US006492506B1

(12) United States Patent
Cole et al.

(10) Patent No.: US 6,492,506 B1
(45) Date of Patent: Dec. 10, 2002

(54) METHOD FOR ISOLATING A POLYNUCLEOTIDE OF INTEREST FROM THE GENOME OF A MYCOBACTERIUM USING A BAC-BASED DNA LIBRARY: APPLICATION TO THE DETECTION OF MYCOBACTERIA

(75) Inventors: Stewart Cole, Clamart (FR); Roland Buchrieser-Brosch, Paris (FR); Stephen Gordon, Paris (FR); Alain Billault, Roissy-en-Brie (FR)

(73) Assignee: Institut Pasteur, Paris (FR)

( * ) Notice: Subject to any disclaimer, the term of this patent is extended or adjusted under 35 U.S.C. 154(b) by 0 days.

(21) Appl. No.: 09/670,314

(22) Filed: Sep. 26, 2000

Related U.S. Application Data

(62) Division of application No. 09/060,756, filed on Apr. 16, 1998, now Pat. No. 6,183,957.

(51) Int. Cl.[7] ........................ C07H 21/02; C07H 21/04; C07H 19/00; C12P 19/34; C12Q 1/08

(52) U.S. Cl. .................... 536/23.1; 536/22.1; 536/24.3; 536/24.31; 536/24.32; 536/24.33; 435/6; 435/7.1; 435/91.1; 435/91.2; 435/252.1

(58) Field of Search .......................... 435/6, 91.1, 91.2; 536/23.1, 24.3, 24.31, 24.32

(56) References Cited

FOREIGN PATENT DOCUMENTS

| | | |
|---|---|---|
| WO | WO93/03187 | 2/1993 |
| WO | WO93/18186 | 9/1993 |
| WO | WO-9723624 A2 * | 7/1997 |
| WO | WO99/54487 | 10/1999 |

OTHER PUBLICATIONS

GenEmbl AD00001 Dec. 3, 1996.*

GenEmbl AD000017 Dec. 10, 1996.*

GenEmbl U00013 Mar. 1, 1994.*

GenEmbl X63508 Nov. 20, 1996.*

Brosch et al., "Use of a Mycobacterium Tuberculosis H37Rv Bacterial Aritificial Chromosome Library for Genome Mapping Sequencing, and Comparative Genomics," *Infection and Immunity*, vol. 66, No. 5, pp. 2221–2229 (May 1998).

Cole et al., "Deciphering the Biology of Mycobacterium Tuberculosis from the Complete Genome Sequence," *Nature*, vol. 393, pp. 537–545 (Jun. 11, 1998).

Cole et al., Novartis Foundation Symposium, pp. 160–177 (1998).

Philipp et al., "Physical Mapping of *Mycobacterium bovis* BCG Pasteur Reveals Differences from the Genome Map of *Mycobacterium tuberculosis* H37Rv and from *M. bovis,*" *Microbiology*, vol. 142:3135–3145 (1996).

Philipp et al., "An Integrated Map of the Genome of the *Tubercle Bacillus, Mycobacterium Tuberculosis* H37Rv, and Comparison with *Mycobacterium leprae,*" *Microbiology*, vol. 93:3132–3137 (1996).

Zimmer et al., "Construction and Characterization of Large–Fragmented Chicken Bacterial Artificial Chromosome Library", *Genomics*, vol. 42:217–226 (1997).

Kim et al., "Construction and Characterization of a Human Bacterial Artificial Chromosome Library," *Genomics*, vol. 34, pp. 213–218 (Jun. 1, 1996).

International Search Report of PCT/IB99/00740.

Philipp et al., "An Integrated Map of the Genome of the *Tubercle Bacilus, Mycobacterium Tuberculosis* H37Rv, and Comparison with *Mycobacterium leprae*," PNAS, vol. 93:3132–3137 (1996).*

* cited by examiner

*Primary Examiner*—Jeffrey Siew
(74) *Attorney, Agent, or Firm*—Finnegan, Henderson, Farabow, Garrett & Dunner, L.L.P.

(57) ABSTRACT

A method for isolating a polynucleotide of interest that is present in the genome of a first mycobacterium strain and/or is expressed by the first mycobacterium strain, where the polynucleotide of interest is also absent or altered in the genome of a second mycobacterium strain and/or is not expressed in the second mycobacterium. The method includes (a) contacting the genomic DNA of the first mycobacterium strain under hybridizing conditions with the DNA of a least one clone that belongs to a bacterial artificial chromosome (BAC) genomic DNA library of the second mycobacterium strain, and (b) isolating the polynucleotide of interest that does not form a hybrid with the DNA of the second mycobacterium strain. This invention further pertains to a *Mycobacterium tuberculosis* strain H37Rv genomic DNA library, as well as a *Mycobactetium bovis* BCG strain Pasteur genomic DNA library, and the recombinant BAC vectors that belong to those genomic DNA libraries. This invention also relates to mycobacterial nucleic acids, and methods and kits for using these nucleic acids to detect mycobacteria in a biological sample.

5 Claims, 12 Drawing Sheets

Figure 1A:
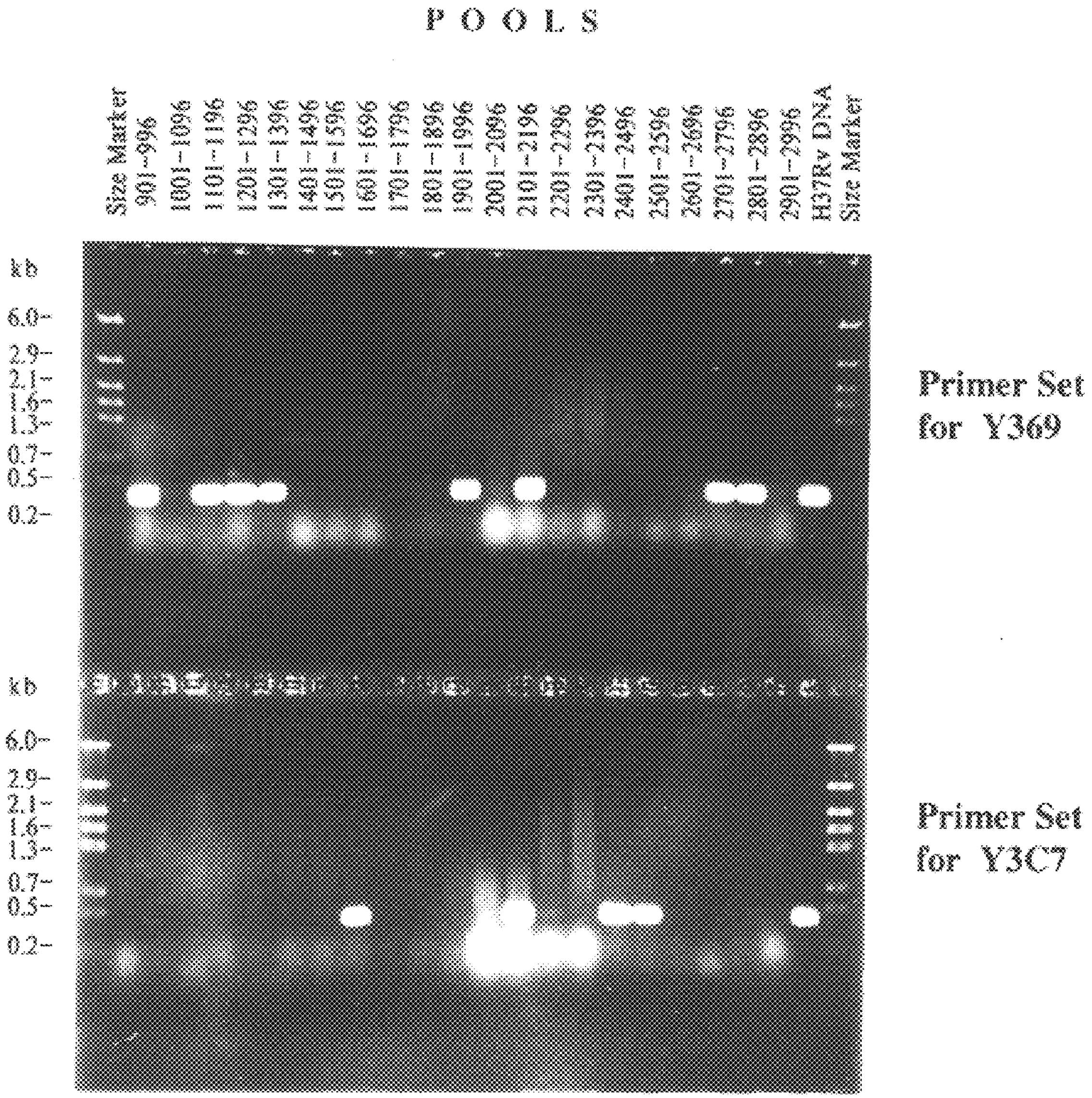

```
(SEQ ID NO. 727) H37Rv .....PTQTLTGRPLIGNGTPGAVGSGATGAPGGWLLGDGGAGGSGAAGSGAPGGAGGAAGLWGT     837273
                 .........::::::::::::::::::::::::::::::::::::::::::::::::::::::::::
(SEQ ID NO. 728) BCG  .......PTQTLTGRPLIGNGTPGAVGSGATGAPGGWLLGDGGAGGSGAAGSGAPGGAGGAAGLWGT

                 H37Rv ...GGAGGAGGSSAGGGGAGGAGGAGGWLLGDGGAGGIGGASTVLGGTGGGGGVGGLWGAGGA   837453
                 ...................................:::::::::::::::::::::::::::::
                 BCG  .....-----------------------------GGAGGIGGASTVLGGTGGGGGVGGLWGAGGA

                 H37Rv ...GGAGGTGLVGGDGGAGGAGGTGGLLAGLIGAGGGHGGTGGLSTNGDGGVGGAGGNAGMLA   837633
                 ........:::::::::::::::::::::::::::::::::::::::::::::::::::::::::
                 BCG  .....GGAGGTGLVGGDGGAGGAGGTGGLLAGLIGAGGGHGGTGGLSTNGDGGVGGAGGNAGMLA

                 H37Rv ...GPGGAGGAGGDGENLDTGGDGGAGGSAGLLFGSGGAGGAGGFGFLGGDGGAGGNAGLLLS   837813
                 ........:::::::::::::::::::::::::::::::::::::::::::::::::::::::::
                 BCG  .....GPGGAGGAGGDGENLDTGGDGGAGGSAGLLFGSGGAGGAGGFGFLGGDGGAGGNAGLLLS

                                                         837897
                 H37Rv ...SGGAGGFGGFGTAGGVGGAGGNAGWLGF------------------------------
                 ........:::::::::::::::::::::::::::...............................
                 BCG  .....SGGAGGFGGFGTAGGVGGAGGNAGWLGFGAGGIGGIGGNANGGAGGNGGTGGQLWGSGGA

                 H37Rv ...--------------GGAGGVGGSAGLIGTGGNGGNGGTGANAGSPGTGGAGGLLLGQNGLNGLP   838047
                 ................:::::::::::::::::::::::::::::::::::::::::::::::::
                 BCG  .....GVEGGAALSVGDTGGAGGVGGSAGLIGTGGNGGNGGTGANAGSPGTGGAGGLLLGQNGLNGLP
```

FIG. 6 pBeloBAC11

(SEQ ID NO. 728) GCGGCCGCAA GGGGTTCGCG TCAGCGGGTG TTGGCGGGTG TCGGGGCTGG
*Not*I restriction site

CTTAACTATG CGGCATCAGA GCAGATTGTA CTGAGAGTGC ACCATATGCG

GTGTGAAATA CCGCACAGAT GCGTAAGGAG AAAATACCGC ATCAGGCGCC

ATTCGCCATT CAGGCTGCGC AACTGTTGGG AAGGGCGATC GGTGCGGGCC

TCTTCGCTAT TACGCCAGCT GGCGAAAGGG GGATGTGCTG CAAGGCGATT
primer T7-BAC1

AAGTTGGGTA ACGCCAGGGT TTTCCCAGTC ACGACGTTGT AAAACGACGG

CCAGTGAATT GTAATACGAC TCACTATAGG GCGAATTCGA GCTCGGTACC
T7-promoter sequence

CGGGGATCCT CTAGAGTCGA CCTGCAGGCA TGCAAGCTTG AGTATTCTAT
primer T7-Belo2 *Hind*III cloning site SP6-promoter AGTGTCACCT AAATAGCTTG GCGTAATCAT GGTCATAGCT GTTTCCTGTG
sequence (complementary strand) primer SP6-Mid (complementary strand)

TGAAATTGTT ATCCGCTCAC AATTCCACAC AACATACGAG CCGGAAGCAT

AAAGTGTAAA GCCTGGGGTG CCTAATGAGT GAGCTAACTC ACATTAATTG
primer SP6-BAC1 (complementary strand)

CGTTGCGCTC ACTGCCCGCT TTCCAGTCGG GAAACCTGTC GTGCCAGCTG

CATTAATGAA TCGGCCAACG CGAACCCCTT GCGGCCGCCC GGGCCGTCGA
*Not*I restriction site

FIG. 7

METHOD FOR ISOLATING A POLYNUCLEOTIDE OF INTEREST FROM THE GENOME OF A MYCOBACTERIUM USING A BAC-BASED DNA LIBRARY: APPLICATION TO THE DETECTION OF MYCOBACTERIA

This is a division of application Ser. No. 09/060,756, filed Apr. 16, 1998 now U.S. Pat. No. 6,183,957 which is Feb. 6, 2000 incorporated herein by reference.

I. BACKGROUND OF THE INVENTION

The present invention pertains to a method for isolating a polynucleotide of interest that is present in the genome of a mycobacterium strain and/or is expressed by said mycobacterium strain and that is absent or altered in the genome of a different mycobacterium strain and/or is not expressed in said different mycobacterium strain, said method comprising the use of at least one clone belonging to a genomic DNA library of a given mycobaterium strain, said DNA library being cloned in a bacterial artificial chromosome (BAC). The invention concerns also polynucleotides identified by the above method, as well as detection methods for mycobacteria, particularly *Mycobacterium tuberculosis*, and kits using said polynucleotides as primers or probes. Finally, the invention deals with BAC-based mycobacterium DNA libraries used in the method according to the invention and particularly BAC-based *Mycobacterium tuberculosis* and *Mycobacterium bovis* BCG DNA libraries.

Radical measures are required to prevent the grim predictions of the World Health Organisation for the evolution of the global tuberculosis epidemic in the next century becoming a tragic reality. The powerfill combination of genomics and bioinformatics is providing a wealth of information about the etiologic agent, *Mycobacterium tuberculosis*, that will facilitate the conception and development of new therapies. The start point for genome sequencing was the integrated map of the 4.4 Mb circular chromosome of the widely-used, virulent reference strain, *M. tuberculosis* H37Rv and appropriate cosmids were subjected to systematic shotgun sequence analysis at the Sanger Centre.

Cosmid clones (Balasubramanian et al., 1996; Pavelka et al., 1996) have played a crucial role in the *M. tuberculosis* H37Rv genome sequencing project. However, problems such as under-representation of certain regions of the chromosome, unstable inserts and the relatively small insert size complicated the production of a comprehensive set of canonical cosmids representing the entire genome.

II. SUMMARY OF THE INVENTION

In order to avoid the numerous technical constraints encountered in the state of the art, as decribed hereabove, when using genomic mycobacterial DNA libraries constructed in cosmid clones, the inventors have attempted to realize genomic mycobacterial DNA libraries in an alternative type of vectors, namely Bacterial Artificial Chromosome (BAC) vectors.

The success of this approach depended on whether the resulting BAC clones could maintain large mycobacterial DNA inserts. There are various reports describing the successful construction of a BAC library for eucaryotic organisms (Cai et al., 1995; Kim et al., 1996; Misumi et al., 1997; Woo et al., 1994; Zimmer et al., 1997) where inserts up to 725 kb (Zimmer et al., 1997) were cloned and stably maintained in the *E. coli* host strain.

Here, it is shown that, surprisingly, the BAC system can also be used for mycobacterial DNA, as 70% of the clones contained inserts in the size of 25 to 104 kb.

This is the first time that bacterial, and specifically mycobacterial, DNA is cloned in such BAC vectors.

In an attempt to obtain complete coverage of the genome with a minimal overlapping set of clones, a Bacterial Artificial Chromosome (BAC) library of *M. tuberculosis* was constructed, using the vector pBeloBAC11 (Kim et al., 1996) which combines a simple phenotypic screen for recombinant clones with the stable propagation of large inserts (Shizuya et al., 1992). The BAC cloning system is based on the *E. coli* F-factor, whose replication is strictly controlled and thus ensures stable maintenance of large constructs (Willets et al., 1987). BACs have been widely used for cloning of DNA from various eucaryotic species (Cai et al., 1995; Kim et al., 1996; Misumi et al., 1997; Woo et al., 1994; Zimmer et al., 1997). In contrast, to our knowledge this report describes the first attempt to use the BAC system for cloning bacterial DNA.

A central advantage of the BAC cloning system over cosmid vectors used in prior art is that the F-plasmid is present in only one or a maximum of two copies per cell, reducing the potential for recombination between DNA fragments and, more importantly, avoiding the lethal overexpression of cloned bacterial genes. However, the presence of the BAC as just a single copy means that plasmid DNA has to be extracted from a large volume of culture to obtain sufficient DNA for sequencing and it is described here in the examples a simplified protocol to achieve this.

Further, the stability and fidelity of maintenance of the clones in the BAC library represent ideal characteristics for the identification of genomic differences possibly responsible for phenotypic variations in different mycobacterial species.

As it will be shown herein, BACs can be allied with conventional hybridization techniques for refined analyses of genomes and transcriptional activity from different mycobacterial species.

Having established a reliable procedure to screen for genomic polymorphisms, it is now possible to conduct these comparisons on a more systematic basis than in prior art using representative BACs throughout the chromosome and genomic DNA from a variety of mycobacterial species.

As another approach to display genomic polymorphisms, the inventors have also started to use selected H37Rv BACs for "molecular combing" experiments in combination with fluorescent in situ hybridization (Bensimon et al., 1994; Michalet et al., 1997). With such techniques the one skilled in the art is enabled to explore the genome of mycobacteria in general and of *M. tuberclosis* in particular for further polymorphic regions.

The availability of BAC-based genomic mycobacterial DNA libraries constructed by the inventors have allowed them to design methods and means both useful to identify genomic regions of interest of pathogenic mycobacteria, such as *Mycobacterium tuberculosis*, that have no counterpart in the corresponding non-pathogenic strains, such as *Mycobacterium bovis* BCG, and useful to detect the presence of polynucleotides belonging to a specific mycobacterium strain in a biological sample.

By a biological sample according to the present invention, it is notably intended a biological fluid, such as plasma, blood, urine or saliva, or a tissue, such as a biopsy.

Thus, a first object of the invention consists of a method for isolating a polynucleotide of interest that is present in the genome of a mycobacterium strain and/or is expressed by said mycobacterium strain and that is absent or altered in the genome of a different mycobacterium strain and/or is not expressed in said different mycobacterium strain, said method comprising the use of at least one clone belonging to a genomic DNA library of a given mycobaterium strain, said DNA library being cloned in a bacterial artificial chromosome (BAC).

The invention is also directed to a polynucleotide of interest that has been isolated according to the above method and in partoular a polynucleotide containing one or several Open Reading Frames (ORFs), for example ORFs encoding either a polypeptide involved in the pathogenicity of a mycobacterium strain or ORFs encoding Polymorphic Glycine Rich Sequences (PGRS).

Such polynucleotides of interest may serve as probes or primers in order to detect the presence of a specific myobacterium strain in a biological sample or to detect the expression of specific genes in a particular mycobacterial strain of interest.

The BAC-based genomic mycobacterial DNA libraries generated by the present inventors are also part of the invention, as well as each of the recombinant BAC clones and the DNA insert contained in each of said recombinant BAC clones.

The invention also pertains to methods and kits for detecting a specific mycobacterium in a biological sample using either at least one recombinant BAC clone or at least one polynucleotide according to the invention, as well as to methods and kits to detect the expression of one or several specific genes of a given mycobacterial strain present in a biological sample.

III. BRIEF DESCRIPTION OF THE FIGURES

In order to better understand the present invention, reference will be made to the appended figures which depicted specific embodiments to which the present invention is in no case limited in scope with.

Figure 1B:
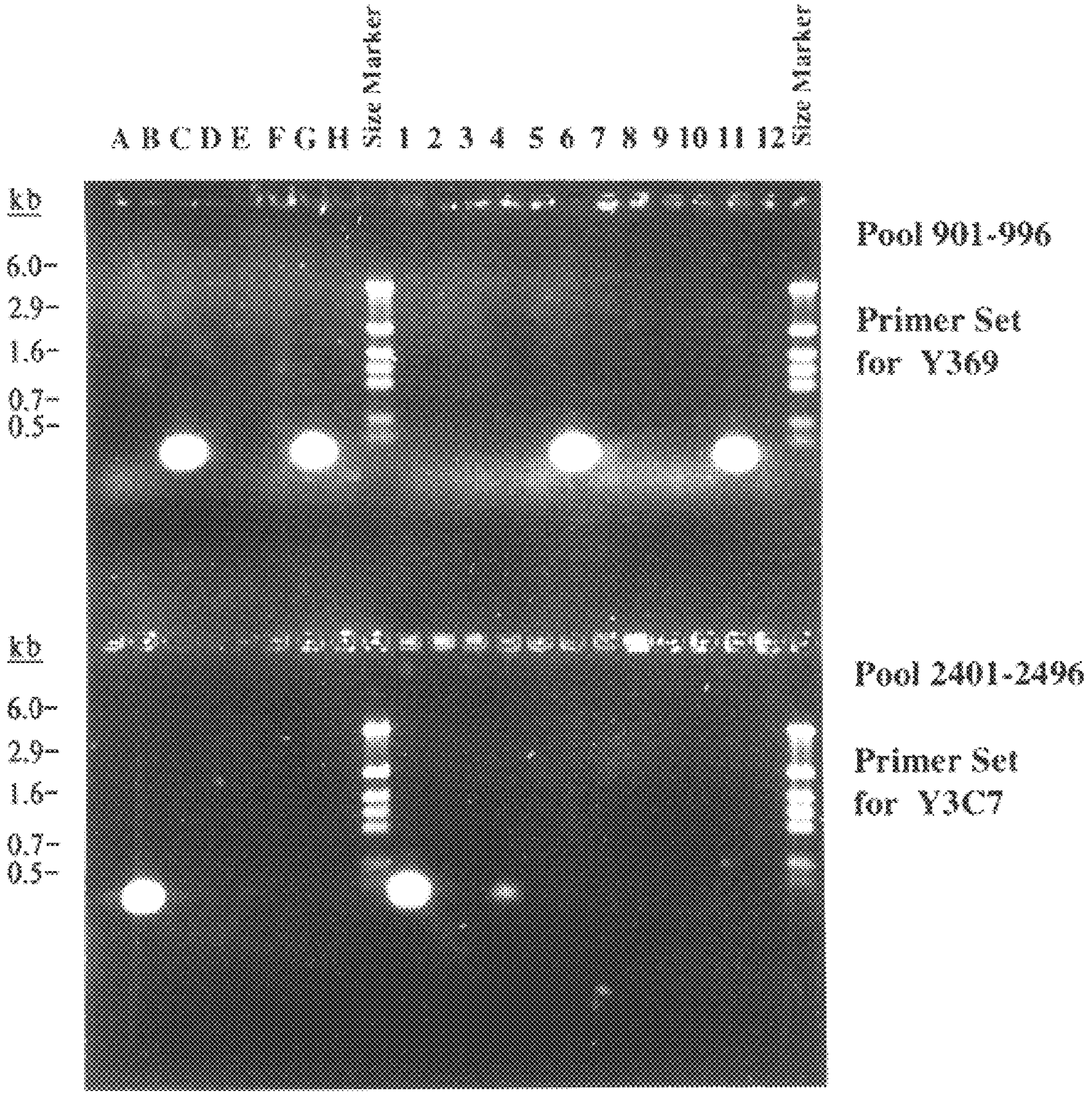

FIGS. 1A and 1B: PCR-screening for unique BAC clones with specific primers for 2 selected genomic regions of the H37Rv chromosome, using 21 pools representating 2016 BACs (Panel A) and sets of 20 subpools from selected positive pools (Panel B).

Figure 2:
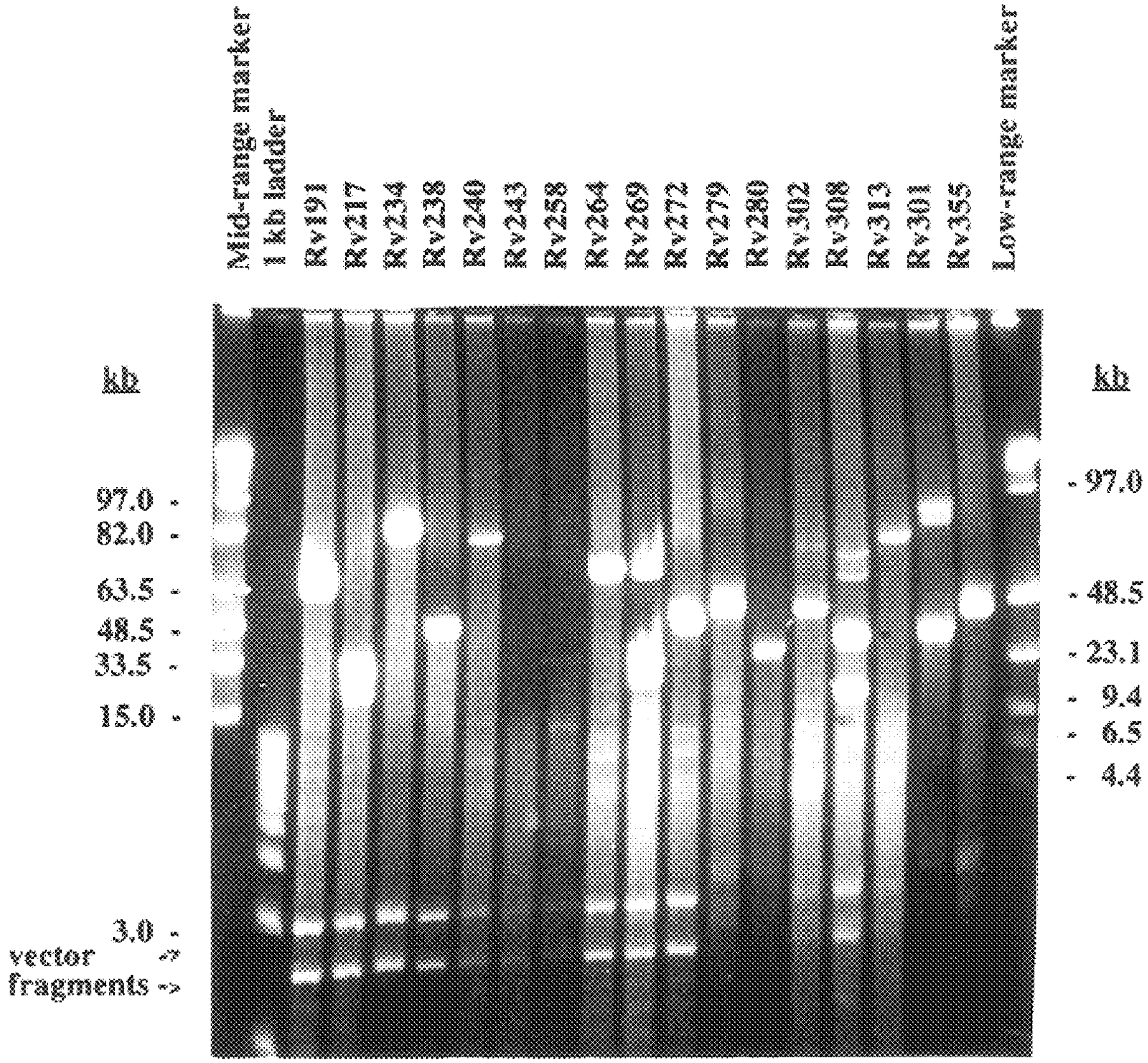
Figure 3A:
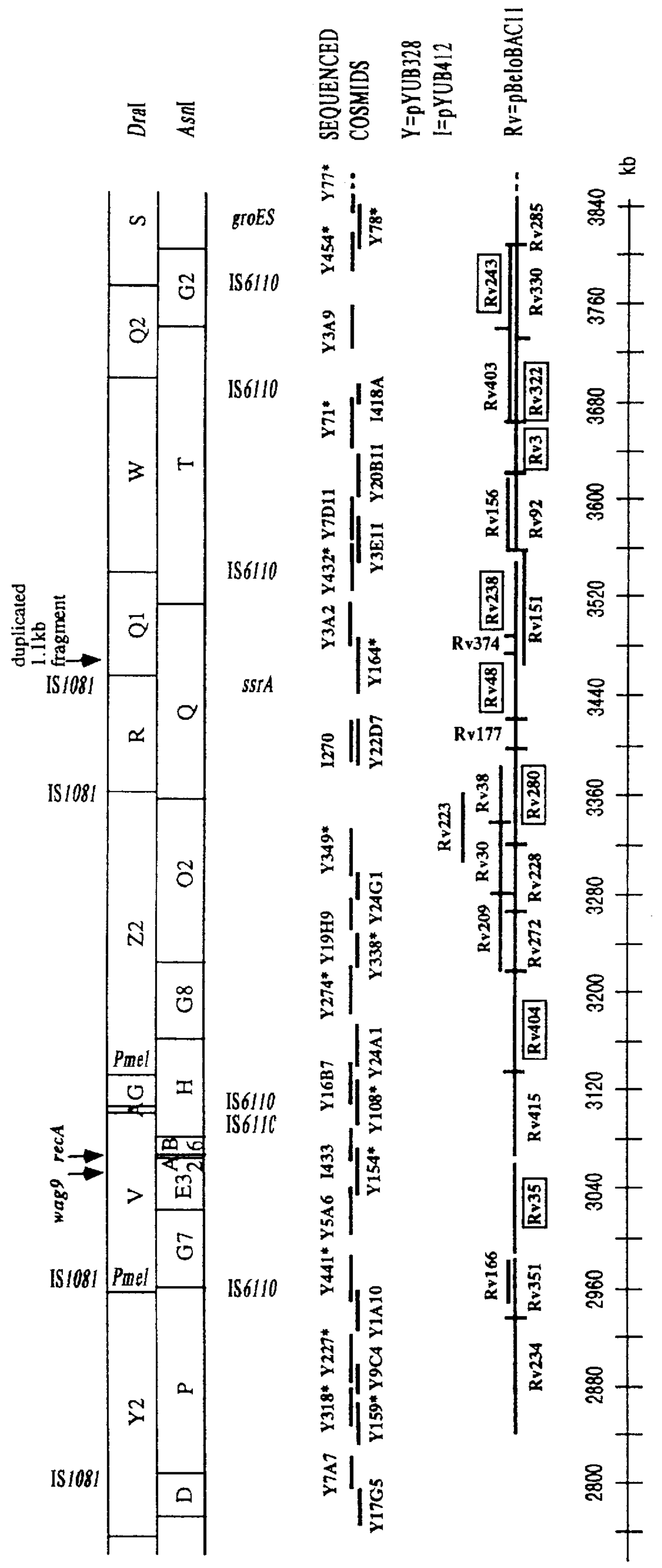
Figure 3B:
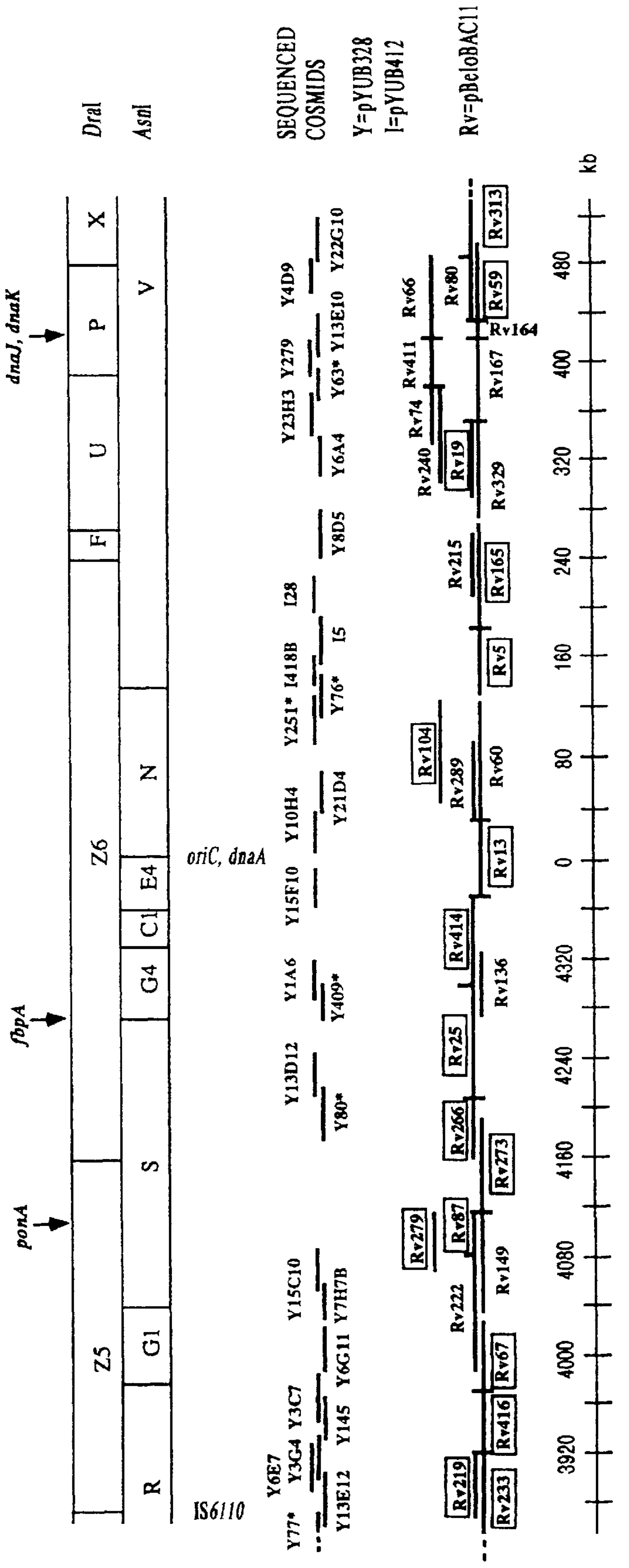
Figure 3C:
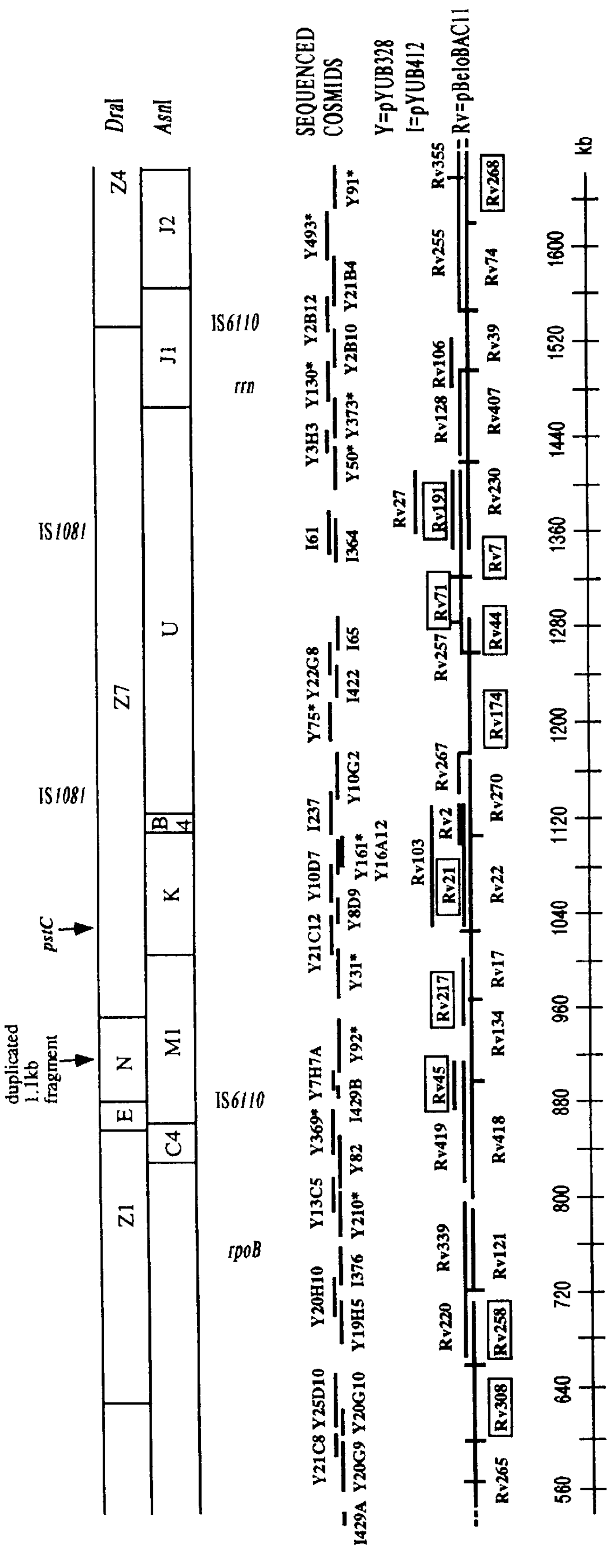
Figure 3D:
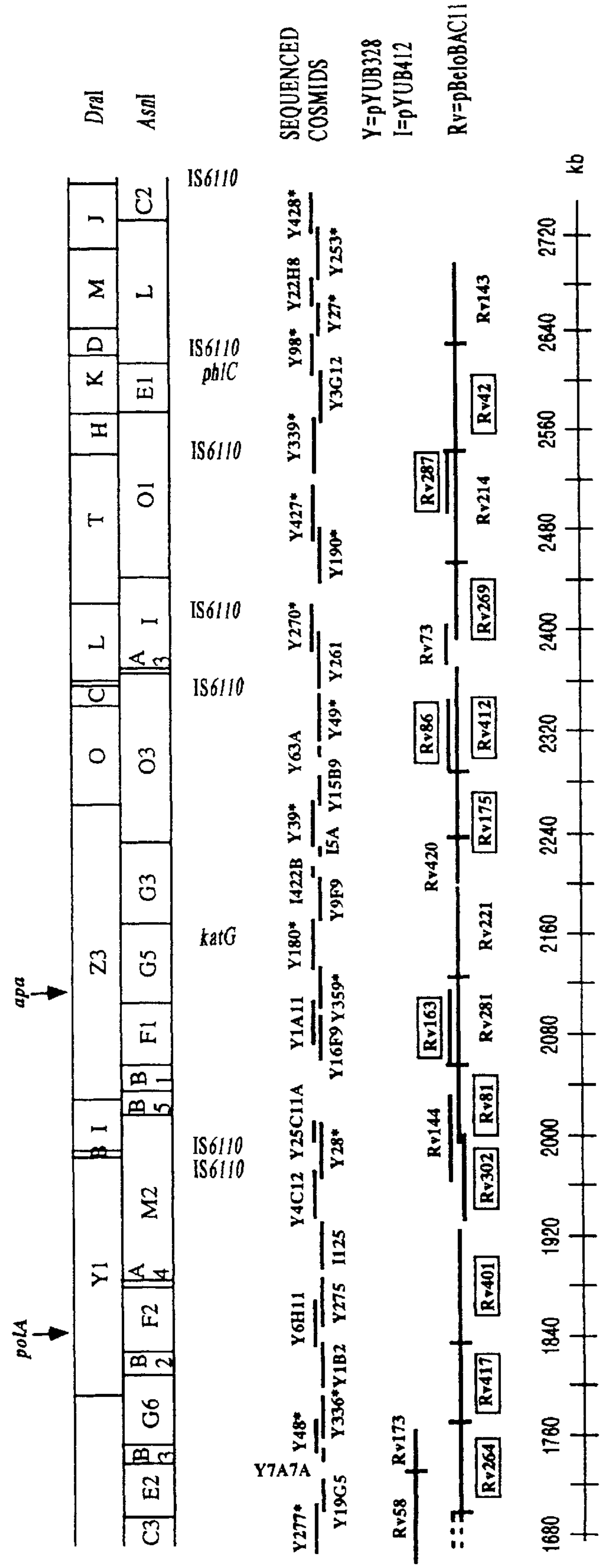

FIG. 2: Pulsed-field gel electrophoresis gel of DraI-cleaved BAC clones used for estimating the insert sizes of BACs.

FIGS. 3A–3D: Minimal overlapping BAC map of *M. tuberclosis* H37Rv superimposed on the integrated physical and genetic map established by Philipp et al. (18). Y- and I-numbers show pYUB328 (2) and pYUB412 (16) cosmids which were shotgun sequenced during the H37Rv genome sequencing project. Y-cosmids marked with * were shown in the integrated physical and genetic map (18). Rv numbers show the position of representative BAC clones relative to sequenced Y- and I-clones. Squared Rv numbers show BACs which were shotgun sequenced at the Sanger Centre.

Figure 4A:
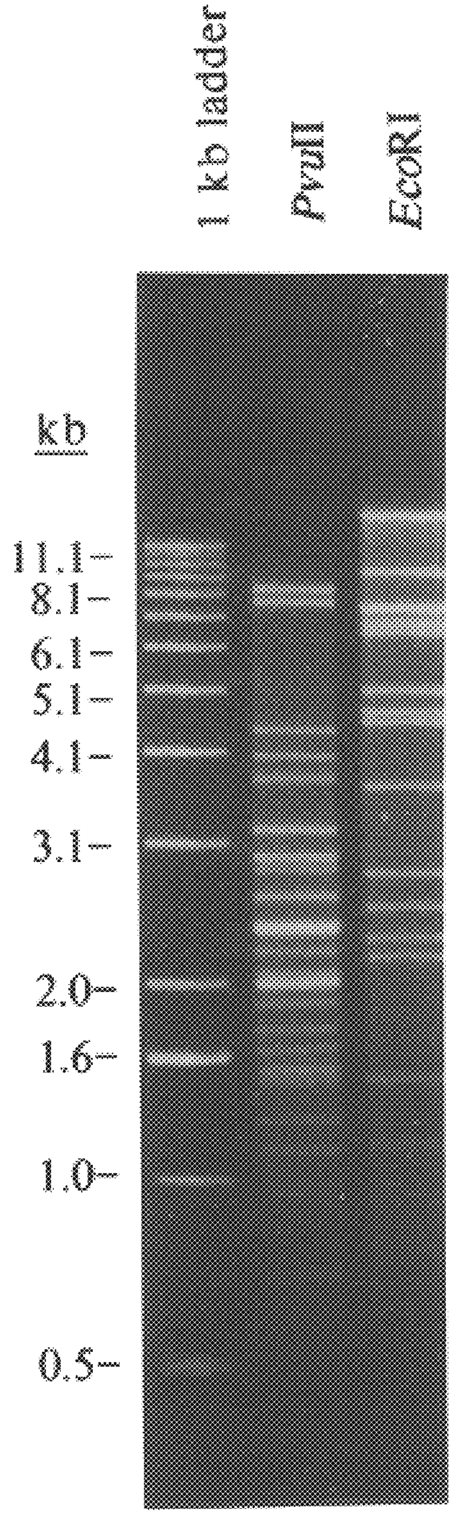
Figure 4B:
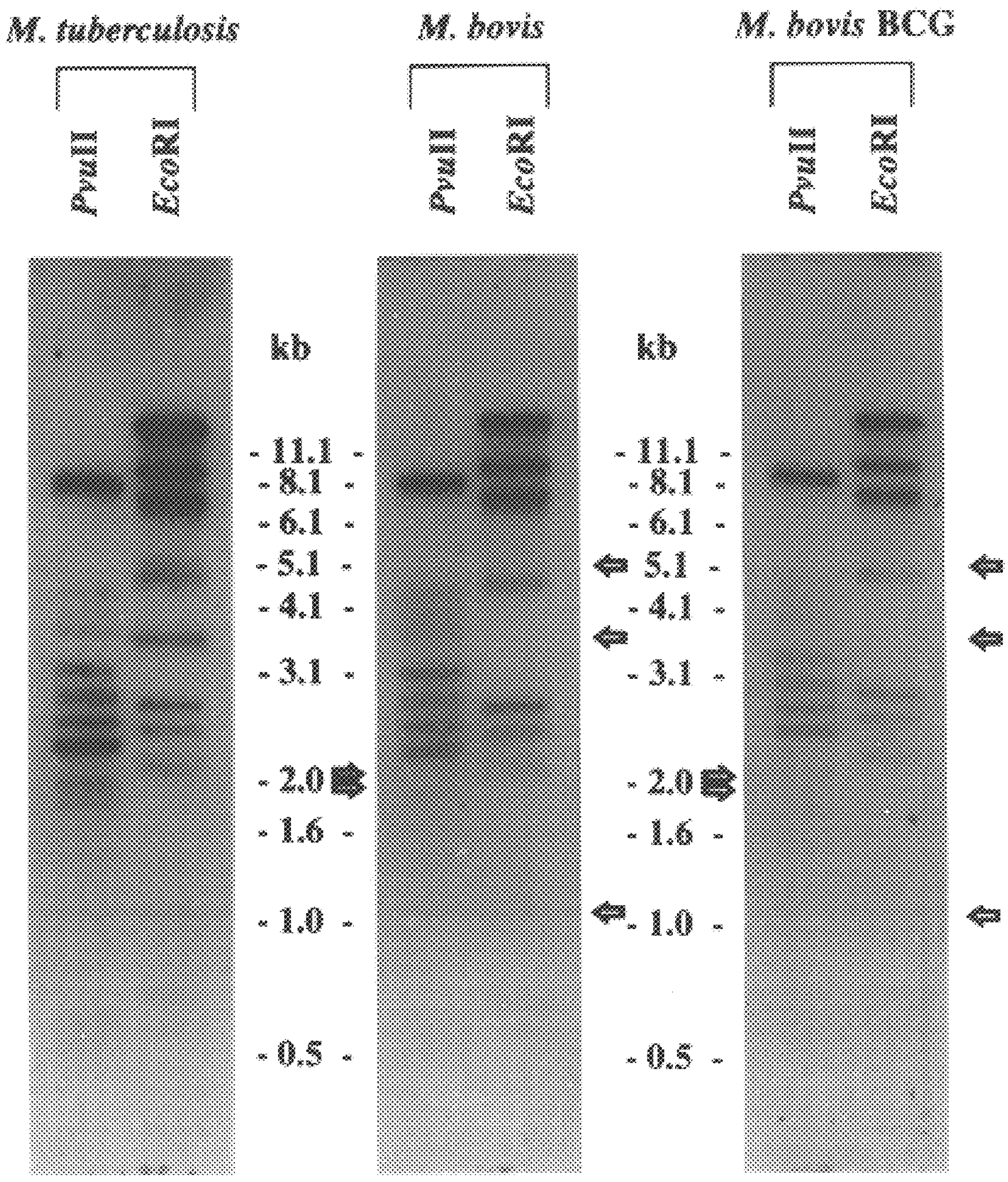

FIGS. 4A and 4B: Ethidium bromide stained gel (Panel A) and corresponding Southern blot (PanelB) of EcoRI and PvuII digested Rv58 DNA hybridized with $^{32}P$ labeled genomic DNA preparations from *M. tuberclosis* H37Rv, *M. bovis* ATCC 19210 and *M. bovis* BCG Pasteur.

Figure 5:
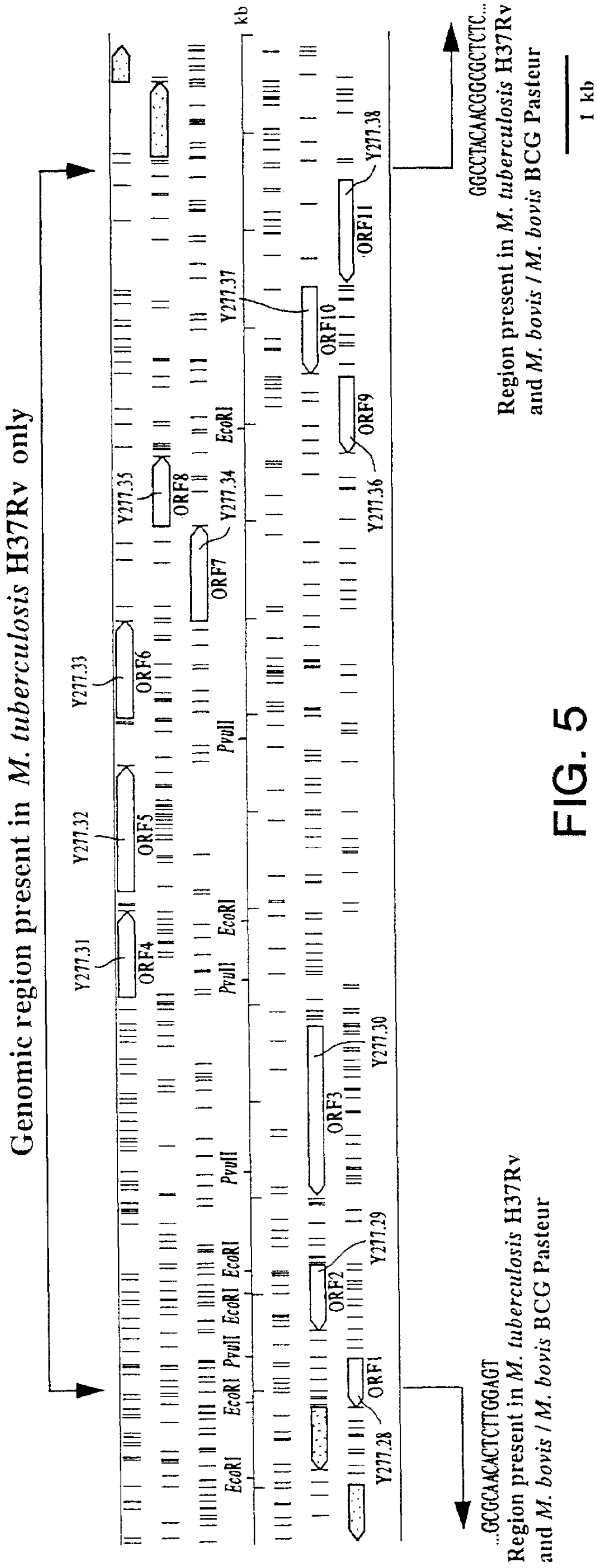

FIG. 5: Organisation of the ORFs in the 12.7 kb genomic region present in *M. tuberculosis* H37Rv but not present in *M. bovis* ATCC 19210 and *M. bovis* BCG Pasteur. Arrows show the direction of transcription of the putative genes. Positions of EcoRI and PvuII restriction sites are shown. Vertical dashes represent stop codons. The 11 ORFs correspond to the ORFs MTCY277.28 to MTCY277.38/ accession number Z79701-EMBL Nucleotide Sequence Data Library. The junction sequences flanking the polymorphic region are shown.

FIG. 6: Variation in the C-terminal part of a PE-PGRS open reading frame in *M. tuberculosis* strain H37Rv relative to *M. bovis* BCG strain Pasteur.

The numbers on the right side of the Figure denote the position of the end nucleotides, taking as the reference the *M. tuberclosis* genome.

FIG. 7: Polynucleotide sequence next to the HindIII cloning site in the BAC vector pBeloBAC11 (Kim et al., 1996) used to clone the inserts of the BAC-based myobacterial genomic DNA library according to the invention.

NotI: location of the NotI restriction sites.

Primer T7-BAC1: nucleotide region recognized by the T7-BAC1 primer shown in Table 1.

T7 promoter: location of the T7 promoter region on the pBeloBac11 vector.

Primer T7-Belo2: nucleotide region recognized by the T7-Belo2 pimer shown in Table 1.

Hind III: the HindIII cloning site used to clone the genomic inserts in the pBeloBAC11 vector.

SP6-Mid primer: nucleotide region recognized by the SP6 Mid primer shown in Table 1.

SP6-BAC1 primer: nucleotide region recognized by the SP6 BAC1 primer shown in Table 1.

SP6 promoter: location of the SP6 promoter region on the pBeloBac11 vector.

IV. DETAILED DESCRIPTION OF THE PREFERRED EMBODIMENTS

As already mentioned hereinbefore, the present invention is directed to a method for isolating a polynucleotide of interest that is present in the genome of a mycobacterium strain and/or is expressed by said mycobacterium strain and that is absent or altered in the genome of a different mycobacterium strain and/or is not expressed in said different mycobacterium strain, said method comprising the use of at least one clone belonging to a genomic DNA library of a given mycobaterium strain, said DNA library being cloned in a bacterial artificial chromosome (BAC).

For this purpose, the inventors have constructed several BAC-based mycobacterial genomic DNA libraries that may be used in order to perform the above described method.

Because it is the first time that mycobacterial genomic DNA has been successfully cloned in BAC type vectors, and because these DNA libraries are then novel and nonobvious, an object of the present invention consists in a myobacterial genomic DNA library cloned in such a BAC type vector.

As an illustrative example, a BAC-based DNA library of *Mycobacterium tuberculosis* has been realized. Forty-seven cosmids chosen from the integrated map of the 4.4 Mb circular chromosome (Philipp et al., 1996a) were shotgun-sequenced during the initial phase of the H37Rv genome sequence project. The sequences of these clones were used as landmarks in the construction of a minimally overlapping BAC map. Comparison of the sequence data from the termini of 420 BAC clones allowed us to establish a minimal overlapping BAC map and to fill in the existing gaps between the sequence of cosmids. As well as using the BAC library for genomic mapping and sequencing, we also tested the system in comparative genomic experiments in order to uncover differences between two closely related mycobacterial species. As shown in a previous study (Philipp et al., 1996b), *M. tuberclosis, M. bovis* and *M. bovis* BCG, specifically BCG Pasteur strain, exhibit a high level of global genomic conservation, but certain polymorphic regions were also detected. Therefore, it was of great interest to find a reliable, easy and rapid way to exactly localize polymorphic regions in mycobacterial genomes using selected BAC clones. This approach was validated by determining the exact size and location of the polymorphisms in the genomic region of DraI fragment Z4 (Philipp et al., 1996b), taking advantage of the availability of an appropriate BAC clone covering the polymorphic region and the H37Rv genome sequence data. This region is located approximately 1.7 Mb from the origin of replication.

The Bacterial Artificial Chromosome (BAC) cloning system is capable of stably propagating large, complex DNA inserts in *Escherichia coli*. As part of the *Mycobacterium tuberculosis* H37Rv genome sequencing project, a BAC library was constructed in the pBeloBAC11 vector and used for genome mapping, confirmation of sequence assembly, and sequencing. The library contains about 5000 BAC clones, with inserts ranging in size from 25 to 104 kb, representing theoretically a 70 fold coverage of the *M. tuberclosis* genome (4.4 Mb). A total of 840 sequences from the T7 and SP6 termini of 420 BACs were determined and compared to those of a partial genomic database. These sequences showed excellent correlation between the estimated sizes and positions of the BAC clones and the sizes and positions of previously sequenced cosmids and the resulting contigs. Many BAC clones represent linking clones between sequenced cosmids, allowing full coverage of the H37Rv chromosome, and they are now being shotgun-sequenced in the framework of the H37Rv sequencing project. Also, no chimeric, deleted or rearranged BAC clones were detected, which was of major importance for the correct mapping and assembly of the H37Rv sequence. The minimal overlapping set contains 68 unique BAC clones and spans the whole H37Rv chromosome with the exception of a single gap of ~150 kb. As a post-genomic application, the canonical BAC set was used in a comparative study to reveal chromosomal polymorphisms between *M. tuberclosis, M. bovis* and *M. bovis* BCG Pasteur, and a novel 12.7 kb segment present in *M. tuberclosis* but absent from *M. bovis* and *M. bovis* BCG was characterized. This region contains a set of genes whose products show low similarity to proteins involved in polysaccharide biosynthesis. The H37Rv BAC library therefore provides the one skilled in the art with a powerfill tool both for the generation and confirmation of sequence data as well as for comparative genomics and a plurality of post-genomic applications.

The above described BAC-based *Mycobacterium tuberculosis* genomic DNA library is part of the present invention and has been deposited in the Collection Nationale de Cultures de Microorganismes (CNCM) on Nov. 19, 1997 under the accession number I-1945.

Another BAC-based DNA library has been constructed with the genomic DNA of *Mycobacterium bovis* BCG, Pasteur strain, and said DNA library has been deposited in the Collection Nationale de Cultures de Microorganismes (CNCM) on Jun. 30, 1998 under the accession number I-2049.

Thus, as a specific embodiment of the above described method for isolating a polynucleotide of interest said method makes use of at least one BAC-based DNA library that has beeen constructed from the genomic DNA of *Mycobacterium tuberculosis*, more specifically of the H37Rv strain and particularly of the DNA library deposited in the accession number I-1945.

In another specific embodiment of the above described method for isolating a polynucleotide of interest said method makes use of at least one BAC-based DNA library has beeen constructed from the genomic DNA of *Mycobacterium bovis* BCG, more specifically of the Pasteur strain and particularly of the DNA library deposited in the accession number I-2049.

In more details, the method according to the invention for isolating a polynucleotide of interest may comprise the following steps:

a) Isolating at least one polynucleotide contained in a clone of a BAC-based DNA library of mycobacterial origin;

b) Isolating:

at least one genomic or cDNA polynucleotide from a mycobacterium, said mycobacterium belonging to a strain different from the strain used to construct the BAC-based DNA library of step a); or alternatively at least one polynucleotide contained in a clone of a BAC-based DNA library prepared from the genome of a mycobacterium that is different from the mycobacterium used to construct the BAC-based DNA library of step a);

c) Hybridizing the at least one polynucleotide of step a) to the at least one polynucleotide of step b);

d) Selecting the at least one polynucleotide of step a) that has not formed a hybrid complex with the at least one polynucleotide of step b);

e) Characterizing the selected polynucleotide.

Following the above procedure, the at least one polynucleotide of step a) may be prepared as follows:

1) Digesting at least one recombinant BAC clone by an appropriate resctriction endonuclease in order to isolate the polynucleotide insert of interest from the vector genetic material;

2) Optionally amplifying the resulting polynucleotide insert;

3) Optionally digesting the polynucleotide insert of step 1) or step 2) with at least one restriction endonuclease.

The above method of the invention allows the one skilled in the art to perform comparative genomics between different strains or species of mycobacteria cells, for example between pathogenic strains or species and their non pathogenic strains or species counterparts, as it is the illustrative case for the genomic comparison between *Mycobacterium tuberculosis* and *Mycobacterium bovis* BCG that is described herein in the examples.

Restriction digests of a given clone of a BAC library according to the invention may be blotted to membranes, and then probed with radiolabeled DNA form another strain or another species of mycobacteria, allowing the one skilled in the art to identify, characterize and isolate a polynucleotide of interest that may be involved in important metabolical and/or physiological pathways of the mycobacterium under testing, such as a polynucleotide functionally involved in the pathogenicity of said given mycobacteria for its host organism.

More specifically, the inventors have shown in Example 6 that when restriction digests of a given clone of the BAC library identified by the CNCM accession number I-1945 are blotted to membranes and then probed with radiolabeled total genomic DNA from, for example, *Mycobacterium bovis* BCG Pasteur, it is observed that restriction fragments that fail to hybridize with the *M. bovis* BCG Pasteur DNA are absent from its genome, hence identifying polymorphic regions between *M. bovis* BCG Pasteur and *M. tuberclosis* H37Rv.

Thus, a further object of the present invention consists in a polynucleotide of interest that has been isolated according to the method described herein before.

In Example 6, a polynucleotide of approximately 12.7 kilobases has been isolated that is present in the genome of *M. tuberclosis* but is absent of the genome of *M. bovis* BCG. This polynucleotide of interest contains 11 ORFs that may be involved in polysaccharide biosynthesis. In particular, two of said ORFs are of particular interest, namely ORF6 (MTCY277.33; Rv1511) that encodes a protein that shares significant homology with bacterial GDP-D-mannose dehydratases, whereas the protein encoded by ORF7 (MTCY277.34; Rv1512) shares significant homology with a nucleotide sugar epimnerase. As polysaccharide is a major constituent of the mycobacterial cell wall, these deleted genes may cause the cell wall of *M. bovis* BCG to differ from that of *M. tuberclosis*, a fact that may have important consequences for both the immune response to *M. bovis* BCG and virulence. Detection of such a polysaccharide is of diagnostic interest and possibly useful in the design of tuberculosis vaccines.

Consequently, the polynucleotide of interest obtained following the method according to the invention may contain at least one ORF, said ORF preferably encoding all or part of a polypeptide involved in an important metabolical and/or physiological pathway of the mycobacteria under testing, and more specifically all or part of a polypeptide that is involved in the pathogenicity of the mycobacteria under testing, such as for example *Mycobacterium tuberculosis*, and more generally mycobacteria belonging to the *Mycobacterium tuberculosis* complex.

The *Mycobacterium tuberculosis* complex has its usual meaning, i.e. the complex of mycobacteria causing tuberculosis which are *Mycobacterium tuberculosis, Mycobacterium bovis, Mycobacterium africanum, Mycobacterium microti* and the vaccine strain *Mycobacterium bovis* BCG.

An illustrative polynucleotide of interest according to the present invention comprises all or part of the polynucleotide of approximately 12.7 kilobases that is present in the genome of *M. tuberclosis* but is absent from the genome of *M. bovis* BCG disclosed hereinbefore. This polynucleotide is contained in clone Rv58 of the BAC DNA library I-1945.

Generally, the invention also pertains to a purified polynucleotide comprising the DNA insert contained in a recombinant BAC vector belonging to a BAC-based mycobacterial genomic DNA library, such as for example the I-1945 BAC DNA library.

Advantageously, such a polynucleotide has been identified according to the method of the invention.

Such a polynucleotide of interest may be used as a probe or a primer useful for specifically detecting a given mycobacterium of interest, such as *Mycobacterium tuberculosis* or *Mycobacterium bovis* BCG.

More specifically, the invention then deals with a purified polynucleotide usefill as probe or a primer comprising all or part of the nucleotide sequence SEQ ID N°1:

```
ACCTGCGCTT GCAGAGATCA AATAGGGCGC ATGGGTCAGC ATAGTACAGG TCGTCGCGCA     60
TCTTTGATGC ATCGGAATAA GATGTCAGGC AATTAAAAGA GAAGCCACGG CGACTCGCGG    120
CATTCAGCAT GTCGAGCGTC GCTTCGATGT GAGCGCACCA TTCCGTGTCC AACGATTTCA    180
GACGAACATT GAATATTCCA CTCGCGACGC TATAGTCCGC CTCCCGATCT ATGCGCGCCG    240
CGCAGATGAA GTCTGCGTTC GCCCGACCTT CGAAACGTAG TGCGGCCGCG CGCACCATTT    300
CGGGGGAGAC GTCGATGCCG GTGTAATCAG TTTTGAAGCC ACGCGCATCT AGGTAGTCCA    360
GTAGAGCCCC ATAGCCACAG CCTAGATCGT TGATCGAAAA TGGGTCCGCC GCATTGACAA    420
TGCGCACCAG CTGGTCAAAG CGCAACGCCT GCCCGGCTTC GCCGTTCCAA TCGACGCCGC    480
GCGGGTGCCG TGTGCTTCGA GTTTCGATGC GTAGTAACGG GCCACGTCAG CGAGCATGGT    540
CGTTGCGTCT TCCGCCATGA AGCTGCCTCA CGATTTGTGT GTGTGGGCGT CGGTGCGTGG    600
GTCCGAGACT ATACCTTCAA CAGTTGCATG CCGAGGCTGC GGCGGGCAAT GACCCAAAAA    660
CCCGCCGGCA CGGTTCGCCG AGCAAGGAAG CGTGGAGACG ATAGATAATT TCACTGGCGA    720
CAGTACCTCA AATAGTCCGG AGCCTCGGCT CCGACGTTAA AGAGCAGATC CAGAATCGAC    760
ACGGCGGGCT CGAACCCTCC CCACAATTGC TTATAATCGC GGTAGCCGTC ATAATCGAAC    840
CAAGTTACCC GGATGCTAAG TTCGTCGAAC ACGCGCTCAT CGACATACGA ACGGGCTGAG    900
GGGCCAGAGA CATATTCGGT CGCTGCGGCC TGTTGGCAGA GGTTGGCCAG TCTCTCGGTC    960
TTGCCGTCGG CTAATTCGTA GTCCCACGAA TTTGCCAGTC GCGTGCTGAT ACCGAGATAA   1020
CTGCAAATCG CATTCAATAG ACGCCTGTTG AGTAAGGAAA GATTCGTGTG CTGTTCTTCG   1080
AGGTAAATCG GCGCGAGCCA GTCAGCGATC TCCGCAAAAT GAGCGGCCGC GCTGTAGTTG   1140
AATTCTAGTG CCCGCCAGTG CGCTTTCGCC CAATCGGTGC CGTCGATCAG CGTCTCACGT   1200
ATCTTTTGAT GGAAACGTCC CTTCACCTGG ACGGGAACAG TTATCCACTG TAACCCCTGG   1260
CTCGTTTTGA TCCGATTTCT GTTTCGCCAA TCACGCTTGG TATATTGCAT GTCATCATAG   1320
```

-continued

ATGATGAATT CATCGACGAA TGCAATCAGG TCAAAATATC CTCGCCAAGG TATGTAATTT 1380

GATTGAACAA TCGCGACTTT CTTCAACGCG GTGTCTCCAA TTTAGAATAA CAAATACGTC 1440

GCGCCCGCGA CAGCTCCGCT GGAGCGAGTT CAAGCGATTC TGCGACATAT TCAATATGGT 1500

GCTCGGGAAG GCCAGGATGG GCCGCGACCC GGGGCGTCCG GTGCGCGATG AACGTCGCAT 1560

CGTCTCCTGT GAGATAATTG CATCCGATCA TATAGGGCTG GCTGCGGCTA GGTTGCTGGC 1620

AAAAAGATAT CGCGGCCGAT CCGTTTCTGG TTTTGTCTTG ATGATCAAAT CCGCTTCCGT 16B0

TCACGAGATC GATTCCTGGT CTTCCCCCAG CGTCGCGATG TCGATAGGTG TCGCGCTTTG 1740

TTCGTACCCG CACTACGCGG CGGCGAGAAC CTCGCCACCG AATCGGGATT GGGGGGAGGA 1800

TACCACTCGG TCGAGGCCCG TCACCGGCCT TCTAGCGGGT TGACCATCAG TGTTTGCAGG 1860

GCCCTATCCC GGTATGGCGC ACCACGGGAT CGGCAGCGTT CCGGTTGCTG GCGTGGTACC 1920

TCGTTGTGGC GCCGTGGTCC ATGTCGATTG AGTGCGTGGA TCAGTGTAAA CCGTTGCGCG 1980

CCATGTTCTG TAGGCACTGG TTCGGGTTGT GGTTAGGCTG CACGGTTGGC AGGTTACCAA 2040

CCACTGAGCC CCTGGGCGGA TGTGAGCTCG GACTCCGCCT ATGGGGTGTA ATTTTGGCAG 2100

ATTGGGCCGG GTCCCCGTGG TGAGGACTCC TCAACCGGAT TGGGTAAGCA TGAGGTGGTG 2160

CTGGCAGCGG TGTCCTGGTC GCTCTCCCGA GTAGGCCCGT TGTGACTGTC ATGTGGGCGA 2220

GCGGGTTTGC GCGCGTAGGA GACGATGATT ACTACGCACG TGACCAACCA CAAGAACGGT 2280

GCCCATGTCA CCGTGGTGAA AACGAGTGGC GTGGTACCGA CTACCCCTTT GGCTCCCAGC 2340

TGTCCATAGA GCGGCACGTA GAACGGCTGG CCCGGGACCG CGACGTTGAC GATGCTCAGC 2400

GCCACGGCCA AACTCACGCA GACGCCGACC GCGCGGCGGC GGTCTCCATG GGCTGCGAGT 2460

TGGTCGAATA TCCCAGCACC AGGAGGCCCG TTGGGGTCTC GGGCTACCAG TGCAGCGATT 2520

GGCAAGACGA AAACGAGATA GTAGAAGGCG ACGTCCGCGG GGGAGAAGGT GGCGGTGGCG 2580

AGCAACACAA TCCCCACCAT GACAGGCGGG ATACGGCGTC CGAGCGCCAG CACGGCGACC 2640

ACGACTATGA CTAGGACAGC AAACCCGATC TGCGTTCGCG GACCAGTGAG GAAACCCTCT 2700

GGGATCTTGC CCGATTGATA GTTCTTGATG CTATCGGGGA TCAGCAGGAG TGCCTTGCCA 2760

AAGGACACGT TCCGCGGGTC TCGAAGCCCT CCGAACGAAC TATTGAACTT GATGATGCCG 2820

TGGATCGACT GTGCGATCGT CCCCGGGAAG CCTCGTGGCC ACAACAGAAA GGCTGCGATA 2880

TTGGACACCA CCACGCCGGT GATCCCGATA CCAGCCCACC GCCATTGTCG AGCCGCCAAC 2940

AACACCACGC CGAGAACGAC GAACTGCGGC TTTACCAGGA CGGCCAAGAT CACCGTGATG 3000

GTGGCGAGGC CCCACCGCTG TCGGGACAAC GCCACGAAGT AAGCCAGCGC GATCGGTACC 3060

ACGAACCCTG TCGAGTTGCC TCGATCGATG ACCCCCCACG CCGGGATGGC CGCGGCGCCC 3120

AGTGTCACGA AGATGACCAC TCGCTCCAGA CCACGTGCCC CCCGGGCCGC CCAGATGGCG 3180

GGAGATATGA CCGCCATCGT TAGGGCGACC AGGTAACAGA TCAGCCCCAA GCGCGGCGCA 3240

CCCAGCCAAT GGCTGGGTAG TCCGAAAATC GCATACGGTA TGCGGGCGGG GGCCCATGCA 3300

GCAACCGCGG TCGGCTGGTA ATCGGCGGGT AGCGAGATCA GGTAGTCCGC GGGATTGGGT 3360

TGAATCCCGG CGGCGGCGAC CATGGCGTAG TCGCTGAAGC AGTGCCGACC GATATTCATG 3420

CCCCAATCAA GCCAACAGTC CCCAGGGACT ACCAAAAGAG TGGAAAAGAC GTCGACCGCG 3480

TACCACTGAC TGAGGGCGTA CGCCGTCGCC GCCGAAATCA CCGACGCCAG CAGGATGGTG 3540

CCGAGCATGA GGGTGCGCTC GGATTGGGAG CCGATCGCCC AGAGCCGCTC CCGGCTCGCG 3600

GTCACGGCAC CGCGCAACAC CTCCGGGGGT CGCTTCATCT GGATTCTCCT CGGTTCTGCG 3660

CGAAACGGTA GCAGAGCGCC ATGGTTGCCA ACGCGGTCGC CGGGCAGTCT AGACCGGATC 3720

-continued

```
TTCCTCGTGG CAACCGACAA CAGGACGTCG TTGCCGAAAG GGCGCTGGGC ACCGACATCT   3780
AGGATGAACC CACAGCCACG CCCCGACGTT ATGCCATGGC GAAGAGCGAC CGGCAGGAGC   3840
GGGAACCCAG TGAAGCGAGC GCTCATCACC GGAATCACAG GACCGGACGG CTCGTATCTC   3900
GCTAAGCTCC CGCTGAAGGG ATATGTGGCC GCTGGTAGCC CGGCCGAGGT CTATTTCTGC   3960
TGGGCGACAC GGAATTATCG CGAATTGTAT GGGTTGCTCG CGGTCAACAG CATCTGGTTC   4020
AATCACGAAT CACCGCGTCA CGGCGAGACA TTCATGACTC GTAATCCTGC ACCATATCGC   4080
GGTCGGCAAC GAGGCGCTGA TCGATGCGCA GACGCTGATG CGCCGGCCCA CCCGGATAGG   4140
TATCAGTATT GGGGCGTTCC GGCCAGCGTA CGAGGCGTGA TCGACCGCGC AATGGGTGTT   4200
TGCGTTGAGT AATAATCTGA ACCGTGTGAA CGCATGCATG GATGGATTCC TTGCCCGTAT   4260
CCGCTCACAT GTTGATGCGC ACGCGCCAGA ATTGCGTTCA CTGTTCGATA CGATGGCGGC   4320
CGAGGCCCGA TTTGCACGCG ACTGGCTGTC CGAGGACCTC GCGCGGTTGC CTGTCGGTGC   4380
AGCATTGCTG GAAGTGGGCG GGGGGGTACT TCTGCTCAGC TGTCAACTGG CGGCGGAGGG   4440
ATTTGACATC ACCGCCATCG AGCCGACGGG TGAAGGTTTT GGCAAGTTCA GACAGCTTGG   4500
CGACATCGTG CTGGAATTGG CTGCAGCACG ACCCACCATC GCGCCATGCA AGGCGGAAGA   4560
CTTTATTTCC GAGAAGCGGT TCGACTTCGC CTTCTCGCTG AATGTGATGG AGCACATCGA   4620
CCTTCCGGAT GAGGCAGTCA GGCGGGTATC GGAAGTGCTG AAACCGGGGG CCAGTTACCA   4680
CTTCCTGTGC CCGAATTACG TATTCCCGTA CGAACCGCAT TTCAATATCC CAACATTCTT   4740
CACCAAAGAG CTGACATGCC GGGTGATGCG ACATCGCATC GAGGGCAATA CGGGCATGGA   4800
TGACCCGAAG GGAGTCTGGC GTTCGCTCAA CTGGATTACG GTTCCCAAGG TGAAACGCTT   4860
TGCGGCGAAG GATGCGACGC TGACCTTGCG CTTCCACCGT GCAATGTTGG TATGGATGCT   4920
GGAACGCGCG CWGACGGATA AGGAATTCGC TGGTCGCCGG GCACAATGGA TGGTCGCTGC   4980
TATTCGCTCG GCGGTGAAAT TGCGTGTGCA TCATCTGGCA GGCTATGTTC CCGCTACGCT   5040
GCAGCCCATC ATGGATGTGC GGCTAACGAA GAGGTAATGA CATGGCGCAA GCGACATCGG   5100
GCATTCGCGC GGCACTTTCG CAACCTGCTG TGTATGAGGC GTATCAGCGG ATTGCGGGCG   5160
CTAAAAGCGG GCTTGCGTGG ATCACAACCG ACCCCATCCA GTCGTTGCCA GGCATGCGTA   5220
CTCTCGACCT CGGTTGCTGG CCAGCGGTGA TACACAGCTC CCCGCCAGTG GACGTGACAT   5280
GTACGAGAGA CGGCATGAGC GCGGAATGTG CGACCGTGCC GTCGAGATGA CCGACGTCGG   5340
CGCTACGGCA GCCCCCACCG GACCTATCGC GCGGGGCAGC GTCGCTCGGG TCGGCGCGGC   5400
GACCGCGTTG GCCGTTGCCT GCGTCTACAC GGTCATCTAT CTGGCGGCCC GCGACCTACC   5460
CCCGGCTTGT TTTTCGATAT TCGCGGTGTT TTGGGGGGCG CTCGGCATTG CCACCGGCGC   5520
CACCCACGGC CTCCTGCAAG AAACGACCCG CGAGGTCCGC TGGGTGCGCT CCACCCAAAT   5580
AGTTGCGGGC CATCGTACCC ATCCGCTGCG GGTGGCCGGG ATGATTGGCA CCGTCGCGGC   5640
CGTCGTAATT GCGGGTAGCT CACCGCTGTG GAGCCGACAG CTATTCGTCG AGGGGCGCTG   5700
GCTGTCCGTG GGGCTACTCA GCGTTGGGGT GGCCGGGTTC TGCGCGCAGG CGACCCTGCT   5760
GGGCGCGCTG GCCGGCGTCG ACCGGTGGAC ACAGTACGGG TCACTGATGG TGACCGACGC   5820
GGTCATCCGG TTGGCGGTCG CCGCGGCAGC GGTTGTGATC GGATGGGGTC TGGCCGGGTA   5880
CTTGTGGGCC GCCACCGCGG GAGCGGTGGC GTGGCTGCTC ATGCTGATGG CCTCGCCCAC   5940
CGCGCGCAGC GCGGCCAGCC TGCTGACGCC CGGGGGAATC GCCACGTTCG TGCGCGGTGC   6000
CGCTCATTCG ATAACCGCCG CGGGTGCCAG CGCGATTCTG GTAATGGGTT TCCCAGTGTT   6060
GCTCAAAGTG ACCTCCGACC AGTTAGGGGC AAAGGGCGGA GCGGTCATCC TGGCTGTGAC   6120
```

-continued

```
CTTGACGCGT GCGCCGCTTC TGGTCCCACT GAGCGCGATG CAAGGCAACC TGATCGCGCA   6180
TTTCGTCGAC CGGCGCACCC AACGGCTTCG GGCGCTGATC GCACCGGCGC TGGTCGTCGG   6240
CGGCATCGGT GCGGTCGGGA TGTTGGCCGC AGGGCTTACC GGTCCCTGGT TGCTGCGTGT   6300
TGGATTCGGC CCCGACTACC AAACTGGCGG GGCGTTGCTG GCCTGGTTGA CGGCAGCGGC   6360
GGTAGCTATC GCCATGCTGA CGCTGACCGG CGCCGCCGCG GTCGCGGCCG CACTGCACCG   6420
GGCGTATTTG CTGGGCTGGG TCAGCGCGAC GGTGGCGTCG ACGCTGTTGC TGCTGCTGCC   6480
GATGCCGCTG GAGACGCGCA CCGTGATCGC GCTGTTGTTC GGTCCAACGG TGGGAATCGC   6540
CATCCATGTG GCCGCGTTGG CGCGGCGACC CGACTGATTT GTGCCCCAGG TCGACAAATC   6600
ACGCCGTCTC GTCAGTGAGC ACTCCGTCCT CGGGTCCGAT CCTTCCAGGA GACGTTGCAA   6660
CCTGATTTGG CTCAAATTGG TGCGCACCGA GGGTCGGGCA CATCGTAGGG TCGCAACAGT   6720
CACATGTGTC ACTGCACCGG GCGACACCCG ATGTCCCGGC TCTCAGCGAC AGCTGTCTGA   6780
CCTGTGGTTT TGTTCCCAAG TTGGTCGTGG CTGTGCGGGA TTGGAGGTGG CGTGGGGGTC   6840
GCGTCGTATG GATTCTCCTC CTCGGTTCCG CGCGAAACGG CCGCAGGCGC AATGGTCACC   6900
AACTTGGCCG CGGTGGAGTC TAGCCTCACA TTTTCCTGGT CGCCCCCGAC AACCAGGAGG   6960
TCGCTGCAGA ACGGGCGTTC CCTACCCACA TCTACTATGA AGCGACAGCG GCGCCCCGCT   7020
GTGATGGCTG AGCATGACCG ACAGAGGCGG GAAGACAGTG AAGCGAGCGC TCATCACCGG   7080
AATCACCGGC CAGGACGGCT CGTATCTCGC CGAACTGCTG CTGGCCAAGG GGTATGAGGT   7140
TCACGGGCTC ATCCGGCGCG CTTCGACGTT CAACACCTCG CGGATCGATC ACCTCTACGT   7200
CGACCCGCAC CAACCGGGCG CGCGGCTGTT TCTGCACTAT GGTGACCTGA TCGACGGAAC   7260
CCGGTTGGTG ACCCTGCTGA GCACCATCGA ACCCGACGAG GTGTACAACC TGGCGGCGCA   7320
GTCACACGTG CGGGTGAGCT TCGACGAACC CGTGCACACC GGTGACACCA CCGGCATGGG   7380
ATCCATGCGA CTGCTGGAAG CCGTTCGGCT CTCTCGGGTG CACTGCCGCT TCTATCAGGC   7440
GTCCTCGTCG GAGATGTTCG GCGCCTCGCC GCCACCGCAG AACGAGCTGA CGCCGTTCTA   7500
CCCGCGGTCA CCGTATGGCG CCGCCAAGGT CTATTCGTAC TGGGCGACCC GCAATTATCG   7560
CGAAGCGTAC GGATTGTTCG CCGTTAACGG CATCTTGTTC AATCACGAAT CACCGCGGCG   7620
CGGTGAGACG TTCGTGACCC GAAAGATCAC CAGGGCCGTG GCACGCATCA AGGCCGGTAT   7680
CCAGTCCGAG GTCTATATGG GCAATCTGGA TGCGGTCCGC GACTGGGGGT ACGCGCCCGA   7740
ATACGTCGAA GGCATGTGGC GGATGCTGCA GACCGACGAG CCCGACGACT TCGTTTTGGC   7800
GACCGGGCGC GGTTTCACCG TGCGTGAGTT CGCGCGGGCC GCGTTCGAGC ATGCCGGTTT   7860
GGACTGGCAG CAGTACGTGA AATTCGACCA ACGCTATCTG CGGCCCACCG AGGTGGATTC   7920
GCTGATCGGC GACGCGACCA AGGCTGCCGA ATTGCTGGGC TGGAGGGCTT CGGTGCACAC   7980
TGACGAGTTG GCTCGGATCA TGGTCGACGC GGACATGGCG GCGCTGGAGT GCGAAGGCAA   8040
GCCGTGGATC GACAAGCCGA TGATCGCCGG CCGGACATGA ACGCGCACAC CTCGGTCGGC   8100
CCGCTTGACC GCGCGGCCCG GGTCTACATC GCCGGGCATC GCGGCCTGGT CGGGTCCGCG   8160
CTGCTACGCA CGTTTGCGGG CGCGGGGTTC ACCAACCTGC TGGTGCGGTC ACGCGCCGAG   8220
CTTGATCTGA CGGATCGGGC CGCGACGTTC GACTTCGTTC TCGAGTCGAG GCCGCAGGTC   8280
GTCATCGACG CGGCGGCCCG GGTCGGCGGC ATCCTGGCCA ACGACACCTA CCCGGCCGAT   8340
TTCCTGTCGG AAAACCTCCA GATCCAGGTC AACCTGCTGG ATGCCGCCGT GGCGGCGCGG   8400
GTGCCGCGGC TGCTGTTCCT GGGCTCGTCG TGCATCTACC CGAAACTCGC CCCGCAGCCG   8460
ATCCCGGAGA GCGCGCTGCT CACCGGTCCG TTGGAGCCGA CCAACGACGC GTACGCGATC   8520
```

-continued

GCCAAAATCG CCGGCATCCT TGCGGTCCAG GCGGTGCGCC GCCAACATGG CCTGCCGTGG 8S80

ATCTCGGCGA TGCCCACCAA CCTGTACGGG CCAGGCGACA ACTTTTCGCC GTCCGGCTCG 8640

CATCTGCTGC CGGCACTCAT CCGCCGCTAT GACGAGGCCA AAGCCAGTGG CGCGCCCAAC 8700

GTGACCAACT GGGGCACCGG CACGCCCCGA CGGGAGTTGC TGCACGTCGA CGACCTGGCG 8760

AGCGCATGCC TGTATCTGCT GGAACATTTC GACGGGCCGA CCCATGTCAA CGTGGGAACC 8820

GGCATCGACC ACACCATCGG CGAGATCGCC GAGATGGTCG CCTCGGCGGT AGGCTATAGC 8880

GGCGAAACCC GCTGGGATCC AAGCAAACCG GACGGAACAC CACGCAAACT GCTGGATGTT 8940

TCGGTGCTAC GGGAGGCGGG ATGGCGGCCT TCGATCGCGC TGCGCGACGG CATCGAGGCG 9000

ACGGTGGCGT GGTATCGCGA GCACGCGGGA ACGGTTCGGC AATGAGGCTG GCCCGTCGCG 9060

CTCGGAACAT CTTGCGTCGC AACGGCATCG AGGTGTCGCG CTACTTTGCC GAACTGGACT 9120

GGGAACGCAA TTTCTTGCGC CAACTGCAAT CGCATCGGGT CAGTGCCGTG CTCGATGTCG 9180

GGGCCAATTC GGGGCAGTAC GCCAGGGGTC TGCGCGGCGC GGGCTTCGCG GGCCGCATCG 9240

TCTCGTTCGA GCCGCTGCCC GGGCCCTTTG CCGTCTTGCA GCGCAGCGCC TCCACGGACC 9300

CGTTGTGGGA ATGCCGGCGC TGTGCGCTGG GCGATGTCGA TGGAACCATC TCGATCAACG 9360

TCGCCGGCAA CGAGGGCGCC AGCAGTTCCG TCTTGCCGAT GTTGAAACGA CATCAGGACG 9420

CCTTTCCACC AGCCAACTAC GTGGGCGCCC AACGGGTGCC GATACATCGA CTCGATTCCG 9480

TGGCTGCAGA CGTTCTGCGG CCCAACGATA TTGCGTTCTT GAAGATCGAC GTTCAAGGAT 9S40

TCGAGAAGCA GGTGATCGCG GGTGGCGATT CAACGGTGCA CGACCGATGC GTCGGCATGC 9600

AGCTCGAGCT GTCTTTCCAG CCGTTGTACG AGGGTGGCAT GCTCATCCGC GAGGCGCTCG 9660

ATCTCGTGGA TTCGTTGGGC TTTACGCTCT CGGGATTGCA ACCCGGTTTC ACCGACCCCC 9720

GCAACGGTCG AATGCTGCAG GCCGATGGCA TCTTCTTCCG GGGCAGCGAT TGACGCGCCG 9780

GCGCGTCAAT CTATTTCGAC ATTCGCGTGA AGACGTTTTC CCAGAATCGA CTGTTGTAGG 9840

CGTAGAACTC CCGGCCGCGT AGGTAGGCAT GTGATATTCG CCTTCCCCCG AACGGGTAGC 9900

GGCGATGAAG GTCGCCCATG CGGCGCAGAT CACCGAAGAC CGCGCTTGGT TCCCGGTGCG 9960

AGCCGACGCC CGTGGTGTCG AACTCGCACA GCACACACCG AATCGTGACC GGCTCGCATA 10020

CCAGCGCGGC CCGCAATATG AATTCCTGGT CGGCGGCGAT CCCGAAATCA AGGTCGTAGC 10080

CACCGATCTT GGCCACCAGC GATGATCCGA AGAACGATGC TTGATGCGGA ACAACCTGCT 10140

TGCCGGCCAG GAATTTGCGC AGGCTGAAAG GTATCGGGCC GCGCACCCGA TCGAGCCCGA 10200

CGAGACGATC CATCCCGAAG CCCCACAATT CGGACACCGG TCCCTTGCCG GATAGCGCCT 10260

CCACGGCCTG GGCTACCACG TCGGGCCCGG AAAAACGATC GGCGGAGTGC AAGAACCACA 10320

ACAGATCACC CGATGCGTGC GCGATGCCCT GGTTCATCGC GTCGTACCGC CCGCCGTCGG 10380

GCTCGGACTG CCAATACGCG AAGCCTGGTT CACACCCGGA CAGGTATGCC ACCACGTCGT 10440

CGCCGCTGCC ACCGTCGATT ACGATGTGCT CGATGCGTCC CCGGTAGCGT TGCGCCCGCA 10500

CACTTTTCAC CGTGCGCTGC AACCCGTCGA GGTCGTTGAA CGAGATCGTT ATCACCGAGA 10560

CGGTCGGAGC AGACGTCACC GAGTTCCCCT AGGTTGCTGG CGGCGATTGT GGATCACCGG 10620

GTCTTGATAC CGATGAAGGT GCCTCGAAGA TTCGCCGCAT AGGAACCTCC GAGCAACGAC 106B0

TCGGCGATGC TTGGTTCCAA GTTGTCGTAC TCCTCCATCA CCAGGTCGAC GCCGACGTCT 10740

TTGATGGCCT GAAGTAGGTG CTCGCGTTGA ATCCAGAATG ACCGGCGATT GTCCCAGGAC 10800

GCCCATTTTG CGGTGTCGCG CTGGCCAAAC GAGCGGTCGT CGGAAAACTC GGTAAACCAC 10860

CTACCGGGAA GTCCCTCATG TTCGGTGGGC GCCGAGAGCA TGAACTTCAC CGGCGCCGGC 10920

-continued

```
CGCCGCAGCA ACCGATCGGT CAATTGTCGT GCCGTCGTGG GCAACCGGAG CCATTTATCG   10980

CTCCGGTTGA TGATCGAGAA GTGCGTCTGG AGAATCAGCA GCTTGTTCGT TACCGACGAG   11040

AGGGTTTCCA GGTATTGCTT CGGATTCTCC AGGTGGTAGA AGAGGCCGCA GCAGAAGACG   11100

GTATCGAAGA GCCCGTGGTT GGCGATGTTG AGGGCGTTGT CGTGGACGAA CCGGAGATTC   11160

GGCAGGTTGG TCTTCGATTT GATGTAGTTG CAGGCCGCCA TGTTCAGCTC GCGAACCTCG   11220

ATCCCGAGGA CCTGAAATCC CATGCGCGCG AACCCGACCG CGTACCCGCC TTCCAAGCAG   11280

CCGACATCGG CCAGGCGTAG GTGGCTCTTG TCCCCGGGAA AGACGGTTTC CAGAATCCCG   11340

CGCGCCGAGA TGAACCAGGA CGATTCGTCT AACGTGCGCG AGGACTCCGG TATCGTCAAG   11400

GTTCCGTCGT CGAGGCGAAC GTTGTGGGCG GTGAATTGTA CCGCGCCGGC CGAATGTTCC   11460

TGTGCCATCA CTTGGTTAGC CCCTTCGGCT GGTCCTGGGT TTGTCGACAT GGTCAGGCTC   11520

GACAGCCGCG TCGGAGCCGG GAGGGCCACA CATCCACGAG CCCCCTGCGG CTCGGCGTCG   11580

CGGCGGCGAG CTTGCGCCAC TGGGTCTTGA GCCGCCGCGC GGGTGTCGCC CCGCGGTGCT   11640

GCAGCGCCAG CATGGCGATC CGGGGATGGC GCGCGATGGT TTCCTGCAGC GCGGCGCGCC   11700

CCTCCGGGCC TGGAACGTTG GCGATCTGGC GAAGGATCCA GTCGGCCATG ACGGCGATGA   11760

GCTCCTCGCG CGCGGGGTCT CCCGGGAACA GGTCGAGCAT CGCGTCAAAC GTCGCCGCAT   11820

GCCCCGGACC CTGCGTCAAC CAGAACTTTG GCGGGTCCAC CACCTGGTTG TGCCACATGC   11880

CTTGGGCGTG GCGGCGATAC ACGGCCATGG TGTCGGGCAA CATGGCGATG TCGCCATGCA   11940

CCGCGTGCCG GACGTGCAGA TACCAGTCCA GGGGCATGAC GTCGGCAGGA ATGTCGTCGT   12000

AGCGCTCGAG GCGACGGTAC ACGGCCGAGT TGGTCTGGAT GAAGTTCATC AAGATCAACG   12060

CATCCAGGCT CAAGTTGCCC CGCACCCGAA CCGGGGGGAA CTTCGAGTCC TTGGCATGGC   12120

CGTCCTCCCA TATCACTCGG ACGGGATGGA AGCACACCGT CGTCTTGGGG TGCCGGTCGA   12180

GGAATGCGAC CTGTTTGCTT AGCTTCAGCG GATCGATCCA GTAGTCGTCC GCCTCGCACA   12240

ACGCGACGTA CTCGCCGCGA GCGGCCGACA GGGCGCCGGT CAGGTTCCCA TTGAGGCCGA   12300

GGTTTTCGGT CCTGAAGATC GGCCGGAACA CGTGCGGGTA CCGCTCGGCG TACTCACGGA   12360

TGATCGCCGG GGTGGCATCG GTCGACGCGT CGTCGGCGAC GATGATCTCC ACCGGGAAGT   12420

CGGTTTGCTG GTCGAGAAAG CTGTCGAAGG CCTGACGGGC GTAGCCCGCC TGGTTGTGAG   12480

TGGTCGAGAC GATGCTCACC TTGGGGCAAA GCTGGGGACT CACCGTCGGC CCTTTTCCTG   12540

CGCGGCCGCA AGGGTATTGC GATGGCGAAC GTGAATCGCC TGTGCCCGCC GGCCGTCGGC   12600

CGTCGTGGCC TGGTGGTCGG CGGACGTACG GCACACGCTG GCGAAGTATA GCGAGGGTGC   12660

ACTGACGTTG GGCTCGAACC GCGTGGCGCG CGGTGTGGGC GCACCGTCTC GAGTCGGTGC   12720

TGGTTGGCTC GC                                                       12732
```

The location, on the *Mycobacterium tuberculosis* chromosome, of the above polynucleotide of sequence SEQ ID N$^{0}$1 has now been ascribed to begin, at its 5' end at nucleotide at position nt 1696015 and to end, at its 3' end, at nucleotide at position nt 1708746.

For diagnostic purposes, this 12.7 kb deletion should allow a rapid PCR screening of tubercle isolates to identify whether they are bovine or human strains. The primers listed in Table 1 are flanking the deleted region and give a 722 bp amplicon in *M. bovis* or *M. bovis* BCG strains, but a fragment of 13,453 bp in *M. tuberclosis* that is practically impossible to amplify under the same PCR conditions. More importantly, assuming that some of the gene products from this region represent proteins with antigenic properties, it could be possible to develop a test that can reliably distinguish between the immune response induced by vaccination with *M. bovis* BCG vaccine strains and infection with *M. tuberclosis* or that the products (e.g. polysaccharides) are specific immunogens.

The invention also provides for a purified polynucleotide usefill as a probe or as a primer, said polynucleotide being chosen in the following group of polynucleotides:

a) a polynucleotide comprising at least 8 consecutive nucleotides of the sequence SEQ ID N$^{0}$1.

b) a polynucleotide whose sequence is fully complementary to the sequence of the polynucleotide defined in a);

c) a polynucleotide that hybridizes under stringent hybridization conditions with the polynucleotide defined in a) or with the polynucleotide defined in b).

For the purpose of defining a polynucleotide or oligonucleotide hybridizing under stringent hybridization conditions, such as above, it is intended a polynucleotide that hybridizes with a reference polynucleotide under the following hybridization conditions:

The hybridization step is realized at 65° C. in the presence of 6×SSC buffer, 5×Denhardt's solution, 0,5% SDS and 100 $\mu$g/ml of salmon sperm DNA.

For technical information, 1×SSC corresponds to 0.15 M NaCl and 0.05M sodium citrate; 1×Denhardt's solution corresponds to 0.02% Ficoll, 0.02% polyvinylpyrrolidone and 0.02% bovine serum albumin.

The hybridization step is followed by four washing steps:

two washings during 5 min, preferably at 65° C. in a 2×SSC and 0.1%SDS buffer;

one washing during 30 min, preferably at 65° C. in a 2×SSC and 0.1% SDS buffer, one washing during 10 min, preferably at 65° C. in a 0.1×SSC and 0.1%SDS buffer A first illustrative useful polynucleotide that is included in the polynucleotide of sequence SEQ ID N°1 is the following polynucleotide of sequence SEQ ID N°2 that corresponds to the Sp6 endsequence of SEQ ID N°1:

```
ATACTCAAGC TTGCCGCAAT CGAAACCAAC CTGTTTGTGC CGCAAGAAAT TACGCCGTGG   60
CCCGGCGCCG ATCAAGAAAC GCCCCGGCGC GCGGCGGTGT CGTCGTATGG CATGACGGGC  120
ACCAATGTGC ACGCCATTGT CGAGCAGGCA CCGGTGCCAG CCCCCGAATC CGGTGCACCA  180
GGCGACACCC CGGCCACACC CGGTATCGAC GGCGCGCTGC TGTTCGCGCT GTCGGCCAGC  240
TCGCAGGACG CGCTGCGGCA AACCGCCGCG CGGCTGGCCG ATTGGGTCT              289
```

A second illustrative useful polynucleotide that is included in the polynucleotide of sequence SEQ ID N°1 is the following polynucleotide of sequence SEQ ID N°3 that corresponds to the T7 endsequence of SEQ ID N°1, located on the opposite strand:

```
TTGGCGGGTT GGCCACACAC CCGCCGGTGA CGGCGACGAT GCTGGGCTGG TTGCGGCCCT   60
GCGCCACCGC GGCTTGCATG CTGGTTGGCT GTCTTGGGAC GATCCCGAAA TAGTCCACGC  120
GGATCTGGTG ATTTTGCGGG CTACCCGCGA TTACCCCGCG CGGCTCGACG AGTTTTTGGC  180
CTGGACTACC CGCGTGGCCA ATCTGCTGAA CTCGCGGCCG GTGGTGGCCT GGAATGTCCA  240
CGCCGTTCAC CTACGTGACC TTGATGGGAT CCGGGGGT                          278
```

The polynucleotide of sequence SEQ ID N°1 contains 11 ORFs, the respective locations of which, taking into account the orientation of each ORF on the chromosome, on the sequence of the *Mycobacterium tunerculosis* chromosome, is given hereafter:

The location of ORF1 is comprised between nucleotide at position nt 1695944 and nucleotide at position nt1696441.

The location of ORF2 is comprised between nucleotide at position nt 1696728 and nucleotide at position nt1697420.

The location of ORF3 is comprised between nucleotide at position nt 1698096 and nucleotide at position nt1699892. ORF3 probably encodes a protein having the characteristics of a membrane protein.

The location of ORF4 is comprised between nucleotide at position nt 1700210 and nucleotide at position nt1701088.

The location of ORF5 is comprised between nucleotide at position nt 1701293 and nucleotide at position nt1702588. ORF5 encodes a protein having the characteristics of a membrane protein.

The location of ORF6 is comprised between nucleotide at position nt 1703072 and nucleotide at position nt1704091. ORF6 encodes a protein having the characteristics of a GDP-D-mannose dehydratase.

The location of ORF7 is comprised between nucleotide at position nt 1704091 and nucleotide at position nt1705056. ORF7 encodes a protein having the characteristics of a nucleotide sugar epimerase involved in colanic acid biosynthesis.

The location of ORF8 is comprised between nucleotide at position nt 1705056 and nucleotide at position nt1705784.

The location of ORF9 is comprised between nucleotide at position nt 1705808 and nucleotide at position nt1706593. ORF9 encodes a protein having the characteristics of colanic acid biosynthesis glycosyl transferase.

The location of ORF10 is comprised between nucleotide at position nt 1706631 and nucleotide at position nt1707524.

The location of ORF11 is comprised between nucleotide at position nt 1707530 and nucleotide at position nt1708648. ORF11 encodes a protein similar to a spore coat polysaccharide biosynthesis.

A polynucleotide of interest obtained by the above-disclosed method according to the invention may also contain at least one ORF that encodes all or part of acidic, glycine-rich proteins, belonging to the PE and PPE families, whose genes are often clustered and based on multiple copies of the polymorphic repetitive sequences. The names PE and PPE derive from the fact that the motifs ProGlu (PE, positions 8, 9) and ProProGlu (PPE, positions 7 to 9) are found near the N-terminus in almost all cases. The PE protein family all have a highly conserved N-terminal domain of ~110 amino acid residues, that is predicted to have a globular structure, followed by a C-terminal segment which varies in size, sequence and repeat copy number. Phylogenetic analysis separated the PE family into several groups, the larger of which is the highly repetitive PGRS class containing 55 members whereas the other groups share very limited sequence similarity in their C-terminal domains. The predicted molecular weights of the PE proteins vary considerably as a few members only contain the ~110 amino acid N-terminal domain while the majority have C-terminal extensions ranging in size from 100 up to >1400 residues. A striking feature of the PGRS proteins is their exceptional glycine content (up to 50%) due to the presence of multiple tandem repetitions of GlyGlyAla or GlyGlyAsn motifs or variations thereof.

Like the PE family, the PPE protein family also has a conserved N-terminal domain that comprises ~180 amino acid residues followed by C-terminal segments that vary considerably in sequence and length. These proteins fall into at least three groups, one of which constitutes the MPTR class characterised by the presence of multiple, tandem copies of the motif AsnXGlyXGlyAsnXGly (SEQ ID NO: 730). The second subgroup contains a characteristic, well-conserved motif around position 350 (GlyXXSerValProXXTrp)(SEQ ID NO: 731), whereas the other group contains proteins that are unrelated except for the presence of the common 180-residue PPE domain. C-terminal extensions may range in size from 00 up to 3500 residues.

One member of the PGRS sub-family, the WHO antigen 22T (Abou-Zeid et al., 1991), a 55 kD protein capable of binding fibronectin, is produced during disease and elicits a variable antibody response suggesting either that individuals mount different immune responses or that this PGRS-protein may not be produced in this form by all strains of *M. tuberculosis*. In other words, at least some PE_PGRS coding sequences encode for proteins that are involved in the recognition of *M. tuberclosis* by the immune system of the infected host Therefore, differences in the PGRS sequences could represent the principal source of antigenic variation in the otherwise genetically and antigenically homogeneous bacterium.

By performing the method of the invention using the *M. tuberclosis* BAC based DNA library I-1945, the inventors have discovered the occurence of sequence differences between a given PGRS encoding ORF (ORF reference on the genomic sequence of *M. tuberclosis* Rv0746) of *M. tuberclosis* and its counterpart sequence in the genome of *M. bovis* BCG.

More precisely, the inventors have determined that one ORF contained in BAC vector N Rv418 of the *M. tuberclosis* BCG I-1945 DNA library carries both base additions and base deletions when compared with the corresponding ORF in the genome of *M. bovis* BCG that is contained in the BAC vector N X0175 of the *M. bovis* BCG I-2049 DNA libary. The variations observed in the base sequences correspond to variations in the C-terminal part of the aminoacid sequence of the PGRS ORF translation product.

As shown in FIG. 6, an amino acid stretch of 29 residues in length is present in this *M. tuberclosis* PGRS (ORf reference Rv0746) and is absent from the ORF counterpart of *M. bovis* BCG, namely the following amino acid sequence:

$NH_2$-GGAGGAGGSSAGGGGAGGAGGAGGWLLGD-COOH (SEQ ID NO: 732).

Furthermore , FIG. 6 shows also that an amino acid stretch of 45 residues in length is absent from this *M. tuberclosis* PGRS and is present in the ORF counterpart of *M. bovis* BCG, namely following amino acid sequence:

$NH_2$-GAGGIGGIGGNANGGAGGNGGTGGQLWGSGGAGVEGGAALSVGDT-COOH (SEQ ID NO: 733).

Similar observations were made with PPE ORF Rv0442, which showed a 5 codon deletion relative to a *M. bovis* amino acid sequence.

Given that the polymorphism associated with the PE-PGRS or PEE ORFS resulted in extensive antigenic variability or reduced antigen presentation, this would be of immense significance for vaccine design, for understanding protective immunity in tuberculosis and, possibly, explain the varied responses seen in different BCG vaccination programmes.

There are several striking parallels between the PGRS proteins and the Epstein-Barr virus-encoded nuclear antigens (EBNA). Both polypeptide families are glycine-rich, contain Gly-Ala repeats that represent more than one third of the molecule, and display variation in the length of the repeat region between different isolates. The Gly-Ala repeat region of EBNA1 has been shown to function as a cis-acting inhibitor of antigen processing and MHC class I-restricted antigen presentation (Levitskaya et al., 1995). The fact that MHC class I knock-out mice are extremely suscepible to *M. tuberclosis* underlines the importance of MHC class I antigen presentation in protection against tuberculosis. Therefore, it is possible that the PE/PPE protein family also play some role in inhibiting antigen presentation, allowing the bacillus to hide from the host's immune system.

As such the novel and nonobvious PGRS polynucleotide from *M. bovis* which is homolog to the *M. tuberclosis* ORF Rv0746, and which is contained in the BAC clone N X0175 (See Table 4 for SP6 and T7 endsequences of clone n° X0175) of the I-2049 *M. bovis* BCG BAC DNA library is part of the present invention, as it represents a starting material in order to define specific probes or primers usefill for detection of antigenic variability in mycobacterial strains, possible inhibition of antigen processing as well as to differentiate *M. tuberculosis* from *M. bovis* BCG.

Thus, a further object of the invention consists in a polynucleotide comprising the following sequence SEQ ID N°4:

```
CCGACCCAGA CACTGACCGG GCGACCGCTG ATCGGCAACG GCACCCCCGG GGCGGTCGGC    60

AGCGGGGCCA CCGGGGCCCC CGGTGGGTGG CTGCTCGGCG ACGGCGGGGC CGGCGGGTCC   120

GGCGCGGCGG GCTCGGGCGC GCCCGGCGGG GCGGGCGGGG CTGCCGGGCT GTGGGGTACC   180

GGCGGGGCCG GCGGGATCGG CGGAGCCAGC ACCGTACTCG GCGGCACCGG CGGGGGAGGC   240

GGGGTCGGTG GGCTGTGGGG CGCCGGTGGG GCCGGCGGGG CCGGTGGAAC CGGCCTTGTT   300

GGTGGCGACG GCGGGGCCGG TGGGGCCGGC GGGACCGGCG GACTGCTGGC CGGGCTGATC   360

GGTGCCGGCG GAGGTCACGG CGGGACCGGC GGGCTCAGCA CTAATGGCGA CGGCGGGGTT   420

GGCGGGGCCG GCGGGAATGC CGGAATGCTC GCCGGGCCGG GCGGCGCCGG CGGAGCCGGC   480
```

```
                              -continued
GGTGACGGCG AAAACCTGGA CACCGGTGGG GACGGCGGGG CCGGCGGTAG CGCAGGGCTG    540

CTGTTCGGCA GCGGCGGCGC CGGCGGCGCC GGCGGATTTG GTTTCCTCGG TGGGGACGGC    600

GGGGCCGGTG GCAACGCCGG GCTGCTGTTG TCCAGCGGCG GGGCCGGCGG GTTCGGCGGG    660

TTCGGCACCG CCGGTGGGGT CGGTGGGGCC GGCGGCAATG CCGGCTGGCT GGGCTTCGGC    720

GGGGCCGGGG GCATCGGCGG AATCGGCGGT AACGCTAACG GGGGCGCCGG TGGGAACGGC    780

GGCACCGGCG GTCAGTTATG GGGTAGCGGC GGCGCCGGCG TCGAAGGCGG CGCAGCCTTA    840

AGCGTCGGCG ACACCGGCGG GGCCGGTGGC GTCGGCGGCA GCGCCGGGCT GATCGGCACC    900

GGCGGCAACG GCGGCAACGG CGGCACCGGC GCCAACGCCG GCAGCCCCGG AACCGGCGGC    960

GCCGGCGGGT TGCTGCTGGG CCAAAACGGG CTCAACGGGT TGCCGTAGCC GGGCGGCACG   1020

GCATGGCTTC CGGGCGTCAA CCACTCGCCG GTGATGCAGA TCGGCTGCGG AGCGGGCCGC   1080

CAAAATGGGG GCCGCCGCGC CAGGTATCTC GGCGAAGATC CCCGGCGCTC GAGCGCTTTG   1140

TCAGAGGCCC GTCGCGGGTC GTCGTGACGA CGGCTATCCG GGCGGTGCGG GTTTCGCGGC   1200

GCGCCCTGTG CCCGGCACCG CCGCCCGTTT GTCGGCAACG CCGCCGCGAC CCGTGAGCCG   1260

TCCAGCAGCT GGCGCCTGCG                                               1280
```

Polynucleotides of interest have been defined by the inventors as useful detection tools in order to differentiate *M. tuberclosis* from *M. bovis* BCG. Such polynucleotides are contained in the 45 aminoacid length coding sequence that is present in *M. bovis* BCG but absent from *M. tuberclosis*. This polynucleotide has a sequence beginning (5' end) at the nucleotide at position nt 729 of the sequence SEQ ID N°4 and ending (3' end) at the nucleotide in position nt 863 of the sequence SEQ ID N°4.

Thus, part of the present invention is also a polynucleotide which is chosen among the following group of polynucleotides:

a) A polynucleotide comprising at least 8 consecutive nucleotides the following nucleotide sequence SEQ ID N°5:

```
GGGCATCGGC GGAATCGGCG GTAACGCTAA CGGGGGCGCC GGTGGGAACG GCGGCACCGG    60

CGGTCAGTTA TGGGGTAGCG GCGGCGCCGG CGTCGAAGGC GGCGCAGCCT TAAGCGTCGG   120

CGACACC                                                             127
``` b) A polynucleotide which sequence is fully complementary to the sequence of the polynucleotide defined in a);

c) A polynucleotide that hybridizes under stringent hybridization conditions with the polynucleotide defined in a) or with the polynucleotide defined in b).

The stringent hybridization conditions for the purpose of defining the above disclosed polynucleotide are defined herein before in the specification.

The invention also provides for a BAC-based *Mycobacterium tuberculosis* strain H37Rv genomic DNA library that has been deposited in the Collection Nationale de Cultures de Microorganismes on Nov. 19, 1997 under the accession number I-1945.

A further object of the invention consists in a recombinant BAC vector which is choosen among the group consisting of the recombinant BAC vectors belonging to the BAC-based DNA library I-1945.

Generally, a recombinant BAC vector of interest may be choosen among the following set or group of BAC vectors contained in the BAC-based DNA library I-1945: Rv101; Rv102; Rv103; Rv104; Rv105; Rv106; Rv107; Rv108; Rv109; Rv10; Rv110; Rv111; Rv112; Rv113; Rv114; Rv115; Rv116; Rv117; Rv118; Rv119; Rv11; Rv120; Rv121; Rv122; Rv123; Rv124; Rv126; Rv127; Rv128; Rv129; Rv130; Rv132; Rv134; Rv135; Rv136; Rv137; Rv138; Rv139; Rv13; Rv140; Rv141; Rv142; Rv143; Rv144; Rv145; Rv146; Rv147; Rv148; Rv149; Rv14; Rv150; Rv151; Rv152; Rv153; Rv154; Rv155; Rv156; Rv157; Rv159; Rv15; Rv160; Rv161; Rv162; Rv163; Rv164; Rv165; Rv166; Rv167; Rv169; Rv16; Rv170; Rv171; Rv172; Rv173; Rv174; Rv175; Rv176; Rv177; Rv178; Rv179; Rv17; Rv180; Rv181; Rv182; Rv183; Rv184; Rv185; Rv186; Rv187; Rv188; Rv18; Rv190; Rv191; Rv192; Rv193; Rv194; Rv195; Rv196; Rv19; Rv1; Rv201; Rv204; Rv205; Rv207; Rv209; Rv20; Rv214; Rv215; Rv217; Rv218; Rv219; Rv21; Rv220; Rv221; Rv222; Rv223; Rv224; Rv225; Rv226; Rv227; Rv228; Rv229; Rv22; Rv230; Rv231; Rv232; Rv233; Rv234; Rv235; Rv237; Rv240; Rv241; Rv243; Rv244; Rv245; Rv246; Rv247; Rv249; Rv24; Rv251; Rv252; Rv253; Rv254; Rv255; Rv257; Rv258; Rv259; Rv25; Rv260; Rv261; Rv262; Rv263; Rv264; Rv265; Rv266; Rv267; Rv268; Rv269; Rv26; Rv270; Rv271; Rv272; Rv273; Rv274; Rv275; Rv276; Rv277; Rv278; Rv279; Rv27; Rv280; Rv281; Rv282; Rv283; Rv284; Rv285; Rv286; Rv287; Rv288; Rv289; Rv28; Rv290; Rv291; Rv292; Rv293; Rv294; Rv295; Rv296; Rv29; Rv2; Rv301; Rv302; Rv303; Rv304; Rv306; Rv307; Rv308; Rv309; Rv30; Rv310; Rv311; Rv312; Rv313; Rv3l4; Rv315; Rv316; Rv317; Rv318; Rv319; Rv31; Rv32; Rv322; Rv327; Rv328; Rv329; Rv32; Rv330; Rv331; Rv333; Rv334; Rv335; Rv336; Rv337; Rv338; Rv339; Rv33; Rv340; Rv341; Rv343; Rv344; Rv346; Rv347; Rv348; Rv349; Rv34; Rv350; Rv351; Rv352; Rv353; Rv354; Rv355; Rv356;

Rv357; Rv358; Rv359; Rv35; Rv360; Rv361; Rv363; Rv364; Rv365; Rv366; Rv367; Rv368; Rv369; Rv36; Rv370; Rv371; Rv373; Rv374; Rv375; Rv376; Rv377; Rv378; Rv379; Rv37; Rv381; Rv382; Rv383; Rv384; Rv385; Rv386; Rv387; Rv388; Rv389; Rv38; Rv390; Rv391; Rv392; Rv393; Rv396; Rv39; Rv3; Rv40; Rv42; Rv413; Rv414; Rv415; Rv416; Rv417; Rv418; Rv419; Rv41; Rv42; Rv43; Rv45; Rv46; Rv47; Rv48; Rv49; Rv4; Rv50; Rv51; Rv52; Rv53; Rv54; Rv55; Rv57; Rv58; Rv59; Rv5; Rv60; Rv61; Rv62; Rv63; Rv64; Rv65; Rv66; Rv67; Rv69; Rv6; Rv70; Rv71; Rv72; Rv73; Rv74; Rv75; Rv76; Rv77; Rv78; Rv79; Rv80; Rv81; Rv82; Rv83; Rv84; Rv85; Rv86; Rv87; Rv88; Rv89; Rv8; Rv90; Rv92; Rv94; Rv95; Rv96; Rv9.

The end sequences of the polynucleotide inserts of each of the above clones corresponding respectively to the sequences adjacent to the T7 promoter and to the Sp6 promoter on the BAC vector are shown in Table 3.

It has been shown by the inventors that the minimal overlapping set of BAC vectors of the BAC-based DNA library I-1945 contains 68 unique BAC clones and practically spans almost the whole H37Rv chromosome with the exception of a single gap of approximately 150 kb.

More specifically, a recombinant BAC vector of interest is choosen among the following set or group of BAC vectors from the BAC-based DNA library I-1945, the location of which vector DNA inserts on the chromosome of *M. tuberclosis* is shown in FIG. 3: Rv234; Rv351, Rv166; Rv35; Rv415; Rv404; Rv209; Rv272; Rv30; Rv228; Rv233; Rb38; Rv280; Rv177; Rv48; Rv374; Rv151; Rv238; Rv156; Rv92; Rv3; Rv403; Rv322; Rv243; Rv330; Rv285; Rv233; Rv219; Rv416; Rv67; Rv222; Rv149; Rv279; Rv87; Rv273; Rv266; Rv25; Rv136; Rv4l4; Rv13; Rv289; Rv60; Rv104; Rv5; Rv165; Rv215; Rv329; Rv240; Rv19; Rv74; Rv411; Rv167; Rv56; Rv80; Rv164; Rv59; Rv313; Rv265; Rv308; Rv220; Rv258; Rv339; Rv121; Rv419; Rv418; Rv45; Rv217; Rv134; Rv17; Rv103; Rv21; Rv22; Rv2; Rv270; Rv267; Rv174; Rv257; Rv44; Rv71; Rv7; Rv27; Rv191; Rv230; Rv128; Rv407; Rv106; Rv39; Rv255; Rv74; Rv355; Rv268; Rv58; Rv173; Rv264; Rv417; Rv401; Rv144; Rv302; Rv81; Rv163; Rv281; Rv221; Rv420; Rv175; Rv86; Rv412; Rv73; Rv269; Rv214; Rv287; Rv42; Rv143.

The polynucleotides disclosed in Table 3 may be used as probes in order to select a given clone of the BAC DNA library I-1945 for further use.

The invention also provides for a BAC-based *Mycobacterium bovis* strain Pasteur genornic DNA library that has been deposited in the Collection Nationale de Cultures de Microorganismes on Jun. 30, 1998 under the accession number I-2049.

A further object of the invention consists in a recombinant BAC vector which is chosen among the group consisting of the recombinant BAC vectors belonging to the BAC-based DNA library I-2049. This DNA library contains approximately 1600 clones. The average insert size is estimated to be 80 kb.

Generally, a recombinant BAC vector of interest may be chosen among the following set or group of BAC vectors contained in the BAC-based DNA library I-2049: X0001; X0002; X0003; X0004; X0006; X0007; X0008; X0009; X0010; X0012; X0013; X0014; X0015; X0016; X0017; X0018; X0019; X0020; X0021; X0175.

The end sequences of the polynucleotide inserts of each of the above clones corresponding respectively to the sequences adjacent to the T7 promoter and to the Sp6 promoter on the BAC vector are shown in Table 4.

The polynucleotides disclosed in Table 4 may be used as probes in order to select a given clone of the BAC DNA library I-2049 for further use.

Are also part of the invention the polynucleotide inserts that are contained in the above described BAC vectors, that are useful as primers or probes.

These polynucleotides and nucleic acid fragments may be used as primers for use in amplification reactions, or as nucleic probes.

PCR is described in the U.S. Pat. No. 4,683,202. The amplified fragments may be identified by an agarose or a polyacrylamide gel electrophoresis, or by a capillary electrophoresis or alternatively by a chromatography technique (gel filtration, hydrophobic chromatography or ion exchange chromatography). The specificity of the amplification may be ensured by a molecular hybridization using, for example, one of the initial primers as nucleic probes.

Amplified nucleotide fragments are used as probes in hybridization reactions in order to detect the presence of one polynucleotide according to the present invention or in order to detect mutations in the genome of the given mycobacterium of interest, specifically a mycobacterium belonging to the *Mycobacterium tuberculosis* complex and more specifically *Mycobacterium tuberculosis* and *Mycobacterium bovis* BCG.

Are also part of the present invention the amplified nucleic fragments (<<amplicons>>) defined herein above.

These probes and amplicons may be radioactively or non-radioactively labeled, using for example enzymes or fluorescent compounds.

Other techniques related to nucleic acid amplification may also be used and are generally preferred to the PCR technique.

The Strand Displacement Amplification (SDA) technique (Walker et al., 1992) is an isothermal amplification technique based on the ability of a restriction enzyme to cleave one of the strands at his recogntion site (which is under a hemiphosphorothioate form) and on the property of a DNA polymerase to initiate the synthesis of a new strand from the 3'OH end generated by the restriction enzyme and on the property of this DNA polymerase to displace the previously synthesized strand being localized downstream. The SDA method comprises two main steps:

a) The synthesis, in the presence of dCTP-alpha-S, of DNA molecules that are flanked by the restriction sites that may be cleaved by an appropriate enzyme.

b) The exponential amplification of these DNA molecules modified as such, by enzyme cleavage, strand displacement and copying of the displaced strands. The steps of cleavage , strand displacement and copy are repeated a sufficient number of times in order to obtain an accurate sensitivity of the assay.

The SDA technique was initially realized using the restriction endonuclease HindIII but is now generally practised with an endonuclease from *Bacillus stearothermophilus* (BSOBI) and a fragment of a DNA polymerase which is devoid of any 5'3'exonuclease activity isolated from *Bacillus cladotenox* (exo-Bca) [=exo-minus-Bca]. Both enzymes are able to operate at 60° C. and the system is now optimized in order to allow the use of dUTP and the decontamination by UDG. When unsing this technique, as described by Spargo et al. in 1996, the doubling time of the target DNA is of 26 seconds and the amplification rate is of $10^{10}$ after an incubation time of 15 min at 60° C.

The SDA amplification technique is more easy to perform than PCR (a single thermostated waterbath device is necessary) and is faster that the other amplification methods.

Thus, another object of the present invention consists in using the nucleic acid fragments according to the invention (primers) in a method of DNA or RNA amplification according to the SDA technique. For performing SDA, two pairs of primers are used: a pair of external primers (B1, B2) consisting of a sequence specific for the target polynucleotide of interest and a pair of internal primers (S1, S2) consisting of a fusion oligonucleotide carrying a site that is recognized by a restriction endonuclease, for example the enzyme BSOBI.

The operating conditions to perform SDA with such primers are described in Spargo et al, 1996.

The polynucleotides of the invention and their above described fragments, especially the primers according to the invention, are useful as technical means for performing different target nucleic acid amplification methods such as:

TAS (Transcription-based Amplification System), described by Kwoh et al. in 1989;

SR (Self-Sustained Sequence Replication), described by Guatelli et al. in 1990.

NASBA (Nucleic acid Sequence Based Amplification), described by Kievitis et al. in 1991.

TMA (Transcription Mediated Amplification).

The polynucleotides according to the invention are also useful as technical means for performing methods for amplification or modification of a nucleic acid used as a probe, such as:

LCR (Ligase Chain Reaction), described by Landegren et al. in 1988 and improved by Barany et al. in 1991 who employ a thermostable ligase.

RCR (Repair Chain Reaction) described by Segev et al. in 1992.

CPR (Cycling Probe Reaction), described by Duck et al. in 1990.

Q-beta replicase reaction, described by Miele et al. in 1983 and improved by Chu et al. in 1986, Lizardi et al. in 1988 and by Burg et al. and Stone et al. in 1996.

When the target polynucleotide to be detected is a RNA, for example a mRNA, a reverse transcriptase enzyme will be used before the amplification reaction in order to obtain a cDNA from the RNA contained in the biological sample. The generated cDNA is subsequently used as the nucleic acid target for the primers or the probes used in an amplification process or a detection process according to the present invention.

The non-labeled polynucleotides or oligonucleotides of the invention may be directly used as probes. Nevertheless, the polynucleotides or oligonucleotides are generally labeled with a radioactive element ($^{32}P$, $^{35}S$, $^{3}H$, $^{125}I$ or by a non-isotopic molecule (for example, biotin, acetylaminofluorene, digoxigenin, 5-bromodesoxyuridin, fluorescein) in order to generate probes that are useful for numerous applications.

Examples of non-radioactive labeling of nucleic acid fragments are described in the french patent N° FR-7810975 or by Urdea et al. or Sanchez-Pescador et al., 1988.

In the latter case, other labeling techniques may be also used such as those described in the french patents FR-2, 422,956 and 2,518,755. The hybridization step may be performed in diffrent ways (Matthews et al., 1988). The more general method consists of immobilizing the nucleic acid that has been extracted from the biological sample onto a substrate (nitrocellulose, nylon, polystyrene) and then to incubate, in defined conditions, the target nucleic acid with the probe. Subsequently to the hybridization step, the excess amount of the specific probe is discarded and the hybrid molecules formed are detected by an appropriate method (radioactivity, fluorescence or enzyme activity measurement).

Advantageously, the probes according to the present invention may have structural characteristics such that they allow the signal amplification, such structural characteristics being, for example, branched DNA probes as those described by Urdea et al. in 1991 or in the European patent N° EP-0225,807 (Chiron).

In another advantageous embodiment of the probes according to the present invention, the latters may be used as <<capture probes>>, and are for this purpose immobilized on a substrate in order to capture the target nucleic acid contained in a biological sample. The captured target nucleic acid is subsequently detected with a second probe which recognizes a sequence of the target nucleic acid which is different from the sequence recognized by the capture probe.

The oligonucleotide probes according to the present invention may also be used in a detection device comprising a matrix library of probes immobilized on a substrate, the sequence of each probe of a given length being localized in a shift of one or several bases, one from the other, each probe of the matrix library thus being complementary to a distinct sequence of the target nucleic acid. Optionally, the substrate of the matrix may be a material able to act as an electron donor, the detection of the matrix poisitons in which an hybridization has occurred being subsequently determined by an electronic device. Such matrix libraries of probes and methods of specific detection of a targer nucleic acid is described in the European patent application N° EP-0713, 016 (Affymax technologies) and also in the U.S. Pat. No. 5,202,231 (Drmanac).

Since almost the whole length of a mycobacterial chromososme is covered by a BAC-based genomic DNA libraries according to the present invention (i.e. 97% of the *M. tuberculosis* chromosome is covered by the BAC library I-1945), these DNA libraries will play an important role in a plurality of post-genomic applications, such as in mycobacterial gene expression studies where the canonical set of BACs could be used as a matrix for hybridization studies. Probing such matrices with cDNA probes prepared from total mRNA will uncover genetic loci induced or repressed under different physiological conditions (Chuang et al., 1993; Trieselmann et al., 1992). As such, the H37Rv BAC library represents a fundamental resource for present and future genomics investigations.

The BAC vectors or the polynucleotide inserts contained therein may be directly used as probes, for example when immobilized on a substrate such as described herein before.

The BAC vectors or their polynucleotide inserts may be directly asdorbed on a nitrocellulose membrane, at predetermined locations on which one or several polynucleotides to be tested are then put to hybridize therewith.

Preferably, a collection of BAC vectors that spans the whole genome of the mycobacteriurn under testing will be immobilized, such as, for example, the set of 68 BAC vectors of the I-1945 DNA library that is described elsewhere in the specification and shown in FIG. 3.

The immobilization and hybridization steps may be performed as described in the present Materials and Methods Section.

As another illustrative embodiment of the use of the BAC vectors of the invention as polynucleotide probes, these vectors may be useful to perform a transcriptional activity analysis of mycobacteria growing in different environmental conditions, for example under conditions in which a stress response is expected, as it is the case at an elevated temperature, for example 40° C.

In this specific embodiment of the invention, Genescreen membranes may be used to immobilize the restriction endonuclease digests (HindIII digests for the BAC DNA library I-1945) of the BAC vectors by tranfer from a gel (Trieselmann et al., 1992).

Alternatively, the BAC vectors may be immobilized for dot blot experiments as follows. First, the DNA concentration of each BAC clone is determined by hybridization of blots of clone DNAs and of a BAC vector concentration standard with a BAC vector specific DNA probe. Hybridization is quantified by the Betascope 603 blot analyzer (Betagen Corp.), which colects beta particles directly from the blot with high efficiency. Then, 0.5 $\mu$g of each clone DNA is incubated in 0.25 M NaOH and 10 mM EDTA at 65° C. for 60 min to denature the DNA and degrade residual RNA contaminants. By using a manifold filtration system (21 by 21 wells), each clone DNA is blotted onto a GeneScreen Plus nylon membrane in the alkaline solution. After neutralization, the blots are baked at 85° C. for 2 h under vacuum. Positive and negative controls are added when necessary. In order to perform this procedure, it may be referred to the article of Chuang et al. (1993).

For RNA extractions, cells grown in a suitable volume of culture medium may, for example, be immediately mixed with an equal volume of crushed ice at −70° C. and spun at 4° C. in a 50 ml centrifugation tube. The cell pellet is then suspended in 0.6 ml of ice-cold buffer (10 mM KCl, 5 mM MgCl, 10 mM Tris; pH 7.4) and then immediately added to 0.6 ml of hot lysis buffer (0.4 M NaCl, 40 mM EDTA, 1% beta-mercaptoethanol, 1% SDS, 20 mM Tris; pH 7.4) containing 100 $\mu$l of water saturated phenol. This mixture is incubated in a boiling water bath for 40 s. The debris are removed by centrifugation. The supernatant is extracted with phenol-chloroform five times, ethanol precipitated, and dried. The dried RNA pellet is dissolved in water before use.

Then labeled total cDNA may be prepared by the following method. The reaction mixture contains 15 $\mu$g of the previously prepared total RNA, 5 $\mu$g of pd($N_6$) (random hexamers from Pharmacia Inc.), 0.5 mM DATP, 0.5 mM dGTP and 0.5 mM DTTP, 5 $\mu$M dCTP, 100 $\mu$Ci of [$\alpha$-$^{32}$P] dCTP (3,000 Ci/mmol), 50 mM Tris-HCl (pH 8.3), 6 mM $MgCl_2$, 40 mM Kcl, 0.5 U of avian myeloblastosis virus reverse transcriptase (Life Science Inc.) in a total volume of 50 $\mu$l. The reaction is allowed to continue overnight at room temperature. EDTA and NaOH are then added to final concentrations of 50 mM and 0.25 M, respectively, and the mixture is incubated at 65° C. for 30 min to degrade the RNA templates. The cDNA is then ready to use after neutralization by adding Hcl and Tris buffer.

The hybridization step may be performed as described by Chuang et al. (1993) and briefly disclosed hereinafter. The DNA dot blot is hybridized to $^{32}$P-labeled total cDNA in a solution containing 0.1% polyvinylpyrrolidone, 0.1% Ficoll, 0.1% sodium $Pp_i$, 0.1% bovine serum albumin, 0.5% SDS, 100 mM NaCl, and 0.1 mM sodium citrate, pH 7.2, at 65° C. for 2 days and then washed with a solution containing 0.1% SDS, 100 mM NaCl, and 10 mM Na-citrate, pH 7.2. The same dot blot is used for hybridization with both control and experimental cDNAs, with an alkaline probe stripping procedure (soaked twice in 0.25M NaOH-0.75 M NaCl at room temperature, 30 min each, neutralized, and completely dried at 65° C. for at least 30 min) between the two hybridizations. Quantification may be done with the Betascope 603 blot analyzer (Betagen Corp.).

As it flows from the above technical teachings, another object of the invention consists in a method for detecting the presence of mycobateria in a biological sample comprising the steps of:

a) bringing into contact the recombinant BAC vector or a purified polynucleotide according to the invention with a biological sample.

b) detecting the hybrid nucleic acid molecule formed between said purified polynucleotide and the nucleic acid molecules contained within the biological sample.

The invention further deals with a method for detecting the presence of mycobacteria in a biological sample comprising the steps of:

a) Bringing into contact the recombinant BAC vector or a purified polynucleotide according to the invention that has been immobilized onto a substrate with a biological sample.

b) Bringing into contact the hybrid nucleic acid molecule formed between said purified polynucleotide and the nucleic acid contained in the biological sample with a labeled recombinant BAC vector or a polynucleotide according to the invention, provided that said polynucleotide and polynucleotide of step a) have non-overlapping sequences.

Another object of the invention consists in a method for detecting the presence of mycobacteria in a biological sample comprising the steps of:

a) Bringing into contact the nucleic acid molecules contained in the biological sample with a pair of primers according to the invention.

b) Amplifying said nucleic acid molecules;

d) detecting the nucleic acid fragments that have been amplified, for example by gel electrophoresis or with a labeled polynucleotide according to the invention.

In one specific embodiment of the above detection and/or amplification methods, said methods comprise an additional step wherein before step a), the nucleic acid molecules of the biological sample have been made available to a hybridization reaction.

In another specific embodiment of the above detection methods, said methods comprise an additional step, wherein, before the detection step, the nucleic acid molecules that are not hybridized with the immobilized purified polynucleotide are removed.

Also part of the invention is a kit for detecting mycobacteria in a biological sample comprising:

a) A recombinant BAC vector or a purified polynucleotide according to the invention;

b) Reagents necessary to perform a nucleic acid hybridization reaction.

The invention also pertains to a kit for detecting a mycobacteria in a biological sample comprising:

a) A recombinant BAC vector or a purified polynucleotide according to the invention that is immobilized onto a substrate.

b) Reagents necessary to perform a nucleic acid hybridization reaction.

c) A purified polynucleotide according to the invention which is radioactively or non-radioactively labeled, provided that said polynucleotide and the polynucleotide of step a) have non-overlapping sequences.

Moreover, the invention provides for a kit for detecting mycobacteria in a biological sample comprising:

a) A pair of purified primers according to the invention;

b) Reagents necessary to perform a nucleic acid amplification reaction;

c) Optionally, a purified polynucleotide according to the invention useful as a probe.

The invention embraces also a method for detecting the presence of a genomic DNA, a cDNA or a mRNA of mycobacteria in a biological sample, comprising the steps of:

a) Bringing into contact the biological sample with a plurality of BAC vectors according to the invention or purified polynucleotides according to the invention, that are immobilized on a substrate;

b) Detecting the hybrid complexes formed.

The invention also provides a kit for detecting the presence of genomic DNA, cDNA or mRNA of a mycobacterium in a biological sample, comprising:

a) A substrate on which a plurality of BAC vectors according to the invention or purified polynucleotides according to the invention have been immobilized;

b) Optionally, the reagents necessary to perform the hybridization reaction.

Additionally, the recombinant BAC vectors according to the invention and the polynucleotide inserts contained therein may be used for performing detection methods based on <<molecular combing>>. Said methods consist in methods for aligning macromolecules, especially DNA and are applied to processes for detecting, for measuring intramolecular distance, for separating and/or for assaying a macromolecule, especially DNA in a sample.

These <<molecular combing>> methods are simple methods, where the triple line S/A/B (meniscus) resulting form the contact between a solvent A and the surface S and a medium B is caused to move on the said surface S, the said macromolecules (i.e. DNA) having a part, especially an end, anchored on the surface S, the other part, especially the other end, being in solution in the solvent A. These methods are particularly fully described in the PCT Application n° PCT/FR 95/00165 files on Feb. 11, 1994 (Bensimon et al.).

When performing the <<molecular combing>> method with the recombinant BAC vectors according to the inventions or their polynucleotide inserts, the latters may be immobilized (<<anchored>>) on a suitable substrate and aligned as described in the PCT Application No. PCT/FR 95/00165, the whole teachings of this PCT Application being herein incorporated by reference. Then, polynucleotides to be tested, preferably under the form of radioactively or non radioactively labeled polynucleotides, that may consist of fragments of genomic DNA, cDNA etc. are brought into contact with the previously aligned polynucleotides according to the present invention and then their hybridization position on the aligned DNA molecules is determined using any suitable means including a microscope or a suitable camera device.

Thus, the present invention is also directed to a method for the detection of the presence of a polynucleotide of mycobacterial origin in a biological sample and/or for physical mapping of a polynucleotide on a genomic DNA, said method comprising:

a) Aligning at least one polynucleotide contained in a recombinant BAC vector according to the invention on the surface of a substrate;

b) Bringing into contact at least one polynucleotide to be tested with the substrate on which the at least one polynucleotide of step a) has been aligned;

c) detecting the presence and/or the location of the tested polynucleotide on the at least one aligned polynucleotide of step a).

The invention finally provides for a kit for performing the above method, comprising:

a) a substrate whose surface has at least one polynucleotide contained in a recombinant BAC vector according to the invention, b) optionally, reagents necessary for labeling DNA;

c) optionally, reagents necessary for performing a hybridization reaction.

In conclusion, it may be underlined that the alliance of such BAC-based approaches such as described in the present specification to the advances in comparative genomics by the availability of an increased number of complete genomes, and the rapid increase of well-characterized gene products in the public databases, will allow the one skilled in the art an exhaustive analysis of the mycobacterial genome.

MATERIALS AND METHODS

1. DNA-preparation. Preparation of *M. tuberclosis* H37Rv DNA in agarose plugs was conducted as previously described (Canard et al., 1989; Philipp et al., 1996b). Plugs were stored in 0.2 M EDTA at 4 C and washed 3 times in 0.1% Triton X-100 buffer prior to use.

2. BAC vector preparation. pBeloBAC11 was kindly provided by Dr. Shizuya, Department of Biology, California Institute of Technology (Pasadena, Calif.). The preparation followed the description of Woo et al., 1994 (Woo et al., 1994).

3. Partial digestion with HindIII. Partial digestion was carried out on plugs, each containing approximately 10 $\mu$g of high molecular weight DNA, after three one hour equilibration steps in 50 ml of HindIII 1×digestion buffer (Boehringer Mannheim, Mannheim, Germany) plus 0.1% Triton X-100. The buffer was then removed and replaced by imliplug of ice-cold HindIII enzyme buffer containing 20 units of HindIII (Boehringer). After two hours incubation on ice, the plugs were transferred to a 37° C. water bath for 30 minutes. Digestions were stopped by adding 500 μl of 50 mM EDTA (pH 8.0).

4. Size selection. The partially digested DNA was subjected to contour-clamped homogenous electric field (CHEF) electrophoresis on a 1% agarose gel using a BioRad DR III apparatus (BioRad, Hercules, Calif.) in 1×TAE buffer at 13° C., with a ramp from 3 to 15 seconds at 6 V/cm for 16 hours. Agarose slices from 25 to 75 kb, 75 to 120 kb and 120 to 180 kb were excised from the gel and stored in TE at 4° C.

5. Ligation and transformation. Agarose-slices containing fractions from 25 to 75 kb, 75 to 120 kb and 120 to 180 kb were melted at 65° C. for 10 minutes and digested with Gelase (Epicentre Technologies, Madison, Wis.), using 1 unit per 100 μl gel-slice. 25–100 ng of the size-selected DNA was then ligated to 10 ng of HindIII digested, dephosphorylated pBeloBAC11 in a 1:10 molar ratio using 10 units of T4 DNA ligase (New England Biolabs, Beverly, Mass.) at 16° C. for 20 hours. Ligation mixtures were heated at 65° C. for 15 minutes, then drop-dialysed against TE using Millipore VS 0.025 mM membranes (Millipore, Bedford, Mass.). Fresh electrocompetent *E. coli* DH 10B cells (Sheng et al., 1995) were harvested from 200 ml of a mid-log ($OD_{550}$=0.5) culture grown in SOB medium. Cells were washed three times in ice-cold water, and finally resuspended in ice-cold water to a cell density of $10^{11}$ cells/ml ($OD_{550}$=150). 1 μl of the ligation-mix was used for electroporation of 30 μl of electrocompetent DH10B *E. coli* using a Eurogentec Easyject Plus electroporator (Eurogentec, Seraing, Belgium), with settings of 2.5 kV, 25 μF, and 99 ½, in 2 mm wide electroporation cuvettes. After electroporation, cells were resuspended in 600 μl of SOC medium, allowed to recover for 45 minutes at 37° C. with gentle shaking, and then plated on LB agar containing 12.5 μg/ml chloramphenicol (CM), 50 μg/ml X-gal, and 25 μg/ml IPTG. The plates were incubated overnight and recombinants (white colonies) were picked manually to 96 well plates. Each clone was inoculated 3 times (2×200 μl and 1×100 μl of 2YT/12.5 μg/ml CM per clone) and incubated overnight. One of the microtiter plates, containing 100 μl culture per well, was maintained as a master plate at −80° C. after 100 ml of 80% glycerol were added to each well, while minipreps (Sambrook et al., 1989) were prepared from the remaining two plates to check for the presence of inserts. Clones containing inserts were then designated "Rv" clones, repicked from the master plate to a second set of plates for storage of the library at −80° C.

6. Preparation of DNA for sizing, direct sequencing and comparative genomics. A modified Bimboim and Doly protocol (Birnboim et al., 1979) was used for extraction of plasmid DNA for sequencing purposes. Each Rv clone was inoculated into a 50 ml Falcon polypropylene tube containing 40 ml of 2YT medium with 12.5 μg/ml of CM and grown overnight at 37° C. with shaking. Cells were harvested by centrifugation and stored at −20° C. The frozen pellet was resuspended in 4 ml of Solution A (50 mM glucose, 10 mM EDTA, 25 mM Tris, pH 8.0) and 4 ml of freshly prepared solution B (0.2 M NaOH, 0.2% SDS) was then added. The solution was gently mixed and kept at room temperature for 5 minutes before adding 4 ml of ice-cold solution C (3M Sodium Acetate, pH 4.7). Tubes were kept on ice for 15 min, and centrifuged at 10,000 rpm for 15 min. After isopropanol precipitation, the DNA pellet was dissolved in 600 μl RNase solution (15 mM Tris HCl pH 8.0, 10 μg/ml RNase A). After 30 minutes at 37° C. the DNA solution was extracted with chloroform:isoarnylalcohol (24:1) and precipitated from the aqueous phase using isopropanol. The DNA pellet was then rinsed with 70% ethanol, air-dried and dissolved in 30 μl distilled water. In general, DNA prepared by this method was clean and concentrated enough to give good quality results by automatic sequencing (at least 300 bp of sequence). For a few DNA preparations, an additional polyethylene glycol (PEG) precipitation step was necessary, which was performed as follows. The 30 μl of DNA solution were diluted to 64 μl, mixed gently and precipitated using 16 μl 4M NaCl and 80 μl of 13% PEG 8000. After 30 min on ice the tubes were centrifuged at 4° C., the pellet carefully rinsed with 70% ethanol, air-dried and diluted in 20 μl of distilled water.

7. Sizing of inserts. Insert sizes were determined by pulsed-field gel electrophoresis (PFGE) after cleavage with Dral (Promega). 100–200 ng of DNA was Dral-cleaved in 20 μl total reaction volume, following the manufacturer's recommendations, then loaded onto a 1% agarose gel and migrated using a pulse of 4 s for 15 h at 6.25 V/cm at 10° C. on an LKB-Pharmacia CHEF apparatus. Mid-range and low-range PFGE markers (New England Biolabs) were used as size standards. Insert sizes were estimated after ethidium bromide staining of gels.

8. Direct sequencing. For each sequencing reaction 7 μl BAC DNA (300–500 ng), 2 μl primer (2 μM), 8 μl reaction mix of the Taq DyeDeoxy Terminator cycle sequencing kit (Applied Biosystems) and 30 μl distilled water were used. After 26 cycles (96° C. for 30 sec; 56° C. for 15 sec; 60° C. for 4 min) in a thermocycler (MJ-research Inc., Watertown, Mass.) DNA was precipitated using 70 μl of 70% ethanol/0.5 mM $MgCl_2$, centrifuged, rinsed with 70% ethanol, dried and dissolved in 2 μl of formamide/EDTA buffer. SP6 and T7 samples of 32 BAC clones were loaded onto 64 lane, 6% polyacrylamide gels and electrophoresis was performed on a Model 373A automatic DNA sequencer (Applied Biosystems) for 12 to 16 hours. The sequences of oligonucleotides used as primers are shown in Table 1.

9. DOP-PCR. As an alternate procedure we used partially degenerate oligonucleotides in combination with vector-specific (SP6 or T7) primers to amplify insert ends of BAC clones, following a previously published protocol for P1 clones (Liu et al., 1995). The degenerate primers Deg2, Deg3, Deg4, Deg6 (Table 1) gave the best results for selected amplification of insert termini.

TABLE 1

| Primers used for PCRs and sequencing | |
|---|---|
| Vector specific Primers for DOP PCR-first amplification step: | |
| SP6-BAC1: | AGT TAG CTC ACT CAT TAG GCA (SEQ ID NO: 734) |
| T7-BAC1: | GGA TGT GCT GCA AGG CGA TTA (SEQ ID NO: 735) |

TABLE 1-continued

| Primers used for PCRs and sequencing | |
|---|---|
| Vector specific Primers (direct sequencing nested primer for second PCR step) | |
| SP6 Mid: | AAA CAG CTA TGA CCA TGA TTA CGC CAA (SEQ ID NO: 736) |
| T7-Belo2: | TCC TCT AGA GTC GAC CTG CAG GCA (SEQ ID NO: 737) |
| Degenerate Primers: | |
| Deg2: | TCT AGA NNN NNN TCC GGC (SEQ ID NO: 738) |
| Deg3: | TCT AGA NNN NNN GGG CCC (SEQ ID NO: 739) |
| Deg4: | CGT TTA AAN NNN NWA GGC CG (SEQ ID NO: 740) |
| Deg6: | GGT ACT AGT NNN NNW TCC GGC (SEQ ID NO: 741) |
| Primers used for the amplification of *M. bovis* DNA in polymorphic chromosomal region of Rv58: | |
| Primer 1: | ACG ACC TCA TAT TCC GAA TCC C (SEQ ID NO: 742) |
| Primer 2: | GCA TCT GTT GAG TAC GCA CTT CC (SEQ ID NO: 743) |

10. Screening by pooled PCR. To identify particular clones in the library which could not be detected by random end-sequencing of the 400 BAC clones, PCR-screening of DNA pools was performed. Primers were designed for regions of the chromosome where no BAC coverage was appearent using cosmid-or H37Rv whole genome shotgun sequences. Primers were designed to amplify approximately 400–500 bp. Ninety-six-well plates containing 200 $\mu$l 2YT/12.5 $\mu$g/ml CM per well were inoculated with 5 $\mu$l of −80° C. glycerol stock cultures each from the master plates and incubated overnight. The 96 clones of each plate were pooled by taking 20 $\mu$l of culture from each well and this procedure was repeated for 31 plates. Pooled cultures were centrifuged, the pellets were resuspended in sterile water, boiled for 5 minutes, centrifuged and the supernatants kept for PCRS. As an initial screening step, the 31 pools of a total of 2976 BACs, representing about two thirds of the library were tested for the presence of a specific clone using appropriate PCR primers. PCR was performed using 10 $\mu$l of supernatant, 5 $\mu$l of assay buffer (100 mM b-mercaptoethanol, 600 mM Tris HCl (pH 8.8), 20 mM $MgCl_2$, 170 mM $(NH_4)_2SO_4$), 5 $\mu$l of Dimethylsulfoxide (DMSO), 5 $\mu$l of dNTPs (20 mM), 5 $\mu$l of water, 10 $\mu$l primer (2 $\mu$M), 10 $\mu$l inverse primer (2 $\mu$M) and 0.2 units off aq DNA polymerase (Boehringer). 32 cycles of PCR (95° C. for 30 s, 55° C. for 1 min 30 s, 72° C. for 2 min) were performed after an initial denaturation at 95° C. 1 min. An extension step at 72° C. for 5 min finished the PCR. If a pool of 96 clones yielded an appropriate PCR product (FIG. 1A), subpools were made to identify the specific clone. Subpools representative for lane A of a 96 well plate were made by pooling clones 1 to 12 from lane A into a separate tube. Subpools for lanes B to H were made in the same way. In addition, subpools of each of the 12 rows (containing 8 clones each) were made, so that for one 96 well plate, 20 subpools were obtained. PCR with these 20 subpools identified the specific clone (FIG. 1B, lower gel portion). If more than one specific clone was present among the 96 clones of one plate (FIG. 1B, upper gel portion), additional PCR reactions had to be performed with the possible candidates (data not shown).

11. Genomic comparisons. DNA from the BAC clone Rv58 was digested with the restriction endonucleases EcoRI and PvuII, and resolved by agarose gel electrophoresis at low voltage overnight (1.5 V/cm). DNA was transferred via the method of Southern to nitrocellulose membranes (Hybond C extra, Amersham) following standard protocols (Sambrook et al., 1989), then fixed to the membranes at 80° C. for 2 hours. The blot was hybridized with $^{32}P$ labelled total genomic DNA from *M. tuberclosis* H37Rv, *M. bovis* type strain (ATCC 19210) or *M. bovis* BCG Pasteur. Hybridization was performed at 37° C. overnight in 50% formamide hybridization buffer as previously described (Philipp et al., 1996b). Results were interpreted from the autoradiograms.

12. Computer analysis. Sequence data from the automated sequencer ABI373A were transferred as binary data to a Digital Alpha 200 station or Sun SparcII station and analysed using TED, a sequence analysis program from the Staden software package (Dear et al., 1991). Proof-read sequences were compared using the BLAST programs (Altschul et al., 1990) to the *M. tuberclosis* H37Rv sequence databases of the Sanger Centre, containing the collected cosmid sequences (TB.dbs) and whole-genome shotgun reads (TB_shotgun_all.dbs) (http://www.sanger.ac.uk/). In addition, local databases containing 1520 cosmid endsequences and the accumulating BAC endsequences were used to determine the exact location of end-sequenced BACs on the physical and genetic map. MycDB (Bergh et al., 1994) and public databases (EMBL, Genbank) were also used to compare new sequences, but to a lesser extent. The organization of the open reading frames (ORFs) in the polymorphic region of clone Rv58 was determined using the DIANA software established at the Sanger Centre.

EXAMPLES

Example 1

Construction of a pBeloBAC11 Library of *M. tuberclosis* H37Rv.

Partial HindIII fragments of H37Rv DNA in the size range of 25 to 180 kb were ligated into pBeloBAC11 and electroporated into strain *E. coli* DH10B. While cloning of fractions I (25 to 75 kb) and II (75 to 120 kb) gave approximately $4\times10^4$ transfornants (white colonies), cloning of fraction III (120 to 180 kb) repeatedly resulted in empty clones. Parallel cloning experiments using partial HindIII digests of human DNA resulted in stable inserts for all three fractions (data not shown), suggesting that the maximum size of large inserts in BAC clones is strongly dependent on the source of the DNA. Analysis of the clones for the presence of inserts revealed that 70% of the clones had an insert of the appropriate size while the remaining 30% of white colonies represented empty or lacZ'-mutated clones. Size determination of randomly selected, Dral-cleaved BACs via PFGE showed that the insert sizes ranged for the majority of the clones between 40 kb and 100 kb with an average size of 70 kb. Clones with inserts of appropriate size were designated with "Rv" numbers, recultured and stored at −80° C. for further use.

Example 2

Direct DNA Sequence Analysis of BACs.

To characterize the BAC clones, they were systematically subjected to insert termini sequencing. Two approaches, direct sequencing of BAC DNA and PCR with degenerate oligonucleotide primers (DOP), adapted to the high G+C content of mycobacterial DNA, were used. In a first screening phase, 50 BAC clones designated Rv1 to Rv50 were analysed using both methods in parallel. Except for two clones, where the sequences diverged significantly, the sequences obtained by the two methods only differed in length. Sequences obtained directly were on average about 350 bp long and for 95% of the clones both the SP6 and T7 endsequences were obtained at the first attempt. Sequences obtained by DOP-PCR were mostly shorter than 300 bp. For 40% of the BACs we obtained only very short amplicons of 50 to 100 base pairs from one end. In two cases the sequence obtained with the DOP-PCR differed from the sequences obtained by direct sequencing, and in these cases *E. coli* or vector sequences were amplified (data not shown). Taking the advantages and disadvantages of both methods into account, we decided to use direct termini sequencing for the systematic determination of the SP6 and T7 end-sequences.

Example 3

Representativity of the Library.

After having determined the end-sequences of 400 BACs a certain redundancy was seen. The majority of clones were represented at least 3 to 4 times. Maximum redundancy was seen in the vicinity of the unique ran operon, as 2.5% of the clones carried identical fragments that bridge the cosmids Y50 and Y130 (FIG. 3, approximate position at 1440 kb). The majority of clones with identical inserts appeared as two variants, corresponding to both possible orientations of the HindIII fragment in pBeloBAC11. This suggests that the redundancy was not the result of amplification during library construction, but due to the limited number of possible combinations of partial HindIII fragments in the given size-range of 25 to 120 kb. To detect rare BAC clones, a pooled PCR protocol was used. Primers were designed on the basis of the existing cosmid sequences and used to screen 31 pools of 96 BAC clones. When positive PCR products of the correct size were obtained, smaller subpools (of 8 or 12 clones each) of the corresponding pool were subsequently used to identify the corresponding clone (FIG. 1). With this approach 20 additional BACs (Rv401–Rv420) were found for the regions where no BACs were found with the initial systematic sequencing approach. The endsequences of these BACs (Rv401–420) were determined by direct sequencing, which confirmed the predicted location of the clones on the chromosome. A 97% coverage of the genome of H37Rv with BAC clones was obtained. Only one region of 150 kb was apparently not represented in the BAC library as screening of all pools with several sets of specific primers did not reveal the corresponding clone. This was probably due to the fact that HindIII fragments of mycobacterial DNA larger than 110 kb are very difficult to establish in *E. coli* and that a HindIII fragment of ~120 kb is present in this region of the chromosome (data not shown).

Example 4

Establishing a BAC Map.

Using all endsequence and shotgun-sequence data from the H37Rv genome sequencing project, most of the BAC clones could then be localized by sequence comparison on the integrated map of the chromosome of *M. tuberclosis* strain H37Rv (Philipp et al., 1996b) and an ordered physical map of the BAC-clones was established. PCR with primers from the termini sequences of selected BACs were used for chromosomal walking and confirmation of overlapping BACs (data not shown). The correct order of BACs on the map was also confirmed more recently, using 40,000 whole genome shotgun reads established at the Sanger Centre. In addition, pulsed-field gel electrophoresis of DraI digests of selected BACs was performed (FIG. 2) in order to see if the approximate fragment size and the presence or absence of DraI cleavage sites in the insert were consistent with the location of the BACs on the physical map (FIG. 3). Comparison of the sequence-based BAC-map with the physical and genetic map, established by PFGE and hybridization experiments (Philipp et al., 1996b), showed that the two maps were in good agreement. The positions of 8 genetic markers previously shown on the physical and genetic map were directly confirmed by BAC-endsequence data (Table 2, FIG. 3). The position of 43 from 47 Y-clones (91%) shown on the physical and genetic map, which were later shotgun sequenced, was confirmed by the BAC endsequences and shotgun sequence data. Four clones (Y63, Y180, Y251, and Y253) were located to different positions than previously thought and this was found to be due to book keeping errors or to chimeric inserts. Their present approximate location relative to the oric is shown in FIG. 3: Y63 at 380 kb, Y63A at 2300 kb, Y180 at 2160 kb, Y251 at 100 kb, and Y253 at 2700 kb. A total of 48 BACs, covering regions of the chromosome, not represented by cosmids were then shotgun sequenced (Cole et al., 1997), and these are squared in FIG. 3. No chimeric BACs were found, which is consistent with the observations of other research groups for other BAC libraries (Cai et al., 1995; Zimmer et al;, 1997). The absence of chimeric BACs was of particular importance for the correct assembly of the *M. tuberculosis* H37Rv sequence. The exact position of the BAC termini sequences on the chromosome will be available via the world wide web

TABLE 2

Identities of genetic markers previously shown on the integrated and genetic map of H37Rv (Phlipp et al., 1996b) which showed perfect sequence homology with BAC end sequences.

| Locus | BAC end sequence | Description of genetic marker | Organism | GenBank Accession n° |
|---|---|---|---|---|
| apa | Rv163SP6 | Secreted alanine-proline-rich antigen | *M. tuberculosis* | X80268 |
| dnaJ, dnaK | Rv164T7 | DnaJ hsp | *M. leprae* | M95576 |
| fop-A | Rv136T7 | Fibronectin binding protein | *M. tuberculosis* | M27016 |
| polA | Rv401T7 | DNA polymerase I | *M. tuberculosis* | L11920 |
| ponA | Rv273T7 | Penicillin binding protein | *M. leprae* | S82044 |
| pstC | Rv103T7 | Putative phosphate transport receptor | *M. tuberculosis* | Z48057 |
| recA | Rv415SP6 | Homologous recombination | *M. tuberculosis* | X58485 |
| wag9 | Rv35SP6 | 35-kDa antigen | *M. tuberculosis* | M69187 |

Example 5

Repetitive Endsequences.

Repetitive sequences can seriously confound mapping and sequence assembly. In the case of the BAC endsequences, no particular problems with repetitive sequences were observed. Although nine clones with one end in an IS1081 (Collins et al., 1991) sequence were identified, it was possible to correctly locate their position on the map using the sequence of the second terminus. Moreover, these BACs were used to determine the exact locations of IS1081 sequences on the map. Five copies of this insertion sequence, which harbors a HindIII cleavage site, were mapped on the previous physical and genetic map. In contrast, BAC endsequence data revealed an additional copy of IS1081 on the *M. tuberculosis* H37Rv chromosome. The additional copy was identified by six clones (Rv27, Rv118, Rv142, Rv160, Rv190, Rv371) which harbored an identical fragment linking Y50 to 1364 (FIG. 3, at ~1380 kb). This copy of IS1081 was not found by previous hybridization experiments probably because it is located near another copy of IS1081, localized on the same DraI fragment Z7 and AsnI fragment U (FIG. 3, at ~1140 kb). Furthermore, the position of a copy of IS1081 previously shown in DraI fragment Y1 (FIG. 3, at ~1840 kb) had to be changed to the region of Y349 (FIG. 3, at ~3340 kb) according to the endsequences of BAC Rv223. The positions of the four other IS1081 copies were confirmed by the sequence data and therefore remained unchanged. In total 6 copies of IS1081 were identified in the H37Rv genome in agreement with the findings of others (Collins et al., 1991).

In addition, a sequence of 1165 bp in length containing a HindIII site was found in two copies in the genome of H37Rv in different regions. The endsequences of BAC clones Rv48 and Rv374, covering cosmid Y164, as well as Rv419 and Rv45, that cover cosmid Y92, had perfect identity with the corresponding parts of this 1165 bp sequence (FIG. 3, at ~3480 kb and 900 kb). Analysis of the sequence did not reveal any homology with insertion sequences or other repetitive elements. However, as each of the two locations showed appropriate BAC coverage, chimerism of the sequenced cosmids Y164 and Y92 can be ruled out as the probable cause.

Example 6

Using BAC Clones in Comparative Genomics.

The minimal overlapping set of BAC clones represents a powerful tool for comparative genomics. For example, with each BAC clone containing on average an insert of 70 kb, it should be possible to cover a 1 Mb section of the chromosome with 15 BAC clones. Restriction digests of overlapping clones can then be blotted to membranes, and probed with radiolabelled total genomic DNA from, for example, *M. bovis* BCG Pasteur. Restriction fragments that fail to hybridize with the *M. bovis* BCG Pasteur DNA must be absent from its genome, hence identifying polymorphic regions between *M. bovis* BCG Pasteur and *M. tuberclosis* H37Rv. The results of such an analysis with clone Rv58 (FIG. 3, at 1680 kb) are shown here. This clone covers a previously described polymorphic genomic region between *M. tuberclosis* and *M. bovis* BCG strains (Philipp et al., 1996a). EcoRI and PvuII digests from clone Rv58, fixed on nitrocellulose membranes, were hybridized with $^{32}P$-labelled total genomic DNA from *M. tuberclosis* H37Rv, *M. bovis* (ATCC 19120), and *M. bovis* BCG Pasteur. FIG. 4 presents the results of this analysis, where it is clear that several restriction fragments from clone Rv58 failed to hybridize with genomic DNA from either *M. bovis* or *M. bovis* BCG Pasteur. On the basis of the various missing restriction fragments, a restriction map of the polymorphic region was established and compared to the H37Rv sequence data. The localization of the polymorphism could therefore be estimated, and appropriate oligonucleotide primers (Table 1) were selected for the amplification and sequencing of the corresponding region in *M. bovis*. The alignment of *M. bovis* and *M. tuberculosis* H37Rv sequences showed that 12,732 bp were absent from the chromosomal region of the *M. bovis* type strain and *M. bovis* BCG Pasteur strain. The G+C content of the polymorphic region is 62.3 mol %, which is the same as the average genome G+C content of the *M. tuberclosis* genome, hence indicating that this region is not a prophage or other such insertion. Subsequent PCR studies revealed that this segment was also absent from the Danish, Russian, and Glaxo substrains of *M. bovis* BCG, suggesting that this polymorphism can be used to distinguish *M. bovis* from *M. tuberclosis*. Analysis of this sequence showed that 11 putative open reading frames (ORFS) are present in *M. tuberclosis*, corresponding to ORFs MTCY277.28 to MTCY277.38/accession number Z79701-EMBL Nucleotide Sequence Data Library (FIG. 5). FASTA searches against the protein and nucleic acid databases revealed that the genes of this region may be involved in polysaccharide biosynthesis. Among these putative genes, the highest score was seen with ORF 6 (MCY277.33), whose putative product shows a 51.9% identity with GDP-D-Mannose dehydratase from *Pseudomonas aeruginosa* (accession number U18320-EMBL Nucleotide Sequence Data Library) in a 320 amino acid overlap. The novel *M. bovis* sequence of the polymorphic region was deposited under accession number AJ003103 in the EMBL Nucleotide Sequence Data Library.

As it appears from the teachings of the specification, the invention is not limited in scope to one or several of the above detailed embodiments; the present invention also embraces all the alternatives that can be performed by one skilled in the same technical field, without deviating from the subject or from the scope of the instant invention.

TABLE 3

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

Clone Rv101 ::::::::::::::Rv101SP6.seq::::::::::::::
AATACTCAAGCTTGCCCAGCCGTCGATGACAAGAAATATGTCCGCAAAAGACTCAGCGGCCGACTTTTGCTCGCAGCTGGCGGTACCGCGCCACCGATTCTATGCCG (SEQ ID NO. 6)
TGGTCGCGGAAAAATGCCTCCCGAAATCGCACGGCCGACTCCAGTTCGGCGAGCATCCGCGATGCCAGCTGCGGCTGCGCCCTGCCGGCCACGGCACCCACATGCG
GCAGTTCGTCCACCTGGGCCAGCGCCCCGCCGCCGAATTCCAAACAATAGAACTGCACCCGGCCCGCATCTGTGGGTAACAGCCAACGCCATGATCAGCGTCCGCAG
CGCGGTTGACTTGCCCGTTTGCGGTGCACCTACGAACGCGACATTGCCTGCGGCCCCGGACAAGTCGATCGTGCGCGGCACCGTGACTGCTCTAACGGGCGATTG
AAATTCCGAT
::::::::::::::Rv101T7.seq::::::::::::::
CCACCCGTGTAATTTGGGATGGGCAAAAAGGCGAAGCACCGCGTGGCCACGAACGCCGGGAGGGACAATCTGGGCGGTTAGGGCTTCTCGCCGGGAAGGCCCGAAC (SEQ ID NO. 7)
GTACGGCGTTTCAACACCTCGCGTCGCCCTCCGACCGCGAACATTCGGGGATGGCAGCAACCTGCTGGCACCCTGGCCGGGCGATGATCTGCAGCGTCGCCGCGGG
TAGTCGCCGCCCGGGCGGCTACACTCTGAAACGCGATGACCATCGATGTGTGGATGCAGCATCCCGACGCAACGGTTCCTACACCGCGATATGTTCGCCTCGCTGC
CCCGGTGGACCGGT Clone Rv102 ::::::::::::::Rv102SP6.seq::::::::::::::
AATACTCAAGCTTTCCGCCGATACCCGCCATGTCGCGCACATCCAGGACTTCTGGGGGGATCCGCTGACAGCGGCGGGATCCCAAGTGCGGATGATCGGGCCGCC (SEQ ID NO. 8)
TACGTCGTGGTGTACCTCGTCGGTAACAACGAAACCGAAGCGTATGACTCGGTCCACGCGGTGCGGCACATGGTGGACACCACACCGCCACCGCACGGGGTGAAGG
CCTATGTCACCGGTCCGGCAGCACTCAATGCCGACCAGGCCGAGGGCGGAGACAAAAGTATCGCTAAGGTCACCGCGATCACCAACATGGTGATCGCAGCAATGTT
GCTAGTGATCTATCGCTCCGTAATTACCGCGGTTCT
::::::::::::::Rv102T7.seq::::::::::::::
GTGCCGTTCCAACCCGAATTGGCTTTCGGCGCCATCGGTGAGGACGGCGTGCGGGTGCTCAACGACGACGTCGTCCGCGGGACACACCTCGATGCTGCCGCCATGG (SEQ ID NO. 9)
ACGCGGTCGAACGCAAGCAGCTGATCGAGCTACAACGCCGCGCGGAACGCTTCCGCCGCGGGCGTGACCGCATCCGTTGACCGGGCGGATCGCGGTGATCGTCGA
TGACGGCATCGCCACCGGAGCGACGGCCAAGGCGGCGTGCCAGGTCGCCCGGGCGCACGGTGCGGACAAGGTGGTGCTGGCGGTCCGATCGGCCCAGACGACATC
GTGGCGAGATTCGCCGGGTACGCCGATGAGGTGGT Clone Rv103 ::::::::::::::Rv103SP6.seq::::::::::::::
AATACTCAAGCTTTCGGCGGAAACGGACACATTGCGAATATTGATGACAAAATAAAAATCATTGATGGTTTGAGTCACCAGGCCGATCAAGCCTTCGCCGAGCCAA (SEQ ID NO. 10)
ATTCCAATCAAGAGGCCCAAGCCCGTACCAATCAGCCCGGCAACGAGGGATTCCGTCATTATCAGCCAAAATAACTGCTCTCGGGTTACACCCAAACAGCGCAATA
TGGCGAAAAACGGTCGCCGTTGCACGACATTAAATGTCACGGTATTGTAGATTAAAAAGATACCCAC
::::::::::::::Rv103T7.seq::::::::::::::
TGCTCCCGAAACCTGGGGTGTGCCTGCTCTGTATGCACGGCATACGGACATCCTTCCCCTGAGACCCGCGGTCGAACCAGCCACGTGTCCATCATAGNGGGTCAA (SEQ ID NO. 11)
CCCCGGCCAAGGGCGACGGCACGCCAAGTTCGCCGACCGTTAACCTAGTGCTGTTAGCTTCATTTGCTGCGATCAAAACAGCTGGTCGGCCGTTAGGAACTGAATT
GAAACTCAACCGATTTGGTGCCGCCGTAGGTGTCCTGGCTGCGGGTGCGCTGGTGTTGTCCGCCTGTGGTAACGACGACAATGTGACCGGGGGAGGTGCAACCACT
GGCCAGGCGTCGGCAAAGGTCGATTGCGGGGGGAAGAAGACACTCAAAGCCAGTGGGT Clone Rv104 ::::::::::::::Rv104SP6.seq::::::::::::::
ATACTCAAGCTTTGCCGACGAGCGGGCGATGTTGATGACGGGAAACCCCAGCGCACAACCGACGATTTTGGCGTAGCCGGCGGACGTCTGCTCGATTCCGATCAGG (SEQ ID NO. 12)
TCGGCGCTCGCATCGAGCATGGCGCCGGCGACGGCTAGCAGCGATCCGCCGTCGTCGAGGAGCACGACACGAGCCGTACGCCCGGCCGTAAGCCGCGCCCAGGATT
CGGCGAAAAACCGTTCTACGTGGCGGGTGTACTGGGTGTCGAATGATTCGTGGGGTGCGTAGGCGTCGCTGCAATCGTCGACATAGATGCCGTCGGGCCGCATCGC
GTCGACAACTCCGGGTGAGTGGAATAGCACTTGCCGATCACCGCGACGTTGCGCGGATGAGGCCGAACCCGAATA
::::::::::::::Rv104T7.seq::::::::::::::
TCCTATGTCCCTGCCGAGCANGTGATCGAACGCGGTGACAGATTTGTCTATCCTGGACCTGACGGTGAGGTCGAAGTTTTCCAGGAATTCGGCAAAATCGGTAAGA (SEQ ID NO. 13)
GCCTGAAGAATTCGGTATCGCCGGACGAAATCTGCGACGCATACGGGGGCATATACGCTTCGGGTTTACGAGATGTCGATGGGGCCGCTGGAGGCTTCACGTCCAT
GGGCCACAAAGGATGTTGTCGGCGCGTACCGTTTTCTGCAGCGGGTGTGGCGCTTGGTCG Clone Rv105 ::::::::::::::Rv105SP6.seq::::::::::::::
ATACTCAAGCTTGATTCCGCCGAAACCGACCGTGAGCACCCCGCCAGCCACCACGCTCGGGTCGGGCGCCGGGCCCGGGCCCGCCAGGCTGCTCCGCTCGGTGATGG (SEQ ID NO. 14)
CACGCCACCGCGACACCACCCGGCTGCGCTACGTCTAACCATTCCAGGCGGAGCTACATCAGCTCGGCCGCCCAGTGTTCGGGCCCTCTTTCCAGGTCGAAGTCTA
TACCGATATGCGCATCCGCAGCCGCCACCCTGGAGAACAGAACGATGCCCTACTAATGCTTGTCTGGCGGGGCC TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | ::::::::::::::Rv105T7.seq:::::::::::::: | |
| | GGTACGCTTCGGTCGCAGTCTGCGAGTGATGCATGACGACCGGGACCTCGTCGGCATCTTCCATAGCCCGCCACACCTTCAGTTGCTCACCGGAATCCAACCGGTA | (SEQ ID NO. 15) |
| | GAAGGTCGGCGAGCGCTCGGCATTGGTCATCGGGATATGCCGCTCGGGACGGTCAGAGCCCTCGGGTCCGGCCAGCACTCCGCAGGCTTCGTCGGGGTGGTCGCGA | |
| | CGCGCATGGGCCACCATCGCATTCACCAGGTCTGCGCGAATCACCAGCACGTAGACGGTTCCTTTCCTAAGCAACACCGAAGTTTCAGGACCCGAATGCTCCGGGA | |
| | AACATGTCACGGTAGGTCGGTATTCCGGCTACCGGCTGA | |
| Clone Rv106 | ::::::::::::::Rv106SP6.seq:::::::::::::: | |
| | GGCGTCAACGGTGTCGGAACCCGCGTCAAGCAATTGGTAGGCCTGCAGTCTGTGAATCAGGCCGACGCTGTGGCCGCCGCGGC | (SEQ ID NO. 16) |
| | ::::::::::::::Rv106T7.seq:::::::::::::: | |
| | GGCTNGCGTACCCGGTACCGGCCGCGGGCCTACCACGTGCCGGAACTGGAAGCGCAGTAAGCCCTCAACGCGCCACCGCTTTGGCCCGCGCGCCCGGCGTAGGCGC | (SEQ ID NO. 17) |
| | ATCGGCGGTGGCCGTGGGGCGGCGCACTGCGACCTCACCAGCGGCTTTCGAGCTTTGTTCGATCAACCGGCCAGCATGGTCGANGATGCATTCGAGACCATATTCG | |
| | AAATTGGTTTCATCGGGGGCCCCGATCCGATGCCCCCTCCCAGTTGCGTGAGCAANCAGCGGAGTCNTCGCGGGATCGATGGCCACGGGGTGTTCAATGGCGGATG | |
| | GTCCGCTGCCCGCCGACTGGCTCTTGCGGGAGAACCGATCTAGCACCACCGATCCGCGCACGTNG | |
| Clone Rv107 | ::::::::::::::Rv107T704.seq:::::::::::::: | |
| | GTAATNTCGCGCACANCCANGACTTCTGGGGGGATCNGCTGACAGTGGNGGATCCCAAATTGCGGATGATCGGGCCGCCNACGTCGTTGTGTACCTCNTCNGTC | (SEQ IN NO. 18) |
| | ACAACNAANCCGAANCGTATGACTCGGTCCACGCGGTGCGGCACATGGTGGACACCACACCGCCACCGCNCGGGGTGAAGGCCTATGTCACCGGTCCGGCAACACT | |
| | CAATGCCGACCAGGCCGANGCCGGACACNANAGTATCNCTAACGTCACCGCGATCACGAGCATGGTGATCGNNCAATGTTNCTANTGATCTATCGCTCCGTAATTA | |
| | CCGCGGTTCTCGTCTTGATCATGGTCGCANCGAACTCCGGCGCAATCCGCGGATTCATCGNCTTGCTCGCCGATCACATATTTTCAGCCTTTCACATTGCAACNAA | |
| | CCTGCTCGTCTCATGGNGATGCGGCGACACGGACTACCGATATCATGCTCGCCGTTACACAATCNCGCCACGCCGCGAAGACNGGAAACGCTTCTACACAATNTTC | |
| | NCGGGACGCCACTNAACTTGGTTCNGGTTTGACATTGCCGCGCATGTNGCCCAGCTTTGCCGGCTCCCCTTA | |
| Clone Rv108 | ::::::::::::::Rv108T704.seq:::::::::::::: | |
| | TGAATTTCCCGATCCCACAATCTCGGTTCAGATACAGGTCGCCATACCCCTTACTTCGGCAACGCTGGGCGGATTGGCCCTGCNGCTGCAGCANACCATCGACGCC | (SEQ ID NO. 19) |
| | ATCGAATTGCCGGCAATCTCGTTCAGCCAATCCATACCCATCGACATTCCGCCGATCGACATCCCGGCCTTCNCCCTTTAACGG | |
| Clone Rv109 | ::::::::::::::Rv109SP6.seq:::::::::::::: | |
| | AACAGCTATGACCATGNTTACGCCAAGCTATTTAGGTAACACTATANAATACTCAAGCTTTTACGGTGATCGCGCATCACCTGGTTCATGAACTGGAAGCAGCGCA | (SEQ ID NO. 20) |
| | NCGCTTCCTTTTCGGCCGCAACATGAGCCAGCCTCTCGTCCGCGGTCNGGTGCAGGTGCTCGGGCAGCTCGGCCGCGACAGCCGCCTGACCCTGAAACCAGCTTCC | |
| | ATATCCCGCGACNAACNACNCCAGTCCGCTACGTAACCCCTCCGCGACTGTCCATGGACAACAGCGCGTTCTCCACCGACCGGGCCCGGGTGTGGGGTGTTTCGGC | |
| | GACCGGCAGCCAGGTGGTCCACACTGCCGACGGGCGCCGCGAGCCGTTCACCGACCAAGCCGCCGAACAAGTCCGCCCGATCGCATACTCCAACCGGTTGCGGTAC | |
| | TGCAGGTCAGCTGGCGTACCTCCTCNTCNCGCTGGCGAAGTCTTFGCTCANCACGTCGCAGAACGGCAAGGAACACGTTCA | |
| | ::::::::::::::Rv109T7.seq:::::::::::::: | |
| | GACCGNNCCATGTTTCCACAATGTGGTGCCAGTNCGGNGGCTACGTGCCATCNANACACTGGCGCAGGCTATCGCACCCGTTATCNGCTACGAACAAATNCGGTA | (SEQ ID NO. 21) |
| | TGCGTTCTTTANCATGAGTCGGCGACCGNCGATCATGGTCGACACCCACGACNGAAATACGCAGATCGCCNTCNAGCNTGTGTGCCGCGGATTATCANGACTGACC | |
| | TCCTGGCTGACCGGNNTGTNTGGTCGCGATGCCTGGCGCCCGGCCGGCGTGNTCGTGGTCGGCTCGGATAGCGAAGTCAGCTAATTCTCGTGGCAGCTCGAAAGGG | |
| | TCCTGCCGGTGCCGGTCTTTGCGCAAACCATGCNCATGTTACGGTCCCTCGGGTGCGGCCTGGCGGCGGC | |
| Clone Rv10 | ::::::::::::::Rv10SP6D2.seq:::::::::::::: | |
| | GGGATGGGCGGGCCCGCTAAACTCTTCGTGTTCCACTAACTCCGGGAGGGNCAATCTCGGGCCGTTATGGCTCACGTCGCGTCGCCCTCCGACCGCGAACATTCGG | (SEQ ID NO. 22) |
| | AGTTGGCAGCAACCTGGTAGCACCCTGGCCGG | |
| | ::::::::::::::Rv10T704.seq:::::::::::::: | |
| | NCCGTCGTTGACAAGTAAATATGTCCGCAAAAGTCTCAGCGGCCGACTTTGCTCGCAGGTGGCGGTACCGCGCCACCGAGTCGATGCCGTGGTCGCGGAAGAATGC | (SEQ ID NO. 23) |
| | CTCCCGAAATCGCACGGCCTTCCCNNTTTAAACGGA | |
| Clone Rv110 | ::::::::::::::Rv110SP6.seq:::::::::::::: | |
| | TTTAGGTGACACTATAGAATACTCAAGCTTTTGGTCTAGCCGGCCGAGCACGATACGGGTGTCATTGGCCACCGGCGGCGGCTGTCCGGGAAATGGCGGGTCCCG | (SEQ ID NO. 24) |
| | GTGGTTTTGCTGATGAGTGCTGAACCGTANTCGAAGTGGGCGGCGTCAGACTCCACCCANCCAGCAGGCAGCGCGAAGCTGAATCCTCCAACCGGGTTGTCNATCC | |
| | GGACAAGTTGGGGTGCGTTTGGGGCAATGACAGGTGGCNGCGGTGCGTTCGGGTCCGCCGGCGGAAGTGCTGCGTTGGGATCNCCCGCTGGGCATTCGGCNTTTT | |
| | GCGGCGGCCGGTGGTNGGGGGGCAACAGGTNTCCCNGTGCGGGTGGCGCTCAACGGTCNACGGCGCAAGCCGCCGTTGTTGGTACCNGGGGCGCTGGCTCCGGATC | |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

GCGTTGGCGGTCNCCGG
::::::::::::::Rv110T7.seq::::::::::::::
CTACACCATCGAATACGACGGCGTCGCCNACTTTCCGCGGTACCCGCTCAACTTTGTGTCGACCCTCAACGCCATTGCCGGCACCTACTACGTGCACTCCAACTAC (SEQ ID NO. 25)
TTCATCCTGACGCCGGAACAAATTGACGCAGCGGTTCCGCTGACCAATACGGTCGGTCCCACGATGACCCAGTACTACATCATTCGCACGGANAACCTGCCGCTGC
TAGAGCCACTGCGATCGGTGCCGATCGTGGGAACCCACTGGCGAACCTGGTTCAACCAAACTTGAANGTGATTGTTAACCTGGGCTACNGCGACCCGGCCTATGG
TTATTCNACCTCNCCGCCCAATGTTGCGACTCCGTTCGGGTTGTTCCCANAAGTCNNCCCGGTCGTCATCGCCGAANCTCTCNTCCCGGGACCCACAGGGAATCNG
CNATTTCNCCTACAAATCANCCACCTCCA
Clone Rv111 ::::::::::::::Rv111T7.seq::::::::::::::
GCATGATCGGCCACCTTTCGGGCCGCCCGGCATACGGCGGCGTACCGATCTCCGCGTCATACACCCGCGGGTAATCGCCGACGGTGCCGGTTCGCGAGCCGAAGGT (SEQ ID NO. 26)
GACGACTCTGATTGAATCGAGTTCCAGGTCCAGCGGGTGGCGCACCAACGGCGCGAGCTCAACGACGTCAATCNCGTTGTCGCTTTCTACGGTCACCGACCCTGGT
GACCGTAGTTCNCCCG
Clone Rv112 ::::::::::::::Rv112SP6.seq::::::::::::::
GACACTATAGAATACTCAAGCTTGCCAACCGCCAGCCTGCATCCGGCGGCGANCACTGCTCCGCCGACCAGTACGAACCAACCTGCGGTGCCCAGGCCATTGACGA (SEQ ID NO. 27)
TGTGCTGGTCGGCGCCCGCGAGTCCGCGCACCATCAACGCCGCGGGCACCACCANGGCGGCCCCACCCTGCACGGCGACGATCATTCCGGCGCCGCTCACGGCGGG
CGGGGCTCGAACANGCACAGCATCAACGTNGTCACCCGGCCGTGACCGGCCCGCATCGTCACACCACCCAAGCCCATTGCCGTCCTCCTCAACNGGGCGACCCGGC
CCGCATCGTCACACGGNCTAAGGCCATTGCCGTCCTCCT
::::::::::::::Rv112T7.seq::::::::::::::
TCGGCGCCATCGGCACCTTCGAGGACCTGTATTTCGACGCCGTGGCCNACCTGAGGTTGGCGGTGGCNAAGTGTGCACCCGGTTGATTCGCTCGGCCTTGCCGGA (SEQ ID NO. 28)
TGCCACCCNGCGCCTGGTGGTCGATCCGCNAANAGACAANTTGTGGTGGANGCTTCTGCTGCCTGCGACACCCACNCGTGGTGGCACCGGGCAGCTTTAGCTGGC
ATGTCCGACCGCGCTGGCCGACNACTCCAGACNTTCCACNAANGGTCGCONNCCCAATGTNCCGNANTGTCTCCGGNTCCCTTTACCNCCCAATGGGCNGNTTCC
ACNGGTTACGGGCCCCNTNCCGGCGGGTCTNCCTCCCAANCTACCAAATACGCCCGACNTTCCGGA
Clone Rv113 ::::::::::::::Rv113SP6.seq::::::::::::::
ATACTCAAGCTTTTATGGTGATCGCGCATCACCTGGTTCATGAACTGGAAGCAGCGCAGCGCTTCCTTTTCGGCCGCAACATGAGCCAGCCTCTCGTCGGCGGTCG (SEQ ID NO. 29)
GGTGCAGGTCTCGGGCAGCTCGGCCGCGAACAGCCCGGCTTGAACCCTGAAAACCNGCTTTCCATATCCCGCGACGAAAGAACGCCAGTTCCGCTACTTAACCCC
TCCGCGAACCGTCCATGGACAACAGCGCGTTCTCCACCAACCGGGCCCGGGTGT
::::::::::::::Rv113T7.seq::::::::::::::
TCGGCTCAGGCCGCGCTGCTGGTAGAGTCGCTGACCGGTGCAGGTTTCGACAATGTGGTGCCGGTTCGGCGGCTACGTGCCATCGAGACACTGGCGCAGGCTATCG (SEQ ID NO. 30)
CACCCGTTATCGGCTACGAAGCAAATCGCGGTATGCGTTCTTGAGCATGAGTCGGCGACCGTCGTCATGGTCGACACCCACGACGGAAAGACGCAGATCGCCGTCA
AGCATGTGTGCCGCGGATTATCAGGACTGACCTCCTGGCTGACCGGCATGTTTGGTCGCGATGCCTGGCGCCCGGCCGGCGTGGTCGTGGTCGGCTCGGATAGCGA
GGTCAGCGAATTCTCGTGGCAGCTCGAAAGGGTCCTGCCGGTGCCGGTCTTTGCGCAAACAATAGCGCAGGTTACGGTCGCGCGGGGTGCGGCCTGGCGGCGGCC
Clone Rv114 ::::::::::::::Rv114SP6.seq::::::::::::::
CAAGCTATTTAGGTGACACTATAGAATACTCAAGCTTCGCGTCTACGCCGGCCCGGAGCATCCGCACAGCGCTCAGCAGCCGGTTCCGTACGANCTCAAGCAGGTG (SEQ ID NO. 31)
GCGCAATGACCGAAACCACCCCAGCCCCGCAAACCCCGGCGGCCCCGGCCGGGCCCGCACAATCGTTCGTGTTGGAGCGGCCCATCCANACCGTTGGGCGCCGTAA
GGANGCCGTGGTACGAATGCGGCTGGTGCCCGGCACCGGCAAGTTCGACCTCAACGGCCGCAGCTTGGANGACTACTTCCCAAACAAGGTGCACCAGCAGTTGATC
AAGGCACCCCTGGTCACCGTGGATCGGGTGGAAAGTTTCGACATCTTTGCCCACCTGGGCGGCGGCGGCCGTCCGGTCAGGCCGGGCCTGCCCTGGGTATCGCCCG
GGCATTGATTCTGGTATCCCCNGAAGAACCG
::::::::::::::Rv114T7.seq::::::::::::::
CGGTTGGCCACCGCTTCTGCGGTGCCGCCGCCGTCGACAATGACCGTGTCGTCCTTGCTGACCACCACGCGTCGGGCCCGAGCCCAGCACCTCCAAGCCCACCTCGC (SEQ ID NO. 32)
GCAGCACCATGCCGGCGTCGGGGTTGACCACCTGGCCACCCGTCACCACCGCCAGGTCCTCAAGGAAACGCTTACGGCGGTCACCGAAGTACGGCCCCTTGACCG
CGACCGCTTTCAACGTCTTGCGAATCGCGTTGACGACCAGCGTCGCCAACG TTCGCCCTCCACGTCTTCAGCCACGATCAGTAGTGGCTTACCGTTCCTGCAAC
CTTTTCCAGCAATGGCAACAGATCGGGAAGCGANCTGATCTTGTCTTGGTGCN
Clone Rv115 ::::::::::::::Rv115SP6.seq::::::::::::::
CCAAGCTATTTAGGTGACACTATAGAATACTCAAGCTTTTGGCTGGGTCGCCTTCGAATTCNGCGTGCACCGCTATGGGTTGCANCAGCGGCTGGCGCCGCACACC (SEQ ID NO. 33)
CCACTGGCCCGGGTGTTTTCGCCCCGAACCCGATCATGGTGAGCGAAAAGGANATTCNCCTGTTCGATGCTGGGATTCGCCACGCCAAGGCATCTANCGATTACT TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | CTCCNCGGGGTGGGAAAAGTGCCCAATCCCCTCCCTCCAACTTTCCNAACAATCATTCCGGTTCCNCCNTCCGGTTGGNGGTAACCNNCCAATAAAACCCCTGCC | |
| | CG | |
| | ::::::::::::::Rv115T7.seq:::::::::::::: | |
| | GCCCGCNCATGGCCAATCCCCGAAGACATCATTGGCCAGTGGCCGGGCGCTAACAGGTTCCAGCCCCCCACCANTGCCGCTCGAACATGCGGTGCAACCCATTCGC | (SEQ ID NO. 34) |
| | AGGCCGGCAGGGAAAGCACCGCGGAAGCCGCAAAGGGCTGCAGTTCCGCGCCCAATAATGTCGTCCGCAACCAGATGCGCTCNAAAACCNCNCCGGCAGTCAGCGC | |
| | ACCCGACGCGANGTCGAAAGACGTCNTCAGCGCGCCCACATGGGGTGCCAATCGGCACGGCAGGTATGCCGCGCGCAACCCGAGCGCGTGGTGCATGCCCACGGTC | |
| | CGCANGANGCGCANCACCCGCCAATGCCGAANCCCACGAAACATCGGGCGCATCCACCTTCAACC | |
| Clone Rv116 | ::::::::::::::Rv116SP6.seq:::::::::::::: | |
| | ATACTCAAGCTTGCCCAGCCGTCGATGACAAGAAATATGTCCGCAAAAGACTCAGCGGCCGACTTTGCTCGCAGCTGGCGGTACCGCGCCACCGAGTCGATGCCGT | (SEQ ID NO. 35) |
| | GGTCGCGGAAGAATGCCTCCCGAATTCGCACGGCCAATTCCATTCCGGGAAGCATCCGCAATGCCAGCTGCGGTTGCCCCCTGCCGGCCACGGCACCCACTTGCGG | |
| | CATTGCGTCCACCTGGGCCAGCGCCCCGCCGCCAAATTCCAAACAATAAAAATTGCACCCGGC | |
| | ::::::::::::::Rv116T7.seq:::::::::::::: | |
| | CCACCCGTGTATTTTGGGATGGGCAAAAAGGCGAAGCACCGCGTGGCCACGAACGCCGGGAGGGACAATCTCGGGCGGCTAGGGCTTCTCGCGGGAAGGCCCGAAC | (SEQ ID NO. 36) |
| | GTACGGCGTTTCAACACGTCGCGTCGCCCTCCGACCGCGAACATTCGGGGATGGCAGCAACCTGGTAGCACCCTGGCCGGGCGATGATCTGCAGCGTCGCCGCGGG | |
| | TAGTCGCCGCCCGGGCGGCTACAGTCTGAAACGCGATGACCATCGATGTGTGGATGCAGCATCCGACGCAACGGTTCCTACACGGCGATATGTTCGCCTCCCTGCC | |
| | CCGT | |
| Clone Rv117 | ::::::::::::::Rv117SP602.seq:::::::::::::: | |
| | CTGCCCATGTTTGGGGACGCCCGACCAGCCGATGCTGGAGGCCTACACGGCCCTTGGTGCGCTGGCCACGGCGACCGAGCGGCTGCAACTGGGCGCGTTGGTGACC | (SEQ ID NO. 37) |
| | GGCAATACCTACCGCAGCCNGACCCCTNTCNCAANAGGATNTTGTTCGCCGGACCCCNCTC | |
| | ::::::::::::::Rv117T704.seq:::::::::::::: | |
| | CCGACTTTCCGCGGTACCCGCTCAACTTTGTGTCGACCCTCAACGCCATTGCCGGCACCTACTACGTGCACTCCAACTACTTCATCCTGACGCCGGAACAAATTGA | (SEQ ID NO. 38) |
| | CGCAGCGGTTCCGCTGACCAATACGGTCGGTCCCACGATGACCCAGTACTACATCATTCGCACGGAGAACCTGCCGCTGCTAGAGCCACTGCGATCGGTGCCGATC | |
| | GTGGGGAACCCACTGGCGAACCTGGTTCAACCAAACTTGAAGGTGATTGTTAACCTGGGCTACGCGACCGCCTTT | |
| Clone Rv118 | ::::::::::::::Rv118SP6.seq:::::::::::::: | |
| | ATACTCAAGCTTTGTCACACCAAGTGTTTCGACCAGGCGCTCCATCCGGCGAGTGGATACTCCCAGCAGGTAGCAGGTCGCCACCACGCTGGTCAGTGCGCGTTCA | (SEQ ID NO. 39) |
| | GCTCGCTTGCGGCGCTGCAGCAGCCATTCGGGGAAATACCTGCCCTGGCGCAGCTGGGGGATCCCAACTTCAATGGTTGCGGCACGGGTGCTAAATTCACGGTGGC | |
| | GGTAGCCGTTGCCCTAATTGGACCGCTCATCGCTGCTTTCGCGGTACCCCGCCCCGCACAGGGCTTCGGCTTCAGCCCCCATCAGGGCGGCAATAAACTTCAAGAG | |
| | CACC | |
| | ::::::::::::::Rv118T7.seq:::::::::::::: | |
| | GAGGCAGCTTCGCCGGCAATTCTACTAGCGAGAAGTCTGGCCCGATACGGATCTGACCGAAGTCGCTGCGGTGCAGCCCACCCTCATTGGCGATGGCGCCGACGAT | (SEQ ID NO. 40) |
| | GGCGCCTGGACCGATCTTGTGCCGCTTGCCGACGGCGACGCGGTAGGTGGTCAAGTCCGGTCTACGCTTGGGCCTTTGCGGACGGTCCCGACGCTGGTCGCGGTTG | |
| | CGCCCGCGAAAGCGGCGGGTCGGGTGCCATCAGGAATGCCTCACCGCCGGCGGCATGCACGGCCAGTGCCGCGGCGATGTCAGCCTCGGGACATCATGCTCGCGTT | |
| | CATACTCCTCGACCAGTCGGCGGAACAGCTCGATTCCCGGACCGCCCAGCGCATTGGTGATGGAATCGGCGAACTTGGCCACCCGCTGGGTGTTGACATCCTCGAC | |
| | GGTGGGCAATTGGCCTCGGTAAGCTTTGCCGCGTAGCTTTTCATC | |
| Clone Rv119 | ::::::::::::::Rv119SP6.seq:::::::::::::: | |
| | ATACTCAAGCTTCACTGACAAGGGACGAATTCGTCGGCCGCCTGTTCGACTGGGTGGTGGCCGAGCTGGTCGCCACCACTCAGGCCGCGGTCACGGCGGTACCGGC | (SEQ ID NO. 41) |
| | GCGGGAGCAAACTCGCGCGGGCATGGCCAACTTCTTGCGGACCATCACCGCAGACGCCCGCTTCGGACCCCTGCTGTCCACCACACAGTTGGCCAACGCATTAATC | |
| | ACCCGCAAGCTTGCGGAATCCACCGCCCTGTTCGC | |
| | ::::::::::::::Rv119T7.seq:::::::::::::: | |
| | TCCATCACCCGATGTGGCNGGAGCACTGCCATGTCGATCTCAACTACCACCTCCGGCCGTGGCGGTTGCGCGCCCCGGGGGGTCCGCGCGAACTCGACGAGGCGGT | (SEQ ID NO. 42) |
| | CGGAGAAATCGCCANCACCCCGCTGAACCGCGACCACCCGCTGTGGGAGATGTACTTCGTTGAGGGGCTTGCCAACCACCGGATCGCGGTGGTTGCCAAAATTCAC | |
| | CATGCGTTGGCTGACGGTGTTGCCTCGGAAACATGATGGCACGGGGGATGGATCTGCCGCCGGGACCGGAGGTCGGCCGCTATGTGCCTGACCCCGCTCCTACCA | |
| | AGCGGCA | |
| Clone Rv11 | ::::::::::::::Rv11SP6.seq:::::::::::::: | |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | AGCTTTGCAGTTGCTGAGTAATGTCGGCCAACGTCACCACAACCGCGATGAATTCAATCATGCCGCCCAGGGCGGCCAACCAATGGTGGCCGCGAGCGGCAGCTC | (SEQ ID NO. 43) |
| | GATCGCAGCGCGGAGGTTGCCGGCCGCCAGTTGATTCACGAACAGGGTGAGGTCATAGGCGGGCAGGATAGTGACGAAGGCAAGACCTCCATCTGCCGTCGGAAGA | |
| | AGTATCGAG | |
| | ::::::::::::::Rv11T7.seq:::::::::::::: | |
| | AGCTTCAGAACAGGCCTGTTGTGGGCGCACCCGGCTCGCCGAGTTCTGCACGCACCGCCTCAAGTGCGGCCCGCACCGCCGGCATCTCCCGGTCACGCAGGGCCGC | (SEQ ID NO. 44) |
| | GGCCCGCGCCGCAGCGACGGCGTGTTCGCGCAGTTCGCCGTCAATGATGCTGACCTGATCGGCCACCCGGGCGTTCTCGGCGTCGTCGCGTTCACTAATCGCGGTG | |
| | CTCAGCAGCGTCTCGACAGCCACCACCCGAGTGGCGACCAGCTGCTCCACCACGGACCGAGCGATGCCCGTC | |
| Clone Rv120 | ::::::::::::::Rv120SP6.seq:::::::::::::: | |
| | ATACTCAAGCTTCAGTTCCTCCACGACGCGTTCCCAAATGAATTTCCCGATCCCACAATCTCGGTTCAGATACAGGTCGCCATACCCCTTACTTCGGCAACGCTGG | (SEQ ID NO. 45) |
| | GCGGATTGGCCCTGCCGCTGCACCAAACCATCAACGCCTTCAAATTGCCGGCAATCTCGTTCAGCCAATCCAT | |
| | ::::::::::::::Rv120T7.seq:::::::::::::: | |
| | GCTCTACGCCGCCTACGGGTCGAACATGCATCCCGAGCAGATGCTCGAGCGCGCACCCCACTCGCCGATGGCCCGGAACCGGCTGGTTACCGGGTGGCGGCTGACG | (SEQ ID NO. 46) |
| | TTCGGCGGCGAGGACATCNGCTGGGAAGGGGCGCTTGCCACCGTCGTCNAAGACCCAAATTCGAAGGTGTTCGTCGTGCTCTACGACATGACCCCGGCGGACGAGA | |
| | AGAACTTGACCGGTGGGAAGGCTCCGAGTTCGGTATCCACCAGAAGATCCGATGCCGCGTGGAGCGCATTTCCTCGGACACCACAACGGGATCCCGTCCTCG | |
| Clone Rv121 | ::::::::::::::Rv121SP6.seq:::::::::::::: | |
| | ATACTCAAGCTTGCCAAAGAGACCTCGTCCACCAAGCAGGACGCGACCGTCGAGGTGGCGATCCGGCTTGGCGTCGACCCGCGTAAGGCAAACCAGATGGTTCGCG | (SEQ ID NO. 47) |
| | GCACGGTCAACCTGCCCACACCGGCACTGGTTAAGAACTGCCCGCGTCGCGGTTTTCGCGGTTGGTGAAAAGGCCAATGCCTGCGTTTGCCGTGGGGGCGGATGTT | |
| | GTCGGGAGTGACAATCTGATCAAAAGGATTCAGGGCGGTTGGCTGGAATTCAATGCCGCAATCGCGACACCGG | |
| | ::::::::::::::Rv121T7.seq:::::::::::::: | |
| | CCACGGCGTGGATCAAGGTACCGGCCGGGATGTTGCGCAATGGCAGGTTGTTGCCCGGCTTGATGTCGGCGTTAGCGCCGGATTCCACCACATCCCCTTGCGAAAG | (SEQ ID NO. 48) |
| | TCCGTTGGGTGCAATGATGTAGCGCTTCTCCCCATCGAGATAGTGGAGCAACGCAATCCGTGCGGTACGGTTCGGGTCGTACTCGATGTGCGCGACCTTGGCGTTG | |
| | ACACCATCTTTGTCATTGCGGCGAAAGTCGATCATCCGGTAAGCGCGCTTATGACCGCCGCCTTTGTGCCGGGTGGTAATCCGGCCATGCGCGTTGCGTCCACCGC | |
| | GACGTGCAGCGGGGCGCACCAGCGACTTCTCCGGGGTTGACCGGGTNATCT | |
| Clone Rv122 | ::::::::::::::Rv122SP602.seq:::::::::::::: | |
| | GCAGCATGACGGCGGTAGCGAACACCGCCGGATGCAGCGCAAGTAGCGTCGATGTGCTCACGGAATCGCCCCGGCACCGCGATCTCGANGATCACCAGTGCCACCC | (SEQ ID NO. 49) |
| | CCTGCAGCGCNACACCGACGATTCCGTACACCGCCACGCCGATCAGGCCCTGGGCCATCTGATTGGAGCTGGCGTANATGGCGGCGATGGTGACGATGGCCAGCGC | |
| | CACATACATTGTGGCGGCCAGAACCACGGCGTTGGGGCGGCGGTCGATGAACACTAGGCGACGCAGATCGCCCGGGGTCAACAGGTTGACCATCAGAAAGCCTGCG | |
| | ACTAGCACGGCGGCGCCACTAGGAGGTACAAGAANGTGGCCACCACCCCATGCAGGATCGGGGTAAGGCTGATGGTCCCGAAATCGACTCCGGCCTAATACATGAC | |
| | TCTCTCCTTTGCGTCATCGCCTTACTTGTGCGCGGAA | |
| Clone Rv | | |
| | ::::::::::::::Rv123SP602.seq:::::::::::::: | |
| | GGGACACACCTCGATGCTGCCGCNATGGACGCGGTCGAACGCAAGCAGCTGATCGAGCTACAACGCCGCGCGGAACGCTTCCGCCGCGGGCGTGACGCATCCCGTT | (SEQ ID NO. 50) |
| | GACCGGCCGGANCNCTCTCTA | |
| | ::::::::::::::Rv123T704.seq:::::::::::::: | |
| | TGGGCGCCTCTTTCGGCCTTCCCNNTTTAAACGNAGCANGACATTCTGGGTATCGAGTTGTACTGGATGGTGTTGGCGATGTCGGTGATCCTGCTCCTGGCGGTGG | (SEQ ID NO. 51) |
| | GATCCGACTACAATCTGCTGCTGATTTCCCGGTTGAAAGAGGAAATTGGGGCCGGATTGAACACCGGAATTATCCGTGCCATGGCTGGTACCGGGGGAGTGGTGAC | |
| | GGCTGCCGGCATGGTGTTCGCCGTTACCATGTCGTTGTTTGTGTTCAGGATTTGCGAATTATTGGTCAGATCGGTACCACCATCGCCTTCCC | |
| Clone Rv124 | ::::::::::::::Rv124SP602.seq:::::::::::::: | |
| | CCGATCGGCGCCGCANCTGGTTGGTGTTNCGGATGAATCGCAGCGAAAATGTAGCTGCGGTGGCGTGTCGTGACTCGTNGGCGTCGACGCTCGTGGCAGCCACCG | (SEQ ID NO. 52) |
| | ANCGGTTGGTCCAGGATCTGGATGGGCAAAGTTGTGCGGCCCGGCCGGTGACGGCCGATGAGCTGACCGAGGTCGACAGCGCCGTGTTGGCTGACTTGGAACCGAC | |
| | ATGGAGTCGCCCCGGTTGGCGTCACCTCAAGCATTTCAATGGTTATGCGACCAGTTTTTGGGTTACGCCGTCAGACATCACGTCGGAGCTTGGATGAGCTGTGTC | |
| | TGCCAGATAGCCCCGAATCGGGACGACCGTGGTCACGGTGCGTCTGACCACTCGGGTCGGGTCGCCCGCGCTATCGGCATGGGTGCGTNATCACAGCGACACGCGC | |
| | CTGCCCAAGGANGTNCGGNCGGACC | |
| | ::::::::::::::Rv124T7D4.seq:::::::::::::: | |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | CGGGTTGCGGATCCACGCGTGCGGGTTGTCAGCAGCTACGGCACTGAACCGCGCCCACAGCTCGCCGATCCGCTTTCGGTGGTTCTCGATCGACTCGCCGTAGGCG | (SEQ ID NO. 53) |
| | ATGCGCAGCGCCTGCTCGAATATCGGGTACACGTAGGCCGGCTTCCCNCTTTA | |
| Clone Rv126 | ::::::::::::::Rv126SP6.seq:::::::::::::: | |
| | CTTGATTTTGATCATCATGACGATCATCACCCTAATTTTGCTACCCGCACTGGTTATCGTGGGTACCGTCGTGCTTTCCATGGGCGCCTCGGTCGGGCTTTCCGTA | (SEQ ID NO. 54) |
| | TTGGTCTGGCAGGACATTCTGGGTATCGATTTGTACTGGATGGTGTTGGCGATGTCGGTGATCCTGCTCCTGGCGGTGGATCCGACTACAATCTGCTGCTGATTT | |
| | CCCGGTTGAAAAAGGAGATTGGGGCGATTGAACACCGGAATTATCCGTGCCATGGCTGGTACCGGGGCAGTGGTGACGGCTGCCGCATGGTGT | |
| | ::::::::::::::Rv126T7.seq:::::::::::::: | |
| | GGGGATCCCTAGATCGACCTGCAGGCATGCAAGCTTGGCGTGTCGTTCCAACCCGAATTGGCTTTCGGCGCCATCGGTGAGGCGGGACCCACCTCGATGCTGCCGC | (SEQ ID NO. 55) |
| | CATGGACGCGGTCGAACGCAAGCAGCTGATCGAGCTACAACGCCGCGCGGAACGCTTCCGCCGCGGGCGTGACCGCATCCCGTTGACCGGGCGGATCGCGGTGATC | |
| | GTCGATGACGGCATCGCCACCGGAGCNACTGTCAAGGCGGCGTGCCAGGTCGCCCGGGCGCACGGTGCGGACAAGGTGGTGCTGGCGGTCCCGATCGGCCCAGACG | |
| | ACATCGTGGCGAGATTCGNGGGGTACGCCGATGAGGTGGTGTGTTTGGCGACGCCGGCGTNGTTCTTCGCCGNCGGGCANGGTTACCGCAACTTCACCCAGACCTC | |
| | CGACGACGAGGTGGTGGCGTCTCTCCTGGATCGTGCTC | |
| Clone Rvl27 | ::::::::::::::Rv127SP6.seq:::::::::::::: | |
| | AAGGCTGCAGGTCGAAGCGGNTGGTTACGACTCCCTGTGTGTGATGGACCAGTTCTACTATCTGCGTCTACACGGCCTTGGTGCGCTGGCCACGGCGACCGAGCG | (SEQ ID NO. 56) |
| | GCTGCAACTGGGCGCGTTGGTGACCGGCAATACCTACCGCAGCCCCGACCCTGCTGGCAAAGATNATCACCACGCTCGACGTGGTTAGCGCCGGTCGAGCGATCCT | |
| | CGGCATTGGAGCCGGCGGGTTTGAACTGGAACACCGCCAGCTCGGCTTCGAGTCCGGCACTTCCAGTGACCGGTTCAACCGGCTCGA | |
| | ::::::::::::::Rv127T.seq:::::::::::::: | |
| | CTTTCCGCGGTACCCGCTCAACTTTGTGTCGACCCTCAACGCCATTGCCGGCACCTACTACGTGCACTCCAACTACTTCATCCTGACGCCGGAACAAATTGACGCN | (SEQ ID NO. 57) |
| | GCGGTTCCGCTGACCAATACGGTCGGTCCCACGATGACCCAGTACTACATCATTCGCACGGAGAACCTGCCGCTGCTACAGCCACTGCGATCGGTGCCGATCGTGG | |
| | GGAACCCACTGGCGAACCTGGTTCAACCAAACTTGAAGGTGATTGTTAACCTGGGCTACGGCGACCCGGCCTATGGTTATTCGACCTCGccGNcCAATGTTGCGAC | |
| | TCCGTTCGGGTTGTTCCAGAAGTCAGCCCGCTCGTCATCGCGGACGCTCTCGTCN | |
| Clone Rv128 | ::::::::::::::Rv128SP6.seq:::::::::::::: | |
| | CGGTCATAGCCCTCGGGTCCGGCCAGCACTCCGCAGCCTTCGTCGGGGTGGTCGCGACGCGCATGGGCCACCATCGCATTCACCAGGTCTGCGCGAATCACCAGCA | (SEQ ID NO. 58) |
| | CGTAGACGGTTCCTTTCCTAAGCAACACCGAAGTTTCACGACCCGAATGCTCCGGGAAACATGTCACGGTAGGTCGGTATTCCGGCTACCGGCTGAGCATTGAGCA | |
| | CGCCGGCCAGCACCGCACGAGCCAGGCAATCAGCCGCCGCCGCACCGATCGCGGTGACCAGCTGAGTCTCCGGAGACAATGCGGCCGGCACGCCGGNCTCCGGCGG | |
| | CACCGCTACNGCGCCCGTGG | |
| | ::::::::::::::Rv128T7.seq:::::::::::::: | |
| | GTGATGGCACGCCACCGCGACACCACCCGGCTGCGCTACNTCGAGCCATACCGGGCGGAGCTACATCGGCTCGGCCGCCCAGTGTTCGGGCCCTCTTTCGAGGTCG | (SEQ ID NO. 59) |
| | AGGTCGATACCGATTTGCGCATCCGCANCCGCNCCCTGGACGACAGAACCGTGCCCTACGAGTGCTTGTCGGGCGGGGCCAAAGAACAGCTTGGCATCCTGGCGCG | |
| | ATTGGCCGGCGCGGCGCTGGTCGCCAAGGACGACGCCGTTCCGGTGCTGATCGACGACGCGCTGGGGTTCACCGATCCGGAGCCACTATCAAGATGGGGGAGGTCT | |
| | CTGACACCATCGGCCCCGACGGACATGTGATCGTGCCGACGTGCAGTCCCACCCCG | |
| Clone Rv129 | ::::::::::::::Rv129SP6.seq:::::::::::::: | |
| | GCGAAAGTCCGTTGGGTGCAATGATGTAGCGCTTCTCCCCATCGAGATAGTGGAGCAACGCAATCCGTGCGGTACGGTTCGGGTCGTACTCGATGTGCGCGACCTT | (SEQ ID NO. 60) |
| | GGCGTTGACACCATCTTTGTCATTGCGGCGAAAGTCGATCATCCGGTNNGCGCGCTTATGACCGCCGCCTTTGTGCCGGGTGGTAATCCGGCCATGCGCGTTGCGT | |
| | CCACCGCGACCGTGCAGCGGGCGCACCAGCGACTTCTCCGGGGTTGACCGGGTGATCTCGGCGAAATCAGATACGCTGGCGCCGCGACGACCAGGCGTCGTGGGCT | |
| | TGTNCTTGCGAATTGNCATGTCTAATCANGTCTTTCTCTCACGCTCTCGTCGCCGGGCTAGGCCGCATTGCCCTGCTCCTCCTCATCGCTTCGCTCTGCATCGTCC | |
| | CCGGGCTAAGCCGTGCCCCGAAA | |
| | ::::::::::::::Rv129T7.seq:::::::::::::: | |
| | GATGGTTCGCGGCACGGTCAACCTGCCACACGGCACTGTGTAAGACTGCCCAGCGTCGCGGTATTCGCGGTTGGTGAAAGGCCGATGCTGCCGTTGCCGCGGGGGCG | (SEQ ID NO. 61) |
| | GATGTTGTCGGGAGTGACGATCTGATCGAGAGGATTCAGGGCGGCTGGCTGGAATTCGATGCCGCGATCGCGAACACCGGATCAGAATGGCCAAAGTCGGTCGCAT | |
| | CGCTCGGGTGCTGGGTCCGCGCGGCCTGATGCCCAACCCGAAACCGGCACCGTCACCGCCGACTCCCCATGGCGTCCCGGATATCAAGGGCCGGCAAATCAACTT | |
| | CCCGGTTGATCAGCAAGGCAACCTGCCTCCNCCTCCGG | |
| Clone Rv130 | ::::::::::::::Rv130SP6.seq:::::::::::::: | |
| | ATACTCAAGCTTCGTCATAAGACCATGGTGCGCTTTCTTTCACCCGTCCAGAGTCGGGGGCATCGGCACCGGCTCGCATCGCATCATCCTCCCACGACGGGCCCT | (SEQ ID NO. 62) |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

CATCAGCTTGGGCCATTTCAATGTACTTGATACCCCGCGCTGCGGGTAGGCCACTGCGACAATTCAAACACGGTGTCACACGGTGAATAGTGTCGAGATGGGCTCT
GATCAACCGTCGCAAACCCGGTTTCGCATCAATAGCGGAATCCCACCGGGTTGCATGGAGGCTGCTGACCTTGGAAAACAAAATTTTTTCATTACAACAAAACAAC
CGCCNCGGAAACTTTGCA
::::::::::::::Rv130T7.seq::::::::::::::
CGAATTCGGCGTGCACCGCTATGGGTTGCAGCAGCGGCTGGCGCCGCACACCCCACTGGCCCGGGTGTTTTCGCCCCGAACCCGGATCATGGTGAGCGAAAAGGAG (SEQ ID NO. 63)
ATTCGCCTGTTCGATGCTGGGATTCGCCACCGCGAGGCCATCGACCGATTACTCGCCACCGGGGTGCGAGAGGTGCCGCAGTCCCGCTCCGTCGACGTCTCCGACG
ATCCATCCGGCTTCCGCCGTCGGGTGGCGGTAGCCGTCGATGAAATCGCTGCCGGCCGCTACCTGCAAGGTGATTCTGTCCCGTTGTGTCGAAGTGCCTTTCGCGA
TCGACTTTCCGTTGACCTACCGGCTGGGGCGTCGGCACAACACCCCGGTGAGGTCGTTTTTGTTGCAGTTGGGCGGAATCCGTGCTCTGGGTTACAGCCCCGAACT
CGTCACGGCGGTGCGCGCCGACGGAGTTGTTATCACCGATCCGTTGGCCGTACCGCGCCTTGGGC
Clone Rv132 ::::::::::::::Rv132SP6.seq::::::::::::::
TCAGACTCCACCCAGCCAGCAGGCAGCGCGAAGCTGAATCCTCCAACCGGGTTGTCGATCCGGACAGGTTGGGGTGCGTTTGGGGCAATGACAGGTGGCGGCGGTG (SEQ ID NO. 64)
CGTTCGGGTCGGCCGGCGGAGGTGCTGCGTTGGGATCGCCCGGCTGGGCATTCNGCGTGTTGGCGGCGGCCGGTGGTGGGGGGCAACAGGTGTCGCCGGTGCGGG
TGGCGCTGCAGCCGTCGACGGCGGCGAAGCGGCCGTTGTGGGTACCGGGGGCGCTGGCTCCGGATCGGCGTTGGCGGTCGCGGGCACCGCAACGGTCACCAAGCTG
GCGCTGGCCATCGCCGCGATAGCCAGTGCCGCCAATCGTCCCTTGCGACGTGTCAAGTNGGGGTCCACCTGATGCATGGCCAAAGAACCTACCGTGTTAACGGCGC
AACNCAAGGACCGCGCCGGTCGCN
::::::::::::::Rv132T7.seq::::::::::::::
TTTCCGCGGTACCCGCTCAACTTTGTGTCNACCCTCAACGCCATTGCCGGCACCTACTACGTNCACTCCAACTACTTCATCCTGACGCCGGAACAAATTGACGCAG (SEQ ID NO. 65)
CGGGTCCGCTGAACAATTCGGTCCGTCCCACGAAAGAACCAGTTTTNCNCTCTTTCNCACGGAGAACCTGCCGCTGCTAGAGCCACTGCGATCGGTGCCGATCGTGG
GGAACCCACTGGCGAACCTGTGTTTCAACCAACACTTAGAGTGTAATTGTAAACCTGGGCTAGGGGAAACCGGCTCTAGTTTTTCCACCNTCTCCGCCCCNTGTTT
CGAATACTCCGTTCGGGTTGTCCCCAAA
Clone Rv134 ::::::::::::::Rv134SP6.seq::::::::::::::
GCTTCCGGCTCGTATGTTGTGTGGAATTGTGACCCGATACCAATTTCACACAGGAAACAGCTATGACCATGATTACGCCAAGCTAGTTAGGTGACACTATACAATA (SEQ ID NO. 66)
CTCAAGCTTGCCGGCTGGTGGGCCGACCACTTCGATGGCACGACCCGTGAACTGCTGCCCGGCCAATTCTTCTTGGTCGCCCGGACCGATGGACCGGGGCTGGGAT
TCCAGAAGGTGCCCGATCCCCTGGGAAAAACCGCGTGCACCTCTACTTCACGACCAACGAC
::::::::::::::Rv134T7.seq::::::::::::::
CCGATCGACTGATGCGCCGACAACCACGCCCCAACAACTGGAATGAACCGTCGTGACCATCATCAGCACGGGGTTGTAGGCGACTTGCGACATGTTCAACCCGCCG (SEQ ID NO. 67)
TACTCGGACGGAATCTTCAAACCGAAACAGCCCAGCTCGGCCAGGCCTTTCACGTACTCGTCGGGGATCTGGGCACCACGCTCGAGGACGCTGCCGTCCACGGTGT
CTAGGAATTCCCGCAGTTTGACCAGAAACGCCTCGGTTCGGGCCTCCTCGGCGTCCGACGGCTTGGGAAATGGGTGTATGAGCCCTACGGGAAACCGGCCCACAAA
GAGTTCTTTGGCGAAGGACGGTTTATCCCAACCACTTTCGCGAGATTCCTCGGCAAGGGCCCGCGCTTGCTCCTCGGTGACCTGAGTTTGCTGTGCCATCGCCGCC
TCCTCCCTGA
Clone Rv135 ::::::::::::::Rv135SP6.seq::::::::::::::
TGCATCCGGCTCGTATGTTGTGTGGAATTGTGAGCGGATAACAATTTCACACAGGAAACAGCTATGACCATGATTACGCCAAGCTATTTAGGTGACACTATAGAAT (SEQ ID NO. 68)
ACTCAAGCTTTTACGGTGATCGCGCATCACCTGGTTCATGAACTGGAAGCAGCGCAGCGCTTCCTTTTCGGCCGCAACATGAGCCAGCCTCTCGTCGGCGGTCGGG
TGCAGGTGCTCGGGCAGCTCGGCCGCGACAGCCGCCTGACCCTGAAACCAGCTTCCATATCCCGCGACGAACGACGCCAGTCCGCTACGTAACCCCTCCGCGACTG
TCCATGGACAACAGCGCGTTCTCCACCGACCGGGCCCGGGTGTGGGGTGTTTCGGCGACCGGCAGCCAGGTGGTCCACACTGCCGACGGGCGCCGCGAGCCGTTCA
CCGACCAGGCCGCCGAGCAAGTCCGCCCGATCGCATACTCC
::::::::::::::Rv135T7.seq::::::::::::::
GGGGGCGCTGCrGGTATAGTCGCTGACCGGTGCAGGTTTCGACAATGTGGTGCCGGTTCGGCGGCTACGTGCCATCGAGACACTGGCGCAGGCTATCGCACCCGTT (SEQ ID NO. 69)
ATCGGCTACGAGCAAATCGCGGTATGCGTTCTTGAGCATGAGTCGGCGACCGTCGTCATGGTCGACACCCACGACGGAAAGACGCAGATCGCCGTCAAGCATGTGT
GCCGCGGATTATCAGGACTGACCTCCTGGCTGACCGGCATGTTTGGTCGCGATGCCTGGCGCCCGGCCGGCGTGGTCGTGGTCGGCTCGGATAGCGAGGTCAGCGA
ATTCTCGTGGCAGCTCGAAAGGGTCCTGCCGGTGCCGGTCTTTGCGCAAACGATGGCGCAGGTTACGGTCGCGCGGGGTGCGGCCTGGCGGCGGCCAGAGCACGAG
TTCACCGATGCGCAGCTAGTGGCGACAGCGTCAGCCAAC
Clone Rv136 ::::::::::::::Rv136SP.seq::::::::::::::
TGCTTCCGGCTCGTATGTTGTGTGGAATTGTGAGCGGATAACAATTTCACACAGGAAACAGCTATGACCATGATTACGCCAAGCTATTTAGGTGACACTATAGAAT (SEQ ID NO. 70)

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | ACTCAAGCTTCCGTACAGGTCGCCTCCAACACGGCGGGGAAGCGACACCAGCCTACCGAGCTTGGAGTCCAGGACGCCAGCGGCGGCGTCGGTCTGCGTCGTGGTG | |
| | CCGCCGGGGTGGCGTTGGCTGGCAACGATCTCCACCCAGCCGGTCGGGTTACCCACGATCTCGGCATAGACGoGGGCCGAGGCCGGTGCGATACCGTATTGCGTCA | |
| | ATTGGGACGCGGTTGTGCATTCGGCTAGCTCGGTTGCCACACCCGTCAGGGGTTCGACGTTGGCGGGTTCGGCGGGCCCCAGCACCGCTGTCACCATGCCCGCCAA | |
| | GCCGACCTGCGGCGCCACCAACT | |
| | ::::::::::::::Rv136T7.seq::::::::::::: | |
| | CGGCATGACCACCGACAGGCCCGACTGGTCGTACCACTCGAACGCCGGGGTGTTGATGTCCCAGCCGCTGAAGTCGTCCTGCGCGCGCAGGCCGTCGAGCAGGTAC | (SEQ ID NO. 71) |
| | AGGGCGGGCGAGTTGGCACCACCACTTTGGAATTGGACCTTATGTCACGGCICCATCGACGGCGACGGCACCTGCAGGTACTCCACCGGCAAGCCCGGCGGGGAAA | |
| | ACGAACCCTGTCAACAAGCTGCATTCTTGCTTCCCTCATCCTCATCTCAACGCATCCATGCATGTTTGGGCGCATCCTGAATTANGTCAGACTGCAGGCGCTGGGC | |
| | CGGCAGTGCTCGTGTATCAACCACAACTTGGGGCGT | |
| Clone Rv137 | ::::::::::::::Rv137SP6.seq::::::::::::: | |
| | TTCCAACCCTAATTGGCTTTCGGCCCCATCCGTGAGGACGGGGTGCGGGTGCTCAACAACAACGTCGTCCGCGGGACACACCTCTATGCTGCCGCCATGGACGCGG | (SEQ ID NO. 72) |
| | TCCAACGCAAGCAGCTGATCGAGCTACAACCCCGCGCGGAACGCTTCCGCCGCGGGCGTGACCGCATCCCGTTGACCGGGCGCATCGCCGTGATCGTCGATGACGG | |
| | CATCGCCACCGGAGCGACGGCCAAGGCGGCGTGCCACGTCGCCCGGGCGCACGGTGCGGACAAGGTGGTGCTGGCGGTCCCGATCGGCCCAAACGACATCGTGGCG | |
| | AGATTCGCCGGGTACGCCGATGAGGTGGTGTGTCTGGCGACGCCGGCGTTGTTCTTCGCCCTCGGGCAGGGTTACCGCAACTTCAC | |
| | ::::::::::::::Rv13T7.seq::::::::::::: | |
| | CAGGCATGCCAGCTTTCCGCCGATACCCGCCATGTCGCGCACATCCAGGACTTCTGGGGGGATCCGCTGACAGCGGCGGGATCCCAAAGTGcGQATGATCGGGCCG | (SEQ ID NO. 73) |
| | CCTACGTCGTGGTGTACCTCGTCGGTAACAACGAAACCGAAGCGTATGACTCGGTCCACGCGGTGCGGCACATGGTGGACACCACACCGCCACCGCACGGGGTGAA | |
| | GGCCTATGTCACCGGTCCGGCAGCACTCAATGCCGACCAGGCCGAGGCCGGAGACAAAAGTATCGCTAAGGTCACCGCCGATCACNAGCATGGTGATCGCAGCAAT | |
| | GTTGCTAGTGATCTATCGCTCCGTAATTACCGCGGTTCTCGTCTTGATCATGGTCGGCATCGACTCGGCCAATCCGCGGATTCATCGCCrTGCTCGCCGAACACAA | |
| | CATTTTCACCTTTCACATTTGCACCAACCTGCTCTTCTCAT | |
| Clone Rv138 | ::::::::::::::Rv138SP6.seq::::::::::::: | |
| | CACTACTCAAGCTCTCTCNTCATTACCACCCCTGTAATTTGGGATGGGCAAAAAGGCGAAGCACCGCTTGGCCACNAACGCCGGGAGGGACAATCTCGGGCGGCTA | (SEQ ID NO. 74) |
| | TGGCTTCTCCCGGGAAGGCCCCAACGTACGGCGTTTCAACACGTCGCGTCGCCCTCCGACCGCGAACATTCGGGGATTGGCACCAACCTGNTACCACCCTGGCCGG | |
| | GCGATGATCTGCAGCGTCGCCGCGGGTAGTCCCCGCCCGGGCGGCTACAGTCTGAAACCCCGATGACCATCGATGTGTGGATGCAGCATCCGACGCAACGGTTCCT | |
| | ACACGGCGGATATGTTCTCCTCGCTGCGCCGCTGGACCGGTGGGTCTATCCCCTGAAACCGACATCCCN | |
| | ::::::::::::::Rv138T7.seq::::::::::::: | |
| | CAGGCATGCAAGCTTTCGTCAGTTCATTGCGCCAGCAGACCAACAAGAGCATCGGGACATACGGAGTCAACTACCCGGCCAACGGTGATTTCTTGGCCGCCGCTGA | (SEQ ID NO. 75) |
| | CGGCGCGAACGACGCCAGCGACCACATTCAGCAGATGGCCAGCGCGTGCCGGGCCACGAGGTTGGTGCTCGGCGGCrACTCCCAGGGTGCGGCCGTGATCGACATC | |
| | GTCACCGCCGCACCACTGCCCGGCCTCGGGTTCACGCAGCCGTTGCCGCCCGCAGCGGACGATCACATCGCCGCGATCGCCCTGTTCGGGAATCCCTCGGGCCGCG | |
| | CTGGCGGGCTGATGAGCGCCCTGACCCCTCAATTCGGGTCCAAGAACATCAACCTCTGCAACAACGGCGACCCATTTGTTCGGACGGCAACCGGTGGCAACGCACC | |
| | TAAGCTACCTGCCCGGGATGA | |
| Clone Pv139 | ::::::::::::::Rv139SP6.seq::::::::::::: | |
| | GTTTATGCACTGGTTAGGTGTTTCCATGAGTTTCATTCTGAACATCCTTTAATCATTGCTTTGCGTTTTTTTATTAAATCTTGCAATTTACTGCAAAGCAACAACA | (SEQ ID NO. 76) |
| | AAATCGCAAAGTCATCAAAAAACCGCAAAGTTGTTTAAAATAAGAGCAACACGTACACAAGGAGATAAGAAGAGCACATACCTCAGTCACTTATTATCACTAGCGC | |
| | CCGCCGCAGCCGTGTAACCGAGCATAGCGAGCGAACTGGCGAGGAAGCAAAGAAGAACTGTTCTGTCAGATAGCTCTTACGCTCAGCGCAAGAAGAAATATCCACC | |
| | GTGGGAACTCCAGGTAGAGGTAC | |
| Clone Rv13 | ::::::::::::::Rv13SP6.seq::::::::::::: | |
| | ATACTCAAGCTTGGGTGTAGCCGATCACCGGAAGTCNCATGATCAGCCACGTTCCGCGCCGCCCGGCATACGGTGGTGTACCGATCTCCGCGTCATACACCCGCGG | (SEQ ID NO. 77) |
| | GTAATCGCCGACGGTGCCGGTTCGGGAGCCAA | |
| | ::::::::::::::Rv13T7.seq::::::::::::: | |
| | AGCTTTATCTGAAAGCGAACAGCTCGCGGCGGCCCACGACGTGCTGCGTCGGATTGCCGGGCGGCGAGATCAATTCCAGGCAGCTCCCGGACAATGCGGCTCTGCT | (SEQ ID NO. 78) |
| | GGCCCGCAACGAAGGACTCGAGGTCACCCCGGTGCCCGGGGTCGTGGTGCACCTGCCGATCGCACAGGTTGGCCCACAACCGGCCGCTTGATGCCCGGTCGGCAAG | |
| | CCCGGCAGTTGCCAAACCCATCGTGATCAGGCTCGGCTCGCGAGTTCGGCGAAGAAATGGTTCGCCTGATCACCTACCATCGGCCA | |
| Clone Rv140 | ::::::::::::::Rv140SP6.seq::::::::::::: | |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | TCAACACGCCGCCAGCCACCACGCGCGGGTCGGGCGCCGGGCCCGGGCCTCCAGGCTNCTCCGCTCGGTGATGGCACGCCACCGCGACACCACCCGGCTGCGCTAC | (SEQ ID NO. 79) |
| | GTCGAGCCATACCGGGCGGAGCTACATCGGCCCGGCCGCCCAGTGTTCGGGCCCTCTCGCCCAGGTCGAGGTCGACACCGATTTGCGCATCCGCAGCCGCACCCTG | |
| | CGACGACAGAACCGCGGCCCTACCCACTGCTTGTCGGGCGGGGGCCAAAGAACCAGCTTGNCATCCTGCCACAATTGGCCGGCGCCG | |
| | ::::::::::::::Rv140T7.seq:::::::::::::: | |
| | CAGGCATGCAAGCTTCACGTCCGTACGGCTCGGGTACGCTTCGGTCGCAGTGTGCGAGTGATAGATGACGACCGGGACCTCGTCGGCATCTTCCATAGCCCGCCAC | (SEQ ID NO. 80) |
| | ACCTTCAGTTGCTCACCGGAATCCAACCGGTAGAAGGTCGGCCAGCGCTCGGCATTGGTCATCGGGATATGCCGCTCGGGACGGTCAGAGCCCTCGGGTCCGGCCA | |
| | GCACTCCGCAGGCTTCGTCGGGGTGGTCGCGACGCGCATGGGCCACCATCGCATTCACCAGGTCTGCGCGAATCACCAGCACGTAGACGGTTCCTTTCCTAAGCAA | |
| | CAC | |
| Clone Rv141 | ::::::::::::::Rv141SP6.seq:::::::::::::: | |
| | AATATTCAAGCTTTCGGCGGAAACGGACNCCTTGCGAACATTGATAACAAAATAGAAATCATTGATGGTTTGAGTCACCAGGCCGATCAAGCCTTCGCCGAGCCAA | (SEQ ID NO. 81) |
| | ATTCCAATCAAGAGGCCCAAGCCCGTACCAATCAGCCCGGCAACGAGGGATTCCGTCNTTATCAGCCNAAATAACTGCTCTCGGGTACCACCCAAACAGCGCAATA | |
| | TGGCGAAAAACGGTCGCCGTTGCACAACATTAAATGTCTCGGTATTGTTGATTAAAAAGATACCCACCACCAGGGCAATCCAACTGAGAGCGGTTAAATTGACCGT | |
| | AAAAACCTCCCGTCATCTGTTT | |
| | ::::::::::::::Rv141T7.seq:::::::::::::: | |
| | CAGGCATGCAAGCTTGCTGCATCTTCCTGTGACTGCTCCCGAAACCTGGGGGTGTGCCTGCTGTGTATGCACGGCATACGGACATCCTTCCCCTGATACCCGCGGT | (SEQ ID NO. 82) |
| | CGAACCAGCCACGTGTCCATCATCAGGGGTCAACCCCGGCCAAGGGCGACGGCACGCCAAGTTCGCCGACCGTTAACCTAGTGCTGTTAGCTTCATTTGCTGCGAG | |
| | CAAAACAGCTGGTCGGCCGTTAGGAACTGAATTGAAACTCAACCGATTTGGTGCGGCCGTAAGTGTCCTGTCTGCGGGTGCGCTGGTGTTGTCCGCGTGTGGTAAC | |
| | GACGACAATGTGACCGGGGGAGGTGCAACCACTGGCCAGGCGTCCGCGAAAGTCCATTGCNGGGGGAAGACAC | |
| Clone Rv142 | ::::::::::::::Rv142IS1081.seq:::::::::::::: | |
| | GAAAGTGCCCCAAGGTGTTGGTGAAACTCGCTGGACGGTCCCCAGGATGTTGGCAGCACATTCACCGGACATGACCGGAGCAAGACCGGACATCCTCCCATACCGT | (SEQ ID NO. 83) |
| | CGTCGCCGTGTACATCCGTAGCCCGTCCTGGCAGGTGCTGGGTTGAACAAAATCAGCCCAACACCTGCCACGACGAAGAAGCGGGTTGCGCTGGCATGTCTTGTCG | |
| | GCTCGGCGATCGAATTCTACGAATTCCTTATCTACGGGACCGCTGCGGCGCTGGTGTTTCCCACCGTGTTCTTCCCACACCTGGATCCCACGGTGGCCGCCGTGGC | |
| | CTCCAAGGGGACATTTGCTGTGGCGTTCCTATCCCGGCCGTTCGGCGCGGCCGTCTTTGGATACTTTGGAGACCGCCTCGGCCGCCAGAAGACCCTGGTCGCCACA | |
| | CTGTTGATCATGGCCCTGGCAACCGTGACTGTTGGGCTGGTTCCACGACAGTGGCCATCGCGC | |
| | ::::::::::::::Rv142SP6.seq:::::::::::::: | |
| | ATATTCAAGCTTTGTCACACCAAGTGTTCCGACCAANCGCTCCATCCGGCGAGTGGATACTCCCAGCAGGTAGCAGGTCGCCACCACGCTGGTCAGTGCGCGTTCA | (SEQ ID NO. 84) |
| | TCTCGCTTGCGGCGCTGCAGCAGCCAGTCCGGGAAATAGCTGCCCTGGCGCAGCTTGGGGATCGCGACGTCGATGGTTGCGGCACGGGTGTCGAAATCACGGTGGC | |
| | GGTAGCCGTTGCGCTGATTGGACCGCTCATCGCTGCGTTCGCGGTAGCCCNCCCCGCACAGGGCGTCGGCTTCAGCCCCCATCCAAGGCGGCGATGAACGTCGAGA | |
| | GCAGCCCGCGCAGCAMTCCGGGCTCGCCTGTGCGAGTTGGTCAGCCAGAAGCTGCTCGGTGTCATMGATGAGAAGAGGTCAGTGCGTCCTTTCCTTCG | |
| | ::::::::::::::Rv142T7.seq:::::::::::::: | |
| | CAGGCATGCAAGCTTTTTGAGCGTCTCGCGGGGCAGCTTCGCCGGCAATTCTACTAGCGAGAAGTCTGGCCCGATACGGATCTGACCGAAGTCGCTGCGGTGCAGC | (SEQ ID NO 85) |
| | CCACCCTCATTGGCGATGGCGCCGACGATGGCGCCTGGACCGATCTTGTGCCGCTTGCCGACGGCGACGCGGTAGGTGGTCAAGTCCGGTCTACGCTTGGGCCTTT | |
| | GCGGACGGTCCCGACGCTGGTCGCGGTTGCGCCGCCAAAGCGGCGGGTCGGGTGCCATCATGAATGCCTCACCGCCGCCGCACTGCACGGCCAGTGCCCCGGCQAT | |
| | GTCAGCCATCGGGACATCATGCTCGCGTTCATACTGCTCGACCAGTCCGCGGAACAGCTCCATTCCACCGCCCAACGC | |
| Clone Rv143 | ::::::::::::::Rv143SP6.seq:::::::::::::: | |
| | ATACTCAAGCTTTTGGCTGGGTCGGCTTCCAATTCAGCGTGCACCGCTATGGGTTGCAGCAGCGGCTGGCNCCGCACACCCCACTGGCCCGGGTGTTTTCGCCCCG | (SEQ ID NO. 86) |
| | AACCCGGATCATGGTGAGCGAAAAGGAGATTCNCCTGTTCGATGCTGGGATTCGCCACCGCGAGGCCATCGACCGATTACTCGCCACCGGGGTGCGAGAGGTGCCG | |
| | CAGTCCCGCTCCGTCGACGTCTCCGACGATCCATCCGGCTTCCGCCGTCGGGTGGCGGTAGCCGTCGATGAAATCGCTGCCGGCCGCTACCACAAGGTGATTCTGT | |
| | CCCGTTGTGTCCAAGTGCCTTTCGCGATCGACTTTCCGTTGACCTACCGGCTGGGGCGTCGGCACAACACCCCGGTGAGGTCGTTTTTGTTGCAGTTGGGCGGAAT | |
| | CCGTGCTCTGGGTTACAGCCCCGAACTCGTCACGGCGGTGCGCCGCCGAC | |
| | ::::::::::::::Rv143T7.seq:::::::::::::: | |
| | CAGGCATGCAAGCTTCAACCTATTGACGCATTGTGCGAACTGACGGCGCCCGCGCATGGCCAATCCGGAAGACCATCATTGGCCAGTGGCCGGGCGCTAACAGGTT | (SEQ ID NO. 87) |
| | CCAGCCCCCCACCAGTGCCCCTCGAACATGCGGTGCAACCCATTCGCAGGCCGGCAGGGAAAGCACCGCGGAAGCCGCAAAGGGCTGCAGTTCCGCGCCCAATAGT | |
| | GTCGTCCGCAACCAGATGCGCTCGAAAACCGCCGCCGGCAGTCAGCGCACCCGACGCGAGGTCGAGAGACGTCGTCAGCGCGCCCACATGGGGTGCCAATCGGCAC | |

TABLE 3-continued

End sequences of the polynucleotide inserts cloned in the named recombinant
BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081
repetitive sequence (Insertion element)
The character <<->> denotes an uncertain base residue.

GGCAGGTAGGCCGCGCGCAACCCCAACGGGTGGTGCATGCCACGGTCCGCAGGAGGCCACCACCC

Clone Rv144 ::::::::::::::Rv144SP6.seq::::::::::::::
ATACTCAAGCTTCCCGGCCGCAGGTGACGGCGCGGCCTAGCGCCACTTGATGCCGCACCCGATCGACGGNCGTTCGGTCGGGGTTGACTGGCCGCCCGGCGAAGG (SEQ ID NO. 88)
GCGTCAACCGCGGCCCGGACGTCGGCGGCCGTCACCGGTCGGCCATTGCCCGGCGGGAGTCGTCGAGCTGACCACGGTAGACAAGTCGGCGCTGGCCGTCGAAGA
CAAACGTGTCGGGTGTGCAGGCCGCGGAGAAGGCGCNGGCGACGTCTCGGGTTTCGTCGTAGAGATACGGGAACGTCCAGCCGTGGCGGCGGCCTCGGCGACCAT
CTGATCGGGCCCGTCCTGCGGGTAGGTGACCACGTCTTACTGGAGATACCGACCATCGGGACCCTTTGATCGGCGAGGTCCCGGCCGACCGTGGCCAATCCGGCG
GCGACGTGTCGCCCGTACCGGCCAGTGGTTC
::::::::::::::Rv144T7.seq::::::::::::::
CAGGCATGCAAGCTTTANCANCATCAACCCCGCCCCGCACCAGCACCGACACGATGTCGATGCCATCGAGGTGAATGTCGAACTGGCNCAAACCATCTGGCGACCG (SEQ ID NO. 89)
CGACCACCGGCAACATGGGTACCGGCGATTTCCGGTGCCAATGCCGACCCGACGGGCCGCTCTCACCGCAGGTGACCTCGATCACCGAGACCAGCCGGCCGTTATA
CTCACGCACCCCTACCGTGTCACGCCCAAAACGGCGCTGGTGGTCGATTGCCGGAGTGCACCCCGCACCCAGTGTCGTGCCCGGATCCGCCGACCAATCCCGCACC
GGCTG Clone Rv145 ::::::::::::::Rv145T7.seq::::::::::::::
ATATTCAACCTTGCACACATTGACGATACCTTGGTCACGAGACCCCAAAAGCTGGCCTCCACCGCGCGCCGGGGACCACGGTCATACCTTGANNCNGCTTTCGATC (SEQ ID NO. 90)
GTTGATGCTGCGTCTTGGTCCGCGGAAACCGCAGGCTGGCATATGCACGTGGGCGCACTGGCGATCTGCGATCCCCACCGATTCGCCCGAATACAGCTTTCAGCGG
CTCCCCCAAGTTGATCATCGACCGGCTGCCGGATATCCCGCACTTGCGGTGGCGGGTCACCGGCGCCCCGCTCGGACTGGACCGGCCGTGGTTCGTCGAGGACCACG
AAC
::::::::::::::Rv145T7.seq::::::::::::::
CAGGCATGCAAGCTTCATGCCCGCGGCATGATAGCCACATGCACGCAATCGAACTCAGCGAAACCGGCGGGCCAGGCGTCTTACGCCACCTCACCAGCGCGCAACC (SEQ ID NO. 91)
TCAACCCGGGCACGGAGACCTCCTGATC Clone Rv146 ::::::::::::::Rv146SP67.seq::::::::::::::
ATACTCAAGCTTGATTTTGATCATCATGATGATCATCACCCGAATTGTGGTAGCCGCAGTGGTTATCGTGGGTACCGTCGTGCTTTCCATGGGCGCCTCTTTCGGG (SEQ ID NO. 92)
CTTTCCGTATTGGTCTGGCAGGACATTCTGGGTATCGAGTTGTACTGGATGGTGTTGGCGATGTCGGTGATCCTGCTCNTGGCGGTGGGATCCGACTACAATCTGC
TGCTGATTTCCCGGTTGAAAGAGGAAATTGGGGCCGGATTGAACACCGGAATTATCCGTGCCATGGCTGGTACCGGGG&AGTGGTGACGGCTGCCGGCATGGTGTT
CGCCGTTACCATGTCGTTGTTTGTGTTCAGCGATTTGCGAATTATTGGTCAGATCGGTACCACCATCGGCCTGGGCTTGCTGTTCGACACCCTCGTCGTGCCTCGT
TCATGAAACCGTCCATTGCTGCCCTGCTGGGACCTGGTTCTGGTGGCCGCTACGGGTGCGCCGCGCCCGGCAGTCAAATCTTCCGCCG
::::::::::::::Rv146T7.seq::::::::::::::
CAGGCATGCAAGCTTGGCGTGCCGTTCCAACCCGAATTGGCTTTCGGCGCCATCGGTGAGGACGGCGTGCGGGTGCTCAACGACGACGTCGTCCGCGGGACACACC (SEQ ID NO. 93)
TCGATGCTGCCGCCATGGACGCGGTCGAACGCAAGCAGCTGATCGAGCTACAACGCCGGGCGGAACGCTTCCGCCGCGGGCGTGACCGCATCCCGTTGACCGGGCG
GATCGCGGTGATCGTCGATGACGGCATCGCCACCGGAGCGACGGCCAAGGCGGCGTGCCAGGTCGCCCGGGCGCACGGTGCGGACAACGTGGTGCTGGCGGTCCCC
ATCGGCCCAGACGACATCGTGGCGAGA Clone Rv147 ::::::::::::::Rv147SP6.seq::::::::::::::
ATACTCAAGCTTTTACGGTGATCGCGATCACCTGGTTCATGAACTGGAAGCAGCGCAGCGCTTCCTTTTCGGCCGCAACATGAGCCAGCCTCTCGTCGGCGGTCG (SEQ ID NO. 94)
GGTGCAGGTGCTCGGGCAGCTCGGCCGCGACAGCCGCCTGACCCTGAAACCAGCTTCCATATCCCGCGACGAACGACGCCAGTCCGCTACGTAACCCCTCCGCGAC
TGTCCATGGACAACAGCGCGTTCTCCACGACCGGGCCCGGGTGTGGGGTGTTTCGGCGACCGGCAGCCANGTGGTCCACACTGCCGAAG
::::::::::::::Rv147T7.seq::::::::::::::
TAGTCGCTGACCGGTGCAGGTTTCGACNATGTGGTGCCGGTTCGGCGGCTACGTGCCATCGAGACACTGGCGCAGGCTATCGCACCCGTTATCGGCTACGAGCAAA (SEQ ID NO. 95)
TCGCGGTATGCGTTCTTGAGCATGAGTCGGCGACCGTCGTCATGGTCGACACCCACGACGGAAAGACGCAGATCGCCGTCTANCNTGTGTGCCGCGGATTATCAGG
ACTGACCTCCTGGCTGACCGGCATGTTTGGTCGCGATGCCTGGCGCCCGGCCGGCGTGGTCGTGGTCGGCTCGG Clone Rv148 ::::::::::::::Rv148SP6.seq::::::::::::::
ATACTCAAGCTTTCCGCCGATACCCGCCCATGTCGCGCACATCCAGAACTTCTGGGGGGATCCGCTGACAGCGGCGGGATCCCAAGTGCGGATGATCGGGCCGCCT (SEQ ID NO. 96)
ACGTCGTGGTGTACCTCGTCGGTAACAACGAAACCGAAGCGTATGACTCGGTCCACGCGGTGCGGCACATGGTGGACACCACACCGCCACGGCACGGGGTGAAGGC
CTATGTCACCGGTCCGGCAGCACTCAATGCCGACCAGGCCGAGGCCGGAGACAAAAGTATCGCTAAGGTCACCGCGATCACGAGCATGGTGATCGCAGCAATGTTG
CTAGTGATCTAATCGCCCCGTAATTACCGCGGTTCTCGTCTTGATCATGGTCGGCATCGACCTCGGCGCAATCCGCGGATTCNTCGCCTTGTCGCCGACCACAACA TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | TTTTCAGCCTTTCAACATTTGCGACAACCTGCTCGTTCTCATGGCGATTGCNGCGAAC | |
| | ::::::::::::::Rv148T7.seq:::::::::::::: | |
| | CAGGCATGCAAGCTTGGCGTGCCGTTCCAACCCCGAATTGGCTTTCGGCGCCATCGGTGAGGACGGCGTGCGGGTGCTCAACGACGACGTCGTCCGCTGGACACAA | (SEQ ID NO. 97) |
| | TCGATGCTGCCGCCATGGACGCGGTCGAACGCAAGCACGTGATCGAGCTACAACGCCGCGCGGAACGCTTCCGCCGCGGGCGTGACCGCATCCCGTTGACCGGGCG | |
| | GATCGCGGTGATCGTCGATGACGGCATCGCCACCGGAGCGACGGCCAAGGCGGCGTGCCAGGTCGCCCGGGCGCACGGTGCGGACAAGGTGGTGCTGGCGGTCCCG | |
| | ATCGGCCCAGACGACATCGTGGCAGATTCGCCGGTACGCCGATGAAGTGGTGTTGTTTGGCGACCCGGCGTTGTT | |
| Clone Rv149 | ::::::::::::::Rv149SP6.seq:::::::::::::: | |
| | ATACTCAAGCTTTGGCATTGTGCACATTTTCCACCCGTGCTCTATTAATGCTGAGCCGCTAATTGTGACCCCAGTCGGGAAACACGCGGAGCACCAAATTCACCGC | (SEQ ID NO. 98) |
| | AGCGGCCGGGGCGGTTCAACTCACCATGGATCGCTCTCGTCGTCTGGTGCTGGACAATCGTCGCTGTAGCGCGTCGCGAACACCTCAGCTTCTGCTGCCGCGGCTT | |
| | CTTCCGGCGATGGTAACCCCCAGGTTTCGCCCACGGTCTTACGTAGCAGTGCGACGCGGTGTTCATCTGCATCGACCTGTTGACTCATCCTGTCAAGGATGAAGGC | |
| | GTACTGGGCCGACTGCGCCTTCTGCCGCGCCAGGTCGGCAATCACCAGGATCTCAGAAACGAGCTGCGACTCACTCTTCCAGGCCACCCTGGCCGAAAGCTCGACA | |
| | TGGTCAATCCGGCCG | |
| | ::::::::::::::Rv149T7.seq:::::::::::::: | |
| | CAGGCATGCAAGCTTGCGGGCCGGAGTGGTTTCGACGGCCGCTCGCTTCTCGGCATCGGTTTGGGCTGTCACCAGCAGTTGGTAGTTCTTCACGTACTGTTGTTCG | (SEQ ID NO. 99) |
| | AGCGTCGAGCCGCCGCGCGTGTCGAGGTCGCCGGACGCGTATCCCGCCAGGCCGGTCAGGGTGCCCTTCCAGTCCACGCCGCTGTGGTCGGCGAACCGCTTATCTT | |
| | CAATCGAGACGATCGCCAGCTTCATCGTGTTGGCGATCTTGTCCGAGGGCACCTCGAACCGGCGCTGCGAGTACAGCCACGCGATCGTGTTGCCCTTCGCGTCGAC | |
| | CATCGTCGATACCGCAGGCACTTGCCCCTC | |
| Clone Rv14 | ::::::::::::::Rv14SP6.seq:::::::::::::: | |
| | ATACTCAAGCTTCCCGGCGGCCAGTACCGAAAGCGCGAACAGCTCGCGGCAGCCCACGACGTGCTGCGTCGGATTGCCGGCGGCGAAATCAATTCCAGGCAGCTCC | (SEQ ID NO. 100) |
| | CGGACAATGCGGCTCTGCTGGCCCGCAACGAAGGACTCGAGGTCACCCCGGTGCCCGGGGTCGTGGTGCACCTGCCGATCGCACAGGTTGGCCCACAACCGGCCGC | |
| | TTGATGCCCGGTCGGCAAGCCCGGCAGTTGCCAAACCCAGCGTGATCAGGGTCGGCTCGCGAGTTCGGCGAAGAAGTGGCTCGGCTGATCACCTACCATCGGCCAG | |
| | GATCTGCGTGTCATCACAACGCTCGCCAAGGAGGTTGTTGTGGTGCTATCGACGGCCTTTAGCCAGATGTTCGGAATCGACTATCCGATAGTGTCCGCGCCAATGG | |
| | ACTTGATCGCCG | |
| | ::::::::::::::Rv14T7.seq:::::::::::::: | |
| | AGCTTCGGTGTAGCCGATCACCGGAAGCCGCATGATCAGCCACGTTTCGCGCCGCCCGGCATACGGCGGCGTACCGATCTCCGCGTCATACACCCGCGGGTAATCG | (SEQ ID NO. 101) |
| | CCGACGGTGCCGGTTCGC&AGCCGAAGGTGACGACGCTGATTGAATCGAGTTCCAGGTCCAGCGGGTGGCGCAGCAACGGCGCGAGCTCAACGACGTCAATCACGT | |
| | TGTCGCTTTCTACGGTCACCGACGCCGTGACCGTAGTCGCCCGGTGCGCTCGGCCGAGAAGTTGCACCGCCACCACCGCGACACCGTCTTGCACGCGGACCCCACC | |
| | CCCGGATCGGTTGTTGGCCAAGGTAATTGGGTCATTCCATTTGACGGGACGCCGACCCCGCAGCCCCAGTACCGCCCACGACCACGCCGGCTGACCCACCACTGTA | |
| | CGAACACCAAGGCGACGCCGA | |
| Clone Rv15 | ::::::::::::::Rv150SP6.seq:::::::::::::: | |
| | ATACTCAAGCTTCGGTGGCTTCGCCCGCCCTGCCGGGTGGACTTCATGACAACGCGGGGGCGATTACCCCCGCTACCGCCAGCAGCATGACGGCGGTACC7AACAC | (SEQ ID NO. 102) |
| | CGCCCGGATGCCTCGCACGTGCCTCGATGTGCTCACGGAATCGCCCCGGCACCGCGATCTCGAGGATCACCAGCGTTACCCCCGGCAGCGCGACACCGACAATTCC | |
| | GTACACCGCCACGCCGATCCGGCCCTGGGCCAGCTGATTGGAGCTGGCG | |
| | ::::::::::::::Rv150T7.seq:::::::::::::: | |
| | CAGGCATGCAAGCTTCCACATGTACGGATCCACGAACATCCCGTTGAACTGACAGGTGCGGCCCGGCTCGATCAGGCCGGCCACTTGTTCTACGCGGTTACCGAAG | (SEQ ID NO. 103) |
| | ATCTCTTCGGTGACCTGCCCGCCGCCGGCCAGCTCGGCCCAGTGCCCGGCGTTGGCCGCCGCGGCGACGATCTTGGCGTCCACGGTGGTCCGGGTCTTGCCCGCTA | |
| | GCACGATCCGCGAGTCGGCCGGTCACCCGGGT | |
| Clone Rv151 | ::::::::::::::Rv151SP6.seq:::::::::::::: | |
| | ATACTCAAGCTTTCCAAGTCCCAAGTGTCGATCATGGCCAAAGAGCTCGACAAAGCCGTAGAGGCGTTTCGGACCCGCCCGCTCGATGCCGGCCCGTATACCTTCC | (SEQ ID NO. 104) |
| | TCGCCGCCGACGCCCTGGTGCTCAAGGTGCGCGAGGCAGGCCGCGTCGTCGGGGTGCACACCTTGATCGCCACCGGCGTCAACGCCGAGGGCTACCGAAAGATCCT | |
| | GGGCATCCAGGTCACCTCCGCCGAAGACGGGGCCGGCTGGCTGGCGTTCTTCCGCGACCTGGTCGCCCGCGGCCTGTCCGGGGTCGCGCTGGTCACCAGCGACGCC | |
| | CACGCCGGCCTGGTGGCCGCGATCGGGGCCACCCTGCCCGCAGCGTGGCAGCGCT | |
| | ::::::::::::::Rv151T7.seq:::::::::::::: | |
| | CAGGCATGCAAGCTTCACACGTAGGCGCGTCGATAAATGACTCCGCCGCGCTTCGCACATCCTCGTAGCGATCCTTGGCGAGCAGGTCAACCGGGCGCTGCCCGT | (SEQ ID NO. 105) |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

CGAGGAGCCGGTTTTTGGCGTGCAGCCACTGGCCGACACCTCGGGGGGTAGGCGAATCCGAGAGCAGGAGGACGAGGTCACGGAGCTGCGCCAGCCGGTCGTACCG
CTCAGGGCGGATGTCGCCGGTCCGCCACCCGCGTACCGCCCGATCGGACACCTGTATGACCGCGGCGACGTC

Clone Rv152 ::::::::::::::Rv152SP6.seq::::::::::::::
CGCGGCGGCGCATTACCCCCGCTACCGTCAGCAGCTTGACGGCGGTAGCGAACACCGCCGGATGCAGCGCAGGTGCGTCTATGTGCACACGGAATCGCCCCGGCAC (SEQ ID NO. 106)
CGCGATCTCGAGGATCACCAGTGCCCGCCCCCTG ::::::::::::::Rv152T7.seq::::::::::::::
GGGATCGAGGAACAGCGCGTTGAACTGATAGGTGCGGCCGGCTCGAGCAGGCCGGCCATTTGTTCGATGCGGTTACCGAAGATCTCTTCGGTGACCTGCCCGCCG (SEQ ID NO. 107)
CCGCCAGCTCGGCCCAGTGCCCGGCGTTGGCCGCCGCGGCCGACGATCTTGGCGTCCACGGTGGTCGGGGTCATGCCCGCGAGCAGGATCGGCGAGCGGCCGGTCA
GCCGGGTGAACTTCGTCGAGAGCTTGACCCTG CGTCGGGGAGGCGAACCACGGTCGGTGCGTATCTCGACCAGGCCCGGGCAACCTCGGGGGTGGCGCCGACGGT
GAACAGGTTGCGCTGGCCACCACGGGTAGCCGCCGGCACTATGCCGATGCCCAGGCCGCGGATCACCGGTGCGGTCAGTCGGGTCAGGATGTCGCCCGGCCCCAGG
TCGAAGATCCAGCGGGCGCCGGCCGCGTGGACACNGGTGATCTCGTCCACCATCGACTTTTCTGATCA Clone Rv153 ::::::::::::::Rv153SP6.seq::::::::::::::
TAACTCAAGGCTTGCGTTGAGGCCCCAGGCCCATCGACGGTTTGGCGGCCTTAAATGCACTGAGGTCGTCAATTGACCCCACAGCGGAAATGCCGACTATTCGCAG (SEQ ID NO. 108)
GCCTCCTTCGCCTTGGCTGCCGGAGAGGGGCTCCGCGGGAACCGCATGCAGGTATATGACCTCGGTTTCTCGGGTGCTACCGGGTGCCTTGTCGAGGATGAACTCG
GCGTTGGAATTGTCCAGCCGGCCCAATTCATCGAGCGCAGATTCGTACACATGGCCGGCGGCGACATACGCTTCACCGTGGATCTGCTCCACACGGAGCGGCCTGT
CGGGATCCTGCTCACGGGTAAAGGAACTTACNTGGCNCTCGGTGCC ::::::::::::::Rv153T7.seq:::::::::::::
CCTTCTGCGCCACCCACACCGTCAACGCCCGCGAAGTCGACGTCGTCCAGGCCATCGGCGGCCTCACGGATGGATTCGGCGCGGACGTGGTGATCGACGCCGTCGG (SEQ ID NO. 109)
CCGACCGGAAACCTACCAGCAGGCCTTCTACGCCCGCGATCTCGCCGGAACCGTTGTGCTGGTGGGTGTGCCGACGCCCGACATGCGCCTGGACATGCCGCTGGTC
GACTTCTTCTCTCACGGCGGTGCGCTGAAGTCGTCGTGGTACGGCGATTGCCTGCCCGAAAGCGACTTCCCCACGCTGATCGACCTTGACCTGCATGGCCGGCTGC
CGCTGCAGCGGTTCGTTTCCGAACGCATCGGGCTCGAAGACGTCGAGGAGGCGTTCCACAAGATGCATGGCGGCAAGGTATTGCGTTCGGTGGTGATGTTGTGATG
GCCGCCATCGAGCGCGTCATCACCCACGG Clone Rv154 ::::::::::::::Rv154SP6.seq:::::::::::::
ATACTCAAGCTTGATTTTGATCATCATGATGATCATCACCCGAAGTGTGGTAGCCGCAGTGGTTATCGTGGGTACCGTCGTGCTTTCCATGGGCGCCTCTTTCGGG (SEQ ID NO. 110)
CTTTCCGTATTGGTCTGGCAGGACATTCTGGGTATCGAGTTGTACTGGATGGTGTTGGCGATGTCGGTGATCCTGCTCCTGGCGGTGGGATCCGACTACAATCTGC
TGCTGATTTCCCGGTTGAAAAAAGAAATTGGGGCCGGATTGAACACCGGAATTATCCGTGCCATGGCTGGTACCGGGGGAGTGGTTACCGCTGCCGGCATGGTGTT
CGCCGTTACCA ::::::::::::::Rv154T7.seq:::::::::::::
ATTGNCTTTCGGCGCCATCGGTGAGGACGGCGTGCGGGTGCTCAACGACGACGTCGTCCGCGGGACACACCTCGATGCTGCCGCCATGGACGCGGTCGAACGCAAG (SEQ ID NO. 111)
CAGCTGATCGAGCTACAACGCCGCGCGGAACGCTTCCGCCGCGGGCGTGACCGCATCCCGTTGACCGGGCGGATCGCGGTGATCGTCGATGACGGCATCGCCACCG
GAGCGACGGCCAAGGCGGCGTGCCAGGTCGCCCGGGCGCACGGTGCGGACAAGGTGGTGCTGGCGGTCCCGATCGGCCCAGACGACATCGTGGCGAGATTCGCCGG
GTACGCCGATGAGGTGGTGTGTTTGGCGACGCCGGCGTTGTTCTTCGCCGTCGGGCAGGGTTACCGCAACTTCACCCAGACCTCCGACGAAGAAGTGGTGGCGTTT
TCTGGATCGTGCTC Clone Rv155 :::::::::::::Rv155SP6.seq:::::::::::::
ATACTCAAGCTTTTCCCGTCCGTCATCGCCCAAGCGCGTGAGGCCGAAGCGGCTGGTTACGACTCCCTGTTTGTGATGGACCACTTCTACCAACTGCCCATGTTGG (SEQ ID NO. 112)
GGACGCCCGACCAGCCGATGCTGGAGGCCTACACGGCCCTTGGTGCGCTGGCCACGGCGACCGAGCGGCTGCAACTGGGCGCGTTGGTGACCGGCAATACCTACCG
CAGCCCGACCCTGCTGGCAAAGATCATCACCACGCTCGACGTGGTTAGCGCCGGTCGAGCGATCCTCGGCATTGGAGCCGGTTGGTTTGAGCTGGAACACCGCCAG
CTCGGCTTCGAGTTCGGCACTTTCAGTGACCGGTTCAACCGGCTCGAANAGGCGCTACAGATCCTCGAGCCAATGGTCAAGGGTGAGCGCCAACGTTTTTCGGCGA
TTGGTACCCACCGA :::::::::::::Rv155T7.seq:::::::::::::
CGGCCACCGGGGCCACTCCGCACAATCTGTACCCGACCAAGATCTACACCATCGAATACGACGGCGTCGCCGACTTTCCGCGGTACCCGCTCAACTTTGTGTCGAC (SEQ ID NO. 113)
CCTCAACGCCATTGCCGGCACCTACTACGTGCACTCCAACTACTTCATCCTGACGCCGGAACAAATTGACGCAGCGGTTCCGCTGACCAATACGGTCGGTCCCACG
ATGACCCAGTACTACATCATTCGCACGGAGAACCTGCCGCTGCTAGAGCCACTGCGATCGGTGCCGATCGTGGGGAACCCACTGGCGAACCTGGTTCAACCAAACT
TGAAGGTGATTGTTAACCTGGGCTACGGCGACCCGGCCTATGGTTATTCGACCTCGCCGCCCAATGTTGCGACTCCGTTCGGGTTGTTCCCAGAGGTCAGCCCGGT TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

CGTCATCGCCGACGCTCTCGTCGCCGGGACCAGCAGGGAATCGGCGATTTCGCCTACA
Clone Rv156 :::::::::::::Rv156SP6.seq:::::::::::::
TCGCCACCGCACCGCGGCGAACGCTCAAAGGCACCTACTGGCACCAAGGCCCCACACGTCACCCTGTGACCTCCTGCGCCGACCCCGCCCGAGGTCCTGGCCGTTA (SEQ ID NO. 114)
CCACCGAACGGGCGAGCCGGGAGTCTGGTACGCATCGAACAAAGAGCAAGGTGCATGGGCGGAGTTGTTCCGCCACTTCGTCGATGACGGGGTCGATCCATTCGAG
GTCCGTCGCCGCGTCGGTCGAGTGGCGGTCACACTCCAGGTACTCGACCTCACAGACGAGAGGACTCGATCCCATCTAGGTGTGGACGAAACAGATCTTCTGTCCG
ACGACTACACCACCACCCAGGCCATCGCCGCCGCCCGCGATGCCAACTTCGACGCCGTACTGGCCCCGGCGGCGGCGCTCCCCGGTTGTCAAACACTTTGCCGTGT
AATCCCATGACGTATCTGCGCAACGACGTGCNCAACNGTGGCTGATGTCNGTGGTGTTGTGGGGTGGGC
:::::::::::::Rv156T7.seq:::::::::::::
TCGCCACCGCACCGCGGCGAACGCTCAAAGGCACCTACTGGCACCAAGGCCCCACACGTCACCCTGTGACCTCCTGCGCCGACCCCGCCCGAGGTCCTGGCCGTTA (SEQ ID NO. 115)
CCACCGAACGGGCGAGCCGGGAGTCTGGTACGCATCGAACAAAGAGCAAGGTGCATGGGCGGAGTTGTTCCGCCACTTCGTCGATGACGGGGTCGATCCATTCGAG
GTCCGTCGCCGCGTCGGTCGAGTGGCGGTCACACTCCAGGTACTCGACCTCACAGACGAGAGGACTCGATCCCATCTAGGTGTGGACGAAACAGATCTTCTGTCCG
ACGACTACACCACCACCCAGGCCATCGCCGCCGCCCGCGATGCCAACTTCGACGCCGTACTGGCCCCGGCGGCGGCGCTCCCCGGTTGTCAAACACTTTGCCGTGT
TCGTTCACGCACTGCCCAACATCGAGCCCGA
Clone Rv157 :::::::::::::Rv157SP6.seq:::::::::::::
ATGAAATAAGAAGAGCACATCCCTCAGTCGGTTATCATCACTAGCGCTCGCCGCACCCGTGTAACCGATCATAGCGAGCGAACTGGCGAGGAAGCAAAGAATATCT (SEQ ID NO. 116)
GTTCTGTCAGATAGCTCTTACGCTCAGCGCAAGAAGAAATATCCCCCGCGGGAACAACTCCAGGTAGAGGTACACACGCGGATAGCCAATTCAGAGTAATAAACTG
TGACACTCACACCCTCATCAATGATGACGAACTACACCCCGATATCCGGTCACATGACGAAGGGAAAGAGAAGGATATCATCTGTGACAAACTGCCCTCAAATTTG
GCTTCCTTAA
Clone Rv159 :::::::::::::Rv159SP6.seq:::::::::::::
ATACTCAAGCTTGTCGAACTCCTTCTTGAATACCGGCCGGCCATCCACAGATGCCCGGAAGAACTTCCAGGTACCCATGGCGGCTGGATCAGGGGGCGGCACAGTT (SEQ ID NO. 117)
GGTCTTGTCCTGCCTCGAGTGGCGTCGTTGTCCGGCTTGGACGGGGCTCCGACGGTACCGGAGGGCAGCGACAAAACACTTATGCACTTGGGCGACCCGCCGAGAC
GGTGCGACACCCATCCCGACGGCACAAGCTCAGCCGCGGCCGCTCTTGTTCTTCGTCGGATCGACATTCACCCACTTCTGACCGGGCTTGGGCGAAGGAAGCAGAA
:::::::::::::Rv159T7.seq:::::::::::::
GGTATAGTCGCTGACCGGTGCAGGTTTCGACAATGTGGTGCCGGTTCGGCGGCTACGTGCCATCGAGACACTGGCGCAGGCTATCGCACCCGTTATCGGCTACGAG (SEQ ID NO. 118)
CAAATCGCGGTATGCGTTCTTGAGCATGAGTCGGCGACCGTCGTCATGGTCGACACCCACGACGGAAAGACGCAGATCGCCGTCAAGCATGTGTGCCGCGGATTAT
CAGGACTGACCTCCTGGCTGACCGGCATGTTTGGTCGCGATGCCTGGCGCCCGGCCGGCGTGGTCGTGGTCGGCTCGGATAGCGAGGTCAGCGAATTCTCGTGGCA
GCTCGAAAGGGTCCTGCCGGTGCCGGTCTTTGCGCAAACGATGGCGCAGGTTACGGTCGCGCGGGGTGCGGCCCTGGCGGCGGCCCA
Clone Rv15 :::::::::::::Rv15SP6D2.seq:::::::::::::
GACACTATATNATACTCAAGCTTCAGGTCAATGTGCGCCAAGCCCTGACGCTGGCCGACCAGGCCACCGCCGCCGGANCCCTNTCTAGA (SEQ ID NO. 119)
:::::::::::::Rv15T7.seq:::::::::::::
CTGTAGCCACCTGTTGCCATCCCCGTCATGCCCGACTCTGGTCATCTCGGATCCGCTGACACCCCGCTAAGGCTGCTCCTCTCGGTGCATTACCTCACCGACGGCG (SEQ ID NO. 120)
AACNCCCCCAGCTTTACGACTATCCGGATGACGGCACCTGGTTGCCGGCTAACTTCACCGTCAGCTTGGACGGCGGCGCTACCGTCGATGGCGCCAGCGGGGCGAT
GGCCGGGCCCGGCGACCGATTCGTCNTCANCCTGTCGCGTGAACTTGCCGACGTCATCGTGGTCGGTGTGGGCACCGTGCGCATTGAGGGCTACTCCGGCGTCCGG
ATGGGTGTCGTCAAGCGCCCGCACCGGCAGGCCCGA
Clone Rv160 :::::::::::::Rv160SP6.seq:::::::::::::
ATACTCAAGCTTCGCACGCTCGGCGCGCGCGGTACCGCCCAGGTCGCCCAACAGATCGTCGATGTTCGCGTCGTCCGCCTCGCGCACGTGGTCTGTCACCAGTCAA (SEQ ID NO. 121)
CGTTAACGCCGCCGCACATGTCCTGCGGCCGGGCAAAAACGTGAAAAACGAGCGGGCGACTGCNATGTCATGACACCGACGGCCGCCGATGGGCCCAGGGTCTGGC
AAATTCGATCTGTGCGGCCAGTGCCAGCAGCGTCGCCTCGTCATACGGCCGGCCGACGAGTTGAACCGACATGGGCAGGCCGTCGCCGTCGAAGTCCCACGGCACC
ACGGGCGCGGGCTGGCCGGTCAGATTCCAAAATTGAAAGTACGGAACCGCTGCACCACCAA
:::::::::::::Rv160T7.seq:::::::::::::
ATCGTTTCGACCAGGCGCTCCATCCGGCGAGTGGATACTCCCAGCAGGTAGCAGGTCGCCACCACGCTGGTCAGTGCGCGTTCAGCTCGCTTGCGGCGCTGCAGCA (SEQ ID NO. 122)
GCCAGTCCGGGAAATAGCTGCCCTGGCGCAGCTTGGGGATCGCGACGTCGATGGTTGCGGCACGGGTGTCGAAATCACGGTGGCGGTAGCCGTTGCGCTGATTGGA
CCGCTCATCGCTGCGTTCGCGGTAGCCCGCCCCGCACAGGGCGTCGGCTTCAGCCCCCATCAAGGCGGCGATGAACGTCGAGAGCAGCCCGCGCAGCAGATCCGGG
CTCGCCTGTGCGAGTTGGTCAGCCAGAAGCTGCTCGGTGTCGATAAGATGANAAGAAGTCATTGCGTTATTTCCT TABLE 3-continued End sequences of the polynucleotide inserts cloned in the named recombinant
BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081
repetitive sequence (Insertion element)
The character <<->> denotes an uncertain base residue.

```
Clone Rv161 ::::::::::::Rv161SP6.seq::::::::::::
            ATACTCAAGCTTGGGTGTTGCCGATCACCGGAAGCCGCATGATCAGCCACGTTTCGCGCCGCCCGGCATACGGCGGCGTACCGATCTCCGCGTCATACACCCGCGG    (SEQ ID NO. 123)
            GTAATCGCCGACGGTGCCGGTTCGCGAGCCGAAGGTGACGACGCTGATTGAATCGAGTTCCAGGTCCAGCGGGTGGCGCAGCAACGGCGCGAGCTCAACNACGTCA
            ATCACGTTGTCGCTTTCTACGGTCACCGACCCGGTGACCGTAGTCGCCCGGTGCGCTCGGCCGAGAAGTTGCACCGCCACCACCGCGACAACGTCTTGCACGCGGA
            CGCCACCCCCCGGAT
            ::::::::::::Rv161T7.seq::::::::::::
            GCGCNAACAGCTCGCGGCAGCCCACGACGTGCTGCGTCGGATTGCCGGCGGCGAGATCAATTCCAGGCAGCTCCCGGACAATGCGGCTCTGCTGGCCCGCAACGAA    (SEQ ID NO. 124)
            GGACTCGAGGTCACCCCGGTGCCCGGGGTCGTGGTGCACCTGCCGATCGCACAGGTTGGCCCACAACCGGCCGCTTGATGCCCGGTCGGCAAGCCCGGCAGTTGCC
            AAACCCAGCGTGATCAGGCTCGGCTCGCGAGTTCGGCGAAAAAGTGGCTCGCCTGATCACCTACCATCGGCCAGGATCTGCGTGTCATCACGACGCTCGCCAAGGA
            GGTTGTTGTGGTGCTATCGACGGCCTTTAGCCAGATGTTCGGAATCGACTATCCGATAGTGTCCGCGCCAATGGACTTGATCGCCGGCGGTGAGCTGGCTGCCGCN
            GT
Clone Rv162 ::::::::::::Rv162SP6.seq::::::::::::
            ATACTCAAGCTTTCTCCGATACCCGCCATGTCGCGCACATCCAGGACTTCTGGGGGGATCCGCTGACAGCGGCGGGATCCCAAAGTGCGGATGATCGGGCCGCCTA    (SEQ ID NO. 125)
            CGTCGTGGTGTACCTCGTCGGTAACAACGAAACCGAAGCGTATGACTCGGTCCACGCGGTGCGGCACATGGTGGACACCACACCGCCACCGCACGGGGTGAAGGCC
            TATGTCACCGGTCCGGCAGCACTCAATGCCGACCAGGCCGAGGCCGGAAACAAAAGTATCGCTAAGGTCACCGCGATCACGAACATGGTGATCGCAGCAATGTTGC
            TAGTGATCTATCGCTCCG
            ::::::::::::Rv162T7.seq::::::::::::
            CCATGAGCACCGCCAGCCGAGCACGAGGCCAAACTCCGCCGACGCAGGCCGGTTGGACTTGTCGTGCTGGACAAGGGGTTTAGCCGCCGAAGCAGTGACGTACATC    (SEQ ID NO. 126)
            GGCGAAGAGCAGTTCGCCTGTCGACCGACGGCGCAAACCGTGAGGCTAGGGAAGCGAGGAGCACATGGCCGCCGACCCGCAATGTACACGCTGCAAGCAAACCATC
            GAACCCGGATGGCTATACATCACCGCCCATCGCCGCGGTCAAGCCGGGATCGTCGATGACGGCGCAGTACTGATTCACGTGCCCGGTGAATGCCGCACCCCGGGGA
            GCACTTTCCGCCAAAACTAACCCGGTTGG
Clone Rv163 ::::::::::::Rv163SP6.seq::::::::::::
            CGGGTGTCATTGGCCACCGGCGGCGGCTGTCCGGGAAATGGCGGGTCCCCGGTGGTTTTGCTGAGGAGTGCTGAACCGTAGTCGAAGTGGGCGGCGTCAGACTCCA    (SEQ ID NO. 127)
            CCCAGCCAGCAGGCAGCGCGAANCTGAATCCTCCAACCGGGTTGTCNATCCGGACAGGTTGGGGTGCGTTTGGGGCAATNACAGGTGGCGGCGGTGCGTTCGGGTC
            GGCCGGCGGAGGTGCTGCNTTGGGATCCCCGGCTGGGCATTCGGCNTGTTGGCGGCGGCCGGTGGTGGGGGGGGCAACACGTGTCNCCGGTGCGGGTGGCCCT
            ::::::::::::Rv163T7.seq::::::::::::
            CCAAGATCTACACCATCGAATACGACGGCGTCGCCGACTTTCCGCGGTACCCGCTCAACTTTGTGTCGACCCTCAACGCCATTGCCGGCACCTACTACGTGCACTC    (SEQ ID NO. 128)
            CAACTACTTCATCCTGACGCCGGAACAANTTGACGCAGCGGTTCCGCTGACCAATACGGTCGGTCCCACGATGACCCAGTACTACATCATTCGCACGGAGAACCTG
            CCGCTGCTAGAGCCACTGCGATCGGTGCCGATCGTGGGGANACCCACTGGCGAACCTGGGTTCAACCAAACTTGAAGGTGATTGTTAACCTGGGCTACGGCGACCC
            GGCCTATGGTTATTCGACCTCGCCGCCCAAATGTTG
Clone Rv164 ::::::::::::Rv164SP6.seq::::::::::::
            AGCTTCCCGAGTTCGGCTTTGGATCAAGACCCCAGTCCGCGGGCGCGATCCGGCNGCTCGGTGACTACATCAAGCCACAAATCGACGGCTTTCGGGGTGCCGATAC    (SEQ ID NO. 129)
            CGATGACGTGGCGGATGTCGAGTGTTGAGTTCTCGGCGGGGCGGATGCTCACCTGGCGATCACCTGCCTCTCGTTGACGATCGATCGTCTATGCCGCCGTCTCTGC
            GGGAACAGGCCNCCAGTACATCGCCACAGACGGGATCCACCCGCATTTCGGCTACGGTTGCTCGTTTCGGTGTTCGGACTAGTCGGTCCTGGTGACGTGCCGGTGA
            TGCGGACCGGTCCTAGCACTGACCAATGGCCAAAATGCGGGC
            ::::::::::::Rv164T7.seq::::::::::::
            CGGGGGGCCTCTTAATAGTGTAGGAAAGAAGCTCTACATATTCAGGAGGATTCACCATGGCTCGTGCGGTCGGGATCGACCTCGGGACCACCAACTCCGTCGTCTC    (SEQ ID NO. 130)
            GGTTCTGGAAGGTGGCGACCCGGTCGTCGTCGCCAACTCCGAGGGCTCCAGGACCACCCCGTCAATTGTCGCGTTCGCCCGCAACGGTGAGGTGCTGGTCTGCCAG
            CCCGCCAAGAACCAGGCAGTGACCAACGTCGATCGCACCGTGCGCTCGGTCAAGCGACACATGGGCAGCGACTGGTCCATAGAGATTGACGGCAAGAAATACACCG
            CGCCGGAGATCAGCGCCCGCATTCTGATGAAGCTGAAGCGCGACGCCGAGGCCTACCTCGGTGAGGACATTACCGACGCGGTTATCACGACGCCCGCCTACTTCAA
            TGACGCCCAGCGTCAGGCCACCAAGGACCCGGCCAGATCGCCGGTCTCACGTGCTGCGG
Clone Rv165 ::::::::::::Rv165SP6.seq::::::::::::
            ATACTCAAGCTTCATAACAGGCCTGTTGTGGGCGCACCCGGCTCGCCGAGTTCTGCACGCACCGCCTCAAGTGCGGCCCGCACCGCCGGCATCTCCCGGTCACGCA    (SEQ ID NO. 131)
            GGGCCGCGGCCCGCGCCGCAGCGACGGCGTGTTCGCGCAGTTCGCCGTCAATGATGCTGACCTGATCGGCCACCCGGGCGTTCTCGGCGTCTTCGCGTTCACTAAT
```

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | CGCGGTGCTCAGCAGCGTCTCGACAGCCACCACCCGAGTGGCGACCAGCTGCTCCACCACGGACCGCAGCGATGCCGTCACCTCACCCGTCCAGCGGTCCACCACG | |
| | ACACGGTCGTGCACCAGCGCGCGGGCATTCACCACCCAGGCGGTCACCGCCAGGCCGATCGCCACACCCGCCACCATCCCCGATGCAGCCAGGCCGGGAGTAAGA | |
| | :::::::::::::Rv165T7.seq::::::::::::: | |
| | CTGGTGCTGGACGGAGCCTAGTACAACTTCCTCTCCAATGCTCTTGCCCCGATCGCGGCGACCAGGATGACCCAGGACATCCTGCCGCCCGAAGTACTGGAAAAGC | (SEQ ID NO. 132) |
| | TCACACCCGAGTTCGTCGCACCGGTGGTGGCCTACCTGTGCACCGAGGAGTGTGCCGACAACCCATCGGTGTACGTCGTCAGTGGTGGTTAGGTGCAGCGAGTTGC | |
| | GCTGTTTGGCAACGACGGCGCCAACTTCGACAAACCGCCGTCNGTACAAGATGTTGCGGCGCGGTGGGCCGAGATCNCCGATCTGTCCGGTGCGAAAATTGCTGGA | |
| | TTCAAGTTGTAGAACTAAAT | |
| Clone Rv166 | :::::::::::::Rv166SP6.seq::::::::::::: | |
| | ATACTCAAGCTTTTCCGGCGTCGTCCACCTGACCCAAAAAGCGCAGGTGCGCCGCCAAACGGCCCGCCTGGCCGCGCAACTGGTCGGCGTCGCCGTGGCCGACAAT | (SEQ ID NO. 133) |
| | CAGTAGCTGGACATCCGGAAACCGCTGCACCACCTTCGGCAGCGCGTCAAGCAAAAACGGCCATTCC | |
| | :::::::::::::Rv166T7.seq::::::::::::: | |
| | TTTCAGATCTCATTTTTATGACATGACTGGAGATCTGTCTAGATTGCAGCTCCTGTGAGCGTGGGTACCGGATTCAAGCCGGTCGGTCACGCCGCGGTGGTACCGG | (SEQ ID NO. 134) |
| | CTTTGCGGCAGTGCTCGGCCTCGAGTTCGGCGATCGCGCGCGAAGTGCGTTTCGCGCACCAAGATCGCGGCCTAATGGCCGGCGATGACCGCGATGACCAGCGCGA | |
| | TCCAGGAAAAACCGTTCCAACCAGTGCTGGGCGGCCATCCCCG | |
| Clone Rv167 | :::::::::::::Rv167SP6.seq::::::::::::: | |
| | ATACTCAAGCTTCCCGACCACAAGTTGAACAGCACCGATTTCGGCGAGCACTTCGTCAACTTCCAGGGTGCCCGCACCAAGTATTTCGACAAGTATTTCCGTCGGG | (SEQ ID NO. 135) |
| | CCGCCGCCGCCGGCGCGCGGCAGGTGGTCATCCTGGCGGCGGGGCTGGACTCCCGCGCGTACCGGCTGCCTTGGCCCGACGGGACCACGGTTTTTGAGCTGGACCG | |
| | CCCGCAGGTCCTTGATTTCAAGCGCGAGGTGCTCGCCAGCCACGGTGCCCAACCGCGCGCCCTGCGCCCGCGA | |
| | :::::::::::::Rv167T7.seq::::::::::::: | |
| | GTGTGCTGTCAATTCAGAGCTGAGCCTGATGCACTCAACTTACTGAGCATGCTAACGCTGGTCGTGCGGGTCTTGTTCCCGCGTGTCGGCAGGGCACACGCTCGGG | (SEQ ID NO. 136) |
| | GCGTAGCTGGGAGAGGCCCCGGTCAAGCCCGGAGAGCAGTGCTCAGTCCGCCAGCTTGACCGACTTTCGATGAGAACGCGCTTCTCGCCGTATTGAACTGGCGTGC | |
| | TGACGGTCGCTGAGCAGCGCTCGCCGAGTGCGGCCGCTGATTCTTTCATCGAGCCAGGAGGCGCATTCGTGTTCGGCCGCCTGCGGGTCGGCCCCATCGTCGACGC | |
| | GATCCGTCACCCACTCCTCGATCAGGTCTGCCTCATCGAACGGGCCAACGGTGCTGTCGGAGTATGTGTGCGTGGGCACGGCGAGCCGGGTGCTGTGGTACACCCA | |
| | CCGTTGCATGACCAAGTTGACGCCTGACTGGCTGAGCACCGCGATCCGCTCACAGGTCGGAACGTTGGTG | |
| Clone Rv169 | :::::::::::::Rv169SP.seq::::::::::::: | |
| | ATACTCAAGCTTTTGGTCTAGCCGGCCGAGCCCGATACAGGTGTCATTGGCCACCGGCGGCGGCTGTCCGGGAAATGGCGGGTCCCCGGTGGTTTTGCTGAGGAGT | (SEQ ID NO. 137) |
| | GCTGAACCGTATGCGAAGTGGGCGGCGTCAGACTCCACCCAGCCAGCAGGCAGCGCGAAACTGAATCCTCCAACCGGGTTGTCGATCCGGACAGGTTGGGGTGCGT | |
| | TTGGGGCAATGACAGGTGGCGGCGGTGCGTCCGGGTCGGCCGGCGGAAGTGCTGCGTTGGGATCGCCCGGCTGGGCATTCTGCGTGTTGGCGGCGGCCGGTGGTGG | |
| | GGGGGCAACAGGTGTCTCCGGTGCGGGTGGCGCTGCACC | |
| | :::::::::::::Rv169T7.seq::::::::::::: | |
| | GGGGCCACTCCGCACAATCTGTACCCGACCAAGATCTACACCATCGAATACGACGGCGTCGCCGACTTTCCGCGGTACCCGCTCAACTTTGTGTCGACCCTCAACG | (SEQ ID NO. 138) |
| | CCATTGCCGGCACCTACTACGTGCACTCCAACTACTTCATCCTGACGCCGGAACAAATTGACGCAGCGGTTCCGCTGACCAATACGGTCGGTCCCACGATGACCCA | |
| | GTACTACATCATTCGCACGGAGAACCTGCCGCTGCTAGAGCCACTGCGATCGGTGCCGATCGTGGGGAACCCACTGGCGAACCTGGTTCAACCAAACTTGAAGGTG | |
| | ATTGTTAACCTGGGCTACGGCGACCCGGCCTATGGTTATTCGACCTCGCCGCCCAATGTTGCGACTCCGTTCGGGTTGTTCCCAGAGGTCAGCCCGGTCGTCATCG | |
| | CCGACGCTCTCGTCGCCGGGACCCAGCACGGAAT | |
| Clone Rv16 | :::::::::::::Rv16SP6.seq::::::::::::: | |
| | TTCTNTCTTCCCNNATTCGTNNNTCTCNTACTACCNGGGCCNCAAAACACCTTGGCNAACGCTCAAAGGCGNTACNGGCACCAAGGCCCCACACGTCACCCTGTGA | (SEQ ID NO. 139) |
| | CCTCCTGCGCCGACCCCGCCCGAGGTCCTGGCCGTTACCACTGAACGGGCGAGCCGGGAGTCTGGTACGCATCGAACAAAGAGCAAGGTGCATGGGCGGAGTTGTT | |
| | CCGCCNCTTTTTTTATGACGGGGTCGATCCATTCGAGGTCCGTCGCCGCGTCGGTCGAGTGGCGGTCACACTCCAGGTACTCGACCTCNCAGACGAGAGGACTCGA | |
| | TCCCATCTANGTGTGGACNAAACAGATCTTCTGTCCGACGACTACACACCACCCAGGCCATCGCCGCCGCCCGCGATGCCAACTTCNACNCCGTNCTGGCCCCGGC | |
| | GGCGGCGCTCCCCGGTTGTCAAACACCTGCCGTGTTCGTTCACNCACTGCCCAACATCNAGCCCGANCNATCCNAGGTCCGTCCAACGCCTCCGCGGCTCNCCAAC | |
| | CTNCTCCCNCTGATCNTCCGCACCAAACACATGCCCGACTCCNTGCNCCNATTGCTTGNATCCCT | |
| | :::::::::::::Rv16T7.seq::::::::::::: | |
| | CCGCTATCGGTCGGTGTGCTTGGCGGCGTCGGTATCAACACCGCCCACGAAATGGGGCACAAGAAGGATTCGCTGGAGCGGTGGCTGTCCAAGATCACCCTCGCCC | (SEQ ID NO. 140) |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | AGACCTGCTACGGGCACTTCTACATCGAGCACAACCGTGGCCATCACGTCCGGGTGTCCACACCGGAGGACCCGGCGTCGGCGCGGTTCGGCGAGACGTTGTGGGA | |
| | GTTCCTGCCCCGCAGTGTTATCGGCGGCTTGCGCTCGGCCGTTCATTTGGAGGCCCAACGGCTGCGTCGGCTCGGCGTCAGCCCCTGGAATCCCATGACGTATCTG | |
| | CGCAACGACGTGCTCAACGCGTGGCTGATGTCGGTGGTGTTGTGGGGTGGGCTGATCGCGGTCTTCGGCCCGGCGCTGATCCCGTTCGTCATCATCCAGGCAGTCT | |
| | TCGGCTTCAG | |
| Clone Rv170 | :::::::::::::Rv170::::::::::::: | |
| | ATACTCATGCTTGCCGAAGTTCCGATGGGTCGCGCCGGCGANCCCAGCGAAGTCGCTAGCGTGGCCGTGTTCTTGGCTTCGGATCTATCCTCGTACATGACCGGCA | (SEQ ID NO. 141) |
| | CCGTGTTGGACGTGACTGGCGGCCGGTTCATATGACACCGAGATCATTGCCACGGTACGGCAATTCGTCAAGAAGGAAATCTTTCCCAATGCACCGGCCCTCGAAC | |
| | GTGGCAACAGCTACCCGCAAGAAATCGTCGATCGGCTGGGTGTTATTGGCTTCGTCGGTCGCCGGCTGCAAGGGTATCGACACCACCGAGTTCATTCTCCGGGCGT | |
| | GCC | |
| | :::::::::::::Rv170T7.seq::::::::::::: | |
| | GGCGTCAACGGTGTCGGCACCGGCGTCCTGCAGTTGGTAGGCCTGCAGTTTGTGCATCAGGCCGATGCCGCGGCCCTCGTGGCCACGCATGTACAGCACCACGCCG | (SEQ ID NO. 142) |
| | CGCCCCTCACGGGCGACCATCGCCAGCGCGGCGTCCAGCTGAGGCCCGCAATCGCAGCGGCGTGACCCAAACACATCGCCGGTCAAGCACTCCGAATGCACCCGGA | |
| | CCAGCACGTCGTCACCGTCGGCGTTGGGCCCGGCGATCTCGCCGCGGACCAGCGCGACATGTTCCACGTCCTCGTAGATGCTGGTGTAGCCGATGGCGCGAATCTC | |
| | CCATGACGAGTCGGAATCCGCGCCTCGGCG | |
| Clone Rv171 | :::::::::::::Rv171SP6.seq::::::::::::: | |
| | ATACTCAAGCTTCGGCCTCGCTGCAGGAGTGGGAGCCGCAGGGCTGGAAATCCGAAAAACGAGCCGGTGATCGCACTGTCGCCGATCGGGGCCGCACCTGGTTGGT | (SEQ ID NO. 143) |
| | GTTACCGATGAATCCGCACCCAAAATGTGGCTGCGGTGGCGTTTCTTGACTCCTTGGCGTCGACTCTTGTGGCAGCCACCGAGCGGTTGGTCCAGGATCTGGATGG | |
| | GCAAAGTTGTGCGGCCCGGCCGGTGACGGCCGATGAGCTGACCGAGGTCGACAGCGCCGTGTTGGCTGACTTGGAACCGACATGGATTCGCCCCGGTTGGCGTCAC | |
| | CTCAAGCATTTCAATGGTTAT | |
| | :::::::::::::Rv171T7.seq::::::::::::: | |
| | ATGCGTCACCCCGATGCGCCCAGATCGGGGCTTCGCAAATAAAGCACGAACAGGCGGGCAAAACGTCTATCTCGGAGCCGGAAGGGCAATCAGCCGACCGTCGACG | (SEQ ID NO. 144) |
| | AACGACACCGGCGATAACCACTTAGGCGTTGAACGGCCGGCCCAAACATTACGCCTCCGTTGATAAGGCTTTCGGTCTCTTCCCCGGTCATCCCAAGCAGGTTGCG | |
| | GCAAATTTGAACGCTTTCCTGTCCGGGCACCGGCCCCGGGCTTTGGGGTCCNTCCGA | |
| Clone Rv172 | :::::::::::::Rv172SP6.seq::::::::::::: | |
| | ATACTCAAGCTTCAATCGCGCCGCCACAATCCAAATATGCGTCTAGCGTCTCGATGAGCGTCGGTCCGGCATCGGCTAGGGGCCGCATCACGTCGGTATGCAGGGC | (SEQ ID NO: 145) |
| | CACGATCGCCCAAGGCGTCGCCCATCAAGGGCGCGTTCGGGCAAAAATTCCCCTATCCAGCACGGGCCGCGGCGCTCCGCNCCAGCCGGCGACGGCGTTCATCCCG | |
| | GAGATCGCCTCGCTAGCGCTGCGGTGCGCCGCGGTCAGCATGGGCGCCGTGGGGCCGATGACCACCGGGGCGT | |
| | :::::::::::::Rv172T7.seq::::::::::::: | |
| | TTCGGCGGGTCTGTAGATTGCGGTCGGCCACCCCACAGGCACTCATGAACCGCAGCCCACGATCGATCTCGGTGG | (SEQ ID NO. 146) |
| Clone Rv173 | :::::::::::::Rv173SP6.seq::::::::::::: | |
| | GCGCACCATCGCCAGTAGGTGCCCGTGGTCGGGCGCGTCGAGCCACCCGAGCGGAAACGCGAGTCCGAACAGCAACAGCAGGACGGGCGCAACCAGGGCGGTGACC | (SEQ ID NO. 147) |
| | ATGCCCCCGGCGCTGAACATCAACCACAGGAAGGGCTCCGCCGAGCGTCCGCGCGACC | |
| | :::::::::::::Rv173T7.seq::::::::::::: | |
| | CATCGTCGAACTTCGGTCCGGGTTGNTAGNACCGCAGCACCAAACGCACCCACCGACCCCCACGCTTCACGCCAACCCTTTAGTTCATTGGCGTGAACAGCAGCGT | (SEQ ID NO. 148) |
| | AGCCGGTTGCCCCGATATATGTGGAAAAATCGTTCGGACGTACAAAAAAAGTTCCTGACGCTGGCGTCAACTCGAAACTGCCTCGGAAGTCAATGATGATCCATCA | |
| | GTCAATATTAAAGTCG | |
| Clone Rv174 | :::::::::::::Rv174SP6.seq::::::::::::: | |
| | ATACTCAAGCTTGTCTGCTGCCTCAGCGTATGCATCCAACAGCGCATCGCGATCAACGATCAGGCGCGCCGATTTCGGGCCGCGGGCAGTGGCACTGGCCAGATGG | (SEQ ID NO. 149) |
| | CCGTTTTTTTCGAGAAACTTCAACGCCTGAGCGCTGCTTCCCATCGAGAGACCGGTGGCCTCTACAACCGATGCGACAGTTGGACCGGCGATGTTCGCCAGCAGCG | |
| | CTTCACATACGGCAAGTNTGGCGCGG | |
| | :::::::::::::Rv174T7.seq::::::::::::: | |
| | TTGTCCAGGCGGGGAATCGGGCAGGGAGACGACACCTTCGTTCGGTTCGATCGTCGCGAACGGGTAGTTGGCCGCGACCACGTTGTTTCGGGTCAGCGCGTTGAAA | (SEQ ID NO. 150) |
| | AGTGTCGACTTGCCGACGTTGGGCAGGCCCACGATCCCCAGGCTCAAGCTCACAGA | |
| Clone Rv175 | :::::::::::::Rv175SP6.seq::::::::::::: | |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | ATACTCATGCTTGGCGCCTGGGTGGCAGCCCACCTGCCCACCACACGGACCGCGGTGCGGACGCGGCTGACGCGCCTGGTGGTCAGCATCGTGGCCGGTCTGCTGT | (SEQ ID NO. 151) |
| | TGTATGCCAACTTCCCGCCGCGCAACTGCTGGTGGGCGGCGGTGGTTGCGCTCGCATTGCTGGCCTGGGTGCTGACCCNCCGCNCNACAACACCGGTGGGTGGGCT | |
| | GGGCTACGGCCTGCTATTCGGCCTGGTGTTCTACGTCTCGTTGTTGCCGTGGATCGGCGAGCTGGTGGGCCCCGGGCCCTGGTTGGCACTGGCGACGACGTNCGCG | |
| | CTGTTCCCCGGCATCTTCGGTCTGTTCGCCGTCGTGGTACCCTGTTGCCGGGTTGGCCC | |
| | :::::::::::::Rv175T7.seq::::::::::::: | |
| | CGCCAATTCACGATATCGTTAACCGATATCCCGAGCCGATAGCTGGCGGGCTCGGGTGGTGGCCAGCGGCGCTGCGACGAAAGGTGTGACCGTCATGAAACAGACA | (SEQ ID NO. 152) |
| | CCACCGGCGGCCGTCGGCCGTCGTCACCTGCTCGAGATCTCAGCATCCGCAGCCGGTGTGATCGCGCTTTCGGCGTGTAGTGGGTCGCCGCCCGACCCCGGCAAAG | |
| | GCCGGCCCGACACAACCCCGGAACAGGAAGTCCCGGTCACCGCGCCCGAAGNACTTGATGCGCGAACNCGGAGTGCTCCAAACGCATCCTGCTGAT | |
| Clone Rv176 | :::::::::::::Rv176SP6.seq::::::::::::: | |
| | ATACTCAAGCTTGGGCACTGACTTCGGTACCCCCTCCGCCTTTGGCCAGCAGCAGCCACAGCGCGGTTCGCGGACCGAACGTGGACATCAATAGCCCGGAATCGGT | (SEQ ID NO. 153) |
| | GTGTGCAAGTTGGTAAACGGTGTTGATCCCAAGCTTTGCCAGCCTTTTCGTAGTCTTGGGCCCCACACCCCACAGTGCTTCGACGGTACGGTCACCCATGATGGCC | |
| | ATCCAGTTGGCATCGGTGAGCTGATAAATGCCAGCTGGTTTCGCCAACCCGGTAGCGATCTTGGCGCGCTGCTTGTTGTCACTGATACCTATCGAGCAAGACAGCC | |
| | CGGTTTGCGACAAAATGACTTTTCGGATCTCTTCGGCGACTTCGATGGGGTCGTCGGGA | |
| | :::::::::::::Rv176T7.seq::::::::::::: | |
| | AAAGTCCTGTGCCGGTTCGCTAAACACCCGGCGGACACTCAGACGGTGCTGGTGGTGCGGCATGGCACCGCGGGCACCAAAGCGCACTTCTCCGGGGGACGACAGC | (SEQ ID NO. 154) |
| | AAGCGACCGCTAGACAAGAGGGGTCGTGCGCAGGCAGAAACGTTGGTACACAGCTGCTGGCGTTCGGCGCCACCGATGTTTATGCCGCCGACCGGGTGCGCTGCCA | |
| | CCAGACGATGGAGCCACTCGCCGCGGAACTGAACGTGACCATACACA | |
| Clone Rv177 | :::::::::::::Rv177SP6.seq::::::::::::: | |
| | ATACTCAAGCTTGGGTTCCACGCCCGCGCAGCCACGCCGTCACCTTTCCACGAGACCTCACCTGCCGATCCGAAATGGAATCGGCCGTGACGGAATTGGCGCACCG | (SEQ ID NO. 155) |
| | AACACCCAACGAGGTGGTGGCTTCGTCGCGAACCGTCACCCGAGTCGCGGCCACCGTGCGCACGGCGACGTTCTACACCCGCACCAAGATCCGAAAGCTGCAAGCT | |
| | CCCAGCACCGATCCCGACGTCATCACCGCTGCCGCCCGGCACGTCCTTGACCTATTCGAGCTGGATCGGCCCGTCCGGTTGCTGGGAGTGCGGTTAGAACTGGCCT | |
| | AGAACCGGCGGGCACACCGCNCCTCCCGCCCCGCAATTCTTGACCGCNCCGGCC | |
| | :::::::::::::Rv177T7.seq::::::::::::: | |
| | CGCGGTTGGCGTAGTTGGACGGGTCGCCCTCCGAGGCCAATGATGACGATGACCACGCCGATCACGATGGCCACCGAGAGGGACAACAACAGAAAGCTGACGAATC | (SEQ ID NO. 156) |
| | CCTCCTTGGCGGCCGGGGCTTTGTGGTCGCCGGTCGCGATGGGCGCGAATTTACGGCCCGCTCCCCCAGGCCGCCGCGAAGCAGGGTCCCCAGCCAGTTGGCGTAG | |
| | GCGGAATTAACGATCAGCGCCACCGCGATAACCTGCCATGCCTCGGGCATATCGATGTGCGGCCAGAACAGGCCGAAC | |
| Clone Rv178 | :::::::::::::Rv178SP6.seq::::::::::::: | |
| | CCAACAAGAGCATCGGGACATACGGAGTCAACTACCCGGCCAACGGTGATTTCTTGGCCGCCGCTGACGGCGCGAACGACGCCAGCGACCACATTCAGCAGATGGA | (SEQ ID NO. 157) |
| | CAGCGCGTGCCGGGCCACGAGGTTGGTGCTCGGCGGCTACTCCCAGGGTGCGGCCGTGATCGACATCGTCACCGCCGCACCACTGCCCGGCCTCGGGTTCACGCAG | |
| | CCGTTGCCGCCCGCAGCGGACGATCACATCGCCGCGATCGCCCTGTTCGGGAATCCCTCGGGCCGCGCTGGCGGGCTGATGAGCGCCCTGACCCCTCAATTCGGGT | |
| | CCAAGACCATCANCCTCTGCAACAACGGCGACCCGATTTGTTCNGACGGCAACCGGTGGCGAGCGCACCTAGGCTACGTGCCCGGGATGACCAACCAGGCGGCGCG | |
| | TTTCGTCGCGAGCAGGATCTAACCGCGAGCCGCCCATAGATTCCCG | |
| | :::::::::::::Rv178T7.seq::::::::::::: | |
| | TAANACCCGTGTAATTTGGGATGGGCAAAAAGGCCAAGCACCGCGTGGCCACGAACGCCGGGAGGGACAATCTCGGGCGGCTAGGGCTTCTCGCGGGAAGGCCCGA | (SEQ ID NO. 158) |
| | ACGTACGGCGTTTCAACACGTCGCGTCNCCCTCCGACCGCGAACATTCGGGGATGGCAGCAACCTGGTAGCNCCCTGGCCGGGCGATGATCTGCAGCGTCGCCGCG | |
| | GGTAGTCGCCGCCCGGGCGGCTACAGTCTGAAACGCGATGACCATCGATGTGTGGATGCAGCATCCGACGCAACGGTTCCTACACGGCGATATGTTCGCCTCGCTG | |
| | CGCCGGTGGACCGGTGGGTCTATCCCGGAGACCGACNTCCCGATCGAAGCGACCGTCTCCTCGATGGACGCCGGCGGCGTCACCCTGGGTTTGCTCACCGCCTGGC | |
| | GTGGCCCCAA | |
| Clone Rv179 | :::::::::::::Rv179SP6.seq::::::::::::: | |
| | GTCCGCAAAAGACTCAGCGGCCGACTTTGCTCGCAGCTGGCGGTACCGCGCCACCGATTCGATGCCGTGGTCGCGGAAGAATGCCTCCCGAAATCGCACGGCCGAC | (SEQ ID NO. 159) |
| | TCCAGTTCGGCGAGCATCCGCGATGCCACGTGCGGCTGCGCCCTGCCGGCCACGGCACCCACATGCGGCAGTTCGTCCACCTGGGCCAGCGCCCCGCCGCCGAAGT | |
| | CCAAACAATAGAACTGCACCCGGCCCGCATCGTGGGTAGCAGCCAACGCCATGATCAGCGTCCGCAGCGCGGTTGACTTGCCCGTTTGCGGTGCACCTACGACCGC | |
| | GACATTGCCTGCGGCCCCGGACAAGTCGATCGTCAGCGGCACCCN | |
| | :::::::::::::Rv179T7.seq::::::::::::: | |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | CGTGGCCACGAACGCCGGGAGGGACANTCTCGGGCGGCTAGGGCTTCTCGCGGGAAGGCCCGAACGTACGGCGTTTCAACACGTCGCGTCGCCCTCCGACCGCGAA | (SEQ ID NO. 160) |
| | CATTCGGGGATGGCAGCAACCTGGCAGCTACCTGGCCGGGCGATGATCTGCAGCGTCGCCGCGGGTAGTCGCCGCCCGGGCGGCTACAGTCTGAAACGCGATGACC | |
| | ATCGATGTGTGGATGCATCATCCGACGCAACGGTTCCTACACGGCGATATGTTCNCCTCGCTGCGCCGGTGGACCGGTGGGTCTATCCC | |
| Clone Rv17 | :::::::::::::Rv17SP6.seq::::::::::::: | |
| | ATACTCAAGCTTTGCGGCGGGCGCCGAAATGTGAACGCACCAAACCCGCCCGCTGCGGGTCGGCGGGCCACTCGACCTCGAATTTCGCCGCCGTGACCATCCAGCC | (SEQ ID NO. 161) |
| | CGACGGCAGTTGGGCACCCGGCCCCCCGGTCGCGGCATAACTGTTGGCGTCGCCGTCATAAAGCTCGAACAGCACCGAAACCGACTCCACCACCGGCCGGTGCGCC | |
| | TCAAAATCCACGCCGATCTCCACATACCGGGAAAACGTCGGTGTCCCATCGGGTTTCGGCTTGCCCGCCAGCTGCACACCACCGGTGGCCTCGGCCACCTTCGCGG | |
| | CCTGAGCGCAGCTACNCATCCTGACGATCATCACCCCGCCCCCGGCTCACGCTTGGCCTCCGTGACCGCACGCATCGCCCGGTTGCGCGCACCGCGACGCCCGTAC | |
| | AGCCGCGCGCAC | |
| | :::::::::::::Rv17T7.seq::::::::::::: | |
| | AGCTTGCCGGGACTGCGGAACAGAAGCGGCGGTTCCTACCGCGGTGTGCGGCCGGCGCGATATCGGCCTTTTTACTAACCGAACCCGATGTGGGCTCCGATCCGGC | (SEQ ID NO. 162) |
| | GCGCATGGCATCGACGGCGACGCCGATCGATGACGGCCAGGCTTACGAGCTTGAGGGTGTGAAGTTGTGGACCACCAACGGTGTGGTAGCGGACCTGCTAGTGGTT | |
| | ATGGCGCGGGTACCGCGCAGTGAAGGGCACCGAGGGGGAATCAGCGCCTTTGTCGTCGAGGCTGATTCGCCCGGGATCACCGTGGAGCGGCGCAACAAGTTCATGG | |
| | GACTGCGTGGCATCNAAAACGGCGTGACCCGGCTTCATCGCGTCNGGGTGCCCAAAGACAACTTGATCGGCA | |
| Clone Rv180 | :::::::::::::Rv180SP6.seq::::::::::::: | |
| | CTCAAGCTTGGCGATGCGGGCTGGCCAAAACTGGCCGGGCGGGGGTTGGCTTGTTCAATCAAGGGTGGGTTGCCG | (SEQ ID NO. 163) |
| | :::::::::::::Rv180T7.seq::::::::::::: | |
| | CCGAAGGCCCGTTCCCGGGCGTTCAGCAAGCGATCGTCGGTTGGCCCACTGCGGGTCGAATCTTGCGGCCGCGCCGGTCGTGGAACGCCCAGGTCACCCGGCGGCG | (SEQ ID NO. 164) |
| | TACC | |
| Clone Rv181 | :::::::::::::Rv181SP6.seq::::::::::::: | |
| | ATACTCAAGCTTTTTCTGCTCATGAAGGTTAGATGCCTGCTGCTTAAGTAATTCCTCTTTATCTGTAAAGGCTTTTTGAAGTGCATCACCTGACCGGGCAAATAG | (SEQ ID NO. 165) |
| | TTCACCGGGGTGAGAAAAAAGAGCAACAACTGATTTAGGCAATTTGGCGGTGTTGATACAGCGGGTAATAATCTTACGTGAAATATTTTCCGCATCAGCCAGCGCA | |
| | GAAATATTTCCAGCAAATTCATTCTGCAATCGGCTTGCATAACGCTGACCACGTTCATAAGCACTTGTTGGGCGATAATCGTTACCCAATCTGGATAATGCAGCCA | |
| | TCTGCTCATCATCCAGCTCGCCAACCAGAACACGATAATCACTTTCGGTAAGTGCAGCAGCTTTACGACGGCGACTCCCATCGGCAATTTCTATGACACCAGATAC | |
| | TCTTCGACCGAACGCCGGTGTCTGTTGACCA | |
| Clone Rv182 | :::::::::::::Rv182SP6.seq::::::::::::: | |
| | CTCAAGCTTGGTGCCGACATGGCCGGGCTGGAGCCCGCGTATGGCAAGGTTCCGCTCAATGTGGTTGTGATGCAGCAGGACTACGTTCGCCTCAATCAGCTCAAAC | (SEQ ID NO. 166) |
| | GTCACCCCCGTGGCGTGCTGCGCAGCATGAAGGTCGGCGCCCGCACGATGTGGGCGAAGGCAACAGGTAAAAACCTGGTCGGCATGGGTCGAGCCCTCATTGGGCC | |
| | GTTGCGGATCGGGTTGCACCGCGCCGGAGTGCCGGTCGAACTCAACACCGCCTTCACCGATCTTTTCGTCAAAATGGCGTCGTGTCCGGGGTATAC | |
| | :::::::::::::Rv182T7.seq::::::::::::: | |
| | CCGAAGCGTGGGAAATCCTGACCGAATACCGCGACGTGCTGGACACTTTGGCCGGCGAGCTGCTGGAAAAGGAGACCCTGCACCGACCCGAGCTGGAAAGCATCTT | (SEQ ID NO. 167) |
| | CGCTGACGTCTAAAAGCGGCCGCGGCTCACCATGTTCGACGACTTCGGTGGCCGGATCCCGTCGGACAAACCGCCCATCAAGACACCCGGGGGAGATCGCGATCGA | |
| | AACGCGGCGAAACTTGGGCC | |
| | :::::::::::::Rv183SP6.seq::::::::::::: | |
| | CGACTCGACAAGCATTCTTGACAGTTGTTTTGGCTCGGCATGGTTAGCCAAGGTTCTGCGGTCCCACCAGATCATCTTGGTCCGGTAGCGCTCGTCCGGGTATGCT | (SEQ ID NO. 168) |
| | GCCGCCGGGATTCTCGCTGCTATTACTCCCCCGAAAAACGCCACCGGTCCAGCGCGTGGGCCGCCGCGGTCCCCATCACAAACTGAACCCCCAACAGGGGACATG | |
| | CTTAGCGGTAGGGCGCGCGCCAAGGCGGCAGCAATCGCATCACTGCGCTGCGCGTCACTATTAACCCACCCGGACTTCACTTCCACGACCCCGAATGGCGCCCGGT | |
| | CATTGATCATCTTGCGCACCGCGGATAATCCGGGATTGCCAGCCCATTCGACTACCGCATGCGAGTCATCGGCTGACCGCAGCGGTCCGATTACCCGAGCGCCCCG | |
| | ANTACATCTCCTCCAATATCAATGGGCGCAA | |
| Clone Rv183 | :::::::::::::Rv183::::::::::::: | |
| | GCGGTNTAGCTTCCCGTCGTACCGGCGACCGCCAGCCGAGAAGCTCGTTTTCCCAGTGTTGCTGGGGATTCTCACGCTGCTGCTGAGTGCGTGCCAGACCGCTTCC | (SEQ ID NO. 169) |
| | GCTTCGGGTTACAACGAGCCGCGGGGCTACGATCGTGCGACGCTGAAGTTGGTGTTCTCCATGGACTTGGGGATGTGCCTGAACCGGTTCACCTACGACTCCAAGC | |
| | TGGCGCCGTCTCGTCCGCAGGTCGTTGCTTGCGATAGCCGGGAGGCCCGGATCCGCAATGACGGATTCCATGCCAACGCTCCGAGTTGCATGCGGATCGACTACGA | |
| | ATTGATCACCCAGAACCATCGGGCGTATTACTGCCTGAAGTACCTGGTGCGGGTCGGATACTGCTATCCGGCGGTGACGACCCCCGGCAAGCCGCCATCCGTGCTG | |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | CTGT | |
| Clone Rv184 | ::::::::::::Rv184SP6.seq:::::::::::: | |
| | CTCAAGCTTGGGCGTGACGGCCACCGGGGCCACTCCGCACAATCTGTACCCGACCAAGATCTACACCATCGAATACGACGGCGTCGCCGACTTTCCGCGGTACCCG | (SEQ ID NO. 170) |
| | CTCAACTTTGTGTCGACCCTCAACGCCATTGCCGGCACCTACTACGTGCACTCCAACTACTTCATCCTGACGCCGGAACAAATTGACGCAGCGGTTCCGCTGACCA | |
| | ATACGGTCGGTCCCACGATGACCCAGTACTACATCATTCGCACGGAGAACCTGCCGCTGCTAAAGCCACTGCGATCGGTGCCGATCGTGGGGAACCCACTGGCGAA | |
| | CCTGGTTCAACCAAACTTGAAGGTGATTGTTAACCTGGGCTACGGCGACCCGGCCTATGGTTATTCC | |
| | ::::::::::::Rv184T7.seq:::::::::::: | |
| | CGGGTGTCATTGGCCACCGGCGGCGGCTGTCCGGGAAATGGCGGGTCCCCGGTGGTTTTGCTGAGGAGTGCTGAACCGTAGTCGAAGTGGGCGGCGTCAGACTCCA | (SEQ ID NO. 171) |
| | CCCAGCCAGCAGGCAGCGCGAAGCTGAATCCTCCAACCGGGTTGTCGATCCGGACAGGTTGGGGTGCGTTTGGGGCAATGACAGGTGGCGGCGGTGCGTTCGGGTC | |
| | GGCCGGCGGAGGTGCTGCGTTGGGATCGCCCGGCTGGGCATTCGGCGTGTTGGCGGCGGCCGGTGGTGGGGGGGCAACANGTGTCGCCGGTGCGGGTGGCGCTGCA | |
| Clone Rv185 | ::::::::::::Rv185SP6.seq:::::::::::: | |
| | NCTTGATATTGGCGTCAACGGTGTCGGCACCGGCGTCCTGCAGTTGGTAGGCCTGCAGTTTGTGCATCAGGCCGATGCCGCGGCCCTCGTGGCCACGCATGTACAG | (SEQ ID NO. 172) |
| | CACCACGCCGCGCCCCTCACGGGCGACCATCGCCAGCGCGGCGTCCAGCTGAGGCCCGCAATCGCAGCGGCGTGACCCAAACACATCGCCGGTCAAGCACTCCGAA | |
| | TGCACCCGGACCAGCACGTCGTCACCGTCGGCGTTGGGCCCGGCGATCTCGCCGCGGACCAGCGCGACATGTTCCACGTCCTCGTAGATGCTGGTGTAGCCGATGG | |
| | CGCGAAACTCCCCATGACGAGTCGGAATCCGCGCCTCGGCGACCCGCTCAATGTGCTTCTCGTGCTTGCGCCGCCATTCGATCAAGTCAGCAATGGTGATCAGCGC | |
| | CAGACCGTGCTCNTCGGCG | |
| | ::::::::::::Rv185T7.seq:::::::::::: | |
| | CATAAGGGCCGGCGTACCCGGTACCGGCCGCGGGCCTACCACGTGCCGGAACTGGAAGCGCAGTAAGCCCTCAACGCGCCACCGCTTTGGCCCGCGCGCCCGGCGT | (SEQ ID NO. 173) |
| | AGGCGCATCGGCGGTGGCCGTGGGGCGGCGCACTGCGACCTCACCAGCGGCTTTCGAGCTTTGTTCGATCAACCGGCCAGCATGGTCGAGGATGCATTCGAGACCA | |
| | TATTCGAAATTGGTTTCATCGGGGGCCCCGATCCGATGCCCCCTCCCAGTTGCGTGAGCAAGCAGCGGAGTCGTCGCGGGATCGATGGCCACGGGGTGTTCAATGG | |
| | CGGATGGTCCGCTGCCCGCCGACTGGCTCTTGCGGGAGAGCCGATCTAGCACCACCGATCCGCGCACGTGGACCGAAACCGCCGAGTAGATGTCGAAAGCGT | |
| Clone Rv186 | ::::::::::::Rv186SP6.seq:::::::::::: | |
| | CGTCCTTTTCCCCAAGATAGAAAGGCAGGAGAGTGTCTTCTGCATGAATATGAAGATCTGGTACCCATCCGTGATACATTGAGGCTGTTCCCTGGGGGTCGTTACC | (SEQ ID NO. 174) |
| | TTCCACNAGCAAAACACGTAGCCCCTTCAGAGCCNNATCCTGAGCAANATGAACAGAAACTGAGGTTTTGTAAACGCCACCTTTATGGGCAGCAACCCCGATCACC | |
| | GGTGGAAATACGTCTTCAGCACGTCGCAATCGCGTACCAAACACATCACGCATATGATTAATTTGTTCAATTGTATAACCAACACGTTGCTCAACCCGTCCTCGAA | |
| | TTTCCATATCCGGGTGCG | |
| Clone Rv187 | ::::::::::::Rv187SP6.seq:::::::::::: | |
| | CTCAAGCTTCATGTCCGTACGGCTCGGGTACGCTTCCGTCGCAGTGTGCGAGTGATAAATGACGACCGGGACCTCGTCGGCATCTTCCATAGCCCGCCACACCTTC | (SEQ ID NO. 175) |
| | AGTTGCTCACCGGAATCCAACCGGTAGAAGGTCGGCGAGCGCTCGGCATTGGTCATCGGGATATGCCGCTCGGGACGGTCAGAGCCCTCGGGTCCGGCCAGCACTC | |
| | CGCAGGCTTCGTCGGGGTGGTCGCGACACGCATGGGCCCCATCGCATTCAC | |
| | ::::::::::::rV187T7.seq:::::::::::: | |
| | NCGCCGCCAGCCACCACGCGCGGGTCGGGCGCCGGGCCCGGGCCGCCAGGCTGCTCCGCTCGGTGATGGCACGCCACCGCGACACCACCCGGCTGCGCTACGTCGA | (SEQ ID NO. 176) |
| | GCCATACCGGGCGGAGCTACATCGGCTCGGCCGCCCAGTGTTCGGGCCCTCTTTCGAGGTCGAGGTCGATACCGATTTGCGCATCCGCAGCCGCACCCTGGACGAC | |
| | AGAACCGTGCCCTACGANTGCTTGTCGGGCGGGGCCAAAGAACAGCTTGGCATCCTGGCGCGATTGGCCGGCGCGGCGCTGGTCTCCAAAGAAGACGCCCTTCCGG | |
| | TGCTGAT | |
| Clone Rv188 | ::::::::::::Rv188SP6.seq:::::::::::: | |
| | CGCCACGTTCATGGGCAACAACCCCGATCACCGGTGGAAATACGTCTTCAGCACGTCGCAATCGCGTACCAAACACATCACGCATATGATTAATTCGTCCAATTGT | (SEQ ID NO. 177) |
| | ATAACCAACACGTTGCTCAACCCGTCCTCGAATTTCCATATCCGGGTGCGGTAGTCGCCCTGCTTTCTCGGCATCTCTGATAGCCTGAGAAGAAACCCCAACTAAA | |
| | TCCGCTCGTTCNCCTATTCTCCAGCGCCGGG | |
| Clone Rv189 | ::::::::::::Rv18SP6.seq:::::::::::: | |
| | ATACTCAAGCTTCAACCGATTGACGCATTGTGCGAACTGACGGCGCCCGCGCATGGCCAATCCGGAAGACCATCATTGGCCAGTGGCCGGGCGCTAACAGGTTCCA | (SEQ ID NO. 178) |
| | GCCCCCCACCAGTGCCGCTCGAACATGCGGTGCAACCCATTCGCAGGCCGGCAGGGAAAGCACCGCGGAAGCCGCAAAGGGCTGCAGTTCCGCGCCCAATAGTGTC | |
| | GTCCGCAACCAGATGCGCTCGAAAACCGCGCCGGCAGTCAGCGCACCCGACGCGAGGTCGAGAGACGTCGTCAGCGCGCCCACATGGGGTGCCAATCGGCACGGCA | |
| | GGTAGGCCGCGCGCAACCCGAACGCGTGGTGCATGCCCACGGTCCGCAGGAGGCGCAGCACCCGCCAATGCCGAAGCCCACGAAACATCGGGCGCATCCACGCTTC | |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | AACCTC | |
| Clone Rv18 | ::::::::::::Rv18T7.seq:::::::::::: | |
| | AGCTTTTGGCAGGGTCTCCTTCGAATTCGGCGTGCACCGCTATGGGTTGCAGCAGCGGCTGGCGCCGCACACCCCACTGGCCCGGGTGTTTTCGCCCCGAACCCGG | (SEQ ID NO. 179) |
| | ATCATGGTGAGCGAAAAGGAGATTCGCCTGTTCGATGCTGGGATTCGCCACCGCGAGGCCATCGACCGATTACTCGCCACCGGGGTGCGAGAGGTGCCGCAGTCCC | |
| | GCTCCGTCGACGTCTCCGACGATCCATCCGGCTTCCGCCGTCGGGTGGCGGTAGCCGTCGATGAAATCGCTGCCGGCCGCTACCACAAGGTGATTCTGTCCCGTTG | |
| | TGTCGAAGTGCCTTTCGCGATCGACTTTCCGTTGACCTACCGGCTGGGGCGTCGGCACAACACCCCGGTGAGGTCGTTTTTGTTGCAGTTGGGCGGAATCCGTGCT | |
| | CTGGGTTACAGCCCGAATCGTCAC | |
| Clone Rv190 | ::::::::::::Rv190SP6.seq:::::::::::: | |
| | ATACTCAAGCTTTGTCACACCAACTGTTTCCACCAGGCGCTCCATCCGGCGAGTGGATACTCCCAGCAGGTAGCAGGTCGCCACCACGCTGGTCAGTGCGCGTTCA | (SEQ ID NO. 180) |
| | GCTCGCTTGCGGCGCTGCAGCAGCCAGTCCGGGAAATAGCTGCCCTGGCGCAGCTTGGGGATCGCGACTTCTATGGTTGCGGCACGGGTGTCGAAATCACGGTGGC | |
| | GGTAGCCGTTGCGCTGATTGGACCGCTCATCGCTGCGTTCGCGGTAGCCCGCCGCGCACAGGGCGTCGGCTTCAGCCCCCATCAAGGCGGCGATGAACGTCGAGAG | |
| | CAGCCCGCGCAGCAGATCCGGGCTCGCCTGTGCGAGTTGGTCAGCCAGAACCTGCTCGGTGT | |
| | ::::::::::::Rv190T7.seq:::::::::::: | |
| | CCTTAAGCCCCGCAGGGCCCGGCACGCGCGGTACCGCCCAGGTCGCCCAACAGATCGTCGATGTTCGCGTCGTCCGCCTCGCGCACGTGGTCTGTCACCAGTCAAC | (SEQ ID NO. 181) |
| | GTTAACGCCGCCGCACATGTCCTGCGGCCGGGCAAAAACGTGAAAAACGAGCGGGCGACTGCAATGTCATGACACCGACGGCCGCCGATGGGCCCAGGGTCTGGCA | |
| | GATTCGATCTGTGCGGCCAGTGCCAGCAGCGTCGCCTCGTCATACGGCCGGCCGACGAGTTGAACCGACATGGGCAGGCCGTCGCCGTCGAAGTCCCACGGCACCA | |
| | CGGCCGCGGGCTGGCCGGTCAGATTCCAGACTTGAAAGTACGGAACCCGCTGCACCACCAGCAGCAACGTCGAAACTGCACCCCGGCGTTGGTAGGCGCCGATGCG | |
| | GGACGGGCCGGTCGCGGCGCCTGGCGTCACAACTACGTCGACATCGTCGAAGATCGACTGGATCGGCTGCTCACACCACTCGGCGGCCGCAGGCCGCCATCCGCCG | |
| | TC | |
| Clone Rv191 | ::::::::::::Rv191SP6.seq:::::::::::: | |
| | AGCTTTTGAGCGTCGCGCGGGGCAGCTTCGCCGGCAATTCTACTAGCGAGAAGTCTGGCCCGATACGGATCTGACCGAAGTCGCTGCGGTGCAGCCCACCCTCAT | (SEQ ID NO. 182) |
| | TGGCGATGGCGCCGACGATGGCGCCTGGACCGATCTTGTGCCGCTTGCCGACGGCGACGCGGTGGGTGGTCAAGTCCGGTCTACGCTTGGGCCTTTGCGGACGGTC | |
| | CCGACGCTGGTCGCGGTTGCGCCGCGAAAGCGGCGGGTCGGGTGCCATCAGGAATGCCTCACCGCCGCGGCACTGCACGGCCAGTGCCGCGGCGATGTCAGCCATC | |
| | GGGACATCATGCTCGCGTTCATACTCCTCGACCAGTCGGCGGAACAGCTCGATTCCCGGACCGCCCAGCGCATTGGTGATGGAATCGGCGAACTTGGCCACCCGCT | |
| | GGGTGTTGACATCCTCGACGGTGGGCAATTGCCCCCGGTAACGTTTGCCGCCT | |
| | ::::::::::::Rv191T7.seq:::::::::::: | |
| | CGGTCCGACCCTGTTCGACGGCTACCTGAATCAACCCGATGCCACCGCCGCGGCGTTCGACGCCGACAGCTGGTACCGCACCGGCGACGTCGCGGTGGTCGACGGC | (SEQ ID NO. 183) |
| | AGTGGGATGCACCGCATCGTGGGACGCGAGTCGGTCGACTTGATCAAGTCGGGTGGATACCGGGTCGGCGCCGGTGAAATTGAAACGGTGCTGCTCGGGCATCCGG | |
| | ACGTGGCGGAGGCGGCAGTCGTCGGGGTGCCCGACGATGATCTAGGCCAGCGGATCGTTGCCTACGTAGTCGGCTCAGCGAATGTCGATGCGGACGGGCTTATCAA | |
| | CTTTGTTGCCCAACAACTTTCGGTGCACAAGCGCCCGCGCGAGGTGCGTATCGTANATGCGCTGCCGCGCAACGCCTTGGGGAAAGTGCTCCAGAACATTGCTGTC | |
| | AGAAGCTGANCTACGCGAATTATCGTGTTACGCTGGA | |
| Clone Rv192 | ::::::::::::Rv192SP6.seq:::::::::::: | |
| | ATACTCAAGCTTGCCGAAGTTCCGATGGGTCGCGCCGGCGAGCCCAGCGAAGTCGCTACCGTGGCCGTGTTCTTGGCTTCGGATCTATCCTCGTTCATGACCGGCA | (SEQ ID NO. 184) |
| | CCGTGTTGGACGTGACTGGCGGCCGGTCCATATGACACCGAGATCATTGCCACGGTACGGCAATTCGTCAAGAAGGAAATCTTTGGGAATGCACCGGCCCTCGAAC | |
| | GTGGCAACAGCTACCCGCAAGAAATCGTCGATCGGCTGGGTGTTATTGGCTTGCTCGGTCGCCGGCTGCAAGGGTATCGACACCACCGAGTTCATTCTCGGGCGTG | |
| | CCGGCGCATTCGAGCTGGCGGTGCGCGCTGCCCAGCACCGTCATAGGTACTTGACGATGGTCCACGTCGGACGAGCGCCTCCACGTCGCTGCCGAACGGTATGCAT | |
| | GGCGGCTACGATTCTC | |
| | ::::::::::::Rv192T7.seq:::::::::::: | |
| | CGGTGTCGGCACCGGCGTCCTGCAGTTGGTAGGCCTGCAGTTTGTGCATCAGGCCGATGCCGCGGCCCTCGTGGCCACGCATGTACAGCACCACGCCGCGCCCCTC | (SEQ ID NO. 185) |
| | ACGGGCGACCATCGCCAGCGCGGCGTCCAGCTGAGGCCCGCAATCGCAGCGGCGTGACCCAAACACATCGCCGGTCAAGCACTCCGAATGCACCCGGACCAGCACG | |
| | TCGTCACCGTCGGCGTTGGGCCCGGCGATCTCGCCGCGGACCAGCGCGACATGTTCCACGTCCTCGTAGATGCTGGTGTAGCCGATGGCGCGAAACTCCCCATGAC | |
| | GAGTCGGAATCCGCGCCTCGGCGACCCGCTCAATGTGCTTCTCGTGCTTGCGCCGCCATTCGATCAAGTCAGCAATGGTGATCAGCGCCAGACCGTGCTCATCGGC | |
| | GAACACCGCAATTCATCGGTGTTGCGCCATCGAGCCCTCATCTTTTTGGCTGACGATCTCGCAAATCGCCCCCGCGGGTTGCAGCCGGCAT | |
| Clone Rv193 | ::::::::::::Rv193SP6.seq:::::::::::: | |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

ATACTCAAGCTTTGGGTGAAAGCCGATCACCGGAAGCCGCATGATCAGCCACGTTTCGCGCCGCCCGGCATACGGCGGCGTACCGATCTCCGCGTCATACACCCGC (SEQ ID NO. 186)
GGGTAATCGCCGACGGTGCCGGTTCGCGAGCCGAAGGTGACGACGCTGATTGAATCGAGTTCCAGGTCCAGCGGGTGGCGCAGCAACGGCGCGAGCTCAACGACGT
CAATCACGTTGTCGCTTTCTACGGTCACCGACCCGGTGACCGTNCTCGCCCGGTGCGCTCGGCCGATAAGTTGCACCGCCACCACCGCGACACCGTCTTGCACGCG
GACCCACCCCCGGATCCGTTGTTGGCC
::::::::::::Rv193T7.seq::::::::::::
AGCTTGCTGGCATCCGCTCCAGTAGCGCCCCGCGCGTGGCTTCCAGCGCCCGCAGATGCTCCATGAGCCGGCCGGTCGAGTCGGCGCCGGCGTTCACCGCCACCCG (SEQ ID NO. 187)
CCAGGAGCTGGCGGCCAGCATCTCCGCCTTCACGCATTGCGCGATCACAGAGAGAATATACGTCTCATATTCGTTGGAGGTCGTCGCAGGCAATCGGTCGATGACG
GATTTGATGGCATCGAGCTGTGCTTCGGCGTAGCCCTCCAGCACGTCGGTATCGCTGTGGCGGTCCACGACGACCGCACCGGCGCGGCGGACAGCCGTCGGGTTGG
ACGNTGTGCGGCGATCAGTCCGGCCAGCTCCGCCTCGGGATCAGCGGC
Clone Rv194 ::::::::::::Rv194SP6.seq::::::::::::
ATACTCAAGCTTGCTGCAGCTTCCTATGACTGCTCCCGAAACCTGGGGGTGTGCCTGCTGTGTATGCACGGCATACGGACATCCTTCCCCTGAGACCCGCGGTCGA (SEQ ID NO. 188)
ACCAGCCACGTGTCCATCATCAGGGGTCAACCCCGGCCAAGGGCGACGGCACGCCAAGTTCGCCGACCGTTAACCTAGTGCTGTTAGCTTCATTTGCTGCGACCAA
AACAGCTGGTCGGCCGTTAGGAACTGAATTGAAACTCAACCGATTTGGTGCCGCCGTAGGTGTCCTGGCTGCGGGTGCGCTGGTGTTGTCCGCGTGTGGTAACNAC
NACAATGTGACCGGGGGAGGTGCAACCACTGGCCAGGCGTCGGCGAAGGTCGATTGCGGGGGGAAGAAGAACTCAAAGCCAGTGGGTCGACGCGCAGGCCAACGC
::::::::::::Rv194T7.seq::::::::::::
AGCTTGACGCGGAGACGGACACATTGCGAACATTGATGACAAAATAGAAATCATTGATGGTTTGAGTCACCAGGCCGATCAAGCCTTCGCCGAGCCAAATTCCAAT (SEQ ID NO. 189)
CAAGAGGCCCAAGCCCGTACCAATCAGCCCGGCAACGAGGGATTCCGTCATTATCAGCCAAAATAACTGCTCTCGGGTTACACCCAAACAGCGCAATATGGCGAAA
AACGGTCGCCGTTGCACGACATTAAATGTCACGGTATTGTAGATTAAAAAGATACCCACCAACAAGGCAATCAAACTGAGAGCGGTTAAATTGACCGTAAAAGCGT
CCGTCATCTGTTTGACGGTGTCCCGTTGGGTATCCGACGTTTCCATACGCACACCGGCCGGCAGTCTTTGTTGGATGCGTGTTGCAGTGGCCTCATCTTTGATGAT
CAAATCGATGTGGCTCAGTCTTCCGGGCA
Clone Rv195 ::::::::::::Rv195SP6.seq::::::::::::
ATACTCAAGCTTCGGCTCAGGCGGCGCTGCTGGTAAAGTCGCTGACCGGTGCAGGTTTCGACAATGTGGTGCCGGTTCGGCGGCTACGTGCCATCGAGACACTGGC (SEQ ID NO. 190)
GCAGGCTATCGCACCCGTTATCGGCTACGAGCAAATCGCGGTATCGCTTCTTGAGCATGAGTCGGCGACCGTCGTCATGGTCGACACCCACGACGGAAAGACGCAG
ATCGCCGTCAAGCATGTGTGCCGCGGATTATCAGGACTGACCTCCTGGCTGACCGGCATGTTTGGTCGCGATGCCTGGCGCCCGGCCGGCGTGGTCGTGGTCCGCT
CGGATAGCGAGGTCAGCGAATTCNCNTGGCAGCTCCAAAGGGTCCTGCCGGTGCCGGTCTTTGCGCAAACNAAGGCNCAGGTTA
::::::::::::Rv195T7.seq::::::::::::
TGATCGCGCATCACCTGCTTCATAAACTGGAAGCAGCGCAGCGCTTCCTTTTCGGCCGCAACATGAGCCAGCCTCTCGTCGGCGGTCGGGTGCAGGTGCTCGGGCA (SEQ ID NO. 191)
GCTCGGCCGCGACAGCCGCCTGACCCTGAAACCAGCTTCCATATCCCGCGACGAACGACGCCAGTCCGCTACGTAACCCCTCCGCGACTGTCCATGGACAACAGCG
CGTTCTCCACCGACCGGGCCCGGGTGTGGGGTGTTTCGGCGACCGGCAGCCAGGTGGTCCACACTGCCGACGGGCGCCGCGAGCCGTTCACCGACCAGGCCGCCGA
GCAAGTCCGCCCGATCGCATACTCCAACCGGTTGCGGTACTGCAGGTTCAGCTGGCGTACTCCTCGTCGCGCTCGGCGAGGTCTTGCTCCAGCACGTCGCANACGG
CAG
Clone Rv196 ::::::::::::Rv196SP6.seq::::::::::::
CAAAGCGCGAACTGCTCGCGGCAGCCCACGACGTGCTGCGTCGGATTGCCGGCGGCGAAATCAATTCCAGGCAGCTCCCGGACAATGCGGCTCTGCTGGCCCGCAA (SEQ ID NO. 192)
CGAAGGACTCGAGGTCACCCCGGTGCCCGGGGTCGTGGTGCACCTGCCGATCGCACAGGTTGGCCCACAACCGGCCGCTTGATGCCCGGTCGGCAAGCCCGGCAGT
TGCCAAACCCAGCGTGATCAGGCTCGGCTCGCGAGTTCCGGGAAGAAGTGGCTCCGCCTGATCACCTACCATCCGCCAGGATCTGCGTGTCTTCACCACGCCCGCC
AAGGAGGTTGTTGTGGTGCTATCGACCGN
::::::::::::Rv196T7.seq::::::::::::
CCGGAAGCCGCATGATCAGCCAAGTTTCGCGCCGCCCGGCATACGGCGGCGTACCGATCTCCGCGTCATACACCCGCGGGTAATCGCCGACGGTGCCGGTTCGCGA (SEQ ID NO. 193)
GCCGAAGGTGACGACGCTGATTGAATCGAGTTCCAGGTCCAGCGGGTGGCGCAGCAACGGCGCGAGCTCAACGACGTCAATCACGTTGTCGCTTTCTACGGTCACC
GACCCGGTGACCGTNGTCGCCCGGTGCGCTCGGCCGAAAANTTGCACCGCCACCACCGCGAAACCGTCTTGCACNCCGGAAGCCACCCCCGATCCGTTGTTGGGCC
AGGTTATTGGGT
Clone Rv19 ::::::::::::Rv19SP6.seq::::::::::::
CCGGAACCGCCGACGGCACGGTATAACGCCTCCGCATATGGGTCGACAACCAGCGGGTCGGACTTCTGGGCTTCTAGCGTTCGCGCNGTCGCGACAAACAGCGCGG (SEQ ID NO. 194)
TCGAACCGACACTCGTTGTGATGTCCTAGCTATCACGTTCGGTACGCACCCAATCGAGTCTAGCGCGGGTAGNTCAGCCCCGATCTCCANGCTCCGCCGAGCCAGG TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | CGC | |
| | :::::::::::::Rv19T7.seq::::::::::::: | |
| | CTGGTTTATGTCCCGTTGAAGTTCCATCACCCGATGTGGCGGGAGCACTGCCAGGTCGATCTCAACTACCACATCCGGCCGTGGCGGTTGCGCGCCCCGGGGGGTC | (SEQ ID NO. 195) |
| | GGCGCGAACTCGACGAGGCGGTCGGAGAAATCGCCAGCACCCCGCTGAACCGCGACCACCCGCTGTGGGAGATGTACTTCGTTGAGGGGCTTGCCAACCACCGGAT | |
| | CGCGGTGGTTGCC | |
| Clone Rv1 | :::::::::::::Rv1SP6D2.seq::::::::::::: | |
| | CCGAGCAGTTGGGAATCGCTCTGCANCAAACCAATATTCTGCGCGACGTCGCGCGACGAGCTGGACCGATTAGGCGTACGCCTCCGNCTGGACGACACCGGGGCAC | (SEQ ID NO. 196) |
| | TCGATGACCCCGACGCCTACGCTCGCAGGATATTGTTCGCCGGACCCCTCTCTAG | |
| | :::::::::::::Rv1T7.seq::::::::::::: | |
| | TATATAATACTCAAGCTTGCCGACGCCAACGCTCGCGCGATGTTGTTAGCCCGACCCGGCTCTTACATGGCACCGGTGCCCCACACGTCAGCCTGTGACGTCCTGC | (SEQ ID NO. 197) |
| | ACCGCGACTCTTTACATAGAATGTGGATTGCCGGATTGGGGATGTCCGGCATCGCTCAATCTGTAGTCCGCGTTGTCCCGCGAGGGCCATGTGGATGGGGGAAGG | |
| | ATCCGTGGCGTCCGGGATCACCATGGGG | |
| Clone Rv201 | :::::::::::::Rv201SP6.seq::::::::::::: | |
| | ATACTCAAGCTTGCCGAAGTTCCGATGGGTCGCGCCGGCGAGCCCAACGAAATCGCTAGCGTGGCCGTGTTCTTGGCTTCGGATCTATCCTCGTACATGACCGGCA | (SEQ ID NO. 198) |
| | CCGTGTTGGACGTGACTGGCGGCCGGTTCATATGACACCGAGATCATTGCCACGGTACGGAAATTCGTCCAGAAGGAAATCTTTCCCAATGCACCGGCCCTCGAAC | |
| | GTGGCAACAGCTACCCGCAAGAAATCGTCAATCGGCTGGGTGTTATTGGCTTGCTCGGTCGCCGGCTGCGAGGGTTTCTACACCACCGAGTTCATTCTCGGGCGTG | |
| | CCGGCGCATTCGAACTGGCGGTGCGCGCTG | |
| | :::::::::::::Rv201T7.seq::::::::::::: | |
| | GCACCGGCGTCCTGCAGTTGGTAGGCCTGCAGTTTGTGCATCAGGCCGATGCCGCGGCCCTCGTGGCCACGCATGTACAGCACCACGCCGCGCCCCTCACGGGCGA | (SEQ ID NO. 199) |
| | CCATCGCCAGCGCGGCGTCCAGCTGAGGCCCGCAATCGCAGCGGCGTGACCCAAACACATCGCCGGTCAAGCACTCCGAATGCACCCGGACCAGCACGTCTTCACC | |
| | GTCGGCGTTGGGCCCGGCGATCTCGCCGCGGACCAACGCGACATGTTCCACGTCCTCGTAGATGCTGGTGTAGCCGATGGCGCGAAACTCCCCANGACAAGTCGGA | |
| | ATCCGCGCCTCGGCGAACCGCTCAATGTGCCTCTCGTGCTTGCGCCGCCATTC | |
| Clone Rv204 | :::::::::::::Rv204SP6.seq::::::::::::: | |
| | TGGTCCGTGTGCGCATACCAATACAACGCGCCGGGCACCTGACGCGGCGGCCGCAACCAATCGGTGGCCATCGCCATCTTCTGCTACCCGGTCAACGGACGCACCT | (SEQ ID NO. 200) |
| | TCTCCTGGCCGACGTAGTGCGCCCACCCGCCGCCGTTGCGTCCCATCGATCCGGTCAAC | |
| Clone Rv205 | :::::::::::::Rv205SP6.seq::::::::::::: | |
| | GGCGTGTTGGCCACCGGGGCCACTCCGCACAATCTGTACCCGACCAAGATCTACACCATCGAATACGACGGCGTCGCCGACTTTCCGCGGTACCCGCTCAACTTTG | (SEQ ID NO. 201) |
| | TGTCGACCCTCAACGCCATTGCCGGCACCTACTACGTGCACTCCAACTACTTCATCCTGACGCCGGAACAAATTGACGCAGCGGTTCCGCTGACCAATACGGTCGG | |
| | TCCCACGATGACCCAGTACTACATCATTCGCACGGAGAACCTGCCGCTGCTAAAGCCACTGGCGATCGGTGCCGATCGTGGGGAACCCACTGGCGAACCTGGTTCA | |
| | ACCAAACTTGAAGGTGATTGTTTACCTGGGCTACGGCGACCCGGCCTATGGTTATTCGACCTCCCCGCCCAA | |
| | :::::::::::::Rv205T7.seq::::::::::::: | |
| | CGTCCGTGNCCCCTCAANCGCGTGNNGCCGAAGCGGCTGGTTACGACTCCCTGTTTGTGATGGACACTTCTACCAACTGCCCATGTTGGGGACGCCCGACCAGCCG | (SEQ ID NO. 202) |
| | ATGCTGGAGGCCTACACGGCCCTTGGTGCGCTGGCCACGGCGACCGANCGGCTGCAACTGGGCGCGTTGGTGACCGGCAATACCTACCGCAGCCCGACCCTGCTGG | |
| | CAAAGATCATCACCACGCTCGACGTGGTTAGCGCCGGTCGAGCGATCCTCGGCATTGGAGCCGGTTGGTTTGAGCTGGAAACACCGCCAGCTCGGCTTCGAGTTCG | |
| | GCACTTTCAGTGACCGGTTCAACCGGCTCGAAGAGGCGCTACAGATCCTCCAGCCAATGGTCAAGGGTGAGCGCCCAACGTTTTTCGGCGATTGGTACACCACCGA | |
| | ATC | |
| Clone Rv207 | :::::::::::::Rv207SP6.seq::::::::::::: | |
| | CCGCTTCCGTGTAACCGAGCANNGCGAGCGANCTGGCGAGGAAGCAAAGAAGAACTGTTCTGTCAGATAGCTCTTACGCTCAGCGCAAGAAGAAATATCCACCGTG | (SEQ ID NO. 203) |
| | GGAAAAACTCCAGGTAGAGGTACACACGCGGATAGCCAATTCAGAGTAATAAACTGTGATAATCAACCCTCATCAATGATGACGAACTATCCCCCGATATCAGGTC | |
| | ACATGACGAAGGGAAAGAGAAGGAAATCAACTGTGACAAACTGCCCTCAAATTTGGCTTCCTTAAAAATTACAGTTCAAAAGTATGAGAAAATCCATGCAGGCTG | |
| | AAGGAAACAGCAAAACTGTGACAAATTACCCTCAGTAGGTCAGAACAAATGTGACGAACCNCCCTCAAATCTGTGACAGATAACCCTCAGACTATCCTGTCGTCAT | |
| | GGAAGTGATATCGCGGAAGGAAAATACGATNTGAGTCGTCTGGCGGCCTTTCTTTTTCTCAATGTATGAGAGCG | |
| Clone Rv209 | :::::::::::::Rv209SP6.seq::::::::::::: | |
| | TGACACCCAACAGAGGGCACTTAAGATGGCAATGCGGCCGCCTACCTGCACGTTTTCGCGATGTCAGAGGATGCCGAGGGAGAACAATGCGAGCACGGCCGCTGAC | (SEQ ID NO. 204) |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | NTTGCTCACCGCTTTGGCGGCGGTGACATTGGTGGTGGTTGCGGGCTGCNAGGCCCGANTCNAGGCCGAAGCATATAGCGCGGCCGACCGCATTTCGTCTCGACCG | |
| | CAAGCGCGACCTCAGCCGCAGCCGGTGGAGCTACTGCTGCGCGCCATCACGCC | |
| | :::::::::::::Rv209T7.seq::::::::::::: | |
| | ACGGGCGACGCTGAGGTGGGCCCGCGGCTATTCATGCTGTCGTCCACGTCCAGCGACGCACTGCGCCAGACGGCCCGCCAACTAGCCACCTGGGTGGAAGAACACC | (SEQ ID NO. 205) |
| | AGGACTGCGTGGCGGCCTCGGATCTGGCCTACACGCTGGCGCGTGGCCGCGCGCACCGGCCGGTGCGCACCGCGGTGGTTGCCGCCAACCTGCCGGAGCTCGTCGA | |
| | GGGTTTGCGCGAGGTGGCCGACGGTGACCCCTCTATGACGCGGCGGTGGGACACTGTGATCTAAGACCGGTCTGGGTCTTCTCCGGGCAAGGGTCTCAGTGGGCGG | |
| | CGATGGGCACCCAATTGCTCGCCAGCGAACCAGTGTTCGCGGCCACCATCG | |
| Clone Rv20 | :::::::::::::Rv20SP6.seq::::::::::::: | |
| | ATACTCAAGCTTCGCGAGATCCGGATGGCACTCACGCTGGACAAGACCTTCACAAAATCTGAAATCCTGACCCGATACTTGAACCTGGTCTCGTTCGGCAATAACT | (SEQ ID NO. 206) |
| | CGTTCGGCGTGCAGGACGCGGCGCAAACGTACTTCGGCATCAACGCGTCCGACCTGAATTGGCAGCAAGCGGCGCTGCTGGCCGGCATGGTGCAATCGACCAGCAC | |
| | GCTCAACCCGTACACCAACCCCGACGGCGCGCTGGCCCGGCGGAACGTGGTCCTCGACACCATGATCNAAAACTTCCCGGGGAGGCGGAGGCGTTGCGTGCCGCCC | |
| | AGGGCGAACCGCTGGGGGTTCTGCCGCAGCCCAATGATTGCCGCGCGGCTGCATCGCGGGCGGCGACCGCCATTCTTCTGCGAATACGTCCAGGAGTACTGTCTCG | |
| | GGGC | |
| | :::::::::::::Rv20T7.seq::::::::::::: | |
| | AGCTTATGTGGCCGCCCACCTACCTTATCTAGCCTAGCTAACTAAATCCAGTGCCGACAGTGCGCGGCTGGCCACCCAGCATGAGGTTATGACCACGGCATATGCC | (SEQ ID NO. 207) |
| | AGCGCGCTGGCGGCGATGCCGACGCTGACCGAGTTGGCCGCTAATCACACCAGCCATGCGGTGTTGCTGGGAACGAATTTCTTTGGAATCAATACGATCCCGATCG | |
| | CGCTCAATGAGGCCGACTATGCGCGGATGTGGATTCAGGCGGCCACCACGATGAGTATCTATGAGGGCACCTCCGATGCGGCGCTGGCGTCNGCACCGCAAACCAC | |
| | ACCGGCTCCGGTACTGTTCAACGGCGGTGCTGGCGTTTGCCAGCGCCTGCCGGCGATCTC | |
| Clone Rv214 | :::::::::::::Rv214SP6.seq::::::::::::: | |
| | ATACTCAAGCTTGCCACCCATGCCGAGCAAGGTCGACTCAGCGATGACGAATTGTTCTTCTTCGCGGTGTTGCTGCTGGTTGCGGGCTATGAGAGCACTGCTCATA | (SEQ ID NO. 208) |
| | TGATTAGCACNTTGTTTCTGACGCTGGCCGACTATCCAGATCAGCTGACACTCCTTGCGCAGCAACCAGACCTGATCCCGTCGGCGATCGAGGAGCACCTCCGCTT | |
| | TATATCGCAATCCAAAACATCTGCCGCACAACGCGCGTCGACTATTCGGTCGGTCAAGCGGTCATCCCGGGA | |
| | :::::::::::::Rv214T7.seq::::::::::::: | |
| | CCGGGGTAGAACGATGCGATCTGGGCCATGTCGACATCGGTGGTACAGGTAAACCGCGCCGTGTGCGCGGTCTCGGAGATCAGAACGTGGTCGCAGTTGACACCGC | (SEQ ID NO. 209) |
| | GGGCTTTCAGCCAGTCGCGATAATCGGCGAAGTCGGCGCCTGCCGCCCCAACTAGCGCGACCTCGCCACCTAGCACACCGATGGCGAAGGCCATGTTTCCGGCCAC | |
| | GCCGCCGCGGTGCATCATCAACTC | |
| Clone Rv215 | :::::::::::::Rv215SP6.seq::::::::::::: | |
| | ATACTCAAGCTTGGCGGCAACGCCACTACCGGGCTCACCAGGTCCTGTGCCGCCACCGCCGGCGCCGAAAGCACCATCAGGTCGTAGTTGTCTGGACGTTCGACAC | (SEQ ID NO. 210) |
| | CGTAAGCGAACACAATGCCGCCGCCCATGCTGTGCCCGAGCACGATGCGCTTGCACCCGGGATATTCCCGGGTGGCGATCCCAACGAGGGTGTCGAAGTCAGCGGT | |
| | GTATCTGAGATGTCTCTCACTATCATCCGTTTGGCACCCGAGCGGGCATGCCCGCGGGGGGTCAAC | |
| | :::::::::::::Rv215T7.seq::::::::::::: | |
| | GTCGACGGCATCAAGGTCCGCAGTGATGGTGTTCATCTCACCCAGGAAGGCGTGAAGTGGCTGATACCGTGGCTTGAGGATTCGGTGCGGGTCGCCAGTTAATCCG | (SEQ ID NO. 211) |
| | CCGTGTGCTCCGGATGAGCGCGACGGTAACCCTGGAATTGTGCTGTGTGCTGGCTGTGTCGTTGTGATGAGCCTGTCTAAGTGGTGCGTAACCGTTTGACGAGCCG | |
| | CGGCCTCGCTGCAAACATTGAAGCCCGCACGTCTGGGTTTGTATTTACACAACGAGGGCGCTCCCCGATCTGGCGCGCGCAACGAGGTGCNCACTATCCATTCGAG | |
| | GTGAACTGGACTCCTTGATGCTCATGCCGGTGCGGTTTTGTC | |
| Clone Rv217 | :::::::::::::Rv217SP6.seq::::::::::::: | |
| | ATACTCAAGCTTGCGTTCGATGAAGTAGTCGTCGGTCAGCGCCGCCTCTTCGAGCTCCTTGGCGATGCCCAGCAAGGAGTCATCGCCGCCGAGCTTGGCCAGGATC | (SEQ ID NO. 212) |
| | TTGTCGGCCTGTTCCTTGACGATGCGGGCCCGCGGATCGTAGTTCTTGTAGACACGATGACCGAAACCCATCAATTTGACCCCGGCCTCGCGGTTCTTGACCTTGC | |
| | GTTACAAACTCGCTGACGTCGTCGCCGCTGTCGCGAATGCCCTC | |
| | :::::::::::::Rv217T7.seq::::::::::::: | |
| | NGTCAAGCCGAGCATGCGCGAGGNAACGACGAACCCAACAAGCCATGGTGGTTGGCGCCGTCGAGAGGTCGGCGGTCGCCACAACGGGAAGATCGCCTTGAGCGTC | (SEQ ID NO. 213) |
| | GCTCGACCGCCGCCTCGAGTTGGGTCATAACGAAGTAGCTGATGCCGATCATGTCGACGTTTCCGTCGCATCAGCGTGCAGCGGCGACCCACTCGACGAGGTCTCG | |
| | GTGCCGCCGCGGCCAGGGCACCAGCAGTGACGATTCCAGGCGCCGTCGGG | |
| Clone Rv218 | :::::::::::::Rv218SP6.seq::::::::::::: | |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | CGATAATCGCTTCCGGTAAGTGCAGCAGCTTTACGACGGCGACTCCCATCGGCAATTTCTATGACACCAGATACTCTTCGACCGAACGCCGGTGTCTGTTGACCAG | (SEQ ID NO. 214) |
| | TCAGTAGAAAAGAAGGGATGAGATCTCCCCGTGCGTCCTCAGTAAGCAGCTCCTGGTCGCGTTCATTACCTGACCATACCCGAGAGGTCTTCTCAACACTATCACC | |
| | CCGGAGCACTTCTAGAGTAAACTTCCCATCCCGACCACATATAGGCTAAGGTAATGGGCATTACCGCGAGCCATTACTCCTACGCGCGCAATTAACGAATCCACCA | |
| | TCGGGGCCGCTGGTGTCN | |
| Clone Rv219 | :::::::::::::Rv219SP6.seq::::::::::::: | |
| | NAATACTCAAGCTTTCTCGTGATTACCACCCGTGTAATTTGGGATGGGCAAAAAGGCGAATCACCGCGTGGCCACAAACGCCGGGAGGGACAATCTCGGGCGGCTA | (SEQ ID NO. 215) |
| | GGGCTTCTCGCGGGAAGGCCCGAACGTACGGCGTTTCAACACGTCGCGTCGCCCTCCGACCGCGAACATTAGGGGATGGCAGCAACCTGGTATCACCCTGGCCGGG | |
| | CAATGATCTGCAGCGTCGCCGCGGGTAGTGNCCGCCCGGGCGGCTAC | |
| | :::::::::::::Rv219T7.seq::::::::::::: | |
| | CCAACTAGAGCATCGGGACATACGGAGTCAACTACCCGGCCAACGGTGATTTCTTGGCCGCCGCTGACGGCGCGAACGACGCCAGCGACCACATTCAGCAGATGGC | (SEQ ID NO. 216) |
| | CAGCGCGTGCCGGGCCACGATGTTGGTGCTCGGCGGCTACTCCCAGGGTGCGGCCGTGATCGACATCGTCACCGCCGCACCACTGCCCGGTCTCGGGTTCACGCAG | |
| | CCGTTGCCGCCCGCAGCGGACGATCACATCGCCGCGATCGCCCTGTTCGGGAATCCCTCGGGGCCGCGCTGGCGGGCTGATGATCGCCCTGACCCCTCAATTCGGG | |
| | TCCAAGA | |
| Clone Rv21 | :::::::::::::Rv21SP6.seq::::::::::::: | |
| | ATACTCAAGCTTGCTGCAGCTTCCTGTGACTGCTCCCGAAACCTGGGGGTGTGCCTGCTGTGTATGCACGGCATACGGACATCCTTCCCCTGAGACCCGCGGTCGA | (SEQ ID NO. 217) |
| | ACCAGCCACGTGTCCATCATCAGGGGTCAACCCCGGCCAAGGGCGACGGCACGCCAAGTTCGCCGACCGTTAACCTAGTGCTGTTAGCTTCATTTGCTGCGAGCAA | |
| | AACAGCTGGTCGGCCGTTAGGAACTGAATTGAAACTCAACCGATTTGGTGCCGCCCGTAAGTGTCCTGGCTGCCGGTGCGCTGGTGTT | |
| | :::::::::::::Rv21T7.seq::::::::::::: | |
| | AGCTTGCGCGGCGTGGCGATCGCGGTTCAAGGCGCGCTCTTCGAGCACAACGAGCGAAGACAGCTCGGCGACGGAGCCTTTATCGACATCCGTTCGGGCTGGCTGA | (SEQ ID NO. 218) |
| | CCGGCGGCGAAGAACTGCTGGACGCGTTGTTGTCGACGGTGCCGTGGCGAGCCGAGCGCCGTCAGATGTACGACCGGGTGGTCGATGTGCCGCGGCTGGTGAGTTT | |
| | TCACGACCTGACCATCGAAGATCCGCCGCATCCGCAGCTGGCGCGGATGCGCC | |
| Clone Rv220 | :::::::::::::Rv220SP6.seq::::::::::::: | |
| | AATACTCAAGCTTGCGCACGACCAGGACGTCGAGTGGCGCTTGCAGTGACTTGGCGACCTCAAAGGCCACCGGTACCCCGCCGCGCGGCAAGCCAAGGACNACNAC | (SEQ ID NO. 219) |
| | GGCCTTGCCGGATAGCTGCGCCAGGCGTTGCGCCAACTGGCGTCCAGCGTCGCCACGATCGTCAAAGAGCTTCATCTGCCGAGTGTGTCGCCATCTCATGGCTCCA | |
| | AATATGGAATTAGGTCCCTGGGCCGACTGACGACAGTCCCTCAGCGACCGGATTGCGCATCCCGCCTTGTACGCTGCTCCGCAAATCCCGGGCTTGCGTCCGCGGA | |
| | AGCGAACTCGGCGGCGCTACGGTGGTGGCTCACTTCGGCCGTGC | |
| | :::::::::::::Rv220T7.seq::::::::::::: | |
| | GGTTGGTGCGGTCCACCTTCGCGGCGGCGGCGCGATATGCCTTGCTGGTCTTGCTCATTTGATATCCAATCTATGGGTCGTGGTTACTCAGCGGGCCGAAGCTGGC | (SEQ ID NO. 220) |
| | CCTCCCACGGGTAGGGCCCTATTCGACGGTGATGCCCATCGACCGAGCGGTACCGGCGATGATCTTGGCCGCAGCGTCGACGTCGTTGGCGTTGAGGTCCGTCTTC | |
| | TTGGTCTCGGCGATTTCGCGGACTTGATCCCAGGTGACTTTGGCGACCTTGGTCTTGTGCGGCTCCGCCGAACCCTTCGCCACACCAGCGGCCTTAAGCAGCAGCT | |
| | TGGCGGCGGGCGGCGTCTTCAGCGTGAAAGTGAAGCTACGGTCTTCATAAACGGTGATCTCCACCGGGATGACGTTGCCGCGCTGGTTCTCCGTCGCGGCGTTGTA | |
| | CGCCTTGCAGAACTCCATGATGTTGACCCGTGCTGACCGAACGCGGGGCCCACTGGCGGGGC | |
| Clone Rv221 | :::::::::::::Rv221SP.seq::::::::::::: | |
| | ATACTCAAGCTTTTCGACCCGCAAGCCGGCGGTGCCCCTCCTCGTTCCGCTGCCCGGTCTGCTCGATCGGTTCGGGGTCGCCGCGCTAGGCCCAATTGCCCGGCTC | (SEQ ID NO. 221) |
| | CTCCTCGGGCCGTTCCACAACCCGCATCGTCGCCGGGCTAGGTTCAAGCCATGCCGGTAAACCCCAGGACGCCAGTGCTGATCGGCTATGGACAGGTCAACCACCG | |
| | AGGCGACATCGACGCCNAAAATCAGTCCATCGAACCCGTCGACCTGATGGCCNCCGCGGCCCGGAAAGCCGCCGAGTCCACCGTGCTCGAAGCGGTGGATTCCATC | |
| | CGTGTGGTGCACATGCTGTCGGCGCATTACCGGAATTCCCGGGCGTCTCCTCGGC | |
| | :::::::::::::Rv221T7.seq::::::::::::: | |
| | NCCTGGTTCATGAACTGGAAGCAGCGCAGCGCTTCCTTTTCGGCCGCAACATGAGCCAGCCTCTCGTCGGCGGTCGGGTGCAGGTGCTCGGGCAGCTCGGCCGCGA | (SEQ ID NO. 222) |
| | CAGCCGCCTGACCCTGAAACCAGCTTCCATATCCCGCGACGAACGACGCCAGTCCGCTACGTAACCCCTCCGCGACTGTCCATGGACAACAGCGCGTTCTCCACCG | |
| | ACCGGGGCCGGGTGTTGGGGTGTTCGGCAACGGCAACCAAGTTGGTCCACACTGCCGACGGGCGCCGCAAATCCGTTCACCGAACCAGGCCGCCNAAACAATTCCG | |
| | CCCGATCCCATAT | |
| Clone Rv222 | :::::::::::::Rv222SP6.seq::::::::::::: | |
| | ATACTCAAGCTTGTCGGGATCAATCTCGAGGGCATCCACGCACGAAAAGTAAACTCTATCAAGCTTTTTGACGACACCCACGGACGCCCCATATATGTTCGGGTGG | (SEQ ID NO. 223) |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | GCAAGAACGGTCCCTACCTGGAACGTTTGGTGGCCGGCGACACCGGTGAGCCCACGCCGCAGCGGGCCAACCTCAGCGACTCGATTACCCCGGACGAACTGACTCT | |
| | ACAGGTGGCCGAAGAGCTCTTTGCCACACCGCAACAGGGACGGACTTTGGGCTTGGACCCAGAAACCGGCCACGAAATCTTTGCCAGGGGAAGGCCGGTTTGGGCC | |
| | TTATGTTACCTATATCCTGCCGGAACCTGCGGCTGATGCGGCCGCGGCCGCTCAGGGAN | |
| | :::::::::::::Rv222T7.seq::::::::::::: | |
| | AGCAGCTAGCCGCGCTCGCCGCGCTGGTCGGTGCGTGCATGCTCGCAGCCGGATGCACCAACGTGGTCGACGGGACCGCCGTGGCTGCCGACAAATCCGGACCACT | (SEQ ID NO. 224) |
| | GCATCAGGATCCGATACCGGTTTCAGCGCTTGAAGGGCTGCTTCTCGACTTGAGCCAGATCAATGCCGCGCTGGGTGCGACATCGATGAAGGTGTGGTTCAACGCC | |
| | AAGGCAATGTGGGACTGGAGCAAGAGCGTGGCCGACAAGAATTGCCTGGGCTATCGACGGTCCAGCACAGGAAAAGGTCTATGCCGGCACCGGGTGGACCGCTATG | |
| | CGCGGCCAACGGCTGGATGACAGCATCGATGACTCCAAGAAACGCGACCACTACGCCATTCAAGCGGTCGTCGGCTTCCCGACCGCACATGATGCCGAAGAATTCT | |
| | ACAGCTCCTCCG | |
| Clone Rv223 | :::::::::::::Rv223IS1081N1400.seq::::::::::::: | |
| | CGCGACTGGCTCCCCGGNCGGCTGCTCGGGTCCGCCGATAGAGACCGGGATGTCGCCCGACGACGGGCAGCCGGGTTGCGTGGGACGGGGCGGGGGTCGGGCAGCC | (SEQ ID NO. 225) |
| | CAAGCAACGGGCTAGTCCCCGAATCCTACGGAGCCGTCACCTACGCCTACGTAATAGTAGCTATCAATAACAGTTGACATACGCAACGATCTGTGAGATCAATATT | |
| | GCCTGACGCATGTCAAGACAGGCGTCAAGACAGGTGTCAATAATTCGCTCCGCTGGTGACGGTAACCGGTCGTGCGGGTGTGTGACGCCTAAGGAAGGAGTGTGGG | |
| | TGGTGACGCTGAGAGTGGTTCCTGAGGGTTTGGCGGCCGCCAGTGCGGCGGTGGAGGCGTTGACCGCACGGCTGGCCGCCGCACACGCTGGCGCGGCGCCGGCGAT | |
| | TACGGCGGTGGTGGCGCCCGCGGCGGATCCGGTGTCGTTGCAGAATGCGGTGGGGTTTAGCGCCTTAAGTAGCCAGCATGCCGCGATCGCCGGCGAAAGGGTCCAA | |
| | GAACTGGGT | |
| | :::::::::::::Rv223SP6.seq::::::::::::: | |
| | ATACTCAAGCTTATTGAACCGCGGGTCGCAGGCAAAGTGGACCTCATAACGACTCGGGTCCAGCGACCGCGCCAACACGAACGGCCGGACGACGTGGGCCAGGGTC | (SEQ ID NO. 226) |
| | GCGGCCTCCCCTACAAACAGGATCCGTTGCCTGCGAACGACAGGCTCCGGTGCGGCGTTGGGCGCCGTGCTCGTCCCAGCGTCCGGTCCCGGGTCGCCGGCGACGC | |
| | TTGTTTCCTCCATACTCGCCCCCTAATCTCGAGGCAGCCCGTACCCGCAGGCAACCTCCCAAAAATGCAATCCCGCAAAATGCAATGCGTCNAGCTATTTCTCACA | |
| | CCGACCGCTAGTTGCGGATCAGAAATCCGTTGGGCGCGGAAGTCCAGCCGAATTTGTTCTCCCGCTCCGCATCATGCTTGTAATCGTTTGGAAATTCATCCTCATA | |
| | TGCCTCGATCGCTTCATAGGGTCCAGGCCCAAACCCGGGCAGGACTGGGTGGCCGTTGATGTTGGAATCCTCCACTACTAGGTATTCACCGGC | |
| | :::::::::::::Rv223T7.seq::::::::::::: | |
| | GTCTCGATCATGGCCAAAGAGCTCGACGAAGCCGTAGAGGCGTTTCGGACCCGCCCGCTCGATGCCGGCCCGTATACCTTCCTCGCCGCCGACGCCCTGGTGCTCA | (SEQ ID NO. 227) |
| | AGGTGCGCGAGGCAGGCCGCGTCGTCGGGGTGCACACCTTGATCGCCACCGGCGTCAACGCCGAGGGCTACCGAGAGATCCTGGGCATCCAGGTCACCTCCGCCGA | |
| | GGACGGGGCCGGCTGGCTGGCGTTCTTCCGCGACCTGGTCGCCCGCGGCCTGTCCGGGGTCGCGCTGGTCACCGGCGACGCCCACGCCGGCCTGGTGGCCGCGATC | |
| | GGCGCCACCCTGCCCGCAGCGGCCTGGCAGCGCTGCAGAACCCACTACGCAGCCAATCTGATGGACGCCACCCCGAAGCCCTCCTGGCCGTGGGTGCGCACCCTGC | |
| | TGCACTCCATCTACGACCAGCCCGACGCCGAATCAGTTGTTGCCAATATGATCGGGTTCTCGAC | |
| Clone Rv224 | :::::::::::::Rv224SP6.seq::::::::::::: | |
| | ATACTCAAGCTTTCGTCAGTTCATGGCGCCAGCAGACCAACAAGAGCATCGGGACATACGGAGTCAACTACCCGGCCAACGGTGATTTCTTGGCCGCCGCTGACGG | (SEQ ID NO. 228) |
| | CGCGAACGACGCCAGCGACCACATTCAGCAAATGGCCAGCGCGTGCCGGGCCACGAGGTTGGTGCTCGGCGGCTACTCCCAGGGTGCGGCCGTGATCAAGATCTTC | |
| | ACCGCCGCACCACTGCCCGGCCTCGGGTTCACGCATCCGTTTGGCCGCCGCC | |
| | :::::::::::::Rv224T7.seq::::::::::::: | |
| | GCCCCGTGTAATTTGGGATGGGCAAAAAGCGAAGCACCGCGTGGCCACGAACGCCGGGAGGGACAATCTCGGGCGGCTAGGGCTTCTCGCGGGAAGGCCCGAACGT | (SEQ ID NO. 229) |
| | ACGGCGTTTCAACACGTCGCGTCGCCCTCCGACCGCGAACATTCGGGGATGGCAGCAACCTGGTAGCACCCTGGCCGGGCGATGATCTGCAGCGTCGCCGCGGGTA | |
| | GTCTCCGCCCGGGCCGC | |
| Clone Rv225 | :::::::::::::Rv225SP6.seq::::::::::::: | |
| | ATACTCAAGCTTCCTTTGACCGAACGCGTCCACCGCACCGTGAGATTGGTGGCGCCATTCGTCGTGGTGTAGCTGCTGTTGGCGGCGTCGCCGTATTGTGCGGGCC | (SEQ ID NO. 230) |
| | AGCCTTGTGCGGGGGCCGCTTCTACCCACAAGTCGGCACTTCCGCAACCGCCCAGCTCGACCGCGAATTACGGCGGCCGCAACGGCCGCCGGAAGGCGTCACGCAA | |
| | TCGCTTATCCTTTCCAGGTTCCCAAATCCTCCGCTTACTTGGGTCCTTCATCGG | |
| | :::::::::::::Rv225T7.seq::::::::::::: | |
| | GGCAGCGGCGACAACCGGAACGTCCGCACGGTGCTCAATCACGGGTGCACGGTGTGCATCAGAATGGCGGGGGTTCGTTGTCGCGGTGAGGCGTTCGGCGAGGAGG | (SEQ ID NO. 231) |
| | TAGTGTCTACCCCTTGCCCGCGGGTTCGTGCGGACTGAAAGGGATTTCATTGGGAACCCACGGCTGCGTATCGCAGGGCCTCGGTGACGTCTGCTTCCTCNAGCTC | |
| | AGGAAGTTCGGCGAGAATCTCGGTGGATGTTATTTGGTCCGCCTAC | |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

Clone Rv226 :::::::::::::Rv226SP6.seq::::::::::::
ATACTCAAGCTTTCTCGGCTTCTCTGATAGCCTGAGAAGAAACCCCAAGTTAATCCGCTGCTTCACCTATTCTCCAGCGCCGGGTTATTTTCCTCGCTTCCGGGCT (SEQ ID NO. 232)
GTCATCATTAAACTGTGCAATGGCGATAGCCTTCGTCATTTCATGACCAGCGTTTATGCACTGGTTAAGTGTTTCCATGAGTTTCATTCTGAACATCCTTTATTCA
TTGTTTTGCGTT Clone Rv227 :::::::::::::Rv227SP6.seq::::::::::::
ATACTCAAGCTTGGTGACCGGCACCGCGATACGTTGCGGCAGGCATCTGGGCTGGCGGTGGTTCGCCGCTCCGAAGCCGTCGAACACCATCGCCAGCGCGGCTTCC (SEQ ID NO. 233)
ACATCAACGACCATTTCGGCCAGCTTGCGGCGCATCAGCGGCTTGTCGATGAGCGCCCCACCGAATGCCCGCCGCTGCCCGGCGTATCACATCGATTCGACCATCG
CGCGGCGCGCGTTGCCGAGGGCGAACGAGGCGGTGCCCAACCGCAATCTGTTTGGTCAGCTCCCTCATGCGGGTTGATTCCTTGCCGTCCGGACGGGCCCGCGTCA
TGCGCTCGGTTCGCC
:::::::::::::Rv227T7.seq::::::::::::
CCGTTGCGCAGCGTGAGCCGATAGTTGACATCCGGCTCGGTGAAGGTGAAATCGATGGCCAGGTCGAGGTCCCATGCGCGTGGGCCATTGATGCCGATCGCCAGGA (SEQ ID NO. 234)
CGTCAAAGATTTGGTCCGGCGTCAGCTGGGCGAAAAACGTGGGCGCCGGGACTTGCCCGGAGCTGCCCGGGTTCCCGTCGCGCAGCTCGGCGGCCCCGGTCAGAAA
GAAATTGCGCCAGGTCGCACACTCCGCGCCGTAGGCCAGCTGCTCCAGGGTGTCGGCATAGAGCCCGCGGGCCGCAGCGTGCTCGCTGTCGGCGAACACCGCATGG
TCGAGAAGCGTTGCCGCCCAACGGGAAATCACCTGCGTCGAAAGCTTCGCGGGCCAGCTCCAGCACTCGGTCGATGCCACCCAACGCGT Clone Rv228 :::::::::::::Rv228SP6.seq::::::::::::
ATACTCAAGCTTGCGGATGTTACCCCTGACAGCGTGAACTATGTCNAAACACACGGCACCGGAACGGTGTTGGGGGACCCCATCGAGTTCGAGTCGCTGGCGGCCA (SEQ ID NO. 235)
CTTATGGCCTGGGTAAAGGCCAGGGCGAGAGCCCGTGCGCATTGGGGTCGGTCAAAACCAACATCGGCCACCTGGAGGCGGCCGCCGGTGTGGCTGGATTCATCAA
GGCGGTGCTGGCGGTGCAACGTGGGCACATTCCCCGCAACTTGCACTTCACCCGGTGGAACCCGGCCATCAACACGTCGGCGACGCGGCTGTTCGTGCCGACCGAA
AGCGCCCCGTGGCCGGCGGCTGCCGGTCCACGCAGGGCTGCGGTGTCATCGTTCGGCCTCAGCGGGACCAA
:::::::::::::Rv228T7.seq::::::::::::
CCGGTAACCAGATCAGCTCGTCGACCTCACTGCCGGGGGTGAATTCCCCACCGGTGCTGCGCGCTGCCCAGTAGTGCACCTTCTTGACGCCTCGAAAAGGGGAGTC (SEQ ID NO. 236)
GGTCGGGTAGGTCACCGTCAGGAGCCGCCTACCCAGGTTGGCGCGGTGACCGGTCTCCTCGAGTATCTCCCGCACCGCCCCCACCGGTGCGGTCTCGCCCGGATCC
ACTTTGCCCTTGGGCAGCGACCAGTCGTCGTAACGGGGGCGGTGAATGACAGCGATCTCGACCGGCCCTTCCGAATCGGCACTGCCGGGTCGCCAGAACACCGCAC
CGGCGGCGTACACAATCCGGCCCGCCGAGCGCCGGCGGGCGGACGANTTCTGGATCGACACCTCAACTCCTGCAGGTCAATTCGGCCAAGCTGCTCGCGGTCGTGG
ATGTGGTC Clone Rv229 :::::::::::::Rv229SP6.seq::::::::::::
ATACTCAAGCTTGATGCCGCCGAAACCGAGCGTGAGCACGCCGCCACCCACCACGCGCGGGTCGGGCGCCGGGCCCGGGCCGCCAGGCTGCTCCGCTCGGTGATGG (SEQ ID NO. 237)
CACGCCACCGCGACACCACCCGGCTGCGCTACGTCGAGCCATACCGGGCGGAGCTACATCGGCTCGGCCGCCCAGTGTTCGGGCCCTCTTTCGAGGTCGAGGTCTA
TACCGATTTGCGCATCCGCAGCCGCACCCTGGTCGTCTCGTACCGTGCCCTACCTCTGCTTGTCGGGCGGGGCCA
:::::::::::::Rv229T7.seq::::::::::::
TCCGTACGGCCCGGGTACGCTTCGGTCGCAGTGTGCGAGTGATAGATGACGACCGGGACCTCGTCGGCATCTTCCATAGCCCGCCACACCTTCAGTTGCTCACCGG (SEQ ID NO. 238)
AATCCAACCGGTAGAAGGTCGGCGAGCGCTCGGCATTGGTCATCGGGATATGCCGCTCGGGACGGTCAGAGCCCTCGGGTCCGGCCAGCACTCCGCAGGCTTCGTC
GGGGTGGTCGCGACGCGCATGGGCCACCATCCATCCACCAGGTCTGCGCGAATCACCCGC Clone Rv22 :::::::::::::Rv22SP6.seq::::::::::::
GGACACATTGCGAACATTGATGACAAAATAGAAATCATTGATGGTTTGAGTCACCAGGCCGATCAAGCCTTCGCCGAGCCAAATTCCAATCAAGAGGCCCAAGCCC (SEQ ID NO. 239)
GTACCAATCAGCCCGGCAACGAGGGATTCCGTCATTATCAGCCAAAATAACTGCTCTCGGGTTACACCCAAACAGCGCAATATGGCGAAAAACGGTCGCCGTTGCA
CGACATTAAATGTCACGGTATTGTAAATTAAAAAGATACCCACCAACAAGGCAATCAAACTGAGAGCGGTTAAATTGACCGTAAAAGCGTCCGTCATCTGTTTCAC
GGTGTCCCGTTGGGTNTCCGACGTTTCCATACGCACACCGGCCGGCAGTCTTTGTTGGATGCGTGTTGCAGTGGCCTCATCTTTGATGATCA
:::::::::::::Rv22T7.seq::::::::::::
GCCTGGCCCAGGTGAAGGCCGACCTCGACGCCAAAGCCGCTGATCCGGCACATGAGTCGGTGGACTGGGACTTGAAGTCGCTGCGATGGGCGTGGAACCGAGCCAA (SEQ ID NO. 240)
AGATGACGTGGCGCCGTGGTGGGCCGAGAATTCCAAGGAGTGCTACTCGTCGGGGTTGGCCGATCTGGCCCAGGGCCTGGCTAATTGGAAAGCTGGCAAGAACGGG
ACCCGCAAAGGCCGGCGGGTGGGCTTCCCGCGATTCAAATCCGGGCGGCGTGATCCTGGCAGGGTGCGGTTCACCACCGGCACCATGCGCATAGAGGATGACCGGC
GCACGATCACGGTCCCGGTGATCGGGCCGCTGCGGGCCAAGGAGAACACCCGCCGGGTGCAACGCCACCTCGTGAGCGGGCGCGCGCAGATCCTGAACATGACCTT
GTCGCAGCGGTGGGG TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

Clone Rv230 ::::::::::::Rv230SP6.seq::::::::::::
TAACTCAAGCTTCAAGTCCGCNGTCCGACCCTGTTCGACGGCTACCTGAATCAACCCGATGCCCCGCCGCGGCGTTCGACCCGACAGCTGGTACCGCACCGGCGAC (SEQ ID NO. 241)
GTCGCGGTGGTCGACGGCAGTGGGATGCACCGCATCGTGGGACGCGAGTCGGTCGACTTGATCAAGTCGGGTGGATACCGGGTCGGCGCCGGTGAAATTCAAACGG
TGCTGCTCGGGCATCCGGACGTGGCGGANGCGGCAGTCGTCGGGGTGCTCGACTATTATCTAGGCCAGCGGATCGTTGCCTACGTAGTCGGCTCAGCGAATGTCGA
TGCGGACGGGCTTATCAACTTTGTTGCCCAACAACTTT
::::::::::::Rv230T7.seq::::::::::::
CCATGTCGCCCAACATATCGTCGATGTTCGCGTCGTCCGCCTCGCGCACGTGGTCTGTCACCAGTCAACGTTAACGCCGCCGCACATGTCCTGCGGCCGGGCAAAA (SEQ ID NO. 242)
ACGTGAAAAACGAGCGGGCGACTGCAATGTCATGACACCGACGCCGCCGATGGGCCCAGGGTCTGGCAGATTCGATCTGTGCGGCCAGTGCCAGCAGCGTCGCCTC
GTCATACGGCCGGCCGACGAGTTGAACCGACATGGGCATGCCGTCGCCGTCGAAGTCCCACGGCACCACGGCCGCGGGCTGGCCGGTCAGATTCCANACTTGAAAG
TACTGAAGCCGCTGCACCACCAG
Clone Rv231 ::::::::::::Rv231SP6.seq::::::::::::
CGAAAGCGTGAAACAGCTCGCGGCAGCCCCCGACGTGCTGCGTCGGATAGCCGGCGGGCGAAGATCAATTCCAGGCAGCTCCCGGACAATGCGGCTCTGCTGGCCC (SEQ ID NO. 243)
GCAACGAAGGACTCGAGGTCACCCCGGTGCCCGGGGTCGTGGTGCACCTGCCGATCGCACAGGTTGGCCCACAACCGGCCGCTTGATGCCCGGTCGGCAAGCCCGG
CAGTTGCCAAACCCAGCGTGATCNTGCTCNGCTCTNTANTTCGGCGAAGAAGTGGCTCGCCTGATCACCTACCATCGGCCAGGATCTGCGTGTCATCACAACGCTC
GCCAAGGAGGTTGTTGTG
::::::::::::Rv231T7.seq::::::::::::
TCCGCCACGCTTCGCGCCGCCCGGCATACGGCGCGTACCGATCTCCGCGTCATACACCGCGGGTAATCGCCGACGGTGCCGGTTCGCGAGCCGAAGGTGACGACGC (SEQ ID NO. 244)
TGATTGAATCGAGTTCCAGGTCCAGCGGGTGGCGCAGCAACGGCGCGAGCTCAACGACGTCAATCACGTTGTCGCTTTCTACGGTCACCGACCCGGTGACCGTAGT
CGCCCGGTGCGCTCGGCCGAGAAGCTGCACCGCCACCACCGCGACACCGTCTTGCACGCGGACCCACCCCGGATCGGTTGTTGGCCAAGGTAATTGGGTCATTCCA
TTTGACGGGACGCCGACCC
Clone Rv232 ::::::::::::Rv232SP6.seq::::::::::::
CATTCTTTAACAGTTGTTTTGGGCTCGGCATGGTTAGCCAACGTTCTGCGGTCCACCATATCATCTTGGTCCGGTAGCGCTCGTCCGGGGTATGCTGCCGCCGGGA (SEQ ID NO. 245)
TTCTCGCTGCTATTACTCCCCCCGAAGAACCGCCACCGGTCCAGCGCGTGGGCCGNCGCGGTCCCATCACAAACTGAACCCCCAACAGGGACATGCTTATCGGTAG
GGCGCGCGCCAAGGCGGCAGCAATCGCATCACTGCGCTCTGCGCGTCACTATTAACCCACCCGGACTTCACTTCCACCACCCCGAATGGCGCCCGGTCATTGATCA
TCTGGCGCACCGCGGATAA
::::::::::::Rv232T7.seq::::::::::::
CGGTGTCCTGCAGTTGGTAGGCCTGCAGTTTGTGCATCATGCCGATGCCGCGGCCTCGTGGCCACGCATGTACAGCACCACGCCGCGCCCCTCACGGGCGAACATC (SEQ ID NO. 246)
GCCAGCGCGGCGTCCAGCTGAAGCCCGCAATCGCAGCGGCGTGACCAAACACATCGCCGGTCAAGCACTCCGAATGCACCGGACCAGCACGTCGTCACCGTCGGCG
TTGGGCCCGGCGATCTCGCCGCGGACCATGCGCGACATGTTCCACGTCCTCGTANATGCTGGTGTAGCCGATGGCGCGAAACTCCCCATGACGAGTCGGAATCCGC
GCCTCGGCGACCCGCTCAATGTGCT
Clone Rv233 ::::::::::::Rv233SP6.seq::::::::::::
CGGCATCTGGCGGCTGAACCTGTTCTTGGGCAACATGCCGAGGATCGCCTCTTCCACCACGCGGTCGGGGTGGCGTTGCATTACCTCACCGATGGTGCGCTTGTGC (SEQ ID NO. 247)
AGGCCGCCGGGATACCCCGAGTGCCGGTAAACCATCTTGTGCTGCAGTTTGTCGCCGCTGATGGCGACCTTGTCGGCGTTGATCACGATNACNAATCACCGCCANC
GACATTGGGGGCGAACGTCGGCTCGTGCTTGCCGCGCAGCAGGCTGGCCGCCGCGACGCAAGGCGCCAACCACCACGTCCGTGGCGTCGATGACGTACCACCATCG
CGTGGTGTCACCCGCCTTGGGC
::::::::::::Rv233T7.seq::::::::::::
GCGGCAAAAATTGAAGCACTCTCNTGGCCACTNCCGCCGGGAGGGACAATCTCGGGCGGCTAGGGCTTCTCGCGGGAAGGCCCGAACGTACTGCGTTTCAACACGTCG (SEQ ID NO. 248)
CGTCGCCCTCCGACCGCGAACATTCTGGGATGGCAGCAACCTGTTAGCACCCTGGCCGGGCGATGATCTGCAGCGTCGCCGCGGGTAGTCGCCCCCGGGCGGCTAC
AGTCTGAAACGCGATGACCATCGATGTGTGGACGCCGCATCCGACNCAACGGTTCCTACACTGTGATATGTTCGCCTCGCTGCGCCGGTGGACGGTGGGTCTATCC
CGGA
Clone Rv234 ::::::::::::Rv234SP6.seq::::::::::::
CGCGTTGAACTGAAGGGGTGCCGCCCGGCTCGAGCAGGCAAGCCATTTGTTCGATGCGGTTACCGAAGATCTCTTCGGTGACTGCCCGCCGCCGGCCAGCTCGGCT (SEQ ID NO. 249)
CAGTGTCCGGCGTTGGTCGCCGCGGCGACAATCTTGGCGTCCACGGTGGTCGGGGTCATGCCCGCGAGCAGGATTGGCGAGCGGNCGGTCAGCCGGGTGAACTTCG
TCAAGAGCTGACGCTGCGGTTGGGGAGGCGAATCATGGTCGGTGCGTAGCCTCGACTAGGCCCGGG TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | :::::::::::::Rv234T7.seq:::::::::::: | |
| | TGACAACGCGGCGGCGATTACCCCGCTACCGCAGCAGCATGACGCGGTAGCGAACACCGCCGGATGCAGCGCAGGTGCGTCGATGTGCTCACGGAATCGCCCCGGC | (SEQ ID NO. 250) |
| | ACCGCGATCTCGAGGATCACCAGTGCCACCCCCTGCAGCGCGACACCGACGATTCCGTACACCGCCACGCCGATCAGGCCCTGGGCCACGTGATTGGAGCTGGCGT | |
| | ATATGGCGGCGATGGTGACGATGGTCATCGCCTCTTACATTGTGGCGGCCAGAACCACGGCGTTGGGGCGGCGGTCGATGAACACTAGGCGACCANATCCCCGGGG | |
| | TCAACAGGTTGACCATCC | |
| Clone Rv235 | :::::::::::::Rv235SP6.seq:::::::::::: | |
| | CGCGGACATCCCGAACGAGGACACGCGACCGCTTCGGTGTGTGATCTATCAGGGCTCGCACCACGCGCAACCGCTTCCGGCTACCTAGACGCGGT | (SEQ ID NO. 251) |
| | :::::::::::::Rv235T7.seq:::::::::::: | |
| | GCATGCGGGTGATGCCGTTCTCAGTGCGCAACAGCGTTCGACGCGGCATACCCAGCCGCACATGCCGTGCACGCCGGNGCCGGGGCGGGAATCT | (SEQ ID NO. 252) |
| Clone Rv237 | :::::::::::::Rv237SP6.seq:::::::::::: | |
| | CTCAAGCTTCAGNCCNTCTAAGCGGTCTGCGCGGCGATCGCAAAGATCGCCCTTTGCCGGCGTTGGGGGCTTCTGCTCGGGGGTGTTGTACACCTTCTCGAACACC | (SEQ ID NO. 253) |
| | TCGGCACCGACACCACCACCGTCGGCTTGAACACCGCCAACATCGGCAGCANATCTTGATGTCCTGGTGAATCCACGGTGACTTTGGAGTGGAAGGCGGCCATACT | |
| | GATCGCGCGCGCCACCACATGAGCTAGCGGCAGGAAAACCAGCAGCCGCTCACCCTTGCGCAGCAGCGTCGGGTGATATGCCTGGCGCCC | |
| | :::::::::::::Rv237T7.seq:::::::::::: | |
| | AGTCGAANGTCAGTCCGGTCTCCTCTCCGACTACGGCCAAGAACTGGGGCGACGGTGTCAGTGCAGAACAGCGGAAACTGGTGGCGCCCTAGGCGAGCGAACGCTC | (SEQ ID NO. 254) |
| | ACAAACGGCGGTGACCGCTTCTGGTCGTGCACCATCGAGCCGTGCCCAGCCCGGCCGCGTGCCGTCAGCCGCATCCACTGGATGCCCTTCTCGGCGGTTTCAATCA | |
| | NGTACAGGCGACGTTCGCCACCATCGTGCCGGGGCACGGTTAGCGAGAAACGCCGACTTCACCGATTGCCTCGGTGATGxxxxx | |
| Clone Rv23 | :::::::::::::Rv23T7.seq:::::::::::: | |
| | AGCTTCGCGGCGTGGCGATCGCGGTTCAAGGCGCGCTCTTCGAGCACAACGAGCGAAGACAGCTCGGCGACGGAGCCTTTATCGACATCCGTTCGGGCTGGCTGAC | (SEQ ID NO. 255) |
| | CGGCGGCGAAGAACTGCTGGACGCGTTGTTGTCGACGGTGCCGTGGCGAGCCGAGCGCCGTCAGATGTNCGACCGGGTGGTCGATGTGCCGCGGCTGGTGAGTTTT | |
| | CACGACCTGACCATCGAAGATCCGCCGCATCCGCAGCTGGCGCGGATGCGCCGGCGGCTCAACGACATCTACGGCGGCGAACTGGGTGAGCCCTTCACCACCGCCG | |
| | GGCTGTGCTACTACCGCGACGGCTCTGACAGCGTCGCCTGGCATGGCGACACCATTGGTCGCGGCAGCACTGAGGACACTATGGTGGCGATCGTCAGCCTCGGCGC | |
| | CACCCGCGTCTTCGCGCTGCGGCCGCGTGG | |
| Clone Rv240 | :::::::::::::Rv240SP6.seq:::::::::::: | |
| | AGCTTCAGCTGATACTCGACCAGCCCCACTCGGGCCAATACGTGAATGTCTAGCATCTTCACCCGTTCACGGGCTANTCGAGTAGTAGACATTGATTAGCCTGAAC | (SEQ ID NO. 256) |
| | GTACCTCCGACGCCAGCTGACGAACGGGTATGACGGATGGATTTCGTGGTGTCGCGCCCGAGGTCAATTCGTTACGGATGTATCTCGGGGCCGGATCGGGGCCGAT | |
| | GTTGGCGGCCGCGGCGGCCTGGGACGGACTATCCGACGAACTGGCGGTGGCGGCGTCGTGGTTTGGGTCGGTGACCTCGGGCCTGGCGGATGCGGCGTGGCGCGGC | |
| | CCGCGGCGGTTGCGATGGCNCGCGCGGT | |
| | :::::::::::::Rv240T7.seq:::::::::::: | |
| | CTGGTCATGGACGTTGCTCCGGTAGTGGCTCACTGCCGATCCTCCTCGTTGAGAGTGCCACCTCAGGGTTGGGTAGGGTTGGGTACTCGAAACCAAGTTACCCACC | (SEQ ID NO. 257) |
| | AGTAACACCGTCAAAATATATCCGTTGCATAGGTCAATGCAAGTTGATGTGAGCTACATTGCACCAACTAACTAACCAACCGGTTGGGTTAGCGGTGATCCTGGCC | |
| | GTGTCGGTCCTCTCACCTGCGGTGATAGCGATCAAATGAAGAATATGCGGAGTCTAGGGCGGCAGCGCCTGGCANCGTAGATCATCGGCTCACGCGGATGCGGCCT | |
| | CTTGGTACGGACATGCGCGCG | |
| Clone Rv241 | :::::::::::::Rv241SP6.seq:::::::::::: | |
| | CTCGTGAGTAGCACCCCTGTAATTTGGGATCGGCAAAAAGGCGAATCACCGCGTGGCCACGACACGCCGGGAGGGACNATCTCGGGCGGCTAGGGCTTCTCGCGGG | (SEQ ID NO. 258) |
| | AAGGCCCGAACGTACGGCGTTTCAACACGTCGCGTCGCCCTCCGACCGCGAACATTCGGGGATGGCAGCAACCTGG | |
| | :::::::::::::Rv241T7.seq:::::::::::: | |
| | GGATCAACTACCGGCCAACGGTGATTCTTGGGCGCCGCTGACGCGCGAACGACCCAGCGACACATTCAGCAGATGGCCAGCGCGTGCCGGGCCACGATGTTGGTGC | (SEQ ID NO. 259) |
| | TCGGCGGCTACTCCCATGGTGCGGCNCGTGATCGACATCGTCACCGCCGCACCACTGCCGGCCTCGGGTTCACGCAGCCGTTGCCGCCCGCAGCGGACGATCACAT | |
| | C | |
| Clone Rv243 | :::::::::::::Rv243SP6.seq:::::::::::: | |
| | AGGACCGTCAGCACGGCGACGTGCTACTCGCCGAGCAGTGGGAATCGCTCTGCAGCAAACCATTACTCTGCGCGACGTTCGAGATGACCTTCTGAATGGACGGATC | (SEQ ID NO. 260) |
| | TACCTGCCGCGCGACGACCTGGACCGCGTATGCGTCCGCCTCCGCCTGGACGACACCGGGGCACTCTATGACCCCGACGGACGGCTCGCGGTACTGCTGCGGTTCA | |
| | CCGCCGACGCCCGCACGGTACGCGTCGGGACTGCGCTGAGTCCANCCTCGACGCCGTAGCGCTGCTGCTGTGCGGCCATGTCTGGCATCTACCGCCGTCGCTCCCT | |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | TGA | |
| | :::::::::::::Rv243T7.seq::::::::::::: | |
| | CGACTCTGTTGGCCACTGCGGGTCGATCTTGCGGCCGCCCCGGTCGTGGAACGCCCAGGTCACCCGGCGGCGCACCGCGGTCAGCGCGTCGTTGGCCAGCGTGGTC | (SEQ ID NO. 261) |
| | ACATGGAAGTGGTCGACGACGAGCTTGGCGTTGGGCAGCAGCCCGGGCGTGCGGATCGCCGAGGCGTATGCAGCGGCGGGGTCGATGGCCACCGTACTGGATGCTC | |
| | TCCCGGAACTGCGGTGTGCGCGCTTGCAGCCATGCCAGCACCGCCGCGCCGCCGCGGCCTTCATGCTGCCCATAAACCCTGATACCGGCCAGGTCGACNAACCNGT | |
| | ATCCCACGGTCAACCC | |
| Clone Rv244 | :::::::::::::Rv244SP6.seq::::::::::::: | |
| | CACACGGACGGCGGTGCGGACGCAGCTGACGCGCATGGTGGTCAGCATCGCGGCCGGTCTGCTGTTGTATGCCTACTTCGCGCCGCGCAAATGCTGGTGGGCGGCG | (SEQ ID NO. 262) |
| | GTGGTGGCGCTCGCATGGCTGGGCTGGGTGCTGACCCAACTCTCGAACCACACCGGTGGGTGGGCTGGGCTATGGCCTGCCATATCGGCCTGGTGTTCTACN | |
| | :::::::::::::Rv244T7.seq::::::::::::: | |
| | CCGATATCCGAGCCGATAGCTGGCGGGCTCGGGTGGTNGCCAGCGGCGCTGCGACGAAAGTGTGACCGTCATGAAACAGACACCACCGGCGGCCGTCGGCCGTCGT | (SEQ ID NO. 263) |
| | CACCTGCTCGAGATCTCAGCATCCGCAGCCGGTGTGATCGCGCTTTCGGCGTGTCGTGGGTCGCCGCCCGAGCCCGGCAAACGCCGGCCCGACACAACCCCGGAAC | |
| | AGGAAGTCCGGTCACCGCGCC | |
| Clone Rv245 | :::::::::::::Rv245SP6.seq::::::::::::: | |
| | GCTTCAGGACAAATTGNATCCCTATGCACCCGTTGTCACGCCGATGAGTGAAGACTGCACGCAATCGCCGGAATCCGGCAAAACCCTGCACAAGCGAAATCAACCG | (SEQ ID NO. 264) |
| | GAGGCTGACAAGGCAACGTCGGTGATCCGTACCGCCTGGTTGGACAAACGGCAGAAGGCGCCTCGTCCGGTCCATCTACGCCGAGCACACTGGTGATAGCGCCATC | |
| | GGCATCGGTGCGGCCACGGTGGAGACGAACGTCCGCNGGCGTCTGGGTCAGTAACCCGCCGACCAGTTCTCGGGCAAGCTGGTCAACATCGGGCGCCACGTCTCCA | |
| | AC | |
| | :::::::::::::Rv245T7.seq::::::::::::: | |
| | GTTTGGCGGCCTTATTGCACTGAGGTCGTCAATTGACCCACAGCGGAAATGCCGACTATTCGCAGGCCTCCTTCGCCTTGGCTGCCGGAGATGGGCTCCGCGGGAA | (SEQ ID NO. 265) |
| | CCGCATGCAGGTATATGACCTCGGTTTCTCGGGTGCTACCGCGTGCCTTGTCGAGGATGAACTCGGCGTTGGAATTGTCCAGCCGGCCCAATTCATCGAGCGCAGA | |
| | TTCGTACACATGGCCGGCGGCGACATACCTTCACCGTGGATCTGCTCCACACGGACCGCCCTGTCGGGATCTGCTCACGGGTAAAGGAATTA | |
| Clone Rv246 | :::::::::::::Rv246SP6.seq::::::::::::: | |
| | GCGCACTCCTCCTTATCGCTCCGCTCTGCATCGTCGCGGCGCGGTCAGGTGCAAACGCCTTCGGGGGTGGGGGTCCTGCGGAGCACACCGGATACGGAGCGCAACG | (SEQ ID NO. 266) |
| | CGTCGCGTTGTGCGGGCAAACAAGTGTGCAGGNNCCAATGCCATGTCCAGCAGCTTATCAGTGTCGAACGTGCGAACGTCGCGCCTTCGCCGGTGCCTGAATCTCT | |
| | ACAAG | |
| | :::::::::::::Rv246T7.seq::::::::::::: | |
| | CGCTGAAAGCCACCATTCGCGGGTCGGGCGCCGGGCTCGGGCCGCCAGGCTGCTCCGCTCGGTCATGGCACGCCACCGCGACACCACCCGGCTGCGCTACGTCGAG | (SEQ ID NO. 267) |
| | CCATACCGGGCGGAGCTACATCGGCTCGGCCGCCTACTCTTCGGGNCCTCTTTCGAGGTCGAGGTCGA | |
| Clone Rv247 | :::::::::::::Rv247SP6.seq::::::::::::: | |
| | TGTAATTTGGGATGGGCAAAAAGCAAANCACCGCGTGGCCACAAACGCGGGGAGGGACAATCTCGGGCGGCTAGGGCTTCTCGCGGGAAGCCCGAAACGTACGGCG | (SEQ ID NO. 268) |
| | TTTCAACACGTCGCGTCGCCTCCGACGCGAAATTCGGG | |
| | :::::::::::::Rv247T7.seq::::::::::::: | |
| | CTTGGGCAACATGCTGAGGATCGCCTTTTTCACCACGCGGTCGGGGTGGCGTTGCATTAGCTCACCGATGGTGCGCTTGTTGCAGGCCGCCGGGATACCCGAGTGCC | (SEQ ID NO. 269) |
| | GGTAAACCATCTTGTGCTGCAGTTTGTCCCGCTGATGGCGACCTTGTCGCGTTGATCACGATGACGAAGTCACCGCCATCGACATTGGGGGCGAACTCGGCTTGTG | |
| | CTTG | |
| Clone Rv249 | :::::::::::::Rv249SP6.seq::::::::::::: | |
| | GCATGCTTCATTATCTAATCTCCAGCCGTGGTTTAATCAGACGATCGAAAATTCATGCAGACGGTCCCAAATAGAAAGACATTCTCCAGGCACCAGTTGAAGAGGT | (SEQ ID NO. 270) |
| | TGATCAATGGTCTGTTCAAAAACAAGTTCTCATCCGGATTGAACTTTACCAACTTCATCCGTTTCATGTACAACATTTTTAGAANCATGCTTC | |
| Clone Rv24 | :::::::::::::Rv24SP6.seq::::::::::::: | |
| | ATACTCAAGCTTGATGCCGCCGAAACCGAGCGTGAGCACGCCGCCAGCCACCACGCGCGGGTCGGGCGCCGGGCCCGGGCCGCCAGGCTGCTCCGCTCGGTGATGG | (SEQ ID NO. 271) |
| | CACGCCACCGCGACACCACCCGGCTGCGCTACGTCTATCCATACCGGGCGGAGCTACATCGGCTCGGCCGCCCATTGTTCNGGCCCTCTTTCGAGGTCGAGGTCTA | |
| | TACCGATTTGCGCATCCG | |
| | :::::::::::Rv24T7.seq::::::::::::: | |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | TCCGTACTGGTCGGGTACGCTTCGGTCGCAGTGTGCGAGTGATAGATGACGACCGGGACCTCGTCGGCATCTTCCATAGCCCGCCACACCTTCAGTTGCTCACCGG | (SEQ ID NO. 272) |
| | AATCCAACCGGTAGAAGGTCGGCGAGCGCTCGGCATTGGTCATCGGGATATGCCGCTCGGGACGGTCAGAACCTCGGGTCCG | |
| Clone Rv251 | :::::::::::::Rv251SP6.seq::::::::::::: | |
| | GTTCTCGCACGATTTCGGATTAGCGGGATGGTCTCAATTGGGTATGCGGGGAAGGCGCTGACATTCGCCGCGATTAGCTGTTTGATGGACCGGGGGTGATTTTTGA | (SEQ ID NO. 273) |
| | TCACGGAAATGGGTGTTTATNCAGGTCGCACGCTTTCATCCGGGGCGGAACG | |
| | :::::::::::::Rv251T7.seq::::::::::::: | |
| | GGGTGTGCCTGCTGTGTATGCACGGCATACGGACATCCTTCCCCTGAAGACCCGCGGTCGAACAGCCACGTGTCCATCATCANGGGGTCAACCCCGGCCAAGGGCG | (SEQ ID NO. 274) |
| | ACGGCACGCCAAGTTCGCCGACCGTTAACCTAGTGCTGTTAGCTTCATTTGCTGCGAGCAAAACAGCTGGTCGGNCGTTAGGAATGAATTGAAACTCAACCGATTT | |
| | GGTGCCGCCGTAGGTGTCCTGGCTG | |
| Clone Rv252 | :::::::::::::Rv252T7.seq::::::::::::: | |
| | ACTACCCGGCCAACGGTGATNTCTTGGCCGCCGCTGACNGCGCGAACGACGCCAGCGACCACATTCAGCAGATGGCCAGCGCGTGCCGGGCCACGANGTTGGTGCT | (SEQ ID NO. 275) |
| | CGGCGGCTACTCCCANGGTGCGGNCGTGATCGACATCNTCACCGCCGCACCACTGCCCGGCCTCGGGTTCACCAGCCGTTGCCGCCCGCAGCGGACGATCACATCG | |
| | CTTTTATTTNNTNTTCNGGAATCCCTCGGGCCGCGCTGGCGGGCTGATGA | |
| Clone Rv253 | :::::::::::::Rv253SP6.seq::::::::::::: | |
| | ACGTCGGGANACTGTTCGCGTTCATCCTCGTCTCGGCGGATTGGTCTGCTGCGCCGGACCGACCGATCTTCAGCGGGGGGTCACGCTCCGTGGGGTGCCGTTACTT | (SEQ ID NO. 276) |
| | CCGATCGCCCAGTGTGCGCGTGCTGTGGCTGATGCTGAACCTCACCGCGTTGANTTGGATCGGTTCGGGATCTGGCTGGTGGCCGGAACGCNATTTATGTCGCTAC | |
| | GGGCGCCGGC | |
| | :::::::::::::Rv253T7.seq::::::::::::: | |
| | GCTCAAAGGCACTACTGGCACCAAGGCCCACACGTCACCTGTGACTCCTGCGCCGACCCGCCCGAGGTCTGGCCGTTACACCGAACGGGCGAGCCGGGAGTTGGTA | (SEQ ID NO. 277) |
| | CCATCGAACAAGACAAGGTGCATGGGCGGAGTTGTTCCGCCACTTCGTCGATGACGGGTC | |
| | CGATACCGGCTGCTTACCGAGACATCCACCATGCCACCCGAATCACCGCACGCGCCGAAATCGCACAACAGCTTGACGCCTTGCAGGTTCCGCGATTGGAATTGCC | (SEQ ID NO. 278) |
| | GACGGTCTCTGACGGCGTCGACCTTGGCAGCCTCTACGAGCTCTCGGAATCACTTGCCCAGCAGGGGGTTCGATGAGTGTCACACCGAAGACCTCGATATGGGCGC | |
| | AATCCTGGCCGACACATCCAACCGGGTGGTTGTGTGCTGCGGCGCCGGTGGGGTCNGCAANACACTACCGCGGCCGCGCTGGCGTTGCGCGCGGCCGAATATGGCC | |
| | GCACTGTGGTCG | |
| | :::::::::::::Rv254T7.seq::::::::::::: | |
| | CGTCGTCGTCGTGGTATGCGATAGCCATCCCGTCGGGCTACTCGCCATCACCGATCAGCTTCGCCCCGAAGCCGCCGCGGCGATTTCCGCTGCGACCAAACTGACC | (SEQ ID NO. 279) |
| | GGGGCCAAACCGGTATTGCTTACCGGCGACAACCGGGCCACCGCCGATCGGCTCGGTGTACANGTTGGCATCGACGACGTACGGGCCGGGCTACTGCCGACGACAA | |
| | NGTCGCAGCCGTGCNGCNGCTGCAAGCTGGAGGTGCCAGATTGACCGTGGTCGGTGACGGTATCAACGACCTCCGGCCTTAGCGGCCGCGCATGTCGCATCGCCAT | |
| | GGGCAGCGCCCGAC | |
| Clone Rv255 | :::::::::::::Rv255SP6.seq::::::::::::: | |
| | GCACGCAATCGAAGTCACCCAAACCGGGCGGGCCAGGCGTCTNACGCCACGTCNACCAGCCGCAACCTCAACCCGGCCACGGCGAGCTCCTGATCAAGGCCGAGGC | (SEQ ID NO. 280) |
| | CATCGGTGTCTACTTCATCGACACCTACTTCCGCTCCGGGCAATATCCGCGCGAACTCCCGTTCGTCATCTGCTCCGAAGTATGCGGCACGGTGGANGCCGTCGGC | |
| | CAGGGGTTAC | |
| | :::::::::::::Rv255T7.seq::::::::::::: | |
| | TCGACTGTGTGGCCACAGATCACGCCCCGCATGCCGAGCACGAGAAATGCGTCGAATTCGCCGCGGGCCGGCCGGCATGCTCGGGTTGCAGACGGCATTGTCGGTG | (SEQ ID NO. 281) |
| | GTGGTGCATACAATGGTGGCGCCGGCTTGTTGANTTNGGCGCGATATCGCGCGGGTGATGAGTGANAACCGGCGTGCA | |
| Clone Rv257 | :::::::::::::Rv257SP6.seq::::::::::::: | |
| | GAACCTGACACCCTGGTCACGGGTGAGCACGGACTTGATTTCTTCNCTATTGGTCGGCGCTGTTGAGCACACCACGCCGCTGACGGCCGTCGCGTCCTCGCTGTGC | (SEQ ID NO. 282) |
| | TCGGTCTGGTGGAGCGCGCTGCCCGCGGCCNAACATCNTAAATCAAGCGTATTCGTCAACAGATATCATCAATGTCGGCGCTGGACTATTCAAATCATCGATATAC | |
| | TGGTGACCTGGTCCTTCGCCATCGATCAATGGCGATAGTCACGCAAATCGTCACGGACATCGTCGGCGTCCCAGCTGGCCCGTGCCAACAGATGCTGCAACCCATC | |
| | GGGGTGGTATCACCGCGGTGCTCGGCGATGGTCCACAATTCTTGCGGTCCAAGCCCNAAACATCCCGGGCATGAATTCACCGGCATGCGCN | |
| | :::::::::::::Rv257T7.seq::::::::::::: | |
| | CTATCGTACCCGCGCCGGTCACCTTCTGGATATCGCCGGCCTGGTCAAGGGGGCGTCCGAGGGAGCCGGGCTGGGTNACAAGTTCCTGGCTCATATCCGCGAATGC | (SEQ ID NO. 283) |
| | GACGCCATTTGTCAGGTGGTGCGGGTGTTCGTCGACGACGACGTGACTCATGTCACCGGACGGGTCGATCCCCAGTCCGACATTGAGGTCGTCGAGACCGAGCTGA | |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | TCCTGGCAGATCTGCAAACCCTGGAGCGGGCCACGGGCCGGCTGGAGAATGAAGCGCGCACCAACAAGGCGCGCAAGCCGGTCTACGAAGCGGCACTGCGTGCCCA | |
| | GCANGTGCTCGACGCCGGGCAAGACGCTGTTCGCCGCGGGGGTGGATGCCGCCGCGTTGCGCGACTGAAACTGCTGACCACCAAGCCCTTCCTGT | |
| Clone Rv258 | :::::::::::::Rv258SP6.seq::::::::::::: | |
| | TACTCAAGCTTCAGGCCGCCACGTCCGCCGTCCGTCGGCGACGTGACCTCGAGCGCCGAGTTCGACTCGACATCGCCGCCGGCGCATGCCGACATGAACGCGGCAC | (SEQ ID NO. 284) |
| | TCACCGCAAGCCCGTCGGACGTCAGGTCGATCGACTCCGCTTCAAGCACCGGATCGTCCGGGCAACTCGCGGCCTCGGCCTGTGCGAACGGCACACCCGTCGTGGC | |
| | GGCNCCCCGCGCGGAACTGGGCTCATCACGGTCGTTGCGAGCCGGTCGCGTCACCGCGTACCGACGCCGTC | |
| | :::::::::::::Rv258T7.seq::::::::::::: | |
| | CCGACATCGAGTGGGCTCGCAGTGACTTGGCGACCTCCAAGCCACCGGTACCCGCCGCGCGGCAAGCCAAGGACGACGACGGCCTTGCCGGATAGCTGCGCCAGGC | (SEQ ID NO. 285) |
| | GTTGCGCCAACTGGCGTCCAGCGTCGCCACGATCGTCAAAGAGCTTCATCTGCCGAGTGTGTCGCCATCTCATGGCTCCAAATATGGAATTAGGTCCCTGGGCCGA | |
| | CTGACGACAGTCCCTCAGCGACCGGATTGCGCATCCCGCCTTGTACGCTACTCCGCAAATCCCGGGCTTGCGTCCGCGGAAGCGAACTCGGCGGCGCTACGTGGTG | |
| | GTTCACTTCGGCCGTGCGCACTCGGATCGACGGGCCGATGGTGGCCGGGCCCGCGCGCTTCTTGGTCATCCGATTGAGT | |
| Clone Rv259 | :::::::::::::Rv259SP6.seq::::::::::::: | |
| | ATACTCAAGCTTGTCGCGGTAAACCGCACGCAGGGCGGTGGGTGCGGTGTCAAAGACACCCACACTTCTTTGCGGTTCGGTGATCTCGACACCGGCCGCGAGCCGA | (SEQ ID NO. 286) |
| | CCACCATGCGCGCGTAGATCGGCGATCAGCGCGTCGGCTATCGCCTGGGTGCCGCCCACCGGAATCGGCCAGCCGACCGAATGGGCCAGCGTTGCCAGCATCAGTC | |
| | CGGCGCCGGCCGACACCAGTGACGGCAACGGTGAAATCGCGTGGGCGGCAACGCCGGTGAACAACGCGCGGGCATCCTCGCCCGCCAACGACCGCCAGGCAGGGTG | |
| | CCTGGGCCATCATCCGCAGCCCGA | |
| | :::::::::::::Rv259T7.seq::::::::::::: | |
| | TGGACTCATAACGATCGGGTCAGCGACGCGCCAACACGAACGGCCGGACGAGTGGGCCAGGGTCGCGCCTCCCCTACAAACAGGATCCGTTGCCTGCGAGCGACAG | (SEQ ID NO. 287) |
| | GCTCCGGTGCGGCGTTGGGCGCCGTGCTCGTCCCAGCGTCCGGTCCCGGGTCGCCGGCGACGCTTGTTTCCTCCATACTCGCCCCCTAATCTCGAGGCAGCCCGTA | |
| | CCCGCAGGCAACCTCCCAAAAATGCAATCCCCCAAAATGCAATGCGTCGAGCTATTTCTCACACCGACCGCTAGTTGCGGATCAGAAATCCGTTGGGCGCGGAAGT | |
| | CCAGCCGAATTTGTTCTCCCGCTCCGCATCATGCTTGTAATCGTTTGGAAATCATCCTCATATGCCTCGATCGCTTCATAGGTCAAGCCCAAACCCGGCAGGATGG | |
| | GTGGCC | |
| Clone Rv25 | :::::::::::::Rv25SP6.seq::::::::::::: | |
| | CTTTACACTTTATGCTTCCGGCTCGTATGTTGTGTGGAATTGTGAGCGGATAACAATTTCACACAGGAAACAGCTATGACCATGATTACGCCAAGCTATTTAGGTG | (SEQ ID NO. 288) |
| | ACACTATAGAATACTCAAGCTTAGTGGTTGCGCACGTAAATTCGTCAGGTGACCGATCCCCTGCTGTCTCACTCGCCTCACAGCGACCACCACGGCTGGCGCTCAA | |
| | GGCGGGCACGTGCGGAGCAGATGAGGAATGTGCGACGTCTTGATGCAGCCTGTCAGAACACCGAGACCCTCGACGAACTTACGATCGAAACCGCTTAGGCCAACCG | |
| | GTGACGGGGGTGTCTTTCCGCGGCTAGGGCGCCTTATCGTCCGAAGGCCGTGGGTGGTGATCGCCTTCTGGGTCGCGCTTGCGGGTCTGCTTGCGCCGACGGTGCC | |
| | GTCCCTGGACCGATCTCCCAGCGGCATCCAGTGGCGATTCTGCCATCGG | |
| | :::::::::::::Rv25T7.seq::::::::::::: | |
| | CAGGCATGCAAGCTTGCGATGTATCAACACGCCGTTGCGCAGCGTGAGCCGATAGTTGACATCCGGCTCGGTGAAGGTGAAATCGATGGCCAGGTCGAGGTCCCAT | (SEQ ID NO. 289) |
| | GCGCGTGGGCCATTGATGCTGATCGCCAGGACGTCAAAGATTTGGTCCGGCGTCAGCTGGGCGAAAAACGTGGGCGCCGGGACTTGCCCGGAGCTGCCCGGGTTCC | |
| | CGTCGCGCAGCTCGGCGGCCCCGGTCAGAAAGAAATTGCGCCAGGTCGCACACTCCGCGCCGTAGGCCAGCTGCTCCACGGTGTCGGCATATAGCCCGCGGGCCGC | |
| | AGCGTGCTCGCTGTCGGCGAACACCGCATGGTCGAGAAGCGTTGCCGCCCAACGGAAATCACTGCGTCAAAGCTTCGCCGGGCCACTCCAGCACTCCGTC | |
| Clone Rv260 | :::::::::::::Rv260SP6.seq::::::::::::: | |
| | ATACTCAAGCTTGACCGACGCTGATCGCACCGCACGCGGGAACCTCAAGGGCACTACTGGCACAAGGGCCCACACGTCAACCTGTTAACTCCTGCGCCGACCCCGG | (SEQ ID NO. 290) |
| | CCGAAGTCCTTGGCGTTAACACCGAACGGGCCAACCCGGGAATTTGGGTTCCATCAAAACAAATAGCAGGTGCCTGGGCGGAGTGTTC | |
| | :::::::::::::Rv260T7.seq::::::::::::: | |
| | GTCGTCGTGTGCTGGGGCGTCCGTATCAGCACGCCCACGAAATGGGGCACAAGAAGGATTCCTGGAACGGTGGCTGTCCAAGATCACCCTCGCCCAAAACTGCTAC | (SEQ ID NO. 291) |
| | GGGCACTTCTACATCGAGCACAACCGTGGCCATCACGTCCGCGGTGTCCACACCGGGAGG | |
| Clone Rv261 | :::::::::::::Rv261SP6w.seq::::::::::::: | |
| | ATATGCCTTGCTGAGCTTTTCGGATCGCAGCGAGTCGTACCCGCGCCGGTCACCTTCGTGGATATCGCCGGCCTGGTCAAGGGGGCGTCCGAGGGAGCCGGGCTGG | (SEQ ID NO. 292) |
| | GTAACAAGTTCCTGGCTCATATCCGCGAATGCGACGCCATTTGTCAGGTGGTGCGGGTGTTCGTCGACAACGACGTGACTCATGTCACCGGACGGGTCGATCCCCA | |
| | GTCCGACATTGAGGTCGTCGAGACCGAGCTGATCCTGGCAGATCTGCAAGCCCTGGAGCGGGCCACGGGGCGGCTNGAA | |
| | :::::::::::::Rv261T7.seq::::::::::::: | |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

GACACCCTGGTCACGGGTGAGCAGGACTCGATTTCTTCGCTATTGGTCGGCGCTGTTGAGGCACAGCACGCCGCTGAGGCCGTCGCGTCCTCGCTGTGCTCGGTCT (SEQ ID NO. 293)
GGTGGAGCGCGCTGCCCGCGGCCGAACATCGTAAATCAAGCGTATTCGTCAACAGATATCATCAATGTCGGCGCTGGACTATTCAAATCATCGATATACTGGTGAC
CTGGTCCTTCGCCATCGATCAATGGCGATAGTCACGCAGATCGTCACGGACATCGTCTGCGTCCCAGCTGGCCCGTGCCAACAGATGCTGCAACCCATCGGGGTGG
TATCNCCGCGGTGCTCGGCGATGGTCCAACAATTCTTGCGGTCCAAGCCCGAAACCATCCGGCCATGAGTTCACCGGCATGGCGCAACGGCTGGTGCCGGGCAAAA
CGCGGCGCGATCGAATTC

Clone Rv262 :::::::::::::Rv262SP6.seq:::::::::::::
TGTAGAAGGTGGGTCCCGTCCAACTTCGCGGCGGCGGCGCGATATGCCTTGCTGGTCTTGCTCATTTGATATCCAATCTATGGGTCGTGGTTACTCAACGGGCCGA (SEQ ID NO. 294)
AGCTGGCCCTCCCACGGGTAGGGTCCTATTCGACGGTGATGTCC
:::::::::::::Rv262T7.seq:::::::::::::
CCCGAATCCGGTGGCCGGCAGGGGGCCTGGCGACGTGGACACCTTCTAACTTGTCTTTACCGGTCACTGTTGCACCCCAACACCTTTAACGACGTGGACGGACGTT (SEQ ID NO. 295)
ACATCGGATTCGACGGTGTCATCCACAGCGTTGCCATTGGGCACACCCACTACGCCAATTTCTCCGACTGGGACACCTACCGCAGCCTCGCCCCACTGCAGGGACT
GTTGTTCCCGCAACGGGCCATCGACATGATCCAGTCGTTGGTGACCGACGCGGAGCAGACTGGTGCGTATCCGCGTTGGGCGCTGGCGAAATTCCGCCACCGGCAT
GAT Clone Rv263 :::::::::::::Rv263SP6.seq:::::::::::::
TTGAGATGCTGGTCGGGATGCCGATGGTTGGAACATGGTCCCCTGGCGTCGAATACGCGCGAGCGCATGAGCTCACCGGTTCGGAACAACGTATCGAAGAACTCGC (SEQ ID NO. 296)
ACTGCTGGCAGATGGTATCTCCGATGTGGTTGTAATTTGTATCCCAACTCTAACTGTGCTATCGGATCTGCGTGAATA
:::::::::::::Rv263T7.seq:::::::::::::
CGTAATCACGATCCCGCTGAGACACTTGACCTTACGGCCGAAGTGACTTCGCTGCTGCTATGCCGACACCCGATTTCCATACGCTGCTGTACACGACGGCCGGGCC (SEQ ID NO. 297)
GGTGGCCTCCATCACGCTCAACCGCCCGGAACAGCTCAACACCATCGTCCCGCCCATGCCCGACGAGATCGAGGCCGCTATCGGGTTGGTCGAACGCGACCAGGAC
ATCAAGGTCATCNTNCTGCGCGGTGGCGGGCGCGCCTTCTCCGGCGG Clone Rv264 CAAGCTTAAGCTGGTTCCGGCCACTCCATGAGCCGTAGTGCAATGGTTCGTGCACGGCGAGGCCGAACTTGCCATAAACATCCCTGACGAAAGTCTCCGGCAAGCC (SEQ ID NO. 298)
GATTGCTTCTTCGGGCCGCTTCTTGTGGATTGTCCGATAACCCGGTCCCTCATGCTGGAAGTTGTGCGCACTCTTTCCTTCCGCGATGTGGGCTAACGACTCGTCA
TTGAGCAAGAAGTACGTGCACAGGCATCGTCCGCCGGGCTTCAGCACGCGGGAGATCTCGTCCAGATAGTGCTCCACGTCCGGNGGGAAACATGTGGGTGAACACC
GAGGTNAGAAACACCNCATCCAACGACGCATCCGGGATATGGAAAGCGAAA
:::::::::::::Rv264T7.seq:::::::::::::
TATGGTCTTCGTCGACCAGTACGTCGTAGGCGCCATGAGCCAGCGACTGAAGCCGCGCCATGCCTGCACGGCCCGCTCATCCAGCGAGGCGGCCATCTCCCGCAGA (SEQ ID NO. 299)
TAGCCTGCCGCCTCGGCGCGCACGCTGTCCGGATCGCGTCCGAGCTCGTCGGCCAGCGCACGCAGCCGCTCGTCATACCATCGGGCATCCAGCAGTTGGGTAACCT
CAACGGGGTCGGTCGCTAGCGGCGTCATTGATTCAGCAACAATACCGATGCGCTGCAGCAACTTTCGCAGTCCGATGCGGCCCACCTCCCGTGCAGTCACTGGCTA
GCCCCCGTCATGCCGGTTGTGTCGATGGCACGGCAGCGGGCTCGTAAACCTGCGGTCTCAGCTCGCTGG Clone Rv265 :::::::::::::Rv265SP6.seq:::::::::::::
GCTTAGCGGTCTTGCTCGAACCGACATTGCGTGCCACTCATGAGCGGGTGGCGGTCGCGGTGCTTACACATCT (SEQ ID NO. 300)
:::::::::::::Rv265T7.seq:::::::::::::
GTATCTGGCGCCTCTCGAATATCCTTGAACGTCCCGCGGTGCCACCCAGATAGATCGCAGCGCCCTGCAATGGAGTTCCCTTTATGGCCTCTCTAGCCTCCCGCTT (SEQ ID NO. 301)
GATCGGCTCGACCCGAGAGATGCCCTCGGGCGTTGCGGGATCTCCCTCCA Clone Rv266 :::::::::::::Rv266SP6.seq:::::::::::::
CTTCACGCCGATCCGCGACCGCGAACGCGACGGTGACGGTGGGCGACAAGGTTCGGTTGGTCGCCGCGGCGCTGGGCGATATCAGCTCACCCGGTTTCGAGGTGTT (SEQ ID NO. 302)
CGGCGACCGGACGGTGCTGCAGACATTCTTGAGCGTCCTCGACCGGCCCGATTCGGCCTTCAACATCGTGACGCCGTATTTCGGCGGTACCGCTCGGCGCCGAGTC
GAAGGCGGCCTGAGCTAAAGCCGGGCATTGCGCGAGTGGTAAACAAGTTCGGTGACTTCGGTTGACCGACTCGACGGGCTCGATCTGGGCGCGCTGGACCGGTATC
TGCGTTCGCTGGGGATCGGGCCNACCGCNANTTGCGTTGCGANCTGATTCCGGTGGAGCTCCAATCTGACTTCCGG
:::::::::::::Rv266T7.seq:::::::::::::
GCAGCTACCGACCCTAGCGACGAGTGTGTTCGCAGCGTCGAATGTGAACGTTCGGCGTGATTCGGCGCGCGGGTTCCCGCTCTCAGCGCACGTTCGGCGCCGAGGN (SEQ ID NO. 303)
GGCTAGTCCCTGGTTAAGCAATGTCTCGGTCGCCGCCAGCAGCGCGCATGTCGCCAACCCGTCNACCGCGTTGCGCATGTCCGGTACCGACGGAAACGACGGCGCG
ATCCGGATGTTCTTGTCGTCCGGATCCTTTCGATACGGGAACGACCCCCCGCCTCGGTCACCGCGATACCAACGTCCTTAGCCAANGCTACNGTCCGGCGCGCGGT
CCCGGGCAACACGTCGAAGCTGATGAANTAACCACCCTTGGGCTCGGTCCAAGANGCGATCTTGGACTCCTTAACCGCTGATNCAA TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

Clone Rv267 :::::::::::::Rv267IS1081N60.seq:::::::::::::
TCCCCATCGGCGCCGGACCGTTTGAAAGTCCAAGCACGGGTGGGATGGAATCGACGACAGTTGAGCGCCGTCGGTGGCCGTGGTCAGCAGCTGTTCGCGAACGCAC (SEQ ID NO. 304)
CAGGTCACATCCCTTCGACATCTCACCGACGTGGCACGGGCGACATCAACAGGAAGATTGACGAATCCCTCGCAGGCGCGGCACGTCCGCAGGCCAACGCCAACTA
CGGGGCCACCAGCGATCCTCCGCTCACGCACCAGCCCAAGCCAGGCTCANCCACCCAAGTCGGCCCGCGCTCTCCCTCGCCCCCTGGTCTCCGGGGCCTTGTTAAA
CAACTACCGGAAGTCCACCAATCCTCGCTGCATCTCGACACCGTCCGCCTCACTCCCTTCCTCCCGCCCCTCTCCACACNACACACCTCTTGCATTAAGGTCACGG
AGCGGTCACTTTTCGTCGGACGAAATTCGCAATCCGGCCGCTCGCCGCCAGAGAT
:::::::::::::Rv267SP6.seq:::::::::::::
CGGAAAGTGGATACTCCCAGCAGGTAGCAGGTCGCCACCACGCTGGTCAGTGCGCGTTCAGCTCGCTTGCGGCGCTGCAGCAGCCAGTCCGGGAAATAGCTGCCCT (SEQ ID NO. 305)
GGCGCAGCTTGGGGATCGCGACGTCGATGGTTGCGGCACGGGTGTCGCAAATCACGGTGGCGGTAGCCGTTGCGCTGATTGGACCGCTCATCGCTGCGTTCGCGGT
AGCCCGCCCCGCACAGGGCGTCGGCTTCAGCCCCCATCAAGGCGGCGA
:::::::::::::Rv267T7.seq:::::::::::::
GGCCGAGTCCAGCACTTCGCACTATGTGCAGACCAAANACCCGGTGGTCGCCGCGCTGCGGCAGCGGCTGGCAACGGCGCCGGTGATCACCGAGTGGTGCGNAGTT (SEQ ID NO. 306)
GCCGACCGGCAGTTCGCCGCGGGCTTACTACGAGAAGGGCCTGCGCGACGTCATCAGGTATCACGTGTCGATGACGTCGAGCGTTAACTTCCCCGACCAGACGGCG
ACCTCGCCGATGGACCCCGCGTTGTACCTGGTGTGGGCGCAAGCTAACGCCGCCGCANGCTATCGGTACTCGGTCGAAGCGCAGCCGGGGTCGCAAGCGCTAGCGG
GCAAGGTCGCGACGATCTCGGTCACCTGGACCAACTACGGCGCTGCTGCCGCCACCGAATAGTGNGTGCCCGGCTACCGGCTGGTGGATTCCACGGGACATGTGGT
TCGGACCTGCCGGCAGCGGTGGAACTGAAGANGCTGGTCT Clone Rv268 :::::::::::::Rv268SP6.seq:::::::::::::
AGCTTCAAGGACATCGTCATCGCGACCAAAACCGCGAGCTAGGTCGGCATCCGGGAAGCATCGCGACACCGTGGCGCCGAGCGCCGCTGCCGGCAGGCCGATTAGG (SEQ ID NO. 307)
CGGGCAGATTAGCCCGCCGCGGCTCCCGGCTCCGATTACGGCGCCCCGAATGGCGTCACCGGCTGGTAACCACGCTTGCGCGCCTGGGCGGCGGCCTGCCGGATCA
GGTGGTATATGCCGACAAAGCCTGCGTGATCGGTCATCACCAACGGTGACAGCAGCCGGTTGTGCACCATCGCNAACGCCACCCCGGTCTCCGGGTCTGTCAN
:::::::::::::Rv268T7.seq:::::::::::::
GCTCGCGGTCCAGCAGCAGACGTGTCTGACCCCGACGCCCGGCCGCCGGTACCGAAACCGGATCGGCCCGCCGATGGCCGCGGCCACGGCGTCTGCCTTACCCGGC (SEQ ID NO. 308)
CCGGATACCAGCAGCCACACCTCGCGGGAACGCTGAATCGCCGGCAGGGTCAAGGTGATTCGGCGTGGCGGCGGTTTCGCGAATCGTCCACCGCCACCACCATGCG
GGTGCTCTCGAAGACGCGGGGCTGTGCGGGAACAGCGAGTTAATGTGGCCCTCGGGCCCCATGCCCAGCAGGTGGACGTCGAAATTCGGCCCGGGTCACCTGGTGC
GGCACTGGCGGCC Clone Rv269 :::::::::::::Rv269SP6.seq:::::::::::::
AGCTTGTCGATCGTCCGGCAGCGTCCGGCGAGTCAAGTCGAAGCCAGTCCGGTCTCCTCTCCGACTACGGCCAAGAACTGGGCGACGGTGTCAGTGCATACCAGCG (SEQ ID NO. 309)
GANACTGGTGGCGCCCTAGGCGAGCGACCGCCTCACAAACGGCGGTGACCGCGTTCTGGTCGTGCACCATCGAGCCGTGCCCATCCCGGCCGCGTGCCGTCAGCCG
CATCCACTGGATGCCCTTCTCGGCGGTTTCAATCAGGTACAGGCGACGTTCGCCANCATCGTGCCGGGGCANGG
:::::::::::::Rv269T7.seq:::::::::::::
TTGGTGATCATCGNCCCAACGACCCCGAGGCGATGTTCTTGCACACCGAGGAGTGTCGCAAGCTGGGGCTGGCCTTCGCCGCCGATCCGTCTCAGCAGCTGGCGAA (SEQ ID NO. 310)
GCTGTCGGGGTGAGGAAATTCGCAGGCTCGTCAACGGTGCTGCTTACTTGTTCACCAACGACTACTAATGGGATCTGCTGCTGTCCAAGACCGGCTGGTCAGANGC
CGATGTGATGGCGCAGATCGACCTGCGGGTGACCACATTGGGTCCTAAGGGTGTCGATTTGGTAGAACCTGACGCACCACCATCCACGTCGGCGTTGGTCCCCGAA
ACAGCCAGACCGA Clone Rv26 :::::::::::::Rv26SP6.seq:::::::::::::
GGCTCGTATGTTGTGTGGAATTGTGAGCGGATAACAATTTCACACAGGAAACAGCTATGACCATGATTACGCCAAGCTATTTAGGTGACACTATAGAATACTCAAG (SEQ ID NO. 311)
CTTGATTTTGATCATCATGATGATCATCACCCGAAGTGTGGTAGCCGCAGTGGTTATCGTGGGTACCGTCGTGCTTTCCATGGGCGCCTCTTTCGGGCTTTCCGTA
TTGGTCTGGCAGGACATTCTGGGTATCGAGTTGTACTGGATGGTGTTGGCGATGTCGGTGATCCTGCTCCTGGCGGTGGGATCCGACTACAATCTGCTGCTGATTT
CCCGGTTGAAAGAGGAAATTGGGGCCGGATTGAACACCGGAATTATCCGTGCCATGGCTGGTACCGGGGGAGTGGTGACGGCTGCCGGCATGGTGTTCGCCGTTAC
CATGTCGTTGTTTGTGTTCAGCGATTTGCGAATT
:::::::::::::Rv26T7.seq:::::::::::::
CAGGCATGCAAGCTTGGCGTGCCGTTCCAACCCGAATTGGCTTTCGGCGCCATCGGTGAGGACGGCGTGCGGGTGCTCAACGACGACGTCGTCCGCGGGACACACC (SEQ ID NO. 312)
TCGATGCTGCCGCCATGGACGCGGTCGAACGCAAGCAGCTGATCGAGCTACAACGCCGCGCGGAACGCTTCCGCCGCGGGCGTGACCGCATCCCGTTGACCGGGCG
GATCGCGGTGATCGTCGATGACGGCATCGCCACCGGAGCGACGGCCAAGGCGGCGTGCCAGGTCNCCCGGGCGCACG TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

Clone Rv270 :::::::::::::Rv270SP6.seq:::::::::::::
GGCATCTTGGCCGCCATGTTAGCCACACTGCCACCGGCTATAGAAGCGATGCGCACCGTCCTGCCAGCACATTGCGGCGCTCCTCCCTGGAAAGCAAGATAACCAA (SEQ ID NO. 313)
GCTCATGCCGTGGTTGTGGGTGGCGTGGTTTGGTTTGGGTAACTTTGG
:::::::::::::Rv270T7.seq:::::::::::::
TCGGCTAATAATCGTCGACGCCGGCCTCCTCTGCAATCGCCTTGGCGGTCGCCGGGTTGTCACCGGTGATCATCACGGTGCGGATGATCATTCGGCGCATTTCGTC (SEQ ID NO. 314)
GAATCGTTCCCGTATGCCCACCTTGACGATGTCCTTCAGATGGACGACGCCGATGGCCCGCGCGCTGCTGTTATCGGTCCATTCCGCAACGACTAGGGGTGTCCCC
CGCCGGAGCTGATGCCGTCGACAATGGCACCCACCTCCTCGGTGGGGTGGGCACCGTGATCGCGAACCCACTTCATCACCGCAGCCGCGGCACCTTGCGGATTCGA
CGGATG
Clone Rv271 :::::::::::::Rv271SP6.seq:::::::::::::
CTCAAGCTTGGAGGCGTGGCGATCGCGGTCCAAGGCGCGCTCTCCGAGCACAACGAGCGAAGACNGCTCGGCGACGGAGCCTTTATCGACNTCCGTTCGGGCTGGC (SEQ ID NO. 315)
TGACGGCGGCNAAATAATGCTGGACTCGTTGTTGTCGACGGTGCCGTGGCGAGCCGAGCGCCGTCAGATGTACGACCGGGTGGTCTATGTGCCGCGGTTGGTGAGT
TTCCACGACCTGACCATCGAAGATCCGCCGCATCCGCTGCTGGCGCGGATGCGCCGGTGGCTCAACTAATTCTACGGCGGCGAACTGGGTNATCCCTTCNCCACCG
TCGG
:::::::::::::Rv271T7.seq:::::::::::::
CCTAGGTCAACCGTACCGTCATCGGATCGGGGTCGACCGCACAGATGGACTGGAGCTTCGGCGAGGTCATCGCCTATGCCTCGCGGGGGGTGACGCTGACCCCGGG (SEQ ID NO. 316)
TGACGTGTTCGGCTCGGGCACGGTGCCCACCTGCACGCTCGTCGAAGCACCTCAGGCCACCGGAAATCATTCCCGGGCTGGCTGCACGACTGCGACGTGGTCACCC
TCCAGGTCGAAGGGCTGGGCGAGACGATGCAGACCGTCCGGACGAGCGGCACTCCTTTTCCGTTGGCTCTTCGGCCGAATCCGGACGCCGAACCCGACCGGCGCGG
GGTCAACCCGGCACCGACGCGGGTGCCGTTTACCCGCGGGCTGCACAAATCCCGACGGGTATGGGCTTTGACCTGCCGACGGGGGA
Clone Rv272 AGCTTGGCGTGACACCAACACAGGGCACTTAAGATGGCAATGCGCCGCCTACCTGCACGTTTTCGCGATGTCAGAGGATGCCGAGGGGAGAACAATGCGAGCACGG (SEQ ID NO. 317)
CCGCTGACGTTGCTCACCGCTTTGGCGGCGGTGACATTGGTGGTGGTTGCGGGCTGCGAGGCCCGAGTCTAGGCCGAAGCATATAGCGCGGCCGACCGCATTTCGT
CTCGACCGCAAGCGCGACCTCAGCCGCAGCCGGTGGAGCTACTGCTGCGCGCCATCACGCCGCCTAGGGCTCCGGCGGCGTCGCCGAACGTCGGGTTTGGCGAACT
GCCTACCCGGGTCCGGCAGGCAACCGAT
:::::::::::::Rv272T7.seq:::::::::::::
TCATGCCGTTGGACCGACCATCGGAGTTAGTTGCCGAACCGCGGGACCACCGCAAGCACCCGGTCCTGGTCGCGCACCGCGTCGGCCAACCGCTTGAGCACCACCA (SEQ ID NO. 318)
CGCCGCAGCCCTCGCCGCGCACGAATCCATCCGCGTTGGCGTCGAAGCTGTTGCATCGGCCGGTCGGTGACAGCGCCGACCACTTGGACAGCGCGATGGCGGTGAA
CGGTGACAAGGTGAGCTGCACCCCGCCCGCCAATGCCACGTCGGTTTCACGCAGGCGAAGCTCTGACACGCCAAGTGAATTGCCACCAGCGACGACGAACAAGCGG
TATCTACGGCGATGG
Clone Rv273 :::::::::::::Rv273SP6.seq:::::::::::::
GGGTCGACTTTCTGCAAGGCGAGGCTACACCGTCGTCGTCGTGGTATGCGATAGCCATCCCGTCGGGCTACTCGCCATCACCGATCAGCTTCGCCCCGAAGCCGCC (SEQ ID NO. 319)
GTGGTGATTTCCGCTGCGACCAAACTGAACGGGGCCAAACCGGTATTGCTTACCGGCGACAACCGGGCCACCGCCGATCGGCTCGGTGTTCAGGTTGGCAT
:::::::::::::Rv273T7.seq:::::::::::::
AATCCGAAATCCTGACCGATACTTGAACCTGGTCTCGTTCGGCAATAACTCGTCGGCGTGCAGGACGCGGCGCAAACGTACTTCGGCATCAACGCGTCCGACCTGA (SEQ ID NO. 320)
ATTGGCAGCAAGCGGCGCTGCTGGCCGGCATGGTGCAATCTAACAGCACGCTCTTCCCGTACACCAACCCCGACGGCGCGCTGGCCCGGGCGGAACGTGGTCCTCG
ACACCATGATCGAAAAACCTTCCCGGGGAGGCGGATGC
Clone Rv274 :::::::::::::Rv274SP6.seq:::::::::::::
TTCCGAATTTCGGGTCCNGGTCATATGACCCTCATGGAAGAAGAAGCGGCCGCCCCGCGCCCGTGCGACGGCGAATGAAAACCCTCACCCAGGCCGCATTGAACGC (SEQ ID NO. 321)
CGACAAGACGGTGGAGCAGGTCGAAGACGTCCTGGACGGTCTGGGTAAGACCATGGCCGAGCTGAACAGCTCGCTGTCACAGCTGAACAGCACCGTGGAGCGCTTG
GAGGACGGTCTGGACCATCTCGAAGGTACCCTGCACAGCCTGGACGATCTCGCGAAACGGCTCATCGTGTTGGTCGAGCCGGTGGAAGCCATCGTCGATCGGATCG
ACTACATCGTGAGCCTCGGCGAAACGGTGATGTCACCGCTGTCGGTC
:::::::::::::Rv274T7.seq:::::::::::::
NCTCGATCTTGGGGTACGTTCGATGAGGCTGCTGACCAACAACCCGGCCAAGCGGGTGGGACTGGATGGATACGGATTGCACATCATCGAGCGCGTGCCGCTGCCG (SEQ ID NO. 322)
GTGCGGGCCAACGCGGAAGAACATCCGTTACCTGATGACCAAGCGTGACAAATTGGGGCACGACTTGGCTGGGTTGGACGATTTTCACGAATCCGTGCATCTGCCC
GGAGAATTCGGCGGTGCCTTGTGAAGGTGGCGCCGGGGTGCCGGATCTGCCGTCGCTGGATCGTCTGGTGTGCGGCTGGCGATTGTCGCCAGCAGCTGGCACGGAA
AGATCTGCGACGCGCTGTTGGACGGCGCCCGCAAGTGGCCGCCGGGTGTGGCCTCGATGACCGACTGTGGTTCGGGTGCTCCGCGCGATCGATAT TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

Clone Rv275 ::::::::::::Rv275SP6.seq::::::::::::
TCATCCCGACCAAAACGCGAGCTAGGTCGGCATCCGGGAAGCATCGCGACACCGTGGCGCCGAGCGCGCTGCCGGCAGGCCGATTAGGCGGGCATATTATCCCGCC (SEQ ID NO. 323)
GCGGCTCCCGGCTCCGAGTACGGCGCCCCGAATGGCGTCACCGGCTGGTAACCGCTCTTGCGCGCCTGGGCGGCGGCCTGCCGGATCAGGTGGTAGATGCCNACAA
AGCCTGCGTGATCGGTCATCACCAACGGTGACAGCAGCCGGTTGTGCACCAAGCGCGAACGCCACCCCGGTCTCCGGGTCTGTCCAACCGATCGACCGCCCAAGCC
CACATGAACAAACCCCGGCATCACGTTGCCGATCGGCATACCGTGA
::::::::::::Rv275T7.seq::::::::::::
TTGGCGGGTTGGCCCAGCAGCCCGCCGGTGACGGCGACGATGCTGGGCTGGTTGCGGCCCTGCGCCACCGCGGCTTGCATGCTGGTTGGCTGTCTTGGGACGATCC (SEQ ID NO. 324)
CGAAATAGTCCACGCGGATCTGGTGATTTTGCGGGCTACCCGCGATTACCCCGCGCGGCTCGACGAGTTTTTGGCCTGGACTACCCGCGTGGCCAATCTGCTGAAC
TCGCGGCCGGTGGTGGCCTGGAATGTCGAGCGCCGTTACCTACGTGACCTGATGGATCGGGGGGTGCCGACCGTGCCCGGCGATGTGTATGTGCCGGGANAGCCGG
TCCGGTTGCCACGCAAAGGCCATGTCTTCGTCGGTCCGACCATCGGTACCGGGACACGGCGCTGTATTGCCCGGTTCGCTGCCGAGTTCGTCGCGCAACTGCACGC
NGGCGGGCCAGCGGTGCTCGTTCANCCCGGAGGTTCCGGTGACGATGATCGTGTTGGTCTCCCT Clone Rv276 ::::::::::::Rv276SP6/seq::::::::::::
GTAGGAGAGAACAAAGACCGTCGATAGGACACGTGTTACGCCGGTAGCTGTCATTGGTATGGGGTGCCGCTGCCGGGGGGCATCTACTCACCCGATCGGTTGTGGG (SEQ ID NO. 325)
AGGCGTTGCTGCGGGGCGACAATCTGGTCACCGAGATCCCCGCCGACCGCTGGGACATCTACGAGTACTACGACCCCGAACCCGGCGTGCCCGGACGCACCGACTG
CAAATGGGGCGCGTACCTCGATAACGTCGGCGACTTTGATCCCGAGTTCTTCGGGATCGGGGAGAAAGAAACGATAGCGATCGATCCGCAGCACCGCTTGTTGCTG
GAAACCTCCTGGGAAGCCATGGAACACGGCGGGCTAACACCGAACCATATGCCTCCCGACANGGGTTTTCGTGGGGTT
::::::::::::Rv276T7.seq::::::::::::
CGAACTGAGCCCATAGAAAGGCAGCGACTAATTCGCTGGGCAAATAGGAAGACCCTTTGTCCTGCCACGTATATTTGTCGACCTCGTTGCGAAGGAAGCGGCTGCG (SEQ ID NO. 326)
ATTGGTGCCCTTTTCCCTGGAGAATCTCTGCCCGGAGCAGGAAGTCTTATGAGTTGACAAGCAGGGGCGCCGCCTTCGCCGGAAATCACATTCTTGGTCTCGTGAA
ATGAGAGCGCTCCCAGGTCGCCGATGCTGCCGAGCGCCCGCCCACGATACGACGCCATCGCGCCTTGGGCCGCGTCTTCGACCACCGCCAGGTTGTGGTGCGTGGC
GATCTTCATGATCGCGTCCATCTCGCAGGCCACCCGGCATAGTGAACGGGGACCATGGCCTCGGTTCGCGGGTGAA Clone Rv277 ::::::::::::Rv277SP6.seq::::::::::::
CTTAGACGCCACCTCCGGGCCGAGCTCCACGGGGTGGATAAGTACGGCCGGATGTGGCCGCAATGGGAAGTTGTTGCCCGCTTGACTGTCCGGGTTAACGCCGGAT (SEQ ID NO. 327)
TCCACCACATCCCCTTGCGAAAGGCCGTTGGGTT
::::::::::::Rv277T7.seq::::::::::::
GATCGCGATCGTCGATGTGGCCATCCGGCTTGGCGTCGACCCGCGTAAGGCAGACCAGATGGTTCGCGGCACGGTCAACCTGCCACACGCACTGGTAAGACTGCCC (SEQ ID NO. 328)
GCGTCGCGGTATTCGCGGTTGGTGAAAAGGCCGATGCTGCCGTTGCCGCGGGGGCTGATGCTGTCGGATCGACGATCTGATCGAGAGGATCAGGGCGGCTGGCTGG
AATTCGATGCCGCGATCGCGATACCGGATT Clone Rv278 ::::::::::::Rv278SP6.seq::::::::::::
AGCTTACGCCGCTTTCGCTTCNGATTTGGGACGCCGCATCGAAAGCGCAGTTGGAAGCGCGGCGCCCGGCTGGTCGAGCTGCTCAAGCAGCCGCAATCCCAGCCCA (SEQ ID NO. 329)
TGCCCGTTGAGGAGCAAGTGGTTTCGATCTTCCTGGGCACCGGCGGTCACCTGGACTCGGTGCCCGTCAAGGATGTCGGCGGTTCGAAACCGAATTACTGGACCAC
ATGCGGGC
::::::::::::Rv278T7.seq::::::::::::
CGACGGGACCTCGTCGCATCTTCCATAGCCCGCCACACCTTCAGTTGCTCACCGGAATCCAACCGGTATAAGGTCGGCGAAGCGCTCGGCATTGGTCATCGGGATA (SEQ ID NO. 330)
TGCCGCTCGGGACGGTCAGATGCCCTCGGGTCCNGCCAGCACTCCTCAGGCTTCGTCGGGGTGGTCGCGACCGCATGGGCCACATCGCATTCACCAGGTCTGCGCG
AATCACCAGCACGTANACGGTTCCTTTCCTAAGCAACACCGAAATTTCAGGACCCGAATGCTCCGGGAAAACATGTCACGGTAAGTCCGGTATTCCGGGTACCGGT
TGAGCATTGA Clone Rv279 ::::::::::::Rv279SP6.seq::::::::::::
CGGCATCGGTTTGGGCTGTCACCAGCAGTTGGTAGTTCTTCACTACTGTTGTTCGAGCGTCGAGCCGCCGCGCGTGTCGAGGTCGCCGGACGCGTACCCGCCAGGC (SEQ ID NO. 331)
CGGTCAGGGTGCCCTTCCAGTCCACGCNGCTGTGGTCGGCTAACCGCTTATCTTCAATCGAGACNATCGCCAGCTTCATCGTGTTGGCGATCTTGTCCGAGGGCAC
CTCGAACCGGCGCTGCGANTACAGCCACGCGATCGTGTTGCCCTTCGCGTCGACCATCGTCGATACCGCAGGCACTTGCCCCTCGAGCAGCTGGGCCGATCCGTTG
GCAACGACCTCAGAGGCACGATTGGACATCAGCCCTAGCCCGCCTGCG
::::::::::::Rv279T7.seq::::::::::::
CCGTCGANGCCGCCGACTTGGCTTGACCGACACCAACATGGCCTGAGGGTGTTCAACAAGACCGTGGCCGACGGGCTGAACATCACCATGAGCGGCATGAGCCACG (SEQ ID NO. 332)

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | CCACCGAGTTCATCATGTTGATCGCCGAAAACCATTGGCGGGTAGCGGAAGAACGGTCGAGGTGCTCTACACCGAGTATTCGAAGTCGAAAGGCCAACCGCTGCTC | |
| | AACGGCGTCAACATCATTTTCGACGGGTTTCTGCGAGGGAGGATGCCACGATGAACTGGATCCAGGTGCTGTTGATCGCGTCGATCATCGGGTTGCTGTTCTACCT | |
| | GTTGCGGTCGCGCCGAAGCGCGCGGTCCGTGCCTGGGTCAAGGTGGGCTATGTCTTGTTCGTGCTCCCGGCATCTATGCCGTGCTGAGA | |
| Clone Rv27 | :::::::::::::Rv27SP6.seq::::::::::::: | |
| | TTACACGNCCTGCTTCCGGCTCGTATGTTGTGTGGAATTGTGAGCGGATAACAATTTCACACAGGAAACAGCTATGACCATGATTACGCCAAGCTATTTAGGTGAC | (SEQ ID NO. 333) |
| | ACTATAGAATACTCAAGCTTTTTGAGCGTCGCGCGGGGCAGCTTCGCCGGCAATTCTACTAGCGAGAAGTCTGGCCCGATNCGGATCTGACCGAAGTCGCTGCGGT | |
| | GCAGCCCACCCTCATTGGCGATGGCGCCGACNATGGCGCCTGGACCGATCTTGTGCCGCTTGCCGACGGNGACGCGGTANGTGGTCAAGTCCGGTCTACNCTTGGG | |
| | CCTTTGCGGACGGTCCCGACGCTGGTCGCGGTTGCGCCGCGGAAAGCGGCGGGTCGGGTGCCATCAGGAATGCCTCACCGCCGCGGCACTGNACGGCCAGTGCCGC | |
| | GGCGATGTCNGCCATCGGGACATCATGCTCGCGTTCATACTCCTCGACC | |
| | :::::::::::::Rv27T7.seq::::::::::::: | |
| | CAGGCATGCAAGCTTTGTCACACCAAGTGTTTCGACCAGGCGCTCCATCCGGCGAGTGGATACTCCCAGCAGGTAGCAGGTCGCCACCACGCTGGTCAGTGCGCGT | (SEQ ID NO. 334) |
| | TCAGCTCGCTTGCGGCGCTGCAGCAGCCAGTCCGGGAAATAGCTGCCCTGGCGCAGCTTGGGGATCGCGACGTCGATGGTTGCGGCACGGGTGTCGAAATCACGGT | |
| | GGCGGTAGCCGTTGCGCTGATTGGACCGCTCATCGCTGCGTTCGCGGTAGCCCGCCCCGCACAGGGCGTCGGCTTCAGCCCCCATCAAGGCGG | |
| Clone Rv280 | :::::::::::::Rv280SP6.seq::::::::::::: | |
| | AGCTTAGCCAGTTTTTCTACTCTTGGGCCCACACCCACAGTGCTTCGACGGTACGGTCACCCATGATGGCCATCCAGTTGGCATCGGTGAGCTGATAAATGCCAGC | (SEQ ID NO. 335) |
| | TGGTTTCGCCAACCCGGTAGCGATCTTGGCGCGCTGCTTGTTGTCACTGATACCTATCGAGCAAGACAGCCCGGTTTGCGACAAGATGACTTTTCGGATCTCTTCG | |
| | GCGACTTCGATGGGGTCGTCGGGAGTCCCGGGCGCCACCGCGAGGTAAGCCTCGTCCCAGCCCCATACCTCGACCGGGTATCCCAGGTCGCGCAATAACGCCACCA | |
| | CCTCCTCGGACGCCGCGTTGTAGGCGGCTGGGTTCGACGGCAAGAAGTGGCCTCAGGGCATCGTCGGCGCGGTCCCAACGGCNTGCCGGCGCGCACACCGTAGGCG | |
| | CGGGGCTC | |
| | :::::::::::::Rv280T7.seq::::::::::::: | |
| | CCGGCGGAACTCAGACGTGCTGGTGGTGCGGCATGGCACCGCGGGCAGCAAAGCGCACTTCTCCGGGGACGACAGCAAGCGACCGCTAGACAAGAGGGGTCGTGCG | (SEQ ID NO. 336) |
| | CAGGCAGAAGCGTTGGTACCACAGCTGCTGGCGTTCGGCGCCACCGATGTTTATGCCGCCGACCGGGTGCGCTGCCACCAGACGATGGAGCCACTCGCCGCGGAAC | |
| | TGAACGTGACCATACACAACGAGCCCACCCTGACCGAAGAGTCCTACGCCAACAACCCCAAACGCGGCCGACACCGAGTGCTGCAGATCGTCGAGCAAGTAGGCAC | |
| | ACCCGTGATCTGCACGCAGGGCAAGGTCATTCCCGATCTGATCACGTGGTGGTGCGAGCGCGACCGTGTGCCCCCGACAGTCCCGCAATCGCAAAGGCAGCACGTT | |
| | GGTGT | |
| Clone Rv281 | :::::::::::::Rv281SP6.seq::::::::::::: | |
| | GTATGGTCAGCTGTCCATCCGGCGCTGTCGGCCGAGCTGCCAGATCTCGTCAGCCCGTAACCGGGTTGCGGGATCCACGCGTGCGGGTTGTCTAC | (SEQ ID NO. 337) |
| | :::::::::::::Rv281T7.seq::::::::::::: | |
| | CCGACTTTCCGCGGGTACCCGCTCAACTTTGTGTCNACCTCAACGCCATTGCCGGCACCTACTACGTGCACTCCAACTACTTCATCCTGACGCCGGAACAAATTGA | (SEQ ID NO. 338) |
| | CGCAGCGGTTCCGCTGACCAATACGGTCGGTCCCACGATGACCCAGTACTACATCATTCGCACGGAGAACCTGCCGCTGCTAGAGCCACTGCGATCGGTGCCGATC | |
| | GTGGGGAACCCACTGGCGAACCTGGTTCAACCAAACTTGAAGGTGATTGTTAACCTGGGCTACGCGACCCGGCCTATGGTTATTCGACCTCGCCGCCCAATGTTGC | |
| | GACTCCGTTCGGTTGTTCCAGAANGTCAGCCCG | |
| Clone Rv282 | :::::::::::::Rv282SP6.seq::::::::::::: | |
| | GCACCGATGTCGGCGAGCACTTCGTCAACTTCCAGGGGTGCCCGCACCAAGTATTTCGACGAGTATTTCCGTCGGGCCGCCGCCGCCGGTGCGCGGCAGGTGGTCA | (SEQ ID NO. 339) |
| | TCCTGGCGGCGGGGCTGGGACTCGCGCGCGTACCGGCTGCCTCGGC | |
| | :::::::::::::Rv282T7.seq::::::::::::: | |
| | TGCACCCAACTTACTGAGCATGCTAACGCTGGTCGTGCGGGTCTTGTTCCCGCGTGTCGGCAGGGCACACGCTCGGGGCGTAGCTGGGAGAGGCCCCGGTCAAGCC | (SEQ ID NO. 340) |
| | CGGAGAGCAGTGCTCAGTCCGCCAGCTTGACCGACTTTCGATGAGAACGCGCTTCTCGCCGTATTGAACTGGCGTGCTGACGGTCGCTGAGCAGCGCTCGCCGAGT | |
| | GCGGCCGCTGATTCTTTCATCGAGCCAGGACGCGCATTCGTGTTCGGCCGC | |
| Clone Rv283 | :::::::::::::Rv283SP6.seq::::::::::::: | |
| | AGCTTACGGCCGGTCGACGCGACGAGTGGTTCATGACACCACAAACCGTCAACGCCTACTACAACCCGGGGATGAACGAAATCGTCTTCCCGCAGCGATTTTACAG | (SEQ ID NO. 341) |
| | CCACCATTTTTCGATCCGCAGGCCGACGAGGCCGCCAACTACGGCGGGATCGGGGCGCGTGATCGGGCACGATGATCGGGCACGGTTTCGACGATAGGGCGCCAAA | |
| | TACGANGGCGACGCAATCTGGTCNATTGGTGGATCGA | |
| | :::::::::::::Rv283T7.seq::::::::::::: | |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | ATGTCGTCACGTCACCACAATCGCGAGGACCCAATCATGCCGCCCAGGGCGGCCAACCCAATGGTGGCCGCGAAGCGGCAGCTCGATCGCAGCGCGGAGGTGCCGG<br>CCGCCAGTTGATTCACGAACAGGGTGAGGTCATAGGCGGGCAGGATAGTGACGAACGCAAGACCTATATCTGCCGTCGGAGTAAGAATCGAGTAGCCGGTCGACCA<br>ACGGAAGCGAAAGTGTCCGCGATGTTGATGAGCGTCGCCGGTTGTGGCGGCGGTGGC | (SEQ ID NO. 342) |
| Clone Rv284 | :::::::::::::Rv284SP6.seq::::::::::::: | |
| | AGCTTCACCAGCGTGCCGATGCTGTTCGCNACACCTCCCTACTATGCGCAATTCGCCGACACGGGTGGCATCAACACGGGCGATAAGGTGGACATCGCTGGGGTGA<br>ACGTCGGGCTGGTGCGCTCGCTGGCAATCCGCGGCAACCGCGTGTTGATCGGATTCTCGTTGCCCGGCAAGACAATCGGGATGCAAAGCCGGGCAGCAATTCGCAC<br>CGACACCATTCTTGGCCGTAAGAACCTGGAAATCGAACCCCGCGGTTCGGAGCCGTTGAAACCCAACGGTTTCCTGCCGTTGGCGCAGAACACTACGCCATACCAA<br>ATCTATGACGCGTTCGTC | (SEQ ID NO. 343) |
| | :::::::::::::Rv284T7.seq::::::::::::: | |
| | CTGCCGCGGTGGCGGTCAGCGCCTGGCAAGTCACCGCACCGCCGTCCGGTTCATCGGCAGGCTCCCCCGAAAAGGGCCCTGGCAACAGAAGGTGATCAATGAGCTC<br>CCGCAGACCTTCGCCGATCTGGGACCGACATACGTGAAGTTCGGCCAGATCATCGCGTCCAGCCCGGGAGCATTCGGTGAGTCGCTGTCGCGGGGAATTCCGCGGC<br>CTGCTCGACCGGGTGCCGCCCGCAAAAACCGACGAGGTGCACAAGCTCTTCGTCGAGGAACTCGGCGACGAGCCGGCCCGGCTGTTCGCCTCCTTCGAGGAAGAAC<br>CGTTCGCGTCTGCGTCCATCGCCCAAGTGCACTACGCGACCTGCGCAGCGGCGAAGAAGTGTGGTCAAGATCCACGGCCGGGCATCCGCCGCCGCGTTT | (SEQ ID NO. 344) |
| Clone Rv285 | :::::::::::::Rv285SP6.seq::::::::::::: | |
| | GATCGTGCCGGCCCCCCGGCGGCAGTAGCAGATCAGCTCGTCGAAATCGCAACAACCAGTCCAGTCGATTTCCATACGGGCGCCGTCAATCAACTCTGCGAACATC<br>GCGATCGGCACCGGAAACCGGCGAGCCGCGTCAGCCAGCGCAACCAGCACCGGGATCGGATGAATCATCAATATTATCAAGTGATTTCCTGATGGCATCGAGCTCG<br>GTGATCTTGGTCTCGGGGGCCAGCTCGCCGTCGGCGACGTCGTCGATCCGGCGGCCGAGCGCATAGACCGCAAATAGTGCCGCTCGCTTTTCGCGCGGCAAGAGTC<br>GGATGCCGTAATATANGTTTCTGGCGGCCGTGCGCGTGATCNACTCGGTGATTCGATACGCCTGTTCATCTCGGTCATGCCGTCCTC | (SEQ ID NO. 345) |
| | :::::::::::::Rv285T7.seq::::::::::::: | |
| | GGTGGCGCAATGACCGAAACCACCCCAGCCCCGCAAACCCCGGCGGCCCCGGCCGGGCCCGCACAATCGTTCGTGTTGGAGCGGCCCATCCAGACCGTTGGGCGCC<br>GTAAGGAGGCCGTGGTACGAGTGCGGCTGGTGCCCGGCACCGGCAAGTTCGACCTCAACGGCCGCAGCTTGGAGGACTACTTCCCAAACAAGGTGCACCAGCAGTT<br>GATCAAGGCACCCCTGGTCACCGTGGATCGGGTGGAAAGTTTCGACATCTTTGCCCACCTGGGCGGCGGCGGCCCGTCGGGTCATGGCCGGCGCGCTGCGCCTGGG<br>TATCGCCCGGGCATTGATTCTNGTATCGCCGGATGACCGGCCCGCGCTGAATAANGCCGGCTTCTTGACCGTGATCCACGCGCCACCGAACGCAAA | (SEQ ID NO. 346) |
| Clone Rv286 | :::::::::::::Rv286SP6.seq::::::::::::: | |
| | CACAATAGATTACTCAAGCTTCGAACCAGCGGCCTTATCACGTATCCCCGCTGAGACCTTGACCCTTAGGGCCGAAGTGACTTCGCTGCTGCTATGCCGACACCCG<br>ATTTCCAGACGCTGCTGTTACACGACGGCCGGGCCGGTGGCCACCATCACGCTCAACCGCCCGGAACAGCTCAACACCATCGTCCCGCCCATGCCCGACGAGATCG<br>AGGCCGCTATCGGGTTGGCCGAGCGCGACCAGGACATCAAGGTCATCGTGCTGCGCGGTGCCGGCCGCGCCTTCTCCGGCGGTTACAACTTCGGCGGCGGGTTCCA<br>ACATTGGGGGCAT | (SEQ ID NO. 347) |
| | :::::::::::::Rv286T7.seq::::::::::::: | |
| | TCAGGACGCTTATGGTTGGCAGATGGTCGCCCTGGCGTCGAATACGCGCGAGCGCATGAGCTCACCGGTTCGGAACAACGTATCGAAGAACGTCGCACTGCTGGCA<br>GATGGTATCTCCGATGTGGTTGTAATTTGTATCCCAACTCTAACTGTGCTATCGGATCAGCGTGAATATCGAGATATTGCGAATGCGATGACAGGCCGCCATTCGG<br>TTTATTCGCTTACGCTTCCCGGGTTCGATTCGTCTGATGCACTGCCGCAAAACGCGGATATGATTGTTGAAACCGTATCTAACGCAATTATTGATGTGGTAGGCGG<br>CAGCTGCCGTTTTGTGCTGTCGGGCTATTCATCGGGTGGGGGTGTTTGGCTATGCCCTCTGCTCCCAT | (SEQ ID NO. 348) |
| Clone Rv287 | :::::::::::::Rv287SP6.seq::::::::::::: | |
| | CGCAGCTGTCGCCGATCTGGTCCGGAATACCTAGCTCCAGGTTCTGAGTGGAGATGAGTGCGGCCATCGAAGTGTTGTCAATGTACTCCAGGATGTCAGGTGCCAG<br>GCCGCTGGCGAGGATCTTGGGCACCGCCGCCATGACTTGGTCGAAGTCGGCGAACGGGGCGAGCACGCTGGCGTCGTGGTC | (SEQ ID NO. 349) |
| | :::::::::::::Rv287T7.seq::::::::::::: | |
| | GTAGTTCGTTCATCCAAACACAGTGCGGTACCGGCTCAAGCGGATCACCGACTTCACCGGGCGCGATCCCACCCAGCCACGCGATGCCTATGTCCTTCGGGTGGCG<br>GCCACCGTGGGTCAACTCAACTATCCGACGCCGCACTGAAGCATCGACAGCAATGCCGTGTCATAGATTCCCTCGCCGGTCAGAGGGGGTCCAGCAGGGGCCCCGG<br>AAAAGATACCAGGGGCGCCGTCGGACCGA | (SEQ ID NO. 350) |
| Clone Rv288 | :::::::::::::Rv288SP6.seq::::::::::::: | |
| | TCCGCTCGCTTCTCCGAGAGGTTGAGTGCCAACGCTCTGCCGATGCCCGAAGCCGGCCCCGGTGATGACGGCGACCTTGCCTTCGAATGAGCTCATTTGACTACTC<br>CCCGTGGTTGTCCCTGCGATTGGTGGAGGTGGCCGCGCAGCCTTGCCCCGAGGTCGGCGATCGCGTCTCGGGCTTCGGGGAGCAGACTGACCTGCAGATGGAAGTC<br>GTGCCACATGCCCGCGAACCGGCGATGCTCGATGCTTGTTTTCGAAGCGGCGCAGGCGGTTTCGATCTTGTCCGCGTCAACACNGATCGGATCGTCGCCCGCGGTC | (SEQ ID NO. 351) |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | TGCATGACGAATGGGCG | |
| | :::::::::::::Rv288T7.seq:::::::::::: | |
| | ATGGGAGGCCACCGATTACCATCTTGCACACACCGATTCCGGGCTATTGATGTCCACGTTCGGTCCGCGAACCGCGCTGTGGCTGCTGCTGGCCAAAGGCGGAGGC | (SEQ ID NO. 352) |
| | GATACCGAAGTCAGTGCCCAAGCTTGGGTTCCACGCTCGCGCAGCCACGCCGTCACCTTTCCACGAGACCTCACCTGCCGATCCGAAATGGAATCGGCCGTGACGG | |
| | AATTGGCGCAGCGAACACTCAACGAGGTGGTGGCTTCGTCGCGAACCGTCACCCGAGTCGCGGTCACCGTGCGCACGGCGACGTTCTACACCCGCACCAAGATCCG | |
| | AAAGCTGCAAGCTCCCAGCACCGATCCCGACGTCATCACCGCTGCCGCCCGGCACGTTCTTGAACCTATTCGAGCTGGAATCGGCCGTCCGGTTGCTGGGAATTGC | |
| | NGTTAAGAACTGGGCCT | |
| Clone Rv289 | :::::::::::::Rv289SP6.seq:::::::::::: | |
| | GCTTTGCGCGCTTCTCCGAGAGGTTGGAGTGCCAACGCTCTGCCGATGCCCGAGCCGGCCCCGGTGATGACGGCGACCTTGCCTTCGAATGAGCTCATTTGACTAC | (SEQ ID NO. 353) |
| | TCCCCGTGGTTGTCCCTGCGATTGGTGGAGGTGGCCGCGCAGCCTTGCCCCGAGGTCGGCGATCGCGTCGCGGGCTTCGGGGAGCAAACTGACCTGCAGATGGAAG | |
| | TCGTGCCACATGCCCGCGAACCGGCGATGCTCGATGCTTGTTTTCGAAGCGGCGCAGGCGGTTCGATCTTGTCCGCGTCAACGCAGATCGGATCGTCGCCCGCGGG | |
| | TCTGCATGAAGAAT | |
| | :::::::::::::Rv289T7.seq:::::::::::: | |
| | CTCACGCAGCCACGCCGTCACCTTTCCACGAAGACCTCACCTGCCGATCCGAAATGGAATCGGCCGTGACGGAAATTGGCGCAGCGAAACACTCAACGAGGTGGTG | (SEQ ID NO. 354) |
| | GCTTCGTCGCGAACCGTCACCCGAGTCGCGGTCACCGTGCGCACGGCGACGTTCTACACCCGCACCAACATCCGAAAGCTGCAAGCTCCCAGCACCGATCCCGACG | |
| | TCATCACCGCTGCCGCCCGGCACGTTCTTGACCTATTCGAGCTGGATCGGCCCGTCCGGTTGCTGGGAGTGCGGTTAGAAACTGGCCTAGAAACCGGCGGGCACAC | |
| | CGCACCTGGGCGGGGN | |
| Clone Rv28 | :::::::::::::Rv28SP6.seq:::::::::::: | |
| | TGCTTCCGGCTCGTATGTTGTGTGGAATTGTGAGCGGATAACAATTTCACACAGGAAACAGCTATGACCATGATTACGCCAAGCTATTTAGGTGACACTATAGAAT | (SEQ ID NO. 355) |
| | ACTCAAGCTTGATGCCGCCGAAACCGAGCGTGAGCACGCCGCCAGCCACCACNCGCGGGTCGGGCGCCGGGCCCGGGTCGCCANGCTGCTCCGCTCGGTGATGGCA | |
| | CGCCACCGCGACACCACCCGGCTGCGCTACGTCGAGCCATACCGGGCGGAGCTACATCGGCTCGGCCGCCCAGTGTTCGGGCCCTCTTTCGAAGTCGAAGTCGATA | |
| | CCGATTGCGCATCCGCNGCCGCA | |
| | :::::::::::::Rv28T7.seq:::::::::::: | |
| | CAGGCATGCAAGCTTCACGTCCGTACGGCTCGGGTACGCTTCGGTCGCAGTGTGCGAGTGATAGATGACGACCGGGACCTCGTCTGCATCTTCCATAGCCCGCCAC | (SEQ ID NO. 356) |
| | ACCTTCAGTTGCTCACCGGAATCCAACCGGTAGAAGGTCGGCGAGCGCTCGGCATTGGTCATCGGGATATGCCGCTCGGGACGGTCAGAACCCTCGGGTCCGGCCA | |
| | GCACTCCGCAGGCTTCGTCGGGGTGGTCGCGACGCGCATGGGCCACC | |
| Clone Rv290 | :::::::::::::Rv290SP6.seq:::::::::::: | |
| | GCTTGTCTATCGTCCCGGCCAGGTCCGGCCAGTCAAGGTCGAAGGCCAGTCCGGTCTCCTCTCCGACTACGGCCAAGAACTGGGCGACGGTGTCAGTGCAGACCAG | (SEQ ID NO. 357) |
| | CGGAAACTGGTGGCGCCCTAGGCGAGCGACCGCCTCACAAACGGCGGTGACCGCGTTCTGGTCGTGCACCATCGAGCCGTGCCCAGCCCGGCCGCGTGCCGTCAGC | |
| | CGCATCCACTGGATGCCCTTCTCGGCGGTTTCAATCAGGTACAGGCGACGTTCGCCACCATCGTGCCGGGGCACGGTTAGCGAGAAACCGCCGACTTCACGATTGC | |
| | CTCGGTGATGCCGTCGAAACAGATCGGGCCT | |
| | :::::::::::::Rv290T7.seq:::::::::::: | |
| | GCGCGCCATGTTGAGGTTGTCCGACGGTGACGACGGTGAACCACAACTGTTTGACCTGTCCGCACACACCGTGTGGATCGGCGAGCGGACCCGACAAATCGATGGC | (SEQ ID NO. 358) |
| | GCGCACATCGCGTTTGCCCAGGTGATTGCTAATCCGGTCGGGGTCAAGTTGGGCCCCAACATGACCCCGGAACTGGCCGTGGAGTACGTCGAGCGGCTCGACCCGC | |
| | ACAATAAGCCGGGCCGGCTGACTTGGTGAGCAGGATGGGCAACCACAAGGTCCGCGATCTGTTGCCACCGATCGTGGAGAACGTCCATGCCACCGGGCATCAGGTC | |
| | ATCTGGC | |
| Clone Rv291 | :::::::::::::Rv291SP6.seq:::::::::::: | |
| | TTGCCTTCCATGCCGAGCAAGGTCGACTCAGCGATGACGAATTGTTCTTCTTCGCGGGTGTTGCTGCTGGTTGCGGGCTATGAGAGCACTGCTCATATGATTAGCA | (SEQ ID NO. 359) |
| | CATTGTTTCTGACGCTGGCCGACTATCCAGATCAGCTGACACTCCTTGCGCAGCAACCAGACCTGATCCCGCCGGCGATCGAGGA | |
| | :::::::::::::Rv291T7.seq:::::::::::: | |
| | CGACGCTGGGCCCAACTGCGACCACCAGGTCCTGGTATGGCAGGACATGGCCGGGTTCAGCGGCGCCAATACCG | (SEQ ID NO. 360) |
| Clone Rv292 | :::::::::::::Rv292SP6.seq:::::::::::: | |
| | TAACGACTCGGGTCCAGCGACCGCGCCAACACNAACGGCCGGACNACGTGGGCCAGGGTCGCGGCCTCCCCTACAAACAGGATCCGTTGCCTGCGAACGACAGGCT | (SEQ ID NO. 361) |
| | CCGGTGCGGCGTTGGGCGCCGTGCTCGTCCCAGCGTCCGGTCCCGGGTCGCCGGCGACGCTTGTTTCCTCCATACTCGCCCCCTAATCTCGAGGCAGCCCGTACCC | |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | GCAGGCAACCTCCCAAAAATGCAATCCCCCAAAATGCAATGCGTCNAGCTATTTCTCACACCGACCGCTAGTTGCGGATCANAAATCCGTTGGGCGCGGA | |
| | :::::::::::::Rv292T7.seq::::::::::::: | |
| | CNTGGCGGTGGGTGCGGTGTCGAACACGACCACACTTCTTTGCGGTTCGGTGATCTCGACACCGGCCGCGAGCCGACCACCATGCGCGCGTAGATCGGCGATCAGC<br>GCGTCGGCTATCGCCTGGGTGCCGCCCACCGGAATCGGCCAGCCGACCGAATGGGCCAGCGTTGCCATCATCAGTCCGGCGCCGGCCGACACCAGTGACGGCAACG<br>GTGAAATCNCGTGGGCGGCAACGCCGGTGAACAACGCGCGGGCATCCTCGCCCGCCAGCGACCGCCAGGCAGGGGTGCCCTGGGCCAGCATCCGCAGCCCGAGACN<br>CAGGACCGANCCCAGTG | (SEQ ID NO. 362) |
| Clone Rv293 | :::::::::::::Rv293SP6.seq::::::::::::: | |
| | GCTTTTCNGATCGCAGCGAGTCGTACCCGCGCCGGTCACCTTCGTGGATATCGCCGGCCTGGTCAAGGGGGCGTCCGAGGGAGCCGGGCTGGGTAACAAGTTCCTG<br>GCTCATATCCGCGAATGCNACGCCATTTGTCAGGTGGTGCGGGTGTTCGTCAACAACNACTTGACTCATGTCACCGGACGGGTCGATCCCCANTCCGACATTGAGG<br>TCGTCGANACCGAGCTGATCCTGGCANATCTGCAAACCCTGGAGCGGGCCACGGGCCGGCTGGAGAAGGAANCGCGCACCAACAAGGCGCGCAAGCCGGTCTACGA<br>CGCGGCACTGCGTGCCCAGCAGGTGCTCGACGCCGGCAANACGCTGTTCGCCGCGGGGGTGGATGCCG | (SEQ ID NO. 363) |
| | :::::::::::::Rv293T7.seq::::::::::::: | |
| | GTCGTACGCCATTNGTCGGTGTGCGCATACCAGTACGACGCGCCGGGCACCTGACGCGGCGGCCGCGACCAGTCGGTGGCCATCGCCATCGTCTGCCACCCGGTCA<br>ACGGACGCACCTTCTCCTGGCCGACGTAGTGCGCCCACCCGCCGCCGTTGCGTCCCATCNATCCGGTCAACATGAGCAGCGCCAACACCGAGCGGTACATGACATC<br>GCTGTGGAACCAGTGACAGATTCCGCCGCCCATGATGATCATCGACCGTCCTCCGGATTCGGTCGCGTTGCGGGCGAAATTCCTTGGCAAACCGGATTGCCTGCGC<br>GGCCGGCACACCGGTGATCGACTCCTGCCAGGCCGGGGTGTTCTGCTGGGTTCGGTCGTGGTACCGGT | (SEQ ID NO. 364) |
| Clone Rv294 | :::::::::::::Rv294SP6.seq::::::::::::: | |
| | GCGAGGCGGTATCGCTTCCCGTCGTACCGGCGACCGCCAGCCGAGAAGCTCGTTTTCCCAGTGTTGCTGGGGATTCTCACGCTGCTGCTGCNTGCGTGCCANACCG<br>CTTCCGCTTCGGGTTACAACGAGCCGCGGGGCTACGATCGTGCGACGCTGAANTTGGTGTTCTCCATGGACTTGGGGATGTGCCTGAACCGGTTCACCTACNACTC<br>CAAGCTGGCGCCGTCTCGTCCGCAGGTCGTTGCTTGCGATAGCCGGGAGGCCCGGATCCGCAATGACGGATTCCATGCCAACGCTCCGAGTTGCATGCGGATCGAA<br>TACNAATTGATCACCCA | (SEQ ID NO. 365) |
| | :::::::::::::Rv294T7.seq::::::::::::: | |
| | TGGGTCTTGCCGGCGAGCCCAGCGAAGTCGCTAGCGTGGCCGTGTTTCTTGGCTTCGGATCTATCCTCGTTACATGACCGGCACCGTGTTGGACGTGACTGGCGGC<br>CGGTTCATATGACACCGAGATCATTGCCACGGTACGGCAATTCGTCAAGAAGGAAATCTTTCCCNATGCACCGGCCCTCGAACGTGGCAACAGCTACCCGCAAGAA<br>ATCGTCGATCGGCTGGGTGTTATTGGCTTGCTCGGTCGCCGGCTGCAAGGGTATCGACACCACCGAGTTCATTCTCGGGCGTGCCGGCGCATTCGAGCTGGCGGTG<br>CGCGCTGCCCAGCACCGTCATAAGTACTTGANGATGGTCAAACGTCGGACGAACCGCCACCACGTCGCTGCCGAACGG | (SEQ ID NO. 366) |
| Clone Rv295 | :::::::::::::Rv295SP6.seq::::::::::::: | |
| | TAGATGCCCAAGCTTGCCNTTANAGACCTCGTCGACCAAGCACGGACGCGACCGTCGAAGGTGGCGAATCCGGGCTTGGCGTCNACCCGCGTAAGGCAGACCAGAT<br>GGTTCGCGGCACGGTCAACCTGCCACACGGCACTGGTAAGACTGCCCGCGTCGCGGTATTCGCGGTTGGTGAAAAGGCCGATGCTGCCGTTGCCGCGGGGGCGGAT<br>GTTGTCGGGAGTGACGATCTGATCGAGAGGATTCAGGGCGGCTGGCTGGA | (SEQ ID NO. 367) |
| | :::::::::::::Rv295T7.seq::::::::::::: | |
| | TCTCCACGGCGTGGATCAAGGTACCGGCCGGGATGTTGCGCAATGGCAGGTTGTTGCCCGGCTTGATGTCTGCGTTAGCGCCGGATTCCACCACATCCCCTTGCGA<br>AAAGTCCGTTGGGTGCAATGATGTAGCGCTTCTCCCCATCGAGATAGTGGAGCAACGCAATCCGTGCGGTACGGTTCGGGTCGTACTCGATGTGCGCGACCTTGGC<br>GTTGACACCATCTTTGTCATTGCGGCGAAAGTCGATCATCCGGTAAGCGCGCTTATGACCGCCGCCTTTGTGCCGGGTNGGTAATCCGGCC | (SEQ ID NO. 368) |
| Clone Rv296 | :::::::::::::Rv296SP6.seq::::::::::::: | |
| | GCCCGGTTCGATCGGGCATGTCCGCAGTCGTCGTTACCGGAGGCGGTCGTGGCCGCGCTAATCGGCGTCGGCGCCGACAAGATGTGGGATATCCGCAATCGGGGCG<br>TCATCCCTGCGGGCGCGCTCCCCCGCGTCCGAGCCTTCGTCGACGCAATCGAGGCAAGTCACGACGCGGATGAGGGGCAGCAGTGAATTACAGCGAGGTCGAGCTG<br>TTGAGTCGCGCTCATCAACTGTTCGCCGGAAACAGTCGGCGACCGGGGTTGGATGCGGGCACCACACCCTACGGGGGATCTGCTGTCTCGGGCTGCCGACCTGAAT<br>GTNGGTGCGGGCANCGCCGGTATCNACTCCCGTGGAACACAGCCGGGGC | (SEQ ID NO. 369) |
| | :::::::::::::Rv296T7.seq::::::::::::: | |
| | CTCGGCGTGGATATCGGTGTAGCCGGCGCCGGTGAANGTCGGCTCCTTACGTCCACTCGACAACAGCTCATAGCGATCCAACCAGTANGCAACCGCCTTCAGCAGT<br>ACAACCGCGCCGGCGAACACTGCGAGTTGAACGCGAGCTGCCTGGGTCAGCATGCCTCTGCCGGTTGTCAGCCGAAGGCCGCCGAACAGGTAATGCGTCAACAGGC<br>TCGCTAGAAACGCCAGAACCACGGCCACGAACAGCCAGTTCAGCACCGACCGGTAGAACGGCAGATCGAAGACGAAAAAACCCAATGTCATAGCCGAATTCGGGGT<br>CCACGATGCCAAAGGTGCCCCCGTGTACAACAACTGAACCTTCACCCA | (SEQ ID NO. 370) |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| Clone | Sequence | SEQ ID |
|---|---|---|
| Clone Rv29 | :::::::::::::Rv29SP6.seq::::::::::::: | |
| | TCCGGCTCGTATGTTGTGTGGAATTGTGAGCGGATAACAATTTCACACAGGAAACAGCTATGACCATGATTACGCCAAGCTATTTAGGTGACACTATAGAATACTC<br>AAGCTTCACGTCCGTACGGCTCGGGTACGCTTCGGTCGCAGTGTGCGAGTGATAGATGACGACCGGGACCTCGTCGGCATCTTCCATAGCCCGCCACACCTTCAGT<br>TGCTCACCGGAATCCAACCGGTAGAAGGTCGGCGAGCGCTCGGCATTGGTCATCGGGATATGCCGCTCGGGACGGTCAGAGCCCTCGGGTCCGGCCAGCACTCCGC<br>AGGCTTCGTCGGGGTGGTCGCGACGCGCATGGGCCACCATCGCATTCACCAGGTCTGCGCGAATCACCAGCACGTAGACGGTTCCTTTCCTAAGCAACACCGAAGT<br>TTCAGGACCGAATGCTCCGGGAAACATGTCA | (SEQ ID NO. 371) |
| | :::::::::::::Rv29T7.seq::::::::::::: | |
| | CAGGCATGCAAGCTTGATGCCGCCGAAACCGAGCGTGAGCACGCCGCCAGCCACCACGCCCGGGTCGGGCGCCGGGCCCGGGCCGCCAGGCTGCTCCGCTCGGTGA<br>TGGCACGCCACCGCGACACCACCCGGCTGCGCTACGTCGAGCCATACCGGGCGGAGCTCCATCCGCTCGGCCGCCAGTGTCCGGGCCCTC | (SEQ ID NO. 372) |
| Clone Rv2 | :::::::::::::Rv2SP6.seq::::::::::::: | |
| | CCTGCATCCGGCTCGTATGTTGTGTGGAATTGTGANCGGATAACAATTTCACACAGGAAACAGCTATGACCATGATTACGCCAAGCTATTTAGGTGACACTATAGA<br>ATACTCAAGCTTCCAATCCCCCTGCCCTGATACGCGTCGGCAACCGTGAACGCGATCTCGGCGACCGTCGGATCGGTTTCATCCCGCACAAAACGCGCGTCGGCTA<br>CGGGGTCGCTTCCGTCGGTCACCACCCAGACGAAGTGGTCGACGTAGTCGACTTCCGACAGGTAGTGCATCAACGCCGGACTGGGAACACNAGCCGACATGAACCG<br>TCGATACAGCGTCTCNCCGGAGAACTGGATGTGTCCGTGCACGGTCCGCTCGCGGTCACCGGGCAGCACGGGGCGTAACATCAGTTGAGTCCCGTCGGCAAGCCGT<br>ACCGGAATCGGGGAGACGA | (SEQ ID NO. 373) |
| | :::::::::::::Rv2T7.seq::::::::::::: | |
| | CAAGATGATCGCCGGTGCCACCCCGATCCGTGCCTCGGTCAGCGCGAACGTGCTTTCCGGTCCGGCGACCACCATGTCGCACGCACCGACCAGGCCGAACCCGCCG<br>GCCCGCACATGCCCGTTGATGGCGCCGACCACCGGCAGCGGCGACTCGACGATGGCGCGCAACAGCGCCGTCATTTCCCGCGCCCGCGCCACCGCCATCCGGTACG<br>GATCACCACCACCACCGCCGGCCTCGCTGAGGTCCGCGCCGGCGCAGAACGTTCCGCCGGTATGCCCCAGCACGACCAGCCGCACCGCCGGATCTGCTTCGGCCGC<br>ACTCAGCCCTTGATGTAGTTGGCTGACCAGCGTGCTCGACAGCGCGTTGCGGTTGTGCGGAGAGTTCAGTGTCAGCCTGGCGAAGGGGCCGCCGCAGGCGGCCGGG<br>CCAGCGTAGTCGACGGGGCTG | (SEQ ID NO. 374) |
| Clone Rv301 | :::::::::::::Rv301SP6.seq::::::::::::: | |
| | CTCAAGCTTCGATCGACAGTACTCCCGCCTTGGGTCTGGTCTTCGAGCTGGTCGGTCATGGTCGGACCTGCTGGTAGTGGGGATCTAACGCAACATGGTCGGGATT<br>CATCATGGTGTACCCGTGATACCCATTCGCAGCTGCCGGTGAAACCCCGCGATGCCGGGATTTCCAGCCGCACTAGGATGTCTAGCCGGCCAGCCGCTGCCGCCGG<br>ACTTCGGGATGTTCGGTATACCACCGATCGGCAATCTTGCNTATCCGCCGATGCTCGAACGCTAGCCACCCCAAACCAACCACTGTGACNACAATC | (SEQ ID NO. 375) |
| | :::::::::::::Rv301T7.seq::::::::::::: | |
| | TGAATTTCCCGATCCCACAATCTCGGTTCAGATACAGGTCGCCATACCCCTTACTTCGGCAACGCTGGGCGGATTGGCCCTGCCGCTGCAGCAGACCATCGACGCC<br>ATCGAATTGCCGGCAATCTCGTTCAGCCAATCCATACCCATCGACATTCCGCCGATCGACATCCCGGCCTCCACTATCAACGGAATTTCGATGTCGGAGGTCGTGC<br>CGATCGATGTGTCCGTCGACATTCCGG | (SEQ ID NO. 376) |
| Clone Rv302 | :::::::::::::Rv302SP6.seq::::::::::::: | |
| | TACTCAAGCTTGAACGCTGCGAGCGAGCCCATGTAGAGCGTTTGGTACCAAACCGATCGGTGGGCCAACTTGCCATGGGCTCACAGCGGCTATCGCGAGCGTGTAG<br>CCGATCATCGGCCAGGCGACGGTGGCCTGAGCGGCAGGGGTTGCCTTATCCATCCTCTTGCGGCATGGTTGCCGCAGGGAGTGCCGGTAAGTCTGGTCGGCAACCT<br>GGCCCGCTGCGGGTTGGGTTCGGATTCCCTCGGCTAGTAAGGTGCTCGCCTGGTGTTACAACGAATCGCTAGACAGCTCTTATCGGGAGTGGCCGTCGCGATCGTT<br>GCGCTGCCGCTGGCGATCGCGTTCGGCNTTACCGCCACCGGAACGTCCCAAGGTGCGCTCATCGGGCTCTACGGCGCCATCTTCGCCGGATTCTTCCCNGCCGTGT<br>TCGGTGG | (SEQ ID NO. 377) |
| | :::::::::::::Rv302T7.seq::::::::::::: | |
| | GCGGTGTCTGAACTTCGCCCGTTCCCTCCAGCGCATTGAGCTTCAGCCCGACCGGCAGGTAGGGAGTCGGCATGCGGTCCTTCGCCCCGACCCCGCTGGCTAAATA<br>GCCACCCCCGAGCGCGGTCACGGTCTTTGCACCGGGACGACGGCATACCGGCAGCGCGAACATCGCCGCGGGCTGCAGCGTGAACGTCGAATACGAGTCGAACAGT<br>GTCGGCGCGTAAAAACCCGAGCCGGCGGTCGCTTCGGTAATCAACGGCTCCTGCGCAACCAGCTGCAANTCNCCGGTGCCACCGGCGTTGACAATCTTGATNTCGG<br>CGACCTCGCGCACCAN | (SEQ ID NO. 378) |
| Clone Rv303 | :::::::::::::Rv303SP6.seq::::::::::::: | |
| | TACTCAGCTTCGGCTCAGGTGGTGCTGCTGGTAAAGTTCNCTGAACGGTGCAGGTTTCGACAATGTGGTGCCGGTTCGGCGGGTACTGCCATCGAGACACTGGCGC<br>AGGCTATCGCACCCGTTATCGGCTACAAACAAATCGCGGTATGCGTTCTTGAGCATGAGTCGGCGACCGTCGTCATGGTCGACACCCACGACGGAAAGACGCAGAT<br>CGCCGTCAAGCNTGTGTGCCGCGGATTATCAGGACTGACCTCCTGGCTGACCGGCNTGTTTGGTCNCGATGCCTGGCGCCCGGCCGGCGT | (SEQ ID NO. 379) |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | :::::::::::::Rv303T7.seq::::::::::::: | |
| | CATCACCTGGTTCATGAAACTGGAAGCAGCGCAGCGCTTCCTTTTCGGCCGCAACATGAGCCAGCCTCTCGTCGGCGGTCGGGTGCAGGTGCTCGGGCAGCTCGGC CGCGACAGCCGCCTGACCCTGAAACCAGCTTCCATATCCCGCGACGAACGACGCCAGTCCGCTACGTAACCCCTCCGCGACTGTCCATGGACAACANCGCGTTCTC CACCGACCGGGCCCGGGTGTGGGGTGTT | (SEQ ID NO. 380) |
| Clone Rv304 | :::::::::::::Rv304SP6.seq::::::::::::: | |
| | CTCAAGCTTCCCGGCGGCCAGTACCGAAAGCGCGAACAGCTCGCGGCAGCCCACAACNTGCTGCGTCGGATTGCCGGCGGCGANATCAATTCCAGGCAGCTCCCGG ACAATGCGGCTCTGCTGGCCCGCAACGAAGGACTCGAGGTCACCCCGGTGCCCGGGGTCGTGGTGCACCTGCCGATCGCACAGGTTGGCCCACAACCGGCCGCTTG ATGCCCGGTCGGCAAGCCCGGCAGTTGCCAAACCCAGCGTGATCAGGCTCGGCTCGCGAGTTCGGCGAAGAAGTGGCTCGCCTGATCACCTACCATCGGCCAGGAT CTGCGTGTCATCACNACGCTCGCCAAGGAGGTTGTTGTGGTGCT | (SEQ ID NO. 381) |
| | :::::::::::::Rv304T7.seq::::::::::::: | |
| | GCCACGTTTCGCGCCGCCCGGCATACGGCGGCGTACCGATCTCCGCGTCATACACCCGCGGGTAATCGCCGACGGTGCCGGTTCGCGAGCCGAAGGTGACGACGCT GATTGAATCGAGTTCCAGGTCCAGCGGGTGGCGCAGCAACGGCGCGAGCTCAACGACGTCAATCACGTTGTCGCTTTCTACGGTCACCGACCCGGTGACCGTAGTC GCCCGGTGCGCTCGGCCGAGAAGTTGCACCGCCACCACCGCGACACCGTCTTGCACGCGGACGCCACCCCCGGATCGGTTGTTGGCCAAGGTAATTGGGTCATTCC ATTTGACGGGACGCCGACCCCGCAGCCCCAGTACCGCCCACGACCACGCCGGCTGACCCCACCACTGTACGAACACCAAGGCGACGCCGACCA | (SEQ ID NO. 382) |
| Clone Rv306 | :::::::::::::Rv306SP6.seq::::::::::::: | |
| | CTCAAGCTTGATGCCGCCTAAACCGAAGCGTGAGCACGCCGCCACCCACCACGCGCGGGTCGGGCGCCGGGCCCGGGCCGCCAGGCTGCTCCGCTCGGTGATGGCA CGCCACCGCGACACCACCCGGCTGCGCTACGTCAAGCCATACCGGGCGGAGCTACATCGGCTCGGCCGCCCAGTGTTCGGGCCCTCTTTCGAGGTCNAGGTCNATA CCGATTTGCGCATCCGCAGCCGCACCCTGGACGACAGAACCGTGCCCTACGAGTGCTTGTCGGGCGGGGCCAAAGAACANCTTGGCATCCTGGCGCGATTGGCCGG CGCGGTCCTGGTC | (SEQ ID NO. 383) |
| | :::::::::::::Rv306T7.seq::::::::::::: | |
| | CTCGGGTACGCTTCGGTCGCAGTGTGCGAGTGATAGATGACGACCGGGACCTCGTCGGCATCTTCCATAGCCCGCCACACCTTCAGTTGCTCACCGGAATCCAACC GGTANAANGTCGGCGAGCGCTCGGCATTGGTCATCGGGATATGCCGCTCGGGACGGTCAGAGCCCTCGGGTCCGGCCAGCACTCCGCAGGCTTCGTCGGGGTGGTC GCGACNCGCATGGGCCACCATCGCATTCACCAGGTCTGCGCG | (SEQ ID NO. 384) |
| Clone Rv307 | :::::::::::::Rv307SP6.seq::::::::::::: | |
| | CTCAAGCTTCAATTCCTCCACGACGCGTTCCCAAATGAATTTCCCGATCCCACAATCTCGGTTCAGATACAGGTCGCCATACCCCTTACTTCGGCAACGCTGGGCG GATTGGCCCTGCCGCTGCAGCAAACCATCGACGCCATCGAATTGCCGGCAATCTCGTTCAGCCAATCCATACCCATCGACATTCCGCCGATCGACATCCCGGCCTC CACTATCAACGGAATTTCGATGTCGGAGGTCGTGCCGATCGATNTNTCCGTCNACATTCCGGNGGTCACCATCACCGGCACCAGNATCGACCCGATTCCGCTGAAC TTCGACGTTCTCAGCAGCGCCGGAACCA | (SEQ ID NO. 385) |
| | :::::::::::::Rv307T7.seq::::::::::::: | |
| | TTAACCCCCGTGGCCTCTACGCCGCCTNCGGGTCGAACATGCATCCCGAGCANATGCTCGAGCGCGCACCCCACTCGCCGATGGCCGGAACCGGCTGGTTACCCGG GTGGCGGCTGACGTTCGGCGGCGAGGACATCGGCTGGGAAGGGGCGCTTGCCACCGTCGTCGAAGACCCAGATTCGAAGGTGTTCGTCGTGCTCTACGACATGACC CCGGCGGACGAGAAGAACCTTGACCGGTGGGAAGGCTCCGAGTTCGGCATCCACCANAAGATCCGATGCCGCGTT | (SEQ ID NO. 386) |
| Clone Rv308 | :::::::::::::Rv308SP6.seq::::::::::::: | |
| | CTCAAGCTTGATTTTGATCATCATGGATGATCATCACCCGAAGTGTGGTAGCCGCAGTGGTTATCGTGGGTACCGTCGTGCTTTCCATGGGCGCCTCTTTCGGGCT TTCCGTATTGGTCTGGCAGGACATTCTGGGTATCGAGTTGTACTGGATGGTGTTGGCGATGTCGGTGATCCTGCTCCTGGCGGTGGGATCCGACTACAATCTGCTG CTGATTTCCCGGTTGAAAAANGAAATTGGGGCCGGATTGAACACCGGAATTATCCGTGCCATGGCTGGTACCGGGGGAGTGGTGACGGCTGCCGGCATGGTGTTCG CCGTTACCATGTCGTTGTTTGTGTTCAGCGATTTGCGAATTATTGGTCAGAT | (SEQ ID NO. 387) |
| | :::::::::::::Rv308T7.seq::::::::::::: | |
| | CGNCCAACCCGAATTGGTTTTCGGCGCCNTCGGTGAGGACGGCGTGCGGGTGCTCAACGACGACGTCGTCCGCGGGACACACCTCGATGCTGCCGCCATGGACGCG GTCGAACGCAAGCAGCTGATCGAGCTACAACGCCGCGCGGAACGCTTCCGCCNCNGGCGTTACCGCATCCCGTTGACCGGGCGGATCGCGGTGATCGTCGATGACG GCATCGCCACCGGAGCGACGGCCAAGGCGGCGTGCCAGGTCGCCCGGGCGCACGGTGCGGACAAGGTGGTGCTGGCGGTCCCGATCGGCCCANACGACATCGTGGC GAGATTCGCCGG | (SEQ ID NO. 388) |
| Clone Rv309 | :::::::::::::Rv309SP6.seq::::::::::::: | |
| | CGTGACTGCCACCGGGGCCACTCCGCAGAATCTGTACCCGACCAAGATCTACACCATCGAATACGACGGCGTCGCCGACTTTCCGCGGTACCCGCTCAACTTTGTG | (SEQ ID NO. 389) |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | TCNACCCTCAACGCCATTGCCGGCACCTACTACGTGCACTCCAACTACTTCATCCTGACGCCGGAACAAATTGACNCAGCGGTTCCNCTGACCAATACGGTCGGTC | |
| | CCACGATGACCCANTACTACNTCATTCGCACGGANAACCTGCCGCTGCTAGAGCCACTGCGATCGGTGCCGATCGTGGGGAACCCACTGGCGAACCTGGTTCAACC | |
| | AAACTTGAAGGTGATTGTTAACCTGGGG | |
| | :::::::::::::Rv309T7.seq::::::::::::: | |
| | TCGCTCAAGCGCNTGAGGCCGAANCGGCTGGTTACGACTCCCTGTTTGTGATGGACCACTTCTACCAACTGCCCATGTTGGGGACGCCCGACCAGCCGATGCTGGA | (SEQ ID NO. 390) |
| | GGCCTACACGGCCCTTGGTGCGCTGGCCACGGCGACCGAGCGGCTGCAACTGGGCGCGTTGGTGACCGGCAATACCTACCGCAGCCCGACCCTGCTGGCAAAGATC | |
| | ATCACCACGCTCGACGTGGTTAGCGCCGGTCGAGCGATCCTCGGCATTGGAGCCGGTTGGTTTGAGCTGGAACACCGCCAGCTCGGCTTCGAGTTCGGCACTTTCA | |
| | GTGACCGGTTCAACCGGCTCGAAAAGGCGCTACANAT | |
| Clone Rv30 | :::::::::::::Rv30SP6.seq::::::::::::: | |
| | ATACTCAAGCTTCCGCTGGGGCCTGTTCAACCATGGCGATCCCGTTGGTCCCGGACATCCCGAACGAGGACACCGCGACCCNCTTCGGTGTGTGATCATTACCGTT | (SEQ ID NO. 391) |
| | GGGCCACTGCGTAACCGCTTGCGGCACAAAGAGCCCGGTCTCGACGTCGGAAAGCTCATCGGGCACCCGATTGAAATGCAGCAGCGGCGGCACCACCCCGTGCCGC | |
| | AGTGACAGAATTGCCTTGATCAGCCCGACGGTCCCCGCCGATGCCGTGCTGTGCCCCATGTTGCTCTTGGCCGATCCAAGCGCGCAGGGGGTGCCCGCGCCATACA | |
| | CCCGCGCCAGGCTGCGGTACTCAATCGGGTCGCCGATTGGCGTACCGGTGCCGTGCGCCTCCACCACACCGACCGTTTCGGGCTG | |
| | :::::::::::::Rv30T7PEG.seq::::::::::::: | |
| | CAACAGCGTTCCAGCGGCATACCACCGCACATGCCGTGCACCCGGCGCCGGGCGGAGTCGCCGCATAACACANGTACACCTTGGGAATCGGTGTGCGCCAGGGATT | (SEQ ID NO. 392) |
| | CNACCGCGGGGTGGGGCCGGCGATCGCGCGCCAGGTCGAGTTGGCGCCGACCGTGATNTCACCGCCGACGTAGTTGGCGTTGTGGTCCGCCATCCGCGCGGCGGGC | |
| | ACGGCGCGGGCCGCCACCACGATGTCACGGAAGCCGGGGGCGAACGCTCGACGACCTGGTTACCGTCTCNGTCGCNTCNANCGTGGACCCGACNGCACGTGGGCAT | |
| | ATGTCCANAACGGACGNGGCCGGTTTCNTCGATGCNGCCGGGGTCCGCGACNTGCGGACNCNCNGNCACACCATCCGCCAGTCCGCGTGGCGTCCCGCCGCGACTC | |
| | TGCCTCGGCCGCGCCA | |
| Clone Rv310 | :::::::::::::Rv310SP6.seq::::::::::::: | |
| | CTCAAGCTTTGNCGACGATCGGGCGATGTCGATGANAGGAAACCCCAGCGCACAACCGACNATTTTGGCGTAGCCGGCGGACNTCTGCTCGATTCCGATCACGTCG | (SEQ ID NO. 393) |
| | GCGCTCGCATCGAGCATGGCGCCGGCGACGGCTAGCAGCGATCCGCCGTCGTCGAGGAACACGACACGAGCCGTACGCCCGGCCGTAAGCCGCGCCCAGGATTCGG | |
| | CGAAAAACCGTTCTACGTGGCGGGTGTACTGGGTGTCCAATGATTCGTGGGGTGCGTAGGCGTCGCTGCAATCGTCGACATAAATGCCGTCGGCCCGCATCGCGTC | |
| | AACAACTCCCGGGTGAGTGGAATANCACTTGCCGA | |
| | :::::::::::::Rv310T7.seq::::::::::::: | |
| | TCCAACGCGGTGACAGATTTGTCTATCCTGGACCTGACGGTGAGGTCGAAGTTTTCCAGGAATTCGGCAAAATCGGTAAGAGCCTGAAGAATTCGGTATCGCCGGA | (SEQ ID NO. 394) |
| | CGAAATCTGCGACGCATACGGGGCAGATACGCTTCGGGTTTACGAGATGTCGATGGGGCCGCTGGAGGCTTCACGTCCATGGGCCACAAAGGATATTATCGGCGCG | |
| | TACCGTTTTCTGCAGCGGGTGTGGCGCTTGGTCGTCGACGAGCACACCGGCGAAACTCGGGTGGCTGACGGCGTGGAACTCGACATCGATACGCTACGGGCGTTGC | |
| | ACCGCACCATCGTCGGCGTGTC | |
| Clone Rv311 | :::::::::::::Rv311SP6.seq::::::::::::: | |
| | CTCGTCCTTGACTACGCCCAGTATCGAAANCCTCCTGTGCCGGTNCGCTAAACACCCGGCGGACACTCANACGGTGCTGGTGGTGCGGCATGGCACCGCGGGCAGC | (SEQ ID NO. 395) |
| | AAAGCGCACTTCTCCGGGGACGACAGCAAGCGACCGCTAGACAAGAGGGGTCGTGCGCAGGCAGAAGCGTTGGTACCACAGCTGCTGGCGTTCGGCGCCACCGATG | |
| | TTTATGCCGCCGACCGGGTGCGCTGCCACCANACNATGGAGCCACTCGCCGCGGAACTGAACGTGACCATACACAACGAGCCCNCCCTGACCGAAGAGTCCTACGC | |
| | CAACAACCCCAAACGCGGCCGACACCGAGTGCTGCAGATCTTCG | |
| | :::::::::::::Rv311T7.seq::::::::::::: | |
| | GTATCGCCTCCNCCTTTGGCCACCAGCAGCCACAGCGCGGTTCGCGGACCGAACGTGGACATCAATAGCCCGGAATCGGTGTGTGCAAGTTGGTAAACGGTGTTGA | (SEQ ID NO. 396) |
| | TCCCAAGCTTTGCCAGCCTTTTCGTAGTCTTGGGCCCCACACCCCACAGTGCTTCGACGGTACGGTCACCCATGATGGCCATCCAGTTGGCATCGGTGAGCTGATA | |
| | GATGCCAGCTGGTTTCGCCAACCCGGTAGCGATCTTGGCGCGCTGCTTGTTGTCACTGATACCTATCGAGCAAGACAGCCCGGTTTGCGACAAGATGACTTTTCGG | |
| | ATCTCTTCNGCGAACTTCCAATGGGGGTCTCCGGGANT | |
| Clone Rv312 | :::::::::::::Rv312SP6.seq::::::::::::: | |
| | CTCAAGCTTTTGGTCTAGCCGGCCGAGCACGATACGGGTGTCCTTGGCCACCGGCGGCGGCTGTCCGGGAAATGGCGGGTCCCCGGTGGTTTTGCTGANGANTGCT | (SEQ ID NO. 397) |
| | GAACCGTAGTCGAAGTGGGCGGCGTCAGACTCCACCCAGCCAGCAGGCAGCGCGAAGCTGAATCCTCCAACCGGGTTGTCGATCCGGACAGGTTGGGGTGCGTTTG | |
| | GGGCAATGACAGGTGGCGGCGGTGCGTTCGGGTCGGCCGGCGGAGGTGCTGCGTTGGGATCNCCCGGCTGGGCATTCGGCNTNTTGGCGGCGGCCGGTGGTGGGGG | |
| | GGCAACANGTGTCCCGGTGCGGGTGGCGCTGC | |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | :::::::::::::Rv312T7.seq:::::::::::: | |
| | ATCTGTACCCGACCAAGATCTACACCATCGAATACGACGGCGTCGCCGACTTTCCGCGGTACCCGCTCAACTTTGTGTCGACCCTCAACGCCATTGCCGGCACCTA | (SEQ ID NO. 398) |
| | CTACGTGCACTCCAACTACTTCATCCTGACGCCGGAACAAATTGACGCAGCGGTTCCGCTGACCAATACGGTCGGTCCCACGATGACCCAGTACTACATCATTCGC | |
| | ACGGAGAACCTGCCGCTGCTAGAGCCACTGCGATCGGTGCCGATCGTGGGGAACCCACTGGCGAACCTGGTTCAACCAAACTTGAAGGTGATTGTTAACCTGGGCT | |
| | ACGGCGACCCGGCCTATGGTTATTCGACCTCGCCGCC | |
| Clone Rv313 | :::::::::::::Rv313SP6.seq:::::::::::: | |
| | CTCAAGCTTGCAATGCGGGTCGGGATGCCCATGGTTGGAANATGGTCGCCCTGGCGTCNAATACGCGCGAGCGCATGAGCTCACCGGTTCGGAACAACGTATCGAA | (SEQ ID NO. 399) |
| | AAACGTCGCACTGCTGGCAGATGGTATCTCCGATGTGGTTGTAATTTGTATCCCAACTCTAACTGTGCTATCGGATCAGCGTGAATATCGANATATTGCGAATGCG | |
| | ATGACAGGCCGCCATTCGGTTTATTCGCTTACGCTTCCCGGGTTCGATTCGTCTGATGCACTGCCGCAAAACGCGGATATGATTGTTGAAACCGTATCTAACGCAA | |
| | TTATTGATGTGGTAGGCGGCAGCTGCCGTTTTGTGCTGTCGG | |
| | :::::::::::::Rv313T7.seq:::::::::::: | |
| | CAAATACACGCCGGACGCACAGGCGGACATCGCCATCCCGAGCACACCCAAAACGGGATACAGGATGGAGGCCAACGCCACGGCCGCGCCCAGGATCACCAACCAC | (SEQ ID NO. 400) |
| | ACCGGCTTGGTCAGCTTGTCGGCGGCGGTATAGGCATCGGGCCGCTGCAACGCAGCATGCACAAACGCGTACACCGCTGTCACCAAGACGGCGACCAGCAATACCA | |
| | GCATGACGGTACCCACGAGGTGGCTCACGCATTCAGACTATGCGGTTTGCATCCAACACG | |
| Clone Rv314 | :::::::::::::Rv314SP6.seq:::::::::::: | |
| | CTCGTCCTTCGGCCTCGCTGCAGGAGTGGGAGCCGCAGGGCTGGAAATCCGAAAAACGAGCCGGTGATCGCACTGTCGCCGATCGGCGCCGCACCTGGTTGGTGTT | (SEQ ID NO. 401) |
| | ACGGATGAATCCGCAGCGAAATGTGGCTGCGGTGGCGTGTCGTGACTCGTTGGCGTCGACGCTGGTGGCAGCCACCGAGCGGTTGGTCCAGGATCTGGATGGGCAA | |
| | AGTTGTGCGGCCCGGCCGGTGACGGCCGATGAGCTGACCGAGGTCGACAGCGCCGTGTTGGCTGACTTGGAACCGACATGGAGTCGCCCCGGTT | |
| | :::::::::::::Rv314T7.seq:::::::::::: | |
| | GTCTAGNCCGCCGAACACGATACGGGTGTCATTGGCCACCGGCGGCGGCTGTCCGGGAAATGGCGGGTCCCCGGTGGTTTTGCTGAAGANTGCTGAACCGTAGTCG | (SEQ ID NO. 402) |
| | AAGTGGGCGGCGTCAGACTCCACCCAGCCAGCAGGCAGCGCGAAGCTGAATCCTCCAACCGGGTTGTCGATCCGGACAGGTTGGGGTGCGTTTGGGGCAATGACAG | |
| | GTGGCGGCGGTGCGTTCGGGTCGGCCGGCGGAAGTGCTGCGTTGGGATCGCCCGGCTGGGCATTCGGCGTGTTGGCGGCGGCCGGTGG | |
| Clone Rv315 | :::::::::::::Rv315SP6.seq:::::::::::: | |
| | ACTCAAGCTTGAGATTGGCGTCAACGGGTGTCGGCACCGGCGTCCTGCAGTTGGTAGGCCTGCAGTTTGTGCATCAGGCCGATGCCGCGGCCCTCGTGGCCACGCA | (SEQ ID NO. 403) |
| | TGTACANCACCACGCCGCGCCCCTCACGGGCGACCATCGCCAGCGCGGCGTCCAGCTGAGGCCCGCAATCGCAGCGGCGTGACCCAAACACATCGCCGGTCAAGCA | |
| | CTCCGAATGCACCCGGACCAGCACGTCG | |
| | TCACCGTCGGCGTTGGGCCCGGCGATCTCGCCGCGGACCAGCGCGACATGTTCCACGTCCTCGTAAATGCTGGTGTANCCGATGGCGCGAAACTCCCCATGACAAN | |
| | TCGGAATCCCGCGCCTCGGCGACCCCGCTCAATGTTGCTTCTCNTGCTTG | |
| | :::::::::::::Rv315T7.seq:::::::::::: | |
| | TCGACNAGCATTCTTGACNGTTGTTTTGGCTCGGCATGGTTAGCCAAGGTTCTGCGGTCCCACCAGATCATCTTGGTCCGGTAGCGCTCGTCCGGGTATGCTGCCG | (SEQ ID NO. 404) |
| | CCGGGATTCTCGCTGCTATTACTCCCCCCGAAGAACGCCACCGGTCCAGCGCGTGGGCCGCCGCGGTCCCCATCACAAACTGAACCCCCAACAGGGGACATGCTTA | |
| | GCGGTAGGGCGCGCGCCAAGGCGGCAGCAATCGCATCACTGCGCTGCGCGTCACTATTAACCCAGCCGGACTTCACTTCCACGACCCCGAATGGCGCCCGGTCATT | |
| | GATCATCTTGCGCACCGCGGATAATCCGGGAT | |
| | TG | |
| Clone Rv316 | :::::::::::::Rv316SP6.seq:::::::::::: | |
| | ACCGGGGCCACTCCGCACAATCTGTACCCGACCAANATCTACACCATCGAATACGACGGCGTCGCCGACTTTCCGCGGTACCCGCTCAACTTTGTGTCNACCCTCA | (SEQ ID NO. 405) |
| | ACGCCATTGCCGGCACCTACTACGTGCACTCCAACTACTTCATCCTGACGCCGGAACAAATTGACGCNGCGGTTCCGCTGACCAATACGGTCGGTCCCACNATGAC | |
| | CCANTACTACATCATTCGCACGGANAACCTGCCGCTGCTAAAGCCACTGCGATCGGTGCCGATCGTGGGGAACCCACTGGCGAACCTGGTTCAACCAAACTTGAAG | |
| | GTNATTGTTNACCTGGGCTACGGCGANCCGGCCTNTGGTTATTCCACCTCNCCGCCCAATGTTTGCNACTCCCGTTCGGGGTTGTTCCCNNAAGGTCAACCC | |
| | :::::::::::::Rv316T7.seq:::::::::::: | |
| | CGCTCAAGCGCNTGAGGCCGAANCGGCTGGTTACGACTCCCTGTTTGTGATGGACCACTTCTACCAACTGCCCATGTTGGGGACGCCCGACCAGCCGATGCTGGAG | (SEQ ID NO. 406) |
| | GCCTACACGGCCCTTGGTGCGCTGGCCACGGCGACCGAGCGGCTGCAACTGGGCGCGTTGGTGACCGGCAATACCTACCGCAGCCCGACCCTGCTGGCAAAGATCA | |
| | TCACCACGCTCGACGTGGTTAGCGCCGGTCGAGCGATCCTCGGCATTGGAGCCGGTTGGTTTGANCTGGAACACCGCCAGCTCGGCTTCGAGTTCGGCACTTTCAG | |
| | TGACCGGTTC | |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

Clone Rv317 :::::::::::::Rv317SP6.seq:::::::::::::
CTCAAGCTTGCGTTCGATGAAGTAGTCGTCGGTCAGCGCCGCCTCTTCGAGCTCCTTGGCGATGCCCAGCAAGGAGTCATCGCCGCCGAGCTTGGCCAGGATCTTG (SEQ ID NO. 407)
TCGGCCTGTTCCTTGACGATGCGGGCCCGCGGATCGTAGTTCTTGTAGACACGATGACCGAAACCCATCAATTTGACCCCGGCCTCGCGGTTCTTGACCTTGCGTA
CAAACTCGCTGACGTCGTCGCCGCTGTCGCGAATGCCCTCGAGCATCTCCAGGACAGCCTGATTGGCGCCGCCATGAAGCGGACCCCATAGTGCGTTGATGCC
:::::::::::::Rv317T7.seq:::::::::::::
GGTCAGGCCGAGCAGGCGCGAGGAACGACGAACCCAACAAGCCATGGTGGTTGGCGCCGTCGAGAGGTCGGCGGTCGCCACAACGGGAAGATCGCCTTGAGCGTCG (SEQ ID NO. 408)
CTCGACCGCCGCCTCGAGTTGGGTCATAACGAAGTAGCTGATGCCGATCATGTCGACGTTTCCGTCGCATCAGCGTGCAGCGGCGACCCACTCNACGAGGTCTCGG
TGCCGCCGCGGCCAGGGCACCAGCAGTGACGAGTCCAGGCGCCGTCGGGCCAAGCAGTCGCGGTGCCANCCGTGGTGGGTCGGGCGATGGTTGGGTGTGCTCATTT
CGGGAACGCCA Clone Rv318 :::::::::::::Rv318SP6.seq:::::::::::::
CTCGAAGCTTTTAACAGCATCAACCCCGCCCCGCACCAGCACCGACACNATGTCGATGCCATCGAGGTGAATGTCGAACTGGCGCAAACCATCGGCGACCGCGACCA (SEQ ID NO. 409)
CCGGCAACATGGGTACCGGCGATTTCCGGTGCCAATGCCGACCCGACGGGCCGCTCTCACCGCAGGTGACCTCGATCACCGAGACCANCCGGCCGTTNTNNTCACG
CACCCCTACCGTGTCACGCCCAAAACGGCGCTGGTGGTCGATTGCCGGAGTGCACCCCNCACCCAGTGTCGTGCCCGGATCC
:::::::::::::Rv318T7.seq:::::::::::::
TGATGCCGCACCCGATCGACGGTCGTTGGTCGGGGTTGACTGGCCGCCCGGCGAAGCAGGGCGTCGACCGCGGCCCGGACGTCGGCGGCCGTCACCGGTCGGCCAT (SEQ ID NO. 410)
TGCCCGGGCGGGAGTCGTCGAGCTGACCACGGTAGACAAGTCGGCGCTGGCCGTCGAAGACNAACGTGTCGGGTGTGCAGGCCGCGGAGAAGGCGCGGGCGACNTC
TTGGGTTTCGTCGTANAGATACGGGAACGTCCAGCCGTGGCGGCGGGCCTCGGCGACCATCTGATCGGGCCCGTCC Clone Rv319 :::::::::::::Rv319SP6.seq:::::::::::::
TTTCGGGCGAGGCGGTATANCTTCCCNTCGTACCGGCGACCGCCAGCCGANAAGCTCGTTTTCCCAGTGTTGCTGGGGATTCTCACGCTGCTGCTGANTGCGTGCC (SEQ ID NO. 411)
AAACCGCTTCCGCTTCGGGTTACAACGAGCCGCGGGGCTACNATCGTGCGACGCTGAAGTTGGTGTTCTCCATGGACTTGGGGATGTGCCTGAACCGGTTCACCTA
CNACTCCAAGCTGGCGCCGTCTCGTCCGCAGGTCGTTGCTTGCGATAGCCGGGAGGCCCGGATCCGCAATGACGGATTCCNTGCCANCGCTCCGAGTTGCNTGCGG
ATCGACTACNAATTGATCACCCANAACCATCGGGCGTNTTACTGCCTGAAGTACCTGGTGCGGGTCGGATACTGCTATCCGGCGGTGACAACCCCGGCAAGC
:::::::::::::Rv319T7.seq:::::::::::::
GTTTTGGCTCGGCATGGTTAGCCAAGGTTCTGCGGTCCCACCAGATCATCTTGGTCCGGTAGCGCTCGTCCGGGTATGCTGCCGCCGGGATTCTCGCTGCTATTAC (SEQ ID NO. 412)
TCCCCCCGAAGAACGCCACCGGTCCAGCGCGTGGGCCGCCGCGGTCCCCATCACAAACTGAACCCCCAACAGGGACATGCTTAGCGGTAGGGCGCGCGCCAAGGCG
GCAGCAATCGCATCACTGCGCTGCGCGTCACTATTAACCCACCCGGACTTCACTTCCACGACCCCGAATGGCGCCCGGTCATTGATCATCTTGCGCACCGCGGATA
ATCCGGGATTGCCAGCCCATTCNACTACCGCATGCGAGTCATCGGCTGACCGCAGCGGTC Clone Rv31 :::::::::::::Rv31SP6.seq:::::::::::::
TCGCCTAGGCGGGCTTCCCCTTCCGTCCGAGCNGTCAGAAGCTCCTATGACAATGCACTACCCGAGACNATCAACGGCCTATGCAATACCNAGCTGATCAAACCCG (SEQ ID NO. 413)
GCAAGCCCTGGCGGTCCATCGAGGATGTCGAGTTGGCCACCGCGCGCTGGGTCGACTGGTTCAACCATCGCCGCCTCTACCGGTACTGCGGCGACATCCCGCCGGT
CTAACTCGACGCCGCCTCACTACGCTCAACGCCAGAGACCANCCGCCGGCTGACGTCTCAGATCAGAGAGTCTCCGGACTCACCGGGGCGGTTCATCCCCACTGTC
GATAGCGTCTGTGGATAACTTTGTCTGCA
:::::::::::::Rv31T7.seq:::::::::::::
GCGCGTNGAACTGATAGGTGCGGCCCGGCTCGAGCANGCCGGCCATTTGTTCGATGCGGTTACCGAAGATCTCTTCGGTGACCTGCCCGCCGCCGGCCAGCTCGGC (SEQ ID NO. 414)
CCAGTGCCCGGCGTTGGCCGCCGCGGCGACAATCTTGGCGTCCACGGTGGTCTGGGTCA Clone Rv321 :::::::::::::Rv321SP6.seq:::::::::::::
CTCAAGCTTCAATACAGAGTTATAAACTGTGATAATCAACCCTCATCAATGATGACNAACTAACCCCCGATATCAGGTCACATGACGAAGGGAAAGAGAAGGAAAT (SEQ ID NO. 415)
CAACTGTGACAAACTGCCCTCAAATTTGGCTTCCTTAAAAATTACAGTTCAAAAAGTATGAGAAAATCCATGCAGGCTGAAGGAAACAGCAATAACTGTGACAAAT
TACCCTCAGTAGGTCAGAACAAATGTGACGAACCACCCTCAAATCTGTGACAGATAACCCTCAGACTATCCTGTCGTCATGGAAGTGATATCGCGGAAGGAAAAT Clone Rv322 :::::::::::::Rv322SP6.seq:::::::::::::
CTCAAGCTTCGATCGACATTACTCCCGCCTTGGGTCTGGTCTCCGAGCTGGTCGGTCATGGTCGGACCTGCTGGTAGTGGGGATCTAACGCAACATGGTCGGGATT (SEQ ID NO. 416)
CATCATGGTGTACCCGTGATACCCATTCGCAGCTGCCGGTGAAACCCCGCGATGCCGGGATTTCCAGCCGCACTAGGATGTCTAGCCGGCCAGCCGCTGCCGCCGG
ACTTCGGGATGTTCGGTATACCANCGATCGGCAATCTTGCGTATCCGCCGATGCTCGAACGCTANCCACGCCAAACCAACCACTGTGACNACAATCGCCACCACAC
CAAAGGTCATGCCCTCGGCGTGATGTCCGGTGCCGAAAGCCGCAAGAGCTCCGACGCCGCC TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

:::::::::::::Rv322T7.seq:::::::::::::
CATTCCCAATTGAATTTCCCNATCCCACAATCTCGGTTCAGATACAGGTCGCCATACCCCTTACTTCGGCAACGCTGGGCGGATTGGCCCTGCCGCTGCAGCANAC (SEQ ID NO. 417)
CATCGACGCCATCGAATTGCCGGCAATCTCGTTCAGCCAATCCATACCCATCGACATTCCGCCGATCGACATCCCGGCCTCCACTATCAACGGAATTTCGATGTCG
GAGGTCGTGCCGATCGATGTGTCCGTCGACATTCCGGCGGTCACCATCACCGGCACCAGGATCGACCCGATTCCGCTGAACTTCGACGTTCTCAGCAGCGCCGGAC
CCATCAACATCTCGATCATCGACATTCCGGCGCTGCCGGGCTTTGGCAACTCGACCGAGCTGCCGTCGTCGGGCTTCTTCAACACCGGCGGCGGTGGCGGCT Clone Rv327 :::::::::::::Rv327SP6.seq:::::::::::::
CTCAAGCTTTCGGCGGAGACGGACANNTTGCGAACATTGATGACAAAATAGAAATCATTGATGGTTTGAGTCACCAGGCCGATCAAGCCTTCGCCGAGCCAAATTC (SEQ ID NO. 418)
CAATCAAGAGGCCCAAGCCCGTACCAATCAGCCCGGCAACGAGGGATTCCGTCATTATCAGCCAAAATAACTGCTCTCGGGTTACACCCAAACAGCGCAATATGGC
GAAAAACGGTCGCCGTTGCACGACATTAAATGTCACGGTATTG
:::::::::::::Rv327T7.seq:::::::::::::
AGCTTAACTGCTCCCTAATACCTGGGGCTGTGCCTGCGGTGTATGCACGGCATACGGACATCCNTCCCCTGAGACCCNCGGTCTAATCAGCCACGTGTCCACCATC (SEQ ID NO. 419)
AGGGGTCAACCCCGGCCAAGGGCGACGGCACCCCAAGTTCGCCGACCGTTAACCTATTGCTGTGAGCTTCATTTGCTGCGAGCAAAACAGTTGGTCGGCCGTTAGG
AACTGAATTGACACTCAACCGATTTGGTGCCNCCGTAGGTGTCCTGGCTGCGGGTGCGCTGGTGTTGTCCGCGTGTGGTAACGACCACAATGTGACCGGGGGAGGT
GCAACCACTGGCCACGCGTCCGCGAATGTCTATTGCGGGGG Clone Rv328 :::::::::::::Rv328SP6.seq:::::::::::::
CTCAAGCTTGGGGTGGCGCTGTCGGTCGGTGTGCTTGGCGGCGTCGGTATCAACACCGCCCACGAAATGGGGCACAAGAAGGATTCGCTGGAGCGGTGGCTGTCCA (SEQ ID NO. 420)
AAATCACCCTCGCCCAGACCTGCTACGGGCACTTCTACATCGAGCACAACCGTGGCCATCACGTCCGGGTGTCCACACCGGAGGACCCGGCGTCGGCGCGGTTCGG
CGAAACGTTGTGGGAGTTCCTGCCCCGCAGTGTTATCGGCGGCTTGCGCTCGGCCGTTCATTTGGAGGCCCAACGGCTGCGTCGGCTCGGCGTCAGCCCCCT
:::::::::::::Rv328T7.seq:::::::::::::
GCACCAAGGCCCCACACGTCACCCTGTGACCTCCTGCGCCGACCCCGCCCGAGGTCCTGGCCGTTACCACCTGAACGGGCGAGCCGGGAGTCTGGTACGCATCGAA (SEQ ID NO. 421)
CAAAGAGCAAGGTGCATGGGCGGAGTTGTTCCGCCACTTCGTCGATGACGGGGTCNATCCATTCGAGGTCCGTCGCCGCGTCGGTCGAGTGGCGGTCACACTCCAG
GTACTCGACCTCACAGACGAGAGGACTCGATCCCATCTAGGTGTGGACGAAACAGATCTTCTGTCCGA Clone Rv329 :::::::::::::Rv329SP6.seq:::::::::::::
TCGCCTCCGCATATGGGTCGACGCCAAGCGGGTCCGGATTTCTGGGCTTCATCGCTCGCGCCGTCGCGACAAACAGCGCGGTCGAACCGACACTCGTTGTGATGTC (SEQ ID NO. 422)
CCAGCTATCACCTTCGGTACGCACCCAATCGACCCTACNCGGCTATCTCAGCCGCGATCTCCAGGCTCCGCCGAGCCAGGTGCATCCCGGTCCGGATCCCACTAAC
CCGGCACCATTGGCGTCN
:::::::::::::Rv329T7.seq:::::::::::::
GTCCTCGAGTGCCGCCGTCGNCACNCCCAGCGCCCGCGCGGCCACTTGGATGCGACCCGTTTCAAGTCCCTTCATCATCTGCGAAAAGCCTTGACCCATGGCTCCG (SEQ ID NO. 423)
CCCAGGATCGCCGAGACCGGCACCCGGAGGTTGTCGAACGACAGCTCGCAGGATTCGACGCCCTTGTAACCCAACTTCGGCAAGTCCCGCGACACCGTGAGTCCCG
GCCCGGGTTCGACGAGCACGATCGACATGCCTTGGTGCCGCGGTGTGGCGTTCGGGTCGG Clone Rv32 :::::::::::::Rv32SP6.seq:::::::::::::
GGCATACCAATGTGGACTTCTGCTCACCCACGATATCCGTGGTCTGATCCGCTGCTGCGGCGGGCTGCNACCTGCNTCTCNGCGGCACCCGTNACTACATGGCNCG (SEQ ID NO. 424)
CGCCGCACGCATACGTCGCGGCGGGACCCACTCCNACTGGTCGACGGTGCTGGCCGCGTGTCCGCANGTCCCNAACCCGGCCGCACCGACGAAACCGGCCGCCGTC
CGTTCTGGACCAACGCTCATGTGCCGTCGGGGTCCATGCTCGACGCCATCGAGACCGTAACCAGCGTCCTCGAGCGGTTCGCCTCCGGCTTCCGTGACATCTTCGT
GGCTGCTCGCGCCGTGCCGCCGCGCGGATGGTCGACCACAACGCCAACCACCTCGGCGGTGACATCACCGTCCGCGCCACTCGACCTGGCGCGCGATCGCGGCCC
:::::::::::::Rv32T7.seq:::::::::::::
GTGAGCAGACCTACGCCNCCTGGTTGCGCCAACTCGGTACCGATCATGGCGCGCNGCCTGTCGTCACCGATACCCAGCGAACAAGACAGCCCGGTCCGCGACAAGA (SEQ ID NO. 425)
TGACTTTCCCGATCTCTTCGGCGACTTCCATGGGGTCGTCCGGAGTCCCGGGCGCCACCGCGAGGTAACCCTCGTCTCAGTCCCATACGCGACCGGGTATCCACGT
CGCGCAACAACGCCACCACCTCCCCAGACGCCNCGTTGTACGCGGCTGGGTTCCACNGCAATAAGTGGCCTCANGGCATCGTCCGGCGGCGGTCCNCAACGCA Clone Rv330 :::::::::::::Rv330SP6.seq:::::::::::::
CTCAAGCTTGAGGTTAACTTTGAACGGATCGAGCTGGACGTTCGAGACGGTGATCGGGCCGAACCTGAATTGTCCGGTAATGCCCAACGCAAAAAGCAGGGTGGTG (SEQ ID NO. 426)
GCCGGGGCGGTGAAACCGGCGTCGGCGGCACCGTCGAAATCTATGTGGATTGCCGGAATGGGGATGTCCGGCACGGCGAAACCGTAGTTCGCTTGTCCCGTGAGGC
CCAGGTGGATGGGGGGAAAGATCCTGGTGTCCGGGATAATAATGGGGCCGATGCCGCCGGTTGAAGTCCACTGGATCGGGAATTCCGGAATCTTGATCCGACGTTC
AGGCCGAACAGGCCCTC TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

::::::::::::Rv330T7.seq:::::::::::
CGGCGACGTCGCGATACGCCGAGCAGTTGGGAATCGCTCTGCAGCAAACCAATATTCTGCGCGACGTTCGAGAGGACTTTTTGAATGGACGGATCTACCTGCCGCG (SEQ ID NO. 427)
CGACGAGCTGGACCGATTAGGCGTACGCCTCCGCCTGGACGACACCGGGGCACTCGATGACCCCGACGGACGGCTCGCGGCNCTGCTGCGGTTCAGTGCCGACCGC
GCCGCAGACTGGTNTTCGCTGGGACTGCGGCTGATTCCACACCTCGACCGCCGCAGCGCTGCCTGCTGTGCGGCCATGTCTGGCATCTACCGCCGTCAGCTCGCCT
TGATCAGAGCATCGCCGGCGGTCGTCTA Clone Rv331 ::::::::::::Rv331SP6.seq:::::::::::
CTATAAAATACTCAAGCTTGATGCCGCCGAAACCGAGCGTGAGCACGCCGCCAGCCACCACGCGCGGGTCGGGCGCCGGGCCCGGGCCGCCAGGCTGCTCCGCTCG (SEQ ID NO. 428)
GTGATGGCACGCCACCGCGACACCACCCGGNTGCGCTACGTCNAGCCATACCGGGCGGAGCTACATCGGCTCGGCCGCCCAGTGTTCGGGCCCTCTTTCGAGGTCN
AGGTCNATACCGATTTGCGCATCCGCAGCCGCACCCTGAACNACANAACCGTGCCCTACTATTGCTTGTCNGGCGGGGCCAAAAAACAGCTTGGCATCCTGGCCCN
ATTGGCCGGCGCGG ::::::::::::Rv331T7.seq:::::::::::
CTTCGGTCGCAGTGTGCGAGTGATAGATGACGACCGGGACCTCGTCGGCATCTTCCATAGCCCGCCACACCTTCAGTTGCTCACCGGAATCCAACCGGTAGAAGGT (SEQ ID NO. 429)
CGGCGAGCGCTCGGCATTGGTCATCGGGATATGCCGCTCGGGACGGTCAGAGCCCTCGGGTCCGGCCAGCACTCCGCAGGCTTCGTCGGGGTGGTCGCGACGCGCA
TGGGCCACCATCGCATTCACCAGGTCTGCGCGAATCNCCANCACGTANACNGTTCCTTTCCTAA Clone Rv333 ::::::::::::Rv333SP6.seq:::::::::::
CTGGCACCAAGGCCCCACACGTCACCCTGTGACCTCCTGCGCCGACCCCGCCCGAGGTCCTGGCCGTTACCACCGAACGGGCGAGCCGGGAGTCTGGTNCGCATCG (SEQ ID NO. 430)
AACAAANAGCAAGGTGCATGGGCGGAGTTGTTCCGCCACTTCGTCGATGACGGGGTCNATCCATTCGAGGTCCGTCGCCGCGTCGGTCNAGTGGCGGTCACACTCC
AGGTACTCGACCTCACAGACNAAAGGACTCNATCCCATCTAGGTGTGGACNAAACAGATCTTCTGTCCGACNACTACACCACCACCCAGGCCATCGCCGCCGCCCG
CGATGCCAACTTCGACGCCGTACTGGCCCCGGCGGGGGGCGCTCCCCGGTTGTCAACACTTGCCGTGTTCNTTCACGCNCTGCCCCACATCCAACCCCAACG Clone Rv334 ::::::::::::Rv334T7.seq:::::::::::
GTTCTTGGGCCCATGCGGAGGTATCGCCGTTTCCACCACGCGGTCGGGGTGGCGTTGCATTAGCTCACCGATGGTGCGCTTGTGCAGGCCGCCGGGATACCCCGAG (SEQ ID NO. 431)
TGCCGGTAAACCATCTTGTGCTGC Clone Rv335 ::::::::::::Rv335SP6.seq:::::::::::
CAATACTCAAGCTTGGCGTGCCGTTCCAACCCGAATTGGCTTTCGGCGCCATCGGTGAGGACGGCGTGCGGGTGCTCAACNAGNACGTCGTCCGCGGGACACACCT (SEQ ID NO. 432)
CGATGCTGCCGCCATGGACGCGGTCGAACGCAAGCAGCTGATCGAGCTACAACGCCGCGCGGAACGCTTCCGCCGCGGGCGTGACCGCATCCCGTTGACCGGGCGG
ATC ::::::::::::Rv335T7.seq:::::::::::
CNTCATGATGATCATCACCCGAAGTGTGGTAGCCGCAGTGGTTATCGTGGGTACCGTCGTGCTTTCCATGGGCGCCTCTTTCGGGCTTTCCGTATTGGTCTGGCAG (SEQ ID NO. 433)
GACATTCTGGGTATCGAGTTGTACTGGATGGTGTTGGCGATGTCGGTGATCCTGCTCCTGGCGGTGGGATCCGACTACAATCTGCTGCTGATTTCCCGGTTGAAAG
AGGAAATTGGGGCCGGATTGAACACCGGAATTATCCGTGCCATGGCTGGTACCGGGGGAGTGGTGACGGCTGCCGGCATGGTGTTCGCCGTTACCATGTCGTTGTT
TGTGTTCAGCGATTTGCGAATTATTGGTCAGATCGGTACCAC Clone Rv336 ::::::::::::Rv336SP6.seq:::::::::::
ATACTCAAGCTTTTACGGTGATCGCNCATCACCTGGTTCATGAACTGGAAGCAGCGCAGCGCTTCCTTTTCGGCCGCAACATGAGCCAGCCTCTCGTCGGCGGTCG (SEQ ID NO. 434)
GGTGCAGGTGCTCGGGCAGCTCGGCCGCNACAGCCGCCTGACCCTGAAACCAGCTTCCATATCCCGCGANNAACGACGCCAGTCCGCTACGTNACCCCTCCGCGAC
TGTCCATGGACAACAGCGCGTTCTCCACCGACCGGGCCCGGGTGTGGGGTNTT ::::::::::::Rv336T7.seq:::::::::::
GCTGGTAGAGTCGCTGACCGGTGCAGGTTTCGACAATGTGGTGCCGGTTCGGCGGCTACGTGCCATCGAGACACTGGCGCAGGCTATCGCACCCGTTATCGGCTAC (SEQ ID NO. 435)
GAGCAAATCGCGGTATGCGTTCTTGAGCATGAGTCGGCGACCGTCGTCATGGTCGACACCCACGACGGAAAGACGCAGATCGCCGTCAAGCATGTGTGCCGCGGAT
TATCAGGACTGACCTCCTGGCTGACCGGCATGTTTGGTCGCGATGCCTGGCG Clone Rv337 ::::::::::::Rv337SP6.seq:::::::::::
GCTTTCCGCCGATACCCGCCATGTCNCGCACATCCAGGACTTCTGGGGGGATCCGCTGACAGCGGCGGGATCCCAAAGTGCGGATGATCGGGCCGCCTACGTCGTG (SEQ ID NO. 436)
GTGTACCTCGTCGGTAACAACGAAACCGAAGCGTATGACTCGGTCCACGCGGTGCGGCACATGGTGGACACCACACCGCCACCGCACGGGGTGAAGGCCTATGTCA
CCGGTCCGGCANCACTCAATGCCGACCAGGCCGAGGCCGGANACAAAANTATCGCTAAGGTCACCGCGATCACNAGCATGGTGATCGCAGCAATGTTGCTAGTGAT
CTATCGCTCCGTAATTA TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | :::::::::::::Rv337T7.seq::::::::::::: | |
| | CTTCCAACCCGAATTGGCTTTCGGCGCCATCGGTGAGGACGGCGTGCGGGTGCTCAACGACGACGTCGTCCGCGGGACACACCTCGATGCTGCCGCCATGGACGCG | (SEQ ID NO. 437) |
| | GTCGAACGCAAGCAGCTGATCGAGCTACAACGCCGCGCGGAACGCTTCCGCCGCGGGCGTGACCGCATCCCGTTGACCGGGCGGATCGCGGTGATCGTCGATGACG | |
| | GCATCGCCACCGGAGCGACGGCCAAGGCGGCGTGCCANGTCGCCCGGGCGCACGGTGCGGACAAGGTGGTGCTGGCGGTCCCGATCGGCCCA | |
| Clone Rv338 | :::::::::::::Rv338SP6.seq::::::::::::: | |
| | TACTCAAGCTTCGCGAGATCCGGATGGCACTCACGCTGGACAAGACCTTCACAAAATCTGAAATCCTGACCCGATACTTGAACCTGGTCTCGTTCGGCAATAACTC | (SEQ ID NO. 438) |
| | GTTCGGCGTGCAGGACGCGGCGCAAACGTNCTTCGGCATCAACGCGTCCGANCTGAATTGGCAGCAAGCGGCGCTGCTGGCCGGCATGGTGCAATCNACCAGCACG | |
| | CTCAACCCGTA | |
| | :::::::::::::Rv338T7.seq::::::::::::: | |
| | CCCACGACTTTCTCCTCGATCAGTTGGATTTGTACGAAGAGGCAACGAAAGCAGTGATCCTCGGGATGGTCGACGCCTACATCGACCCGCCGTTCACGCCGCACAG | (SEQ ID NO. 439) |
| | CCTGCTAGATGCGCTGGGCGAGCAGGTCCCACAGTTCGCCGCTAAGGCACGGCGTCTGTTCCCGTCCGGATCGCCATTCGGCCTCGGCGTCCTGCTCCCATTCGAT | |
| | CAATAGGGCTGGCAGCTCCGTCGGCAGGGGCCTACGCCTCACCCCGTCACG | |
| Clone Rv339 | :::::::::::::Rv339SP6.seq::::::::::::: | |
| | CTCAAGCTTATGCGCGCCGGCCGAGGTCTGCTCACGGCAACCCCTGAAGTTTAGGGGACNACCTACTCAGCGCAAAATTTCGCTAATGTGAGTCCGCCCCACCAGG | (SEQ ID NO. 440) |
| | GGNANATCAACCCATGTCGATCATGATCTACCCGGATACCGGATTGGCGGTAGCGCCCACGATCGTCNAAATNTCCGCCTGAATCATCGGATAGCTGATCCGGCGT | |
| | CAACGCGTTTTGANTTCACCGCGCAACAGCCGCCAGGCCGGCCCGCANCGANCCGATCTCNTCGGGCCGCATGGGCCCCAATCTTNTCG | |
| | :::::::::::::Rv339T7.seq::::::::::::: | |
| | GTGTGTGGTGGAACCCATCTGAGCAGTGTGCCAAACCGGGGCAGACAGCTCCCAATTGACGTGAGCCCGCTCACTTGCTGGGTAAGCGTC | (SEQ ID NO. 441) |
| Clone Rv33 | :::::::::::::Rv33SP6.seq::::::::::::: | |
| | CTTTACACTTCCTGCATCCGGCTCGTATGTTGTGTGGAATTGTGAGCGGATAACAATTTCACACAGGAAACAGCTATGACCATGATTACGCCAAGCTATTTAGGTG | (SEQ ID NO. 442) |
| | ACACTATAGAATACTCAAGCTTGGGCGTGACGGCCACCGGGGCCACTCCGCACCATCTGTACCCGACCAAGATCTAC | |
| | :::::::::::::Rv33T7.seq::::::::::::: | |
| | CAGGCATGCAAGCTTTAGCTGCCCGAATGCGTCACCCCGATGCGCCCAGATCGGGGCTTCGCAGATAAAGCACGAACAGGCGGGCAAAACGTCNATCTCGGAGCCG | (SEQ ID NO. 443) |
| | GAAGGGCAATCAGCCGACCGTCGACGAACGACACCGGCGAGACCACTTAGGCAGTGACGGCCGGCCCGAACATTACGCGCTCGTTGATTAGGCGTTCGGTCTCGTC | |
| | CGCGGTCATGCCGAGCAGCTTGCGGCAGATCTGAACGCTGTCCTGTCCGGGCAGCGGCGCCGGGCGTTGGGGTGCCTGCCCGAATGTGACGAAACGGAGCCGGACC | |
| | CGTCTCGGCGGGCCGCGGACGGCGATCCGC | |
| Clone Rv340 | :::::::::::::Rv340SP6.seq::::::::::::: | |
| | CNCAAGCTTGCGGATGTTACCCCTGACAGCCTGAACTATGTCNAAACACACGGCACCGGAACGGTGTTGGGGGACCCCATCGANTTCGAGTCGCTGGCGGCCACTT | (SEQ ID NO. 444) |
| | ATGGCCTGGGTAAAGGCCAGGGCNANAGCCCGTGCGCATTGGGGTCGGTCAAAACCAACATCGGCCACCTGGAGGCGGCCGCCGGTGTGGCTGGATNCATCAAGGC | |
| | GGTGCTGGCGGTGCAACGTGGGCACATTCCCCGCAACTTGCACTTCACCCGGTGGAACCCGGCCATCNACGCGTCGGCNACGCGGCTGTTCGTGCCNACCNAAAAC | |
| | CCCCCGTGGCCGGCGGC | |
| | :::::::::::::Rv340T7.seq::::::::::::: | |
| | GGAACCGGTAACCAGATCAGCTCGTCGACCTCACTGCCGGGGGTGAATTCCCCACCGGTGCTGCGCGCTGCCCAGTAGTGCACCTTCTTGACGCCTCGAAAAGGGG | (SEQ ID NO. 445) |
| | AGTCGGTCGGGTAGGTCACCGTCAGGAGCCGCCTACCCAGGTTGGCGCNATAGCCGGTCTCCTCGAGTATCTCCCGCACCGCCCCCACCGGTGCGGTCTCACCCAN | |
| | ATCCACTTTGCCCTTGGGCAGCGACCAGTCGTCGTANCNGGGGCGGTGAATGACAACGATCTCGACCGGCCCTTCCN | |
| Clone Rv341 | :::::::::::::Rv341SP6.seq::::::::::::: | |
| | TACTCAAGCTTCAGAACAGGCCTGTTGTGGGCNCACCCGGCTCGCCGAGTTCTGCACGCACCGCCTCAAGTGCGGCCCGCACCGCCGGCATCTCCCGGTCACGCAG | (SEQ ID NO. 446) |
| | GGCCGCGGCCCGCGCCGCAGCGACGGCGTGTTCGCGCAGTTCGCCGTCAATGATGCTGACCTGATCGGCCACCCGGGCGTTCTCGGCGTCGTCGCGTTCACTAATC | |
| | GCGGTGCTCAGCAGCGTCTCGACAGCCACCACCCGAGTGGCGACCAGCTGC | |
| | :::::::::::::Rv341T7.seq::::::::::::: | |
| | TAATGTCTTGCCAACGTCACCACAATCGCGATGAATTCAATCATGCCGCCCAGGGCGGCCAACCCAATGGTGGCCGCGAGCGGCAGCTCGATCGCAGCGCGGAGGT | (SEQ ID NO. 447) |
| | TGCCGGCCGCCAGTTGATTCACGAACAGGGTGAGGTCATAGGCGGGCAGGATAGTGACGAAGGCAAGACCTATATCTGCCGTCGGAAGAAGAATCGAGTAGCCGGT | |
| | CGACACAACGGAAGCGAAAGTGTCCGCGATGTTGATGAGCGTCGCCGGTTGTGGCGGCGGTGGCGGC | |
| Clone Rv343 | :::::::::::::Rv343SP6.seq::::::::::::: | |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | TACTCAAGCTTTCGTCAGTTCATCGCGCCAGCAGACCAACAAGAGCATCGGGACATACGGAGTCAACTACCCGGCCAACGGTGATTTCTTGGCCGCCGCTGACGGC | (SEQ ID NO. 448) |
| | GCGAACGACGCCAGCGACCACATTCAGCANATGGCCAGCGCGTGCCGGGCCACGAGGTTGGTGCTCGGCGGCTACTCCCAGGGTGCGGCCGTGATCGACATCGTCA | |
| | CCGCCGCACCACTGCCCGGCCTCGGGTTCACGCAGCCGTTGCCGCCCGCAGCGGANNATCACATCGCCGCGATCGCCCTGTTC | |
| | :::::::::::::Rv343T7.seq::::::::::::: | |
| | CCACCCGTGTAATTTGGGATGGGCNAAAAGGCNAAGCACCGCGTGGCCACGAACGCCGGGAGGGACAATCTCGGGCGGCTAGGGCTTCTCGCGGGAAGGCCCGAAC | (SEQ ID NO. 449) |
| | GTACGGCGTTTCAACACGTCGCGTCGCCCTCCGACCGCGAACATTCGGGGATGGCAGCAACCTGGTAGCACCCTGGCCGGGCGATGATCTGCAGCGTCGCCGCGGG | |
| | TAGTCGCCGCCCGGGCGGCTACAGTCTGAAACGCGATGACCATCGATGTGTGGATGCAGCATCCGACG | |
| Clone Rv344 | :::::::::::::Rv344SP6.seq::::::::::::: | |
| | TCAAGCTTTAGCTGCCCGAATCCGTCANCCCGATGCNCCCAGATCGGGGCTTCGCANATAAAGCACNAACAGGCGGGCAAAACGTCNATCTCGGAGCCGGAAGGGC | (SEQ ID NO. 450) |
| | AATCANCCGACCGTCNACAAACGACACCGGCGANACCACTTAGGCAGTGACGGCCGGCCCGAACATTACNCGCTCGTTGATTAGGCGTTCGGTCTCGTCCGCGGTC | |
| | ATGCCGAGCAGCTTGCGGCANATCTGAACGCTGTCCTGTCCGGGCAGCGGCGCCGGGCGTTGGGGTGCCTGCGGAATGTGACNAAACGGAGCCGGACCCNTCTCGG | |
| | CG | |
| | :::::::::::::Rv344T7.seq::::::::::::: | |
| | CCGGGGCCACTCCGCACAATCNGTACCNNACCAANATCTACACCATCGAATACGACGGCGTCGCCGANTTTCCGCGGTACCCGCTCAACTTTGTGTCGACCCTCAA | (SEQ ID NO. 451) |
| | CGCCATTGCCGGCACCTACTACGTGCACTCCAACTACTTCATCCTGACGCGGAACAAATNGACGCNTCGGTTCCGCTGACCAATACGGTCGGTCCC | |
| Clone Rv346 | :::::::::::::Rv346SP6.seq::::::::::::: | |
| | NCTGGCCTTTGGTCCACACTAANACAATACTCAAGCTTCCGGCCGCAGAGCCGCCAACTCACGATATCGTTAACCGATATCCCGAGCCGATAGCTGGCGGGCTCGG | (SEQ ID NO. 452) |
| | GTGGTGGCCAGCGGCGCTGCGACNAAAGGTGTGACCGTCATGAAACAGACACCACCGGCGGCCGTCGGCCGTCGTCACCTGCTCGANATCTCAGCATCCGCAGCCG | |
| | GTGTGATCGCGCTTTCGGCGTGTNGTGGGTCNCCGCCCGAGCCCGGCAAAGGCCGGCCCGACACAACCCCGGAAC | |
| | :::::::::::::Rv346T7.seq::::::::::::: | |
| | CATCTGCCCACCACACGGACCGCGGTGCGGACGCGGCTGACGCGCCTGGTGGTCAGCATCGTGGCCGGTCTGCTGTTGTATGCCAGCTTCCCGCCGCGCAACTGCT | (SEQ ID NO. 453) |
| | GGTGGGCGGCGGTGGTTGCGCTCGCATTGCTGGCCTGGGTGCTGACCCACCGCGCGACGACACCGGTGGGTGGGCTGGGCTACGGCCTGCTATTCGGCCTGGTGTT | |
| | CTACGTCTCGTTGTTGCCGTGGATCGGCGAGCTGGTGGGCCCCGGGCCCTGGTTGGCACT | |
| Clone Rv347 | :::::::::::::Rv347SP6.seq::::::::::::: | |
| | GACAATACTCAAGCTTGACTGGCCACCCACCGGCATGACCACCGACAGGCCCGACTGGTCGTACCACTCGAACGCCGGGGTGTTGATGTCCCAGCCGCTGAANTCG | (SEQ ID NO. 454) |
| | TCCTGCGCGCGCAGGCCGTCNAACAGGTACAGGGCGGGCGAATTGGCACCACCACTTTGGAATTGGACCTTGATGTCACGGCCCATCGACGGCGACGGCACCTGCA | |
| | GGTACTCCACCGGCAAGCCCGGCCGGGAAAATGCCCCCGCGGTCNCCGTGCCACCGACGGCGCCGANCAAACCCGACACTAGGGCCGCGCCNACGGCCCCGACCAC | |
| | NANTCNACGCGACATACCCGTGACGGCGCCACNAACCCTGTCAACA | |
| | :::::::::::::Rv347T7.seq::::::::::::: | |
| | CCTCCAACTCGGCGGGGAAGCGACNCCAGCCTACCGAGCTTGGAGTCCANGACGCCAGCGGCGGCGTCGGTCTGCGTCGTGGTGCCGCCGGGGTGGCGTTGGCTGG | (SEQ ID NO. 455) |
| | CAACGATCTCCACCCAGCCGGTCGGGTTACCCACGATCTCGGCATANACGCGGGCCGAGGCCGGTGCGATACCGTATTGCGTCAATTGGGACGCGGTTGTGCATTC | |
| | GGCTAGCTCGGTTGCCACACCCGTCAGGGGTTCGACGTTGGCGGGTTCGGCGGGCCCCANCACCGCTGTCACCATGCCCGCCAAGCCGACCTGCGGCGCCACCAAC | |
| | TGCAGCACCANCATGTCGCCGTCGCGCGCCGCGATCACATGG | |
| Clone Rv348 | :::::::::::::Rv348SP6.seq::::::::::::: | |
| | CTCAAGCTTTTTGAGCGTCGCGCGGGGCANCTTCGCCGGCAATTCTACTANCGAGAANTCTGGCCCGATACGGATCTGACCGAANTCGCTGCGGTGCANCCCACCC | (SEQ ID NO. 456) |
| | TCATTGGCGATGGCGCCGACNATGGCGCCTGGACCGATCTTGTGCCGCTTGCCGACGGCGACGCGGTAGGTGGTCAAGTCCGGTCTACGCTTGGGCCTTTGCGGAC | |
| | GGTCCCGACGCTGGTCGCGGTTGCGCCGCNAAAGCGGCGGGTCGGGTGCCATCAGGAATGCCTCNCCGCCGCGGCACTGCACGGCCAGTGCCGCGGCGA | |
| | :::::::::::::Rv348T7.seq::::::::::::: | |
| | CNCCAGCTTGATTGGTCTGGTTGCATTGGCCAGCTGCGCGAGCCTGGCTCACTTCAACTACGACGACCGCAAACAATTGCCGCCTTCGGATCCGAGTTCGGTTGGG | (SEQ ID NO. 457) |
| | TACGCGGCAATGGAGCACCATTTCTCGGTGAATCAGACTATTCCTGAGTACTTGATCATCCACTCTGCACACGACCTGCGAACCCCGCGCGGCCTTGCCGACCTGG | |
| | AGCAGCTGGCGCAACGTGTGAGCCAGATCCCAGGCGTTGCCATGGTTCGCGGTGTGACCCGGCCAAACGGGGAAAC | |
| Clone Rv349 | :::::::::::::Rv349SP6.seq::::::::::::: | |
| | CAATACTCAAGCTTGACTGGGCCCGCACCTTCGGCGCCACCCACACCGTCAACGCCCGCGAAGTCNACGTCGTCCAGGCCATCGGCGGCCTCACGGATGGATTCGG | (SEQ ID NO. 458) |
| | CGCGGACGTGGTGATCGACGCCGTCGGCCGACCGGAAACCTACCAGCAGGCCTTCTACGCCCGCGATCTCGCCGGAACCGTTGTGCTGGTGGGTGTTCCNACGCCC | |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | GACATGCGCCTGGACATGCCGCTGGTCNACTTCTTCTCTCACGG | |
| | :::::::::::::Rv349T7.seq:::::::::::: | |
| | TCGACGGTTTGGCGGCCTTAAATGCACTGAGGTCGTCAATTGACCCCACAGCGGAAATGCCGACTATTCGCAGGCCTCCTTCGCCTTGGCTGCCGGAGAGGGGCTC | (SEQ ID NO. 459) |
| | CGCGGGAACCGCATGCAGGTATATGACCTCGGTTTCTCGGGTGCTACCGCGTGCCTTGTNTANGATNANCTCGGCGTTGGAATTGTCCAGCCGGCCCAATTCATCG | |
| | AGCGCANATTCGTACACNTGGCCGGCGGCGACATACGCTTCACCGTGGATCTGCTCCACACGGACCGCCCTGTCGGGATCCTGCTCACGGGTAANGGAACTTACGT | |
| | GGCACTCGG | |
| Clone Rv34 | :::::::::::::Rv34SP6.seq:::::::::::: | |
| | GACCACGCCAGGCTAATCACGTGACGCTACCGAATACCCTNCCTAGTGGTGCAGGCTCCCGCTGGAAATGGCCCTGTACCAACTCGCGCACCGGTGCCAG | (SEQ ID NO. 460) |
| | :::::::::::::Rv34T7.seq:::::::::::: | |
| | CGGCACCCGACCCCTTTGAGCCGTCCGCCGTGGCCGCGGTGGAACTGGCCGACGAGGGACTGATCGTGCTGGGCAAATTGGTCGATGGCACGCTGGCCGCCGATCT | (SEQ ID NO. 461) |
| | GAAGGTCN | |
| Clone Rv350 | :::::::::::::Rv350SP6.seq:::::::::::: | |
| | CTCAAGCTTGCCGTTACCCCGACTTCCGGAGGGACACCATGAGCACCGCCAGCCGAGCACGAGGCCAAACTCCGCCGACGCAGGCCGGTTGGACTTGTCGTGCTGG | (SEQ ID NO. 462) |
| | ACAAGGGGTTTAGCCGCCGAAGCAGTGACGTACATCGGCGAAAAGCAGTTCGCCTGTCGACCGACGGNGCNNACCGTGAGGCTAGGGAAGCGAGGAGCACATGGCC | |
| | GCCGACCCGCAATGTACACGCTGCAAGCAAACCATCGAACCCGGATGGCTATNCNTCACCGCCCATCGCCGCGGT | |
| | :::::::::::::Rv350T7.seq:::::::::::: | |
| | CATGTCGCGCACATCCAGGACTTCTGGGGGGATCCGCTGACAGCGGCGGGATCCCAAAGTGCGGATGATCGGGCCGCCTACGTCGTGGTGTACCTCGTCGGTAACA | (SEQ ID NO. 463) |
| | ACGAAACCGAAGCGTATGACTCGGTCCACGCGGTGCGGCACATGGTGGACACCACACCGCCACCGCACGGGGTGAAGGCCTATGTCACCGGTCCGGCAGCACTCAA | |
| | TGCCGACCAGGCCGAGGCCGGAGACAAAAGTATCGCTAAGGTCACCGCGATCACGAGCATGGTGATCGCAGCAATG | |
| Clone Rv351 | :::::::::::::Rv351SP6.seq:::::::::::: | |
| | ATACTCAAGCTTCGGTACGGTGGCGGGCCGTGCTGCTGGCCGCGGTCGCGGCGTGCGCGGCCTGCGGTCTCGTTTACNAGCTCGCGCTGCTGACACTGGCGGCNAG | (SEQ ID NO. 464) |
| | CCTGAACGGCGGCGGGATCGTGGCCACCTCCCTGATCGTCGCGGGCTACATAGCCGCGCTGGGAGCAGGCGCCTTGCTGATCAAGCCGCTACTTGCACACGCGGCC | |
| | ATCGCGTTCATCGCCGTGGAGGCGGTGCTGGGCATCATCGGCG | |
| | :::::::::::::Rv351T7.seq:::::::::::: | |
| | TGTCAAGTCCTTTCAGATCTCNTTTTTATGACATGACTGGAGATCTGTCTAGATTGCAGCTCCTGTGAGCGTGGGTACCGGATTCAAGCCGGTCGGTCACGCCGCG | (SEQ ID NO. 465) |
| | GTGGTACCGGCTTTGCGGCAGTGCTCGGCCTCGAGTTCGGCGATCGCGCGCGAAGTGCGTTCGCGCAGCAAGATCGCGGCCGTAATGCCGGCGATGACCGCGATGA | |
| | CCAGCGCGATCCAGGAGAACCGTTCCAACCAGTGCTGGGCGGCCATCCCGGCGAAGTAGACCAGTGCAGTGGTGCC | |
| Clone Rv352 | :::::::::::::Rv352SP6.seq:::::::::::: | |
| | CAATACTCAAGCTTCAAAACAGGCCTGTTGTGGGCGCACCCGGCTCGCCGAGTTCTGCACGCACCGCCTCAANTGCGGCCCGCACCGCCGGCATCTCCCGGTCACG | (SEQ ID NO. 466) |
| | CAGGGCCGCGGCCCGCGCCGCANCGACGGNGTGTTCGCGCAGTTCGCCGTCAATGATGCTGACCTGATCGGCCACCCGGGCGTTCTCGGCGTCGTCNCGTTCACTA | |
| | ATCGCGGTGCTC | |
| | :::::::::::::Rv352T7.seq:::::::::::: | |
| | TACGCTGGCGCTGGAGGGAGCCANNTACAACATCCACGCCAATGCTCTTGCCCCGATCGCGGCGACCAGGATGACCCAGGACATCCTGCCGCCCGAAGTACTGGAA | (SEQ ID NO. 467) |
| | AAGCTCACACCCGAGTTCGTCGCACCGGTGGTGGCCTACCTGTGCACCGAGGAGTGTGCCGACAACGCATCGGTGTACGTCGTCGGTGGTGGCAAGGTGCAGCGAG | |
| | TTGCGCTGTTTGGCAACGACGGCGCCAACTTCGACAAACCGCCGTCGGTACAAGATGTTGCGGCGCGGTGGGCCGAGATCACCGATCTGTCCGGTGCGAAAATTGC | |
| | TG | |
| Clone Rv353 | :::::::::::::Rv353SP6.seq:::::::::::: | |
| | GCTTTTCCCGTCCGTCNNCGCTCAACCGCGTGAGGCCGAAGCGGNTGGTTACGACTCCCTGTTTGTGATGGACCACTTCTACCAACTGCCCATGTTGGGGACNCCC | (SEQ ID NO. 468) |
| | GACCAGCCGATGCTGGAGGCCTACACGGCCCTTGGTGCGCTGGCCACGGCGACCGANCGGCTGCNNNTGGGCGCGTTGGTGACCGGCAATACCTACCGCAGCCCGA | |
| | CCCTGCTGGCAAANATCATCACCACGCTCGACGTGGTTAGCGCCGGTCGAGCGATCCTCGGCATTGGAGCCGGTTGGTTTGANCTGGAAC | |
| | :::::::::::::Rv353T7.seq:::::::::::: | |
| | CNGCTTTTTAATGGCCTTGACNTGGGCGNGCCGGCCACCGGGGCCACTCCGCACAATCTGTACCCGACCAAGATCTACACCATCGAATACGACGGCGTCGCCGACT | (SEQ ID NO. 469) |
| | TTCCGCGGTACCCGCTCAACTTTGTGTCGACCCTCAACGCCATTGCCGGCACCTACTACGTGCACTCCAACTACTTCATCCTGACGCCGGAACAAATTGACGCAGC | |
| | GGTTCCGCTGACCAATACGGTCGGTCCCAAGATGACCCAGTACTACATCATTCGCACGGAGAACCTGCCGCTGCTAGAGCCACTGCGATCGGTGCCGATCGTGGGG | |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | AACCCACTGGCGAACCTGGTTCAACCAAACTTGAAGGTGATTGTTAACCTGGGCTACGGCGACCCGGCCTATG | |
| Clone Rv354 | ::::::::::::Rv354SP6.seq:::::::::::: | |
| | CTCAAGCTTGCCGGGAGGGTGCATGGCCGACTCGGATTTACCCACCANGGGGCGCCAACGCGGTGTCCGCGCCGTCNAGCTGAACGTTGCTGCCCGCCTGGAGAAC | (SEQ ID NO. 470) |
| | CTGGCGCTGCTGCGCACCCTGGTCGGCGCCATCGGCACCTTCGAGGACCTGGATTTCGACGCCGTGGCCGACCTGAGGTTGGCGGTGGACGAGGTGTGCACCCGGT | |
| | TGATTCGCTCGGCCTTGCCGGATGCCACCCTGCGCCTGGTGGTCGATCCGCGAAAANACGAANTTGTGGTGGAGGCTTCTGCTGCCTGCGACACCCACNACGTGGT | |
| | GGCACCGGGCAGCTTTAGCTGGCAT | |
| | ::::::::::::Rv354T7.seq:::::::::::: | |
| | CCGACGCCGTCGTGGCCACCAACACCGCGACCAGCACCGTGACCCGGACCGGGGTGCCGCGCGAACCGGTCTTGGCCAATTGCCGCGGCACCAAGCCGTCGCGCGC | (SEQ ID NO. 471) |
| | CATGGCGAACAGCACGCGGCATTGCCCGAGCATCAACACCATCACCACCGTGGTAAGCCCGGCCAGCGCGCCGACGGAGATGATGCCGCTGGCCCAGTACACCCCG | |
| | TTGGCCTGGAACGCGGTGGCCAGATTTGCCGGCCCGCGGCCCGGTACGGTCCGCAGTTGGGTGTATGGAACCATGCCCGACAGCACCACCG | |
| Clone Rv355 | ::::::::::::Rv355SP6.seq:::::::::::: | |
| | TTNACTGGCCTTTGGTCCACACTAGACAATACTCAAGCTTCCAGGACATCGTCATCGCGACCAAAACCGCGAGCTAGGTCGGCATCCGGGAAGCATCGCGACACCG | (SEQ ID NO. 472) |
| | TGGCGCCGAGCGCCGCTGCCGGCAGGCCGATTAGGCGGGCAAATTAGCCCGCCGCGGCTCCCGGCTCCGANTACGGCGCCCCGAATGGCGTCACCGGCTGGTAACC | |
| | ACGCTTGCGCGCCTGGGCGGCGGCCTGCCGGATCAGGTGGTAAATGCCGACA | |
| | ::::::::::::Rv355T7.seq:::::::::::: | |
| | NGACGTCTTCCATCCGCGCGTCGTTTTGGCGGGTTGGCCACAGCAGCCCGCCGGTGACGGCGACGATGCTGGGCTGGTTGCGGCCCTGCGCCACCGCGGCTTGCAT | (SEQ ID NO. 473) |
| | GCTGGTTGGCTGTCTTGGGACGATCCCGAAATAGTCCACGCGGATCTGGTGATTTTGCGGGCTACCCGCGATTACCCCGCGCGGCTCGACGAGTTTTTGGCCTGGA | |
| | CTACCCGCGTGGCCAATCTGCTGAACTCGCGGCCGGTGGTGGCCTGGAATGTCGAGCGCCGTTACCTA | |
| Clone Rv356 | ::::::::::::Rv356SP6.seq:::::::::::: | |
| | CTTCCTCCTGAGTACCNCCCGTNTACTTTGGGATGGGTAAAAAGGCGAATCNCCGTTTGGTCACGAACGCCGGGAGGGACAATCTCGGGCGGCTGGGGCCTCTCGC | (SEQ ID NO. 474) |
| | GGGAANGCCCGAATGTACGGTGTCTCGACACTTCCCNTCCCCCTCCG | |
| | ::::::::::::Rv356T7.seq:::::::::::: | |
| | GAGCATCGGGACNTACGGAGTCAACTACCCGGCCAACGGTGATTTCTTGGCCGCCGCTGACGGCGCGAACGACGCCNGCGACCACATTCAGCAGATGGCCAGCGCG | (SEQ ID NO. 475) |
| | TGCCGGGCCACGAGGTTGGTGCTCGGCGGCTACTCCCAGGGTGCGGCCNTGATCNACATCGTCACCGCCGCACCACTGCCCGGCCTCGGGTTCACGCAGCCGTTGC | |
| | CGCCCNCAGCGGACGATCACNTCGCCGCGATCGCC | |
| Clone Rv357 | ::::::::::::Rv357SP6.seq:::::::::::: | |
| | TACTCATGANCATCCTTTAATCANNGCTTTGCGTTTTTTTATTAAATCTTGCAATTTACTGCAAAGCAACAACAAAATCGCAAAGTCATCAAAAAACCGCAAAGTT | (SEQ ID NO. 476) |
| | GTTTAAAATAAGAGCANCACTACAAAAGGAGATAAGAAGAGCACATACCTCAGTCACTTATTATCACTAGCGCTCGCCGCAGCCGTGTAACCGAGCATAGCGAGCG | |
| | AACTGGCGAGGAAGCAAAGAAGAACTGTTCTGTCAGATAGCTCTTACGCNCA | |
| Clone Rv358 | ::::::::::::Rv358SP6.seq:::::::::::: | |
| | CTCAAGCTTCAGGTCAATGTGCNCCAAGCCCTGACGCTGGCCGACCAGGCCACCGCCGCCGGANACNCTGCCAAGGCCACCGAATACAACAACGCCGCCGAGGCGT | (SEQ ID NO. 477) |
| | TCGCANCCCAGCTGGTGACCGCCGAGCANANCGTCAAAAACCTCAAGACGCTGCATGACCAGGCGCTTANCNCCGCANCTCAGGCCAAGAAGGCCGTCNAACGAAA | |
| | TGCGATGGTGCTGCACCANAAGATCGCCGAGCGAACCAAGCTGCTCAGCCNG | |
| | ::::::::::::Rv358T7.seq:::::::::::: | |
| | CATGGTGGCACTGTAGCGACGTGCTGCAATCAAGGTCATGCCCGACTCTGGTCAGCTCGGANCCGCTGACACCCCGCTAAGGCTGCTCAGCTCGGTGCATTACCTC | (SEQ ID NO. 478) |
| | ACCGACGGCGAACTCCCCCAGCTTTACGACTATCCGGATGACGGCACCTGGTTGCGGGCGAACTTCATCATCAGCTTGGACGGCGGCGCTACCGTCGATGGCACCA | |
| | GCGGGGCGATGGCCGGGCCCGGCGACCGATTCGTCTTCAACCTGTTGCGTGAACTTGCCGACGTCATCGTGGTCGGCGTGGGCACCGTGCGCATTGAGGGCTACTC | |
| | CGGCGTCCGGATGGGTGTCGTCCAGCGCCAGCAC | |
| Clone Rv359 | ::::::::::::Rv359SP6.seq:::::::::::: | |
| | TACTCAAGCTTGCGGGTGATCGCCTTGGTCAACGGCACCGTGATCGGATCGGGGTCNACCGCACAAATGGACTGGAGCTTCGGCGAANTCATCGCCTATGCCTCGC | (SEQ ID NO. 479) |
| | GGGGGGTGACGCTGACCCCGGGTGACNTGTTCGGCTCGGGCACGGTGCCCACCTGCACGCTCGTCTATCACCTCNGGCCACCGGAATCATTCCCGGGCTGG | |
| | ::::::::::::Rv359T7.seq:::::::::::: | |
| | GTTGGNGCCTCGTCGGCGAACAGTTCTCGCACGATTTCCGGATTAGCGGGACTGGTCACCAGTTGGGTATGCGGGAAGGCGCTGACGTTCGCCGCGATTAGCTGTT | (SEQ ID NO. 480) |
| | TGATGGACGCGGTGGTGATGTTCTGATCACGGAACTGGCTGTAATAGCCCAGGGTCGCCACGCTTTCATCCGGGCCCGGACCCGGCGCACCGAGCGTGTCGCGCAG | |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | GTATGCGACGTGATTTTCGCTGAAGTCCCCGTACCCGGAGAACT | |
| Clone Rv35 | :::::::::::::Rv35SP6.seq::::::::::::: | |
| | TGCTTCCGGCTCGTATGTTGTGTGGAATTGTGANCGGATAACAATTTCACACAGGAAACAGCTATGACCATGATTACGCCAAGCTATTTAGGTGACACTATAGAAT | (SEQ ID NO. 481) |
| | ACTCAAGCTCCAGGTCAATGTGCGCCAAGCCCTGACGCTGGCCGACCAGGCCACCGCCGCCGGAGACGCTGCCTTTGTCACCGAATACAACAACGCCGCCGAGGCG | |
| | TTCGCAGCCCAGCTGGTGACCGCCGAGCAGAGCGTCGAAGACCTCAAGACGCTGCATGACCAGGCGCTTAGCGCCGCAGCTCAGGCCAAGAATGCCGTCGAACGAA | |
| | ATGCGATGGTGCTGCGGCATAAGATCGCCGAGCGAACCAAGCTGCTCAGCCAGCTCGAGCAGGCGAAGATGCACGAGCA | |
| | :::::::::::::Rv35T7.seq::::::::::::: | |
| | CAGGCATGCAAGCTTCGGAGGCAGACCCGTGCATGGTGGCACTGTAGCGACGTGCTGCAATCAAGGTCATGCCCGACTCTGGTCAGCTCGGAGCCGCTGACACCCC | (SEQ ID NO. 482) |
| | GCTAAGGCTGCTCAGCTCGGTGCATTACCTCACCGACGGCGAACTCCCCCAGCTTTACGACTATCCGGATGACGGCACCTGGTTGCGGGCGAACTTCATCAGCAGC | |
| | TTGGACGGCGGCGCTACCGTCGATGGCACCAGCGGGGCGATGGCCGGGCCCGGCGACCGATTCGTCTTCAACCTGTTGCGTGAACTTGCCGACGTCATCGTGGTCG | |
| | GCGTGGGCACCGTGCGCATTGAAGGCTACTCCGGCGTCCGGATGGGTGTCGTCCATCGCCA | |
| Clone Rv360 | :::::::::::::Rv360SP6.seq::::::::::::: | |
| | TACTCAAGCTTGGGGTGGCGCTGTCGGTCGGTGTGCTTGGCGGCGTCGGTATCAACACCGCCCACGAAATGGGGCACAAGAAGGATTCGCTGGAGCGGTGGCTGTC | (SEQ ID NO. 483) |
| | CAAAATCACCCTCGCCCANACCTGCTACGGGCACTTCTACATCGAGCACAACCGTGGCCATCACGTCCGGGTGTCCACACCGGAGGACCCGGCGTCGGCGCGGTTC | |
| | GGCNAAACGTTGTGGGANTTCCTGCCCCGCANTGTTATCGGCGGCTTGCGCT | |
| | :::::::::::::Rv360T7.seq::::::::::::: | |
| | GGCCATCGCCACCGCNCCGCGGCGAACGCTCAAAGGCACCTACTGGCACCAAGGCCCCACACGTCACCCTGTGACCTCCTGCGCCGACCCCGCCCGAGGTCCTGGC | (SEQ ID NO. 484) |
| | CGTTACCACCGAACGGGCGAGCCGGGAGTCTGGTACGCATCGAACAAAGAGCAAGGTGCATGGGCGGAGTTGTTCCGCCACTTCGTCGATGACGGGGTCGATCCAT | |
| | TCGAGGTCCGTCGCCGCGTCGGTCGAGTGGCGGTCACACTCCANGTACTCGACCTCACAGACGAGAGGACTCGATCCCATCTAGGTGTGGACGAAACAGATCTTCT | |
| | GTCCGACGACTACACCACCACCCAGGCCATCGC | |
| Clone Rv361 | :::::::::::::Rv361SP6.seq::::::::::::: | |
| | GCTTGCGGGTGATCGCCTTGGTCAACGGCACCGTGATCGGATCGGGGTCNACCGCNCAGATGGACTGGANCTTCGGCGAANTCNTCGCCTATGCCTCGCGGGGGGT | (SEQ ID NO. 485) |
| | GACCCTGACCCCGGGTGACNTGTTCGGCTCGGGCACGGTGCCCACCTGCACGCTCGTCAAGCACCTCNGGCCACCGGAATCATTCCCGGGCTGGCTGCACNACGGC | |
| | GACNTGGTCNCCCTCCAGGTCGAAGGGCTGGGCNAAACAANGCAGACCGTCCGGACAANCGGCACTCCTTTTCCGTTGGCTCTTCGGCCGAATCCGGACGCCNAAC | |
| | CCGACCGGCG | |
| | :::::::::::::Rv361T7.seq::::::::::::: | |
| | GTTCTCGCACGATTTCCGGATTAGCGGGACTGGTCACCAGTTGGGTATGCGGGAAGGCGCTGACGTTCGCCGCGATTAGCTGTTTGATGGACGCGGTGGTGATGTN | (SEQ ID NO. 486) |
| | CTGATCACGGAACTGGCTGTAATANCCCAGGGTCGCCNCGCTTTCATCCGGGCCCGGACCCGGCGCACCGAGCGTGTCGCGCAGGTATGCGACGTGATTTTCGCTG | |
| | AAGTCCCCGTACCCGGAGAACTCGAACACGCTGAGGCGCTCGTCACCGTCGTNNCGGCGACCAAGCGCGGCGAGCAACTGCGCAAAATCGTTAAGANAGGTCGAAT | |
| | CGTTGAAATTCGGCACCACCTGCACC | |
| Clone Rv363 | :::::::::::::Rv363SP6.seq::::::::::::: | |
| | CACAAGACAATACTCAAGCTTCAGGTCAATGTGCNCCAAGCCCTGACGCTGGCCGACCAGGCCACCGCCGCCGGANACGCTGCCAAGGCCACCGAATACAACAACG | (SEQ ID NO. 487) |
| | CCGCCGAGGCGTTCGCAGCCCAGCTGGTGACCGCCGAGCANANCGTCNAAAACCTCAAGACGCTGCATGACCAGGCGCTTANCGCCNCAGCTCAGGCCAAGAAGGC | |
| | CGTCGAACGAAATGCGATGGTGCTGCAGCANAANATCGCCGANCGAACCAAGCTGCTCAGCCAGCTCGAGCAG | |
| | :::::::::::::Rv363T7.seq::::::::::::: | |
| | CCACCCGTGCATGGTGGCACTGTAGCGACGTGCTGCAATCAAGGTCATGCCCGACTCTGGTCAGCTCGGAGCCGCTGACACCCCGCTAAGGCTGCTCAGCTCGGTG | (SEQ ID NO. 488) |
| | CATTACCTCACCGACGGCGAACTCCCCCAGCTTTACGACTATCCGGATGACGGCACCTGGTTGCGGGCGAACTTCATCAGCAGCTTGGACGGCGGCGCTACCGTCG | |
| | ATGGCACCAGCGGGGCGATGGCCGGGCCCGGCGACCGATTCGTCTTCAACCTGTTGCGTGAACTTGCC | |
| Clone Rv364 | :::::::::::::Rv364SP6.seq::::::::::::: | |
| | GCTTTCCGCCGATACCCNCCATGTCCCGCACATCCAGGACTTCTGGGGGGATCCGCTGACAGCGGCGGGATCCCAAAGTGCGGATGATCGGGCCGCCTACGTCGTG | (SEQ ID NO. 489) |
| | GTGTACCTCGNCGGTAACAACGAAACCGAANCGTATGACTCNGTCCACGCGGTG | |
| | :::::::::::::Rv364T7.seq::::::::::::: | |
| | CAACCCGANTTGGCTTTCGGCGCCNTCGGTGAGGACGGCGTGCGGGTGCTCAACGACGACGTCGTCCGCGGGACACACCTCGATGCTGCCGCCATGGACGCGGTCG | (SEQ ID NO. 490) |
| | AACGCAAGCAGCTGATCGATCTACNACGCCGNGNGGAACGCTTCNGCCGCGGGCGTGACCGCNTCCCGTT | |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

Clone Rv365 :::::::::::::Rv365SP6.seq:::::::::::::
GGGATGGGCAAAAAGGCGAAGCACCGCGTGGCCACGAACGCCGGGAGGGACAATCTCGGGCGGCTAGGGCTTCTCGCGGGAAGGCCCGAACGTACGGCGTTTCAAC (SEQ ID NO. 491)
ACGTCGCGTCGCCCTCCGACCGCGAACATTCGGGGATGGCAGCAACCTGGTAGCACCCTGGCCGGGCGATGATCTGCCAGCGTCCCCGCGGGTAGTCGCCGCCCGG
GCGG
:::::::::::::Rv365T7.seq:::::::::::::
CAGCAGACCAACAAGAGCATCGGGACATACGGAGTCAACTACCCGGCCAACGGTGATTTCTTGGCCGCCGCTGACGGCGCGAACGACGCCAGCGACCACATTCAGC (SEQ ID NO. 492)
AGATGGCCAGCGCGTGCCGGGCCACGAGGTTGGTGCTCGGCGGCTACTCCCACGGTT Clone Rv366 :::::::::::::Rv366SP6.seq:::::::::::::
CTCAAGCTTGACTGGCCACCCACCGGCATGACCACCGACAGGCCCGACTGGTCGTACCACTCGAACGCCGGGGTGTTTGA (SEQ ID NO. 493)
:::::::::::::Rv366T7.seq:::::::::::::
TTGGTGCCCGGAATGGCGAGTCCCATTTANTCGCTGATTTGTTTGAACAGCGACGAAACCGGTGTTGAAAATGTCGCCTGGGTCGGGGATTCCCTCTCCAAGCAAG (SEQ ID NO. 494)
AGTAACTGGCCCCAAATAAAGTTACTCGTCGTCTTGCAAAGACCGCTACCCGATGCCATTTATGTGTTTCCTTACGCTCNNNNTTCCGGTGCGCCATCATTATCTG
CACCTTTGCACTGCACATTGAGCTTAGCAGCGCTCG Clone Rv367 :::::::::::::Rv367T7.seq:::::::::::::
GAATTNGCTTTCGGCGCCATCGGCCCAGGACCGCGTGCGGGTGCTCAACGACGACGTCGTCCGCGGGACACACCTCGATGCTGCCGCCATGGACGCGGTCGAACGC (SEQ ID NO. 495)
AAGCAGCTGATCGAGCTACAACGCCGCGCGGAACGCTTCCGCCGCGGGCGTGACCGCATCCCGTTGACCGGGCGGATCGCNGTGATCGTCGATGACGGCATCGCCA
CCGGAGCGACGGCCAAGGCGGCGTGCCAGGTCGCCCGGGCGCACGGTGCGGACAAGGTGGTGCTGGCGGTCCCGATCGGCCCAGACGACATCGTGGCGAGATTCGC
CGGGTACGCCGATGAAGTGGTGT Clone Rv368 :::::::::::::Rv368SP6.seq:::::::::::::
TAAAGCTTTCGTCAGTTCATNGNGCCCCCGGACCAACAAAAGCATCGGGACATACGGAGTCAACTACCCGGCCAACGGTGATTTCTTGGCCGCCGCTGACGGCGCN (SEQ ID NO. 496)
AACGACGCCAGCGACCACATTCAGCAGATGGCCAGCGCGTGCCGGGCCACGAGGTTGGTGCTCGGCGGCTACTCCCAGGGTGCGGCCGTGATCNACATCGTCACCG
CCGCACCACTGCCCGGCCTCGGGTTCACGCAGCCGTTGCCGCCCGCAGCGGACGATCACNTCGCCGCGATCGCCCTGTTCGGGAATCCCTCGGGCCGCGCTGGCGG
GCTGATGAGCGCCCTGACCCCTCAATTCGGGTCCAANACCATCNACCTCTGCAACAACGGCGACCCGATTTGTTCGGACGGCAACCGGTGGCGANCGCACCT
:::::::::::::Rv368T7.seq:::::::::::::
CCGGGAGGGACCATCNCGGGCGGCTNCGGCTTCTCTCCGGAAGGTTCTANNGTNNNGCGTTTCNACNCTTCCCGTCGCCCTGCGACCGCCGAACATTCGGGGTATG (SEQ ID NO. 497)
GNNGCANCCTGTNAGCATCCNGGCCGGGC Clone Rv369 :::::::::::::Rv369SP6.seq:::::::::::::
CTCAAGCTTCCGCATCAGATCGCTATAGAACCGGTGCGCGTCCCCACCGAGTGGCTGGTCGCCTTCCAGCACGATCGTTACCGCGTTATCGGAATCAAACTCNCCG (SEQ ID NO. 498)
AACACCTGACCAACGCGCTTGATCGCCTGAATCGATGCGGCGTCGCTGGGGCTCATCGATACCGAGTGTGCTTTTCCGACCACTTCCAGTTGCGGTACGGCGAGAT
TGACAAAGGCGGTGAAGCCCAGCCAGAGCAGGACGATCACCNCCGCAAACCGGCGGATTTGCCCG
:::::::::::::Rv369T7.seq:::::::::::::
GCTTGGCAGCCTGCGGCTGGGCGCCCTNGAGCTCTTCGATCTGGATCTCCGGACTCGAGATGCTCACTTGCCCGGCCGTGGACGTACCCATTGCGGCCGGGACCCC (SEQ ID NO. 499)
AGCGCCCCAGGTGACCAGCGAGTTGGGCTGCACGCTGACCGGCCCGTCGGGGTCGACGCCGGTAACGGTCAGCAGCTCCGANGTCCNNCTGATCCCGACCGCAGCT
GCCAATGCGCGGCTGGCAGCCGACGTGGATGTGCCGGGGCCTAGATCGCGGGGCAGCAGCGAGACCGCGTCACCGACGGTCATCACCTTGCCGAGTTTNGGCCTGC
CGCAN Clone Rv36 :::::::::::::Rv36SP6.seq:::::::::::::
GCTTCCGGCTCGTATGTTGTGTGGAATTGTGAGCGGATAACAATTNCACACAGGAAACAGCTATGACCATGATTACGCCAAGCTATCTAGGTGACACTATAGAATA (SEQ ID NO. 500)
CTCAAGCTTGAGCCATCGGGCTATCAGCTGGTTGATGTCCCG
:::::::::::::Rv36T7.seq:::::::::::::
CAGGCATGCAAGCTTGTCGTCTATCACATCCGACCACCAACCGCCCGACGGCTCGGCAGAACGCCTCCGCATATGGGTCGACGACCAGCGGGTCGGACTTCTGGGC (SEQ ID NO. 501)
TGCCAGCGCTCGCGCCGTCGCGACAAACAGCGCGGTCGAACCGACACTCCTTGTGATGTCCCACCTATCACCTTCGGTACGCACCCAATCGACCCTACGCGGCTAG
CTCAGCCCCGATCTTCCAGAGCTCCGCCCG Clone Rv370 :::::::::::::Rv370SP6.seq:::::::::::::
GCTTTTTGAGCGTCGCGCGGGGCGGCTTCCCCGGCAATTCTACTAGCGAGAAGTCTGGCCCGATACGGATCTGACCGAAGTCGCTGCGGTGCAGCCCACCCTCATT (SEQ ID NO. 502)

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | GGCGATGGCGCCGACNATGGCGCCTGGACCGATCTTGTGCCGCTTGCCGACGGCGACGCGGTAGGTGGTCAATTCCGGTCTACGCTTGGGCCTTTGCGGACGGTCC | |
| | CGACGCTGGTCGCGGTTG | |
| | :::::::::::::Rv370T7.seq::::::::::::: | |
| | CGANCCTGTTCGACGGCTACCTGAATCACCCCGATNCCACCGCCGCGGCGTTCGACGCCGACAGCTGGTACCGCACCGGCGACGTCGCGGTGGTCGACGGCAGTGG | (SEQ ID NO. 503) |
| | GATGCACCGCATCGTGGGACGCGAGTCGGTCGACTTGATCAAGTCGGGTGGATACCGGGTCGGCGCCGGTGAAATTGAAACGGTGCTGCTCGGGCATCCGGACGTG | |
| | GCGGAGGCGGCAGTCGTCGGGGT | |
| Clone Rv371 | :::::::::::::Rv371SP6.seq::::::::::::: | |
| | NAAGCTTTGTCACACCAAGTGTTTCNACCAGNCGCTCCATCCGGCGAAGTGGATACTCCCAGCAGGTAGCAGGTCGCCACCACGCTGGTCAGTGCGCGTTCAGCTC | (SEQ ID NO. 504) |
| | GCTTGCGGCGCTGCAGCAGCCAGTCCGGGAAATAGCTGCCCTGGCG | |
| | :::::::::::::Rv371T7.seq::::::::::::: | |
| | CGCTGGNCGCCGGCGCTGGGCTGCGGTAACCAATTACCACAACACTTTTCGGTAGCCGAACAGCGGCGCGTACCAGCGAAATGGCACAGCCACCGCAGTCGCCGAC | (SEQ ID NO. 505) |
| | ATCCCGCGAAGATGTGGCAGATTTTCGTGCGGTCGAGCCGGCGAAGGCCTAGCGTCATTGTTGCCTGGCAAGGTTGCTGGGCCCGG | |
| Clone Rv373 | :::::::::::::Rv373SP6.seq::::::::::::: | |
| | CTCAAGCTTCTTCTGCCCCTTGCCGTTNCGGATNACATCCCGCAGCGACTCGGCTTCGGCGTCGATGTCGAAGTTCTCGATCAGCTTCTGGATCGACTCCGCGCCC | (SEQ ID NO. 506) |
| | ATGGCACCGGTGAAGTACTCGCCGTAGCGGTCGACNAGTTCGCGGTAGAGGTTTTCGTCNACNATCAGCTGCTTGGGCGCCANCTTGGTGAAAGTGCTCCAAATGT | |
| | CCTCCAACCGGTCCAGCTCACGCTGCGCGCGGTCACGGATCTGGCGCATCTCGCGCTCGCCGCCGTCGCGAACTTGCGCCGCGCATCGGCCTTGGGGCCC | |
| | :::::::::::::Rv373T7.seq::::::::::::: | |
| | GTTCACACCTACCTACTATGCCNCAATTCNCCGACACGGGTGGCATCAACACGGGCGATAAGGTGGAAATCGCTGGGGTGAACGTCGGGCTGGTGCGCTCGCTGGC | (SEQ ID NO. 507) |
| | AATCCGCGGCAACCGCGTGTTGATCGGATTCTCGTTGCCCGGCAAGACAATCGGGATGCAAAGCCGGGCAGCAATTCNCNCCNACACCATTCTTGGCCGTAAGAAC | |
| | CTGGAGATCGAACCCCGCGGTTCGGAGCCGTTGAAACCCAACGGTTTCCTGCCGTTGGCGCANACCACTACGCCATACCAAATC | |
| Clone Rv374 | :::::::::::::Rv374SP6.seq::::::::::::: | |
| | CTCAAGCTTTACGCCGACGCCGGCCTACACAACACCAAGGAAACGATTGCCTACTGCCGAATCGGGGAACGGTCCTCGCACACCTGGTTCGTGTTGCGGGAATTAC | (SEQ ID NO. 508) |
| | TCGGACACCAAAACGTCAAGAACTACGACGGCAGTTGGACAGAATACGGCTCCCTGGTGGGCGCCCCGATCGAGTTGGGAAGCTGATATGTGCTCTGGACCC | |
| | :::::::::::::Rv374T7.seq::::::::::::: | |
| | TCCCNCATGGGATAACGGGTTTAGATTTCNACAACGGCACCGTGTTTCTCAACAAGCCGGTCATCAGCTGGGCCGGCGACAACGGTATCTACTTCACCCGCTTTCG | (SEQ ID NO. 509) |
| | CCCGTACAAGAAAAACCACTAGGCCACCATCGAGTCCAAGAACAACCACCTGGTCCGCAAGTACGCGTTCTACTACCGCTATGACACCGCCGAGGAACGCGCCGTG | |
| | CTCAACCGGATGTGGAAGCTGGTCAACGACCGCCTCAACTACCTCACCCCGACCATCAAACCGATC | |
| Clone Rv375 | :::::::::::::Rv375SP6.seq::::::::::::: | |
| | CTCAAGCTTGGGTGTTGCCGATCACCGGAAGCCNCATGATCAGCCACGTTTCGCGCCGCCCGGCATACGGCGGCGTACCGATCTCCGCGTCATACACCCGCGGGTA | (SEQ ID NO. 510) |
| | ATCGCCGACGGTGCCGGTTCGCGAGCCGAAGGTGACAACGCTGATTGAATCNAGTTCCANGTCCAGCGGGT | |
| | :::::::::::::Rv375T7.seq::::::::::::: | |
| | TNAACAGCTCGCGGCAGCCCACGACCTGCTGCGTCGGATTGCCGGCGGCGAGATCAATTCCAGGCAGCTCCCGGACAATGCGGCTCTGCTGGCCCGCAACGAANGA | (SEQ ID NO. 511) |
| | CTCGAGGTCACCCCGGTGCCCGGGGTCGTGGTGCACCTGCCGATCGCACAGGTTGGCCCACAACCGGCCGCTTGATGNNNNGTCGGCAAGCCCGGCAGTNGCCAAA | |
| | CCCAGCGTGATCANGCTCGGCTCGCGAGTTCGGCGAANAAGTGGCTCGCCTGATCACCTACCATCGGCCANGATCTGCGTGTCA | |
| Clone Rv376 | :::::::::::::Rv376SP6.seq::::::::::::: | |
| | GCCANCCGGCTTGGCGTCGACTCCCGTTCNGCACATCATACGGTCCCCGGTACTGTCCAACTGCGCCGGTGCGCTAGCCAAACGTCACGACTCTCAGTGATCCCAG | (SEQ ID NO. 512) |
| | TTCGTGATCCGGCCGGTGGCGCCGCTGCGGCGGGGGCTNATNTACTTCGGACTNATTATCTCATCCAAAGGACACCGGGCCGGTGGCTGGAATCCCATGGTGCGAT | |
| | CGGCCACACAN | |
| | :::::::::::::Rv376T7.seq::::::::::::: | |
| | CCGACCTGGTATCTTCCGATAGCGCGCGTTGATATCCGGTCTGATCTCCTGCCCTTAACGCCGGATCTCAGCAGGTCCCCATGCAAAGATCCGAGGTGTCCCNGAT | (SEQ ID NO. 513) |
| | CTAGGGGTCCTCGTCCTCCAGATGATGGAGCAAGTCGGCCC | |
| Clone Rv377 | :::::::::::::Rv377SP6.seq::::::::::::: | |
| | CTCAAGCTTCGGCTCAGGCGGCGCTGCCGGTAACGTCGCTGACCGGTGCAGGTTTCGACAATGTGGTGCCGGTTCGGCGGCTACGTGCCATCAAGACACTGGCGCA | (SEQ ID NO. 514) |
| | GGCTATCGCACCCGTTATCGGCTACAAACAAATCGCGGTATGC | |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | :::::::::::::Rv377T7.seq::::::::::::: | |
| | CATCACCTGNTTCATGAACTGGAAGCACCGCAGCGCTTCCTTTTCGGCCGCAACATGAGCCAGCCTCTCGTCGGCGGTCGGGTGCAGGTGCTCGGGCAGCTCGGCC | (SEQ ID NO. 515) |
| | GCGACAGCCGCCTGACCCTGAAACCAGCTTCCATATCCCGCGACGAACGACGCCAGTCCGCTACGTAACCCCTCCGCGACTGTCCATGGACAACAGCGCGTTCTCC | |
| | ACCGACCGGGCCCGGGTGTGGGGTGT | |
| Clone Rv378 | :::::::::::::Rv378SP6.seq::::::::::::: | |
| | AGCTTAGCTTCCCGCCCCGGCAATAGGGCTCCAGCTCATCCGGTGTGACCAGATAGGGGCCCAGGGTGATACCGCTGTCTTTGCCCTTGGCCTGTCCGATGCGCAG | (SEQ ID NO. 516) |
| | CTGGCCCTCCAGCATCTGCAGGTCCCGTGCGGACCAGTCGTTGAAAATGGTATAGCCGATGATCGACCG | |
| | :::::::::::::Rv378T7.seq::::::::::::: | |
| | CCNGAACAGAAGCGGNGGTTCCTACCGCGGTGTGCGGCCGGCGCGATATCGGCCTTTTTACTAACCGAACCCGATGTGGGCTCCGATCCGGCGCGCATGGCATCGA | (SEQ ID NO. 517) |
| | CGGCGACGCCGATCGATGACCGCCAGGCTTACCACCTT | |
| Clone Rv379 | :::::::::::::Rv379SP6.seq::::::::::::: | |
| | CTCAAGCTTGCGCGACTCGACAAGCATTCTTGACAGTTGTTTTGGCTCGGCATGGTTAGCCAAGGTTCTGCGGTCCCACCAGATCATCTTGGTCCGGTAGCGCTCG | (SEQ ID NO. 518) |
| | TCCGGGTATGCTGCCGCCGGGATTCTCGCTGCTATTACTCCCCCCGAAGAACGCCACCGGTCCAGCGC | |
| | :::::::::::::Rv379T7.seq::::::::::::: | |
| | GCNAGGCGGTATAGCTTCCCGTCGTACCGGCGACCGCCAGCCGAGAAGCTCGTTTTCCCAGTGTTGCTGGGGATTCTCACGCTGCTGCTGAGTGCGTGCCAGACCG | (SEQ ID NO. 519) |
| | CTTCCGCTTCGGGTTACAACGAGCCGCGGGGCTACGATCGTGCGACGCTGAAGTTGGTGTTCTCCATGGACTTGGGGATGT | |
| Clone Rv37 | :::::::::::::Rv37SP6.seq::::::::::::: | |
| | GTGTGGAACCGTGAGCGGATAACAATTTCACACAGGAAACAGCTNTGACCTTGATTACGCCAAGCTATTTAGGTGAGGCTATATTAATACTCAAGATTGCGGTCGA | (SEQ ID NO. 520) |
| | GCACATCGGCCCAAGAACCGCCGAAGGCACGGCGGAACGCCTGCGGCACATGGGGCGACGACCAGCGGGTCGGACTTCTGGGCTGTCCAGCCGGATCGCGCCGTCG | |
| | CGA | |
| | :::::::::::::Rv37T7.seq::::::::::::: | |
| | CACTGTCAGTACATATGCGCCGCTCCTCCTCATCGCTGCGCTCGGCATCGTCGCCGGCGGTCATGGCGTCACCCTACCCAAGCCGAACGCGAAACGAGAACGTGTT | (SEQ ID NO. 521) |
| | CCATTATTAGGGTGTGAGCACCAATACCAGATTGCTCACCAGGAACTCACGCAGCACCGGGACGGATGTCAGCCACCACGCCCATCTGGGGTGGTAGCGGGGAAAT | |
| | ACGGCTAACGCGGCTCCGGTGCCGGCAGCCCAGCGCAGACCCTCGGCGGCGGACACGGCAAACAACGACGACCCATAGTTGTTCTTTGCCGGATGGCCGTGTTTGC | |
| | GGACATATCGGGCGGCGGCGCGGGCGCCGCCGAGGTAGTGGCTGAGGCCCATCTCGTGCCCGCCGAATGGCCCCAGCCAAACCGTGTA | |
| Clone Rv381 | :::::::::::::Rv381SP6.seq::::::::::::: | |
| | CTCAAGCTTTTACGGTGATCGCGCATCACCTGGTTCATGAACTGGAAGCAGCGCAGCGCTTCCTTTTCGGCCGCAACATGAGCCANCCTCTCGTCGGCGGTCGGGT | (SEQ ID NO. 522) |
| | GCAGGTGCTCGGGCAGCTCGGCCGCGACAGCCGCCTGACCCTGAAACCAGCTTCCATATCCCGCGACNAACGAC | |
| | :::::::::::::Rv381T7.seq::::::::::::: | |
| | CTCAGAAGCCGCTAGCTGGTAGAGTCGCTGACCGGTGCACGTGGCGNCAATGTGCGCTGCCGGTTCGCG | (SEQ ID NO. 523) |
| Clone Rv382 | :::::::::::::Rv382SP6.seq::::::::::::: | |
| | CTCAAGCTTGCGCTCATCAAGCGCGAACAGCAGGGCGGTCGGCTGGTCGCCATGACGGGTGACGGGACCAATGACGCACCCGCGCTCGCGCAAGCCGATGTCGGGG | (SEQ ID NO. 524) |
| | TGGCNATNAATACCGGCACCCAGGCGGCCCGGGAAGCCGGCAACATGGTCNATCTCCACTCC | |
| | :::::::::::::Rv382T7.seq::::::::::::: | |
| | ACTTCTATTTCGACTGGTGTGCTGTGGCGCGATCCGACTGCCGGCGTGGTCAAGGCCGGCCAGTTGTGGGATNCCACAGGCAC | (SEQ ID NO. 525) |
| Clone Rv383 | :::::::::::::Rv383SP6.seq::::::::::::: | |
| | GCTTGTCGTATTCCGTGGCACTGTCAGACATATGCGCCGCTCCTCCTCATCGCTGCGCTCGGCATCGTCGCCGGCGGTCATGGCGTCACCCTACCCAAGCCGAACG | (SEQ ID NO. 526) |
| | CGAAACGAGAACGTGTTCCATTATTAGGGTGTGAGCACCAATACCAGATTGCTCACCAGGAACTCAC | |
| | :::::::::::::Rv383T7.seq::::::::::::: | |
| | CGATATTCGTCGGCCGCGTTGTCTCGACTGGGTCGCGT | (SEQ ID NO. 527) |
| Clone Rv384 | :::::::::::::Rv384SP6.seq::::::::::::: | |
| | GACCTCGGCCACCAAGCCGGACGCGACCGTCGAGGTGGCGATCCGGCTTGGCGTCGACCCGCGTAAGGCAGACCAGATGGTCCGCGGCACGGCCANCCTGCCACAC | (SEQ ID NO. 528) |
| | GGCACTGGTAAGACTGCCCGCGTCGCGGCN | |
| | :::::::::::::Rv384T7.seq::::::::::::: | |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | CCGGAAGTCTAGGGGACGACCTACTCAGCGCAAAATGTCGCTAATGTGAGTCCGCCCCACCAGGGCAGATCAACCCATGTCGATGATGACCTACCCGGATACCGGA | (SEQ ID NO. 529) |
| | TTGGCGGT | |
| Clone Rv385 | ::::::::::::Rv385SP6.seq:::::::::::: | |
| | AGCTTCAGTTCCTCCACGACGCGTTCCCAAATGAATTTCCCGATCCCACAATCTCGGTTCAGATACAGGTCGCCATACCCCTTACTTCGGNAACGCTGGGCGGATT | (SEQ ID NO. 530) |
| | GGCCCTGCCGCTG | |
| | ::::::::::::Rv385T7.seq:::::::::::: | |
| | CCGCCTACGGGTCGAACATGCATCCCGAGACCGATGCTCGAGCGCGCACCCCACTCGCCGATGGCCGGAACCGGCTGGTTACCCGGGTGGCGGCTGACC | (SEQ ID NO. 531) |
| Clone Rv386 | ::::::::::::Rv386SP6.seq:::::::::::: | |
| | GCGGCTGGTTACGACTCCCTGTTTGTGATGGACCACTTCTACCAACTGCCCATGTTGGGGACGCCCGACCAGCCGATGCTGGAGGCCTACACGGCCCTTGGTGCGC | (SEQ ID NO. 532) |
| | TGGCCACGGCGACCGAGCGGCTGCAACTGGGCGCNTTGGTNACCGGCAATACCTACCGCAGCCCGACCCTGCTGGCAAAGATCATCACCACGCTCGACGTGGTTAG | |
| | CGCCGGTCGAGCGATCCTCGGCATTGGAGCCGGTTGGTTTGAGCTGGAACACCGCCAGCTCGGCTTCGAGTTCGGCACTTTCAGTGACCGGTTCAN | |
| | ::::::::::::Rv386T7.seq:::::::::::: | |
| | GCCTTTCCGCACAATCTGTACCCCAGGACCNTCTAAAAAATCGAATACGACGGCGTCGCCGACTTTCCGCGGTACCCGCTCAACTTTGTGTCGACCCTCAACGCCA | (SEQ ID NO. 533) |
| | TTGCCGGCACCTACTACGTGCACTCCAACTACTTCATCCTGACGCCGGAACAAATTGACGCAGCGGTTCCGCTGACCANTNNTGTCGGTCCCACGATGACCCAGTA | |
| | CTACATCATTCGCACGGAGAACCTGCCGCTGCTAGAGCCACTGCGATCGGTGCCGATCGTGGGGAACCCACTGGCGAACCTGGTTCAACCAAACTTGAAGGTGATT | |
| | GTTAACCTGG | |
| Clone Rv387 | ::::::::::::Rv387T7.seq:::::::::::: | |
| | GCAGACCAACAAGATGCATCGGGATCATACGCCGTCAACTACCCGGCCAACGGTGATTTCTTGGCCGCCGCCCAC | (SEQ ID NO. 534) |
| Clone Rv388 | ::::::::::::Rv388SP6.seq:::::::::::: | |
| | CTCAAGCTTGCCAAAGAGACCTCGTCCACCAAGCNGGACGCGACCGTCNAGGTGGCGATCCGGCTTGGCGTCCACCCGCGTAAGGCANACCANATGGTTCGCGGCA | (SEQ ID NO. 535) |
| | CGGTCAACCTGCCACACGGCACTGGTAANACTGCCCGCGTCGCGGTATTCGCGGTTGGTGAAAAGGCCGATGCTGCCGTTGCCGCGGGGGCGGATGTTGTCGGGAG | |
| | TGACAATCTGATCGANAGGATTCAGGGCGGCTGGCTGGAATTCGATGCCGCGATCGCGACACCGGATCAGATGGCCAAAGTCGGTCNCATCGCTCGGGTGCTGGGT | |
| | C | |
| | ::::::::::::Rv388T7.seq:::::::::::: | |
| | CCACGGCGTGGATCAAGGTACCGGCCGGGATGTTGCGCAATGGCAGGTTGTTGCCCGGCTTGATGTCGGCGTTAGCGCCGGATTCCACCACATCCCCTTGCGAAAG | (SEQ ID NO. 536) |
| | TCCGTTGGGTGCAATGATGTAGCGCTTCTCCCCATCGAGATAGTGGAGCAACGCAATCCGTGCGGTACGGTTCGGGTCNTACTCGATGTGCGCGACCTTGGCGTTG | |
| | ACACCATCTTTGTCATTGCGGCGAAAGTCGATCATCCGGTAAGCGCGCTTATGACCGCCGCCTTTGTGCCGGGTGGTAATCCGGCCATGCGCGTTGCGTC | |
| Clone Rv389 | ::::::::::::Rv389SP6.seq:::::::::::: | |
| | GGCGGCTGCGTCGGCGAGATGATCGCCCGGTGCCACCCCGATCCGTGCCTCGGTCAGCGCCAACGTGCTTTCCGGTCCGGCGACCACCATGTCGCATGCGCCGAC | (SEQ ID NO. 537) |
| | ::::::::::::Rv389T7.seq:::::::::::: | |
| | GCAATCGCCTTGGCGGTCGCCGGGTTGTCACCGGTGATCATCNCGGNGCGGATGCTCATNCGGCGCATTTCGTCNAATCGTTCCCGTATGCCCACCTTGACGATGT | (SEQ ID NO. 538) |
| | CCTTCATATGGACCACGCCGATGGCCCNCGCGCTNCTG | |
| Clone Rv38 | ::::::::::::Rv38SP6.seq:::::::::::: | |
| | CCGGCTCGTATGTTGTGTGGAATTGTGAGCGGATAACAATTTCACACAGGAAACAGCTATGACCATGATTACGCCAAGCTATTTAGGTGACACTATAGAATACTCA | (SEQ ID NO. 539) |
| | AGCTTCCACATCGGTATGCCAAAGCATTGCGCCGCTATCGATTTCGCGCTGGCATCGCCAAGGTGGACTTCTTGCTCAGCGACGAGATCCCGTGGTCGGATCCGCG | |
| | GCTGCGGCGGGCTGCGACCCTGCATCTCGGCGGCACCCGTGACCAGATGGCGCGCGCCGAGGCAGACGTCGCGGCGGGACGCCACGCCGACTGGCCGATGGTGCTG | |
| | GCCGCGTGTCCGCACGTCGCCGACCCCGGCCGCATCGACGAAACCGGCCGCCGTCCGTTCTGGACCTATGCCCACGTGCCGTCGGGGTCCACGCTCGACGCGACCG | |
| | AGACCGT | |
| | ::::::::::::Rv38T7.seq:::::::::::: | |
| | CGCGTCCACCGCAGCGTGAGATTGGTGGCGCCATTCGTCGTGGTGTAGCTGCTGTTGGCGGCGTCGCCGTATTGTGCGGGCCAGCCTTGTGCGGGGGCCGCTTCTA | (SEQ ID NO. 540) |
| | CCCACGAGTCGGCACTTCCGCAACCGCCCAGCTCGACCGCGATTACGGCGGCCGCAACGGCCGCCGGAAGGCGTCTCGCAAGCGCCTTATCCTTTCGCAGGTTCCC | |
| | AGATCCTTCCGCTACGTGGGTCGCTCATCGGCGGGCCCGGCCGAATGAGTACAGGTGAGGGTAACCGCTACAAATGAAGTTGGTCAGTGCTGGCCAACTGTGTAAT | |
| | GGTTGCCCGGCTCGGGTCACCACGTACATTCTGGCAAGGCGGGCGAGATTCGGTTCCTCGCGTCCTTGGCCGGTGGCGGTTCCCGGTTGTCCGTGGGCGTGTCGTG | |
| | TACGTGGTGTAAGTGTCGTGAACTCCTCAGTTTGGGCT | |

TABLE 3-continued

End sequences of the polynucleotide inserts cloned in the named recombinant
BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081
repetitive sequence (Insertion element)
The character <<->> denotes an uncertain base residue.

Clone Rv390 ::::::::::::Rv390SP6.seq:::::::::::
CTCAAGCTTGCGCTGGATCTGGCGGCTGAGCCTGTTCTTGGGCAACATGCCGAGGGATCGCCTTTTCCACCACGCGGTCGGGGTGGCGTTGCATTAGCTCACCGAT (SEQ ID NO. 541)
GGTGCGCTTGTGCAGGCCGCCGGGATACCCCGAGTGCCGGTAAACCATCTTGTGCTGCAGTTTGTCGCCGCTGATGGCGACCTTGTCGGCGTTGATCACNATGACN
AAGTCACCGCCATCGACATTGGGGGCGAACGTCGGCTTGTGCTTGCCGCGCAGCAGGTTGGCCGCCGCGACGGCAAGGCGGCCAANCACCACGTC
::::::::::::Rv390T7.seq::::::::::::
TTTGGGATGGGCAAAAAGGCGAAGCNCCGCGTGGCCACGAACGCCGGGAGGGACAATCTCGGGCGGCTAGGGCTTCTCGCGGGAAGGCCCGAACGTACGGCGTTTC (SEQ ID NO. 542)
AACACGTCGCGTCGCCCTCCGACCGCGAACATTCGGGGATGGCAGCAACCTGGTAGCACCCTGGCCGGGCGATGATCTGCAGCGTCGCCGCGGGTAGTCGCCGCCC
GGGCGGCTACAGTCTGAAACGCGATGACCATCGATGTGTGGATGCAGCATCCGACGCAACGGTTCCTACACGGCGATATGTTCGCCTCGCTGCGCCGGTGGACCGG
TGGGTCTATCCCGGA
Clone Rv391 ::::::::::::Rv391SP6.seq::::::::::::
CTCAAGCTTCGTCATAAGACCATGGTGCGCTTTCTTTCACCCGTCCANAGTCGGGGGCATCCGCACCGGCTCGCATCGCATCATCCTCCCACGACGGGCCGCTCAT (SEQ ID NO. 543)
CAGCTTGGGCCATTTCAATGTACTTGATACCCCGCGCTGCGGGTAGGCCACTGCNACAATTCAAACACGGTGTCACACGGTGAATANTGTCNANATGGGCTCTGAT
CAACCGTCNCAAACCCGGTTTC
::::::::::::Rv391T7.seq::::::::::::
GAATTCTGCGTGCACCGCTATGGGTTGCAGCAGCGGCTGGCGCCGCACACCCCACTGGCCCGGGTGTTTTCGCCCCGAACCCGGATCATGGTGAGCGAAAAGGAGA (SEQ ID NO. 544)
TTCGCCTGTTCGATGCTGGGATTCGCCACCGCGAGGCCATCGACCGATTACTCGCCACCGGGGTGCGAGAGGTGCCGCAGTCCCGCTCCGTCGACGTCTCCGACGA
TCCATCCGGCTTCCGCCGTCGGGTGGCGGTAGCCGTCGATGAAATCGCTGCCGGCCGCTACCACAAGGTGATTCTGTCCCGTTGTGTCGAAGTGCCTTTCGCGATC
GACTTTCCGTTGACCTACCGGCTGGGGCGTCTGCACAACACCCCGGTGAGGTCGTTTTTGTTGCAGTTGGGCGGAATCCGTGCTCTGGGTTACAGCCCCGAACTCG
TCNCGGCGGTGCGCGC
Clone Rv392 ::::::::::::Rv392SP6.seq::::::::::::
GCAGTTGGGAATCGCTCTGCAGCAAAGGANTATTCTGCGCGACGTTCGAGAGGACTNTTTGAATGGACGGATCTACCTGCCGCGCGACGAGCTGGACCGATTAGGC (SEQ ID NO. 545)
GTACNCCTCCGCCTGGACGACTCCGGGGCACTCGATGACCCCGACGGACGGCTCGCGGCACTGCTGCGGTTCANTGCCNACCGCGCCGCANACTGGTATTCGCTGG
GACTGCGGCTGATTCCACACCTCGACCGCCGCAGCGCTGCCTGCTGTGCGGCCATGTCTGGCATCTACCGCCGTCNGCTCGCCTTGATCAGACCATCGCCGGCGGT
CGTCTACCATCGGCGAATCTCTCTGTTCGGGACTGAANAANGCCCAAGTGGCGGCGGCAGCACTGGNCTCTTCGGTAACCTGCNGACCGCCCATTGGACCGCTACC
G
::::::::::::Rv392T7.seq::::::::::::
TTGATCTGGACGTCTGAGACGGTGATCGGNCCGAACCTGAATTGTCCGGTAATGCCCAGCGCAGAAAGCANGGTGGTGGCCGGGGCGGTGAANCCGGCGTCGGCGG (SEQ ID NO. 546)
CACCGTCGAAGTCGATGTGGATTGCCGGAATGGGGATGTCCGGCACGGCGAAGCCGTAGTTCGCTTGTCCCGTGAGGCCCANGTGGATGGGGGGAAGGATCGTGGT
GTCCGGGATGATAATGGGGCCGATGCCGCCGGTTGAAGTCCAGTGGATCGGGAATTCGGGAATCGTGATGCCGACGTTCAGGCCGAACAGGCCCTCCAAGTTGCCT
CGCCACNAGATGCCGTTGCTGAAGTTGCCCGACATGAGGGCGCCGGTGTCCACATTGCCCGAATTGGCGACGCCGGTGTTGGC
Clone Rv393 ::::::::::::Rv393SP6.seq::::::::::::
CACGTAGGCGCCGTCCATAAATNACTCCGCCGCGCTTCGCACATCCTCGTANCGATCCTTGGCGAGCAGGTCAACCGGGCGCTGCCCGTCNAGGAGCCGGTTTTTG (SEQ ID NO. 547)
GCGTGCAGCCACTGGCCGACACCTCGGGGGGTAAGCGAATCCGAGAGCAGGAGGACNAGGTCACGAANCTGCGCCAGCCGGTCGTACCGCTCAGGGCGGATGTCGC
CGGTCCGCCACCCGCGTACCGCCCGATCGGACACCTGTATGACCGCGGCGACNTCGACCTGGGTGACGCCGAAGGGTTTCAGGGCATCNACNATCTCGCTGGCCTC
GACCGCCCGGTCCAGGGTGACCGCCATCGTGGTTCCTCCGCAACTTCCGGTTCTACTACCGTAAACGCTACCG
::::::::::::Rv393T7.seq::::::::::::
CGGGGAACGGTCCTCGCACACCTGGTTCGTGTTGCGGGAATTACTCGGACANCAAAACGTCAAGAACTACGACGGCAGTNGGACAGAANACGGCTCCCTGGTGGGC (SEQ ID NO. 548)
GCCCCGATCGAGTTGGGAAGCTGATATGTGCTCTGGACCCAAGCAAGGACTGACATTGCCGGCCAGCGTCGACCTGGAAAAAGAAACGGTGATCACCGGCCGCGTA
GTGGACGGTGACGGCCAGGCCGTGGGCGGCGCGTTTCGTGCGGCTGCTGGGACNCCTCCGACGAGTTCACCGCCGGGAGGTCGTCGCGTCGGCCACCGGGCGAATT
TCCGGTTCTTCGCCGCGCCCCGGGATCCTGGGACCGCNGGCGCGCGCTGTT
Clone Rv396 ::::::::::::Rv396SP6.seq::::::::::::
CTCAAGCTTTGTCCGACAAGCGTTCCCGGGCGGTCAGCAAGCGAACGTCGGTTGGCCCACTGCGGGTCGATATTGCCGCCAGGGA (SEQ ID NO. 549)
::::::::::::Rv396T7.seq::::::::::::
CGTCAGCACGGCGACGTCGCGNTACGCCGAGCAGTTACACAATCGCTCTGCAGCAAACCAATATTCTGCGCGACGTTCGAGAGGACTTCTTGATTGGACTG (SEQ ID NO. 550)

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| Clone Rv39 | :::::::::::::Rv39SP6.seq::::::::::::: | |
| | CTGCATCCGGCTCGTATGTTGTGTGGAATTGTGAGCGGATAACAATTTCACACAGGAAACAGCTATGACCATGATTACGCCAAGCTATTTAGGTGACACTATAGAA | (SEQ ID NO. 551) |
| | TACTCAAGCTTCGCGCAGCGGCGGGTTGACCCGGTTCACGCCGTCATAGCTGGCCAATCTGGCATCGTCGATCANCATGTGGTGGGGGGTGACCTCGGCGGTGATC | |
| | GAAATACCCTGGTCCTTATCCCATTTCAGGATTTCGACGGTGCCCGCGGCCGACGCGTGACAGATGTGCACCCGGGCGCCGGCGTCACGGGCCAGCAAGGCGTCGC | |
| | GGGCGACGATCGATTCCTCGGCGGCCCGCGGCCATCCCGCCAGGCCCAGCCGCGCCGCCATGGGTCCCTCGTGCGCGACGGCGCCGACCGTCAGCCGGGGCTCCTC | |
| | GGCGTGCTGGGCGATCAGCACGCCCAAACCGGTG | |
| | :::::::::::::Rv39T7.seq::::::::::::: | |
| | CCGACGCGCACTACGTGCTGGTGTCCACCCGCGACCCGCACCGGCACGAGCTACGCAGCTACCGCATCGTCGATGGCGCTGTCACCGAGGAACCTGTCAATGTCGT | (SEQ ID NO. 552) |
| | CGAGCAGTACTGAACCGTTCCGAGAAAGGCCAGCATGAACGTCACCGTATCCATTCCGACCATCCTGCGGCCCCACACCGGCGGCCAGAAGAGTGTCTCGGCCAGC | |
| | GGCGATACCTTGGGTGCCGTCATCAGCGACCTGGAGGCCAGCTATTCGGGCATTTCCGAGCGCCTGATGGACCCGTCTTCCCCAGGTAAGTTGCACCGCTTCGTGA | |
| | ACATCTACGTCAACGACGAAGACGTGCGGTTCTCCGGCGGCTTGGCCACCGCGATCGCTGACGGTGACTCGGTCACCATCCTCCCCGCCGTGGCCGGTGGGTGAGC | |
| | GGACACATGACACGATACGACTCACTGTTGCATGCCTTG | |
| Clone Rv3 | :::::::::::::Rv3SP6.seq::::::::::::: | |
| | TGCTTCCGGCTCGTATGTTGTGTGGAATTGTGAGCGGATAACAATTTCACACAGGAAACAGCTATGACCATGATTACGCCAAGCTATTTAGGTGACACTATAGAAT | (SEQ ID NO. 553) |
| | ACTCAAGCTTGCCGGGAGGGTGCATGGCCGACTCGGATTTACCCACCAAGGGGCGCCAACGCGGTGTCCGCGCCGTCGAGCTGAACGTTGCTGCCCGCCTGGAGAA | |
| | CCTGGCGCTGCTGCGCACCCTGGTCGGCGCCATCGGCACCTTCGAGGACCTGGATTTCGACGCCGTGGCCGACCTGAGGTTGGCGGTGGACGANGTGTGCACCCGG | |
| | TTGATTCGCTCGGCCTTGCCGGATGCCACCCTGCGCCTGGTGGTCGATCCGCGAAAAGACGAAGTTGTGGTGGAGGCTTCTGCTGCCTGCGACACCCACGACGTGG | |
| | TGGCACGGGCAGCTTTAGCTGGCATTCCT | |
| | :::::::::::::Rv3T7.seq::::::::::::: | |
| | GGAAACACCGNCGCCGTCGTGGCCACCAACACCGCGACCAGCACCGTGACCCGGACCGGGGTGCCGCGCGAACCGGTCTTGGCCAATTGCCGCGGCACCAAGCCGT | (SEQ ID NO. 554) |
| | CGCGCGCCATGGCGAACAGCACGCGGCATTGCCCGAGCATCAACACCATCACCACCGTGGTAAGCCCGGCCAGCGCGCCGACGGAGATGATGCCGCTGGCCCAGTA | |
| | CACCCCGTTGGCCTGGAACGCGGTGGCCAGATTTGCCGGCCCGCGGCCCGGTACGGTCCGCAGTTGGGTGTATGGAACCATGCCCGACAGCACCACCGATACCGCG | |
| | ACGTAGAGAAGGGTCACGACCCCCAGCGACGCGAGAATCCCTCGAGGGACGTCTCGTTGAGGACGCTTGGTCTCCTCGGCCATGGTGGCCACGATGTCAAACCCGA | |
| | TAAACGCGAAGAACACGATCGATGCCCGGCCAGCACGCCGTA | |
| Clone Rv40 | :::::::::::::Rv40SP6.seq::::::::::::: | |
| | CCTGCTTCCGGCTCGTATGTTGTGTGGAATTGTGAGCGGATAACAATTTCACACAGGAAACAGCTATGACCATGATTACGCCAAGCTATTTAGGTGACACTATAGA | (SEQ ID NO. 555) |
| | ATACTCAAGCTTGTCCTCGGGCGTGGCCTCGGCCAAGAAATCGTCGACGCCGGCCTCCTGTGCAATCGCCTTGGCGGTCGCCGGGTTGTCACCGGTGATCATCACG | |
| | GTGCGGATGCTCATTCGGCGCATTTCGTCGAAGCGTTCCCGTATGCCCACCTTGACGATGTCCTTCAGATGGACGACGCCGATGGCCCGCGCGCTGCTGTTATCGG | |
| | TCCATTCCGCAACGACTAGGGGTGTCCCCCCGCCGGAGCTGATGCCGTCGACAATGGCACCCACCTCCTCAGTGGGGTGGCCACCGTGATCGCAAAACCACTTCAT | |
| | CACCGCAGCCGCGGCACCTTGCGGATCCGAACGGATGCGCTC | |
| | :::::::::::::Rv40T7.seq::::::::::::: | |
| | TTCGTTCGATGGCGCCGCCCCGGCTACGGTTTGACCTGTGGGTGTCGAATTGGGGTCAAATTCCGAGGTCGGCGCGCTAAGAGTGGTCATCCTGCACCGCCCGGGG | (SEQ ID NO. 556) |
| | GCCGAACTGCGCCGGCTCACACCGCGCAACACCGACCAGCTGCTGTTCGACGGCCTGCCCTGGGTATCCCGCGCGCATGACGAGCACGACGAATTCGCCGAGCTGC | |
| | TGGCTTCCCGCGGTGCGGAAGTGCTGTTGCTGTCGGACCTGTTGACTGAGGCACTACATCACAGCGGGGCCGCCCGCATGCAGGGGATCGCCGCTGCCGTCGACGC | |
| | ACCGCGGCTGGGACTGCCGCTGGCGCAAGAACTTTCGGCCTACCTGCGTATCTCGACCCAAGCANGTTGGCGCATGTGCTGACGCCGGCATGACTTCAACGAACTC | |
| | CCNTCCGACACGCCGAACGAAGTGTCGTTGGTGTTGCGTATGC | |
| Clone Rv412 | :::::::::::::Rv412SP6.seq::::::::::::: | |
| | GCGGCGAGTGTGGTGGGTGCCGAACACGAATCCAACGACGCACTGGCGGAGAGATACCACTTGCTGTACTGGAAGCACGTGCTGATGATCTCCCGTGGAATGTGCC | (SEQ ID NO. 557) |
| | TCGCCGCCGTCTATCGAAAACAGTGAGCATGCTGCG | |
| | :::::::::::::Rv412T7.seq::::::::::::: | |
| | CAACCGCGCTCGGCGCGTCTGGGCCTTCCGCCGGCTCCGCCGACAATTCTATCTCTGGATCAGCGGGGCTCTCCGGGCCGGCCTCCGCGAACTCAACAGGCCGCGC | (SEQ ID NO. 558) |
| | CTTCCGGCCGAAACATTCCCTAGCCATATATGATCGCACCTCGATACACGATCTGGCGGCAACACCGCAAAGCGTCCGACGGGCCCAACCTCCGCAATTCAGGTAT | |
| | CCGGG | |
| Clone Rv413 | :::::::::::::Rv413SP6.seq::::::::::::: | |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | GAAGGTCGGCGAAGGTGTGGCTGGNTGCCGATCACGAATCCAATGATGCAGTGGTCGGAAGATATTAGCCACTTGCTGTTCTGGAGACAGGTGCTGATGATCTCCC | (SEQ ID NO. 559) |
| | GTGGAATGTCCCTCGACTCCGTCTATCGAAATCTGTGAACA | |
| | :::::::::::::Rv413T7.seq::::::::::::: | |
| | TCCTGCGCTCTGGGCCATTCTCGGGTCTGCCGACAATTCTATCTCTGGATCTGTGGGGCTCTCTTGGCCGGCCTCNGCGATCTCTTCANGGCGCGCCTTCCGGCCG | (SEQ ID NO. 560) |
| | AAACATTCCCTATCCATATATGATCGCACCTCTATACACCGTTTGGCGGCAACACCGCAAAGTGTCTGTCG | |
| Clone Rv414 | :::::::::::::Rv414SP6.seq:::::::::::: | |
| | AGCTTTACGCTGGCGTATCAGCGTTGGGGCCGCTGCCATTTCGGTCGCCCAACGCGTTGCCAGCTCCCTGCGCTGTCAGGGCTTGCGCGCCAAACTGGCCACCGCA | (SEQ ID NO. 561) |
| | ACAAACTTGGCTGAGCTTGATC | |
| | :::::::::::::Rv414T7.seq::::::::::::: | |
| | CTCTATCTGGCGTCACATTCGCAATCTTTAGATTGCAGATATCGATAAAATCACCCGCGCGACAAGACCGCCATGTCATCCTTTCGATGTTATTTCGCCGGCCTGG | (SEQ ID NO. 562) |
| | GGAAAGCGCAACGACGTTGCCTACACGTTCCGCCGT | |
| Clone Rv415 | :::::::::::::Rv415SP6.seq:::::::::::: | |
| | AGCTTTNCCTTGCATCTGCACCCCGATCCACGTCAGCCACGTCGGCGTTCTCCACCAAGAAGTTGCGGGCATTCTCCTTGCCCTGGCCGAGCTGCTCGCCCTCGTA | (SEQ ID NO. 563) |
| | GGTGAACCAGGCACCCGACTTGCGGATGAGGCCCTGATCCACACCCATGTCGATCAGCGAGCCCTCCCTGCTGATTCCCTTGCCGTAGAGGATGTCGAACTCGGCC | |
| | TGCTTGAAGGGGGGCGAACAGTTGTGCACGACAACCCCTTCGGCGACGAGGGTGTGCAGTTCCTCGACCTCGAGGTCGAACGTTCGTGCCCGCCGCGTTGGCAGCA | |
| | CTTCTCGGATCACGGAATAGCGGANTTCTTCCGCCAGCATGTCGTGCAGGAATTTGTCATCCAGGGCATCCGCGAGCGCCTGCACGCG | |
| | :::::::::::::Rv415T7.seq::::::::::::: | |
| | ACTGTCNAGGGAATGCTTCGCAGCATCTACCTGCAGTCGCTTGTGCATAAGCGGACGGCCCNACCTGTTCGTGTTCCGGGACACCAGACGCGGGAGCACCGGCAGT | (SEQ ID NO. 564) |
| | ACGGCGAAAGGTTTGAGCGGAAGGAGTTGCGCAAATCGGGGCGCCCCAACACCCGTCCGCAAGACGCGGTCAACGACCTGTTTCAGGCGATCAGGGTCACCGACTC | |
| | ACCTGCACTGAGAACAAGCGATCTGCTGATCTGCCAGAAGATGGACATGAATGTCCACGGCAAGCCTGATGGCCTGCCGCTCTTCCGGGAATGTTTGGC | |
| Clone Rv416 | :::::::::::::Rv416SP6.seq::::::::::::: | |
| | TGAATTATGATCCCGACACAACTGCATCANTTTAGCCGCGTCGNGATGCTATCCGCCGACGGTTTGGANCNGGTCCGTGTCGTTCGTGTTGATCTCACCCGAAGTT | (SEQ ID NO. 565) |
| | GTGTCCGCCGCCGCCGGGGATCTAGCGAACGTGGGATCGACAATCAGCGCCGCCAACAAGGCGGCAGCGGCTGCGACCACGCAGGTGCTGGCCGCGGGCGCCGATN | |
| | AGGTGTCAGCGCGCATCGCGGCGCTGTTTGGTATGTACGGCCTGNAATATCCGGCGATCAGTGCGCAAGTTGCCGCGTATCACCANCAGTCCGTGCAG | |
| | :::::::::::::Rv416T7.seq::::::::::::: | |
| | AACGGGGACCNCAAGAAACCATTCAANAACGAGGGGTCGTCACCAACGTCGAAACCGACGGTTGCCAGCCGGCCCACGATATTGCGTGCTCGAGGGTCCGCTGTAC | (SEQ ID NO. 566) |
| | CCTCACCGAACGTGAGTCCCACACCGCGGAGGCGGGCGACTCTGGCGTCGTTAGCAGCCGAGCTCAAGGTGTCCCGCACCACTGTCTCGAATGCTTTTAACCGACC | |
| | GGATCAGCTCTCCGCCGATCTACGTGAACGAGTGCTTGCCACGGCCAAGCGACTGGGCTATGCCGGACCGGATCCGGTGGCGCGATCGTTGCGGACCCGCAAAGCC | |
| | GGTGCGGT | |
| Clone Rv417 | :::::::::::::Rv417SP6.seq::::::::::::: | |
| | AGCTTTGGAGCCNCNCCGANCCNCCGGTACGCCCCGCCACCGCCGTACCCGGCACCCGACCCCTTTGAGCCGTTCGCCGTGGCCGCGGTGGANCTGGCCGACGAGG | (SEQ ID NO. 567) |
| | GACTGATCGTGCTGGGCAAAGTGGTCGATGGCACGCTGGCCGCCGATCTGAAGGTCGGCATGGAGATGGAGCTGACGACCATGCCGCTGTTCGCCGACNACGACGG | |
| | TGTGCAGCGCATCGTCTACGCGTGGCGGATCCCATCGCGCGCCGGCGACNATGCANAGCGCANCGATGCTGAGGAGCGGCGCCGATGAGGATGAGCGCGCCGGAAC | |
| | CCGTTTACNTCCTGGGTGCCGGTATGCACCCGTGGGGGAAATGGGGTAATGACTTC | |
| | :::::::::::::Rv417T7.seq::::::::::::: | |
| | TTCTCNCATCGTTCGTACTNNGATGGGACGCTGCTGCCCGAGGCGATCCTGGCCAACCGGCTCTCGCCGGCGCTGACCTTCGGCGGGGCGAACCTGAACTTCTTTC | (SEQ ID NO. 568) |
| | CGATGGGCGCTTGGGCCAAACGTACCGGGGCTATCTTCATTCGGCGTCAGACGAAAGATATTCCCGTCTACCGCTTCGTATTACGTGCTTACGCCGCGCAGCTGGT | |
| | GCAAAACCATGTCAACCTCACCTGGTCGATCGAAGGGGGTCGGACCAGAACGGGCAAGCTACGGCCACCGGTGTTCGGGATCCTGCGTTACATCACCGATGCGGTC | |
| | GACGAAATCGACGGTCCCGAAGTGTATTTGGTGCCGACCTCGATCGTGTACGAACAGCTGCACGAAGTGGAAGCCATGACCACCGAAGCCTATGGCGCCGTGAA | |
| Clone Rv418 | :::::::::::::Rv418SP6.seq::::::::::::: | |
| | TTCTTCCGGGTACCGCTGATCGGCGGCACCATCACGCACCCGGTGCAGGGCGAGGCGGCCGCCGGTGTGGTGTTGCTACGGCCGGCCAGCCCGGGTACCGGTGTGA | (SEQ ID NO. 569) |
| | TCGCCGGTGGTGCGGCCCGCGCGGTGCTGGAATGTGCGGGGGTGCACGACATCTTGGCCAAGTCGCTGGGCAGTGACAACGCGATCAATGTGGTGCACGCCACCGT | |
| | GGCCGCGCTCAAGCTGCTGCACCGTCCGGAGGAGGTGGCGGCGCGCCGCGGTTTGCCAATAGAAGACGTCCCCCCGGCCGGGATGCTG | |
| | :::::::::::::Rv418T7.seq::::::::::::: | |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | GTCGAAAGTGACCATCTCTACCTTGAGTGCCATACCGCCCGACCCTATGCCTCGGATAGCTCGGCGGAAAGAAACGCTTGCAGTGCCGCCGAATAGGCGGCTACGT<br>CGTGAGCGCCCATCAACTCTCGCGCGGAGTGCATCGCCAGCTGGGCGGCGCCGACGTCGACCGTGGGGATTCCGGTGCGCGCCGCGGCCAACGGCCCGATCGTCGA<br>CCCGCACGGCAGATCGGCGCGATGTTCGTAACGCTGCATAGGCACTCCCGCGCGCTGGCAGGCCAGTTGCGAAACGCCCCCGCCGGGTGCCTTCCGTCGGTTGGCT<br>TTACCGCAAATTTGGGGTTGCCCCT | (SEQ ID NO. 570) |
| Clone Rv419 | :::::::::::::Rv419SP6.seq:::::::::::: | |
| | AAAGCCACGGAAACGATTGCCTACTGCCGAATCGGGGAACGGTCCTCGCACACCTGGTTCGTGTTGCGGGAATTACTCGGACACCAAAACGTCAAGAACTACGACG<br>GCAGTTGGACAGAATACGGCTCCCTGGTGGGCGCCCCGATCGAGTTGGGAAACTGATATGTGCTCTGGACCCAAGCAAGGACTGACATTGCCGGCCAGCGTCTACC<br>TGGAAAAA | (SEQ ID NO. 571) |
| | :::::::::::::Rv419T7.seq:::::::::::: | |
| | TTTCGCCACCGCNAGGTCGTGCGCGTTCCAGAAAAGCGTGGTTTCGCCGGGCGCGAGGATTCGACGGTCCAACTGACCAGCCGGTCCCGCCACCCGTTAGGCAGGA<br>TCGCGGTGTCTATATGTTCGCCCTCGGCATAAACGCCATTGCTGCGGTGAAAATCGGACATCTCGCCGATTGCCACGTCTACATGATCCGCTTTGTCCCGCGCCGG<br>GTCGTTGACAAACGCGATGTCNGCCTCCTGGGAAGCGGTGGC | (SEQ ID NO. 572) |
| Clone Rv41 | :::::::::::::Rv14SP6.seq:::::::::::: | |
| | TCGCCAAGTGGATTCGTGCTCACCNACGAGATCCGTGGTCGGATCCGCNGCTGCGGCGGGCTGCGACCCTGCATCTCGGCGGCACCCGTGACCAAATGGCGCGCGC<br>CGAAGCAGACGTCTCGGCGGGACGCCACGCCGACTGGCCGATGGTGCTGGCCGCGTGTCCGCNCGTCNCCGACCCCGGCCGCATCNACCAAACCGGCCGCCGTCCG<br>TTCTGGACCTATCCCACGTGCCNTCGGGGTCCACGCTCGACGCGACCGANAACGTAACCAGCGTCCTCGANCGGTTCGCCCCCGGCTTCCGTGACATCGTGGTGGC<br>GGCCGCGCCGT | (SEQ ID NO. 573) |
| | :::::::::::::Rv41T7.seq:::::::::::: | |
| | GTACCGTCACCATGATCGCCCCCATCGGCATCGGTGAGCTGATAGATCCCAGCCGGTTTCGCCAACCCCGGAGCGATCTTGGCGCGCTGCTNGTNGTCNCTGANAC<br>NTAGCCACCAACAGAGCCCGGTGTGCGACAAGANGACTGATCGGATCTCTCCGGACACNTCGAGGGGGTCNTCAGGAGNCCGGGCGCCACCCCGAGGTAAGCCTCC<br>GCCCAGCCTCACACCGCGACCGGGTATCNCAAGTCGCGCAATAANCCCACCACCTCCTCGGACCCCACGTTGTATGCGGCTGGGT | (SEQ ID NO. 574) |
| Clone Rv42 | :::::::::::::Rv42SP6.seq:::::::::::: | |
| | ATACTCAAGCTTAGACCTCACTGATGTGGCGGGACGCGGGAGATAACCGCGGTTCGAGCCGTTCAACAGTGGTGGTTCCCACACCAGTTGTTTGCCTTTGCGAAGT<br>AAAGCGATTCGATTTGCTCGAAAAGAGGGCTGGCTGCTCGTGAGGGACATCCATGGCCGATACCTCAGCGATCTCAACGGTCAAGCGACTGCATGTTTGGCGCAAG<br>GTATCGCTAAGCATAGGTTCGTGACGGATTTGACAGCAAGAGCTTTCCAAAGATTGCTGTCCACATANTGATTCGCATCTCTACACCTCTTCGCCGGTGCTGTCAA<br>GAGCCATTCGAATCAGTTATCTCGCTCGTGCTTGGAANAAATTTTCCCAGCCTGCGTTGGACAAACCGCGTCGCCAAAGCGGT | (SEQ ID NO. 575) |
| | :::::::::::::Rv42T7.seq:::::::::::: | |
| | AGCTTCCCGAGAAACAGTGCATTCCCTAAGCAGCCCGTTGTCACGCCGATGAGTGAAGAGTGCACGCAATCGCCGGAATCCGGCAAAGCCCTGCACAAGCGAAATC<br>AACCCGGAGGCTGACAAGGCAACGTCGGTGATCCGTACCGCCTGGTTGGACAAACGGCAGAAGGCGGCCTCGTCCGGTCCATCTACGCCGAGCACACTGGTGATAG<br>CGCGCATCGGCATCGGTGCGGCCACGGTGGAGACGACGTCCGCGGGCGTCTGGGTCAGTAACCCGCCGACCAGTTCTCGGGCAAGCTGGTCGACCATCGGGCGCCA<br>CGTCTCCAACGCGCCACGCGCCATACCTGGTGCCAGTTGCTTGCGCATCCGGGTGTGCGCCGGCGGATCGGACGTCGCAGAAACGCAGCCACCCCGTGAGAAGTGA<br>CCCACGGCGCTGGACACGTGTCTGGTTAC | (SEQ ID NO. 576) |
| Clone Rv43 | :::::::::::::Rv43SP6.seq:::::::::::: | |
| | CGGCCGGGATGTGCGCAATGGCAGGTTGTCGCCCGGCTTGATGTCGGCGTTAGCGCCGGATTCCACCACATCCCCTTGCGAAAGTCCGTTGGGTGCAATGATGTAN<br>CGCTTCTCCCCATCGAGATAGTGGAGCAACGCAATCCGTGCGGTACGGTTCGGGTCGTACTCGATGTGCGCGACCTTGGCGTTGACACCATCTTTGTCATGGCGGC<br>GAAAGTCGATCATCCGGTAAGCGCGCTTATGACCGCCGCCTTTGTGCCNGGTGGTAATCCGGCCATGCGCGTTGCGTCCACCGCGACCGTGCAGCGGGCGCACCAG<br>CGACNTCTCCGGGGTTGACCGGGTGATCTCGGCGAAATCAGATACGCTGGCGCCGCGACGACCAGGCGTCGTGGGCTTGTACTTGCGAATTGCCATGGTCTAATCA<br>GGTCTTTCTCTCACCTCTCGTCGCCGGGCTAGGGCGCATTGCCTGCTCCT | (SEQ ID NO. 577) |
| | :::::::::::::Rv43T7.seq:::::::::::: | |
| | TAGCGGTGTAACCAACTCCCGGGTCACCACCCGCAAACCTCTTGCGGCAACAGCACCGTCGACGCGTCAACCGGGCTGCCCGGAATCCTGTGGATGGGCATCGAGT<br>GCATGGTCACGACGTCCCCGACGCGGCCGGTGGCAACGACAAGTGGCCCGGATGCACCACAAATGACGGCCGCACACCGGTGGGGACGGCCAGCACGAGAGCCGTG<br>TCGCCGAAGTCGACGCTAATGCCGTAGGCATTGGCCGTCACAACAGGCGACGCCCCGCGTACCACCGAGTCCACGGNGGTTGGGCGGTCTCCTCGGCCAACCAGGC<br>GTGAACCCGGCGGATCCGAATGCAGCAAGACCCGTGGGC | (SEQ ID NO. 578) |
| Clone Rv44 | :::::::::::::Rv44-2ndSP6.seq:::::::::::: | |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

CCATTGGTCGGTGTGCGCATACCANTACNACGCGCCGGGCACCTGACGCGGCGGCCGCAACCATTCGGTGGCCATCGCCATCGTCTGCCACCCGGTCAACGGACGC (SEQ ID NO. 579)
ACCTTCTCCTGGCCGACCTAGTGCGCCCACCCGCCGCCGTTGCGTCCCATCGATCCGGTCAACATGAGCAGCGCCAACACCGAGCGGTACATGACATCTGCTGTGG
AACCAGTGACANATTCCGCCGCCCATGATGATCNTCGACCGTCCTCCGGATTCGGTC
:::::::::::::Rv44-2ndT7.seq:::::::::::::
GCCGGCCTGGTCAAAGGGGCGTCCGAAGGANCCGGGCTGGGTAACAAGTTCCTGGCTCATATCCGCGAATGCGACGCCATTTGTCAGGTGGTGCGGGTGTTCGTCG (SEQ ID NO. 580)
ACGACNACGTGACTCATGTCACCGGACGGGTCGATCCCCAGTCCGACATTGAGGTCGTCGAGACCGAGCTGATCCTGGCAGATCTGCAAACCCTGGAGCGGGCCAC
GGGCCGGCTGGAGAANGAAGCNGCACCAACAAGGCGCGCAAGCCGGTCTACGACCCGGC
Clone Rv45 :::::::::::::Rv45SP6.seq:::::::::::::
GATCCACTGACCACGATGACATATCGAAATGCTCGACGATTCCGATGGCGATCAAGGCCACGATGCCCTGGCCGTTGGGCGGTATCTGGTGGATGGTGTACCCGCG (SEQ ID NO. 581)
GTAGGTTCCCGTGATCGTGTCGACCCAGTCCACGCGATGGGCGGCGAGGTCGTCGGCACGCATCACCCCGCCGTNTGCCGCCGAGTGCGCCTCGAGTTTGGCGGCC
AGCTCTCCCCGGTAGAACTCTCACCGTTGGTCGCCGCGATCTTCTCTANCGTCGCCGCGTGGTCAGGAAAGGTAAACAGCTCACCGGGTTTCGGCGCTCGTCCGCC
GGGCATGAACGCATCTGCGAATCCGGGCTGGGATGCGAACAACGGACCTGTGCCG
:::::::::::::Rv45T7.seq:::::::::::::
TCTACTGCCGAATCGGGGAACGGTCCTCGCCCACCNGGTTCGTGTTGCCGGAATTACTCAGGACACCGAAACGTCGAGAACTACGAGCGGAGTTGGACANAATACC (SEQ ID NO. 582)
GCTCCCNGGTGGGCGCCCCCATCGANTTGGGAAGCNGAAATGTGCTCTGGACCCCACCCAAGAATGACATTGCCGGCCGCCCTCCAACTGGAAATAGAAACNGTGA
TCACCCGCCGCGTTCTTGGAAGGAATGGCATGCCCTGGGCCGGGCGTTCCTTCCGCTGCCGGACTCCTCCCACCAATTCACCGCCGAAGGCGTCCCGTCTGC
Clone Rv46 :::::::::::::Rv46SP6.seq:::::::::::::
ATACTCAAGCTTCTGTCACCGAAATCCCGCATGGGATAACGGGTTTAGATTTCGACAACGGGACCGTGTTTCTCAACAAGCCGGTCATCAGCTGGGCCGGCGACAA (SEQ ID NO. 583)
CGGTATCTACTTCACCCGCTTTCGCCCGT
:::::::::::::Rv46T7.seq:::::::::::::
CTGGCTCAAGCGCTCGGCGCGCAGGTGAACTCGGACCGGCTCGACGTCGCCGAACGCGAGGCGGTGCTGGCCCACGCCGACGCCGTCGTCGCACATATCGGCACCG (SEQ ID NO. 584)
TGCACAAGTCTACAACAACGCCGGCATCGCGTACAACGGCAACGTCGACAAGTCGGAGTTCAAGGACATCGAGCGCATCATCGACGTCGACTTCTGGGGCGTCCTC
CACGGGCCC
Clone Rv47 :::::::::::::Rv47SP6.seq:::::::::::::
CCGCCCTCCGCATTATGGGTCAAGAACCATCGGGTCGGACTTCTGGGCTTCCAACGCTCGCGCCGTCCCN (SEQ ID NO. 585)
:::::::::::::Rv47T7.seq:::::::::::::
CCGTGGCACTGTCAGACATATGCGCCGCTCCTCCTCATCGCTGCGCTCGGCATCGTCGCCGGCGGTCATGGCGTCACCCTACCCAAGCCGAACGCGAAACGAGAAC (SEQ ID NO. 586)
GTGTTCCATTATTAGGGTGTGAGCACCAATACCAGATTGCTCACCAGGAACTCACGCAGCACCGGGACGGATGTCGGCCACCACGCCCATCTGGGGTGGTAGCGGG
GAAATACCGCTAACGCGGCTCCGGTGCCG
Clone Rv48 :::::::::::::Rv48SP6.seq:::::::::::::
TACTCAAGCTTGTCCAAATATCGAAGCGTCGGGTCGCGAGGCTCGGTCGGCAGCTCCAGCAAAACCCGCTCCACCCCTAGATGCCGGTATCCCTCAAGGTCTTTAT (SEQ ID NO. 587)
CCGCCGCTTCACCCCACTGGCACACGGTCACCGGCACGTCGCCCCCGGCCATGGCGCGCAACCGCTGAAGCGGACCCGACAGCCGCTGCGGTGATGGACTGATCGC
GATCCACCCGGCATTGAGCCGGGCTATCCGCGGGAAGTTCGCCGGTCCCCCGCCCACATACAGCGGAGGATAGGGCTTTGTCACCGGCTTCGGCCAGCAGTAGATC
GGATCGAAGTCCACATATGTCCCATGGAATTCCGCCTGCTCCTGCGTTCAGATCTCGATTATCGCGCGCAACCGCTCATCGATCACACGTCCGCGCACCGCAGGGT
CCACACCATGGTTGGCGACTTCTTCGCGCAACCAGCCACACCCACGCCGAAACGAAACCGTCCCTGCG
:::::::::::::Rv48T7.seq:::::::::::::
CAGGCATCGAAGCTTGGCCAACTCCTCATCGGACTTGAAGGTGCCGTCCTCGTTGGCGGCCCTGCTCCACGGCACGTTGATGGCACCAGGAATGTGTCCGGGCCGC (SEQ ID NO. 588)
TGGCTTTGTTCCTGCGGCAGGTGCGCGGGGGCCAGGATCTTGCCGGAGAACTCGTCGGGAGAGCGCACGTCGATGAGGTTCTTGACGTTGATGGCCGCCAGGACCT
CGTCGCGGAATGCCCGAATCGTGTTATCCGGCGGGGANGCGGTGTAGGAAGTCACCGGCCGGCTGACCGGGTCGCTGGACAGCGGGCGTCCGTCGAGCTCC
Clone Rv49 :::::::::::::Rv49SP6.seq:::::::::::::
ATACTCAAGCTTCAAAACAGGCCTGTTGTGGGCGCACCCGGCTCGCCGAGTTCTGCACGCACCGCCTCAAGTGCGGCCCGCACCGCCGGCATCTCCCGGTCACGCA (SEQ ID NO. 589)
GGGCCGCGGCCCGCGCCGCAGCGACGGCGTGTTCGCGCAGTTCGCCGTCAATGATGCTGACCTGATCGGCCACCCGGGCGGTCTCGGCGTCGTCCCGTTCACTAAT
CGCGGTGCTCAGCAGCGTCTCGACAGCCACCACCCGAGTGGAGACCAGATGCNCCACCACGGACCGCAGCGATGCCAGTCACCTCACCCGTCC
:::::::::::::Rv49T7.seq:::::::::::::

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | CAGGCATGCAAGCTTTGCAGTTGCTGAGTAATGTCGGCCAACGTCACCACAATCGCGATGAATTCAATCATGCCGCCCAGGGCGGCCAACCCAATGGTGGCCGCGA<br>GCGGCAGCTCGATCGCAGCGCGGAGGTTGCCGGCCGCCAGTTGATTCACGAACAGGGTGAGGTCATAGGCGGGCAGGATAGTGACGAAGGCAAGACCTAGATCTGC<br>CGTCGGAAGAAGAATCGAGTATCCGGTCGACACAACGGAAGCGAAAGTGTCCGCGATGTTGATGAGCGTCGCCGGTTGTGGCGGCGGTGGCGGCGGTAGCACCGTC<br>CGCACATACCGCGGGAACGCGGGCATCCGAATTTGGGGCAGGGTGTTCAAGGCGGCTGGCAACTCACCATGAATCT | (SEQ ID NO. 590) |
| Clone Rv4 | :::::::::::::Rv4SP6.seq::::::::::::: | |
| | CCGGCTCGTATGTTGTGTGGAATTGTGACCGGATAACAATTTCACACAGGAAACAGCTATGACCATGATTACGCCAAGCTATTTAGGTGACACTATAGAATACTCA<br>AGCTTGGCCGCAGGGCCGAGTCGATTGGTCGCGGTCGCCTCGACAGTTAGCTTATGCAATGCTAACTTCGGGGCAAAGTTCAGGCGGATCGGCCGATGGCGGGCGT<br>AGGTGAAGGAGACAGCGGAGGCGTGGAGCGTGATGACATTGGCATGGTGGCCGCTTCCCCCGTCGCGTCTCGGGTAAATGGCAAGGTAGACGCTGACGTCGTCGGT<br>CGATTTGCCACCTGCTGCCGTGCCCTGGGCATCGCGGTTTACCAGCGTAAACGTCCGCCGGACCTGGCTGCCGCCCGGTCTGGTTTCGCCGCGCTGACCCGCGTCG<br>CCCATGACAGTGCGACCCTGNACCGGGCTGGCC | (SEQ ID NO. 591) |
| | :::::::::::::Rv4T7.seq::::::::::::: | |
| | GTGTGCTGTCAATTCAGAGCTGAGCCTGATGCACTCAACTTACTGAGCATGCTAACGCTGGTCGTGCGGGTCTTGTTCCCGCGTGTCGGCAGGGCACACGCTCGGG<br>GCGTAGCTGGGAGAGGCCCCGGTCAAGCCCGGAGAGCAGTGCTCAGTCCGCCAGCTTGACCGACTTTCGATGAGAACGCGCTTCTCGCCGTATTGAACTGGCGTGC<br>TGACGGTCGCTGAGCAGCGCTCGCCGAGTGCGGCCGCTGATTCTTTCATCGAGCCAGGAGGCGCATTCGTGTTCGGCCGCCTGCGGGTCGGCCCCATCGTCGACGC<br>GATCCGTCACCCACTCCTCGATCAGGTCTGCCTCATCGAACGGGCCAACGGTGCTGTCGGAGTAAGTGTGCGTGGGCACGCGAGCCGGGTGCTGTGGTACACCCAC<br>CGTTGCATGAACAA | (SEQ ID NO. 592) |
| Clone Rv50 | :::::::::::::Rv50SP6.seq::::::::::::: | |
| | ATACTCAAGCTTCACCAGGCGCCGGCGGGCCGCGGCGCCAAGCCAGGCAGCCGCGCTCGGCGCGTCGGGGCCTTCCGCCGGCTCGGCCGACAGTTCGATCTCTGGA<br>TCGGCGGGGCTCTCCGGGCCGGCCTCGGCGACCTCAGCGGGCCGCGCCTTCCGGCCGAACCATTCCCTAGCCATAGATAACCGCACCTCAATGCACGGTTTGGCGG<br>CAACCCGG | (SEQ ID NO. 593) |
| | :::::::::::::Rv50T7.seq::::::::::::: | |
| | AGCTTCCGTCACGACCCGCCCTCGCCGGTGCCGGCGCCATCGGTCATCGGATCTCATGACGACGTCACGTAGGCCCGCTAGCCGCGAGCGGGCGCGGTCAACTGGC<br>GAGGCGGCGGCGACGTGACTGAGCTGGCCGAGCTGGACCGGTTCACCGCGGAACTACCGTTCTCGCTCGACGACTTTCAGCAGCGGGCTTGCAGCGCGCTGGAACG<br>CGGCCACGGTGTTGCTGGTGTGCGCGCCGACCGGCGCTGGCAAGACGGTGGTCG | (SEQ ID NO. 594) |
| Clone Rv51 | :::::::::::::Rv51SP6.seq::::::::::::: | |
| | ATACTCAAGCTTGCCGGGACCGCGGAACAGAACCGGCGGTTCCTACCGCGGTGTGCGGCCGGCGCGATATCGGCCTCCCGACTAACCGAACCCGATGTGGGCTCC | (SEQ ID NO. 595) |
| | :::::::::::::Rv51T7.seq::::::::::::: | |
| | ACGTTGGCTCTGCCGGAACGTATTTCCAGCGGCACGCATTCGGCGTGGGTGCCGGGCGCCGAGTTGCGTCGCTGGGATCACGCAGCAGTCGCCGGCGGCTGCCGTC<br>GGGCTATGAATTGCACCGAGCCGGAAAATCCNCAC | (SEQ ID NO. 596) |
| Clone Rv52 | :::::::::::::Rv52SP6.seq::::::::::::: | |
| | ATACTCAAGCTTGTCGTATTCCGTGGCACTGTCAGACATATGCGCCGCTCCTCCTCATCGCTGCGCTCGGCATCGTCGCCGGCGGTCATGGCGTCACCCTACCCAA<br>GCCGAACGCGAAACGAGAACGTGTTCCATTATTAGGGTGTGAGCACCAATACCAGATTGCTCACCAGGAACTCACGCAGCACCGGGACGGATGTCAGCCACCACCC<br>CCATCTGGGGTGGTAGCGGGGA | (SEQ ID NO. 597) |
| | :::::::::::::Rv52T7.seq::::::::::::: | |
| | CGTTGGTAGCCCGATATGCATAGTGTATCTTACTGAACATGATTTCCATTATGGAGCCCGGGGTGCCGGCAGCGCGAACGGTGCGCCGTCAGACGCGGGCGGCACT<br>GACCAGGGTGTTGCGGGCGAACATCGGCCCGGCTTCGGATTCCGGTCCGGGTACCGGGCGACCCACCGCTTCGAGGTC | (SEQ ID NO. 598) |
| Clone Rv53 | :::::::::::::Rv53SP6.seq::::::::::::: | |
| | ATACTCAAGCTTGGCCAACTCCTCATCGGACTTGAAGGTGCCGTCCTCGTTGGCGGCCCTGCTCCACGGCACGTTGATGGCACCAGGAATGTGTCCGGGCCGCTGG<br>CTTTGTTCCTGCGGCAGGTGCGCGGGGGCCATGATCTTGCCGGAAAACTCGTCGGGAGAGCGCACGTCGATGAGGTTCTTGACGTTGATGGCCGCCAGGACCTCGT<br>CGCGGAATGCCCGAATCGTGTTATCCGGCGGGGAGGCGGTGTATGAGGTCACCGGCCGGCTGACCGGGTCGCTGGACAGCGGGCGTCCGTCCAGCTCCCACTTCTT<br>GCGGGCGCCGTCCAACNACTTGACTTCTCCTGG | (SEQ ID NO. 599) |
| | :::::::::::::Rv53T7.seq::::::::::::: | |
| | ATATCTTAAGCGTCGGGTCCCGAGGCTCGGTCGGCAGCTCCAGCAAAACCCGCTCCACCCCTAGATGCCGGTATCCCTCAAGGTCTTTAGCCGCCGCTTCACCCCA<br>CTGGCACACGGTCACCGGCACGTCGCCCCCGGCCATGGCGCGCAACCGCTGAAGCGGACCCGACAGCCGCTGCGGTGATGGACTGATCGCGATCCACCCGGCATTG | (SEQ ID NO. 600) |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | AGCCGGGCTATCCGCGGGAAGTTCGCCGGTCCCCCGCCCACATACAGCGGAGGATAGGGCTTTGTCACCGGCTTCGGCCAGCAGTAGATCGGATCGAAGTCCACAT | |
| | ATGTCCCATGGAATTCCGCCTGCTCCTGCGTCCAGATCTCGATTATCGCGCGCAACCGCTCATCGATCACACGTCCGCGCACCGCAGGGTCCACACCATGGTTGGC | |
| | GACTTCTTCGCGCA | |
| Clone Rv54 | :::::::::::::Rv54SP6.seq::::::::::::: | |
| | ATACTCAAGCTTGTCGCGGTAAACCCGCAGCAGGGCGGTGGGTGCGGTGTCAAAAACAACCACACTTCTTTGCGGTTCGGTGATCTCGACACCGGCCGCGAGCCGA | (SEQ ID NO. 601) |
| | CCACCATGCGCGCGTAAATCGGCGATCAGCGCGTCGGCTATCGCCTGGGTGCCGCCCACCGGAATCGGCCAGCCGACCGAATGGGCCAGCGTTGCCAGCATCAGTC | |
| | CGGCGCCGGCCGACACCAGTGACGGCAACGGTGAAATCGCGTGGGCGGCAACGCCGGTGAACAACGCGCGGGCATCCTCGCCCGCCAGCGACCGCCAGGCAGGGGT | |
| | GCCCTGGGCCAGCATCCGCAGCCCGAGACGCAGGACCGAGCCCAGTGCAGTAGGCAAAGACCGCTTGTCGGAGACATGAACTCCACGACCGT | |
| | :::::::::::::Rv54T7.seq::::::::::::: | |
| | AGCTTATTGAACCGCGGGTCGCAGGCAAAGTGGACCTCATAACGACTCGGGTCCAGCGACCGCGCCAACACGAACGGCCGGACGACGTGGGCCAGGGTCGCGGCCT | (SEQ ID NO. 602) |
| | CCCCTACAAACAGGATCCGTTGCCTGCGAGCGACAGGCTCCGGTGCGGCGTTGGGCGCCGTGCTCGTCCCAGCGTCCGGTCCCGGGTCGCCGGCGACGCTTGTTTC | |
| | CTCCATACTCGCCCCCTAATCTCGAGGCAGCCCGTACCCGCAGGCAACCTCCCAAAAATGCAATCCCCCAAAATGCAATGCGTCGAGCTATTTCTCACACCGACCG | |
| | CTAGTTGCGGATCAGAAATCCGTTGGGCGCGGAAGTCCAGCCGAATTTGTTCTCCCGCTCCGCATCATGCTTGTAATCGTTTGGAAATTCATCCTCATATGCCTCG | |
| | ATCGCTTCATAGGGTCCAGGCCAAACCGGGCA | |
| Clone Rv55 | :::::::::::::Rv55SP6.seq::::::::::::: | |
| | CTTCCGGCTCGTATGTTGTGTGGAATTGTGAGCGGATAACAATTTCACACAGGAAACAGCTATGACCATGATTACGCCAAGCTATTTAGGTGACACTATAGAATAC | (SEQ ID NO. 603) |
| | TCAAGCTTGGCCACCTCGCGGTGTGTGGTGGAACCCATCTGAGCAGTGTGCCAAACCGGGGCAGACAGCTCCCAATTGACGTGAGCCCGCTCACTTGCTGGGTAAG | |
| | CGTCG | |
| | :::::::::::::Rv55T7.seq::::::::::::: | |
| | TAGCGCCCCCTCCCGGGCGGAGCTCCACGGCGTGGATCAAGGTACCGGCCGGGATGTTGCGCAATGGCAGGTTGTTGCCCGGCTTGATGTCGGCGTTAGCGCCGGA | (SEQ ID NO. 604) |
| | TTCCACCACATCCCCTTGCGAAAGTCCGTTGGGTGCAATGATGTAGCGCTTCTCCCCATCGAGATAGTGGAGCAACGCAATCCGTGCGGTACGGTTCGGGTCGTAC | |
| | TCGATGTGCGCGACCTTGGCGTTGACACCATCTTTGTCATTGCGGCGAAAGTCGATCATCCGGTAAGCGCGCTTATGACCGCCGCCTTTGTGCCGGGTGGTAATCC | |
| | GGCCATGCGCGTTGCGTCCACCGCGACCGTGCAGCGGGCGCACCAGCGACTTCTCCGGGGTTGACCGGGTGATCTCGGCGAAATCAGATACGCTGGCGCCGCGACG | |
| | ACCAAGCGTCGTGGGCTTGTTCTTGCGAATTGCATGTCTAATCAGGTCTTTCTC | |
| Clone Rv56 | :::::::::::::Rv56SP6.seq::::::::::::: | |
| | TGAAACTAATATAATACTCAAGCTTGCCAAAGAAGACCTCGTCGACCAAGCAGGACGCGACCGTCGAGGTGGCGATCCGGCTTGGCGTCGACCCGCGTAAGGCAAAC | (SEQ ID NO. 605) |
| | CAGATGGTTCGCGGCACGGTCAACCTGCCACACGGCACTGGTAAGACTGCCCGCGTCGCGGTATTCGCGGTTGGTGAAAAGGCCGATGCTGCCGTTGCCGCGGGGGG | |
| | CGGATGTTGTCGGGAGTGACGATCTGATCGAAAGGATTCAGGGCGGCTGGCTGGAATTCGATGCCGCGATCGCGACACCGGATCAGATGGCCAAAGTCGGTCGCAT | |
| | CGCTCGGGTGCTGGGTCCGCGCGGCCTGATGCCCAACCCGAAAACCGGCACCGTCACCGCCGACGTCGCCAAGGCCGTCGCGGACATCAAGGGCGGCAAGATCAAC | |
| | TTCCGGGTTGACAAGCAGGCCAACCTGCACTTCTC | |
| | :::::::::::::Rv56T7.seq::::::::::::: | |
| | GCTGAGCTCCACGGCGTGGATCAAGGTACCGGCCGGGATGTTGCGCAATGGCAGGTTGTTGCCCGGCTTGATGTCGGCGTTAGCGCCGGATTCCACCACATCCCCT | (SEQ ID NO. 606) |
| | TGCGAAAGTCCGTTGGGTGCAATGATGTAGCGCTTCTCCCCATCGAGATAGTGGAGCAACGCAATCCGTGCGGTACGGTTCGGGTCGTACTCGATGTGCGCGACCT | |
| | TGGCGTTGACACCATCTTTGTCATTGCGGCGAAAGTCGATCATCCGGTAAGCGCGCTTATGACCGCCGCCTTTGTGCCGGGTGGTAATCCGGCCATGCGCGTTGCG | |
| | TCCACCGCGACCGTGCAGCGGGCGCACCAGCGACTTCTCCGGGGTTGACCGGGTGATCTCGGCGAAATCAGATACGCTGGCGCCGCGACGACCAGGCGTCGTGGGC | |
| | TTGTACTTGCGAATTGCCATGTCTAATCAGGTCTTTCTCT | |
| Clone Rv57 | :::::::::::::Rv57SP6.seq::::::::::::: | |
| | ATACTCAAGCTTGTTGGTGACCTCGCCGGCGAACAGTTCTCGCACGATTTCCGGATTAGCGGGACTGGTCACCAGTTGGGTATGCGGGAAGGCGCTGACGTTCGCC | (SEQ ID NO. 607) |
| | GCGATTAGCTGTTTGATGGACGCGGCGGTGATGTCCTGATCACGGAACTGGCTGTAATAGCCCAGGGTCGCCACGCTTCCATCCGGGCCCGGACCCGGC | |
| | :::::::::::::Rv57T7.seq::::::::::::: | |
| | GATGATCGCCGGTGCCACCCCGATCCGTGCCTCGGTCAGCGCGAACGTGCTTTCCGGTCCGGCGACCACCATGTCGCACGCACCGACCAGGCCGAACCCGCCGGCC | (SEQ ID NO. 608) |
| | CGCACATGCCCGTTGATGGCGCCGACCACCGGCAGCGGCGACTCGACGATGGCGCGCAACAGCGCCGTCATTTCCCGCGCCCGCGCCACCGCCATCCGGTACGGAT | |
| | CACCACCACCTCCGCCGGCCTCGCTGAGGTCC | |
| Clone Rv58 | :::::::::::::Rv58SP6.seq::::::::::::: | |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

ATACTCAAGCTTGCCGCAATCGAAACCAACCTGTTTGTGCCGCAAGAAATTACGCCGTGGCCCGGCGCCGATCAAGAAACGCCCCGGCGCGCGGCGGTGTCGTCGT (SEQ ID NO. 609)
ATGGCATGACGGGCACCAATGTGCACGCCATTGTCGAGCAGGCACCGGTGCCAGCCCCCGAATCCGGTGCACCAGGCGACACCCCGGCCACACCCGGTATCGACGG
CGCGCTGCTGTTCGCGCTGTCGGCCAGCTCGCAGGACGCGCTGCGGCAAACCGCCGCGCGGCTGGCCGATTGGGTCT
:::::::::::::Rv58T7.seq::::::::::::
TTGGCGGGTTGGCCACANCANCCCGCCGGTGACGGCGACGATGCTGGGCTGGTTGCGGCCCTGCGCCACCGCGGCTTGCATGCTGGTTGGCTGTCTTGGGACGATC (SEQ ID NO. 610)
CCGAAATAGTCCACGCGGATCTGGTGATTTTGCGGGCTACCCGCGATTACCCCGCGCGGCTCGACGAGTTTTTGGCCTGGACTACCCGCGTGGCCAATCTGCTGAA
CTCGCGGCCGGTGGTGGCCTGGAATGTCCANCGCCGTTCACCTACGTGACCTTGATGGGATCCGGGGGNT Clone Rv59
:::::::::::::Rv59SP6.seq::::::::::::
NCGTGGACACCGGTGTCGANCGCCACCAGCCGCATGTCTGCANGTCNATTCCGTCCTCGGCAACATCTTGAATGCCGAGCAGCGCCTGGGCGTGATCGGCAACCGG (SEQ ID NO. 611)
GGATGACCGCTCGCCGATCCGCTCGACAATCCCGGCGGCACGTGACATGCCGGCGGACGGCTCGACGAGCTGGAACTTCAGCGACGACGATCCGGAATTGATCACC
AGCACGGTGCTACTCATGGACCCCTGCGCCTGAATCCCGTGATGGCCACGGTGTTGACTATTCGTCGACAGTGCACCCGAGATAGTCTTCACGGCTGCGT
:::::::::::::Rv59T7.seq::::::::::::
CATGTATTGCCGTGCTCACGGCGCCACGCTCGATGGTTTCTCGAAGTCTCCGGGCTGGTGTACAGCTTCTCGTTGATCTCGTTCGCCACGCCGTCCTCTTCCCGCC (SEQ ID NO. 612)
GACGACCCGATCTCGATCTCCANAATGATCTTGGCGGCCGCCGCCGCCTTGAGCAGCTCCTGGGCGATGGCCAGGTTCTCATCGATGGGCACTGCCGACCGTCCCA
CATGTGCGACGGAACAAAGATGTCACCTTGCTCACGCGTGCGCNAGATCNCANAAGGGCCGGACATACTGTCNACTTGTCCTTGGGCAGTGGTCCGTGTCAGCCCA
CGTGACGGGTACTTGGCGCGATAACGTGGTG Clone Rv5
:::::::::::::Rv5SP6.seq::::::::::::
GCCACCACGACCCGGCCGTAACTCTGCTCACGGAAATGCGGCCAGGCCGCGCGTAGCACGTGGTATCCGCCATAAAGGTGCACCTTAAGCACGGCGTCCCAATTCT (SEQ ID NO. 613)
CGAACGACATCTTGTGGAAGGTGCCGTCGCGCAAGATCCCGGCGTTGCTCACCACACCGTGCACGGCGCCGAATTCGTCAAGCGCGGTCTTGATGATGTTCGCTGC
GCCGTCCTCGGTGGCGACGCTGTCCTTAGTTGGCGACCGCCCGGCCCCCCTTGTCGCGAATCTCGGCGACGACCTCATCGGCCATCGCCGAACGGCGCCCGTGCCC
GTCGCGGGCGCCACCGAGGTCGTTGACCACGA
:::::::::::::Rv5T7.seq::::::::::::
CAGGCATGCAACCTTTGTCCACACGGCGTCTACTCCGTGCAAGGTCCGACCGCTTCCACGTCCCGCCGTGACGGTGCTCCATCTCCCTCAGCAACGCGTGAAGTGG (SEQ ID NO. 614)
TCCGATCCCGCGGCTTCAGG Clone Rv60
:::::::::::::Rv60SP6.seq::::::::::::
GTTGAGACGCAACCAGCGCACAACGACGATTTGGCGTAGCGGCGGACGTCTGCTCGATTCGATCACGTCGCGCTCGCATCGAGCATGGCCCGCGACGCTACACGAT (SEQ ID NO. 615)
CGCCGTCGTCGATGACACGACCGAGCCGTACGCCGGCCGTAAGCCGCGCCAGGATTCGGCGAAAAACGTCTACGTGGCGGGTGTACTGGGTGTCGAATGATTCGTG
GGGTGCGTATGCGTCCTGCAATCGTCGACATAGATCCGTCGCCGCATCGCGTCGACAACTCCGGGTGAGTGGAATACACTTGCCGATCACGCGACGTGCGCGGATC
GATGCCGACCGAAATACGACCACATGGCTCTTGTTGCNCAGTGTTGGCGGCATCAAATACCCTCAGTGCCGTCCGAC
:::::::::::::Rv60T7.seq::::::::::::
TTNCCGCCTTNACGCCTACTCCNAGACGATGCTCGACGCGTGTGAGCACACGGCGCTGCTGTAGACGGCACGGCGCAGCTGGATCGCGCTTGGTGCACCCAAGCCT (SEQ ID NO. 616)
CTACGCGCGTCGCTGCGTCGTCATCGGGTACCGAACATATTCCGGTCGTTGCGCAGAGTGTGCATGTGCGGCTCTTGTGAACGAACATAGCAAAGCGTATATGTCT
GTGGCGGCTCTGCAGATATCGCGATAATACGTATATACATAAGGTGGCGCGCGATCTATCGGTATATCCGTTATGGCGGACGTGCGTGAGCGTGAGTCGCGGCGCA
TCGCGCACTTCGCGATCGCGTGACTGGTCCTCGCGACTGCGCGCATGCGTAGC Clone Rv61
:::::::::::::Rv61SP6.seq::::::::::::
GGTGATGACGCACTTGCTTCGAATGAGTCATTGACTACTCCCGTGGTTGTCCTGCGATGGTGGAGTGCCGCGCAGCCTTGCCCGANGTCGCGATCGCGTCGCGGGC (SEQ ID NO. 617)
TTCGGGGAGCAGACTGACCTGCAGATGGAAGTCGTGCCACATGCCCGCGAACGGCGAGCTCGATGCTTGTTTTCGAAGNGCGCANGCGGTTTCGATCTTGTCCGCG
TCAACGCAGATCGGATCTCGCCGCGGTCTGCATGACGATGGGCGCAGGCCCGCTCATGTCCCGTAGACGGGGAGATACGGGCAGCCGCGGATCGAGACCTACGTAG
CGCGGCGCCCATCGTGCCATCGACGAAGAATGACGGATCGCGCAGCGCCGTCGCGTCGCTTCGATGTCACGCGAGATCGCCACGGCAGATCAGCGATGCGCGGGC
:::::::::::::Rv61T7.seq::::::::::::
CGGTACGCCGGCAACAAACGCCTTGTGACGAGCGCGTCCGAGCGGTCATCGGCCTCCACCGTCATGCACAGCTCCTTCTCCAGGTCTACGCCGACGTCGCGGTCCA (SEQ ID NO. 618)
CATTGGTGAGCTTGGCGAATGCCTCGGCAACCTCGTCGAAATGCGCCTCCGCGTCCGCATCGAAGGTCGCCATGTCAAAGATCAACTCGACGTAGTAGCTAGTTAC
CGCATCAGGTCAGTGTTTGCTGGCCTCGGAGTCCGGCCGAACAATGGCCATTTCCCGCGACTCTAGAATCCAGTCATCGTCTCGGTGACGACGCCTTGCCGATCAC
ATAGCTCGACCGGATCGGAGAGAATCTGGTTCTCGT TABLE 3-continued End sequences of the polynucleotide inserts cloned in the named recombinant
BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081
repetitive sequence (Insertion element)
The character <<->> denotes an uncertain base residue.

Clone Rv62 :::::::::::::Rv62SP6.seq:::::::::::::
ATACTCAAGCTTAAGCGCAGCAGTACCGGCGGTGCCTGGGCATCCCAGCAAAACGGGGAGCTCAACGAACGATTCCTGAACGAAGGGTCGTCCACCAACCTCCAAA (SEQ ID NO. 619)
CCGAACGGTTGCCAGCCCCGGC
:::::::::::::Rv62T7.seq:::::::::::::
GCAAGTCCGCTCAATGTGGTTGTGATCACANGACTACGTCGCCTCAATCAGCTCAAACGTCACCCCGTGGCGTGCTGCGCAGCATGAAGGTCGGCGCCCGCACGAT (SEQ ID NO. 620)
GTGGGCGAAGCAACAGGTAATAACTGGTCGGCATGGGTCAACCCTCATTGGGCCGTTGCGGATCGGGTGCACGCCCGGAGTGCCGGTCGAACTCAACACCGCCTTC
ACCGATCTTTTCGTCGAAAATGGCGGTCGTGTCGGGGTATACGTCCGCGATCCCACGAGGCGGAATCCGCTGAGCCGCACTGA Clone Rv63 :::::::::::::Rv63SP6.seq:::::::::::::
ATACTCAAGCTTCGCGCCCTCAAGCGGCTGAAGGTGGTTCCGGCGTNCCAACNGTCGGGCAACTCGCCGATGGGCATGGTGCTCGACNCCGTCCCGGTGATCCCGC (SEQ ID NO. 621)
CGGAGCTGCGCCCGATGGTGCAGCTCGACGGCGGCCGGTTCGCCNCGTCCGACTTGAACGACCTGTACCGCAGGGTGATCAACCGCNACNNANNGNTGAAAAGGCT
GATCGATCTGGGTGCGCCGGAAATCATCGTCAACAACNAGAANCGGATGCTGCNGGAATCCGTGGACGCGCTGTTCGACAATGGCCGCCGCGGCCGGCCCGTCACC
GGGCCGGGCAACCGTCCGCTCAAGTCGCTTTCCGATCTGCTCA
:::::::::::::Rv63T7.seq:::::::::::::
TGCGCATGGCAGTTGTTGCCGGCTTGAGTCGCGTTAGCGCGGATTCCACCACATCCCTTGCGAAGTCGTGGGTGCAATGATGTAGCGCTTCTCCCATCGAGATAGT (SEQ ID NO. 622)
GGAGCAACGCAATCCGTGCGTACGTTGGGTCGTACTCGAGTGCGCANCTTGGCGTTGACACCATCTTTGTCATTGCGGCGAAGTCGATCATCCGGTAAGCGCGCTT
ATCGACGCCGCCTCTGTGCCGGGTGGTAATCCGGCCATGCGCTTGCGTCCACCGCGACGTGCAGCGGGCGCACACCGACTTCTCCGGGTGACGGGTGATCTCGGCG
AATCAGAACCTGGCGCGCGACACAGCGTCGTGGCTGTACTTGC Clone Rv64 :::::::::::::Rv64SP6.seq:::::::::::::
TGGGTGATCAGATACTGGCTAGTTGGTCGGGTGGGGTGATCGAAGATCGCGGTGGCCGGCAGCGTTACTGCGGTGACGCTGTTAAGCGGTTACGTACTCCACGGCA (SEQ ID NO. 623)
CTCAANGAATTANATCCCGAATCGGCAAACCCTGGCCAGCGTCGAGTCCGCAGCGCCGTCGCGCCCCCCACCGCTGCGGCATGCTCACATACCACCTCGATCGCTG
CGGGAGTTGCTCGTCGGCCGACCGACCGGCCAGCCGGGCGGCAAACCGGAGGACCCAAGATTCAGCACCACCATCGCTAGCCCGATCTGGCCGCGCGTGG
:::::::::::::Rv64T7.seq:::::::::::::
TCGTAGCGGTTGCGACCANTCCGCGGACAGCTCCGCCACGCGACGGGTCGGGATCACCGCGGTCAAACCACCGAGCGGCGAGGATCTCTGGCCGTCGACGTGACCG (SEQ ID NO. 624)
CGCACGGCCGCGGTGATGGCCAGTCCCGACCGCCGTTCCACTTGGCGTACGCGCTGGATGTGTTGTGCCGCAACGGAATCCCACCTCAATTATGACCTCGTTGTGG
GCGAGCGCGGTATCGTACGCCCGACCAGGAATCGTCGATGCTATCTCACGTCACCGAAGGCCTCTCCCAGCACACCGCATCCAGAACGTGCACACNGTCGACATGT
CTCGGCGGATCCGCCTGCAGAACGAACGCCANGTGCGCTGTGCGACACGGGTCGCGATCACCGCTCGCACGCGGAGATCGGCACACGCGCAGCGCATCGATCATAA
TCTCTCGATGCGGTCTCCACCACCGAACAG Clone Rv65 :::::::::::::Rv65SP6.seq:::::::::::::
ATACTCAAGCTTCGCTGAGGTGGTGGGGCACGATCACGTCACCGCACCGCTGTCGGTGGCGCTGGATGCCGGCCGGATCAACCACGCGTACCTGTTCTCTGGGCCG (SEQ ID NO. 625)
CGTGGCTGCGGAAAGACGTCGTCAGCGCGTATCCTGGCNCGGTCGTTGAACTGTGCGCAGGGCCCTACCGCCAACCCGTGCGGGGTCTGCGAATCCTGCGTTTCGT
TGGCGCCCAACGCCCCCGGCAGCATCGACGTGGTAGAGCTGGATGCCGCCAGCCACGGCGGCGTGGACGACACCCGCGAGCTGCGGGACCGCGCGTTCTATGCGCC
GGTCCACTCACGGTACCGGGTATTTATCGTCGACGAGGCGCACATGGT
:::::::::::::Rv65T7.seq:::::::::::::
GCACTCACGCTGGTACAAGACCTTCACAAAATCTGAAATCCTGACCCGATACTTGAACCTGGTCTCGTTCGGCAATAACTCGTTCGGCGTGCAGGACGCGGCGCAA (SEQ ID NO. 626)
ACGTACTTCGGCATCAACGCGTCCGACCTGAATTGGCAGCAAGCGGCGCTGCTGGCCGGCATGGTGCAATCGACCAGCACGCTCAACCCGTACACCAACCCCGACG
GCGCGCTGGCCCGGCGGAACGTGGTCCTCGACACCATGATCGAGAACCTTCCCGGGGAGGCGGAGGCGTTGCGTGCCGCCAAGGCCGATCCGCTGGGGGTACTGCC
GCAGCCCAATGAGTTGCCGCGCGGCTGCATCGCGGCCGGCGACCG Clone Rv66 :::::::::::::Rv66SP6.seq:::::::::::::
ATACTCAAGCTTGTATAAAAAGATCGGTGAGCGCATCGATTCGCTCCGCCGGGTTTGCCGCTGCGGCGGCGGAGCTGCCGTGACCGTCTATTTGGGTGATCAGATA (SEQ ID NO. 627)
CTGGGCTAGTTCGGTCGGGGTGGGGTGATCGAAGATCGCGGTGGCCGGCAGCGTTACTGCGGTGACGGCTGTTAAGCGGTTACGTACCTCCACGGCACTCAAGGAA
TTAAATCCCGAATCGGCAAACGCCTGGCCAGCGTCGAATCCGGCAGCGCCGTCGCGCCCCAGCACCGCTGCGGCATGCTCACATACCACCTCCATCGCTGCGGCGA
ATTGCTCGTCGGCCGACCGACCGGCCAGCCGGGCGGCAAACCCGGAAGA
:::::::::::::Rv66T7.seq:::::::::::::
CCTCATCATATGCCGATAGAGCTCTACATATTCAGGAGATCACCATGGCTCGTGCGGTCGGGATCGACTCGGGACCACCAACTCCGTCGTCTCGGTTCTGGAANGT (SEQ ID NO. 628)

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | GGCGACCNGGTCGTCGTCGCCAACTCCGGAGGGCTCCAGGACCACCCGTCAATTGTCGCGTTCGCCCGCAACGGTGAGGTGCTGGTCNGCCAGCCCGCCAAGAACA | |
| | GGCAGTGACCAACGTCGATCGCACCGTGCGCTCGGTCAAGCGACCATGGGCAGCGACTGGTCCATAGAGATTGACGCAAGAAATACACGCCCGGAGATCTCGCCGC | |
| | ATTCTGATGAACTGAACGCGACCCGAGGCTACTCGGTGANGACATNACGACGCGTTATCACACCCCGCCTNCTTCAATGACCCCACGTCNGGCACCAAGGACCCGG | |
| | CAATCGCGGCTCACTTGNGCGATNGTCNACAACCAACGCGNCGCCTGGCTACGGGCTCAACAAGGCANAAGACACAATCCGCTCTCGATTGGTG | |
| Clone Rv67 | :::::::::::::Rv67SP6.seq::::::::::::: | |
| | ATACTCAAGCTTATCGAGGCGGCGCATACCGAAGCGTGGGAAATCCAGACCGAATACCGCGACGTGCTGGACACTTTGGCCGGCGAGCTGCTGGAAAAGGAGACCC | (SEQ ID NO. 629) |
| | TGCACCGACCCGAGCTGGAAAGCATCTTCGCTGACGTCGAAAAGCGGCCGCGGCTCACCATGTTCGACAACTTCGGTGGCCGGATCCCGTCGGACAAACCGCCCAT | |
| | CAAGACACCCGGCGAGCTCGCGATCGAACGCGGCGAACCTTGGCCCCAGCCGGTCCCCGAGCCGGCGTTCAAGGCGGCGATTGCGCATGCTACCCAAGCCGCTGAG | |
| | GCCGCCCGGTCCGACCCGGCCAAACCGGGCACGGCGCCAACGGTTCGCCCGCCGGCACCACCGGTCCGGTGACCGCAGTACGGTCCCCCCAGCCTGACTACCGTGC | |
| | CCCGGCGGGCT | |
| | :::::::::::::Rv67T7.seq::::::::::::: | |
| | TGGCCGGGCTGGTAGCCCGCGTATGGCAAGGTTCCGCTCAATGTGGTTGTGATGCAGCAGGACTACGTTCGCCTCAATCAGCTCAAACGTCACCCCCGTGGCGTGC | (SEQ ID NO. 630) |
| | TGCGCAGCATGAAGGTCGGCGCCCGCACGATGTGGGCGAAGGCAACAGGTAAGAACCTGGTCGGCATGGGTCGAGCCCTCATTGGGCCGTTGCGGATCGGGTTGCA | |
| | GCGCGCCGGAGTGCCGGTCGAACTCAACACCGCCTTCACCGATCTTTTCGTCGAAAATGGCGTCGTGTCCGGGGTATACGTCCGCGATTCCCACGAGGCGGAATCC | |
| | GCTGAGCCGCAGCTGATCCGGGCTCGCCGCGGCGTGATCCTGGCCTGTGGTGGTTTCGAGCATAACGAGCAGATGCGAAT | |
| Clone Rv68 | :::::::::::::Rv68SP6.seq::::::::::::: | |
| | GTCCAGTCAAGCATCGGTCCTCTCCGACTACGCCAAGANTGGCGACGTGTCAGTGCANACAGCGGANATGGTGGCGCCTATGCGTCGACGCTCACAAACNGCGGTG | (SEQ ID NO. 631) |
| | ANCGCGTTCTGGTCGTGCACCATCGAGCCGTGCCAGCCCGGCCGCGTGCCGTCAGCCGCATCCACTGGATGCCTTCTCGGNGTTTCAATCANGTACANGCGACGTT | |
| | CGCCACCATCGTGCCGGGGCACGGTTAGCGAGAAACCGCCGACTTCACCGATTGCCTCGGTGATGCCGTCGAACAGATCGGGCCTATTGTCGACAGCCAGTGTGAT | |
| | NCGTATTTGCCGCCGTGCTCCTCGTCGCAACGATGCGAACACAGATCCGTGGNGGACGATAGCGGCTGACAANGTGGGGGCAACACAATCACATGCCACATTTCTT | |
| | CATTTCACGCCCACAACCCAGACTTCGTCTCGATGNGCCG | |
| | :::::::::::::Rv68T7.seq::::::::::::: | |
| | CACGCGGTCTGGCCCGATCCGAAGATCCCTTTGCCGGCGTGGCGGCTCTGCTCGGCGGTGTTGTACACTTCTCGAACACCTCGGCACCGACACCACCACCGTNGCT | (SEQ ID NO. 632) |
| | TGAACACCGCCAACATCGGCAGCAGATCTTGATGGTCCTGGTGAATCCCACGGTGACTTTGGAGTGGAAGGCGCCATACTGATCGCCGCGCCAGCACATGAGCTAG | |
| | CGGCAGGAAAACCAGCAGCCGCTCACCTTGCGCAGCAGCGTCNGGTGATATGCCTGGCGCCCTTAATCTCGTGAACCAGTTGGATTGGGTCAACTGGCAGCCTTGG | |
| | GTCTCCGGTGGTGCCGANGTGTANATAAGCTCCCGGGTCCGTCAACGTANTGCGCAGGCGGCGGTTACTCGGCGGGTCAACGAGCCCCGCTCGTGAGCNATCAGCC | |
| | TTTGGACCGAACGGGATTCATACTCCGCAGGCGGCCCTCCGAAATCGGCACATGTCCTTTGATCGTTCGCAACAN | |
| Clone Rv69 | :::::::::::::Rv69T7D3.seq::::::::::::: | |
| | GGCCATGTCACATCGGTGGTACAGGTAAACCGCGCCGTGTGCGCGGTCTCGGAGATCAGAACGTGGTCGCAGTTGAACCGCGGGCTTTCAGCCAGTCGCGATAATC | (SEQ ID NO. 633) |
| | GGCGGAAGTCGGCGCCTGCCGCCCCAACTAGCGCGACTCGCCACCTAGCACACCGATGGCGAAGGCCATGTNTCCGGCCACGCCGCCGCGGTGCATCACCAAGTCA | |
| | TCGACTAGGAAGCTAAGCGACANCTTGTGCAGGTGTTCGGGCAGTAGCTGCTCGGAAAATCGGCTGGAAACCGCATCAAATGGTCGGTCCAATCGAACCGGTTACC | |
| | CGATCGTCACAAAAATCTCGTCCT | |
| Clone Rv6 | :::::::::::::Rv6SP6.seq::::::::::::: | |
| | GGGTCTACAACCACCGGGTCTGACTTCTGGGCTTCCACCGCTCGCGCCGTCGCGACAAACAGCGCGGTCGAACCGACACTCGTTGTGATGTCCCAGCTATCACCTC | (SEQ ID NO. 634) |
| | CGGTAGGCACCCAATCGACCCTACCCGGCTATCTCACCCCCGATCTCCAGGCTCCGCCGATCCATGCGCATCCCGGTCCGGATCCC | |
| | :::::::::::::Rv6T7.seq::::::::::::: | |
| | CAGGCATGCAAGCTTGTCGTATTCCGTGGCACTGTCAGACATATGCGCCGCTCCTCCTCATCGCTGCGCTCGGCATCGTCGCCGGCGGTCATGGCGTCACCCTACC | (SEQ ID NO. 635) |
| | CAAGCCGAACGCGAAACGAGAACGTGTTCCATTATTAGGGTGTGAGCACCAATACCAGATTGCTCACCAGGAACTCACGCAGCACCGGGACGGATGTCAGCCACCA | |
| | CGCCCATCTGGGGTGGTAGCGGGGAAATACGGCTAACGCGGCTCCGGTGCCGGCAGCCCAGCGCAGACCCTCGGCGGCGGACACGGCTAACAACGACGACCCATAG | |
| | TTGTTCTTTGCCGGATGGCCGTGTTTGCTGACATATCGGGCGCGGCGCCGGCGCCGCC | |
| Clone Rv70 | :::::::::::::Rv70SP6D2.seq::::::::::::: | |
| | NCTACGCTGCTGAATGTTGTGCGCCGGAGGANCTCAAGACCCACGCGGTTGTACGCGGACNTGCGACATGTTCAACCGCCGGA | (SEQ ID NO. 636) |
| | :::::::::::::Rv70T7D3.seq::::::::::::: | |
| | CTAACCAACAAGCCATGGTGGTTGGCGCCGTCGAGAGGTCGGCGGTCGCCACAACGGGAAGATCGCCTTGAGCGTCGCTCGACCGCCGCCTCGAGTTGGGTCATAA | (SEQ ID NO. 637) |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

CGAAGTACTGATGCCGATCATGTCGACGTGTCCGTCGCATCAGCGTGCAGCGGCGACCCCTCGACGAGCCTCGGTGCCGCCGCGGCCAGGGCACCAGCTGTTTTAG
CGCATTGTGCTCCGCCGGTAATAAAGGANGTCGGTCGCCTCCGCTGCTGTGGTTGCGGAATAACATCTTCCCTTCCTGCAACAGGATGAGAATGGTTTTAATTGCT
C

Clone Rv71 :::::::::::::Rv71SP6.seq:::::::::::::
CTAAGCTTTCGGGTCCGCCGCCACTAGTACCGCGTTGCCGGCCCCGCCGACCTAGAATCTTCCGCCCATTGCCGTTTCCTCCCGCCGCCGGGTT (SEQ ID NO. 638)
:::::::::::::Rv71T7.seq:::::::::::::
TCTGGTGCCGGGTGTGCCGACGGGTCCGTCCGCCTCTGCTTCAGTGATTCTGTGATGCGACCGGCAACGTCCTCGTTGTTCGGTGTCTATGTGGTCCGTCTCTCCT (SEQ ID NO. 639)
TGTTCCGCATACGATT Clone Rv72 :::::::::::::Rv72SP6D2.seq:::::::::::::
GCGATCGNTNACCACAAGGGCGCAACCGTTCGCGCGTCGACTGAACGTGCTGCCGCCTGGAGAACTGGCGCTGCTGCCACCTGGTCGGCGCATCGGCACTTCGAGG (SEQ ID NO. 640)
ACTGGATTTCGACGCGTGGCCCGACCTGANGTNGGCGGTGGACNNGTGTGCACCCGGTTGATTCCTCGGCCTTGCCGGGATGCCACCTGCGCCTGGTGGTCGAT
:::::::::::::Rv72T7D3.seq:::::::::::::
CGTGACCGGACGGGGTGCCGCGCGAACCGGTCTTGGCCAATTGCCGGGGACTGGGGCTGGAGTATAAAGCGGGCCTGTTGCCGGAAGATAAAGTCAAAGCGGTGAC (SEQ ID NO. 641)
CGAGCTGAATCAACATGCGCCGCTGGCGATGGTCGGTGACGGTATTAACGACCGCCAGCGATGAAAGCTGCCGCCATCGGGATTGCAATGGTAGCGGCACAGACT
GGCGCTGGAAACCGCCGACGCACATTAACCATAACCACCTGCGCGGCTGGTGCAAATGATTGAACTGGCACGNCCACTCACGCCAATATCCGCCAGAACATCACTA
TTGCGCTGGG Clone Rv73 :::::::::::::Rv73SP6.seq:::::::::::::
ATACTCAAGCTTCTTACCCANAGCATGAACCCCGCCGTCCAATGCCGCCACCGTGGTGCTGTCGGCCGGCCGGGTGCGGGCACAATCGCCGAGTTCGGCGAACAGA (SEQ ID NO. 642)
TCCTCGAAGGTCTTCACGGCCAGCGATTGTTGCACGTGTCAGCCAGCCAAGTCACGGTGGTTTGACGCCACACGTTCGCCACCGCCGCGCCGCGCATTAGGGCATC
CTAATATAGGTTAGGCTACCCTANTTATTCCTGTGGTCNAAGGAGGCAGCCGAACGTGACCTTCCCGATGTGGTTCGCAGTTCCGCCGGAAGTGCCGTCAGCATGG
CTGTCCACCGGCATGGGCCCCGGTCCGCTGCTGGCCGCGGCCAGGGCGTGGCACGCGCTGGCCGCGCAATACACCGAAATTGCAACGGAACTCGCAAGCGTGCTCG
CTGCGGTGCAGGCAACTCGTGGCAGGGGCCCAGCGCCGACGGTTCGTCNTCCCCATCAACCGTTCCGTATTGGCTAACCACCTGCACGGTGGCACCGCACAACGCC
GCCACAAACGCGCCCCGGTATAC
:::::::::::::Rv73T7.seq:::::::::::::
GGCCGAACTTAATCGGTTGTTGGCGGCTGCCGAGTTGGGTCACTCGGGGGGTGTGCACTGGCACATGGTGGGCCGGATTCAACGCAACAAAGCCGGGTCGCTGGCT (SEQ ID NO. 643)
CGCTGGGCGCACACCGCTCACTCGGTGGACAGCTCGCGGTTGGTGACCGCGCTGGATCGGGCGGTTGTTGCGGCGCTGGCCGAACACCGTCGTGGCGAGCGGCTGC
GGGTTTACGTCCAGGTCAGCCTCGACGGTGACGGATCCCGGGGCGGCGTCGACAGCACGACGCCCGGCGCCGTAGACCGGATTTGCGCGCAGGTGCAGGAGTCAGA
GGGCCTCGAACTGGTCGGGTTGATGGGCATTCCGCCGCTGGATTGGGACCCGACGAAGCCTTTGACCGGCTGCAATCGGAGCACAACCGGGTGCGTGCGATGTTCC
CGCACGCGATCGGTCTGTCGCGGGCATGTCCAACAACTTGAAATCCCGTCAACATGGTCGAC Clone Rv74 :::::::::::::Rv74SP6.seq:::::::::::::
GCTTCCCCTGATACTCGACCAGCCCCACTCGGGCCAATACGTGAATGTCCTAGCATTTTTCACCCGTTCACGGGCTAGTCGAGTAGTAGACGATTGATTAGCCTGA (SEQ ID NO. 644)
ACGTACCTCCGACGGCCAGCTGACGAACGGGTTTGACGGA
:::::::::::::Rv74T7D3.seq:::::::::::::
TCAGCTGTCTGTAGAAGGGCTGGCGATACTGTGCACTGTCTGATATCGCNNCGTNGTGGGACTATNCAGNCCATNANGATGCGGTTCNGNNNNTGCAGAGNATCCT (SEQ ID NO. 645)
GGNACACATNCGGTTCACGTTAATCANCATCGCGANTTNCTNCGTNTTCGATTANTTCTGCTAACGNNTCTNNNAGTGCCTGCGGGTCGACTCTAGAG Clone Rv75 :::::::::::::Rv75SP6D2.seq:::::::::::::
NCTCTGCCGGGCNAGAGCGCAGAGTCGGACGGCTTCGTCGATCGTGAAGCGACCNTGCGATGANCAGATATCGNTNACACTGCTCANAAACTTCGGATCATCGNTG (SEQ ID NO. 646)
ATACACAGGCCAACGGGTAGCGGTTGTCCAACCGCTTCGTCAACGANATGGGATCGTGACGANCCTACGCTCGCAGGATATGTCGCNGACCNGNTCTAGANAN
:::::::::::::Rv75T7D3.seq:::::::::::::
CACTTCATGCTCGTGCGTTGGCNTCGATTTGCNCGAGNGGTTAGCTCCTCGAGTGNGTGACGTATCACTCCGGCNGACTANCCGTATCNGCGTCCCGCACCGGTCA (SEQ ID NO. 647)
ACTGGTCTAGCCACACCGGGGAGAATNCNGCAGGCCNGCTATCGACCNATCACGGCTTGTCGNNAAGATAGNCAGCC Clone Rv76 :::::::::::::Rv76SP6.seq:::::::::::::
ATACTCAAGCTTGCCAACCGCCACCCTGCATCCGGGGGGCGAGCACTGCTCCGCCGACCAGTACGAACCAACCTGCGGTGCCCAGGCCATTGACAATGTGCTGGTC (SEQ ID NO. 648)
GGCGCCCGCGAGTTCTAGCACAGCAACGCCGCGGCCACCACAGGGGCG TABLE 3-continued End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | :::::::::::::Rv76T7.seq::::::::::::: | |
| | CGGTCGGTGTGCTTGGCGGCGTCGGTATCAACACCGCCCACGAAATGGGGCACAAGAAGGATTCGCTGGAGCGGTGGCTGTCCAAGATCACCCTCGCCCAGACCTG CTACGGGCACTTCTACATCGAGCACAACCGTGGCCATCACGTCCGGGTGTCCACACCGGAAGACCCGGCGTCGGCGCGGTTCGGCAAAACTTTGTGGGATTTCCCG CCCCCCC | (SEQ ID NO. 649) |
| Clone Rv77 | :::::::::::::Rv77SP6.seq::::::::::::: | |
| | AATACTCAAGCTTCGCGGAGGTGGTGGGGCAGGAGCACGTCACCGCGCCGCTGTCGGTGGCGCTGGATGCCGGCCGGATCAACCACGCGTACCTGTTCTCTGGGCC GCGTGGCTGCGGAAAGACGTCGTCAGCGCGTATCCTGGCGCGGTCGTTGAACTGTGCGCAGGGCCCTACCGCCAACCCGTGCGGGGTCTGCGAATCCTGCGTTTCG TTGGCGCCCAACGCCCCCGGCAGCATCGACGTGGTAGAGCTGGATGCCGCCAGCCACGGCGGCGTGGAGCAACCCCGCGAGCTGCGGGACCGCCC | (SEQ ID NO. 650) |
| | :::::::::::::Rv77T7.seq::::::::::::: | |
| | GATGGCACTCACGCTGGACAAGACCTTCACAAAATCTGAAATCCTGACCCGATACTTGAACCTGGTCTCGTTCGGCAATAACTCGTTCGGCGTGCAGGACGCGGCG CAAACGTACTTCGGCATCAACGCGTCCGACCTGAAATTGGCAGCAAACCGGCGCTGCTGGGCCGGGCATGGTGCAATCCGAACAAGCACGCTCAACCCGTACACCA ACCCCGAAGGGCCGCTGGCCCGGCGGAACCTTGTCCTCCA | (SEQ ID NO. 651) |
| Clone Rv78 | :::::::::::::Rv78SP6.seq::::::::::::: | |
| | AACAGCTATGACCATGATTACGCCAAGCTATTTAGGTGACACTATAGAATACTCAAGCTTCTGGGCGTCGTGGTGCCCGGCCTGCCGGTGCAGGAACTGGATTTTA CTGCCATCTCTCGCGACCCTGAGGTGGTCCAGGCTTACAACACCGACCCACTCGTGCACCACGGACGGGTTCCGGCCGGGATTGGCCGCGCGCTGCTGCANGTGGG CGAGACCATGCCGCGGCGANCACCGGCATTGACCGCGCCGCTGCTAGTGCTGCACGGCACCGATGACCGGCTGATCCCCATCGAAGGCAGCCGTCGCCTGGTCNAA TGTNTNGGATCNGCCGACGTGCANCTGAANGANTATCCCCGGCTGTNCCACNAGGTGTTCAACGAACCGGANCGCAACCAAGTG | (SEQ ID NO. 652) |
| | :::::::::::::Rv78T7.seq::::::::::::: | |
| | CAAGGCATACGCCAAGACCCAAGGGATCGCAGTCACCTCCGTCAACGGCCTGGTCGCCGGCCACGGGTCCGTGCAGGAGACGTGGCTGGCCATGCAAAGCGCCGCC GCCTTATCAGGAACGCCCCGGCTTGTCGGCTTTTCCTGCATCGACACATTTCCGGAGGTGTTGTGGTTGGCGCANCGCGCGAGACAGGCCTGGGATGGCGTGCGCA TCGTCATCGGGAATGCGATGGCAACACTGAACTACGAGCGCATCCTGCGCCAGCATGACTGTTTCGACTACGTCGTCGTTGGCGACGGGGANGTAGCGTTCACCAA GCTGGCCTTGGCCCTGGCGAATGACCTGCGGTTGACGACTCCCGGGACTAACCCGCCGTANTGAGCAAGGACAGATTCTGCGCACACCCTCCTCGCTGGTCGACCT TGACA | (SEQ ID NO. 653) |
| Clone Rv79 | :::::::::::::Rv79SP6.seq::::::::::::: | |
| | AACAGCTATGACCATGATTACGCCAAGCTATTTAGGTGACACTATAGAATACTCAAGCTTGCCGGTGATCTGGGTGGCCAACTCGGCGGGCACCATCTCCATCACG ACNGCAAACGCTCCGGCTTCGGCGACAGCGATCGCGTCTGCGATNGTTTGTTCGGCGGCGTCTCCGCGGCCCTGCACCCGGAAGCCGCCCAAGGTGTTGACNCTTT GCGGGGTGAAGCCGATGTGTGCCATCACCGGGATNCCCGCCGCGGTCAGACANGCGATTTGCTCGGCCACCCGCTCACCGCCCTCGANCTTGACNGCATGTGCGCC GCCGTCCTTGAAGAAACCGGTGGCGGNGGCAACCC | (SEQ ID NO. 654) |
| | :::::::::::::Rv79T7.seq::::::::::::: | |
| | CGTTGAGATCCAGCTGCGCACTGTGCAGCGCCTCGGTGGTCTGCTCGGCCTGCCGGGATAACTCGTTGAGCTTGGCCAGCGCGTCGTCGGCCGGATCAGCCAGCAC ATTCGCGGCCAGGACGCCGGAGGAGACGGTGAAGCTCGCAAAGAAACCTATGGCGGACCGCATGATTACACGCGCGATCAACCACCTCTGGTCGAGCCTCAAAATT TGCTTCCTTAAACGGGCCATCGACGGATGACGTCGAGCTGGTTTAGGTCTCAAACAGGTTACGAAACGATCTCGGAATTGTCCAAAAGGGGAAGTTAAGAAAATGG ATAGATTTCTACCATTTCGCTGTGGACGATCGTACTTCTGCTATAGGGCTCCAGGGGCATCGACACGCAACGACCTTACGCGACACCGGATCCGCGCTGGCGGCGG AACGGCACCANGCGCAACCGAAGGGCCAATCCGACATCGG | (SEQ ID NO. 655) |
| Clone Rv7 | :::::::::::::Rv7SP6.seq::::::::::::: | |
| | ATACTCAAGCTTATCTAGGCGCCAGCTTGATTGGTCTGGTTGCATTGGCCAGCTGCGCGAGCCTGGCTCACTTCAACTACAACAACCGCAAACAATTGCCGCCTTC GGATCCGAGTTCGGTTGGGTACGCGGCAATGGANCACCATTTCTCGGTGAATCAGACTATTCCTGAGTACTTGATCATCCACTCTGCACACGACCTGCGAACCCCG CGCGGCCTTGCCGACCTGGAGCAGCTGGCGCAACGTGTGAGCCANATCCCAGGCGTTGCCATGGTTCGCGGTGTGACCCGGCCAAACGGGGAAACCCTTGAACAGG CCCGGGCGACATACCAAGCCGGCCAAGTTGGCAACCGGCTGGGCGGCGCGTCGCGAATGATCGATGAGCGCACCGGCGACCTGAATCGGCTGGCATCGGGTGCCAA CCTGTTGGCCGACAATCTCGGTGACTTCGCGGTCAAGTCAGCCGGGCCGTTGCGGGTGTCCGCAGCCTTGTCCAGCCCCTCGCTTACTCCA | (SEQ ID NO. 656) |
| | :::::::::::::Rv7T7.seq::::::::::::: | |
| | CAGGCATGCAAGCTTTTTGAGCGTCGCGCGGGGCAGCTTCGCCGGCAATTCTACTAGCGAGAAGTCTGGCCCGATACGGATCTGACCGAAGTCGCTGCGGTGCAGC CCACCCTCATTGGCGATGGCGCCGACGATGGCGCCTGGACCGATCTTGTGCCGCTTGCCGACGGCGACGCGGTAGGTGGTCAAGTCCGGTCTACGCTTGGGCCTTT GCGGACGGTCCCGACGCTGGTCGCGGTTGCGCCGCGAAAGCGGCGGGTCGGGTGCCATCAGGAATGCCTCACCGCCGCGGCACTGCACGGCCAGTGCCCGCGGCGA | (SEQ ID NO. 657) |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | TTCAGCCATCGGGACATCATGCTCGCTTCATACTCCTCGACCAGTCGGCGGAACAGCTCGATTCCCGGAACGCCCACGCATGGTG | |
| Clone Rv80 | :::::::::::::Rv80SP6.seq::::::::::::: | |
| | AACAGCTATGACCATGATTACGCCAAGCTATTTAGGTGACACTATAGAATACTCAAGCTTGTAGAAAAAGATCGGTGAGCGCATCGATTCGCTCCGCCGGGTTTGC CGCTGCGGCGGCGGAGCTGCCGTGACCGTCTATTTGGGTGATCAGATACTGGGCTAGTTCGGTCGGGGTGGGGTGATCGAAGATCGCGGTGGCCGGCAGCGTTACT GCGGTGACAGCTGTTAAGCGGTTACGTATCTCCACGGCACTCAAGGAATTAAATCCCGAATCGGCAAACGCCTGGCCAGCGTCNAGTCCGGCAGCGCCGTCNCGCC CCAGCACCGCTGCGGCATGCTCACATACCACCTCGATCGCTGCGGCGANTTGCTCGTCNGCCGACCGACCGGCCANCCGGGCGGCAAACCCNGAAGACCCAAGAAT TCATCACCACCATCGCTAGC | (SEQ ID NO. 658) |
| | :::::::::::::Rv80T7.seq::::::::::::: | |
| | CCTTCTTGACACCCACCTCGCCATCGACCTTGAGCACTCCGTCGTAGTTGGTGAACATGTGACCGGCGATCGGGCGGGTGAACGCGTACTGGGTGTCGGTGTCGAC GTTCATCTTCACCACGCCGTAGCGCAGCGCCTCCTCGATCTCCGACTTAAGCGAACCCGAGCCGCCGTGGAACACGAAATCNAACGGCTTGGCGTCNGCCGGCAGT CCGAGCTTGGCCGCCGCCACCTGTTGCCCTTGCGCAAGGATGTCNGGGCGAANCTTGACGTTGCCGGGCTTGTANACGCCATGCACGTTGCCGAACGTCNCGGCCA GCANGTATTTGCCGTGCTCACCGGCGCCCANCGCCTCGATGGTTTTCTCGAAGTCCTCCGGGCTGGTGTACAGCTTCTCGTTGATCTCGTTCGCCACGCCGTCCTC TTCGCCGCCGACG | (SEQ ID NO. 659) |
| Clone Rv81 | :::::::::::::Rv81SP6.seq::::::::::::: | |
| | AACAGCTATGACCATGATTACGCCAAGCTATTTAGGTGACACTATAGAATACTCAAGCTTGGAAAGGAGATCCCCGGGAACCTGGTGGCAACCCCGCCATTGGGGT TGTTGGGATTGCCGATCAGCGTGAANGAAAGCTCGTCTGGAGACAGCGGGTCGGCCGAAGCCGCAAGATTGGCCATCACTAGTGACGANATCGTGGCGCTCTGCGA GTANCCNAAGACAGTGACGTTGTTNCCGGCGGCAATTTGCTGCCGAATCGCACTTTCGAGAATGACNGCACCCTGCGCCACCGANGAATCNAAAGTGAGGTTCTTG ATCACGACCACCGGGTNGAGCCCTTGGGGCGTGAAGANCGCCTGCGCNATAACACCCGGGACGCTGCCACTCATGTNCAGCGCGTTCGCGANCTCNACATATCT | (SEQ ID NO. 660) |
| | :::::::::::::Rv81T7.seq::::::::::::: | |
| | TCCTGGTGATCGANGGCCGCGGTTCCGGCCGAAAATCCGGTTCGGGTTCGGGTCGCGGTTCCAACTTGANCGCGGTCCGCAGCTGATTCACCGTGGCAACGCCGGC CAACTGCGCATAATGCGCATCCGAACCCTCACCCGCCCGCCCCGCGATCACCCCAACCTGATCCAACGACAACCGCCCCTCCCGCATACCCCGGGCGCAGCGCGGA AACTCCGGCAACCGCCGCGCCACCGTGGCGATCGTGTGGGCGTTGCCTGACGAACANCCCATCTTCCAGGCCACCAACCCCGCCACCGACCGCGCCCCCGTCACAC CCCACAACCCGTCGCGATCCAGCTCAGCCACGATCTCCACAATGCGCCCATCAATCGCATTGCGCTGAACGGGCAACTCCGCCAACTCCTCCAA | (SEQ ID NO. 661) |
| Clone Rv82 | :::::::::::::Rv82SP6.seq::::::::::::: | |
| | AACAGCTATGACCATGATTACGCCAAGCTATTTAGGTGACACTATAGAATACTCAAGATCTGGTACCCATCCGTGATACATTGAGGCTGTTCCCTGGGGGTCGTTA CCTTCCACGAGCAAAACACGTAGCCCCTTCAGAGCCAGATCCTGAGCAAGATGAACAGAAACTGAGGTTTTGTAAACGCCACCTTTATGGGCAGCAACCCCGATCA CCGGTGGAAATACGTCTTCAGCACGTCGCAATCGCGTACCAAACACATCACGCATATGATTAATTTGTTCAATTGTATAACCAACACGTTGCTCAACCCGTCCTCG AATTTCCATATCCGGGTGCGGTAGTCGCCCTGCTTTCTCGGCATCTCTGATAGCCTGAGAAGAAACCCCAACTAAATCCGCTGCTTCACCTATTCTCCAGCGCCGG GTTATTTTCCTCGCTTCCGGGCTGTCATCATTAAACTGTGCAA | (SEQ ID NO. 662) |
| Clone Rv83 | :::::::::::::Rv83SP6.seq::::::::::::: | |
| | AACAGCTATGACCATGATTACGCCAAGCTATTTAGGTGACACTATAGAATACTCAAGCTTANCGCCACCTCCCGGGCGGAACTCCACGGCGTGGATNAAGGTACCG GCCGGGATGTTGCGCAATGGCAGGTTGTTGCCCGGCTTGANGTCCGCGTTAGCGCCGGATTCCACCACATCCCCTTGCGAAANTCCGTTGGGTNCNATGATGTNNC GCTTCTCCCCNTCNANATAATGGANCAACGCNATCCGTGCGGTACGGTTCGGGTCNTACTCCATGTNCGCGACCTTGGCGTTGANACCATCTTTGTCATTGCGGCG AAAGTCNATCATCCGGTNAGCNCGCNTATGANCGCCGCCTTTGTGCCGGGTGGTAATCCGGCCATGCGCNTTGCGTCCACCGCGAACGTGCAACGGGGGCNCCAAC GANTTCTCCNGGGTTGAACCGGTNATCT | (SEQ ID NO. 663) |
| | :::::::::::::Rv83T7.seq::::::::::::: | |
| | TGTGTGTGGTGGTAACCCATCTGAGCAGTGTGCCAAACCGGGGCAGCCAGCTCCCAATTGACGTGAGCCCGCTCACTTGCTGGGTAAGCGTCG | (SEQ ID NO. 664) |
| Clone Rv84 | :::::::::::::Rv84SP6.seq::::::::::::: | |
| | AACAGCTATGACCATGATTACGCCAAGCTATTTAGGTGACACTATANAATACTCAAGCTTGCGGGTNATNGCCTTGGTCAACGGCACCGTGATCGGATCNGGGTCT ACCGCACACATNGACTGGAGCTTCGGCGAANTCATCGCCTATGCCTCGCGGGGGGTGACGCTGANCCCNGGTGACNTGTTCNGCTCNGGCACGGTGCCCACCTGCA CGCTCNTCNAACACCTCANGCCACCGGAATCATTCCNGGCTGGCTGCACGANAGCGANNTTGTCNCCCTCCAAAGTCTAAAGGCTGGGCGANANAAGCANAACGTC CCGACNAACGGCACTCCTTTTCCNTTTGCTCTTC | (SEQ ID NO. 665) |
| | :::::::::::::Rv84T7.seq::::::::::::: | |
| | GAAATCATTGATGGTTTGAGTCACCAGGCCGATCAAGCCTTCGCCGAGCCAAATTCCAATCAAGAGGCCCAAGCCCGTACCAATCAGCCCGGCAACGAGGGATTCC | (SEQ ID NO. 666) |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | GTCATTATCAGCCAAAATAACTGCTCTCGGGTTACACCCAAACAGCGCAATATGGCGAAAAACGGTCGCCGTTGCACGACATTAAATGTCACGGTATTGTAGATTA<br>AAAAGATACCCACCAACAANGCAATCAAACTGAGAGCGGTTAAATTGACCGTAAAAGCGTCCGTCATCTGTTTGACNGTGTCCCGTTGGGTATCCGACGTTTCCAT<br>ACGCACACCGGCCGGCAGTCTTTGTTGGATGCGTNTTGCAATGGCCTCATCTTTGATGATCAAATCGATGTNGCTCAGTCTTCCGGGCATATGGAACAACTCTTGG<br>GCCGTGGAAATATCAGCAATGATA | |
| Clone Rv85 | :::::::::::::Rv85SP6.seq::::::::::::: | |
| | CTTTCGCCCAGGCCGGCGCGGATGTCCTCATCGCTTCACGAACATCATCCGAGCTTGACGCTGTCGCCGAACAGATCCGCGCTGCCGGCCGCCGCGCCCACACCGT<br>TGCCGCCGATCTGGCCCATCCCGAGGTGACCGCGCAGCTGGCTGGTCAGGCCGTCGGAGCTTTCGGGAAGCTCGACATCGTCGTCAACAACGTTGGCGGCACCATG<br>CCCAACACGCTGCTAAGCACCTCGACCAANGACCTCGCGGACGCCTTCGCCTTCAACGTGGGCACCGCCCACGCGCTGACCGTCGCGGCGGTGCCGTTGATGCTGG<br>AACACTCCGGCGGCGGCAGCGTGATCAACATCAGCTCCACCATGGGCCGGCTGGCGGCGCGGGGTTTC | (SEQ ID NO. 667) |
| | :::::::::::::Rv85T7.seq::::::::::::: | |
| | TGTGGGCTCCGATCCGGCGCGCATGGCATCGACGGCGACGCCGATCGATGACGGCCAGGCTTACGAGCTTGAGGGTGTGAAGTTGTGGACCACCAACGGTGTGGTA<br>GCGGACCTGCTAGTGGTTATGGCGCGGGTACCGCGCAGTGAAGGGCNCCGAGGGGGAATCANCGCCTTTGTCGTCGAGGCTGATTCGCCCGGGATCACCGTGGAGC<br>GGCGCAACAAGTTCATGGGACTGCGTGGCATCGAAAACGGCGTGACCCGGCTTCNTCGCGTCAGGGTGCCCAAAGACAACTTGATCGCANGGAAGCGACGGTCTGA<br>AGATCGCGCTGACCACACTCAACGCCGGACGGCTGTCCCTACCGGCGATCCAACCGGAGT | (SEQ ID NO. 668) |
| Clone Rv86 | :::::::::::::Rv86SP6.seq::::::::::::: | |
| | GAGCTGGCCGAGCTGGACCGGTTCACCGCGGAACTACCGTTCTCGCTCGACGACTTTCAGCAGCGGGCTTGCAGCGCGCTGGAACGCGGCCACGGTGTGCTGGTGT<br>GCGCGCCGACCGGCGCTGGCAAGACAGTGGTCGGCGAGTTCGCCGTGCACCTGGCGCTGGCGGCCGGCAGTAAATGTTTCTACACCACGCCGCTGAAAGCCCTGAG<br>CAACCAAAAGCACACCGATCTCACAGCACGCTACGGCCGTGACCAGATCTGGCTGCTGACCGGTGACCTGTCNGTCAACGGCAACCGCCGGTGGTGGTGATGACCA<br>CCGAAATGCTGCGCAACATGCTCTAC | (SEQ ID NO. 669) |
| | :::::::::::::Rv86T7.seq::::::::::::: | |
| | GATCTCTGGATCGGCGGGGCTCTCCGGGCCGGCCTCGGCGACCTCAGCGGGCCGCGCCTTCCGGCCGAACCATTCCCTAGCCATAGATGACCGCACCTCGATGCAC<br>GGTTTGGCGGCAACGCGGCAAGGCGTCNGTCGGGCCCAGCCGCGGCAATGCGGGTACCCGGGAGCGCGGGTCNGTANACCANCGCTGGACTGCGTCGCGCGGTGCG<br>TCNACNTCAAAGTCCCCGGCGTCCCATATCGCGTATGACGCGGGCGCGCCCGGCACCANGGGTGCCGATCCGGCCGTCTCGAACACCACCGGCCCGCCAGCCGCCG<br>CGGGTCCGGCAGCNAACCCGCCCGCGCCGATACCCGCTGCCCGCGTGCGTGATTGACCGCCGCGCGCACGCTGGCCANGGATCAAAGCCCGTG | (SEQ ID NO. 670) |
| Clone Rv87 | :::::::::::::Rv87SP6.seq::::::::::::: | |
| | GGACGCGTAGCCCGCCAGGCCGGTCAGGGTGCCCTTCCAGTCCACGCCGCTGTGGTCGGCGAACCGCTTATCTTCAATCGAGACGATCGCCAGCTTCATCGTGTTG<br>GCGATCTTGTCCGAGGGCACCTCGAACCGGCGCTGCGAGTNCAGCCACGCGATCGTGTTGCCCTTCGCGTCGACCATCGTCGATACCGCAGGCACTTGCCCCTCGA<br>GCAGCTGGGCCGAGCCGTTGGCAACGACCTCAGANGCACGATTGGACATCAGCCCTAGCCCGCCTGCGAACGGGAACGTCAGCGCAGTGGCGACGACACTGGCCAA<br>CAGACAGCACCCAGCCAGCTTCAGAACGGTGATCGCGGCCGGGAAGCGCTCGGGCATGCGTNCTACAGTAGCGACCTCCTGTCACTCCACGTGCCGCTCGGTCCAA<br>TAGAATCTTTCCGCGGGCGGGTGAATCTCTGCNGGATCGGGGCNGGCGC | (SEQ ID NO. 671) |
| | :::::::::::::Rv87T7.seq::::::::::::: | |
| | GCTCGTTGCCGGCGGCGATCTCGTCGAGCTCGTCTTCCATCGCCGCGGTGAAGTCGTAGTCGACGAGCCGACCGAAATGCTGCTCGAGCAGACCGGTTACCGCGAA<br>CGCCACCCATGACGGCACCAGTGCACTGCCCTTCTTGTGCACGTNGCCGCGATCCTGGATGGTCTTGATGATCGACGANTAGGTCGACGGGCGGCCGATGCCCAGC<br>TCCTCGAGCGCTTTGACCAGCGACGCCTCNGTGTNNCGGGCCGGCGGGTTGGTGGCATGGCCGTCTGGGGTCAACTCGACNATGTCCAACCGTTGACCCGGGGTCA<br>GATGGGGCAGTCGCCGCTCGGCATCGTCAGCCTCGCCGC | (SEQ ID NO. 672) |
| Clone Rv88 | :::::::::::::Rv88SP6.seq::::::::::::: | |
| | GTCTTTCGATGGCTGCTTCTTCGGCGCTGACGCTGGCGATCTATCACCCCCAGCAGTTCGTCTACGCGGGAGCGATGTCGGGCCTGTTGGACCCCTCCCAGGCGAT<br>GGGTCCCACCCTGATCGGCCTGGCGATGGGTGACGCTGGCGGCTACAAGGCCTCCGACATGTGGGGCCCGAAGGAGGACCCGGCGTGGCAGCGCAACGACCCGCTG<br>TTGAACGTCNGGAANCTGATCGCCAACNACACCCNCGTCTGGGTGTACTGCGGCAACNGCAAGCCGTCGGATCTGGGTGGCAACAACCTGCCGGCCAAGTTCCTCG<br>AGGGCTTCGTGCGGACCATCAACATCAAGTTCCAAGACGCCTACAACGCCNGTGGCGGCCACAACCGCGTGTTCGACTTCCCGG | (SEQ ID NO. 673) |
| | :::::::::::::Rv88T7.seq::::::::::::: | |
| | GCCAGGTCGAGGTCCCATGCGCGTGGGCCATTGATGCTGATCGCCAGGACGTCAAANATTTGGTCCGGCGTCAGCTGGGCGAAAAACGTGGGCCCCAGGACTTGCC<br>CGGAGCTGCCCGGGTTCCCGTCGCGCAGCTCGGCGGCCCCGGTCAGAAANAAATTGCGCCAGGTCGCACACTCCGCGCCGTANGCCAGCTGCTCCAGGGTGTCGGC<br>ATAGAGCCCGCGGGCCGCAGCGTGCTCGCTGTCGGCGAACACCGCATGGTCGAGAAGCGTTGCCGCCCAACGGAAATCACCTGCGTCNAANGCTTCGCGGGCCAAC | (SEQ ID NO. 674) |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | TCCAGCACTCGGTCGATG | |
| Clone Rv89 | ::::::::::::Rv89SP6.seq:::::::::::: | |
| | NAAACGTTCCGGCTTNGGTGCCGGGCGCTTATTTGCGTCTCTGGGATCACNCTCAGTCGCCGGCGGCTGCCGTTGGGCTATNANTTGCACCGANCCGGAAAATCCG | (SEQ ID NO. 675) |
| | CACNANAACTGCNAGTAGCGGCCTGCAGAANTGCATCCTCGGCGAANCNGACTACCGGTGGACANCNACAAGCGCCGCCGAACAACGCACTGGCCCGAGGGATNGG | |
| | CGTCTATCGGCCCCGCCCGTCGAACTNGGAACAGACNGTGCGGTTCTACCGTGATCTGGTGGGAATGCTCNACCANACCTTCCCNANNGCTACGGAACNACGGCGC | |
| | GATATTCNGCCNTCCCANCTCGAGCCTGACNCTNGATATCGTCGANNCTCACCATCNCGATCNGCTGTGCCGGTNTTGCTCGGACTN | |
| | ::::::::::::Rv89T7.seq:::::::::::: | |
| | CGAACGACGAACNCCNCAAGCCATGGTGGTTGGCGCCGTCAAAAGGTCCGCGGTCGCCACTACTGGAAAATCGCCTTGAGCGTCNCTCGACCNCCGCCTCGAGTTG | (SEQ ID NO. 676) |
| | GGTCNTAACGAAATACCTGATGCCGATCANGTCNACGTCTCCGTCGCNNCAACGTGCAGCGGCGACCCACTCTACNANGTCTCGGTNCCGCCNCGGCCAGNGCACC | |
| | ACCAGTGACNAATCCNTGCGCCNTCGGGCCNAGCANTCCCGGTGCNACCGNGGTGGGTCCGGCGATGGTNGGGTGTNCTCNNTACNGGAACGCCAGCGCNATCANC | |
| | ATCGGCANACTCNCGTCGATGTGCCGCGGCGCAACCATCCCCCACAATGATCNGGTGCGTCTGATCAGGCN | |
| Clone Rv8 | ::::::::::::Rv8SP6D.seq:::::::::::: | |
| | TTAGGCGTGACGGCCACCGGGGCCACTCCGCACAATCTGTACCCGACCAAGATCTACACCATCGAATACGACGGCGTCGCCGACTTTCCGCGGTACCCGCTCAACT | (SEQ ID NO. 677) |
| | TTGTGTCGACCCTCAACGCCATTGCCGGC | |
| | ::::::::::::Rv8T7D4.seq:::::::::::: | |
| | CGTCACCCCGATGCGCCCAGATCGGGGCTTCGCAGATAAAGCACGAACTGGCGGGCAAAACGTCGATCTCGGAGCCGGAAGGGCAATCAGCCGACCGTCGACGAAC | (SEQ ID NO. 678) |
| | GACACCGGCGAGACCACTTAGGCAGTGACGGCCT | |
| Clone Rv90 | ::::::::::::Rv90SP6.seq:::::::::::: | |
| | CTTTTCNCGATGTCTCATGATNCCNANGGAGAACNNTGCNANCNCNGCCGCTGACNTNGCNCACCGCTNTGGCNGNGGTGACATTGGTGGTGGTTGCGGGCTGCNA | (SEQ ID NO. 679) |
| | CGCCCGACTCGANGCCGANCCATNTNTTGCGGCCGACCGCNTNTCGTCTCNACCGCANNCCCNATCTCNGCCGCNCCCGGTGGANCTACNGCTNCTTCGCCATCTC | |
| | TCGCCNATGGCTCCNGCGNNTCGCNCAACGTNTGGTTTGGTNANCTGCCTACCTGGTCNT | |
| | ::::::::::::Rv90T7.seq:::::::::::: | |
| | GCTGCGCCAGTCGTTCGGTGCGGTCATGCCGTTGGACCNACCATCGGAGTTAGTTGCCGAACCGCGGACCACCGCAAGCACCCGGTCCTGGTCGCGCACCGCGTCG | (SEQ ID NO. 680) |
| | GCCAACCGCTTGAGCACCACCACGCCGCAGCCCTCGCCGCGCACGAATCCATCCGCGTTGGCGTCNAANCTGTNGCATCGGTCGGTCGGTGACAGCGCCGACCACT | |
| | TGGACAGCGCGATGGCGGTGAACGGTNANTAGGTGACCTGCCNCCNCGCCCGCCAATGCCCACCTCCGCTTCACNCATGCGAATGGTCTGACACGCCNAGTGAATT | |
| | GCCACCAGCGACAACAAAAATCGGTATCTNCNGCGACGGCGGACACGCNATCCCNACTGATACTCGATCCGCCCCACCGCTTGNANCTCCGGGTTCCNGTGCTCAT | |
| | GTACCNTCATGTCGGTCTGCGCNCGATATTGACGATCGTGTTTCCCACGANNANAGANCCTCATCACGCCGGTTCGAGTGCCG | |
| Clone Rv91 | ::::::::::::Rv91SP6.seq:::::::::::: | |
| | CTGTGTGCGGNCGGCGCGATATCGGCCTTTTTACTAACCGAACCCGATGTGGGCTCCGATCCGGCGCGCATGGCATCTACNGCGACGCCGATCGATGACGGCCAGG | (SEQ ID NO. 681) |
| | CTTACGAGCTTGAGGGTGTGAANTTGTGGACCNCCAACGGTGTGGTAGCGGACCTGCTANTGGTTATGGCGCGGGTACCGCGCAGTGAANGGCACCGAGGGGGAAT | |
| | CANCGCCTTTGTCGTCTANGCTGATTCTCCCGGGATCACCNTGGAGCGCNCCNCNANTTCATGGGACTGCGTGGCATCCAANACGGCGTGACCGGCTTCATCCNTC | |
| | NGGGTGCCCAAAGACAACTTGATCNGCNNGGAAGCGACGTCTGAANATCGCGCTGATCNCACTCAACGCCGGACGCTGTCCTACCGGCGATCGCACCGGANTTGCC | |
| | AANCGGCGCTNANNATNCGCGNGAATGNCCGTCCACNANTGCATGG | |
| | ::::::::::::Rv91T7.seq:::::::::::: | |
| | TGGGGTGCCGGGCGCCGAGTTGCGTCCCTGGGATCACGCAGAGTCGCCGGCGGCTGCCGTTGGGCTATGAATTGCACCGAGCCGGAAAATCCGCANCAAAACTGCG | (SEQ ID NO. 682) |
| | AGTAGCGGCCTGCAGAAGTGCANCCTCGGCGAAACGGAGTACGGTGGACAACGAAAAGCGCCGCCGAACNACGCACTGGCCCGAGGGATTGGCGTCAATCGGCCCC | |
| | GCCCGTCGAACTTGGAAGANACANTGCGGTTCTACCGTGATCTGGTGGGAATGCTCCAACNNACCTTCNCCGAAAGCTACGGAAGCNACGGCGCGATNTTCGGCCT | |
| | TCCCAGCTCGACCTGACGCTGGAAATCG | |
| Clone Rv92 | ::::::::::::Rv92SP6.seq:::::::::::: | |
| | NGGCNGGGAAGTTAATGCCCTACTGGTTCNATGCTCNCACNTCNCCNGTGACNNCCTGCNCCGACCCGCCGAGGTCCTGNCCGTNACCACCGANCNGGCGATCCGG | (SEQ ID NO. 683) |
| | GACTCTNGTACGCATCCAACANNGANCAACGTGCACGGGCGGAGTNGTNCCGCCACTTCGNCNATGACGGGGTCGATCCNTTCGACGTCCGTCGCCGCGTCGGTCG | |
| | AGTGGCGGTCACNCTCCNNGTACTCGACCNCACNGACGAGAGGACTCGANCCCATCTACGTGTGGACGAAACANATCTTCTGTCCNACGACTACACCACCACCCAG | |
| | GCCATCGCCGNCGCCCGCGANGCCCCTTCGACGCCNTACTGGTCCNGNGGNGGCGCTCTCCGGTTGTCTNNCNCNTGNCGTGTTCCTTCACNCACTGCCCNACATC | |
| | GANCCCGAGCNATNCNANGTCCGTCAATC | |

TABLE 3-continued

End sequences of the polynucleotide inserts cloned in the named recombinant BAC vectors contained in the I-1945 *M. tuberculosis* H37Rv genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

| | | |
|---|---|---|
| | :::::::::::::Rv92T7.seq:::::::::::::<br>GGACACTGTTCGCGTGCCCCTCGTCAAAGCCGGAGTGGTCGTGCTGCGCCGGACCCGACCCGACCTTCAGCGGGGGTTCACAGCTCCGTGGGTGCCGTTACTTCCG<br>ATCGCCGCAGTGTGCGCGTGCCTGTGGCTGATGCTGAACCTCACCGCGTTGACTTGGATCCGGTTCGGGATCTGGCTGGTGGCCGGAACCGCGATTTATGTCNGCT<br>ACGGGCGCCGGCACTCGGCGCATGGCCTTCGGCAAGCNCNANANAACGCGACCCGGAGGTGTTGAACTAGCTTCGCCGCGTATTTACAAATTGCNTTATATGTCTA<br>CACATAAGACGCAAACTGCTCTATTGTCAANTCCCANCGTGGTGTGGCNCATGAAGATGTTTGG | (SEQ ID NO. 684) |
| Clone Rv94 | :::::::::::::Rv94SP6.seq:::::::::::::<br>TCCTTCTCGGTATCGGTTTGGGCTGTCACCANCAGTTGGTAGTTCTTCACGTNCTGTTGTTCGAGCGTCNAGCCGTCGCGCGTGTCNANGTCNCCGGACGCGTATC<br>CCGCCAGGCCGGTCANGGTGCCCTTCCANTCCACGCCGCTGTGGTCGGCGAACGCTNATCTTCAATCGAGACCATCGCCAGCTTCATCNTGTTGGCGATCTTGTCN<br>NACGGCACCTCNAACCGGCGCTNCTAGTACNCCACNCNATCNTGTTNCCTTCNCGTCNACATCCTCGATNCCNCNTGCACTTTCCCTCGANCNCCTGGGCCGAGCC<br>GTTGGCANTNACCTCNGAGCCCCATTGGACATCANCCCANCCCGCCTGCGAACGGGAACGTCAGCNCNCTGGCGACAACCTGGCCAACAN | (SEQ ID NO. 685) |
| | :::::::::::::Rv94T7.seq:::::::::::::<br>CACNCCGTGATCGCNAGCCCCNGTAGAAATNGTTGAGCCAGTTGGTGCGGCGCTCGTTGCCGGCGGTNATCTCGTCGAGCTCNTCTTCCATCGCCGCGGTGAAGTC<br>GTACTCGACNCGCCGACCNAAATGCTGCTCNAGCAGACCGGTTACCNNNAACNCCNCCTCNTGACNGCACCAGTGCNCTGCCCTTCTTGTGCACGTACCCGCNATC<br>CTGGATGGTCTTGATGATCNACTANTNTGTCGACGGGCGGCCGATGCCCATCTCCTCNAGCGCTTTGACCAGCGACNCCTCGGTGTATCGGGCCGGCGGGTTNGTG<br>GCATGGCCGTCTGGGGTCANCTCNACNATNTTCANCCGTTGACCCGGGGTCACA | (SEQ ID NO. 686) |
| Clone Rv95 | :::::::::::::Rv95SP6.seq:::::::::::::<br>TGGCCTTCTTGNCANGGGCNNACATNNGCTATNGCGAGCGTGTAACCGATCATCNTCCNGGCGACTGTGGCCTGANCGGCAAGGGTNGCCTNATTCNTCCTCCTGN<br>GGCATGGTTNCCACACGGAATGNCGGTAAGTCTGGTCGGCAACCTGGCCCGCTGCGGGTTGGGTTCGGATTCGCTCGGCTANTAAGGTGCTCGCCTGGTGTNACNA<br>CTAATCNCNATATACNCTTANCGGGAGTNGNCGTCCCGATCCTNGCCCTGCCGCNGGCGATCNCGTTCGCANCACCGCCACCGGAACTCNCAANGTGCGCTCATCG<br>GGCTCTACGCGCCATCTTCCCCGGATTCTTCGCGGCNGNGTNCCGNGGGACCCCGGACTGTGACNGGCCCAACGGCTCATCATCG | (SEQ ID NO. 687) |
| | :::::::::::::Rv95T7.seq:::::::::::::<br>CCGGATAGCGGTGTCTGAACTTCGCCCGTTCCCTCCANCGCATTGAGCTTCAGCCCGACCGGCAGGTNNGGAGTCGGCATGCGGTCCTTCGCCCCGACCCCGCTGG<br>CTAAATANCCACCCCCGAGCGCGGTCACGGTCTTTGCACCGGGACGACGCATACCGGCAGCGCGAACATCNCCGCGGGCTGCAGCNTGAACGTCCAATACCANTCN<br>AACAGTGTCCGCGCGTNAAAACCCGANCCGGCGGTCGCTTCNGTAATCAACGGCTCCTGCGCAACCAGCTGCAAGTCGCCGGTGCCACCGGCGTTGACGATCTTCA<br>TGTCTGCGANCTCGCGCACCAGCTCGACGGCCCGGGCA | (SEQ ID NO. 688) |
| Clone Rv96 | :::::::::::::Rv96SP6.seq:::::::::::::<br>CCTCCCGACCACATACAGGCAAAGTAATGGCATTACCGCGAGCCATTACTCCTACGCGCGCAATTAACGAATCCACCATCGGGGCAGCTGGTGTCGATAACGAAGT<br>ATCTTCAACCGGTTGAGTATTGAGCGTATGTTTTGGAATAACAGGCGCACGCTTCATTATCTAATCTCCCAGCGTGGTTTAATCAGACGATCGAAAATTTCATTGC<br>AGACAGGTTCCCAAATAGAAAGAGCATTTCTCCAGGCACCAGTTGAAGAGCGTTGATCAATGGCCTGTTCAAAAACAGTTCTCATCCGGATCTGACCTTTACCAAC<br>TTCATCCGTTTCACGTACAACATTTTTTAGAACCATGCTTCCCCAGGCATCCCGAATTTGCTCCTCCATCCACGGGGACTGAGAGCCATTACTATTGCTGTATTTG<br>GTAAGCAAAATACGT | (SEQ ID NO. 689) |
| Clone Rv9 | :::::::::::::Rv9SP6.seq:::::::::::::<br>CTTCACNTCCGTACGGCTCGGGTACGCTTCGGTCNCATTGTGCGAGTGATAGATGACGACCGGGACCTCGTCGGCATCTTCCATAGCCCGCCACACCTTCAGTTGC<br>TCACCGGAATCCAACCGGTANAAGGTCGGCGANCGCTCNGCATTGGTCATCGGGATATGCCGCTCGGGACGGTCANAGCCCTCGGGTCCGGCCAGCACTCCGCAGG<br>CTTCGTCGGGGTGGTCGCGACGCGCATGGGCCACCATCGCATTCACCAGGTCTGCGCGAATCACCAGCACGTANACGGTTCCTTTCCTAAGCAACACCGAANTTTC<br>AGGACCCGAATGCTCCGGGAAACATGTCACGGTAGGTCGGTATTCCGGCTACCGGCTGANCATTGAGCACGCCGGCCAGCACCGCACGAACCAGGCAATCAGCCGC<br>CGCCGCACCCGACCGCGG | (SEQ ID NO. 690) |
| | :::::::::::::Rv9T7.seq:::::::::::::<br>CAGGCATGCAAGCTTGATGCCGCCGAAACCGAGCGTGAGCACGCCGCCAGCCACCACGCGCGGGTCGGGCGCCGGGCCCGGGCCGCCAGGCTGCTCCGCTCGGTGA<br>TGGCACGCCACCGCGACACCACCCGGCTGCGCTACGTCGAGCCATACCGGGCGGAGCTACATCGGCTCGGCCGCCCAGTGTTCGGGCCCTCTTTCGAGGTCGAGGT<br>CGATACCGATTTGCGCATCCGCAGCCGCACCCTGGACGACAGAACCGTGCCCTACGAATTGCTTGTCGGGCGGGGCCAAAGAACAGCTTGGCATCCTGGCGCGATT<br>GGCCGGCGCGGCGCTGGTCGCCAAGGAAGACCCGTTCCGGTGCTGAT | (SEQ ID NO. 691) |

TABLE 4

End sequences of the polynucleotide inserts cloned in the named recombinant BAC vectors contained in the I-2049 *M. bovis* strain Pasteur genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

Clone X0001
::::::::::X0001SP6.seq:::::::::
AAG-
TCGGGTTTCCACACGCGCGGTTTGACCCTAGTCATATGTAATCATGTGTACCATGTGCGGGCGCTTTTCGACGGC
CGCGAACCACCGGA-ATTTCCTGTGATTTCACTGCATGCGTACCATCTGGCACAATTGAGCA-TTGTCT-TCGCGG
TGGTCGG-CGGGTTGCGTGCCGCCTGCTGCGA-ATGCACCA-TAAGCCCGAACCCACCGGCTTGGTGACCACCGC
ACGCTGCGTGTGGGGGTAACCACTCCGCGACCCCAAGGATGGTCATTTCCAATGAACCGGCTGGACTTCGTCC
A-A (SEQ ID NO. 692)

::::::::::X0001T7.seq::::::::::
GTCGCGGTTCGATCGACCCGATCTTCACCTCGTAACCTCGATGCTTAGCAGGATCCAGCTTGACCGCGTTTGGCT
CTACCCACTCTTTGAGTGGCGCCGTCGCCTGTGCCCCATCGGTGTTCATGACGAACGCTTCGAAAGACTTCCTCT
TGTGAGCCGGAATGTCTGCGTAAAGAAGTTCCATGTCCGGGAAGTAGACCCGGTCGCCCTCCACGTGGTACTCC
TTCGAGGTCCGCTTCTCGCCGGATCCGATAAACACCGGCCCCAGGCACCGCAGCGTGAGTTCGAACGGCTTCAG
GTAGGTGTTCATGCGGCGGACTCCGGGAGTGCGAGAAATAGCGGTCGCGCGTAGCTGTAGACCGGATGGTTTCC
GCCCAGGCTGACGTCGAAGATGCCTCCTTGGAAGGGGCGCGA (SEQ ID NO. 693)

Clone X0002
::::::::::X0002SP6.seq:::::::::
AACTCAAGTTTTTACGGTGATCGCGCATCACCTGGTTCATGAACTGGAAGCAGCGCAGCGCTTCCTTTTCGGCCG
CAACATGAGCCAGCCTCTCGTCGGCGGTCGGGTGCAGGTGCTCGGGCAGCTCGGCCGCGACAGCCGCCTGACC
CTGAAACCAGCTTCCATATCCCGCGAC-
AACGACGCCAGTCCGCTACGTAACCCCTCCGCGACTGTCCATGGACAACAGCGCGTTCTCCACCGACCGGGCCC
GGGTGT (SEQ ID NO. 694)

::::::::::X0002T7.seq:::::::::
GTGCAGGTTTCGACAATGTGGTGCCGGTTCGGCGGCTACGTGCCATCGAGACACTGGCGCA-GCTATCGCACCC
GTTATCGGCTGCGAGCAAATCGCGGTATGCGTTCTTGAGCATGAGTCGGCGACCGTCGTCATGGTCGACACCCA
CGACGGAAAGACGCAGATCGCCGTCAAGCATGTGTGCCGCGGATTATCAGGACTGACCTCCTGGCTGACCGGCA
TGTTTGGTCGCGATGCCTGGCGCCCGGCCGGCGTGGTCGTGGTCGGCTCGGATAGCGAGGTCAGCGAATTCTCG
TGGCAGCTCGAAAGGGTCCTGCCGGTGCCGGT (SEQ ID NO. 695)

Clone X0003
::::::::::X0003SP6.seq:::::::::
TTCGAGTCATGCGCCCGCCTCGACCACGAA-ATGCACGTCGGGTTCGATCGACCCGATCTTCACCTCGTAACCTC
GATGCTTAGCAGGATCCAGCTTGACCGCGTTTGGCTCTACCCACTCTTTGAGTGGCGCCGTCGCCTGTGCCCCAT
CGGTGTTCATGACGAACGCTTCGAAAGACTTCCTCTTGTGAGCCGGAATGTCTGCGTAAAGAAGTTCCATGTCC
GGGAAGTAGACCCGGTCGCCCTCCACGTGGTACTCCTTCGAGGTCCGCTTCTC (SEQ ID NO. 696)

::::::::::X0003SP6.seq:::::::::
GTCATGTGTACCATTTGCGGGCGCTTTTCGACGGCCGCGAAACACCGGAGATTTCCTGTGATTTCACTGCATGCG
TACCGTCTGGCACAATTGAGCAGTTGTCTGTCGCGGTGGTCGGCCGGGTTGCGTGCCGCCTGCTGCGAGATGCA
CCAATAAGCCCGAACCCACCGGCTTGGTGACCACCGCACGCTGCGTGTGGGGGTAACCACGCCGCGACCCCA
AGGATGGTCATTTCCAATGAACCGGCTGGACTTC-TCAACAA (SEQ ID NO. 697)

Clone X0004
::::::::::X0004T7.seq:::::::::
AACAGCGCGGTTGAACTGATAGGTGCGGCCCGGCTCGAGCAGGCCGGGCCATTTGTTCGATGCGGTTACCGAAA
GATCTCTTCGGTGACCTGCCCGCCGCCGGCCAGCTCGGCCCAGTGCCCGGCGTTGGCCGCCGCGGCGACGATCT
TGGCGTCCACGGTGGTCGGGG (SEQ ID NO. 698)

Clone X0006
::::::::::X0006T7.seq:::::::::
GCATCTGGGCTGGCGGTGGTTCGCCGCTCCGAAGCCGTCGAACACCATCGCCAGCGCGGCTTCCACATCAACGA
CCATTTCGGCCAGCTTGCGGCGCATCAGCGGCTTGTCGATGAGCGCCCCACCGAATGCCCGCCGCTGCCCGGCG
TA-CACAGCGATTCGACCAGCGCGGCGCGCGTTGCCGAGGGCGAACGAAGCGGTGCCCAACCGCAATCTGTT
GGTCAGCTCCATCATGCGGGTGAGTCCCTTGCCG (SEQ ID NO. 699)

Clone X0007
::::::::::X0007SP6.seq:::::::::
ATCGGTTTCCAGCAACAGCCGATCGACGGCTTCGCCCA-GGCCGCTCCCGGGCGACCCGACCATTGCTGTCGCC
GCGTAACGCCATCACGGATGACGCGCAGTTCGTCGCTGTCTAGCTCCACCATCGCCTGCACACCGGCGGCCAG-
ACCCATTGGCCGTCGCACTCGTA-
AGCAGGTAATCCTCGTCGACGGACTCGGTAACCACCGCCGCCAGCTCCGCTGCCAGGTCGGCGGGGTTGACACC
GGCGGGCATCGGGATGGACGACGACGCGGTGCTGACGGCGCCTGTC (SEQ ID NO. 700)

::::::::::X0007T7.seq:::::::::
AGCGGTTTCCCA-GCGATGTGCTGTGAGCGCCGCACCACCAGCGCCGACGCTAAGGATGGAACGCACGGCAT
CTTCTGACGCGTAACCGCGTTGTGATCGCGAGCTGAGGAGACGGTATGGGGAGGGTTCTCGGAGGCCATCTGG
GATGTTGATGTCTGTCGATCTTGAGCCGGTGCAACTCGTCGGCCCGGACGGTACGCCGACGGCCGAACGCCGCT TABLE 4-continued End sequences of the polynucleotide inserts cloned in the named recombinant BAC vectors contained in the I-2049 *M. bovis* strain Pasteur genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

ACCACCGTGACCTTCCTGAGGAAACGCTGCGTTGGCTCTACGAGATGATGGTGGTCACCCGCGAGCTGGATACC
GAATTCGTCAATCTGCACG (SEQ ID NO. 701)

Clone X0008
::::::::::X0008SP6.seq:::::::::
CAAGCTTCCACAGGTAGGGATCGAGGAACAGCGCGTTGAACTGATAGGTGCGGCCCGGCTCGAGCAGGCCGGC
CATTTGTTCGATGCGGTTACCGAAAATCTCTTCGGTGACCTGCCCGCCGCCGGCCAGCTCGGCCCAGTGCCCGG
CGTTGGCCGCCGCGGCAACGATCTTGGCGTCCACGGTGGTCGGGGTCATGCCCGCGAGCAGGATCGGCGAGCG
GCCGGTCAGCCGGGTGAACTTCGTCGAAAGCTTGACCCTGCCGTCGGGGAGGCGAACCACGGTCGGTGCGTAN
CTCCACCAAGCCCGGGCAACCTCGGGGGTGGCGCC (SEQ ID NO. 702)

::::::::::X0008T7.seq:::::::::
TGGACCTCATGACAACGCGGCGGCGATTACCCCCGCTACCGCCAGCAGCATGACGGCGGTAGCGAACACCGCC
GGATGCAGCGCAGGTGCGTCGATGTGCTCACGGAATCGCCCCGGCACCGCGATCTCGAGGATCACCAGTGCCAC
CCCCTGCAGCGCGACACCGACGATTCCGTACACCGCCACGCCGATCAGGCCCTGGGCCAGCTGGCGTATATGGC
GGCGATGGTGACGATGGCCAGCGCCACATACATTGTGGCGGCCAGAACCACGGCGTTGGGGCGGCGGTCGATG
AACACTAGGCGACGCAGATCGCCCGGGGTCAACAGGTTGACCATCAGAAAGCCTGCGA (SEQ ID NO. 703)

Clone X0009
::::::::::X0009SP6.seq:::::::::
TTTGGTGCGGCCGGCAATCAACTTC-
GCTC-CAGCGGTITCCCAGGCGGGATGTGCTGTGAGCGCCGCACCACCAGCGCCGACGCTAAGGATGGAACGCA
CGGCATCTTCTGACGCGTAACCGCGTTGTGATCGCGAGCTGAGGAGACGGTATGGGGGAGGGTTCTCGGAGGC
CATCTGGGATGTTGATGTCTGTCGATCTTGAGCCGGTGCAACTCGTCGGCCCGGACGGTACGCCGACGGCCGAA
CGCCGCTACCACCGTGACCTTCCTGAGGAAACGCTGCGTTGGCTCTACGATATGATGGTGGTCACCCG
(SEQ ID NO. 704)

::::::::::X0009T7.seq:::::::::
CGCCCAGGGCCGCTCCCGGGCGACCCGACCATTGCTGTCGCCGCGTAACGCCATCACGGATGACGCGCAGTTCG
TCGCTGTCTAGCTCCACCATCGCCTGCACACCGGCGGCCAGGACCCATTGGCCGTCGCACTCGTAGAGCAGGTA
ATCCTCGTCGACGGACTCGGTAACCACCGCCGCCAGCTCCGCTGCCAGGTCGGCGGGGTTGACACCGGCGGGC
ATCGGGATGGACGACGACGCGGTGCTGACGGCGCCTGTCGCGACGCTGAGCTCGGACACAGCTAGTAAATGTA
GCCTAACCTACTTAATGGGTCGCAGCCCCCCGGGGTCGTCGCATGTCCAACGTTGCTCGACTGGAAGAAAATGC
TCGTCGGGGAGCAAATGGCACC (SEQ ID NO. 705)

Clone X0010
AATACTCAATCCTTGATCGGTTTCCAGCAACAGCCGATCGACGGCTTCGCCCAGGGCCGCTCCCGGGCGACCCGA
CCATTGCTGTCGCCGCGTAACGCCATCACGGATGACGCGCAGTTCGTCGCTGTCTAGCTCCACCATCGCCTGCA
CACCGGCGGCCAGGACCCATTGGCCGTCGCACTCGTAGAGCAGGTAATCCTCGTCGACGGACTCGGTAACCACC
GCCGCCAGCTCCGCTGCCAGGTCGGCGGGGTTGACACCGGCGGGCATCGGGATGGACGACGACGCGGTGCTGA
CGGCGCCTGTCGCGACTCTGAGCTCGG (SEQ ID NO. 706)

::::::::::X0010T7.seq:::::::::
GGATGTGCTGTGAGCGCCGCACCACCAGCGCCGACGCTAAGGATGGAACGCACGGCATCTTCTGACGCGTAACC
GCGTTGTGATCGCGAGCTGAGGAGACGGTATGGGGGAGGGTTCTCGGAGGCCATCTGGGATGTTGATGTCTGTC
GATCTTGAGCCGGTGCAACTCGTCGGCCCGGACGGTACGCCGACGGCCGAACGCCGCTACCACCGTGACCTTCC
TGAGGAAACGCTGCGTTGGCTCTACGAGATGATGGTGGTCACCCGCGAGCTGGATACCGAATTCGTCAATCTGC
AGCGCCAGGGGGAAGCTGGCGTTGTACACGCCCTGTCGCGGGCAGGAAGCCGCGCAGGTGGGTGCGGCGGCTT
GCCTACGCAAAACCGACTGGTTGTTCCCC (SEQ ID NO. 707)

Clone X0012
::::::::::X0012SP6.seq:::::::::
ATCACGACAACAGCGACGGTGTGTCGGATCAGCGGCCCCCGTTGCCGGGCAATGTTGAGGCGTTTCTGCGTCTG
GTTGAGGCCGGCTGGGAC-
CCGAGGTGGCTCGTCGGCCACATGGGCAGCACACCACCGTGGTGATGCATCTAGACGTGCAGGACCGTGCCGCT
GGCCTGCA (SEQ ID NO. 708)

::::::::::X0012T7.seq:::::::::
GCGGCTACGTGCCATCGAGACACTGGCGCAGGCTATCGCACCCGTTATCGGCTGCGAGCAAATCGCGGTATGCG
TTCTTGAGCATGAGTCGGCGACCGTCGTCATGGTCGACACCCACGACGGAAAGACGCAGATCGCCGTCAAGCAT
GTGTGCCGCGGATTATCAGGACTGACCTCCTGGCTGACCGGCATGTTTGGTCGCGATGCCTG
(SEQ ID NO. 709)

Clone X00013
::::::::::X0013T7.seq:::::::::
TACAAGCGGCACCTCGCCGGTGAACTGACCGTTCGCACGCTGCGCACCGCCGCCGGGCGCGTGCTCGGCGCGC
CGGCGGCCCCCGAGGCCTGAGAGGGGAACCAACCATGCAGGTGAACATGACGGTAAACGGCGAGCCCGTCACC
GCCGAGGTCGAACCCCGGATGCTGCTGGTCCATTTTCTCCGTGATCAGCTGCGGCTCACCGGAACTCACTGGGG
CTGTGATACCAGCAACTGCGGGACATGCGTGGTGGAGGTCGACGGCGTGCCGGTGAAATCCTGCACGATGCTCG
CCGTGATGGCCTCCGGGC (SEQ ID NO. 710)

TABLE 4-continued

End sequences of the polynucleotide inserts cloned in the named recombinant BAC vectors contained in the I-2049 *M. bovis* strain Pasteur genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

Clone X0014
::::::::::X0014T7.seq:::::::::
AGCGGCTGGTTACGACTCCCTGTITGTGATGGACCACTTCTACCAACTGCCCATGTTGGGGACGCCCG-
CC-TCCGATGCTGGAAGCCTACACTGCCCTTGGTGCGCTGGCC-C-GACCGAGCGGCTGCAACTGGGCGC-
TTGGTGAC-GCCAATACCTACCGCACCCC-ACCCTGCTGG-CAAA
ATCATCACCACGCTCGACTTGGTTAGCGCCGGTCGACGATCCTCGGCATTGGAACCGGTTGGTTT-
(SEQ ID NO. 711)

Clone X0015
::::::::::X0015SP6.seq:::::::::
ACGCGCGCCGATCATATCTGCTATGGATGTACAATTCAGCTCTTGCTGTTATACCAGTATATGGTGTACTATTTG
ATCTATGCTGACGTGTGAGATGCGGGAATCGGCCCTGGCTCGACTCGGCCGGGCTCTGGCTGATCCGACGCGGT
GCCGGATTCTGGTGGCGTTGCTGGATGGCGTTTGCTATCCCGGCCAGCTAGCTGCGCACCTCGGGTTGACCCGA
TCGAATGTGTCCAACCATCTGTCGTGTTTGCGGGGCGGGCTGGTA-
TCCCAACCTATGAGGGCCGGCAGGTTCGGTAT (SEQ ID NO. 712)

::::::::::X0015T7.seq:::::::::
CCGCGCTGCTGCTGACGTCGGTCGAACGTGCGACACGTCTGCGAATACCGGCCGAACGCTGGGTITATCCACAG
GCTGGCACCGACGCCCACGACACACCGGCCGTCGCCGACCGCCACCGACTGCATCGGTCGACGGCCATTCGGAT
CGCCGGTGCCCGGGCGCTGGAACTGGCTGGGCTGGGGCTCGATGACATCGAATACGTCGACCTGTATTCGTGCT
TTCCCTCCGCTGTCCAAGTCGCCGCAATCGAACTCGGCCTGGACACCGACGATCCTGCCCGCCCGCTGACCGTC
ACCGGGGGCCTGACCTTCGCCGGCGGGCCGTGGAGCAATTACGTCACGCACTCCAT (SEQ ID NO. 713)

Clone X0016
::::::::::X0016SP6.seq:::::::::
CAGGCGTGCAATGACCTGCACTGCGCCGGA-A-TCCCTAACCCACTAAACCGGGGCCGCTCACAAGCCGTGCAGC
TCGGTCAGCGTCAGGTGCGCGACCAGGAA-
TAAATGAGCAGACCCGTGCCGTCAACGATGGTGGCGATCATCGGCCCCGAAACGATGGCCGGGTC
ATGCGCAACTTCTTCAGCAGCGGCGGAAGGACGGCACCACCAGCGAC-ACCACACCACGAT
(SEQ lD NO. 714)

::::::::::X00016T7.seq:::::::::
GCGAA-CACTTCGTCAACTTCCAGGGCTGCCCGCACCAAGTATTTCGACGAGTATTTCCGTCGGGCCGCCGCCGC
CGGCGCGCGGCAGGTGGTCATCCTGGCGGCGGGGCTGGACTCGCGCGCGTACCGGCTGCCTTGGCCCGACGGG
ACCACGGTTTTTGAGCTGGACCGCCCGCAGGTCCTTGATTTCAAGCGCGAGGTGCTCGCCAGCCACGGTGCCCA
ACCGCGCGCCCTGCGCCGCGAGATCGCCGTCGACCTGCGTGACGATTGGCCACAAGCCTTGCGGGACAGTGGTT
TCGATGCGGCTGCACCGTCGGCATGGATTGCCGAAGGGCT (SEQ ID NO 715)

Clone X0017
::::::::::X0017SP6.seq:::::::::
TTGGGC-TTGCCC-CAATA-GGCCCCAATCAAAAGCCGAGCAGGTGGAACCTA-CGCATTCGCCTC-TCGT-TGTGC
ACCCGAGCCATCGCACGCGCGGGAATTCCCGGAT-TC-CCGTATTCTCCGGCGGCCGGGCTAACCCATCCCA-GCC
GAACGGTTGGCTC-TGCCGTGGGTCCCGTGTTGGCCGATCGGGGCGTCACCGGGGGTGCTCGGGTGCGG
TGACCATGGC-AACTGCCCC-ATGGGCCGACCCTGGTGCAGATAAACCTG (SEQ ID NO. 716)

::::::::::X0017T7.seq:::::::::
TGGTGGAGGTCCCCACCAA-ACCCGGCCGTAACTCTGCTCACGGAAATGCGG-CAGGCCGCGCGTAGCACGTGGT
ATCCGCCATAAAGGTGCACCTTAAGCACGGCGTCCCAATTCTCGAACGACATCTTGTGGAAGGTGCCGTCGCGC
AAGATCCCGGCGTTGCTCACCACACCGTGCACGGCGCCGAATTCGTCAAGCGCGGTCTTGATGATGTTCGCTGC
GCCGTCCTCGGTGGCGACGCTGTCGGTA-TTGGCGACCGCCCGGCCCCCCTTGTCGCGAAATCTCGGCGACGAC
CTCATCGGCCATCGCCGAACCGGGCCCCCG (SEQ ID NO. 717)

Clone X0018
::::::::::X0018SP6.seq:::::::::
GCCGGCCAAACTGGCCGGCGGGGTTGCTGTC-TCAAGGTGGGTTCCGCCACCAA-ACC
CACTCAAGGATCGCAAGGAAAGC-
TCAAGGATGCGGTCGCGGCCGCCAAGGCCGCGGTCAAGGAGGGCATCGTCCCTGGTGGGGA-CCTCCCTCATC
CACCAGGCCCGCAAGGCGCTGACCGAACTGC-TGCGTC-C-GACCGGTGACAA-GTCCTCGGTGTCCACGTGT-CTC
CGAAGCCCTTGCCGCTCCGTTGTTCTGGATC-CC-CCAAC-CTGGTTGGACGGCTC
GTGGTGGTCAACAAGGTCAGCGAGCTACCCGCCGGGCATGGGCTGAACGTGA (SEQ ID NO. 718)

Clone X0018
::::::::::X0018T7.seq:::::::::
CGAACCT-
AATTGTCCTGTAATGCCCAGCTCACCAA-GCATGGCTGGTGGCCGGGGCGGTGAAGCCGGCGTCTGCGGCACCG
TCCAACTC-ATGTGGAT-GCCGGAATGGGGATGTCCGG-ACGGCGAATCCGTA-
TTCGCTTGTCCCGTGAGGCCCAGGTGGATGGGGGGAAGGATC-TGGTGTCCGGGATGAT
ATGGGGCCGATGCCGCCGGTTGAAGTCCACTGGATCGGGAATTCGGGAATCGTGAT
CCGACGTTCAGGCCGAAC (SEQ ID NO. 719)

TABLE 4-continued

End sequences of the polynucleotide inserts cloned in the named recombinant BAC vectors contained in the I-2049 *M. bovis* strain Pasteur genomic DNA library.
RvXXXSP6 corresponds to the SP6 endsequence of the clone RvXXX;
RvXXXT7 corresponds to the T7 endsequence of the clone RvXXX.
RvXXXIS 1081 corresponds to a region located close to a copy of the IS1081 repetitive sequence (Insertion element)
The character <<->> denotes an uncertain base residue.

Clone X0019
:::::::::X0019SP6.seq:::::::::
CTAACGGAATGAAAGCCCTGGTGGCCGT-TCGGCGGTGGCCGTCGTCGCACTGCTCGGTGTATCTTCCGCCCAAG
CTGATCCCGAGGCGGATCCCGGCGCAGGTGAGGCCAACTATGGTGGCCCCCCAAGTTCCCCACGTCTTGTCGAT
CACACCGAATGGGCGCA-
TGGGGAATTCTGCCCAGCCTCCGGGTCTACCCGTCCCAAGTTGGGCGTACA-CTCCCGCCGCCTCGGGATGGCC
GCTGCCGACCCGGCCTGGGCC-AGGTTCTCGCGCTGTCACCGGAAGCCGACACTGCCGGC (SEQ ID NO. 720)

:::::::::X0019T7.seq:::::::::
CCGCGGGACAC-CCTC-ATGCTGCCGCCATGGACGCGGTCGAACGCAAGCAGCTGATCGAGCTACAACGCCGCG
CGGAACGCTTCCGCCGCGGGCGTGACCGCATCCCGTTGACCGGGCGGATCGCGGTGATCGTCGATGACGGCATC
GCCACCGGAGCGACGGCCAAGGCGGCGTGCCAGGTCGCCCGGGCGCACGGTGCGGACAAGGTGGTGCTGGCG
GTCCCGATCGGCCCA-ACGACATCGTGGCGAAGATTCGCCGGGTACGCCGATGATGTGGTGTGTTTGGCGACGC
CGGCGTTGT (SEQ ID NO. 721)

Clone X0020
:::::::::X0020T7.seq:::::::::
CTCTGGGACCGGCCACGGTGCC-CCGGCGTTCCCGGACGTGCTGCGCCAGGTGTCCGGCGGCCGCGTGCATGGT
GTTCCCGGATCGGCCGCTGGCCAGAGCCCACCGGTGAATCTGGCGCCTGGCCGACCACCGTGCGCCGTAGGCTT
GCGATCGTGCAGCGCTGGCGTGGCCAGGACGAGATCCCGACGGATTGGGGCAGATGCGTGCTCACCATCGGGG
TATTTGACGGCGTGCACCGCGGGCACGCCGAACTGATCGCGCACGCGGTCAAAGGCGGC (SEQ ID NO.722)

Clone X0021
:::::::::X0021SP6.seq:::::::::
AATACTCAAGCTTTCGTCAGTTCATTGCGCCAGCAGACCAACAA-AGCATCGGGACATACGGA-TCAACTACCCG
GCCAACGGTGATTTCTTGGCCGCCGCTGACGGCGCGAACGACGCCAGCGACCAC-TTCAGCAAATGGCCA-CGCG
TGCCGGGCCACGAGGTTGGTGCTCGGCGGCTACTCCCAGGGTGCGGCCGTGATC-ACATC-TCACCGCCGCACCA
CTGCCCGGCCTCGGGTTCACGCAGCCGTTGCCGCCCGCAGCGGAC-
ATCACATCGCCGCGATCGCCCTGTTCGGGAATCCCTC-GGCCGCGCTGGCGGGCTGATTAAC
(SEQ ID NO. 723)

:::::::::X002lT7.seq:::::::::
TGCCGCGGATTTGGCTGGGTGCCCAATATTCAGAATCGGGCCTTTCTTTTTGCGCGACAATAAGGTCACAGTAAA
CCCTCGTTTTGTGAGATGCGGCCCGGGCCGGGCGAA-TCGACCTCGAGTGAATGGATCTCGAGTGAATGGACAG
GGCATCGCCTACGAGTCGCATCCCCATCCAACAGACCGGTGCTCTTGCATCGGACCCTGAAGGTCCCGCACGGA
GGGTGTGGTTGCCGGCGCGGGGTCACGGTGCGGTAGCGACGTAGTGTTTGAACGAATTTCTTGATGCTCCAACC
TGTITGGTGTTCAATCCAGTTCT (SEQ ID NO. 724)

Clone X0175
...X0175SP6...
AA-CTTGCGCGCTCGGCCGGGTC-AGCATCCAGCTGCTCGGCAAGGAGGCCAGCTACC-TCGCTGCGTATGCCCA
GCGGTGAGATCCGCCGGGTC-ACGTCCGCTGCCGCGCGACCGTCGGCGAAGTGGGCAATGCCGAGCAGGCAAAC
ATCAACTGGGGCAAGGCCGGTCGGATGCGGTGGAAGGGCAAGCGCCCGTCGGTCCGGGGCGTGGTGAT-AACC
CGGTC-ACCACCCGCACGGCGGTGGTGAGGGTAAAACCTCCGGCGGCCGTCACCCGGTTAGCCCGTGGGGCAA
(SEQ ID NO. 725)

...X0175...
A-TCGAAAGTGACCATCTCTACCTTGAGTGCCATACCGCCCGACCCTATGCCTCGGATAGCTCGGCGGAAAGAAA
CGCTTGCAGTGCCGCCGAATAGGCGGCTACGTCGTGAGCGCCCATCAACTCTCGCGCGGAGTGCATCGCCAGCT
GGGCGGCGCCGACGTCGACCGTGGGGATTCCGGTGCGCGCCGCGGCCAACGGCCCGATCGTCGACCCGCACGG
CAGATCGGCGCGATGTTCGTAACGCTGCAThGGCACTCCCGCGCGCTGGCAGGCCAGTGCGAACGCCGCCGCG
GTGCGTCCG (SEQ ID NO. 726)

References

Altschul, S. F., W. Gish, W. Miller, E. W. Myers, and D. J. Lipman. 1990. Basic local alignment search tool. J. Mol. Biol. 215:403–10.

Balasubramanian, V., M. S. Pavelka, Jr., S. S. Bardarov, J. Martin, T. R. Weisbrod, R. A. McAdam, B. R. Bloom, and W. R. Jacobs, Jr. 1996. Allelic exchange in Mycobacterium tuberculosis with long linear recombination substrates. J. Bacteriol. 178:273–279.

Barany F., 1991, Proc. Natl. Acad. Sci. USA, 88:189–193.

Bensimon, A., A. Simon, A. Chiffaudel, V. Croquette, F. Heslot, and D. Bensimon. 1994. Alignment and sensitive detection of DNA by a moving interface. Science. 265:2096–2098.

Bergh, S., and S. T. Cole. 1994. MycDB: an integrated mycobacterial database. Mol. Microbiol. 12:517–534.

Bimboim, H. C. and J. Doly. 1979. A rapid alkaline extraction procedure for screening recombinant plasmid DNA. Nucleic Acids Res. 7:1513–1523.

Burg J. L. et al., 1996, Mol. and Cell. Probes, 10:257–271.

Cai, L., J. F. Taylor, R. A. Wing, D. S. Gallagher, S. S. Woo, and S. K. Davis. 1995. Construction and characterization of a bovine bacterial artificial chromosome library. Genomics. 29:413–425.

Canard, B., and S. T. Cole. 1989. Genome organization of the anaerobic pathogen Clostridium perfingens. Proc. Natl. Acad. Sci. USA 86:6676–6680.

Chu B. C. F. et al., 1986, Nucleic Acids Res., 14:5591–5603.

Chuang S. et al., 1993. Global regulation of gene expression in Escherichia coli. J. Bact., 175(7): 2026–2036.

Chuang, S., D. L. Daniels, and F. R. Blattner. 1993. Global regulation of gene expression in *Escherichia coli*. J. Bacteriol. 175:2026–2036.

Cole, S.T., R. Brosch, K. Eiglmeier, T. Garnier, S. V. Gordon, C. Churcher, D. Harris, K. Badcock, D. Basharn, D. Brown, T. Chillingworth, R. Connor, R. Davies, K. Devlin, T. Feltwell, S. Holroyd, S. Gentles, K. Jagels, J. McLean, S. Moule, L. Murphy, K. Oliver, J. Osborne, J. Parkhill, M. Quail, M-A. Rajandream, J. Rogers, S. Rutter, K. Seeger, J. Skelton, R. Squares, S. Squares, J. Sulston, K. Taylor, S. Wlitehead and B. G. Barrell. 1997. Genome Sequence of Mycobacterium tuberculosis H37Rv. Microbial Comparative Genomics, 2:174.

Collins, D. M., and D. M. Stephens. 1991. Identification of an insertion sequence, IS1081, in Mycobacterium bovis. FEMS Microbiol. Lett. 67:11–15.

Cousins D. et al., 1998, 36(1): 168–170.

De Wit D. et al., 1990, J. Clin. Microbiol., 28: 2437–2441.

Dear, S., and R. A. Staden. 1991. Sequence assembly and editing program for the efficient management of large projects. Nucleic Acids Res. 19:3907–3911.

Duck P. et al., 1990, Biotechniques, 9:142–147.

Guateli J.C. et al., 1990, Proc. Natl. Acad. Sci. USA, 87:1874–1878.

Kievitis T. et al., 1991, J. Virol. Methods, 35:273–286.

Kim, U. J., B. W. Birren, T. Slepak, V. Mancino, C. Boysen, H. L. Kang, M. I. Simon, and H. Shizuya. 1996. Construction and characterization of a human bacterial artificial chromosome library. Genomics. 34:213–218.

Kwoh D.Y. et al., 1989, Proc. Natl. Acad. Sci. USA, 86:1173–1177.

LandegrenU. et al., 1988, Science, 241:1077–1080.

Liu, Y. G., and R. F. Whittier. 1995. Thermal asymmetric interlaced PCR: automatable amplification and sequencing of insert end fragments from P1 and YAC clones for chromosome walking. Genomics. 25:674–681.

Lizardi P. M. et al., 1988, Bio/technology, 6:1197–1202.

Matthews J.A. et al., 1988, Anal. Biochem., 169:1–25.

Michalet, X., R. Ekong, F. Fougerousse, S. Rousseaux, C. Schurra, N. Hornigold, M. Vanslegtenhorst, J. Wolfe, S. Povey, J. S. Beckmann, and A. Bensimon. 1997. Dynamic molecular combing—stretching the whole human genome for high-resolution studies. Science. 277:1518–1523.

Misumi, D. J., D. L. Nagle, S. H. McGrail, B. J. Dussault, Jr., J. S. Smutko, H. Chen, O. Charlat, G. M. Duyk, C. Ebeling, L. Baldini., G. A. Carlson, and K. J. Moore. 1997. The physical and genetic map surrounding the Lyst gene on mouse chromosome. Genomics. 40:147–150.

Pavelka, M. S., Jr., and W. R Jacobs, Jr. 1996. Biosynthesis of diaminopimelate, the precursor of lysine and a component of peptidoglycan, is an essential function of Mycobacterium smegmatis. J. Bacteriol. 178:6496–6507.

Philipp, W. J., S. Nair, G. Guglielmi, M. Lagranderie, B. Gicquel, and S. T. Cole. 1996a Physical mapping of Mycobacterium bovis BCG pasteur reveals differences from the genome map of Mycobacterium tuberculosis H37Rv and from M. bovis. Microbiology. 142:3135–3145.

Philipp, W. J., S. Poulet, K. Eighneier, L. Pascopella, V. Balasubramanian, B. Heym, S. Bergh, B. R. Bloom, W. R. Jacobs, Jr., and S. T. Cole. 1996b. An integrated map of the genome of the tubercle bacillus, Mycobacterium tuberculosis H37Rv, and comparison with Mycobacterium leprae. Proc. Natl. Acad. Sci. USA. 93:3132–3137.

Poulet S. et al., 1995, Arch. Microbiol., 163: 87–95.

Ross BC, 1992, J. Clin. Microbiol., 30: 942–946.

Sambrook, J., E. F. Fritsch, and T. Maniatis. 1989. Molecular cloning: a laboratory manual, 2nd ed. Cold Spring Harbor Laboratory, NY: Cold Spring Harbor. N.Y.

Sanchez-Pescador R., 1988, J. Clin. Microbiol., 26(10) :1934–1938.

Segev D., 1992, in <<Non-radioactive Labeling and Detection of Biomolecules>>. Kessler C. Springer Verlag, Berlin, New-York, 197–205.

Sheng, Y., V. Mancino, and B. Birren. 1995. Transformation of Escherichia coli with large DNA molecules by electroporation. Nucleic Acids Res. 23:1990–1996.

Shinnick T. M. et al., 1987, J. Bact., 169(3): 108–1088.

Shizuya, H., B. Birren, U. J. Kim, V. Mancino, T. Slepak, Y. Tachiiri, and M. Simon. 1992. Cloning and stable maintenance of 300-kilobase-pair fragments of human DNA in *Escherichia coli* using an F-factor-based vector. Proc. Natl. Acad. Sci. USA. 89:8794–8797.

Spargo C. A. et al., 1996, Mol. and Cell. Probes, 10:247–256

Stone B. B. et al., 1996, Mol. and Cell. Probes, 10:359–370.

Trieselman B.A. et al., 1992. Transcriptionnally active regions in the genome of the archaebacterium Haloferax volcanii. J. Bact., 174: 30–34.

Trieselmann, B. A., and R. L. Charlebois. 1992. Transcriptionally active regions in the genome of the archaebacterium Haloferax volcanii. J. Bacteriol. 174:30–34.

Urdea M. S. et al., 1991, Nucleic Acids Symp. Ser., 24:197–200.

Urdea M. S., 1988, Nucleic Acids Research, 11: 4937–4957.

Van Soolingen D., 1993, J. Clin. Microbiol., 31: 1987–1995.

Willets, N., and R. Skurray. 1987. Structure and fimction of the F-factor and mechanism of conjugation. In Escherichia coli and Salmonella Typhimurium: Cellular and Molecular Biology (F.C. Neidhardt, Ed) Vol.2 ppl 10–1 133, Am. Soc. Microbiol., Washington, D.C.

Woo, S. S., 3. Jiang, B. S. Gill, A. H. Paterson, and R. A. Wing. 1994. Construction and characterization of a bacterial artificial chromosome library of Sorghum bicolor. Nucleic Acids Res 22:4922–4931.

Zimmer, R., and A. M. V. Gibbins. 1997. Construction and characterization of a large-fragment chicken bacterial artificial chromosome library. Genomics. 42:217–226.

What is claimed is:

1. A purified polynucleotide consisting of SEQ ID NO:1.

2. A purified polynucleotide, comprising SEQ ID NO:2.

3. A purified polynucleotide, comprising SEQ ID NO:3.

4. A purified polynucleotide comprising SEQ ID NO:4.

5. A purified polynucleotide comprising SEQ ID NO:5.

* * * * *

UNITED STATES PATENT AND TRADEMARK OFFICE

CERTIFICATE OF CORRECTION

PATENT NO. : 6,492,506 B1

DATED : December 10, 2002

INVENTOR(S) : Stewart Cole et al.

It is certified that error appears in the above-identified patent and that said Letters Patent is hereby corrected as shown below:

Title page,
Item [57], ABSTRACT,
Line 9, "a least" should read -- at least --.
Line 15, "*Mycobactetium bovis*" should read -- *Mycobacterium bovis* --.

Signed and Sealed this

Eighth Day of April, 2003

JAMES E. ROGAN
*Director of the United States Patent and Trademark Office*

SEQUENCE LISTING

```
<160> NUMBER OF SEQ ID NOS: 743

<210> SEQ ID NO 1
<211> LENGTH: 12732
<212> TYPE: DNA
```

-continued

<213> ORGANISM: Mycobacterium tuberculosis

<400> SEQUENCE: 1
acctgcgctt gcagagatca aatagggcgc atgggtcagc atagtacagg tcgtcgcgca 60
tctttgatgc atcggaataa gatgtcaggc aattaaaaga gaagccacgg cgactcgcgg 120
cattcagcat gtcgagcgtc gcttcgatgt gagcgcacca ttccgtgtcc aacgatttca 180
gacgaacatt gaatattcca ctcgcgacgc tatagtccgc ctcccgatct atgcgcgccg 240
cgcagatgaa gtctgcgttc gcccgacctt cgaaacgtag tgcggccgcg cgcaccattt 300
cgggggagac gtcgatgccg gtgtaatcag ttttgaagcc acgcgcatct aggtagtcca 360
gtagagcccc atagccacag cctagatcgt tgatcgaaaa tgggtccgcc gcattgacaa 420
tgcgcaccag ctggtcaaag cgcaacgcct gcccggcttc gccgttccaa tcgacgccgc 480
gcgggtgccg tgtgcttcga gtttcgatgc gtagtaacgg gccacgtcag cgagcatggt 540
cgttgcgtct tccgccatga agctgcctca cgatttgtgt gtgtgggcgt cggtgcgtgg 600
gtccgagact ataccttcaa cagttgcatg ccgaggctgc ggcgggcaat gacccaaaaa 660
cccgccggca cggttcgccg agcaaggaag cgtggagacg atagataatt tcactggcga 720
cagtacctca aatagtccgg agcctcggct ccgacgttaa agagcagatc cagaatcgac 780
acggcgggct cgaaccctcc ccacaattgc ttataatcgc ggtagccgtc ataatcgaac 840
caagttaccc ggatgctaag ttcgtcgaac acgcgctcat cgacatacga acgggctgag 900
gggccagaga catattcggt cgctgcggcc tgttggcaga ggttggccag tctctcggtc 960
ttgccgtcgg ctaattcgta gtcccacgaa tttgccagtc gcgtgctgat accgagataa 1020
ctgcaaatcg cattcaatag acgcctgttg agtaaggaaa gattcgtgtg ctgttcttcg 1080
aggtaaatcg gcgcgagcca gtcagcgatc tccgcaaaat gagcggccgc gctgtagttg 1140
aattctagtg cccgccagtg cgctttcgcc caatcggtgc cgtcgatcag cgtctcacgt 1200
atcttttgat ggaaacgtcc cttcacctgg acgggaacag ttatccactg taacccctgg 1260
ctcgttttga tccgatttct gtttcgccaa tcacgcttgg tatattgcat gtcatcatag 1320
atgatgaatt catcgacgaa tgcaatcagg tcaaaatatc ctcgccaagg tatgtaattt 1380
gattgaacaa tcgcgacttt cttcaacgcg gtgtctccaa tttagaataa caaatacgtc 1440
gcgcccgcga cagctccgct ggagcgagtt caagcgattc tgcgacatat tcaatatggt 1500
gctcgggaag gccaggatgg gccgcgaccc ggggcgtccg gtgcgcgatg aacgtcgcat 1560
cgtctcctgt gagataattg catccgatca tatagggctg gctgcggcta ggttgctggc 1620
aaaaagatat cgcggccgat ccgtttctgg ttttgtcttg atgatcaaat ccgcttccgt 1680
tcacgagatc gattcctggt cttcccccag cgtcgcgatg tcgataggtg tcgcgctttg 1740
ttcgtacccg cactacgcgg cggcgagaac ctcgccaccg aatcgggatt gggggggagga 1800
taccactcgg tcgaggcccg tcaccggcct tctagcgggt tgaccatcag tgtttgcagg 1860
gccctatccc ggtatggcgc accacgggat cggcagcgtt ccggttgctg gcgtggtacc 1920
tcgttgtggc gccgtggtcc atgtcgattg agtgcgtgga tcagtgtaaa ccgttgcgcg 1980
ccatgttctg taggcactgg ttcgggttgt ggttaggctg cacggttggc aggttaccaa 2040
ccactgagcc cctgggcgga tgtgagctcg gactccgcct atggggtgta attttggcag 2100
attgggccgg gtccccgtgg tgaggactcc tcaaccggat tgggtaagca tgaggtggtg 2160
ctggcagcgg tgtcctggtc gctctcccga gtaggcccgt tgtgactgtc atgtgggcga 2220
gcgggtttgc gcgcgtagga gacgatgatt actacgcacg tgaccaacca caagaacggt 2280

-continued

```
gcccatgtca ccgtggtgaa aacgagtggc gtggtaccga ctaccccttt ggctcccagc   2340
tgtccataga gcggcacgta gaacggctgg cccgggaccg cgacgttgac gatgctcagc   2400
gccacggcca aactcacgca gacgccgacc gcgcggcggc ggtctccatg ggctgcgagt   2460
tggtcgaata tcccagcacc aggaggcccg ttggggtctc gggctaccag tgcagcgatt   2520
ggcaagacga aaacgagata gtagaaggcg acgtccgcgg gggagaaggt ggcggtggcg   2580
agcaacacaa tccccaccat gacaggcggg atacggcgtc cgagcgccag cacggcgacc   2640
acgactatga ctaggacagc aaacccgatc tgcgttcgcg gaccagtgag gaaaccctct   2700
gggatcttgc ccgattgata gttcttgatg ctatcgggga tcagcaggag tgccttgcca   2760
aaggacacgt tccgcgggtc tcgaagccct ccgaacgaac tattgaactt gatgatgccg   2820
tggatcgact gtgcgatcgt ccccgggaag cctcgtggcc acaacagaaa ggctgcgata   2880
ttggacacca ccacgccggt gatcccgata ccagcccacc gccattgtcg agccgccaac   2940
aacaccacgc cgagaacgac gaactgcggc tttaccagga cggccaagat caccgtgatg   3000
gtggcgaggc cccaccgctg tcgggacaac gccacgaagt aagccagcgc gatcggtacc   3060
acgaaccctg tcgagttgcc tcgatcgatg accccccacg ccgggatggc cgcggcgccc   3120
agtgtcacga agatgaccac tcgctccaga ccacgtgccc cccgggccgc ccagatggcg   3180
ggagatatga ccgccatcgt tagggcgacc aggtaacaga tcagccccaa gcgcggcgca   3240
cccagccaat ggctgggtag tccgaaaatc gcatacggta tgcgggcggg ggcccatgca   3300
gcaaccgcgg tcggctggta atcggcgggt agcgagatca ggtagtccgc gggattgggt   3360
tgaatcccgg cggcggcgac catggcgtag tcgctgaagc agtgccgacc gatattcatg   3420
ccccaatcaa gccaacagtc cccagggact accaaaagag tggaaaagac gtcgaccgcg   3480
taccactgac tgagggcgta cgccgtcgcc gccgaaatca ccgacgccag caggatggtg   3540
ccgagcatga gggtgcgctc ggattgggag ccgatcgccc agagccgctc ccggctcgcg   3600
gtcacggcac cgcgcaacac ctccgggggt cgcttcatct ggattctcct cggttctgcg   3660
cgaaacggta gcagagcgcc atggttgcca acgcggtcgc cgggcagtct agaccggatc   3720
ttcctcgtgg caaccgacaa caggacgtcg ttgccgaaag ggcgctgggc accgacatct   3780
aggatgaacc cacagccacg ccccgacgtt atgccatggc gaagagcgac cggcaggagc   3840
gggaacccag tgaagcgagc gctcatcacc ggaatcacag gaccggacgg ctcgtatctc   3900
gctaagctcc cgctgaaggg atatgtggcc gctggtagcc cggccgaggt ctatttctgc   3960
tgggcgacac ggaattatcg cgaattgtat gggttgctcg cggtcaacag catctggttc   4020
aatcacgaat caccgcgtca cggcgagaca ttcatgactc gtaatcctgc accatatcgc   4080
ggtcggcaac gaggcgctga tcgatgcgca gacgctgatg cgccggccca cccggatagg   4140
tatcagtatt ggggcgttcc ggccagcgta cgaggcgtga tcgaccgcgc aatgggtgtt   4200
tgcgttgagt aataatctga accgtgtgaa cgcatgcatg gatggattcc ttgcccgtat   4260
ccgctcacat gttgatgcgc acgcgccaga attgcgttca ctgttcgata cgatggcggc   4320
cgaggcccga tttgcacgcg actggctgtc cgaggacctc gcgcggttgc ctgtcggtgc   4380
agcattgctg gaagtgggcg ggggggtact tctgctcagc tgtcaactgg cggcggaggg   4440
atttgacatc accgccatcg agccgacggg tgaaggtttt ggcaagttca gacagcttgg   4500
cgacatcgtg ctggaattgg ctgcagcacg acccaccatc gcgccatgca aggcggaaga   4560
ctttatttcc gagaagcggt tcgacttcgc cttctcgctg aatgtgatgg agcacatcga   4620
```

-continued

```
ccttccggat gaggcagtca ggcgggtatc ggaagtgctg aaaccggggg ccagttacca   4680
cttcctgtgc ccgaattacg tattcccgta cgaaccgcat ttcaatatcc caacattctt   4740
caccaaagag ctgacatgcc gggtgatgcg acatcgcatc gagggcaata cgggcatgga   4800
tgacccgaag ggagtctggc gttcgctcaa ctggattacg gttcccaagg tgaaacgctt   4860
tgcggcgaag gatgcgacgc tgaccttgcg cttccaccgt gcaatgttgg tatggatgct   4920
ggaacgcgcg ctgacggata aggaattcgc tggtcgccgg gcacaatgga tggtcgctgc   4980
tattcgctcg gcggtgaaat tgcgtgtgca tcatctggca ggctatgttc ccgctacgct   5040
gcagcccatc atggatgtgc ggctaacgaa gaggtaatga catggcgcaa gcgacatcgg   5100
gcattcgcgc ggcactttcg caacctgctg tgtatgaggc gtatcagcgg attgcgggcg   5160
ctaaaagcgg gcttgcgtgg atcacaaccg accccatcca gtcgttgcca ggcatgcgta   5220
ctctcgacct cggttgctgg ccagcggtga tacacagctc cccgccagtg gacgtgacat   5280
gtacgagaga cggcatgagc gcggaatgtg cgaccgtgcc gtcgagatga ccgacgtcgg   5340
cgctacggca gcccccaccg gacctatcgc gcggggcagc gtcgctcggg tcggcgcggc   5400
gaccgcgttg gccgttgcct gcgtctacac ggtcatctat ctggcggccc gcgacctacc   5460
cccggcttgt ttttcgatat tcgcggtgtt ttgggggggcg ctcggcattg ccaccggcgc   5520
cacccacggc ctcctgcaag aaacgacccg cgaggtccgc tgggtgcgct ccacccaaat   5580
agttgcgggc catcgtaccc atccgctgcg ggtggccggg atgattggca ccgtcgcggc   5640
cgtcgtaatt gcgggtagct caccgctgtg gagccgacag ctattcgtcg aggggcgctg   5700
gctgtccgtg ggctactcca gcgttggggt ggccgggttc tgcgcgcagg cgaccctgct   5760
gggcgcgctg gccggcgtcg accggtggac acagtacggg tcactgatgg tgaccgacgc   5820
ggtcatccgg ttggcggtcg ccgcggcagc ggttgtgatc ggatggggtc tggccgggta   5880
cttgtgggcc gccaccgcgg gagcggtggc gtggctgctc atgctgatgg cctcgcccac   5940
cgcgcgcagc gcggccagcc tgctgacgcc cgggggaatc gccacgttcg tgcgcggtgc   6000
cgctcattcg ataaccgccg cgggtgccag cgcgattctg gtaatgggtt tcccagtgtt   6060
gctcaaagtg acctccgacc agttaggggc aaagggcgga gcggtcatcc tggctgtgac   6120
cttgacgcgt gcgccgcttc tggtcccact gagcgcgatg caaggcaacc tgatcgcgca   6180
tttcgtcgac cggcgcaccc aacggcttcg ggcgctgatc gcaccggcgc tggtcgtcgg   6240
cggcatcggt gcggtcggga tgttggccgc agggcttacc ggtccctggt tgctgcgtgt   6300
tggattcggc cccgactacc aaactggcgg ggcgttgctg gcctggttga cggcagcggc   6360
ggtagctatc gccatgctga cgctgaccgg cgccgccgcg gtcgcggccg cactgcaccg   6420
ggcgtatttg ctgggctggg tcagcgcgac ggtggcgtcg acgctgttgc tgctgctgcc   6480
gatgccgctg gagacgcgca ccgtgatcgc gctgttgttc ggtccaacgg tgggaatcgc   6540
catccatgtg gccgcgttgg cgcggcgacc cgactgattt gtgccccagg tcgacaaatc   6600
acgccgtctc gtcagtgagc actccgtcct cgggtccgat ccttccagga gacgttgcaa   6660
cctgatttgg ctcaaattgg tgcgcaccga gggtcgggca catcgtaggg tcgcaacagt   6720
cacatgtgtc actgcaccgg gcgacacccg atgtcccggc tctcagcgac agctgtctga   6780
cctgtggttt tgttcccaag ttggtcgtgg ctgtgcggga ttggaggtgg cgtgggggtc   6840
gcgtcgtatg gattctcctc ctcggttccg cgcgaaacgg ccgcaggcgc aatggtcacc   6900
aacttggccg cggtggagtc tagcctcaca ttttcctggt cgcccccgac aaccaggagg   6960
tcgctgcaga acgggcgttc cctacccaca tctactatga agcgacagcg gcgccccgct   7020
```

-continued gtgatggctg agcatgaccg acagaggcgg gaagacagtg aagcgagcgc tcatcaccgg 7080
aatcaccggc caggacggct cgtatctcgc cgaactgctg ctggccaagg ggtatgaggt 7140
tcacgggctc atccggcgcg cttcgacgtt caacacctcg cggatcgatc acctctacgt 7200
cgacccgcac caaccgggcg cgcggctgtt tctgcactat ggtgacctga tcgacggaac 7260
ccggttggtg accctgctga gcaccatcga acccgacgag gtgtacaacc tggcggcgca 7320
gtcacacgtg cgggtgagct tcgacgaacc cgtgcacacc ggtgacacca ccggcatggg 7380
atccatgcga ctgctggaag ccgttcggct ctctcgggtg cactgccgct tctatcaggc 7440
gtcctcgtcg gagatgttcg gcgcctcgcc gccaccgcag aacgagctga cgccgttcta 7500
cccgcggtca ccgtatggcg ccgccaaggt ctattcgtac tgggcgaccc gcaattatcg 7560
cgaagcgtac ggattgttcg ccgttaacgg catcttgttc aatcacgaat caccgcggcg 7620
cggtgagacg ttcgtgaccc gaaagatcac cagggccgtg gcacgcatca aggccggtat 7680
ccagtccgag gtctatatgg gcaatctgga tgcggtccgc gactggggt acgcgcccga 7740 atacgtcgaa ggcatgtggc ggatgctgca gaccgacgag cccgacgact tcgttttggc 7800
gaccgggcgc ggtttcaccg tgcgtgagtt cgcgcgggcc gcgttcgagc atgccggttt 7860
ggactggcag cagtacgtga aattcgacca acgctatctg cggcccaccg aggtggattc 7920
gctgatcggc gacgcgacca aggctgccga attgctgggc tggagggctt cggtgcacac 7980
tgacgagttg gctcggatca tggtcgacgc ggacatggcg gcgctggagt gcgaaggcaa 8040
gccgtggatc gacaagccga tgatcgccgg ccggacatga acgcgcacac ctcggtcggc 8100
ccgcttgacc gcgcggcccg ggtctacatc gccgggcatc gcggcctggt cgggtccgcg 8160
ctgctacgca cgtttgcggg cgcggggttc accaacctgc tggtgcggtc acgcgccgag 8220
cttgatctga cggatcgggc cgcgacgttc gacttcgttc tcgagtcgag gccgcaggtc 8280
gtcatcgacg cggcggcccg ggtcggcggc atcctggcca acgacaccta cccggccgat 8340
ttcctgtcgg aaaacctcca gatccaggtc aacctgctgg atgccgccgt ggcggcgcgg 8400
gtgccgcggc tgctgttcct gggctcgtcg tgcatctacc cgaaactcgc cccgcagccg 8460
atcccggaga gcgcgctgct caccggtccg ttggagccga ccaacgacgc gtacgcgatc 8520
gccaaaatcg ccggcatcct tgcggtccag gcggtgcgcc gccaacatgg cctgccgtgg 8580
atctcggcga tgcccaccaa cctgtacggg ccaggcgaca acttttcgcc gtccggctcg 8640
catctgctgc cggcactcat ccgccgctat gacgaggcca aagccagtgg cgcgcccaac 8700
gtgaccaact ggggcaccgg cacgccccga cgggagttgc tgcacgtcga cgacctggcg 8760
agcgcatgcc tgtatctgct ggaacatttc gacgggccga cccatgtcaa cgtgggaacc 8820
ggcatcgacc acaccatcgg cgagatcgcc gagatggtcg cctcggcggt aggctatagc 8880
ggcgaaaccc gctgggatcc aagcaaaccg gacggaacac cacgcaaact gctggatgtt 8940
tcggtgctac gggaggcggg atggcggcct tcgatcgcgc tgcgcgacgg catcgaggcg 9000
acggtggcgt ggtatcgcga gcacgcggga acggttcggc aatgaggctg gcccgtcgcg 9060
ctcggaacat cttgcgtcgc aacggcatcg aggtgtcgcg ctactttgcc gaactggact 9120
gggaacgcaa tttcttgcgc caactgcaat cgcatcgggt cagtgccgtg ctcgatgtcg 9180
gggccaattc ggggcagtac gccaggggtc tgcgcggcgc gggcttcgcg ggccgcatcg 9240
tctcgttcga gccgctgccc gggccctttg ccgtcttgca gcgcagcgcc tccacggacc 9300
cgttgtggga atgccggcgc tgtgcgctgg gcgatgtcga tggaaccatc tcgatcaacg 9360

-continued

```
tcgccggcaa cgagggcgcc agcagttccg tcttgccgat gttgaaacga catcaggacg   9420
cctttccacc agccaactac gtgggcgccc aacgggtgcc gatacatcga ctcgattccg   9480
tggctgcaga cgttctgcgg cccaacgata ttgcgttctt gaagatcgac gttcaaggat   9540
tcgagaagca ggtgatcgcg ggtggcgatt caacggtgca cgaccgatgc gtcggcatgc   9600
agctcgagct gtctttccag ccgttgtacg agggtggcat gctcatccgc gaggcgctcg   9660
atctcgtgga ttcgttgggc tttacgctct cgggattgca acccggtttc accgaccccc   9720
gcaacggtcg aatgctgcag gccgatggca tcttcttccg gggcagcgat tgacgcgccg   9780
gcgcgtcaat ctatttcgac attcgcgtga agacgttttc ccagaatcga ctgttgtagg   9840
cgtagaactc ccggccgcgt aggtaggcat gtgatattcg ccttcccccg aacgggtagc   9900
ggcgatgaag gtcgcccatg cggcgcagat caccgaagac cgcgcttggt tcccggtgcg   9960
agccgacgcc cgtggtgtcg aactcgcaca gcacacaccg aatcgtgacc ggctcgcata  10020
ccagcgcggc ccgcaatatg aattcctggt cggcggcgat cccgaaatca aggtcgtagc  10080
caccgatctt ggccaccagc gatgatccga agaacgatgc ttgatgcgga acaacctgct  10140
tgccggccag gaatttgcgc aggctgaaag gtatcgggcc gcgcacccga tcgagcccga  10200
cgagacgatc catcccgaag ccccacaatt cggacaccgg tcccttgccg gatagcgcct  10260
ccacggcctg ggctaccacg tcgggcccgg aaaaacgatc ggcggagtgc aagaaccaca  10320
acagatcacc cgatgcgtgc gcgatgccct ggttcatcgc gtcgtaccgc ccgccgtcgg  10380
gctcggactg ccaatacgcg aagcctggtt cacacccgga caggtatgcc accacgtcgt  10440
cgccgctgcc accgtcgatt acgatgtgct cgatgcgtcc ccggtagcgt tgcgcccgca  10500
cacttttcac cgtgcgctgc aacccgtcga ggtcgttgaa cgagatcgtt atcaccgaga  10560
cggtcggagc agacgtcacc gagttcccct aggttgctgg cggcgattgt ggatcaccgg  10620
gtcttgatac cgatgaaggt gcctcgaaga ttcgccgcat aggaacctcc gagcaacgac  10680
tcggcgatgc ttggttccaa gttgtcgtac tcctccatca ccaggtcgac gccgacgtct  10740
ttgatggcct gaagtaggtg ctcgcgttga atccagaatg accggcgatt gtcccaggac  10800
gcccattttg cggtgtcgcg ctggccaaac gagcggtcgt cggaaaactc ggtaaaccac  10860
ctaccgggaa gtccctcatg ttcggtgggc gccgagagca tgaacttcac cggcgccggc  10920
cgccgcagca accgatcggt caattgtcgt gccgtcgtgg gcaaccggag ccatttatcg  10980
ctccggttga tgatcgagaa gtgcgtctgg agaatcagca gcttgttcgt taccgacgag  11040
agggtttcca ggtattgctt cggattctcc aggtggtaga agaggccgca gcagaagacg  11100
gtatcgaaga gcccgtggtt ggcgatgttg agggcgttgt cgtggacgaa ccggagattc  11160
ggcaggttgg tcttcgattt gatgtagttg caggccgcca tgttcagctc gcgaacctcg  11220
atcccgagga cctgaaatcc catgcgcgcg aacccgaccg cgtacccgcc ttccaagcag  11280
ccgacatcgg ccaggcgtag gtggctcttg tccccgggaa agacggtttc cagaatcccg  11340
cgcgccgaga tgaaccagga cgattcgtct aacgtgcgcg aggactccgg tatcgtcaag  11400
gttccgtcgt cgaggcgaac gttgtgggcg gtgaattgta ccgcgccggc cgaatgttcc  11460
tgtgccatca cttggttagc cccttcggct ggtcctgggt ttgtcgacat ggtcaggctc  11520
gacagccgcg tcggagccgg gagggccaca catccacgag ccccctgcgg ctcggcgtcg  11580
cggcggcgag cttgcgccac tgggtcttga gccgccgcgc gggtgtcgcc ccgcggtgct  11640
gcagcgccag catggcgatc cggggatggc gcgcgatggt ttcctgcagc gcggcgcgcc  11700
cctccgggcc tggaacgttg gcgatctggc gaaggatcca gtcggccatg acggcgatga  11760
```

-continued gctcctcgcg cgcggggtct cccgggaaca ggtcgagcat cgcgtcaaac gtcgccgcat 11820
gccccggacc ctgcgtcaac cagaactttg gcgggtccac cacctggttg tgccacatgc 11880
cttgggcgtg gcggcgatac acggccatgg tgtcgggcaa catggcgatg tcgccatgca 11940
ccgcgtgccg gacgtgcaga taccagtcca ggggcatgac gtcggcagga atgtcgtcgt 12000
agcgctcgag gcgacggtac acggccgagt tggtctggat gaagttcatc aagatcaacg 12060
catccaggct caagttgccc cgcacccgaa ccggggggaa cttcgagtcc ttggcatggc 12120
cgtcctccca tatcactcgg acgggatgga agcacaccgt cgtcttgggg tgccggtcga 12180
ggaatgcgac ctgtttgctt agcttcagcg gatcgatcca gtagtcgtcc gcctcgcaca 12240
acgcgacgta ctcgccgcga gcggccgaca gggcgccggt caggttccca ttgaggccga 12300
ggttttcggt cctgaagatc ggccggaaca cgtgcgggta ccgctcggcg tactcacgga 12360
tgatcgccgg ggtggcatcg gtcgacgcgt cgtcggcgac gatgatctcc accgggaagt 12420
cggtttgctg gtcgagaaag ctgtcgaagg cctgacgggc gtagcccgcc tggttgtgag 12480
tggtcgagac gatgctcacc ttggggcaaa gctggggact caccgtcggc ccttttcctg 12540
cgcggccgca agggtattgc gatggcgaac gtgaatcgcc tgtgcccgcc ggccgtcggc 12600
cgtcgtggcc tggtggtcgg cggacgtacg gcacacgctg gcgaagtata gcgagggtgc 12660
actgacgttg ggctcgaacc gcgtggcgcg cggtgtgggc gcaccgtctc gagtcggtgc 12720
tggttggctc gc 12732

<210> SEQ ID NO 2
<211> LENGTH: 289
<212> TYPE: DNA
<213> ORGANISM: Mycobacterium tuberculosis

<400> SEQUENCE: 2
atactcaagc ttgccgcaat cgaaaccaac ctgtttgtgc cgcaagaaat tacgccgtgg 60
cccggcgccg atcaagaaac gccccggcgc gcggcggtgt cgtcgtatgg catgacgggc 120
accaatgtgc acgccattgt cgagcaggca ccggtgccag cccccgaatc cggtgcacca 180
ggcgacaccc cggccacacc cggtatcgac ggcgcgctgc tgttcgcgct gtcggccagc 240
tcgcaggacg cgctgcggca aaccgccgcg cggctggccg attgggtct 289

<210> SEQ ID NO 3
<211> LENGTH: 278
<212> TYPE: DNA
<213> ORGANISM: Mycobacterium tuberculosis

<400> SEQUENCE: 3
ttggcgggtt ggccacacac ccgccggtga cggcgacgat gctgggctgg ttgcggccct 60
gcgccaccgc ggcttgcatg ctggttggct gtcttgggac gatcccgaaa tagtccacgc 120
ggatctggtg attttgcggg ctacccgcga ttaccccgcg cggctcgacg agtttttggc 180
ctggactacc cgcgtggcca atctgctgaa ctcgcggccg gtggtggcct ggaatgtcca 240
cgccgttcac ctacgtgacc ttgatgggat ccgggggt 278

<210> SEQ ID NO 4
<211> LENGTH: 1280
<212> TYPE: DNA
<213> ORGANISM: Mycobacterium tuberculosis

<400> SEQUENCE: 4

-continued

```
ccgacccaga cactgaccgg gcgaccgctg atcggcaacg gcacccccgg ggcggtcggc     60

agcggggcca ccggggcccc cggtgggtgg ctgctcggcg acggcggggc cggcgggtcc    120

ggcgcggcgg gctcgggcgc gcccggcggg gcgggcgggg ctgccgggct gtggggtacc    180

ggcggggccg gcgggatcgg cggagccagc accgtactcg gcggcaccgg cgggggaggc    240

ggggtcggtg ggctgtgggg cgccggtggg gccggcgggg ccggtggaac cggccttgtt    300

ggtggcgacg gcggggccgg tggggccggc gggaccggcg gactgctggc cgggctgatc    360

ggtgccggcg gaggtcacgg cgggaccggc gggctcagca ctaatggcga cggcggggtt    420

ggcggggccg gcgggaatgc cggaatgctc gccgggccgg gcggcgccgg cggagccggc    480

ggtgacggcg aaaacctgga caccggtggg gacggcgggg ccggcggtag cgcagggctg    540

ctgttcggca gcggcggcgc cggcggcgcc ggcggatttg gtttcctcgg tggggacggc    600

ggggccggtg gcaacgccgg gctgctgttg tccagcggcg gggccggcgg gttcggcggg    660

ttcggcaccg ccggtggggt cggtggggcc ggcggcaatg ccggctggct gggcttcggc    720

ggggccgggg gcatcggcgg aatcggcggt aacgctaacg gggggcgccgg tgggaacggc    780

ggcaccggcg gtcagttatg ggtagcggc ggcgccggcg tcgaaggcgg cgcagcctta    840

agcgtcggcg acaccggcgg ggccggtggc gtcggcggca gcgccgggct gatcggcacc    900

ggcggcaacg gcggcaacgg cggcaccggc gccaacgccg gcagccccgg aaccggcggc    960

gccggcgggt tgctgctggg ccaaaacggg ctcaacgggt tgccgtagcc gggcggcacg   1020

gcatggcttc cgggcgtcaa ccactcgccg gtgatgcaga tcggctgcgg agcgggccgc   1080

caaaatgggg gccgccgcgc caggtatctc ggcgaagatc cccggcgctc gagcgctttg   1140

tcagaggccc gtcgcgggtc gtcgtgacga cggctatccg ggcggtgcgg gtttcgcggc   1200

gcgccctgtg cccggcaccg ccgcccgttt gtcggcaacg ccgccgcgac ccgtgagccg   1260

tccagcagct ggcgcctgcg                                                1280
```

```
<210> SEQ ID NO 5
<211> LENGTH: 127
<212> TYPE: DNA
<213> ORGANISM: Mycobacterium tuberculosis

<400> SEQUENCE: 5

gggcatcggc ggaatcggcg gtaacgctaa cgggggcgcc ggtgggaacg gcggcaccgg     60

cggtcagtta tggggtagcg gcggcgccgg cgtcgaaggc ggcgcagcct taagcgtcgg    120

cgacacc                                                               127
```

```
<210> SEQ ID NO 6
<211> LENGTH: 434
<212> TYPE: DNA
<213> ORGANISM: Mycobacterium tuberculosis

<400> SEQUENCE: 6

aatactcaag cttgcccagc cgtcgatgac aagaaatatg tccgcaaaag actcagcggc     60

cgactttgct cgcagctggc ggtaccgcgc caccgattct atgccgtggt cgcggaaaaa    120

tgcctcccga aatcgcacgg ccgactccag ttcggcgagc atccgcgatg ccagctgcgg    180

ctgcgccctg ccggccacgg cacccacatg cggcagttcg tccacctggg ccagcgcccc    240

gccgccgaat tccaaacaat agaactgcac ccggcccgca tcgtgggtaa cagccaacgc    300

catgatcagc gtccgcagcg cggttgactt gcccgtttgc ggtgcaccta cgaacgcgac    360

attgcctgcg gccccggaca agtcgatcgt gcgcggcacc cgtgactgct ctaacgggcg    420
```

-continued attgaaattc cgat 434

<210> SEQ ID NO 7
<211> LENGTH: 332
<212> TYPE: DNA
<213> ORGANISM: Mycobacterium tuberculosis

<400> SEQUENCE: 7
ccacccgtgt aatttgggat gggcaaaaag gcgaagcacc gcgtggccac gaacgccggg 60
agggacaatc tcgggcggtt agggcttctc gcgggaaggc ccgaacgtac ggcgtttcaa 120
cacctcgcgt cgccctccga ccgcgaacat tcggggatgg cagcaacctg ctggcaccct 180
ggccgggcga tgatctgcag cgtcgccgcg ggtagtcgcc gcccgggcgg ctacactctg 240
aaacgcgatg accatcgatg tgtggatgca gcatcccgac gcaacggttc ctacaccgcg 300
atatgttcgc ctcgctgccc cggtggaccg gt 332

<210> SEQ ID NO 8
<211> LENGTH: 354
<212> TYPE: DNA
<213> ORGANISM: Mycobacterium tuberculosis

<400> SEQUENCE: 8
aatactcaag ctttccgccg atacccgcca tgtcgcgcac atccaggact tctgggggga 60
tccgctgaca gcggcgggat cccaaagtgc ggatgatcgg gccgcctacg tcgtggtgta 120
cctcgtcggt aacaacgaaa ccgaagcgta tgactcggtc cacgcggtgc ggcacatggt 180
ggacaccaca ccgccaccgc acggggtgaa ggcctatgtc accggtccgg cagcactcaa 240
tgccgaccag gccgagggcg gagacaaaag tatcgctaag gtcaccgcga tcaccaacat 300
ggtgatcgca gcaatgttgc tagtgatcta tcgctccgta attaccgcgg ttct 354

<210> SEQ ID NO 9
<211> LENGTH: 353
<212> TYPE: DNA
<213> ORGANISM: Mycobacterium tuberculosis

<400> SEQUENCE: 9
gtgccgttcc aacccgaatt ggctttcggc gccatcggtg aggacggcgt gcgggtgctc 60
aacgacgacg tcgtccgcgg gacacacctc gatgctgccg ccatggacgc ggtcgaacgc 120
aagcagctga tcgagctaca acgccgcgcg gaacgcttcc gccgcgggcg tgaccgcatc 180
ccgttgaccg ggcggatcgc ggtgatcgtc gatgacggca tcgccaccgg agcgacggcc 240
aaggcggcgt gccaggtcgc ccgggcgcac ggtgcggaca aggtggtgct ggcggtcccg 300
atcggcccag acgacatcgt ggcgagattc gccgggtacg ccgatgaggt ggt 353

<210> SEQ ID NO 10
<211> LENGTH: 279
<212> TYPE: DNA
<213> ORGANISM: Mycobacterium tuberculosis

<400> SEQUENCE: 10
aatactcaag ctttcggcgg aaacggacac attgcgaata ttgatgacaa aataaaaatc 60
attgatggtt tgagtcacca ggccgatcaa gccttcgccg agccaaattc caatcaagag 120
gcccaagccc gtaccaatca gcccggcaac gagggattcc gtcattatca gccaaaataa 180
ctgctctcgg gttacaccca aacagcgcaa tatggcgaaa aacggtcgcc gttgcacgac 240

-continued attaaatgtc acggtattgt agattaaaaa gatacccac 279

<210> SEQ ID NO 11
<211> LENGTH: 376
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 11
tgctcccgaa acctgggggt gtgcctgctc tgtatgcacg gcatacggac atccttcccc 60
tgagacccgc ggtcgaacca gccacgtgtc catcatagng ggtcaacccc ggccaagggc 120
gacggcacgc caagttcgcc gaccgttaac ctagtgctgt tagcttcatt tgctgcgatc 180
aaaacagctg gtcggccgtt aggaactgaa ttgaaactca accgatttgg tgccgccgta 240
ggtgtcctgg ctgcgggtgc gctggtgttg tccgcgtgtg gtaacgacga caatgtgacc 300
gggggaggtg caaccactgg ccaggcgtcg gcaaaggtcg attgcggggg gaagaagaca 360
ctcaaagcca gtgggt 376

<210> SEQ ID NO 12
<211> LENGTH: 393
<212> TYPE: DNA
<213> ORGANISM: Mycobacterium tuberculosis

<400> SEQUENCE: 12
atactcaagc tttgccgacg agcgggcgat gttgatgacg ggaaacccca gcgcacaacc 60
gacgattttg gcgtagccgg cggacgtctg ctcgattccg atcacgtcgg cgctcgcatc 120
gagcatggcg ccggcgacgg ctagcagcga tccgccgtcg tcgaggagca cgacacgagc 180
cgtacgcccg gccgtaagcc gcgcccagga ttcggcgaaa aaccgttcta cgtggcgggt 240
gtactgggtg tcgaatgatt cgtggggtgc gtaggcgtcg ctgcaatcgt cgacatagat 300
gccgtcgggc cgcatcgcgt cgacaactcc gggtgagtgg aatagcactt gccgatcacc 360
gcgacgttgc gcggatgagg ccgaacccga ata 393

<210> SEQ ID NO 13
<211> LENGTH: 272
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 13
tcctatgtcc ctgccgagca ngtgatcgaa cgcggtgaca gatttgtcta tcctggacct 60
gacggtgagg tcgaagtttt ccaggaattc ggcaaaatcg gtaagagcct gaagaattcg 120
gtatcgccgg acgaaatctg cgacgcatac gggggcatat acgcttcggg tttacgagat 180
gtcgatgggg ccgctggagg cttcacgtcc atgggccaca aaggatgttg tcggcgcgta 240
ccgttttctg cagcgggtgt ggcgcttggt cg 272

<210> SEQ ID NO 14
<211> LENGTH: 286
<212> TYPE: DNA
<213> ORGANISM: Mycobacterium tuberculosis -continued

<400> SEQUENCE: 14
atactcaagc ttgattccgc cgaaaccgac cgtgagcacc ccgccagcca ccacgctcgg 60
gtcgggcgcc gggcccgggc cgccaggctg ctccgctcgg tgatggcacg ccaccgcgac 120
accacccggc tgcgctacgt ctaaccattc caggcggagc tacatcagct cggccgccca 180
gtgttcgggc cctctttcca ggtcgaagtc tataccgata tgcgcatccg cagccgccac 240
cctggagaac agaacgatgc cctactaatg cttgtctggc ggggcc 286

<210> SEQ ID NO 15
<211> LENGTH: 357
<212> TYPE: DNA
<213> ORGANISM: Mycobacterium tuberculosis

<400> SEQUENCE: 15
ggtacgcttc ggtcgcagtc tgcgagtgat gcatgacgac cgggacctcg tcggcatctt 60
ccatagcccg ccacaccttc agttgctcac cggaatccaa ccggtagaag gtcggcgagc 120
gctcggcatt ggtcatcggg atatgccgct cgggacggtc agagccctcg ggtccggcca 180
gcactccgca ggcttcgtcg gggtggtcgc gacgcgcatg ggccaccatc gcattcacca 240
ggtctgcgcg aatcaccagc acgtagacgg ttcctttcct aagcaacacc gaagtttcag 300
gacccgaatg ctccgggaaa catgtcacgg taggtcggta ttccggctac cggctga 357

<210> SEQ ID NO 16
<211> LENGTH: 83
<212> TYPE: DNA
<213> ORGANISM: Mycobacterium tuberculosis

<400> SEQUENCE: 16
ggcgtcaacg gtgtcggaac ccgcgtcaag caattggtag gcctgcagtc tgtgaatcag 60
gccgacgctg tggccgccgc ggc 83

<210> SEQ ID NO 17
<211> LENGTH: 383
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 17
ggctngcgta cccggtaccg gccgcgggcc taccacgtgc cggaactgga agcgcagtaa 60
gccctcaacg cgccaccgct ttggcccgcg cgcccggcgt aggcgcatcg gcggtggccg 120
tggggcggcg cactgcgacc tcaccagcgg ctttcgagct ttgttcgatc aaccggccag 180
catggtcgan gatgcattcg agaccatatt cgaaattggt ttcatcgggg gccccgatcc 240 gatgcccccct cccagttgcg tgagcaanca gcggagtcnt cgcgggatcg atggccacgg 300
ggtgttcaat ggcggatggt ccgctgcccg ccgactggct cttgcgggag aaccgatcta 360
gcaccaccga tccgcgcacg tng 383

<210> SEQ ID NO 18
<211> LENGTH: 603
<212> TYPE: DNA
<213> ORGANISM: Mycobacterium tuberculosis
<220> FEATURE:
<221> NAME/KEY: unsure -continued
<222> LOCATION: (various positions within the sequence)
<223> OTHER INFORMATION: applicants are uncertain of bases designated as "n"

<400> SEQUENCE: 18
cgtaatntcg cgcacancca ngacttctgg ggggatcngc tgacagtggt nggatcccaa 60
attgcggatg atcgggccgc cnacgtcgtt gtgtacctcn tcngtcacaa cnaanccgaa 120
ncgtatgact cggtccacgc ggtgcggcac atggtggaca ccacaccgcc accgcncggg 180
gtgaaggcct atgtcaccgg tccggcaaca ctcaatgccg accaggccga ngccggacac 240
nanagtatcn ctaacgtcac cgcgatcacg agcatggtga tcgnncaatg ttnctantga 300
tctatcgctc cgtaattacc gcggttctcg tcttgatcat ggtcgcancg aactccggcg 360
caatccgcgg attcatcgnc ttgctcgccg atcacatatt ttcagccttt cacattgcaa 420
cnaacctgct cgtctcatgg ngatgcggcg acacggacta ccgatatcat gctcgccgtt 480
acacaatcnc gccacgccgc gaagacngga aacgcttcta cacaatnttc ncgggacgcc 540
actnaacttg gttcnggttt gacattgccg cgcatgtntg cccagctttg ccggctcccc 600
tta 603

<210> SEQ ID NO 19
<211> LENGTH: 190
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 19
tgaatttccc gatcccacaa tctcggttca gatacaggtc gccatacccc ttacttcggc 60
aacgctgggc ggattggccc tgcngctgca gcanaccatc gacgccatcg aattgccggc 120
aatctcgttc agccaatcca tacccatcga cattccgccg atcgacatcc cggccttcnc 180
cctttaacgg 190

<210> SEQ ID NO 20
<211> LENGTH: 506
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 20
aacagctatg accatgntta cgccaagcta tttaggtaac actatanaat actcaagctt 60
ttacggtgat cgcgcatcac ctggttcatg aactggaagc agcgcancgc ttccttttcg 120
gccgcaacat gagccagcct ctcgtccgcg gtcnggtgca ggtgctcggg cagctcggcc 180
gcgacagccg cctgaccctg aaaccagctt ccatatcccg cgacnaacna cnccagtccg 240
ctacgtaacc cctccgcgac tgtccatgga caacagcgcg ttctccaccg accgggcccg 300
ggtgtggggt gtttcggcga ccggcagcca ggtggtccac actgccgacg ggcgccgcga 360
gccgttcacc gaccaagccg ccgaacaagt ccgcccgatc gcatactcca accggttgcg 420
gtactgcagg tcagctggcg tacctcctcn tcncgctcgg cgaagtcttg ctccancacg 480
tcgcagaacg gcaaggaaca cgttca 506

-continued

<210> SEQ ID NO 21
<211> LENGTH: 388
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 21
gaccgnncca tgtttccaca atgtggtgcc agtncggngg ctacgtgcca tcnanacact 60
ggcgcaggct atcgcacccg ttatcngcta cgaacaaatc ncggtatgcg ttctttanca 120
tgagtcggcg accgncgatc atggtcgaca cccacgacng aaatacgcag atcgccntcn 180
agcntgtgtg ccgcggatta tcangactga cctcctggct gaccggnntg tntggtcgcg 240
atgcctggcg cccggccggc gtgntcgtgg tcggctcgga tagcgaagtc agctaattct 300
cgtggcagct cgaaagggtc ctgccggtgc cggtctttgc gcaaaccatg cncatgttac 360
ggtccctcgg gtgcggcctg gcggcggc 388

<210> SEQ ID NO 22
<211> LENGTH: 138
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 22
gggatgggcg ggcccgctaa actcttcgtg ttccactaac tccgggaggg ncaatctcgg 60
gccgttatgg ctcacgtcgc gtcgccctcc gaccgcgaac attcggagtt ggcagcaacc 120
tggtagcacc ctggccgg 138

<210> SEQ ID NO 23
<211> LENGTH: 142
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 23
nccgtcgttg acaagtaaat atgtccgcaa aagtctcagc ggccgacttt gctcgcaggt 60
ggcggtaccg cgccaccgag tcgatgccgt ggtcgcggaa gaatgcctcc cgaaatcgca 120
cggccttccc nntttaaacg ga 142

<210> SEQ ID NO 24
<211> LENGTH: 441
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 24

-continued

```
tttaggtgac actatagaat actcaagctt ttggtctagc cggccgagca cgatacgggt     60

gtcattggcc accggcggcg gctgtccggg aaatggcggg tccccggtgg ttttgctgat    120

gagtgctgaa ccgtantcga agtgggcggc gtcagactcc acccanccag caggcagcgc    180

gaagctgaat cctccaaccg ggttgtcnat ccggacaagt tggggtgcgt ttggggcaat    240

gacaggtggc ngcggtgcgt tcgggtccgc cggcggaagt gctgcgttgg gatcncccgc    300

tgggcattcg gcntttttgc ggcggccggt ggtngggggg caacaggtnt cccngtgcgg    360

gtggcgctca acggtcnacg gcgcaagccg ccgttgttgg taccnggggc gctggctccg    420

gatcgcgttg gcggtcnccg g                                              441
```

<210> SEQ ID NO 25
<211> LENGTH: 453
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 25

```
ctacaccatc gaatacgacg gcgtcgccna ctttccgcgg tacccgctca actttgtgtc     60

gaccctcaac gccattgccg gcacctacta cgtgcactcc aactacttca tcctgacgcc    120

ggaacaaatt gacgcagcgg ttccgctgac caatacggtc ggtcccacga tgacccagta    180

ctacatcatt cgcacggana acctgccgct gctagagcca ctgcgatcgg tgccgatcgt    240

ggggaaccca ctggcgaacc tggttcaacc aaacttgaan gtgattgtta acctgggcta    300

cngcgacccg gcctatggtt attcnacctc nccgcccaat gttgcgactc cgttcgggtt    360

gttcccanaa gtcnncccgg tcgtcatcgc cgaanctctc ntcccgggac ccacagggaa    420

tcngcnattt cncctacaaa tcanccacct cca                                 453
```

<210> SEQ ID NO 26
<211> LENGTH: 228
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 26

```
gcatgatcgg ccacctttcg ggccgcccgg catacggcgg cgtaccgatc tccgcgtcat     60

acacccgcgg gtaatcgccg acggtgccgg ttcgcgagcc gaaggtgacg actctgattg    120

aatcgagttc caggtccagc gggtggcgca ccaacggcgc gagctcaacg acgtcaatcn    180

cgttgtcgct ttctacggtc accgaccctg gtgaccgtag ttcncccg                 228
```

<210> SEQ ID NO 27
<211> LENGTH: 357
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 27

-continued

```
gacactatag aatactcaag cttgccaacc gccagcctgc atccggcggc gancactgct     60

ccgccgacca gtacgaacca acctgcggtg cccaggccat tgacgatgtg ctggtcggcg    120

cccgcgagtc cgcgcaccat caacgccgcg ggcaccacca nggcggcccc accctgcacg    180

gcgacgatca ttccggcgcc gctcacggcg ggcggggctc gaacangcac agcatcaacg    240

tngtcacccg gccgtgaccg gcccgcatcg tcacaccacc caagcccatt gccgtcctcc    300

tcaacngggc gacccggccc gcatcgtcac acggnctaag gccattgccg tcctcct       357
```

<210> SEQ ID NO 28
<211> LENGTH: 384
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 28

```
tcggcgccat cggcaccttc gaggacctgt atttcgacgc cgtggccnac ctgaggttgg     60

cggtggacna agtgtgcacc cggttgattc gctcggcctt gccggatgcc acccngcgcc    120

tggtggtcga tccgcnaana gacaanttgt ggtggangct tctgctgcct gcgacaccca    180

cnacgtggtg gcaccgggca gctttagctg gcatgtcctg accgcgctgg ccgacnactc    240

cagacnttcc acnaanggtc gccnncccaa tgtnccgnan tgtctccggn tccctttacc    300

ncccaatggg cngnttccac nggttacggg ccccntnccg gcgggtctnc ctcccaanct    360

accaaatacg cccgacnttc cgga                                           384
```

<210> SEQ ID NO 29
<211> LENGTH: 266
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 29

```
atactcaagc ttttatggtg atcgcgcatc acctggttca tgaactggaa gcagcgcagc     60

gcttcctttt cggccgcaac atgagccagc ctctcgtcgg cggtcgggtg caggtgctcg    120

ggcagctcgg ccgcgaacag cccggcttga accctgaaaa ccngctttcc atatcccgcg    180

acgaaagaac gccagttccg ctacttaacc cctccgcgaa ccgtccatgg acaacagcgc    240

gttctccacc aaccgggccc gggtgt                                         266
```

<210> SEQ ID NO 30
<211> LENGTH: 423
<212> TYPE: DNA
<213> ORGANISM: Mycobacterium tuberculosis

<400> SEQUENCE: 30

```
tcggctcagg ccgcgctgct ggtagagtcg ctgaccggtg caggtttcga caatgtggtg     60

ccggttcggc ggctacgtgc catcgagaca ctggcgcagg ctatcgcacc cgttatcggc    120

tacgaagcaa atcgcggtat gcgttcttga gcatgagtcg gcgaccgtcg tcatggtcga    180

cacccacgac ggaaagacgc agatcgccgt caagcatgtg tgccgcggat tatcaggact    240

gacctcctgg ctgaccggca tgtttggtcg cgatgcctgg cgcccggccg gcgtggtcgt    300
```

-continued

```
ggtcggctcg gatagcgagg tcagcgaatt ctcgtggcag ctcgaaaggg tcctgccggt    360

gccggtcttt gcgcaaacaa tagcgcaggt tacggtcgcg cggggtgcgg cctggcggcg    420

gcc                                                                  423
```

<210> SEQ ID NO 31
<211> LENGTH: 455
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 31

```
caagctattt aggtgacact atagaatact caagcttcgc gtctacgccg gcccggagca     60

tccgcacagc gctcagcagc cggttccgta cganctcaag caggtggcgc aatgaccgaa    120

accaccccag ccccgcaaac cccggcggcc ccggccgggc ccgcacaatc gttcgtgttg    180

gagcggccca tccanaccgt tgggcgccgt aaggangccg tggtacgaat gcggctggtg    240

cccggcaccg gcaagttcga cctcaacggc cgcagcttgg angactactt cccaaacaag    300

gtgcaccagc agttgatcaa ggcaccccctg gtcaccgtgg atcgggtgga aagtttcgac   360

atctttgccc acctgggcgg cggcggccgt ccggtcaggc cgggcctgcc ctgggtatcg    420

cccgggcatt gattctggta tccccngaag aaccg                               455
```

<210> SEQ ID NO 32
<211> LENGTH: 371
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 32

```
cggttggcca ccgcttctgc ggtgccgccg ccgtcgacaa tgaccgtgtc gtccttgctg     60

accaccacgc gtcgggccga gcccagcacc tccaagccca cctcgcgcag caccatgccg    120

gcgtcggggt tgaccacctg gccacccgtc accaccgcca ggtcctcaag gaaacgcctt    180

acggcggtca ccgaagtacg gccccttgac cgcgaccgct ttcaacgtct tgcgaatcgc    240

gttgacgacc agcgtcgcca acgcttcgcc ctccacgtct tcagccacga tcagtagtgg    300

cttacccgtt cctgcaacct tttccagcaa tggcaacaga tcgggaagcg anctgatctt    360

gtcttggtgc n                                                         371
```

<210> SEQ ID NO 33
<211> LENGTH: 320
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 33

```
ccaagctatt taggtgacac tatagaatac tcaagctttt ggctgggtcg ccttcgaatt     60

cngcgtgcac cgctatgggt tgcancagcg gctggcgccg cacaccccac tggcccgggt    120
```

-continued

```
gttttcgccc cgaacccgga tcatggtgag cgaaaaggan attcncctgt tcgatgctgg    180

gattcgccac gccaaggcat ctancgatta ctctccncgg ggtgggaaaa gtgcccaatc    240

cccctccctc caactttccn aacaatcatt ccggttccnc cntccggttg gnggtaaccn    300

nccaataaaa cccctgcccg                                                320
```

<210> SEQ ID NO 34
<211> LENGTH: 383
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 34

```
gcccgcncat ggccaatccc cgaagacatc attggccagt ggccgggcgc taacaggttc     60

cagcccccca ccantgccgc tcgaacatgc ggtgcaaccc attcgcaggc cggcagggaa    120

agcaccgcgg aagccgcaaa gggctgcagt tccgcgccca ataatgtcgt ccgcaaccag    180

atgcgctcna aaaccncncc ggcagtcagc gcacccgacg cgangtcgaa agacgtcntc    240

agcgcgccca catggggtgc caatcggcac ggcaggtatg ccgcgcgcaa cccgagcgcg    300

tggtgcatgc ccacggtccg cangangcgc ancacccgcc aatgccgaan cccacgaaac    360

atcgggcgca tccaccttca acc                                            383
```

<210> SEQ ID NO 35
<211> LENGTH: 275
<212> TYPE: DNA
<213> ORGANISM: Mycobacterium tuberculosis

<400> SEQUENCE: 35

```
atactcaagc ttgcccagcc gtcgatgaca agaaatatgt ccgcaaaaga ctcagcggcc     60

gactttgctc gcagctggcg gtaccgcgcc accgagtcga tgccgtggtc gcggaagaat    120

gcctcccgaa ttcgcacggc caattccatt ccgggaagca tccgcaatgc cagctgcggt    180

tgccccctgc cggccacggc acccacttgc ggcattgcgt ccacctgggc cagcgccccg    240

ccgccaaatt ccaaacaata aaaattgcac ccggc                               275
```

<210> SEQ ID NO 36
<211> LENGTH: 322
<212> TYPE: DNA
<213> ORGANISM: Mycobacterium tuberculosis

<400> SEQUENCE: 36

```
ccacccgtgt attttgggat gggcaaaaag gcgaagcacc gcgtggccac gaacgccggg     60

agggacaatc tcgggcggct agggcttctc gcgggaaggc ccgaacgtac ggcgtttcaa    120

cacgtcgcgt cgccctccga ccgcgaacat tcggggatgg cagcaacctg gtagcaccct    180

ggccgggcga tgatctgcag cgtcgccgcg ggtagtcgcc gcccgggcgg ctacagtctg    240

aaacgcgatg accatcgatg tgtggatgca gcatccgacg caacggttcc tacacggcga    300

tatgttcgcc tccctgcccc gt                                             322
```

<210> SEQ ID NO 37
<211> LENGTH: 167
<212> TYPE: DNA
<213> ORGANISM: Mycobacterium tuberculosis -continued
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 37
ctgcccatgt ttggggacgc ccgaccagcc gatgctggag gcctacacgg cccttggtgc 60
gctggccacg gcgaccgagc ggctgcaact gggcgcgttg gtgaccggca atacctaccg 120
cagccngacc cctntcncaa naggatnttg ttcgccggac cccnctc 167

<210> SEQ ID NO 38
<211> LENGTH: 287
<212> TYPE: DNA
<213> ORGANISM: Mycobacterium tuberculosis

<400> SEQUENCE: 38
ccgactttcc gcggtacccg ctcaactttg tgtcgaccct caacgccatt gccggcacct 60
actacgtgca ctccaactac ttcatcctga cgccggaaca aattgacgca gcggttccgc 120
tgaccaatac ggtcggtccc acgatgaccc agtactacat cattcgcacg gagaacctgc 180
cgctgctaga gccactgcga tcggtgccga tcgtggggaa cccactggcg aacctggttc 240
aaccaaactt gaaggtgatt gttaacctgg gctacgcgac cgccttt 287

<210> SEQ ID NO 39
<211> LENGTH: 322
<212> TYPE: DNA
<213> ORGANISM: Mycobacterium tuberculosis

<400> SEQUENCE: 39
atactcaagc tttgtcacac caagtgtttc gaccaggcgc tccatccggc gagtggatac 60
tcccagcagg tagcaggtcg ccaccacgct ggtcagtgcg cgttcagctc gcttgcggcg 120
ctgcagcagc cattcgggga aatacctgcc ctggcgcagc tgggggatcc caacttcaat 180
ggttgcggca cgggtgtcaa attcacggtg gcggtagccg ttgccctaat tggaccgctc 240
atcgctgctt tcgcggtacc ccgccccgca cagggcttcg gcttcagccc ccatcagggc 300
ggcaataaac ttcaagagca cc 322

<210> SEQ ID NO 40
<211> LENGTH: 471
<212> TYPE: DNA
<213> ORGANISM: Mycobacterium tuberculosis

<400> SEQUENCE: 40
gaggcagctt cgccggcaat tctactagcg agaagtctgg cccgatacgg atctgaccga 60
agtcgctgcg gtgcagccca ccctcattgg cgatggcgcc gacgatggcg cctggaccga 120
tcttgtgccg cttgccgacg gcgacgcggt aggtggtcaa gtccggtcta cgcttgggcc 180
tttgcggacg gtcccgacgc tggtcgcggt tgcgccgcga aagcggcggg tcgggtgcca 240
tcaggaatgc ctcaccgccg cggcactgca cggccagtgc cgcggcgatg tcagccatcg 300
ggacatcatg ctcgcgttca tactcctcga ccagtcggcg gaacagctcg attcccggac 360
cgcccagcgc attggtgatg gaatcggcga acttggccac ccgctgggtg ttgacatcct 420
cgacggtggg caattgcgcc tcggtaagct ttgccgcgta gccttttcat c 471

<210> SEQ ID NO 41
<211> LENGTH: 247

-continued

<212> TYPE: DNA
<213> ORGANISM: Mycobacterium tuberculosis

<400> SEQUENCE: 41
atactcaagc ttcactgaca agggacgaat tcgtcggccg cctgttcgac tgggtggtgg 60
ccgagctggt cgccaccact caggccgcgg tcacggcggt accggcgcgg gagcaaactc 120
gcgcgggcat ggccaacttc ttgcggacca tcaccgcaga cgcccgcttc ggacccctgc 180
tgtccaccac acagttggcc aacgcattaa tcacccgcaa gcttgcggaa tccaccgccc 240
tgttcgc 247

<210> SEQ ID NO 42
<211> LENGTH: 325
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 42
tccatcaccc gatgtggcng gagcactgcc atgtcgatct caactaccac ctccggccgt 60
ggcggttgcg cgccccgggg ggtccgcgcg aactcgacga ggcggtcgga gaaatcgcca 120
ncaccccgct gaaccgcgac cacccgctgt gggagatgta cttcgttgag gggcttgcca 180
accaccggat cgcggtggtt gccaaaattc accatgcgtt ggctgacggt gttgcctcgg 240
caaacatgat ggcacggggg atggatctgc cgccgggacc ggaggtcggc cgctatgtgc 300
ctgaccccgc tcctaccaag cggca 325

<210> SEQ ID NO 43
<211> LENGTH: 221
<212> TYPE: DNA
<213> ORGANISM: Mycobacterium tuberculosis

<400> SEQUENCE: 43
agctttgcag ttgctgagta atgtcggcca acgtcaccac aaccgcgatg aattcaatca 60
tgccgcccag ggcggccaac ccaatggtgg ccgcgagcgg cagctcgatc gcagcgcgga 120
ggttgccggc cgccagttga ttcacgaaca gggtgaggtc ataggcgggc aggatagtga 180
cgaaggcaag acctccatct gccgtcggaa gaagtatcga g 221

<210> SEQ ID NO 44
<211> LENGTH: 285
<212> TYPE: DNA
<213> ORGANISM: Mycobacterium tuberculosis

<400> SEQUENCE: 44
agcttcagaa caggcctgtt gtgggcgcac ccggctcgcc gagttctgca cgcaccgcct 60
caagtgcggc ccgcaccgcc ggcatctccc ggtcacgcag ggccgcggcc cgcgccgcag 120
cgacggcgtg ttcgcgcagt tcgccgtcaa tgatgctgac ctgatcggcc acccgggcgt 180
tctcggcgtc gtcgcgttca ctaatcgcgg tgctcagcag cgtctcgaca gccaccaccc 240
gagtggcgac cagctgctcc accacggacc gcagcgatgc ccgtc 285

<210> SEQ ID NO 45
<211> LENGTH: 179
<212> TYPE: DNA
<213> ORGANISM: Mycobacterium tuberculosis

<400> SEQUENCE: 45
atactcaagc ttcagttcct ccacgacgcg ttcccaaatg aatttcccga tcccacaatc 60
tcggttcaga tacaggtcgc catacccctt acttcggcaa cgctgggcgg attggccctg 120
ccgctgcacc aaaccatcaa cgccttcaaa ttgccggcaa tctcgttcag ccaatccat 179

<210> SEQ ID NO 46
<211> LENGTH: 315
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 46
gctctacgcc gcctacgggt cgaacatgca tcccgagcag atgctcgagc gcgcacccca 60
ctcgccgatg gccggaaccg gctggttacc cgggtggcgg ctgacgttcg gcggcgagga 120
catcngctgg gaaggggcgc ttgccaccgt cgtcnaagac ccaaattcga aggtgttcgt 180
cgtgctctac gacatgaccc cggcggacga gaagaacctt gaccggtggg aaggctccga 240
gttcggtatc caccagaaga tccgatgccg cgtggagcgc atttcctcgg acaccacaac 300
gggatcccgt cctcg 315

<210> SEQ ID NO 47
<211> LENGTH: 285
<212> TYPE: DNA
<213> ORGANISM: Mycobacterium tuberculosis

<400> SEQUENCE: 47
atactcaagc ttgccaaaga gacctcgtcc accaagcagg acgcgaccgt cgaggtggcg 60
atccggcttg gcgtcgaccc gcgtaaggca aaccagatgg ttcgcggcac ggtcaacctg 120
cccacaccgg cactggttaa gaactgcccg cgtcgcggtt ttcgcggttg gtgaaaaggc 180
caatgcctgc gtttgccgtg ggggcggatg ttgtcgggag tgacaatctg atcaaaagga 240
ttcagggcgg ttggctggaa ttcaatgccg caatcgcgac accgg 285

<210> SEQ ID NO 48
<211> LENGTH: 369
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 48
ccacggcgtg gatcaaggta ccggccggga tgttgcgcaa tggcaggttg ttgcccggct 60
tgatgtcggc gttagcgccg gattccacca catccccttg cgaaagtccg ttgggtgcaa 120
tgatgtagcg cttctcccca tcgagatagt ggagcaacgc aatccgtgcg gtacggttcg 180
ggtcgtactc gatgtgcgcg accttggcgt tgacaccatc tttgtcattg cggcgaaagt 240
cgatcatccg gtaagcgcgc ttatgaccgc cgcctttgtg ccgggtggta atccggccat 300
gcgcgttgcg tccaccgcga cgtgcagcgg gcgcaccagc gacttctccg gggttgaccg 360 ggtnatctc 369

<210> SEQ ID NO 49
<211> LENGTH: 461
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 49
gcagcatgac ggcggtagcg aacaccgccg gatgcagcgc aagtagcgtc gatgtgctca 60
cggaatcgcc ccggcaccgc gatctcgang atcaccagtg ccaccccctg cagcgcnaca 120
ccgacgattc cgtacaccgc cacgccgatc aggccctggg ccatctgatt ggagctggcg 180
tanatggcgg cgatggtgac gatggccagc gccacataca ttgtggcggc cagaaccacg 240
gcgttggggc ggcggtcgat gaacactagg cgacgcagat cgcccggggt caacaggttg 300
accatcagaa agcctgcgac tagcacggcg gcgccactag gaagtacaag aangtggcca 360
ccaccccatg caggatcggg gtaaggctga tggtcccgaa atcgactccg gcctaataca 420
tgactctctc ctttgcgtca tcgccttact tgtgcgcgga a 461

<210> SEQ ID NO 50
<211> LENGTH: 127
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 50
gggacacacc tcgatgctgc cgcnatggac gcggtcgaac gcaagcagct gatcgagcta 60
caacgccgcg cggaacgctt ccgccgcggg cgtgacgcat cccgttgacc ggccggancn 120
ctctcta 127

<210> SEQ ID NO 51
<211> LENGTH: 305
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 51
tgggcgcctc tttcggcctt cccnntttaa acgnagcang acattctggg tatcgagttg 60
tactggatgg tgttggcgat gtcggtgatc ctgctcctgg cggtgggatc cgactacaat 120
ctgctgctga tttcccggtt gaaagaggaa attggggccg gattgaacac cggaattatc 180
cgtgccatgg ctggtaccgg gggagtggtg acggctgccg gcatggtgtt cgccgttacc 240
atgtcgttgt ttgtgttcag cgatttgcga attattggtc agatcggtac caccatcgcc 300
ttccc 305

<210> SEQ ID NO 52
<211> LENGTH: 449
<212> TYPE: DNA
<213> ORGANISM: Mycobacterium tuberculosis
<220> FEATURE:

-continued

<221> NAME/KEY: unsure
<222> LOCATION: (various positions within the sequence)
<223> OTHER INFORMATION: applicants are uncertain of bases designated
as "n"

<400> SEQUENCE: 52
ccgatcggcg ccgcanctgg ttggtgttnc ggatgaatcc gcagcgaaaa tgtagctgcg 60
gtggcgtgtc gtgactcgtn ggcgtcgacg ctcgtggcag ccaccgancg gttggtccag 120
gatctggatg ggcaaagttg tgcggcccgg ccggtgacgg ccgatgagct gaccgaggtc 180
gacagcgccg tgttggctga cttggaaccg acatggagtc gccccggttg gcgtcacctc 240
aagcatttca atggttatgc gaccagtttt tgggttacgc cgtcagacat cacgtcggag 300
acttggatga gctgtgtctg ccagatagcc ccgaatcggg acgaccgtgg tcacggtgcg 360
tctgaccact cgggtcgggt cgcccgcgct atcggcatgg gtgcgtnatc acagcgacac 420
gcgcctgccc aaggangtnc ggncggacc 449

<210> SEQ ID NO 53
<211> LENGTH: 160
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 53
cgggttgcgg atccacgcgt gcgggttgtc agcagctacg gcactgaacc gcgcccacag 60
ctcgccgatc cgctttcggt ggttctcgat cgactcgccg taggcgatgc gcagcgcctg 120
ctcgaatatc gggtacacgt aggccggcct tcccncttta 160

<210> SEQ ID NO 54
<211> LENGTH: 308
<212> TYPE: DNA
<213> ORGANISM: Mycobacterium tuberculosis

<400> SEQUENCE: 54
cttgattttg atcatcatga cgatcatcac cctaattttg ctacccgcac tggttatcgt 60
gggtaccgtc gtgctttcca tgggcgcctc tttcgggctt tccgtattgg tctggcagga 120
cattctgggt atcgatttgt actggatggt gttggcgatg tcggtgatcc tgctcctggc 180
ggtgggatcc gactacaatc tgctgctgat ttcccggttg aaaaaggaaa ttggggccgg 240
attgaacacc ggaattatcc gtgccatggc tggtaccggg ggagtggtga cggctgccgg 300
catggtgt 308

<210> SEQ ID NO 55
<211> LENGTH: 460
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 55
ggggatccct agatcgacct gcaggcatgc aagcttggcg tgtcgttcca acccgaattg 60
gctttcggcg ccatcggtga ggcgggacac acctcgatgc tgccgccatg gacgcggtcg 120

-continued

```
aacgcaagca gctgatcgag ctacaacgcc gcgcggaacg cttccgccgc gggcgtgacc    180

gcatcccgtt gaccgggcgg atcgcggtga tcgtcgatga cggcatcgcc accggagcna    240

ctgtcaaggc ggcgtgccag gtcgcccggg cgcacggtgc ggacaaggtg gtgctggcgg    300

tcccgatcgg cccagacgac atcgtggcga gattcgncgg gtacgccgat gaggtggtgt    360

gtttggcgac gccggcgtng ttcttcgccg ncgggcangg ttaccgcaac ttcacccaga    420

cctccgacga cgaggtggtg gcgtctcctg gatcgtgctc                          460
```

<210> SEQ ID NO 56
<211> LENGTH: 299
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 56

```
aaggctgcag gtcgaagcgg ntggttacga ctccctgtgt gtgatggacc agttctacta     60

tctgcgtcta cacggccctt ggtgcgctgg ccacggcgac cgagcggctg caactgggcg    120

cgttggtgac cggcaatacc taccgcagcc ccgaccctgc tggcaaagat natcaccacg    180

ctcgacgtgg ttagcgccgg tcgagcgatc ctcggcattg gagccggcgg gtttgaactg    240

gaacaccgcc agctcggctt cgagtccggc acttccagtg accggttcaa ccggctcga     299
```

<210> SEQ ID NO 57
<211> LENGTH: 373
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 57

```
ctttccgcgg tacccgctca actttgtgtc gaccctcaac gccattgccg gcacctacta     60

cgtgcactcc aactacttca tcctgacgcc ggaacaaatt gacgcngcgg ttccgctgac    120

caatacggtc ggtcccacga tgacccagta ctacatcatt cgcacggaga acctgccgct    180

gctacagcca ctgcgatcgg tgccgatcgt ggggaaccca ctggcgaacc tggttcaacc    240

aaacttgaag gtgattgtta acctgggcta cggcgacccg gcctatggtt attcgacctc    300

gccgnccaat gttgcgactc cgttcgggtt gttccagang tcagcccggt cgtcatcgcc    360

gacgctctcg tcn                                                       373
```

<210> SEQ ID NO 58
<211> LENGTH: 338
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 58

```
cggtcatagc cctcgggtcc ggccagcact ccgcaggctt cgtcggggtg gtcgcgacgc     60

gcatgggcca ccatcgcatt caccaggtct gcgcgaatca ccagcacgta gacggttcct    120
```

-continued

```
ttcctaagca acaccgaagt ttcacgaccc gaatgctccg ggaaacatgt cacggtaggt    180

cggtattccg gctaccggct gagcattgag cacgccggcc agcaccgcac gagccaggca    240

atcagccgcc gccgcaccga tcgcggtgac cagctgagtc tccggagaca atgcggccgg    300

cacgccggnc tccggcggca ccgctacngc gcccgtgg                            338


<210> SEQ ID NO 59
<211> LENGTH: 374
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 59

gtgatggcac gccaccgcga caccacccgg ctgcgctacn tcgagccata ccgggcggag     60

ctacatcggc tcggccgccc agtgttcggg ccctctttcg aggtcgaggt cgataccgat    120

ttgcgcatcc gcanccgcnc cctggacgac agaaccgtgc cctacgagtg cttgtcgggc    180

ggggccaaag aacagcttgg catcctggcg cgattggccg gcgcggcgct ggtcgccaag    240

gacgacgccg ttccggtgct gatcgacgac gcgctggggt tcaccgatcc ggagcgacta    300

tcaagatggg ggaggtctct gacaccatcg gccccnacgg acatgtgatc gtgccgacgt    360

gcagtcccac cccg                                                      374


<210> SEQ ID NO 60
<211> LENGTH: 448
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 60

gcgaaagtcc gttgggtgca atgatgtagc gcttctcccc atcgagatag tggagcaacg     60

caatccgtgc ggtacggttc gggtcgtact cgatgtgcgc gaccttggcg ttgacaccat    120

ctttgtcatt gcggcgaaag tcgatcatcc ggtnngcgcg cttatgaccg ccgcctttgt    180

gccgggtggt aatccggcca tgcgcgttgc gtccaccgcg accgtgcagc gggcgcacca    240

gcgacttctc cggggttgac cgggtgatct cggcgaaatc agatacgctg gcgccgcgac    300

gaccaggcgt cgtgggcttg tncttgcgaa ttgncatgtc taatcangtc tttctctcac    360

gctctcgtcg ccgggctagg ccgcattgcc ctgctcctcc tcatcgcttc gctctgcatc    420

gtccccgggc taagcccgtg ccccgaaa                                       448


<210> SEQ ID NO 61
<211> LENGTH: 356
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 61

gatggttcgc ggcacggtca acctgccaca cggcactggt aagactgccc gcgtcgcggt     60
```

-continued

```
attcgcggtt ggtgaaaagg ccgatgctgc cgttgccgcg ggggcggatg ttgtcgggag    120

tgacgatctg atcgagagga ttcagggcgg ctggctggaa ttcgatgccg cgatcgcgaa    180

caccggatca gaatggccaa agtcggtcgc atcgctcggg tgctgggtcc gcgcggcctg    240

atgcccaacc cgaaaaccgg caccgtcacc gccgactccc catggcgtcc cggatatcaa    300

gggccggcaa atcaacttcc cggttgatca gcaaggcaac ctgcctccnc ctccgg        356


<210> SEQ ID NO 62
<211> LENGTH: 336
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 62

atactcaagc ttcgtcataa gaccatggtg cgctttcttt cacccgtcca gagtcggggg     60

catccgcacc ggctcgcatc gcatcatcct cccacgacgg gccgctcatc agcttgggcc    120

atttcaatgt acttgatacc ccgcgctgcg ggtaggccac tgcgacaatt caaacacggt    180

gtcacacggt gaatagtgtc gagatgggct ctgatcaacc gtcgcaaacc cggtttcgca    240

tcaatagcgg aatcccaccg ggttgcatgg aggctgctga ccttggaaaa caaaattttt    300

tcattacaac aaaacaaccg ccncggaaac tttgca                              336


<210> SEQ ID NO 63
<211> LENGTH: 489
<212> TYPE: DNA
<213> ORGANISM: Mycobacterium tuberculosis

<400> SEQUENCE: 63

cgaattcggc gtgcaccgct atgggttgca gcagcggctg gcgccgcaca ccccactggc     60

ccgggtgttt tcgccccgaa cccggatcat ggtgagcgaa aaggagattc gcctgttcga    120

tgctgggatt cgccaccgcg aggccatcga ccgattactc gccaccgggg tgcgagaggt    180

gccgcagtcc cgctccgtcg acgtctccga cgatccatcc ggcttccgcc gtcgggtggc    240

ggtagccgtc gatgaaatcg ctgccggccg ctacctgcaa ggtgattctg tcccgttgtg    300

tcgaagtgcc tttcgcgatc gactttccgt tgacctaccg gctggggcgt cggcacaaca    360

ccccggtgag gtcgtttttg ttgcagttgg gcggaatccg tgctctgggt tacagccccg    420

aactcgtcac ggcggtgcgc gccgacggag ttgttatcac cgatccgttg gccgtaccgc    480

gccttgggc                                                            489


<210> SEQ ID NO 64
<211> LENGTH: 448
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 64

tcagactcca cccagccagc aggcagcgcg aagctgaatc ctccaaccgg gttgtcgatc     60

cggacaggtt ggggtgcgtt tggggcaatg acaggtggcg gcggtgcgtt cgggtcggcc    120

ggcggaggtg ctgcgttggg atcgcccggc tgggcattcn gcgtgttggc ggcggccggt    180
```

-continued ggtggggggg caacaggtgt cgccggtgcg ggtggcgctg cagcggtcga cggcggcgaa 240
gcggccgttg tgggtaccgg gggcgctggc tccggatcgg cgttggcggt cgcgggcacc 300
gcaacggtca ccaagctggc gctggccatc gccgcgatag ccagtgccgc caatcgtccc 360
ttgcgacgtg tcaagtnggg gtccacctga tgcatggcca aagaacctac cgtgttaacg 420
gcncaacnca aggaccgcgc cggtcgcn 448

<210> SEQ ID NO 65
<211> LENGTH: 346
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 65
tttccgcggt acccgctcaa ctttgtgtcn accctcaacg ccattgccgg cacctactac 60
gtncactcca actacttcat cctgacgccg gaacaaattg acgcagcggg tccgctgaac 120
aattcggtcc gtcccacgaa agaaccagtt ttncntcttt cncacggaga acctgccgct 180
gctagagcca ctgcgatcgg tgccgatcgt ggggaaccca ctggcgaacc tgtgtttcaa 240
ccaacactta gagtgtaatt gtaaacctgg gctaggggaa accggctcta gtttttccac 300
cntctccgcc ccntgtttcg aatactccgt tcgggttgtc cccaaa 346

<210> SEQ ID NO 66
<211> LENGTH: 277
<212> TYPE: DNA
<213> ORGANISM: Mycobacterium tuberculosis

<400> SEQUENCE: 66
gcttccggct cgtatgttgt gtggaattgt gaccggatac caatttcaca caggaaacag 60
ctatgaccat gattacgcca agctagttag gtgacactat acaatactca agcttgccgg 120
ctggtgggcc gaccacttcg atggcacgac ccgtgaactg ctgcccggcc aattcttctt 180
ggtcgcccgg accgatggac cgcggctggg attccagaag gtgcccgatc ccgcccctgg 240
gaaaaaccgc gtgcacctct acttcacgac caacgac 277

<210> SEQ ID NO 67
<211> LENGTH: 434
<212> TYPE: DNA
<213> ORGANISM: Mycobacterium tuberculosis

<400> SEQUENCE: 67
ccgatcgact gatgcgccga caaccacgcc ccaacaactg gaatgaaccg tcgtgaccat 60
catcagcacg cggttgtagg cgacttgcga catgttcaac ccgccgtact cggacggaat 120
cttcaaaccg aaacagccca gctcggccag gcctttcacg tactcgtcgg ggatctgggc 180
accacgctcg aggacgctgc cgtccacggt gtctaggaat tcccgcagtt tgaccagaaa 240
cgcctcggtt cgggcctcct cggcgtccga cggcttggga aatgggtgta tgagccctac 300
gggaaaccgg cccacaaaga gttctttggc gaaggacggt ttatcccaac cactttcgcg 360
agattcctcg gcaagggccc gcgcttgctc ctcggtgacc tgagtttgct gtgccatcgc 420
cgcctcctcc ctga 434

-continued

<210> SEQ ID NO 68
<211> LENGTH: 465
<212> TYPE: DNA
<213> ORGANISM: Mycobacterium tuberculosis

<400> SEQUENCE: 68
tgcatccggc tcgtatgttg tgtggaattg tgagcggata acaatttcac acaggaaaca 60
gctatgacca tgattacgcc aagctattta ggtgacacta tagaatactc aagcttttac 120
ggtgatcgcg catcacctgg ttcatgaact ggaagcagcg cagcgcttcc ttttcggccg 180
caacatgagc cagcctctcg tcggcggtcg ggtgcaggtg ctcgggcagc tcggccgcga 240
cagccgcctg accctgaaac cagcttccat atcccgcgac gaacgacgcc agtccgctac 300
gtaacccctc cgcgactgtc catggacaac agcgcgttct ccaccgaccg ggcccgggtg 360
tggggtgttt cggcgaccgg cagccaggtg gtccacactg ccgacgggcg ccgcgagccg 420
ttcaccgacc aggccgccga gcaagtccgc ccgatcgcat actcc 465

<210> SEQ ID NO 69
<211> LENGTH: 463
<212> TYPE: DNA
<213> ORGANISM: Mycobacterium tuberculosis

<400> SEQUENCE: 69
gggggcgctg ctggtatagt cgctgaccgg tgcaggtttc gacaatgtgg tgccggttcg 60
gcggctacgt gccatcgaga cactggcgca ggctatcgca cccgttatcg gctacgagca 120
aatcgcggta tgcgttcttg agcatgagtc ggcgaccgtc gtcatggtcg acacccacga 180
cggaaagacg cagatcgccg tcaagcatgt gtgccgcgga ttatcaggac tgacctcctg 240
gctgaccggc atgtttggtc gcgatgcctg gcgcccggcc ggcgtggtcg tggtcggctc 300
ggatagcgag gtcagcgaat tctcgtggca gctcgaaagg gtcctgccgg tgccggtctt 360
tgcgcaaacg atggcgcagg ttacggtcgc gcggggtgcg gcctggcggc ggccagagca 420
cgagttcacc gatgcgcagc tagtggcgac agcgtcagcc aac 463

<210> SEQ ID NO 70
<211> LENGTH: 447
<212> TYPE: DNA
<213> ORGANISM: Mycobacterium tuberculosis

<400> SEQUENCE: 70
tgcttccggc tcgtatgttg tgtggaattg tgagcggata acaatttcac acaggaaaca 60
gctatgacca tgattacgcc aagctattta ggtgacacta tagaatactc aagcttccgt 120
acaggtcgcc tccaacacgg cggggaagcg acaccagcct accgagcttg gagtccagga 180
cgccagcggc ggcgtcggtc tgcgtcgtgg tgccgccggg gtggcgttgg ctggcaacga 240
tctccaccca gccggtcggg ttacccacga tctcggcata gacgcgggcc gaggccggtg 300
cgataccgta ttgcgtcaat tgggacgcgg ttgtgcattc ggctagctcg gttgccacac 360
ccgtcagggg ttcgacgttg gcgggttcgg cgggccccag caccgctgtc accatgcccg 420
ccaagccgac ctgcggcgcc accaact 447

<210> SEQ ID NO 71
<211> LENGTH: 460
<212> TYPE: DNA
<213> ORGANISM: Mycobacterium tuberculosis
<220> FEATURE:
<221> NAME/KEY: unsure
<222> LOCATION: (various positions within the sequence)

-continued

<223> OTHER INFORMATION: applicants are uncertain of bases designated as "n"

<400> SEQUENCE: 71

```
cggcatgacc accgacaggc ccgactggtc gtaccactcg aacgccgggg tgttgatgtc     60
ccagccgctg aagtcgtcct gcgcgcgcag gccgtcgagc aggtacaggg cgggcgagtt    120
ggcaccacca ctttggaatt ggaccttgat gtcacggccc atcgacggcg acggcacctg    180
caggtactcc accggcaagc ccggccggga aaatgccccc gcggtcgccg tgccaccgac    240
ggcgccgacc agacccgaca ctagggccgc gccgacggcc ccgaccacga gtcgacgcga    300
catacccgtg acggcgccac gaaccctgtc aacaagctgc attcttgctt ccctcatcct    360
catctcaacg catccatgca tgtttgggcg catcctgaat tangtcagac tgcaggcgct    420
gggccggcag tgctcgtgta tcaaccacaa cttcgggcgt                          460
```

<210> SEQ ID NO 72
<211> LENGTH: 404
<212> TYPE: DNA
<213> ORGANISM: Mycobacterium tuberculosis

<400> SEQUENCE: 72

```
ttccaaccct aattggcttt cggccccatc cgtgaggacg gggtgcgggt gctcaacaac     60
aacgtcgtcc gcgggacaca cctctatgct gccgccatgg acgcggtcca acgcaagcag    120
ctgatcgagc tacaaccccg cgcggaacgc ttccgccgcg ggcgtgaccg catcccgttg    180
accgggcgga tcgcggtgat cgtcgatgac ggcatcgcca ccggagcgac ggccaaggcg    240
gcgtgccacg tcgcccgggc gcacggtgcg gacaaggtgg tgctggcggt cccgatcggc    300
ccaaacgaca tcgtggcgag attcgccggg tacgccgatg aggtggtgtg tctggcgacg    360
ccggcgttgt tcttcgccct cgggcagggt taccgcaact tcac                      404
```

<210> SEQ ID NO 73
<211> LENGTH: 465
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 73

```
caggcatgca agctttccgc cgatacccgc catgtcgcgc acatccagga cttctggggg     60
gatccgctga cagcggcggg atcccaaagt gcggatgatc gggccgccta cgtcgtggtg    120
tacctcgtcg gtaacaacga aaccgaagcg tatgactcgg tccacgcggt gcggcacatg    180
gtggacacca caccgccacc gcacggggtg aaggcctatg tcaccggtcc ggcagcactc    240
aatgccgacc aggccgaggc cggagacaaa agtatcgcta aggtcaccgc cgatcacnag    300
catggtgatc gcagcaatgt tgctagtgat ctatcgctcc gtaattaccg cggttctcgt    360
cttgatcatg gtcggcatcg actcggccaa tccgcggatt catcgccttg ctcgccgaac    420
acaacatttt cacctttcac atttgcacca acctgctctt ctcat                    465
```

<210> SEQ ID NO 74
<211> LENGTH: 387
<212> TYPE: DNA
<213> ORGANISM: Mycobacterium tuberculosis
<220> FEATURE:
<221> NAME/KEY: unsure -continued
<222> LOCATION: (various positions within the sequence)
<223> OTHER INFORMATION: applicants are uncertain of bases designated as "n"

<400> SEQUENCE: 74
cactactcaa gctctctcnt cattaccacc cctgtaattt gggatgggca aaaaggcgaa 60
gcaccgcttg gccacnaacg ccgggaggga caatctcggg cggctatggc ttctcccggg 120
aaggccccaa cgtacggcgt ttcaacacgt cgcgtcgccc tccgaccgcg aacattcggg 180
gattggcacc aacctgntac caccctggcc gggcgatgat ctgcagcgtc gccgcgggta 240
gtccccgccc gggcggctac agtctgaaac cccgatgacc atcgatgtgt ggatgcagca 300
tccgacgcaa cggttcctac acggcggata tgttctcctc gctgcgccgg tggaccggtg 360
ggtctatccc ctgaaaccga catcccn 387

<210> SEQ ID NO 75
<211> LENGTH: 445
<212> TYPE: DNA
<213> ORGANISM: Mycobacterium tuberculosis

<400> SEQUENCE: 75
caggcatgca agctttcgtc agttcattgc gccagcagac caacaagagc atcgggacat 60
acggagtcaa ctacccggcc aacggtgatt tcttggccgc cgctgacggc gcgaacgacg 120
ccagcgacca cattcagcag atggccagcg cgtgccgggc cacgaggttg gtgctcggcg 180
gctactccca gggtgcggcc gtgatcgaca tcgtcaccgc cgcaccactg cccggcctcg 240
ggttcacgca gccgttgccg cccgcagcgg acgatcacat cgccgcgatc gccctgttcg 300
ggaatccctc gggccgcgct ggcgggctga tgagcgccct gacccctcaa ttcgggtcca 360
agaacatcaa cctctgcaac aacggcgacc catttgttcg gacggcaacc ggtggcaacg 420
cacctaagct acttgcccgg gatga 445

<210> SEQ ID NO 76
<211> LENGTH: 345
<212> TYPE: DNA
<213> ORGANISM: Mycobacterium tuberculosis

<400> SEQUENCE: 76
gtttatgcac tggttaggtg tttccatgag tttcattctg aacatccttt aatcattgct 60
ttgcgttttt ttattaaatc ttgcaattta ctgcaaagca acaacaaaat cgcaaagtca 120
tcaaaaaacc gcaaagttgt ttaaaataag agcaacacgt acacaaggag ataagaagag 180
cacatacctc agtcacttat tatcactagc gcccgccgca gccgtgtaac cgagcatagc 240
gagcgaactg gcgaggaagc aaagaagaac tgttctgtca gatagctctt acgctcagcg 300
caagaagaaa tatccaccgt ggggaaaaac tccaggtaga ggtac 345

<210> SEQ ID NO 77
<211> LENGTH: 139
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 77
atactcaagc ttgggtgtag ccgatcaccg gaagtcncat gatcagccac gttccgcgcc 60

-continued

```
gcccggcata cggtggtgta ccgatctccg cgtcatacac ccgcgggtaa tcgccgacgg    120

tgccggttcg cgagccgaa                                                 139


<210> SEQ ID NO 78
<211> LENGTH: 298
<212> TYPE: DNA
<213> ORGANISM: Mycobacterium tuberculosis

<400> SEQUENCE: 78

agctttatcg aaagcgcgaa cagctcgcgg cggcccacga cgtgctgcgt cggattgccg     60

gcggcgagat caattccagg cagctcccgg acaatgcggc tctgctggcc cgcaacgaag    120

gactcgaggt caccccggtg cccggggtcg tggtgcacct gccgatcgca caggttggcc    180

cacaaccggc cgcttgatgc ccggtcggca agcccggcag ttgccaaacc catcgtgatc    240

aggctcggct cgcgagttcg gcgaagaaat ggttcgcctg atcacctacc atcggcca      298


<210> SEQ ID NO 79
<211> LENGTH: 300
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 79

tcaacacgcc gccagccacc acgcgcgggt cgggcgccgg gcccgggcct ccaggctnct     60

ccgctcggtg atggcacgcc accgcgacac cacccggctg cgctacgtcg agccataccg    120

ggcggagcta catcggcccg gccgcccagt gttcgggccc tctcgcccag gtcgaggtcg    180

acaccgattt gcgcatccgc agccgcaccc tgcgacgaca gaaccgcggc cctacccact    240

gcttgtcggg cgggggccaa agaaccagct tgncatcctg ccacaattgg ccggcgcccg    300


<210> SEQ ID NO 80
<211> LENGTH: 321
<212> TYPE: DNA
<213> ORGANISM: Mycobacterium tuberculosis

<400> SEQUENCE: 80

caggcatgca agcttcacgt ccgtacggct cgggtacgct tcggtcgcag tgtgcgagtg     60

atagatgacg accgggacct cgtcggcatc ttccatagcc cgccacacct tcagttgctc    120

accggaatcc aaccggtaga aggtcggcca gcgctcggca ttggtcatcg ggatatgccg    180

ctcgggacgg tcagagccct cgggtccggc cagcactccg caggcttcgt cggggtggtc    240

gcgacgcgca tgggccacca tcgcattcac caggtctgcg cgaatcacca gcacgtagac    300

ggttcctttc ctaagcaaca c                                              321


<210> SEQ ID NO 81
<211> LENGTH: 340
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 81

aatattcaag ctttcggcgg aaacggacnc cttgcgaaca ttgataacaa aatagaaatc     60
```

attgatggtt tgagtcacca ggccgatcaa gccttcgccg agccaaattc caatcaagag 120
gcccaagccc gtaccaatca gcccggcaac gagggattcc gtcnttatca gccnaaataa 180
ctgctctcgg gtaccaccca aacagcgcaa tatggcgaaa aacggtcgcc gttgcacaac 240
attaaatgtc tcggtattgt tgattaaaaa gatacccacc accagggcaa tccaactgag 300
agcggttaaa ttgaccgtaa aaacctcccg tcatctgttt 340

<210> SEQ ID NO 82
<211> LENGTH: 394
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 82
caggcatgca agcttgctgc atcttcctgt gactgctccc gaaacctggg ggtgtgcctg 60
ctgtgtatgc acggcatacg gacatccttc ccctgatacc cgcggtcgaa ccagccacgt 120
gtccatcatc aggggtcaac cccggccaag ggcgacggca cgccaagttc gccgaccgtt 180
aacctagtgc tgttagcttc atttgctgcg agcaaaacag ctggtcggcc gttaggaact 240
gaattgaaac tcaaccgatt tggtgccgcc gtaagtgtcc tgtctgcggg tgcgctggtg 300
ttgtccgcgt gtggtaacga cgacaatgtg accgggggag gtgcaaccac tggccaggcg 360
tccgcgaaag tccattgcng ggggaagaag acac 394

<210> SEQ ID NO 83
<211> LENGTH: 487
<212> TYPE: DNA
<213> ORGANISM: Mycobacterium tuberculosis

<400> SEQUENCE: 83
gaaagtgccc caaggtgttg gtgaaactcg ctggacggtc cccaggatgt tggcagcaca 60
ttcaccggac atgaccggag caagaccgga catcctccca taccgtcgtc gccgtgtaca 120
tccgtagccc gtcctggcag gtgctgggtt gaacaaaatc agcccaacac ctgccacgac 180
gaagaagcgg gttgcgctgg catgtcttgt cggctcggcg atcgaattct acgaattcct 240
tatctacggg accgctgcgg cgctggtgtt tcccaccgtg ttcttcccac acctggatcc 300
cacggtggcc gccgtggcct ccaaggggac atttgctgtg gcgttcctat cccggccgtt 360
cggcgcggcc gtctttggat actttggaga ccgcctcggc cgccagaaga ccctggtcgc 420
cacactgttg atcatgggcc tggcaaccgt gactgttggg ctggttccac gacagtggcc 480
atcgcgc 487

<210> SEQ ID NO 84
<211> LENGTH: 418
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 84
atattcaagc tttgtcacac caagtgttcc gaccaancgc tccatccggc gagtggatac 60

-continued

```
tcccagcagg tagcaggtcg ccaccacgct ggtcagtgcg cgttcatctc gcttgcggcg    120

ctgcagcagc cagtccggga aatagctgcc ctggcgcagc ttggggatcg cgacgtcgat    180

ggttgcggca cgggtgtcga aatcacggtg gcggtagccg ttgcgctgat tggaccgctc    240

atcgctgcgt tcgcggtagc ccnccccgca cagggcgtcg gcttcagccc ccatccaagg    300

cggcgatgaa cgtcgagagc agcccgcgca gcaaatccgg gctcgcctgt gcgagttggt    360

cagccagaag ctgctcggtg tcataagatg agaagaggtc agtgcgtcct ttccttcg      418
```

<210> SEQ ID NO 85
<211> LENGTH: 399
<212> TYPE: DNA
<213> ORGANISM: Mycobacterium tuberculosis

<400> SEQUENCE: 85

```
caggcatgca agctttttga gcgtctcgcg gggcagcttc gccggcaatt ctactagcga     60

gaagtctggc ccgatacgga tctgaccgaa gtcgctgcgg tgcagcccac cctcattggc    120

gatggcgccg acgatggcgc ctggaccgat cttgtgccgc ttgccgacgg cgacgcggta    180

ggtggtcaag tccggtctac gcttgggcct ttgcggacgg tcccgacgct ggtcgcggtt    240

gcgccgccaa agcggcgggt cgggtgccat catgaatgcc tcaccgccgc cgcactgcac    300

ggccagtgcc ccggcgatgt cagccatcgg gacatcatgc tcgcgttcat actcctcgac    360

cagtccgcgg aacagctcca ttcccggacc gcccaacgc                           399
```

<210> SEQ ID NO 86
<211> LENGTH: 474
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 86

```
atactcaagc ttttggctgg gtcgccttcc aattcagcgt gcaccgctat gggttgcagc     60

agcggctggc nccgcacacc ccactggccc gggtgttttc gccccgaacc cggatcatgg    120

tgagcgaaaa ggagattcnc ctgttcgatg ctgggattcg ccaccgcgag gccatcgacc    180

gattactcgc caccggggtg cgagaggtgc cgcagtcccg ctccgtcgac gtctccgacg    240

atccatccgg cttccgccgt cgggtggcgg tagccgtcga tgaaatcgct gccggccgct    300

accacaaggt gattctgtcc cgttgtgtcc aagtgccttt cgcgatcgac tttccgttga    360

cctaccggct ggggcgtcgg cacaacaccc cggtgaggtc gtttttgttg cagttgggcg    420

gaatccgtgc tctgggttac agccccgaac tcgtcacggc ggtgcgccgc cgac          474
```

<210> SEQ ID NO 87
<211> LENGTH: 383
<212> TYPE: DNA
<213> ORGANISM: Mycobacterium tuberculosis

<400> SEQUENCE: 87

```
caggcatgca agcttcaacc tattgacgca ttgtgcgaac tgacggcgcc cgcgcatggc     60

caatccggaa gaccatcatt ggccagtggc cgggcgctaa caggttccag ccccccacca    120

gtgccgctcg aacatgcggt gcaacccatt cgcaggccgg cagggaaagc accgcggaag    180

ccgcaaaggg ctgcagttcc gcgcccaata gtgtcgtccg caaccagatg cgctcgaaaa    240
```

-continued

```
ccgccgccgg cagtcagcgc acccgacgcg aggtcgagag acgtcgtcag cgcgcccaca    300

tggggtgcca atcggcacgg caggtaggcc gcgcgcaacc ccaacgcgtg gtgcatgcca    360

cggtccgcag gaggccacca ccc                                            383
```

<210> SEQ ID NO 88
<211> LENGTH: 455
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 88

```
atactcaagc ttcccggccg caggtgacgg cgcggcctag cgccacttga tgccgcaccc     60

gatcgacggn cgttggtcgg ggttgactgg ccgcccggcg agcagggcgt caaccgcggc    120

ccggacgtcg gcggccgtca ccggtcggcc attgcccggg cgggagtcgt cgagctgacc    180

acggtagaca agtcggcgct ggccgtcgaa gacaaacgtg tcgggtgtgc aggccgcgga    240

gaaggcgcng gcgacgtctc gggtttcgtc gtagagatac gggaacgtcc agccgtggcg    300

gcgggcctcg gcgaccatct gatcgggccc gtcctgcggg taggtgacca cgtccttact    360

ggagataccg accatcggga ccctttgatc ggcgaggtcc cggccgaccg tggccaatcc    420

ggcggcgacg tgtcgcccgt accggccagt ggttc                                455
```

<210> SEQ ID NO 89
<211> LENGTH: 429
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 89

```
caggcatgca agctttanca ncatcaaccc cgccccgcac cagcaccgac acgatgtcga     60

tgccatcgag gtgaatgtcg aactggcnca aaccatctgg cgaccgcgac caccggcaac    120

atgggtaccg gcgatttccg gtgccaatgc cgacccgacg ggccgctctc accgcaggtg    180

acctcgatca ccgagaccag ccggccgtta tactcacgca cccctaccgt gtcacgccca    240

aaacggcgct ggtggtcgat tgccggagtg caccccgcac ccagtgtcgt gcccggatcc    300

gccgaccaat cccgcaccca cgtcgccaaa cccgaaatca ccgtgatgcc gtggtaactg    360

accaccgaca gtaacgtcac tacggccgcc acgccgacgc cgaaccacca cgcacatgat    420

gatcggctg                                                            429
```

<210> SEQ ID NO 90
<211> LENGTH: 321
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 90

```
atattcaacc ttgcacacat tgacgatacc ttggtcacga gaccccaaaa gctggcctcc     60
```

-continued

```
accgcgcgcc ggggaccacg gtcatacctt ganncngctt tcgatcgttg atgctgcgtc    120

ttggtccgcg gaaaccgcag gctggcatat gcacgtgggc gcactggcga tctgcgatcc    180

ccaccgattc gcccgaatac agctttcagc ggctccccaa gttgatcatc gaccggctgc    240

cggatatccc gcacttgcgg tggcgggtca ccggcgcccc gctcggactg gaccggccgt    300

ggttcgtcga ggaccacgaa c                                              321


<210> SEQ ID NO 91
<211> LENGTH: 134
<212> TYPE: DNA
<213> ORGANISM: Mycobacterium tuberculosis

<400> SEQUENCE: 91

caggcatgca agcttcatgc ccgcggcatg atagccacat gcacgcaatc gaactcagcg     60

aaaccggcgg gccaggcgtc ttacgccacc tcaccagcgc gcaacctcaa cccggccacg    120

gagacctcct gatc                                                      134


<210> SEQ ID NO 92
<211> LENGTH: 513
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 92

atactcaagc ttgattttga tcatcatgat gatcatcacc cgaattgtgg tagccgcagt     60

ggttatcgtg ggtaccgtcg tgctttccat gggcgcctct ttcgggcttt ccgtattggt    120

ctggcaggac attctgggta tcgagttgta ctggatggtg ttggcgatgt cggtgatcct    180

gctcntggcg gtgggatccg actacaatct gctgctgatt tcccggttga aagaggaaat    240

tggggccgga ttgaacaccg gaattatccg tgccatggct ggtaccgggg gagtggtgac    300

ggctgccggc atggtgttcg ccgttaccat gtcgttgttt gtgttcagcg atttgcgaat    360

tattggtcag atcggtacca ccatcggcct gggcttgctg ttcgacaccc tcgtcgtgcc    420

tcgttcatga aaccgtccat tgctgccctg ctgggacctg gttctggtgg ccgctacggg    480

tgcgcccgcg cccggcagtc aaatcttccg ccg                                 513


<210> SEQ ID NO 93
<211> LENGTH: 345
<212> TYPE: DNA
<213> ORGANISM: Mycobacterium tuberculosis

<400> SEQUENCE: 93

caggcatgca agcttggcgt gccgttccaa cccgaattgg ctttcggcgc catcggtgag     60

gacggcgtgc gggtgctcaa cgacgacgtc gtccgcggga cacacctcga tgctgccgcc    120

atggacgcgg tcgaacgcaa gcagctgatc gagctacaac gccgcgcgga acgcttccgc    180

cgcgggcgtg accgcatccc gttgaccggg cggatcgcgg tgatcgtcga tgacggcatc    240

gccaccggag cgacggccaa ggcggcgtgc caggtcgccc gggcgcacgg tgcggacaac    300

gtggtgctgg cggtccccat cggcccagac gacatcgtgg cgaga                    345


<210> SEQ ID NO 94
<211> LENGTH: 302
<212> TYPE: DNA
```

-continued

<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 94
atactcaagc ttttacggtg atcgcgcatc acctggttca tgaactggaa gcagcgcagc 60
gcttcctttt cggccgcaac atgagccagc ctctcgtcgg cggtcgggtg caggtgctcg 120
ggcagctcgg ccgcgacagc cgcctgaccc tgaaaccagc ttccatatcc cgcgacgaac 180
gacgccagtc cgctacgtaa cccctccgcg actgtccatg gacaacagcg cgttctccac 240
cgaccgggcc cgggtgtggg gtgtttcggc gaccggcagc cangtggtcc acactgccga 300
ag 302

<210> SEQ ID NO 95
<211> LENGTH: 286
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 95
tagtcgctga ccggtgcagg tttcgacnat gtggtgccgg ttcggcggct acgtgccatc 60
gagacactgg cgcaggctat cgcacccgtt atcggctacg agcaaatcgc ggtatgcgtt 120
cttgagcatg agtcggcgac cgtcgtcatg gtcgacaccc acgacggaaa gacgcagatc 180
gccgtctanc ntgtgtgccg cggattatca ggactgacct cctggctgac cggcatgttt 240
ggtcgcgatg cctggcgccc ggccggcgtg gtcgtggtcg gctcgg 286

<210> SEQ ID NO 96
<211> LENGTH: 482
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 96
atactcaagc tttccgccga tacccgccat gtcgcgcaca tccagaactt ctgggggggat 60 ccgctgacag cggcgggatc ccaaagtgcg gatgatcggg ccgcctacgt cgtggtgtac 120
ctcgtcggta acaacgaaac cgaagcgtat gactcggtcc acgcggtgcg gcacatggtg 180
gacaccacac cgccaccgca cggggtgaag gcctatgtca ccggtccggc agcactcaat 240
gccgaccagg ccgaggccgg agacaaaagt atcgctaagg tcaccgcgat cacgagcatg 300
gtgatcgcag caatgttgct agtgatctat cgccccgtaa ttaccgcggt tctcgtcttg 360
atcatggtcg gcatcgacct cggcgcaatc cgcggattcn tcgccttgct cgccgaccac 420
aacattttca gcctttcaac atttgcgaca acctgctcgt tctcatggcg attgcngcga 480
ac 482

<210> SEQ ID NO 97
<211> LENGTH: 395
<212> TYPE: DNA

-continued

<213> ORGANISM: Mycobacterium tuberculosis

<400> SEQUENCE: 97
caggcatgca agcttggcgt gccgttccaa cccgaattgg ctttcggcgc catcggtgag 60
gacggcgtgc gggtgctcaa cgacgacgtc gtccgctgga cacacctcga tgctgccgcc 120
atggacgcgg tcgaacgcaa gcagctgatc gagctacaac gccgcgcgga acgcttccgc 180
cgcgggcgtg accgcatccc gttgaccggg cggatcgcgg tgatcgtcga tgacggcatc 240
gccaccggag cgacggccaa ggcggcgtgc caggtcgccc gggcgcacgg tgcggacaag 300
gtggtgctgg cggtcccgat cggcccagac gacatcgtgg cgagattcgc cgggtacgcc 360
gatgaagtgg tgttgtttgg cgacccggcg ttgtt 395

<210> SEQ ID NO 98
<211> LENGTH: 439
<212> TYPE: DNA
<213> ORGANISM: Mycobacterium tuberculosis

<400> SEQUENCE: 98
atactcaagc tttggcattg tgcacatttt ccacccgtgc tctattaatg ctgagccgct 60
aattgtgacc ccagtcggga aacacgcgga gcaccaaatt caccgcagcg gccggggcgg 120
ttcaactcac catggatcgc tctcgtcgtc tggtgctgga caatcgtcgc tgtagcgcgt 180
cgcgaacacc tcagcttctg ctgccgcggc ttcttccggc gatggtaacc cccaggtttc 240
gcccacggtc ttacgtagca gtgcgacgcg gtgttcatct gcatcgacct gttgactcat 300
cctgtcaagg atgaaggcgt actgggccga ctgcgccttc tgccgcgcca ggtcggcaat 360
caccaggatc tcagaaacga gctgcgactc actcttccag gccaccctgg ccgaaagctc 420
gacatggtca atccggccg 439

<210> SEQ ID NO 99
<211> LENGTH: 348
<212> TYPE: DNA
<213> ORGANISM: Mycobacterium tuberculosis

<400> SEQUENCE: 99
caggcatgca agcttgcggg ccggagtggt ttcgacggcc gctcgcttct cggcatcggt 60
ttgggctgtc accagcagtt ggtagttctt cacgtactgt tgttcgagcg tcgagccgcc 120
gcgcgtgtcg aggtcgccgg acgcgtatcc cgccaggccg gtcagggtgc ccttccagtc 180
cacgccgctg tggtcggcga accgcttatc ttcaatcgag acgatcgcca gcttcatcgt 240
gttggcgatc ttgtccgagg gcacctcgaa ccggcgctgc gagtacagcc acgcgatcgt 300
gttgcccttc gcgtcgacca tcgtcgatac cgcaggcact tgcccctc 348

<210> SEQ ID NO 100
<211> LENGTH: 436
<212> TYPE: DNA
<213> ORGANISM: Mycobacterium tuberculosis

<400> SEQUENCE: 100
atactcaagc ttcccggcgg ccagtaccga aagcgcgaac agctcgcggc agcccacgac 60
gtgctgcgtc ggattgccgg cggcgaaatc aattccaggc agctcccgga caatgcggct 120
ctgctggccc gcaacgaagg actcgaggtc accccggtgc ccggggtcgt ggtgcacctg 180
ccgatcgcac aggttggccc acaaccggcc gcttgatgcc cggtcggcaa gcccggcagt 240
tgccaaaccc agcgtgatca ggctcggctc gcgagttcgg cgaagaagtg gctcgcctga 300

-continued tcacctacca tcggccagga tctgcgtgtc atcacaacgc tcgccaagga ggttgttgtg 360
gtgctatcga cggcctttag ccagatgttc ggaatcgact atccgatagt gtccgcgcca 420
atggacttga tcgccg 436

<210> SEQ ID NO 101
<211> LENGTH: 445
<212> TYPE: DNA
<213> ORGANISM: Mycobacterium tuberculosis

<400> SEQUENCE: 101
agcttcggtg tagccgatca ccggaagccg catgatcagc cacgtttcgc gccgcccggc 60
atacggcggc gtaccgatct ccgcgtcata cacccgcggg taatcgccga cggtgccggt 120
tcgcgagccg aaggtgacga cgctgattga atcgagttcc aggtccagcg ggtggcgcag 180
caacggcgcg agctcaacga cgtcaatcac gttgtcgctt tctacggtca ccgacccggt 240
gaccgtagtc gcccggtgcg ctcggccgag aagttgcacc gccaccaccg cgacaccgtc 300
ttgcacgcgg acgccacccc cggatcggtt gttggccaag gtaattgggt cattccattt 360
gacgggacgc cgaccccgca gccccagtac cgcccacgac cacgccggct gacccaccac 420
tgtacgaaca ccaaggcgac gccga 445

<210> SEQ ID NO 102
<211> LENGTH: 261
<212> TYPE: DNA
<213> ORGANISM: Mycobacterium tuberculosis

<400> SEQUENCE: 102
atactcaagc ttcggtggct tcgcccgccc tgccgggtgg acttcatgac aacgcggggg 60
cgattacccc cgctaccgcc agcagcatga cggcggtacc taacaccgcc cggatgcctc 120
gcacgtgcct cgatgtgctc acggaatcgc cccggcaccg cgatctcgag gatcaccagc 180
gttacccccg gcagcgcgac accgacaatt ccgtacaccg ccacgccgat ccggccctgg 240
gccagctgat tggagctggc g 261

<210> SEQ ID NO 103
<211> LENGTH: 244
<212> TYPE: DNA
<213> ORGANISM: Mycobacterium tuberculosis

<400> SEQUENCE: 103
caggcatgca agcttccaca tgtacggatc cacgaacatc ccgttgaact gacaggtgcg 60
gcccggctcg atcaggccgg ccacttgttc tacgcggtta ccgaagatct cttcggtgac 120
ctgcccgccg ccggccagct cggcccagtg cccggcgttg gccgccgcgg cgacgatctt 180
ggcgtccacg gtggtccggg tcttgcccgc tagcacgatc cgcgagtcgg ccggtcaccc 240
gggt 244

<210> SEQ ID NO 104
<211> LENGTH: 376
<212> TYPE: DNA
<213> ORGANISM: Mycobacterium tuberculosis

<400> SEQUENCE: 104
atactcaagc tttccaagtc ccaagtgtcg atcatggcca aagagctcga caaagccgta 60
gaggcgtttc ggacccgccc gctcgatgcc ggcccgtata ccttcctcgc cgccgacgcc 120

-continued

```
ctggtgctca aggtgcgcga ggcaggccgc gtcgtcgggg tgcacacctt gatcgccacc    180

ggcgtcaacg ccgagggcta ccgaaagatc ctgggcatcc aggtcacctc cgccgaagac    240

ggggccggct ggctggcgtt cttccgcgac ctggtcgccc gcggcctgtc cggggtcgcg    300

ctggtcacca gcgacgccca cgccggcctg gtggccgcga tcggggccac cctgcccgca    360

gcggcctggc agcgct                                                    376
```

```
<210> SEQ ID NO 105
<211> LENGTH: 284
<212> TYPE: DNA
<213> ORGANISM: Mycobacterium tuberculosis

<400> SEQUENCE: 105

caggcatgca agcttcacac gtaggcgccg tcgataaatg actccgccgc gcttcgcaca     60

tcctcgtagc gatccttggc gagcaggtca accgggcgct gcccgtcgag gagccggttt    120

ttggcgtgca gccactggcc gacacctcgg ggggtaagcg aatccgagag caggaggacg    180

aggtcacgaa gctgcgccag ccggtcgtac cgctcagggc ggatgtcgcc ggtccgccac    240

ccgcgtaccg cccgatcgga cacctgtatg accgcggcga cgtc                     284
```

```
<210> SEQ ID NO 106
<211> LENGTH: 140
<212> TYPE: DNA
<213> ORGANISM: Mycobacterium tuberculosis

<400> SEQUENCE: 106

cgcggcggcg cattaccccc gctaccgtca gcagcttgac ggcggtagcg aacaccgccg     60

gatgcagcgc aggtgcgtct atgtgcacac ggaatcgccc cggcaccgcg atctcgagga    120

tcaccagtgc ccgccccctg                                                140
```

```
<210> SEQ ID NO 107
<211> LENGTH: 491
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 107

gggatcgagg aacagcgcgt tgaactgata ggtgcggccc ggctcgagca ggccggccat     60

ttgttcgatg cggttaccga agatctcttc ggtgacctgc ccgccgccgg ccagctcggc    120

ccagtgcccg gcgttggccg ccgcggcgac gatcttggcg tccacggtgg tcggggtcat    180

gcccgcgagc aggatcggcg agcggccggt cagccgggtg aacttcgtcg agagcttgac    240

cctgccgtcg gggaggcgaa ccacggtcgg tgcgtatctc gaccaggccc gggcaacctc    300

gggggtggcg ccgacggtga acaggttgcg ctggccaccg cgggtagccg ccggcactat    360

gccgatgccc aggccgcgga tcaccggtgc ggtcagtcgg gtcaggatgt cgcccggccc    420

caggtcgaag atccagcggg cgccggccgc gtggacacng gtgatctcgt ccaccatcga    480

ctttctgatc a                                                         491
```

```
<210> SEQ ID NO 108
<211> LENGTH: 364
<212> TYPE: DNA
<213> ORGANISM: Mycobacterium tuberculosis
<220> FEATURE:
```

-continued

<221> NAME/KEY: unsure
<222> LOCATION: (various positions within the sequence)
<223> OTHER INFORMATION: applicants are uncertain of bases designated
as "n"

<400> SEQUENCE: 108
taactcaagg cttgcgttga ggccccaggc ccatcgacgg tttggcggcc ttaaatgcac 60
tgaggtcgtc aattgacccc acagcggaaa tgccgactat tcgcaggcct ccttcgcctt 120
ggctgccgga gaggggctcc gcgggaaccg catgcaggta tatgacctcg gtttctcggg 180
tgctaccgcg tgccttgtcg aggatgaact cggcgttgga attgtccagc cggcccaatt 240
catcgagcgc agattcgtac acatggccgg cggcgacata cgcttcaccg tggatctgct 300
ccacacggac cgccctgtcg ggatcctgct cacgggtaaa ggaacttacn tggcnctcgg 360
tgcc 364

<210> SEQ ID NO 109
<211> LENGTH: 453
<212> TYPE: DNA
<213> ORGANISM: Mycobacterium tuberculosis

<400> SEQUENCE: 109
ccttctgcgc cacccacacc gtcaacgccc gcgaagtcga cgtcgtccag gccatcggcg 60
gcctcacgga tggattcggc gcggacgtgg tgatcgacgc cgtcggccga ccggaaacct 120
accagcaggc cttctacgcc cgcgatctcg ccggaaccgt tgtgctggtg ggtgtgccga 180
cgcccgacat gcgcctggac atgccgctgg tcgacttctt ctctcacggc ggtgcgctga 240
agtcgtcgtg gtacggcgat tgcctgcccg aaagcgactt ccccacgctg atcgaccttg 300
acctgcatgg ccggctgccg ctgcagcggt tcgtttccga acgcatcggg ctcgaagacg 360
tcgaggaggc gttccacaag atgcatggcg gcaaggtatt gcgttcggtg gtgatgttgt 420
gatggccgcc atcgagcgcg tcatcaccca cgg 453

<210> SEQ ID NO 110
<211> LENGTH: 329
<212> TYPE: DNA
<213> ORGANISM: Mycobacterium tuberculosis

<400> SEQUENCE: 110
atactcaagc ttgattttga tcatcatgat gatcatcacc cgaagtgtgg tagccgcagt 60
ggttatcgtg ggtaccgtcg tgctttccat gggcgcctct ttcgggcttt ccgtattggt 120
ctggcaggac attctgggta tcgagttgta ctggatggtg ttggcgatgt cggtgatcct 180
gctcctggcg gtgggatccg actacaatct gctgctgatt tcccggttga aaaaagaaat 240
tggggccgga ttgaacaccg gaattatccg tgccatggct ggtaccgggg gagtggttac 300
cgctgccggc atggtgttcg ccgttacca 329

<210> SEQ ID NO 111
<211> LENGTH: 438
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 111
attgnctttc ggcgccatcg gtgaggacgg cgtgcgggtg ctcaacgacg acgtcgtccg 60

-continued

```
cgggacacac ctcgatgctg ccgccatgga cgcggtcgaa cgcaagcagc tgatcgagct    120

acaacgccgc gcggaacgct tccgccgcgg gcgtgaccgc atcccgttga ccgggcggat    180

cgcggtgatc gtcgatgacg gcatcgccac cggagcgacg gccaaggcgg cgtgccaggt    240

cgcccgggcg cacggtgcgg acaaggtggt gctggcggtc ccgatcggcc cagacgacat    300

cgtggcgaga ttcgccgggt acgccgatga ggtggtgtgt ttggcgacgc cggcgttgtt    360

cttcgccgtc gggcagggtt accgcaactt cacccagacc tccgacgaag aagtggtggc    420

gttttctgga tcgtgctc                                                  438
```

<210> SEQ ID NO 112
<211> LENGTH: 438
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 112

```
atactcaagc ttttcccgtc cgtcatcgcc caagcgcgtg aggccgaagc ggctggttac     60

gactccctgt ttgtgatgga ccacttctac caactgccca tgttggggac gcccgaccag    120

ccgatgctgg aggcctacac ggcccttggt gcgctggcca cggcgaccga gcggctgcaa    180

ctgggcgcgt tggtgaccgg caatacctac cgcagcccga ccctgctggc aaagatcatc    240

accacgctcg acgtggttag cgccggtcga gcgatcctcg gcattggagc cggttggttt    300

gagctggaac accgccagct cggcttcgag ttcggcactt tcagtgaccg gttcaaccgg    360

ctcgaanagg cgctacagat cctcgagcca atggtcaagg gtgagcgcca acgtttttcg    420

gcgattggta cccaccga                                                  438
```

<210> SEQ ID NO 113
<211> LENGTH: 482
<212> TYPE: DNA
<213> ORGANISM: Mycobacterium tuberculosis

<400> SEQUENCE: 113

```
cggccaccgg ggccactccg cacaatctgt acccgaccaa gatctacacc atcgaatacg     60

acggcgtcgc cgactttccg cggtacccgc tcaactttgt gtcgaccctc aacgccattg    120

ccggcaccta ctacgtgcac tccaactact tcatcctgac gccggaacaa attgacgcag    180

cggttccgct gaccaatacg gtcggtccca cgatgaccca gtactacatc attcgcacgg    240

agaacctgcc gctgctagag ccactgcgat cggtgccgat cgtggggaac ccactggcga    300

acctggttca accaaacttg aaggtgattg ttaacctggg ctacggcgac ccggcctatg    360

gttattcgac ctcgccgccc aatgttgcga ctccgttcgg gttgttccca gaggtcagcc    420

cggtcgtcat cgccgacgct ctcgtcgccg ggaccagcag ggaatcggcg atttcgccta    480

ca                                                                   482
```

<210> SEQ ID NO 114
<211> LENGTH: 388
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated -continued as "n"

<400> SEQUENCE: 114
atactcaagc ttggggtggc gctgtcggtc ggtgtgcttg gcggcgtcgg tatcaacacc 60
gcccacgaaa tggggcacaa gaaggattcg ctggagcggt ggctgtccaa aatcaccctc 120
gcccagacct gctacgggca cttctacatc gagcacaacc gtggccatca cntccgggtg 180
tccacaccgg aggacccggc gtcggcgcgg ttcggcgaaa cgttgtggga gttcctgccc 240
cgcagtgtta tcggcggctt gcgctcggcc gttcatttgg aggcccaacg gctgcgtcgg 300
ctcggcgtca gcccctggaa tcccatgacg tatctgcgca acgacgtgcn caacncgtgg 360
ctgatgtcng tggtgttgtg gggtgggc 388

<210> SEQ ID NO 115
<211> LENGTH: 455
<212> TYPE: DNA
<213> ORGANISM: Mycobacterium tuberculosis

<400> SEQUENCE: 115
tcgccaccgc accgcggcga acgctcaaag gcacctactg gcaccaaggc cccacacgtc 60
accctgtgac ctcctgcgcc gaccccgccc gaggtcctgg ccgttaccac cgaacgggcg 120
agccgggagt ctggtacgca tcgaacaaag agcaaggtgc atgggcggag ttgttccgcc 180
acttcgtcga tgacggggtc gatccattcg aggtccgtcg ccgcgtcggt cgagtggcgg 240
tcacactcca ggtactcgac ctcacagacg agaggactcg atcccatcta ggtgtggacg 300
aaacagatct tctgtccgac gactacacca ccacccaggc catcgccgcc gcccgcgatg 360
ccaacttcga cgccgtactg gccccggcgg cggcgctccc cggttgtcaa acactttgcc 420
gtgttcgttc acgcactgcc caacatcgag cccga 455

<210> SEQ ID NO 116
<211> LENGTH: 328
<212> TYPE: DNA
<213> ORGANISM: Mycobacterium tuberculosis

<400> SEQUENCE: 116
atgaaataag aagagcacat ccctcagtcg gttatcatca ctagcgctcg ccgcacccgt 60
gtaaccgatc atagcgagcg aactggcgag gaagcaaaga atatctgttc tgtcagatag 120
ctcttacgct cagcgcaaga agaaatatcc cccgcgggaa caactccagg tagaggtaca 180
cacgcggata gccaattcag agtaataaac tgtgacactc acaccctcat caatgatgac 240
gaactacacc ccgatatccg gtcacatgac gaagggaaag agaaggatat catctgtgac 300
aaactgccct caaatttggc ttccttaa 328

<210> SEQ ID NO 117
<211> LENGTH: 318
<212> TYPE: DNA
<213> ORGANISM: Mycobacterium tuberculosis

<400> SEQUENCE: 117
atactcaagc ttgtcgaact ccttcttgaa taccggccgg ccatccacag atgcccggaa 60
gaacttccag gtacccatgg cggctggatc agggggcggc acagttggtc ttgtcctgcc 120
tcgagtggcg tcgttgtccg gcttggacgg ggctccgacg gtaccggagg gcagcgacaa 180
aacacttatg cacttgggcg acccgccgag acggtgcgac acccatcccg acggcacaag 240
ctcagccgcg gccgctcttg ttcttcgtcg gatcgacatt cacccacttc tgaccgggct 300

-continued

```
tgggcgaagg aagcagaa                                          318


<210> SEQ ID NO 118
<211> LENGTH: 405
<212> TYPE: DNA
<213> ORGANISM: Mycobacterium tuberculosis

<400> SEQUENCE: 118

ggtatagtcg ctgaccggtg caggtttcga caatgtggtg ccggttcggc ggctacgtgc     60

catcgagaca ctggcgcagg ctatcgcacc cgttatcggc tacgagcaaa tcgcggtatg    120

cgttcttgag catgagtcgg cgaccgtcgt catggtcgac acccacgacg gaaagacgca    180

gatcgccgtc aagcatgtgt gccgcggatt atcaggactg acctcctggc tgaccggcat    240

gtttggtcgc gatgcctggc gcccggccgg cgtggtcgtg gtcggctcgg atagcgaggt    300

cagcgaattc tcgtggcagc tcgaaagggt cctgccggtg ccggtctttg cgcaaacgat    360

ggcgcaggtt acggtcgcgc ggggtgcggc cctggcggcg gccca                     405


<210> SEQ ID NO 119
<211> LENGTH: 89
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as “n”

<400> SEQUENCE: 119

gacactatat natactcaag cttcaggtca atgtgcgcca agccctgacg ctggccgacc     60

aggccaccgc cgccggancc ctntctaga                                       89


<210> SEQ ID NO 120
<211> LENGTH: 354
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as “n”

<400> SEQUENCE: 120

ctgtagccac ctgttgccat ccccgtcatg cccgactctg gtcatctcgg atccgctgac     60

accccgctaa ggctgctcct ctcggtgcat tacctcaccg acggcgaacn cccccagctt    120

tacgactatc cggatgacgg cacctggttg ccggctaact tcaccgtcag cttggacggc    180

ggcgctaccg tcgatggcgc cagcggggcg atggccgggc ccggcgaccg attcgtcntc    240

ancctgtcgc gtgaacttgc cgacgtcatc gtggtcggtg tgggcaccgt gcgcattgag    300

ggctactccg gcgtccggat gggtgtcgtc aagcgcccgc accggcaggc ccga          354


<210> SEQ ID NO 121
<211> LENGTH: 379
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as “n”

<400> SEQUENCE: 121
```

-continued

```
atactcaagc ttcgcacgct cggcgcgcgc ggtaccgccc aggtcgccca acagatcgtc     60

gatgttcgcg tcgtccgcct cgcgcacgtg gtctgtcacc agtcaacgtt aacgccgccg    120

cacatgtcct gcggccgggc aaaaacgtga aaaacgagcg ggcgactgcn atgtcatgac    180

accgacggcc gccgatgggc ccagggtctg gcaaattcga tctgtgcggc cagtgccagc    240

agcgtcgcct cgtcatacgg ccggccgacg agttgaaccg acatgggcag gccgtcgccg    300

tcgaagtccc acggcaccac gggcgcgggc tggccggtca gattccaaaa ttgaaagtac    360

ggaaccgctg caccaccaa                                                 379


<210> SEQ ID NO 122
<211> LENGTH: 393
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 122

atcgtttcga ccaggcgctc catccggcga gtggatactc ccagcaggta gcaggtcgcc     60

accacgctgg tcagtgcgcg ttcagctcgc ttgcggcgct gcagcagcca gtccgggaaa    120

tagctgccct ggcgcagctt ggggatcgcg acgtcgatgg ttgcggcacg ggtgtcgaaa    180

tcacggtggc ggtagccgtt gcgctgattg gaccgctcat cgctgcgttc gcggtagccc    240

gccccgcaca gggcgtcggc ttcagccccc atcaaggcgg cgatgaacgt cgagagcagc    300

ccgcgcagca gatccgggct cgcctgtgcg agttggtcag ccagaagctg ctcggtgtcg    360

ataagatgan aagaagtcat tgcgttattt cct                                 393


<210> SEQ ID NO 123
<211> LENGTH: 333
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 123

atactcaagc ttgggtgttg ccgatcaccg gaagccgcat gatcagccac gtttcgcgcc     60

gcccggcata cggcggcgta ccgatctccg cgtcatacac ccgcgggtaa tcgccgacgg    120

tgccggttcg cgagccgaag gtgacgacgc tgattgaatc gagttccagg tccagcgggt    180

ggcgcagcaa cggcgcgagc tcaacnacgt caatcacgtt gtcgctttct acggtcaccg    240

acccggtgac cgtagtcgcc cggtgcgctc ggccgagaag ttgcaccgcc accaccgcga    300

caacgtcttg cacgcggacg ccaccccccg gat                                 333


<210> SEQ ID NO 124
<211> LENGTH: 426
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 124
```

-continued

```
gcgcnaacag ctcgcggcag cccacgacgt gctgcgtcgg attgccggcg gcgagatcaa     60

ttccaggcag ctcccggaca atgcggctct gctggcccgc aacgaaggac tcgaggtcac    120

cccggtgccc ggggtcgtgg tgcacctgcc gatcgcacag gttggcccac aaccggccgc    180

ttgatgcccg gtcggcaagc ccggcagttg ccaaacccag cgtgatcagg ctcggctcgc    240

gagttcggcg aaaaagtggc tcgcctgatc acctaccatc ggccaggatc tgcgtgtcat    300

cacgacgctc gccaaggagg ttgttgtggt gctatcgacg gcctttagcc agatgttcgg    360

aatcgactat ccgatagtgt ccgcgccaat ggacttgatc gccggcggtg agctggctgc    420

cgcngt                                                               426
```

<210> SEQ ID NO 125
<211> LENGTH: 336
<212> TYPE: DNA
<213> ORGANISM: Mycobacterium tuberculosis

<400> SEQUENCE: 125

```
atactcaagc tttctccgat acccgccatg tcgcgcacat ccaggacttc tgggggggatc     60

cgctgacagc ggcgggatcc caaagtgcgg atgatcgggc cgcctacgtc gtggtgtacc    120

tcgtcggtaa caacgaaacc gaagcgtatg actcggtcca cgcggtgcgg cacatggtgg    180

acaccacacc gccaccgcac ggggtgaagg cctatgtcac cggtccggca gcactcaatg    240

ccgaccaggc cgaggccgga aacaaaagta tcgctaaggt caccgcgatc acgaacatgg    300

tgatcgcagc aatgttgcta gtgatctatc gctccg                              336
```

<210> SEQ ID NO 126
<211> LENGTH: 347
<212> TYPE: DNA
<213> ORGANISM: Mycobacterium tuberculosis

<400> SEQUENCE: 126

```
ccatgagcac cgccagccga gcacgaggcc aaactccgcc gacgcaggcc ggttggactt     60

gtcgtgctgg acaaggggtt tagccgccga agcagtgacg tacatcggcg aagagcagtt    120

cgcctgtcga ccgacggcgc aaaccgtgag gctagggaag cgaggagcac atggccgccg    180

acccgcaatg tacacgctgc aagcaaacca tcgaacccgg atggctatac atcaccgccc    240

atcgccgcgg tcaagccggg atcgtcgatg acggcgcagt actgattcac gtgcccggtg    300

aatgccgcac cccggggagc actttccgcc aaaactaacc cggttgg                   347
```

<210> SEQ ID NO 127
<211> LENGTH: 315
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 127

```
cgggtgtcat tggccaccgg cggcggctgt ccgggaaatg gcgggtcccc ggtggttttg     60

ctgaggagtg ctgaaccgta gtcgaagtgg gcggcgtcag actccaccca gccagcaggc    120

agcgcgaanc tgaatcctcc aaccgggttg tcnatccgga caggttgggg tgcgtttggg    180

gcaatnacag gtggcggcgg tgcgttcggg tcggccggcg gaggtgctgc nttgggatcc    240

ccggctgggc attcggcntg ttggcggcgg ccggtggtgg ggggggcaac acgtgtcncc    300
```

-continued ggtgcgggtg gccct 315

<210> SEQ ID NO 128
<211> LENGTH: 354
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 128
ccaagatcta caccatcgaa tacgacggcg tcgccgactt tccgcggtac ccgctcaact 60
ttgtgtcgac cctcaacgcc attgccggca cctactacgt gcactccaac tacttcatcc 120
tgacgccgga acaanttgac gcagcggttc cgctgaccaa tacggtcggt cccacgatga 180
cccagtacta catcattcgc acggagaacc tgccgctgct agagccactg cgatcggtgc 240
cgatcgtggg ganacccact ggcgaacctg ggttcaacca aacttgaagg tgattgttaa 300
cctgggctac ggcgacccgg cctatggtta ttcgacctcg ccgcccaaat gttg 354

<210> SEQ ID NO 129
<211> LENGTH: 360
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 129
agcttcccga gttcggcttt ggatcaagac cccagtccgc gggcgcgatc cggcngctcg 60
gtgactacat caagccacaa atcgacggct ttcggggtgc cgataccgat gacgtggcgg 120
atgtcgagtg ttgagttctc ggcggggcgg atgctcacct ggcgatcacc tgcctctcgt 180
tgacgatcga tcgtctatgc cgccgtctct gcgggaacag gccnccagta catcgccaca 240
gacgggatcc acccgcattt cggctacggt tgctcgtttc ggtgttcgga ctagtcggtc 300
ctggtgacgt gccggtgatg cggaccggtc ctagcactga ccaatggcca aaatgcgggc 360

<210> SEQ ID NO 130
<211> LENGTH: 483
<212> TYPE: DNA
<213> ORGANISM: Mycobacterium tuberculosis

<400> SEQUENCE: 130
cggggggcct cttaatagtg taggaaagaa gctctacata ttcaggagga ttcaccatgg 60
ctcgtgcggt cgggatcgac ctcgggacca ccaactccgt cgtctcggtt ctggaaggtg 120
gcgacccggt cgtcgtcgcc aactccgagg gctccaggac caccccgtca attgtcgcgt 180
tcgcccgcaa cggtgaggtg ctggtctgcc agcccgccaa gaaccaggca gtgaccaacg 240
tcgatcgcac cgtgcgctcg gtcaagcgac acatgggcag cgactggtcc atagagattg 300
acggcaagaa atacaccgcg ccggagatca gcgcccgcat tctgatgaag ctgaagcgcg 360
acgccgaggc ctacctcggt gaggacatta ccgacgcggt tatcacgacg cccgcctact 420
tcaatgacgc ccagcgtcag gccaccaagg acccggccag atcgccggtc tcacgtgctg 480
cgg 483

<210> SEQ ID NO 131
<211> LENGTH: 423
<212> TYPE: DNA
<213> ORGANISM: Mycobacterium tuberculosis

<400> SEQUENCE: 131

```
atactcaagc ttcataacag gcctgttgtg ggcgcacccg gctcgccgag ttctgcacgc     60

accgcctcaa gtgcggcccg caccgccggc atctcccggt cacgcagggc cgcggcccgc    120

gccgcagcga cggcgtgttc gcgcagttcg ccgtcaatga tgctgacctg atcggccacc    180

cgggcgttct cggcgtcttc gcgttcacta atcgcggtgc tcagcagcgt ctcgacagcc    240

accacccgag tggcgaccag ctgctccacc acggaccgca gcgatgccgt cacctcaccc    300

gtccagcggt ccaccacgac acggtcgtgc accagcgcgc gggcattcac cacccaggcg    360

gtcaccgcca ggccgatcgc cacacccgcc accatccccg atgcagccag gccgggagta    420

aga                                                                  423
```

<210> SEQ ID NO 132
<211> LENGTH: 338
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 132

```
ctggtgctgg acggagccta gtacaacttc ctctccaatg ctcttgcccc gatcgcggcg     60

accaggatga cccaggacat cctgccgccc gaagtactgg aaaagctcac acccgagttc    120

gtcgcaccgg tggtggccta cctgtgcacc gaggagtgtg ccgacaaccc atcggtgtac    180

gtcgtcagtg gtggttaggt gcagcgagtt gcgctgtttg gcaacgacgg cgccaacttc    240

gacaaaccgc cgtcngtaca agatgttgcg gcgcggtggg ccgagatcnc cgatctgtcc    300

ggtgcgaaaa ttgctggatt caagttgtag aactaaat                            338
```

<210> SEQ ID NO 133
<211> LENGTH: 173
<212> TYPE: DNA
<213> ORGANISM: Mycobacterium tuberculosis

<400> SEQUENCE: 133

```
atactcaagc ttttccggcg tcgtccacct gacccaaaaa gcgcaggtgc gccgccaaac     60

ggcccgcctg gccgcgcaac tggtcggcgt cgccgtggcc gacaatcagt agctggacat    120

ccggaaaccg ctgcaccacc ttcggcagcg cgtcaagcaa aaacggccat tcc           173
```

<210> SEQ ID NO 134
<211> LENGTH: 255
<212> TYPE: DNA
<213> ORGANISM: Mycobacterium tuberculosis

<400> SEQUENCE: 134

```
tttcagatct catttttatg acatgactgg agatctgtct agattgcagc tcctgtgagc     60

gtgggtaccg gattcaagcc ggtcggtcac gccgcggtgg taccggcttt gcggcagtgc    120

tcggcctcga gttcggcgat cgcgcgcgaa gtgcgtttcg cgcaccaaga tcgcggccta    180

atggccggcg atgaccgcga tgaccagcgc gatccaggaa aaaccgttcc aaccagtgct    240
```

-continued

```
gggcggccat ccccg                                                    255


<210> SEQ ID NO 135
<211> LENGTH: 285
<212> TYPE: DNA
<213> ORGANISM: Mycobacterium tuberculosis

<400> SEQUENCE: 135

atactcaagc ttcccgacca caagttgaac agcaccgatt tcggcgagca cttcgtcaac     60

ttccagggtg cccgcaccaa gtatttcgac aagtatttcc gtcgggccgc cgccgccggc    120

gcgcggcagg tggtcatcct ggcggcgggg ctggactccc gcgcgtaccg gctgccttgg    180

cccgacggga ccacggtttt tgagctggac cgcccgcagg tccttgattt caagcgcgag    240

gtgctcgcca gccacggtgc ccaaccgcgc gccctgcgcc cgcga                     285


<210> SEQ ID NO 136
<211> LENGTH: 494
<212> TYPE: DNA
<213> ORGANISM: Mycobacterium tuberculosis

<400> SEQUENCE: 136

gtgtgctgtc aattcagagc tgagcctgat gcactcaact tactgagcat gctaacgctg     60

gtcgtgcggg tcttgttccc gcgtgtcggc agggcacacg ctcggggcgt agctgggaga    120

ggccccggtc aagcccggag agcagtgctc agtccgccag cttgaccgac tttcgatgag    180

aacgcgcttc tcgccgtatt gaactggcgt gctgacggtc gctgagcagc gctcgccgag    240

tgcggccgct gattctttca tcgagccagg aggcgcattc gtgttcggcc gcctgcgggt    300

cggccccatc gtcgacgcga tccgtcaccc actcctcgat caggtctgcc tcatcgaacg    360

ggccaacggt gctgtcggag tatgtgtgcg tgggcacggc gagccgggtg ctgtggtaca    420

cccaccgttg catgaccaag ttgacgcctg actggctgag caccgcgatc cgctcacagg    480

tcggaacgtt ggtg                                                     494


<210> SEQ ID NO 137
<211> LENGTH: 357
<212> TYPE: DNA
<213> ORGANISM: Mycobacterium tuberculosis

<400> SEQUENCE: 137

atactcaagc ttttggtcta gccggccgag cccgatacag gtgtcattgg ccaccggcgg     60

cggctgtccg ggaaatggcg ggtccccggt ggttttgctg aggagtgctg aaccgtatgc    120

gaagtgggcg gcgtcagact ccacccagcc agcaggcagc gcgaaactga atcctccaac    180

cgggttgtcg atccggacag gttggggtgc gtttggggca atgacaggtg gcggcggtgc    240

gtccgggtcg gccggcggaa gtgctgcgtt gggatcgccc ggctgggcat tctgcgtgtt    300

ggcggcggcc ggtggtgggg gggcaacagg tgtctccggt gcgggtggcg ctgcacc       357


<210> SEQ ID NO 138
<211> LENGTH: 458
<212> TYPE: DNA
<213> ORGANISM: Mycobacterium tuberculosis

<400> SEQUENCE: 138

ggggccactc cgcacaatct gtacccgacc aagatctaca ccatcgaata cgacggcgtc     60

gccgactttc cgcggtaccc gctcaacttt gtgtcgaccc tcaacgccat tgccggcacc    120

tactacgtgc actccaacta cttcatcctg acgccggaac aaattgacgc agcggttccg    180
```

-continued

```
ctgaccaata cggtcggtcc cacgatgacc cagtactaca tcattcgcac ggagaacctg    240

ccgctgctag agccactgcg atcggtgccg atcgtgggga acccactggc gaacctggtt    300

caaccaaact tgaaggtgat tgttaacctg ggctacggcg acccggccta tggttattcg    360

acctcgccgc ccaatgttgc gactccgttc gggttgttcc cagaggtcag cccggtcgtc    420

atcgccgacg ctctcgtcgc cgggacccag cacggaat                            458
```

<210> SEQ ID NO 139
<211> LENGTH: 595
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 139

```
ttctntcttc ccnnattcgt nnntctcnta ctaccngggc cncaaaacac cttggcnaac     60

gctcaaaggc gntacnggca ccaaggcccc acacgtcacc ctgtgacctc ctgcgccgac    120

cccgcccgag gtcctggccg ttaccactga acgggcgagc cgggagtctg gtacgcatcg    180

aacaaagagc aaggtgcatg ggcggagttg ttccgccnct ttttttatga cggggtcgat    240

ccattcgagg tccgtcgccg cgtcggtcga gtggcggtca cactccaggt actcgacctc    300

ncagacgaga ggactcgatc ccatctangt gtggacnaaa cagatcttct gtccgacgac    360

tacacaccac ccaggccatc gccgccgccc gcgatgccaa cttcnacncc gtnctggccc    420

cggcggcggc gctccccggt tgtcaaacac ctgccgtgtt cgttcacnca ctgcccaaca    480

tcnagcccga ncnatccnag gtccgtccaa cgcctccgcg gctcnccaac ctnctcccnc    540

tgatcntccg caccaaacac atgcccgact ccntgcnccn attgcttgna tccct         595
```

<210> SEQ ID NO 140
<211> LENGTH: 434
<212> TYPE: DNA
<213> ORGANISM: Mycobacterium tuberculosis

<400> SEQUENCE: 140

```
ccgctatcgg tcggtgtgct tggcggcgtc ggtatcaaca ccgcccacga aatggggcac     60

aagaaggatt cgctggagcg gtggctgtcc aagatcaccc tcgcccagac ctgctacggg    120

cacttctaca tcgagcacaa ccgtggccat cacgtccggg tgtccacacc ggaggacccg    180

gcgtcggcgc ggttcggcga gacgttgtgg gagttcctgc cccgcagtgt tatcggcggc    240

ttgcgctcgg ccgttcattt ggaggcccaa cggctgcgtc ggctcggcgt cagcccctgg    300

aatcccatga cgtatctgcg caacgacgtg ctcaacgcgt ggctgatgtc ggtggtgttg    360

tggggtgggc tgatcgcggt cttcggcccg gcgctgatcc cgttcgtcat catccaggca    420

gtcttcggct tcag                                                      434
```

<210> SEQ ID NO 141
<211> LENGTH: 321
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

-continued

<400> SEQUENCE: 141
atactcatgc ttgccgaagt tccgatgggt cgcgccggcg ancccagcga agtcgctagc 60
gtggccgtgt tcttggcttc ggatctatcc tcgtacatga ccggcaccgt gttggacgtg 120
actggcggcc ggttcatatg acaccgagat cattgccacg gtacggcaat tcgtcaagaa 180
ggaaatcttt cccaatgcac cggccctcga acgtggcaac agctacccgc aagaaatcgt 240
cgatcggctg ggtgttattg gcttgctcgg tcgccggctg caagggtatc gacaccaccg 300
agttcattct ccgggcgtgc c 321

<210> SEQ ID NO 142
<211> LENGTH: 348
<212> TYPE: DNA
<213> ORGANISM: Mycobacterium tuberculosis

<400> SEQUENCE: 142
ggcgtcaacg gtgtcggcac cggcgtcctg cagttggtag gcctgcagtt tgtgcatcag 60
gccgatgccg cggccctcgt ggccacgcat gtacagcacc acgccgcgcc cctcacgggc 120
gaccatcgcc agcgcggcgt ccagctgagg cccgcaatcg cagcggcgtg acccaaacac 180
atcgccggtc aagcactccg aatgcacccg gaccagcacg tcgtcaccgt cggcgttggg 240
cccggcgatc tcgccgcgga ccagcgcgac atgttccacg tcctcgtaga tgctggtgta 300
gccgatggcg cgaatctccc atgacgagtc ggaatccgcg cctcggcg 348

<210> SEQ ID NO 143
<211> LENGTH: 339
<212> TYPE: DNA
<213> ORGANISM: Mycobacterium tuberculosis

<400> SEQUENCE: 143
atactcaagc ttcggcctcg ctgcaggagt gggagccgca gggctggaaa tccgaaaaac 60
gagccggtga tcgcactgtc gccgatcggg gccgcacctg gttggtgtta ccgatgaatc 120
cgcacccaaa atgtggctgc ggtggcgttt cttgactcct tggcgtcgac tcttgtggca 180
gccaccgagc ggttggtcca ggatctggat gggcaaagtt gtgcggcccg gccggtgacg 240
gccgatgagc tgaccgaggt cgacagcgcc gtgttggctg acttggaacc gacatggatt 300
cgccccggtt ggcgtcacct caagcatttc aatggttat 339

<210> SEQ ID NO 144
<211> LENGTH: 269
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 144
atgcgtcacc ccgatgcgcc cagatcgggg cttcgcaaat aaagcacgaa caggcgggca 60
aaacgtctat ctcggagccg gaagggcaat cagccgaccg tcgacgaacg acaccggcga 120
taaccactta ggcgttgaac ggccggccca aacattacgc ctccgttgat aaggctttcg 180
gtctcttccc cggtcatccc aagcaccttg cggcaaattt gaacgctttc ctgtccgggc 240
accggccccg ggctttgggg tccntccga 269

<210> SEQ ID NO 145

-continued

<211> LENGTH: 285
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 145
atactcaagc ttcaatcgcg ccgccacaat ccaaatatgc gtctagcgtc tcgatgagcg 60
tcggtccggc atcggctagg ggccgcatca cgtcggtatg cagggccacg atcgcccaag 120
gcgtcgccca tcaagggcgc gttcgggcaa aaattcccct atccagcacg ggccgcggcg 180
ctccgcncca gccggcgacg gcgttcatcc cggagatcgc ctcgctagcg ctgcggtgcg 240
ccgcggtcag catgggcgcc gtggggccga tgaccaccgg ggcgt 285

<210> SEQ ID NO 146
<211> LENGTH: 75
<212> TYPE: DNA
<213> ORGANISM: Mycobacterium tuberculosis

<400> SEQUENCE: 146
ttcggcgggt ctgtagattg cggtcggcca ccccacaggc actcatgaac cgcagcccac 60
gatcgatctc ggtgg 75

<210> SEQ ID NO 147
<211> LENGTH: 164
<212> TYPE: DNA
<213> ORGANISM: Mycobacterium tuberculosis

<400> SEQUENCE: 147
gcgcaccatc gccagtaggt gcccgtggtc gggcgcgtcg agccacccga gcggaaacgc 60
gagtccgaac agcaacagca ggacgggcgc aaccagggcg gtgaccatgc ccccggcgct 120
gaacatcaac cacaggaagg gctccgccga gcgtccgcgc gacc 164

<210> SEQ ID NO 148
<211> LENGTH: 228
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 148
catcgtcgaa cttcggtccg ggttgntagn accgcagcac caaacgcacc caccgacccc 60
cacgcttcac gccaaccctt tagttcattg gcgtgaacag cagcgtagcc ggttgccccg 120
atatatgtgg aaaaatcgtt cggacgtaca aaaaaagttc ctgacgctgg cgtcaactcg 180
aaactgcctc ggaagtcaat gatgatccat cagtcaatat taaagtcg 228

<210> SEQ ID NO 149
<211> LENGTH: 238
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

-continued

<400> SEQUENCE: 149
atactcaagc ttgtctgctg cctcagcgta tgcatccaac agcgcatcgc gatcaacgat 60
caggcgcgcc gatttcgggc cgcgggcagt ggcactggcc agatggccgt ttttttcgag 120
aaacttcaac gcctgagcgc tgcttcccat cgagagaccg gtggcctcta caaccgatgc 180
gacagttgga ccggcgatgt tcgccagcag cgcttcacat acggcaagtn tggcgcgg 238

<210> SEQ ID NO 150
<211> LENGTH: 162
<212> TYPE: DNA
<213> ORGANISM: Mycobacterium tuberculosis

<400> SEQUENCE: 150
ttgtccaggc ggggaatcgg gcagggagac gacaccttcg ttcggttcga tcgtcgcgaa 60
cgggtagttg gccgcgacca cgttgtttcg ggtcagcgcg ttgaaaagtg tcgacttgcc 120
gacgttgggc aggcccacga tccccaggct caagctcaca ga 162

<210> SEQ ID NO 151
<211> LENGTH: 377
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 151
atactcatgc ttggcgcctg ggtggcagcc cacctgccca ccacacggac cgcggtgcgg 60
acgcggctga cgcgcctggt ggtcagcatc gtggccggtc tgctgttgta tgccaacttc 120
ccgccgcgca actgctggtg ggcggcggtg gttgcgctcg cattgctggc ctgggtgctg 180
acccnccgcn cnacaacacc ggtgggtggg ctgggctacg gcctgctatt cggcctggtg 240
ttctacgtct cgttgttgcc gtggatcggc gagctggtgg gccccgggcc ctggttggca 300
ctggcgacga cgtncgcgct gttccccggc atcttcggtc tgttcgccgt cgtggtaccc 360
tgttgccggg ttggccc 377

<210> SEQ ID NO 152
<211> LENGTH: 308
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 152
cgccaattca cgatatcgtt aaccgatatc ccgagccgat agctggcggg ctcgggtggt 60
ggccagcggc gctgcgacga aaggtgtgac cgtcatgaaa cagacaccac cggcggccgt 120
cggccgtcgt cacctgctcg agatctcagc atccgcagcc ggtgtgatcg cgctttcggc 180
gtgtagtggg tcgccgcccg accccggcaa aggccggccc gacacaaccc cggaacagga 240
agtcccggtc accgcgcccg aagnacttga tgcgcgaacn cggagtgctc caaacgcatc 300
ctgctgat 308

<210> SEQ ID NO 153
<211> LENGTH: 377

-continued

<212> TYPE: DNA
<213> ORGANISM: Mycobacterium tuberculosis

<400> SEQUENCE: 153
atactcaagc ttgggcactg acttcggtac cccctccgcc tttggccagc agcagccaca 60
gcgcggttcg cggaccgaac gtggacatca atagcccgga atcggtgtgt gcaagttggt 120
aaacggtgtt gatcccaagc tttgccagcc ttttcgtagt cttgggcccc acaccccaca 180
gtgcttcgac ggtacggtca cccatgatgg ccatccagtt ggcatcggtg agctgataaa 240
tgccagctgg tttcgccaac ccggtagcga tcttggcgcg ctgcttgttg tcactgatac 300
ctatcgagca agacagcccg gtttgcgaca aaatgacttt tcggatctct tcggcgactt 360
cgatggggtc gtcggga 377

<210> SEQ ID NO 154
<211> LENGTH: 259
<212> TYPE: DNA
<213> ORGANISM: Mycobacterium tuberculosis

<400> SEQUENCE: 154
aaagtcctgt gccggttcgc taaacacccg gcggacactc agacggtgct ggtggtgcgg 60
catggcaccg cgggcagcaa agcgcacttc tccgggggac gacagcaagc gaccgctaga 120
caagaggggt cgtgcgcagg cagaaacgtt ggtacacagc tgctggcgtt cggcgccacc 180
gatgtttatg ccgccgaccg ggtgcgctgc caccagacga tggagccact cgccgcggaa 240
ctgaacgtga ccatacaca 259

<210> SEQ ID NO 155
<211> LENGTH: 372
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 155
atactcaagc ttgggttcca cgcccgcgca gccacgccgt cacctttcca cgagacctca 60
cctgccgatc cgaaatggaa tcggccgtga cggaattggc gcaccgaaca cccaacgagg 120
tggtggcttc gtcgcgaacc gtcacccgag tcgcggccac cgtgcgcacg gcgacgttct 180
acacccgcac caagatccga aagctgcaag ctcccagcac cgatcccgac gtcatcaccg 240
ctgccgcccg gcacgtcctt gacctattcg agctggatcg gcccgtccgg ttgctgggag 300
tgcggttaga actggcctag aaccggcggg cacaccgcnc ctgggcgggg cgaattcttg 360
accgcnccgg cc 372

<210> SEQ ID NO 156
<211> LENGTH: 290
<212> TYPE: DNA
<213> ORGANISM: Mycobacterium tuberculosis

<400> SEQUENCE: 156
cgcggttggc gtagttggac gggtcgccct ccgaggccaa tgatgacgat gaccacgccg 60
atcacgatgg ccaccgagag ggacaacaac agaaagctga cgaatccctc cttggcggcc 120
ggggctttgt ggtcgccggt cgcgatgggc gcgaatttac ggcccgctcc cccaggccgc 180
cgcgaagcag ggtccccagc cagttggcgt aggcggaatt aacgatcagc gccaccgcga 240

-continued taacctgcca tgcctcgggc atatcgatgt gcggccagaa caggccgaac 290

<210> SEQ ID NO 157
<211> LENGTH: 470
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 157
ccaacaagag catcgggaca tacggagtca actacccggc caacggtgat ttcttggccg 60
ccgctgacgg cgcgaacgac gccagcgacc acattcagca gatggccagc gcgtgccggg 120
ccacgaggtt ggtgctcggc ggctactccc agggtgcggc cgtgatcgac atcgtcaccg 180
ccgcaccact gcccggcctc gggttcacgc agccgttgcc gcccgcagcg gacgatcaca 240
tcgccgcgat cgccctgttc gggaatccct cgggccgcgc tggcgggctg atgagcgccc 300
tgacccctca attcgggtcc aagaccatca ncctctgcaa caacggcgac ccgatttgtt 360
cngacggcaa ccggtggcga gcgcacctag gctacgtgcc cgggatgacc aaccaggcgg 420
cgcgtttcgt cgcgagcagg atctaaccgc gagccgccca tagattcccg 470

<210> SEQ ID NO 158
<211> LENGTH: 434
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 158
taanacccgt gtaatttggg atgggcaaaa aggccaagca ccgcgtggcc acgaacgccg 60
ggagggacaa tctcgggcgg ctagggcttc tcgcgggaag gcccgaacgt acggcgtttc 120
aacacgtcgc gtcnccctcc gaccgcgaac attcggggat ggcagcaacc tggtagcncc 180
ctggccgggc gatgatctgc agcgtcgccg cgggtagtcg ccgcccgggc ggctacagtc 240
tgaaacgcga tgaccatcga tgtgtggatg cagcatccga cgcaacggtt cctacacggc 300
gatatgttcg cctcgctgcg ccggtggacc ggtgggtcta tcccggagac cgacntcccg 360
atcgaagcga ccgtctcctc gatggacgcc ggcggcgtca ccctgggttt gctcaccgcc 420
tggcgtggcc ccaa 434

<210> SEQ ID NO 159
<211> LENGTH: 363
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 159
gtccgcaaaa gactcagcgg ccgactttgc tcgcagctgg cggtaccgcg ccaccgattc 60
gatgccgtgg tcgcggaaga atgcctcccg aaatcgcacg gccgactcca gttcggcgag 120
catccgcgat gccagctgcg gctgcgccct gccggccacg gcacccacat gcggcagttc 180

-continued gtccacctgg gccagcgccc cgccgccgaa gtccaaacaa tagaactgca cccggcccgc 240
atcgtgggta gcagccaacg ccatgatcag cgtccgcagc gcggttgact tgcccgtttg 300
cggtgcacct acgaccgcga cattgcctgc ggccccggac aagtcgatcg tcagcggcac 360 ccn 363

<210> SEQ ID NO 160
<211> LENGTH: 301
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 160
cgtggccacg aacgccggga gggacantct cgggcggcta gggcttctcg cgggaaggcc 60
cgaacgtacg gcgtttcaac acgtcgcgtc gccctccgac cgcgaacatt cggggatggc 120
agcaacctgg cagctacctg gccgggcgat gatctgcagc gtcgccgcgg gtagtcgccg 180
cccgggcggc tacagtctga aacgcgatga ccatcgatgt gtggatgcat catccgacgc 240
aacggttcct acacggcgat atgttcncct cgctgcgccg gtggaccggt gggtctatcc 300
c 301

<210> SEQ ID NO 161
<211> LENGTH: 436
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 161
atactcaagc tttgcggcgg gcgccgaaat gtgaacgcac caaacccgcc cgctgcgggt 60
cggcgggcca ctcgacctcg aatttcgccg ccgtgaccat ccagcccgac ggcagttggg 120
cacccggccc cccggtcgcg gcataactgt tggcgtcgcc gtcataaagc tcgaacagca 180
ccgaaaccga ctccaccacc ggccggtgcg cctcaaaatc cacgccgatc tccacatacc 240
gggaaaacgt cggtgtccca tcgggtttcg gcttgcccgc cagctgcaca ccaccggtgg 300
cctcggccac cttcgcggcc tgagcgcagc tacncatcct gacgatcatc accccgcccc 360
cggctcacgc ttggcctccg tgaccgcacg catcgcccgg ttgcgcgcac cgcgacgccc 420
gtacagccgc gcgcac 436

<210> SEQ ID NO 162
<211> LENGTH: 390
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 162
agcttgccgg gactgcggaa cagaagcggc ggttcctacc gcggtgtgcg gccggcgcga 60
tatcggcctt tttactaacc gaacccgatg tgggctccga tccggcgcgc atggcatcga 120

-continued cggcgacgcc gatcgatgac ggccaggctt acgagcttga gggtgtgaag ttgtggacca 180
ccaacggtgt ggtagcggac ctgctagtgg ttatggcgcg ggtaccgcgc agtgaagggc 240
accgaggggg aatcagcgcc tttgtcgtcg aggctgattc gcccgggatc accgtggagc 300
ggcgcaacaa gttcatggga ctgcgtggca tcnaaaacgg cgtgacccgg cttcatcgcg 360
tcngggtgcc caaagacaac ttgatcggca 390

<210> SEQ ID NO 163
<211> LENGTH: 75
<212> TYPE: DNA
<213> ORGANISM: Mycobacterium tuberculosis

<400> SEQUENCE: 163
ctcaagcttg gcgatgcggg ctggccaaaa ctggccgggc gggggttggc ttgttcaatc 60
aagggtgggt tgccg 75

<210> SEQ ID NO 164
<211> LENGTH: 110
<212> TYPE: DNA
<213> ORGANISM: Mycobacterium tuberculosis

<400> SEQUENCE: 164
ccgaaggccc gttcccgggc gttcagcaag cgatcgtcgg ttggcccact gcgggtcgaa 60
tcttgcggcc gcgccggtcg tggaacgccc aggtcacccg gcggcgtacc 110

<210> SEQ ID NO 165
<211> LENGTH: 455
<212> TYPE: DNA
<213> ORGANISM: Mycobacterium tuberculosis

<400> SEQUENCE: 165
atactcaagc tttttctgc tcatgaaggt tagatgcctg ctgcttaagt aattcctctt 60
tatctgtaaa ggctttttga agtgcatcac ctgaccgggc aaatagttca ccggggtgag 120
aaaaaagagc aacaactgat ttaggcaatt tggcggtgtt gatacagcgg gtaataatct 180
tacgtgaaat attttccgca tcagccagcg cagaaatatt tccagcaaat tcattctgca 240
atcggcttgc ataacgctga ccacgttcat aagcacttgt tgggcgataa tcgttaccca 300
atctggataa tgcagccatc tgctcatcat ccagctcgcc aaccagaaca cgataatcac 360
tttcggtaag tgcagcagct ttacgacggc gactcccatc ggcaatttct atgacaccag 420
atactcttcg accgaacgcc ggtgtctgtt gacca 455

<210> SEQ ID NO 166
<211> LENGTH: 309
<212> TYPE: DNA
<213> ORGANISM: Mycobacterium tuberculosis

<400> SEQUENCE: 166
ctcaagcttg gtgccgacat ggccgggctg gagcccgcgt atggcaaggt tccgctcaat 60
gtggttgtga tgcagcagga ctacgttcgc ctcaatcagc tcaaacgtca cccccgtggc 120
gtgctgcgca gcatgaaggt cggcgcccgc acgatgtggg cgaaggcaac aggtaaaaac 180
ctggtcggca tgggtcgagc cctcattggg ccgttgcgga tcgggttgca ccgcgccgga 240
gtgccggtcg aactcaacac cgccttcacc gatcttttcg tcaaaaatgg cgtcgtgtcc 300
ggggtatac 309

-continued

<210> SEQ ID NO 167
<211> LENGTH: 232
<212> TYPE: DNA
<213> ORGANISM: Mycobacterium tuberculosis

<400> SEQUENCE: 167
ccgaagcgtg ggaaatcctg accgaatacc gcgacgtgct ggacactttg gccggcgagc 60
tgctggaaaa ggagaccctg caccgacccg agctggaaag catcttcgct gacgtctaaa 120
agcggccgcg gctcaccatg ttcgacgact tcggtggccg gatcccgtcg gacaaaccgc 180
ccatcaagac acccggggga gatcgcgatc gaaacgcggc gaaacttggg cc 232

<210> SEQ ID NO 168
<211> LENGTH: 455
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 168
cgactcgaca agcattcttg acagttgttt tggctcggca tggttagcca aggttctgcg 60
gtcccaccag atcatcttgg tccggtagcg ctcgtccggg tatgctgccg ccgggattct 120
cgctgctatt actccccccg aaaaacgcca ccggtccagc gcgtgggccg ccgcggtccc 180
catcacaaac tgaaccccca acaggggaca tgcttagcgg tagggcgcgc gccaaggcgg 240
cagcaatcgc atcactgcgc tgcgcgtcac tattaaccca cccggacttc acttccacga 300
ccccgaatgg cgcccggtca ttgatcatct tgcgcaccgc ggataatccg ggattgccag 360
cccattcgac taccgcatgc gagtcatcgg ctgaccgcag cggtccgatt acccgagcgc 420
cccgantaca tctcctccaa tatcaatggg cgcaa 455

<210> SEQ ID NO 169
<211> LENGTH: 428
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 169
gcggtntagc ttcccgtcgt accggcgacc gccagccgag aagctcgttt tcccagtgtt 60
gctggggatt ctcacgctgc tgctgagtgc gtgccagacc gcttccgctt cgggttacaa 120
cgagccgcgg ggctacgatc gtgcgacgct gaagttggtg ttctccatgg acttggggat 180
gtgcctgaac cggttcacct acgactccaa gctggcgccg tctcgtccgc aggtcgttgc 240
ttgcgatagc cgggaggccc ggatccgcaa tgacggattc catgccaacg ctccgagttg 300
catgcggatc gactacgaat tgatcaccca gaaccatcgg gcgtattact gcctgaagta 360
cctggtgcgg gtcggatact gctatccggc ggtgacgacc cccggcaagc cgccatccgt 420
gctgctgt 428

<210> SEQ ID NO 170
<211> LENGTH: 385
<212> TYPE: DNA
<213> ORGANISM: Mycobacterium tuberculosis -continued

<400> SEQUENCE: 170
ctcaagcttg ggcgtgacgg ccaccggggc cactccgcac aatctgtacc cgaccaagat 60
ctacaccatc gaatacgacg gcgtcgccga ctttccgcgg tacccgctca actttgtgtc 120
gaccctcaac gccattgccg gcacctacta cgtgcactcc aactacttca tcctgacgcc 180
ggaacaaatt gacgcagcgg ttccgctgac caatacggtc ggtcccacga tgacccagta 240
ctacatcatt cgcacggaga acctgccgct gctaaagcca ctgcgatcgg tgccgatcgt 300
ggggaaccca ctggcgaacc tggttcaacc aaacttgaag gtgattgtta acctgggcta 360
cggcgacccg gcctatggtt attcc 385

<210> SEQ ID NO 171
<211> LENGTH: 318
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 171
cgggtgtcat tggccaccgg cggcggctgt ccgggaaatg gcgggtcccc ggtggttttg 60
ctgaggagtg ctgaaccgta gtcgaagtgg gcggcgtcag actccaccca gccagcaggc 120
agcgcgaagc tgaatcctcc aaccgggttg tcgatccgga caggttgggg tgcgtttggg 180
gcaatgacag gtggcggcgg tgcgttcggg tcggccggcg gaggtgctgc gttgggatcg 240
cccggctggg cattcggcgt gttggcggcg gccggtggtg ggggggcaac angtgtcgcc 300
ggtgcgggtg gcgctgca 318

<210> SEQ ID NO 172
<211> LENGTH: 443
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 172
ncttgatatt ggcgtcaacg gtgtcggcac cggcgtcctg cagttggtag gcctgcagtt 60
tgtgcatcag gccgatgccg cggccctcgt ggccacgcat gtacagcacc acgccgcgcc 120
cctcacgggc gaccatcgcc agcgcggcgt ccagctgagg cccgcaatcg cagcggcgtg 180
acccaaacac atcgccggtc aagcactccg aatgcacccg gaccagcacg tcgtcaccgt 240
cggcgttggg cccggcgatc tcgccgcgga ccagcgcgac atgttccacg tcctcgtaga 300
tgctggtgta gccgatggcg cgaaactccc catgacgagt cggaatccgc gcctcggcga 360
cccgctcaat gtgcttctcg tgcttgcgcc gccattcgat caagtcagca atggtgatca 420
gcgccagacc gtgctcntcg gcg 443

<210> SEQ ID NO 173
<211> LENGTH: 420
<212> TYPE: DNA
<213> ORGANISM: Mycobacterium tuberculosis

<400> SEQUENCE: 173

-continued

```
cataagggcc ggcgtacccg gtaccggccg cgggcctacc acgtgccgga actggaagcg     60

cagtaagccc tcaacgcgcc accgctttgg cccgcgcgcc cggcgtaggc gcatcggcgg    120

tggccgtggg gcggcgcact gcgacctcac cagcggcttt cgagctttgt tcgatcaacc    180

ggccagcatg gtcgaggatg cattcgagac catattcgaa attggtttca tcgggggccc    240

cgatccgatg ccccctccca gttgcgtgag caagcagcgg agtcgtcgcg ggatcgatgg    300

ccacggggtg ttcaatggcg gatggtccgc tgcccgccga ctggctcttg cgggagagcc    360

gatctagcac caccgatccg cgcacgtgga ccgaaaccgc cgagtagatg tcgaaagcgt    420
```

<210> SEQ ID NO 174
<211> LENGTH: 336
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 174

```
cgtccttttc cccaagatag aaaggcagga gagtgtcttc tgcatgaata tgaagatctg     60

gtacccatcc gtgatacatt gaggctgttc cctgggggtc gttaccttcc acnagcaaaa    120

cacgtagccc cttcagagcc nnatcctgag caanatgaac agaaactgag gttttgtaaa    180

cgccaccttt atgggcagca accccgatca ccggtggaaa tacgtcttca gcacgtcgca    240

atcgcgtacc aaacacatca cgcatatgat taatttgttc aattgtataa ccaacacgtt    300

gctcaacccg tcctcgaatt tccatatccg ggtgcg                              336
```

<210> SEQ ID NO 175
<211> LENGTH: 264
<212> TYPE: DNA
<213> ORGANISM: Mycobacterium tuberculosis

<400> SEQUENCE: 175

```
ctcaagcttc atgtccgtac ggctcgggta cgcttccgtc gcagtgtgcg agtgataaat     60

gacgaccggg acctcgtcgg catcttccat agcccgccac accttcagtt gctcaccgga    120

atccaaccgg tagaaggtcg gcgagcgctc ggcattggtc atcgggatat gccgctcggg    180

acggtcagag ccctcgggtc cggccagcac tccgcaggct tcgtcggggt ggtcgcgaca    240

cgcatgggcc accatcgcat tcac                                           264
```

<210> SEQ ID NO 176
<211> LENGTH: 325
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 176

```
ncgccgccag ccaccacgcg cgggtcgggc gccgggcccg ggccgccagg ctgctccgct     60

cggtgatggc acgccaccgc gacaccaccc ggctgcgcta cgtcgagcca taccgggcgg    120

agctacatcg gctcggccgc ccagtgttcg ggccctcttt cgaggtcgag gtcgataccg    180

atttgcgcat ccgcagccgc accctggacg acagaaccgt gccctacgan tgcttgtcgg    240

gcggggccaa agaacagctt ggcatcctgg cgcgattggc cggcgcggcg ctggtctcca    300
```

-continued

```
aagaagacgc ccttccggtg ctgat                                          325


<210> SEQ ID NO 177
<211> LENGTH: 243
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 177

cgccacgttc atgggcaaca accccgatca ccggtggaaa tacgtcttca gcacgtcgca     60

atcgcgtacc aaacacatca cgcatatgat taattcgtcc aattgtataa ccaacacgtt    120

gctcaacccg tcctcgaatt tccatatccg ggtgcggtag tcgccctgct ttctcggcat    180

ctctgatagc ctgagaagaa accccaacta aatccgctgc ttcncctatt ctccagcgcc    240

ggg                                                                  243


<210> SEQ ID NO 178
<211> LENGTH: 430
<212> TYPE: DNA
<213> ORGANISM: Mycobacterium tuberculosis

<400> SEQUENCE: 178

atactcaagc ttcaaccgat tgacgcattg tgcgaactga cggcgcccgc gcatggccaa     60

tccggaagac catcattggc cagtggccgg gcgctaacag gttccagccc cccaccagtg    120

ccgctcgaac atgcggtgca acccattcgc aggccggcag ggaaagcacc gcggaagccg    180

caaagggctg cagttccgcg cccaatagtg tcgtccgcaa ccagatgcgc tcgaaaaccg    240

cgccggcagt cagcgcaccc gacgcgaggt cgagagacgt cgtcagcgcg cccacatggg    300

gtgccaatcg gcacggcagg taggccgcgc gcaacccgaa cgcgtggtgc atgcccacgg    360

tccgcaggag gcgcagcacc cgccaatgcc gaagcccacg aaacatcggg cgcatccacg    420

cttcaacctc                                                           430


<210> SEQ ID NO 179
<211> LENGTH: 448
<212> TYPE: DNA
<213> ORGANISM: Mycobacterium tuberculosis

<400> SEQUENCE: 179

agcttttggc agggtctcct tcgaattcgg cgtgcaccgc tatgggttgc agcagcggct     60

ggcgccgcac accccactgg cccgggtgtt ttcgccccga acccggatca tggtgagcga    120

aaaggagatt cgcctgttcg atgctgggat tcgccaccgc gaggccatcg accgattact    180

cgccaccggg gtgcgagagg tgccgcagtc ccgctccgtc gacgtctccg acgatccatc    240

cggcttccgc cgtcgggtgg cggtagccgt cgatgaaatc gctgccggcc gctaccacaa    300

ggtgattctg tcccgttgtg tcgaagtgcc tttcgcgatc gactttccgt tgacctaccg    360

gctggggcgt cggcacaaca ccccggtgag gtcgtttttg ttgcagttgg gcggaatccg    420

tgctctgggt tacagcccga atcgtcac                                       448


<210> SEQ ID NO 180
<211> LENGTH: 380
<212> TYPE: DNA
<213> ORGANISM: Mycobacterium tuberculosis
```

<400> SEQUENCE: 180
atactcaagc tttgtcacac caactgtttc caccaggcgc tccatccggc gagtggatac 60
tcccagcagg tagcaggtcg ccaccacgct ggtcagtgcg cgttcagctc gcttgcggcg 120
ctgcagcagc cagtccggga aatagctgcc ctggcgcagc ttggggatcg cgacttctat 180
ggttgcggca cgggtgtcga aatcacggtg gcggtagccg ttgcgctgat tggaccgctc 240
atcgctgcgt tcgcggtagc ccgccccgca cagggcgtcg gcttcagccc ccatcaaggc 300
ggcgatgaac gtcgagagca gcccgcgcag cagatccggg ctcgcctgtg cgagttggtc 360
agccagaacc tgctcggtgt 380

<210> SEQ ID NO 181
<211> LENGTH: 532
<212> TYPE: DNA
<213> ORGANISM: Mycobacterium tuberculosis
<400> SEQUENCE: 181
ccttaagccc cgcagggccc ggcacgcgcg gtaccgccca ggtcgcccaa cagatcgtcg 60
atgttcgcgt cgtccgcctc gcgcacgtgg tctgtcacca gtcaacgtta acgccgccgc 120
acatgtcctg cggccgggca aaaacgtgaa aaacgagcgg gcgactgcaa tgtcatgaca 180
ccgacggccg ccgatgggcc cagggtctgg cagattcgat ctgtgcggcc agtgccagca 240
gcgtcgcctc gtcatacggc cggccgacga gttgaaccga catgggcagg ccgtcgccgt 300
cgaagtccca cggcaccacg gccgcgggct ggccggtcag attccagact tgaaagtacg 360
gaacccgctg caccaccagc agcaacgtcg aaactgcacc ccggcgttgg taggcgccga 420
tgcgggacgg gccggtcgcg gcgcctggcg tcacaactac gtcgacatcg tcgaagatcg 480
actggatcgg ctgctcacac cactcggcgg ccgcaggccg ccatccgccg tc 532

<210> SEQ ID NO 182
<211> LENGTH: 477
<212> TYPE: DNA
<213> ORGANISM: Mycobacterium tuberculosis
<400> SEQUENCE: 182
agctttttga gcgtcgcgcg gggcagcttc gccggcaatt ctactagcga gaagtctggc 60
ccgatacgga tctgaccgaa gtcgctgcgg tgcagcccac cctcattggc gatggcgccg 120
acgatggcgc ctggaccgat cttgtgccgc ttgccgacgg cgacgcggtg ggtggtcaag 180
tccggtctac gcttgggcct ttgcggacgg tcccgacgct ggtcgcggtt gcgccgcgaa 240
agcggcgggt cgggtgccat caggaatgcc tcaccgccgc ggcactgcac ggccagtgcc 300
gcggcgatgt cagccatcgg gacatcatgc tcgcgttcat actcctcgac cagtcggcgg 360
aacagctcga ttcccggacc gcccagcgca ttggtgatgg aatcggcgaa cttggccacc 420
cgctgggtgt tgacatcctc gacggtgggc aattgccccc ggtaacgttt gccgcct 477

<210> SEQ ID NO 183
<211> LENGTH: 461
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 183

-continued

```
cggtccgacc ctgttcgacg gctacctgaa tcaacccgat gccaccgccg cggcgttcga     60

cgccgacagc tggtaccgca ccggcgacgt cgcggtggtc gacggcagtg ggatgcaccg    120

catcgtggga cgcgagtcgg tcgacttgat caagtcgggt ggataccggg tcggcgccgg    180

tgaaattgaa acggtgctgc tcgggcatcc ggacgtggcg gaggcggcag tcgtcggggt    240

gcccgacgat gatctaggcc agcggatcgt tgcctacgta gtcggctcag cgaatgtcga    300

tgcggacggg cttatcaact ttgttgccca acaactttcg gtgcacaagc gcccgcgcga    360

ggtgcgtatc gtanatgcgc tgccgcgcaa cgccttgggg aaagtgctcc agaacattgc    420

tgtcagaagc tganctacgc gaattatcgt gttacgctgg a                         461
```

```
<210> SEQ ID NO 184
<211> LENGTH: 440
<212> TYPE: DNA
<213> ORGANISM: Mycobacterium tuberculosis

<400> SEQUENCE: 184

atactcaagc ttgccgaagt tccgatgggt cgcgccggcg agcccagcga agtcgctacc     60

gtggccgtgt tcttggcttc ggatctatcc tcgttcatga ccggcaccgt gttggacgtg    120

actggcggcc ggtccatatg acaccgagat cattgccacg gtacggcaat tcgtcaagaa    180

ggaaatcttt cccaatgcac cggccctcga acgtggcaac agctacccgc aagaaatcgt    240

cgatcggctg ggtgttattg gcttgctcgg tcgccggctg caagggtatc gacaccaccg    300

agttcattct cgggcgtgcc ggcgcattcg agctggcggt gcgcgctgcc cagcaccgtc    360

ataggtactt gacgatggtc cacgtcggac gagcgcctcc acgtcgctgc cgaacggtat    420

gcatggcggc tacgattctc                                                440
```

```
<210> SEQ ID NO 185
<211> LENGTH: 515
<212> TYPE: DNA
<213> ORGANISM: Mycobacterium tuberculosis

<400> SEQUENCE: 185

cggtgtcggc accggcgtcc tgcagttggt aggcctgcag tttgtgcatc aggccgatgc     60

cgcggccctc gtggccacgc atgtacagca ccacgccgcg cccctcacgg gcgaccatcg    120

ccagcgcggc gtccagctga ggcccgcaat cgcagcggcg tgacccaaac acatcgccgg    180

tcaagcactc cgaatgcacc cggaccagca cgtcgtcacc gtcggcgttg ggcccggcga    240

tctcgccgcg gaccagcgcg acatgttcca cgtcctcgta gatgctggtg tagccgatgg    300

cgcgaaactc cccatgacga gtcggaatcc gcgcctcggc gacccgctca atgtgcttct    360

cgtgcttgcg ccgccattcg atcaagtcag caatggtgat cagcgccaga ccgtgctcat    420

cggcgaacac cgcaattcat cggtgttgcg ccatcgagcc ctcatctttt tggctgacga    480

tctcgcaaat cgcccccgcg ggttgcagcc ggcat                               515
```

```
<210> SEQ ID NO 186
<211> LENGTH: 345
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as “n”

<400> SEQUENCE: 186
```

-continued

```
atactcaagc tttgggtgaa agccgatcac cggaagccgc atgatcagcc acgtttcgcg      60

ccgcccggca tacggcggcg taccgatctc cgcgtcatac acccgcgggt aatcgccgac     120

ggtgccggtt cgcgagccga aggtgacgac gctgattgaa tcgagttcca ggtccagcgg     180

gtggcgcagc aacggcgcga gctcaacgac gtcaatcacg ttgtcgcttt ctacggtcac     240

cgacccggtg accgtnctcg cccggtgcgc tcggccgata agttgcaccg ccaccaccgc     300

gacaccgtct tgcacgcgga cccacccccg gatccgttgt tggcc                     345


<210> SEQ ID NO 187
<211> LENGTH: 366
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 187

agcttgctgg catccgctcc agtagcgccc cgcgcgtggc ttccagcgcc cgcagatgct      60

ccatgagccg gccggtcgag tcggcgccgg cgttcaccgc cacccgccag gagctggcgg     120

ccagcatctc cgccttcacg cattgcgcga tcacagagag aatatacgtc tcatattcgt     180

tggaggtcgt cgcaggcaat cggtcgatga cggatttgat ggcatcgagc tgtgcttcgg     240

cgtagccctc cagcacgtcg gtatcgctgt ggcggtccac gacgaccgca ccggcgcggc     300

ggacagccgt cgggttggac gntgtgcggc gatcagtccg gccagctccg cctcgggatc     360

agcggc                                                                366


<210> SEQ ID NO 188
<211> LENGTH: 423
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 188

atactcaagc ttgctgcagc ttcctatgac tgctcccgaa acctgggggt gtgcctgctg      60

tgtatgcacg gcatacggac atccttcccc tgagacccgc ggtcgaacca gccacgtgtc     120

catcatcagg ggtcaacccc ggccaagggc gacggcacgc caagttcgcc gaccgttaac     180

ctagtgctgt tagcttcatt tgctgcgagc aaaacagctg gtcggccgtt aggaactgaa     240

ttgaaactca accgatttgg tgccgccgta ggtgtcctgg ctgcgggtgc gctggtgttg     300

tccgcgtgtg gtaacnacna caatgtgacc gggggaggtg caaccactgg ccaggcgtcg     360

gcgaaggtcg attgcggggg gaagaagaac tcaaagccag tgggtcgacg cgcaggccaa     420

cgc                                                                   423


<210> SEQ ID NO 189
<211> LENGTH: 453
<212> TYPE: DNA
<213> ORGANISM: Mycobacterium tuberculosis

<400> SEQUENCE: 189

agcttgacgc ggagacggac acattgcgaa cattgatgac aaaatagaaa tcattgatgg      60
```

-continued tttgagtcac caggccgatc aagccttcgc cgagccaaat tccaatcaag aggcccaagc 120
ccgtaccaat cagcccggca acgagggatt ccgtcattat cagccaaaat aactgctctc 180
gggttacacc caaacagcgc aatatggcga aaaacggtcg ccgttgcacg acattaaatg 240
tcacggtatt gtagattaaa aagataccca ccaacaaggc aatcaaactg agagcggtta 300
aattgaccgt aaaagcgtcc gtcatctgtt tgacggtgtc ccgttgggta tccgacgttt 360
ccatacgcac accggccggc agtctttgtt ggatgcgtgt tgcagtggcc tcatctttga 420
tgatcaaatc gatgtggctc agtcttccgg gca 453

<210> SEQ ID NO 190
<211> LENGTH: 402
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 190
atactcaagc ttcggctcag gcggcgctgc tggtaaagtc gctgaccggt gcaggtttcg 60
acaatgtggt gccggttcgg cggctacgtg ccatcgagac actggcgcag gctatcgcac 120
ccgttatcgg ctacgagcaa atcgcggtat gcgttcttga gcatgagtcg gcgaccgtcg 180
tcatggtcga cacccacgac ggaaagacgc agatcgccgt caagcatgtg tgccgcggat 240
tatcaggact gacctcctgg ctgaccggca tgtttggtcg cgatgcctgg cgcccggccg 300
gcgtggtcgt ggtccgctcg gatagcgagg tcagcgaatt cncntggcag ctccaaaggg 360
tcctgccggt gccggtcttt gcgcaaacna aggcncaggt ta 402

<210> SEQ ID NO 191
<211> LENGTH: 427
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 191
tgatcgcgca tcacctgctt cataaactgg aagcagcgca gcgcttcctt ttcggccgca 60
acatgagcca gcctctcgtc ggcggtcggg tgcaggtgct cgggcagctc ggccgcgaca 120
gccgcctgac cctgaaacca gcttccatat cccgcgacga acgacgccag tccgctacgt 180
aacccctccg cgactgtcca tggacaacag cgcgttctcc accgaccggg cccgggtgtg 240
gggtgtttcg gcgaccggca gccaggtggt ccacactgcc gacgggcgcc gcgagccgtt 300
caccgaccag gccgccgagc aagtccgccc gatcgcatac tccaaccggt tgcggtactg 360
caggttcagc tggcgtactc ctcgtcgcgc tcggcgaggt cttgctccag cacgtcgcan 420
acggcag 427

<210> SEQ ID NO 192
<211> LENGTH: 347
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated -continued as “n”

<400> SEQUENCE: 192
caaagcgcga actgctcgcg gcagcccacg acgtgctgcg tcggattgcc ggcggcgaaa 60
tcaattccag gcagctcccg gacaatgcgg ctctgctggc ccgcaacgaa ggactcgagg 120
tcaccccggt gcccggggtc gtggtgcacc tgccgatcgc acaggttggc ccacaaccgg 180
ccgcttgatg cccggtcggc aagcccggca gttgccaaac ccagcgtgat caggctcggc 240
tcgcgagttc cgggaagaag tggctccgcc tgatcaccta ccatccgcca ggatctgcgt 300
gtcttcacca cgcccgccaa ggaggttgtt gtggtgctat cgaccgn 347

<210> SEQ ID NO 193
<211> LENGTH: 330
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 193
ccggaagccg catgatcagc caagtttcgc gccgcccggc atacggcggc gtaccgatct 60
ccgcgtcata cacccgcggg taatcgccga cggtgccggt tcgcgagccg aaggtgacga 120
cgctgattga atcgagttcc aggtccagcg ggtggcgcag caacggcgcg agctcaacga 180
cgtcaatcac gttgtcgctt tctacggtca ccgacccggt gaccgtngtc gcccggtgcg 240
ctcggccgaa aanttgcacc gccaccaccg cgaaaccgtc ttgcacnccg gaagccaccc 300
ccgatccgtt gttgggccag gttattgggt 330

<210> SEQ ID NO 194
<211> LENGTH: 215
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 194
ccggaaccgc cgacggcacg gtataacgcc tccgcatatg ggtcgacaac cagcgggtcg 60
gacttctggg cttctagcgt tcgcgcngtc gcgacaaaca gcgcggtcga accgacactc 120
gttgtgatgt cctagctatc acgttcggta cgcacccaat cgagtctagc gcgggtagnt 180
cagccccgat ctccangctc cgccgagcca ggcgc 215

<210> SEQ ID NO 195
<211> LENGTH: 225
<212> TYPE: DNA
<213> ORGANISM: Mycobacterium tuberculosis

<400> SEQUENCE: 195
ctggtttatg tcccgttgaa gttccatcac ccgatgtggc gggagcactg ccaggtcgat 60
ctcaactacc acatccggcc gtggcggttg cgcgccccgg ggggtcggcg cgaactcgac 120
gaggcggtcg gagaaatcgc cagcaccccg ctgaaccgcg accacccgct gtgggagatg 180
tacttcgttg aggggcttgc caaccaccgg atcgcggtgg ttgcc 225

-continued

<210> SEQ ID NO 196
<211> LENGTH: 161
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 196
ccgagcagtt gggaatcgct ctgcancaaa ccaatattct gcgcgacgtc gcgcgacgag 60
ctggaccgat taggcgtacg cctccgnctg gacgacaccg gggcactcga tgaccccgac 120
gcctacgctc gcaggatatt gttcgccgga cccctctcta g 161

<210> SEQ ID NO 197
<211> LENGTH: 240
<212> TYPE: DNA
<213> ORGANISM: Mycobacterium tuberculosis

<400> SEQUENCE: 197
tatataatac tcaagcttgc cgacgccaac gctcgcgcga tgttgttagc ccgacccggc 60
tcttacatgg caccggtgcc ccacacgtca gcctgtgacg tcctgcaccg cgactcttta 120
catagaatgt ggattgccgg attggggatg tccggcatcg ctcaatctgt agtccgcgtt 180
gtcccgcgag ggccatgtgg atggggggaa ggatccgtgg cgtccgggat caccatgggg 240

<210> SEQ ID NO 198
<211> LENGTH: 348
<212> TYPE: DNA
<213> ORGANISM: Mycobacterium tuberculosis

<400> SEQUENCE: 198
atactcaagc ttgccgaagt tccgatgggt cgcgccggcg agcccaacga aatcgctagc 60
gtggccgtgt tcttggcttc ggatctatcc tcgtacatga ccggcaccgt gttggacgtg 120
actggcggcc ggttcatatg acaccgagat cattgccacg gtacggaaat tcgtccagaa 180
ggaaatcttt cccaatgcac cggccctcga acgtggcaac agctacccgc aagaaatcgt 240
caatcggctg ggtgttattg gcttgctcgg tcgccggctg cgagggtttc tacaccaccg 300
agttcattct cgggcgtgcc ggcgcattcg aactggcggt gcgcgctg 348

<210> SEQ ID NO 199
<211> LENGTH: 371
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 199
gcaccggcgt cctgcagttg gtaggcctgc agtttgtgca tcaggccgat gccgcggccc 60
tcgtggccac gcatgtacag caccacgccg cgcccctcac gggcgaccat cgccagcgcg 120
gcgtccagct gaggcccgca atcgcagcgg cgtgacccaa acacatcgcc ggtcaagcac 180
tccgaatgca cccggaccag cacgtcttca ccgtcggcgt tgggcccggc gatctcgccg 240
cggaccaacg cgacatgttc cacgtcctcg tagatgctgg tgtagccgat ggcgcgaaac 300
tccccangac aagtcggaat ccgcgcctcg gcgaaccgct caatgtgcct ctcgtgcttg 360

-continued

```
cgccgccatt c                                                         371


<210> SEQ ID NO 200
<211> LENGTH: 165
<212> TYPE: DNA
<213> ORGANISM: Mycobacterium tuberculosis

<400> SEQUENCE: 200

tggtccgtgt gcgcatacca atacaacgcg ccgggcacct gacgcggcgg ccgcaaccaa     60

tcggtggcca tcgccatctt ctgctacccg gtcaacggac gcaccttctc ctggccgacg    120

tagtgcgccc acccgccgcc gttgcgtccc atcgatccgg tcaac                    165


<210> SEQ ID NO 201
<211> LENGTH: 390
<212> TYPE: DNA
<213> ORGANISM: Mycobacterium tuberculosis

<400> SEQUENCE: 201

ggcgtgttgg ccaccggggc cactccgcac aatctgtacc cgaccaagat ctacaccatc     60

gaatacgacg gcgtcgccga ctttccgcgg tacccgctca actttgtgtc gaccctcaac    120

gccattgccg gcacctacta cgtgcactcc aactacttca tcctgacgcc ggaacaaatt    180

gacgcagcgg ttccgctgac caatacggtc ggtcccacga tgacccagta ctacatcatt    240

cgcacggaga acctgccgct gctaaagcca ctggcgatcg gtgccgatcg tggggaaccc    300

actggcgaac ctggttcaac caaacttgaa ggtgattgtt tacctgggct acggcgaccc    360

ggcctatggt tattcgacct ccccgcccaa                                     390


<210> SEQ ID NO 202
<211> LENGTH: 427
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 202

cgtccgtgnc ccctcaancg cgtgnngccg aagcggctgg ttacgactcc ctgtttgtga     60

tggacacttc taccaactgc ccatgttggg gacgcccgac cagccgatgc tggaggccta    120

cacggccctt ggtgcgctgg ccacggcgac cgancggctg caactgggcg cgttggtgac    180

cggcaatacc taccgcagcc cgaccctgct ggcaaagatc atcaccacgc tcgacgtggt    240

tagcgccggt cgagcgatcc tcggcattgg agccggttgg tttgagctgg aaacaccgcc    300

agctcggctt cgagttcggc actttcagtg accggttcaa ccggctcgaa gaggcgctac    360

agatcctcca gccaatggtc aagggtgagc gcccaacgtt tttcggcgat tggtacacca    420

ccgaatc                                                              427


<210> SEQ ID NO 203
<211> LENGTH: 498
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 203
```

-continued

```
ccgcttccgt gtaaccgagc anngcgagcg anctggcgag gaagcaaaga agaactgttc     60

tgtcagatag ctcttacgct cagcgcaaga agaaatatcc accgtgggaa aaactccagg    120

tagaggtaca cacgcggata gccaattcag agtaataaac tgtgataatc aaccctcatc    180

aatgatgacg aactatcccc cgatatcagg tcacatgacg aagggaaaga gaaggaaatc    240

aactgtgaca aactgccctc aaatttggct tccttaaaaa ttacagttca aaaagtatga    300

gaaaatccat gcaggctgaa ggaaacagca aaactgtgac aaattaccct cagtaggtca    360

gaacaaatgt gacgaaccnc cctcaaatct gtgacagata accctcagac tatcctgtcg    420

tcatggaagt gatatcgcgg aaggaaaata cgatntgagt cgtctggcgg cctttctttt    480

tctcaatgta tgagagcg                                                  498


<210> SEQ ID NO 204
<211> LENGTH: 265
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 204

tgacacccaa cagagggcac ttaagatggc aatgcggccg cctacctgca cgttttcgcg     60

atgtcagagg atgccgaggg agaacaatgc gagcacggcc gctgacnttg ctcaccgctt    120

tggcggcggt gacattggtg gtggttgcgg gctgcnaggc ccgantcnag gccgaagcat    180

atagcgcggc cgaccgcatt tcgtctcgac cgcaagcgcg acctcagccg cagccggtgg    240

agctactgct gcgcgccatc acgcc                                          265


<210> SEQ ID NO 205
<211> LENGTH: 369
<212> TYPE: DNA
<213> ORGANISM: Mycobacterium tuberculosis

<400> SEQUENCE: 205

acgggcgacg ctgaggtggg cccgcggcta ttcatgctgt cgtccacgtc cagcgacgca     60

ctgcgccaga cggcccgcca actagccacc tgggtggaag aacaccagga ctgcgtggcg    120

gcctcggatc tggcctacac gctggcgcgt ggccgcgcgc accggccggt gcgcaccgcg    180

gtggttgccg ccaacctgcc ggagctcgtc gagggtttgc gcgaggtggc cgacggtgac    240

ccctctatga cgcggcggtg ggacactgtg atctaagacc ggtctgggtc ttctccgggc    300

aagggtctca gtgggcggcg atgggcaccc aattgctcgc cagcgaacca gtgttcgcgg    360

ccaccatcg                                                            369


<210> SEQ ID NO 206
<211> LENGTH: 428
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 206

atactcaagc ttcgcgagat ccggatggca ctcacgctgg acaagacctt cacaaaatct     60
```

-continued

```
gaaatcctga cccgatactt gaacctggtc tcgttcggca ataactcgtt cggcgtgcag    120

gacgcggcgc aaacgtactt cggcatcaac gcgtccgacc tgaattggca gcaagcggcg    180

ctgctggccg gcatggtgca atcgaccagc acgctcaacc cgtacaccaa ccccgacggc    240

gcgctggccc ggcggaacgt ggtcctcgac accatgatcn aaaacttccc ggggaggcgg    300

aggcgttgcg tgccgcccag ggcgaaccgc tgggggttct gccgcagccc aatgattgcc    360

gcgcggctgc atcgcgggcg gcgaccgcca ttcttctgcg aatacgtcca ggagtactgt    420

ctcggggc                                                             428
```

<210> SEQ ID NO 207
<211> LENGTH: 378
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 207

```
agcttatgtg gccgcccacc taccttatct agcctagcta actaaatcca gtgccgacag     60

tgcgcggctg gccacccagc atgaggttat gaccacggca tatgccagcg cgctggcggc    120

gatgccgacg ctgaccgagt tggccgctaa tcacaccagc catgcggtgt tgctgggaac    180

gaatttcttt ggaatcaata cgatcccgat cgcgctcaat gaggccgact atgcgcggat    240

gtggattcag gcggccacca cgatgagtat ctatgagggc acctccgatg cggcgctggc    300

gtcngcaccg caaaccacac cggctccggt actgttcaac ggcggtgctg gcgtttgcca    360

gcgcctgccg gcgatctc                                                  378
```

<210> SEQ ID NO 208
<211> LENGTH: 284
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 208

```
atactcaagc ttgccaccca tgccgagcaa ggtcgactca gcgatgacga attgttcttc     60

ttcgcggtgt tgctgctggt tgcgggctat gagagcactg ctcatatgat tagcacnttg    120

tttctgacgc tggccgacta tccagatcag ctgacactcc ttgcgcagca accagacctg    180

atcccgtcgg cgatcgagga gcacctccgc tttatatcgc aatccaaaac atctgccgca    240

caacgcgcgt cgactattcg gtcggtcaag cggtcatccc ggga                     284
```

<210> SEQ ID NO 209
<211> LENGTH: 236
<212> TYPE: DNA
<213> ORGANISM: Mycobacterium tuberculosis

<400> SEQUENCE: 209

```
ccggggtaga acgatgcgat ctgggccatg tcgacatcgg tggtacaggt aaaccgcgcc     60

gtgtgcgcgg tctcggagat cagaacgtgg tcgcagttga caccgcgggc tttcagccag    120

tcgcgataat cggcgaagtc ggcgcctgcc gccccaacta gcgcgacctc gccacctagc    180

acaccgatgg cgaaggccat gtttccggcc acgccgccgc ggtgcatcat caactc        236
```

<210> SEQ ID NO 210
<211> LENGTH: 278
<212> TYPE: DNA
<213> ORGANISM: Mycobacterium tuberculosis

<400> SEQUENCE: 210
atactcaagc ttggcggcaa cgccactacc gggctcacca ggtcctgtgc cgccaccgcc 60
ggcgccgaaa gcaccatcag gtcgtagttg tctggacgtt cgacaccgta agcgaacaca 120
atgccgccgc ccatgctgtg cccgagcacg atgcgcttgc acccgggata ttcccgggtg 180
gcgatcccaa cgagggtgtc gaagtcagcg gtgtatctga gatgtctctc actatcatcc 240
gtttggcacc cgagcgggca tgcccgcggg gggtcaac 278

<210> SEQ ID NO 211
<211> LENGTH: 360
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 211
gtcgacggca tcaaggtccg cagtgatggt gttcatctca cccaggaagg cgtgaagtgg 60
ctgataccgt ggcttgagga ttcggtgcgg gtcgccagtt aatccgccgt gtgctccgga 120
tgagcgcgac ggtaaccctg gaattgtgct gtgtgctggc tgtgtcgttg tgatgagcct 180
gtctaagtgg tgcgtaaccg tttgacgagc cgcggcctcg ctgcaaacat tgaagcccgc 240
acgtctgggt ttgtatttac acaacgaggg cgctccccga tctggcgcgc gcaacgaggt 300
gcncactatc cattcgaggt gaactggact ccttgatgct catgccggtg cggttttgtc 360

<210> SEQ ID NO 212
<211> LENGTH: 256
<212> TYPE: DNA
<213> ORGANISM: Mycobacterium tuberculosis

<400> SEQUENCE: 212
atactcaagc ttgcgttcga tgaagtagtc gtcggtcagc gccgcctctt cgagctcctt 60
ggcgatgccc agcaaggagt catcgccgcc gagcttggcc aggatcttgt cggcctgttc 120
cttgacgatg cgggcccgcg gatcgtagtt cttgtagaca cgatgaccga aacccatcaa 180
tttgaccccg gcctcgcggt tcttgacctt gcgttacaaa ctcgctgacg tcgtcgccgc 240
tgtcgcgaat gccctc 256

<210> SEQ ID NO 213
<211> LENGTH: 262
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 213
ngtcaagccg agcatgcgcg aggnaacgac gaacccaaca agccatggtg gttggcgccg 60
tcgagaggtc ggcggtcgcc acaacgggaa gatcgccttg agcgtcgctc gaccgccgcc 120

-continued tcgagttggg tcataacgaa gtagctgatg ccgatcatgt cgacgtttcc gtcgcatcag 180
cgtgcagcgg cgacccactc gacgaggtct cggtgccgcc gcggccaggg caccagcagt 240
gacgattcca ggcgccgtcg gg 262

<210> SEQ ID NO 214
<211> LENGTH: 336
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 214
cgataatcgc ttccggtaag tgcagcagct ttacgacggc gactcccatc ggcaatttct 60
atgacaccag atactcttcg accgaacgcc ggtgtctgtt gaccagtcag tagaaaagaa 120
gggatgagat ctccccgtgc gtcctcagta agcagctcct ggtcgcgttc attacctgac 180
catacccgag aggtcttctc aacactatca ccccggagca cttctagagt aaacttccca 240
tcccgaccac atataggcta aggtaatggg cattaccgcg agccattact cctacgcgcg 300
caattaacga atccaccatc ggggccgctg gtgtcn 336

<210> SEQ ID NO 215
<211> LENGTH: 259
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 215
naatactcaa gctttctcgt gattaccacc cgtgtaattt gggatgggca aaaaggcgaa 60
tcaccgcgtg gccacaaacg ccgggaggga caatctcggg cggctagggc ttctcgcggg 120
aaggcccgaa cgtacggcgt ttcaacacgt cgcgtcgccc tccgaccgcg aacattcggg 180
gatggcagca acctggtatc accctggccg ggcaatgatc tgcagcgtcg ccgcgggtag 240
tgnccgcccg ggcggctac 259

<210> SEQ ID NO 216
<211> LENGTH: 325
<212> TYPE: DNA
<213> ORGANISM: Mycobacterium tuberculosis

<400> SEQUENCE: 216
ccaactagag catcgggaca tacggagtca actacccggc caacggtgat ttcttggccg 60
ccgctgacgg cgcgaacgac gccagcgacc acattcagca gatggccagc gcgtgccggg 120
ccacgatgtt ggtgctcggc ggctactccc agggtgcggc cgtgatcgac atcgtcaccg 180
ccgcaccact gcccggtctc gggttcacgc agccgttgcc gcccgcagcg gacgatcaca 240
tcgccgcgat cgccctgttc gggaatccct cggggccgcg ctggcgggct gatgatcgcc 300
ctgacccctc aattcgggtc caaga 325

<210> SEQ ID NO 217
<211> LENGTH: 300
<212> TYPE: DNA
<213> ORGANISM: Mycobacterium tuberculosis -continued

<400> SEQUENCE: 217
atactcaagc ttgctgcagc ttcctgtgac tgctcccgaa acctgggggt gtgcctgctg 60
tgtatgcacg gcatacggac atccttcccc tgagacccgc ggtcgaacca gccacgtgtc 120
catcatcagg ggtcaacccc ggccaagggc gacggcacgc caagttcgcc gaccgttaac 180
ctagtgctgt tagcttcatt tgctgcgagc aaaacagctg gtcggccgtt aggaactgaa 240
ttgaaactca accgatttgg tgccgcccgt aagtgtcctg gctgccggtg cgctggtgtt 300

<210> SEQ ID NO 218
<211> LENGTH: 265
<212> TYPE: DNA
<213> ORGANISM: Mycobacterium tuberculosis

<400> SEQUENCE: 218
agcttgcgcg gcgtggcgat cgcggttcaa ggcgcgctct tcgagcacaa cgagcgaaga 60
cagctcggcg acggagcctt tatcgacatc cgttcgggct ggctgaccgg cggcgaagaa 120
ctgctggacg cgttgttgtc gacggtgccg tggcgagccg agcgccgtca gatgtacgac 180
cgggtggtcg atgtgccgcg gctggtgagt tttcacgacc tgaccatcga agatccgccg 240
catccgcagc tggcgcggat gcgcc 265

<210> SEQ ID NO 219
<211> LENGTH: 362
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 219
aatactcaag cttgcgcacg accaggacgt cgagtggcgc ttgcagtgac ttggcgacct 60
caaaggccac cggtaccccg ccgcgcggca agccaaggac nacnacggcc ttgccggata 120
gctgcgccag gcgttgcgcc aactggcgtc cagcgtcgcc acgatcgtca aagagcttca 180
tctgccgagt gtgtcgccat ctcatggctc caaatatgga attaggtccc tgggccgact 240
gacgacagtc cctcagcgac cggattgcgc atcccgcctt gtacgctgct ccgcaaatcc 300
cgggcttgcg tccgcggaag cgaactcggc ggcgctacgg tggtggctca cttcggccgt 360
gc 362

<210> SEQ ID NO 220
<211> LENGTH: 486
<212> TYPE: DNA
<213> ORGANISM: Mycobacterium tuberculosis

<400> SEQUENCE: 220
ggttggtgcg gtccaccttc gcggcggcgg cgcgatatgc cttgctggtc ttgctcattt 60
gatatccaat ctatgggtcg tggttactca gcgggccgaa gctggccctc ccacgggtag 120
ggccctattc gacggtgatg cccatcgacc gagcggtacc ggcgatgatc ttggccgcag 180
cgtcgacgtc gttggcgttg aggtccgtct tcttggtctc ggcgatttcg cggacttgat 240
cccaggtgac tttggcgacc ttggtcttgt gcggctccgc cgaacccttc gccacaccag 300
cggccttaag cagcagcttg gcggcgggcg gcgtcttcag cgtgaaagtg aagctacggt 360
cttcataaac ggtgatctcc accgggatga cgttgccgcg ctggttctcc gtcgcggcgt 420

-continued tgtacgcctt gcagaactcc atgatgttga cccgtgctga ccgaacgcgg ggcccactgg 480
cggggc 486

<210> SEQ ID NO 221
<211> LENGTH: 373
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 221
atactcaagc ttttcgaccc gcaagccggc ggtgcccctc ctcgttccgc tgcccggtct 60
gctcgatcgg ttcggggtcg ccgcgctagg cccaattgcc cggctcctcc tcgggccgtt 120
ccacaacccg catcgtcgcc gggctaggtt caagccatgc cggtaaaccc caggacgcca 180
gtgctgatcg gctatggaca ggtcaaccac cgaggcgaca tcgacgccna aaatcagtcc 240
atcgaacccg tcgacctgat ggccnccgcg gcccggaaag ccgccgagtc caccgtgctc 300
gaagcggtgg attccatccg tgtggtgcac atgctgtcgg cgcattaccg gaattcccgg 360
gcgtctcctc ggc 373

<210> SEQ ID NO 222
<211> LENGTH: 331
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 222
ncctggttca tgaactggaa gcagcgcagc gcttcctttt cggccgcaac atgagccagc 60
ctctcgtcgg cggtcgggtg caggtgctcg ggcagctcgg ccgcgacagc cgcctgaccc 120
tgaaaccagc ttccatatcc cgcgacgaac gacgccagtc cgctacgtaa cccctccgcg 180
actgtccatg gacaacagcg cgttctccac cgaccggggc cgggtgttgg ggtgttcggc 240
aacggcaacc aagttggtcc acactgccga cgggcgccgc aaatccgttc accgaaccag 300
gccgccnaaa caattccgcc cgatcccata t 331

<210> SEQ ID NO 223
<211> LENGTH: 377
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 223
atactcaagc ttgtcgggat caatctcgag ggcatccacg cacgaaaagt aaactctatc 60
aagctttttg acgacaccca cggacgcccc atatatgttc gggtgggcaa gaacggtccc 120
tacctggaac gtttggtggc cggcgacacc ggtgagccca cgccgcagcg ggccaacctc 180
agcgactcga ttaccccgga cgaactgact ctacaggtgg ccgaagagct ctttgccaca 240
ccgcaacagg gacggacttt gggcttggac ccagaaaccg gccacgaaat ctttgccagg 300

-continued

```
ggaaggccgg tttgggcctt atgttaccta tatcctgccg gaacctgcgg ctgatgcggc    360

cgcggccgct cagggan                                                   377


<210> SEQ ID NO 224
<211> LENGTH: 436
<212> TYPE: DNA
<213> ORGANISM: Mycobacterium tuberculosis

<400> SEQUENCE: 224

agcagctagc cgcgctcgcc gcgctggtcg gtgcgtgcat gctcgcagcc ggatgcacca     60

acgtggtcga cgggaccgcc gtggctgccg acaaatccgg accactgcat caggatccga    120

taccggtttc agcgcttgaa gggctgcttc tcgacttgag ccagatcaat gccgcgctgg    180

gtgcgacatc gatgaaggtg tggttcaacg ccaaggcaat gtgggactgg agcaagagcg    240

tggccgacaa gaattgcctg ggctatcgac ggtccagcac aggaaaaggt ctatgccggc    300

accgggtgga ccgctatgcg cggccaacgg ctggatgaca gcatcgatga ctccaagaaa    360

cgcgaccact acgccattca agcggtcgtc ggcttcccga ccgcacatga tgccgaagaa    420

ttctacagct cctccg                                                    436


<210> SEQ ID NO 225
<211> LENGTH: 539
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 225

cgcgactggc tccccggncg gctgctcggg tccgccgata gagaccggga tgtcgcccga     60

cgacgggcag ccgggttgcg tgggacgggg cgggggtcgg gcagcccaag caacgggcta    120

gtccccgaat cctacggagc cgtcacctac gcctacgtaa tagtagctat caataacagt    180

tgacatacgc aacgatctgt gagatcaata ttgcctgacg catgtcaaga caggcgtcaa    240

gacaggtgtc aataattcgc tccgctggtg acggtaaccg gtcgtgcggg tgtgtgacgc    300

ctaaggaagg agtgtgggtg gtgacgctga gagtggttcc tgagggtttg gcggccgcca    360

gtgcggcggt ggaggcgttg accgcacggc tggccgccgc acacgctggc gcggcgccgg    420

cgattacggc ggtggtggcg cccgcggcgg atccggtgtc gttgcagaat gcggtggggt    480

ttagcgcctt aagtagccag catgccgcga tcgccggcga aagggtccaa gaactgggt     539


<210> SEQ ID NO 226
<211> LENGTH: 517
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 226

atactcaagc ttattgaacc gcgggtcgca ggcaaagtgg acctcataac gactcgggtc     60

cagcgaccgc gccaacacga acggccggac gacgtgggcc agggtcgcgg cctcccctac    120

aaacaggatc cgttgcctgc gaacgacagg ctccggtgcg gcgttgggcg ccgtgctcgt    180
```

-continued

```
cccagcgtcc ggtcccgggt cgccggcgac gcttgtttcc tccatactcg ccccctaatc    240

tcgaggcagc ccgtacccgc aggcaacctc ccaaaaatgc aatcccgcaa aatgcaatgc    300

gtcnagctat ttctcacacc gaccgctagt tgcggatcag aaatccgttg ggcgcggaag    360

tccagccgaa tttgttctcc cgctccgcat catgcttgta atcgtttgga aattcatcct    420

catatgcctc gatcgcttca tagggtccag gcccaaaccc gggcaggact gggtggccgt    480

tgatgttgga atcctccact actaggtatt caccggc                             517
```

<210> SEQ ID NO 227
<211> LENGTH: 488
<212> TYPE: DNA
<213> ORGANISM: Mycobacterium tuberculosis

<400> SEQUENCE: 227

```
gtctcgatca tggccaaaga gctcgacgaa gccgtagagg cgtttcggac ccgcccgctc     60

gatgccggcc cgtatacctt cctcgccgcc gacgccctgg tgctcaaggt gcgcgaggca    120

ggccgcgtcg tcggggtgca caccttgatc gccaccggcg tcaacgccga gggctaccga    180

gagatcctgg gcatccaggt cacctccgcc gaggacgggg ccggctggct ggcgttcttc    240

cgcgacctgg tcgcccgcgg cctgtccggg gtcgcgctgg tcaccggcga cgcccacgcc    300

ggcctggtgg ccgcgatcgg cgccaccctg cccgcagcgg cctggcagcg ctgcagaacc    360

cactacgcag ccaatctgat ggcagccacc ccgaagccct cctggccgtg ggtgcgcacc    420

ctgctgcact ccatctacga ccagcccgac gccgaatcag ttgttgccaa tatgatcggg    480

ttctcgac                                                             488
```

<210> SEQ ID NO 228
<211> LENGTH: 264
<212> TYPE: DNA
<213> ORGANISM: Mycobacterium tuberculosis

<400> SEQUENCE: 228

```
atactcaagc tttcgtcagt tcatggcgcc agcagaccaa caagagcatc gggacatacg     60

gagtcaacta cccggccaac ggtgatttct tggccgccgc tgacggcgcg aacgacgcca    120

gcgaccacat tcagcaaatg gccagcgcgt gccgggccac gaggttggtg ctcggcggct    180

actcccaggg tgcggccgtg atcaagatct tcaccgccgc accactgccc ggcctcgggt    240

tcacgcatcc gtttggccgc cgcc                                           264
```

<210> SEQ ID NO 229
<211> LENGTH: 229
<212> TYPE: DNA
<213> ORGANISM: Mycobacterium tuberculosis

<400> SEQUENCE: 229

```
gccccgtgta atttgggatg ggcaaaaagc gaagcaccgc gtggccacga acgccgggag     60

ggacaatctc gggcggctag ggcttctcgc gggaaggccc gaacgtacgg cgtttcaaca    120

cgtcgcgtcg ccctccgacc gcgaacattc ggggatggca gcaacctggt agcaccctgg    180

ccgggcgatg atctgcagcg tcgccgcggg tagtctccgc ccgggccgc                229
```

<210> SEQ ID NO 230
<211> LENGTH: 266
<212> TYPE: DNA
<213> ORGANISM: Mycobacterium tuberculosis

<400> SEQUENCE: 230

-continued atactcaagc ttcctttgac cgaacgcgtc caccgcaccg tgagattggt ggcgccattc 60
gtcgtggtgt agctgctgtt ggcggcgtcg ccgtattgtg cgggccagcc ttgtgcgggg 120
gccgcttcta cccacaagtc ggcacttccg caaccgccca gctcgaccgc gaattacggc 180
ggccgcaacg gccgccggaa ggcgtcacgc aatcgcttat cctttccagg ttcccaaatc 240
ctccgcttac ttgggtcctt catcgg 266

<210> SEQ ID NO 231
<211> LENGTH: 258
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 231
ggcagcggcg acaaccggaa cgtccgcacg gtgctcaatc acgggtgcac ggtgtgcatc 60
agaatggcgg gggttcgttg tcgcggtgag gcgttcggcg aggaggtagt gtctacccct 120
tgcccgcggg ttcgtgcgga ctgaaaggga tttcattggg aacccacggc tgcgtatcgc 180
agggcctcgg tgacgtctgc ttcctcnagc tcaggaagtt cggcgagaat ctcggtggat 240
gttatttggt ccgcctac 258

<210> SEQ ID NO 232
<211> LENGTH: 224
<212> TYPE: DNA
<213> ORGANISM: Mycobacterium tuberculosis

<400> SEQUENCE: 232
atactcaagc tttctcggct tctctgatag cctgagaaga aaccccaagt taatccgctg 60
cttcacctat tctccagcgc cgggttattt tcctcgcttc cgggctgtca tcattaaact 120
gtgcaatggc gatagccttc gtcatttcat gaccagcgtt tatgcactgg ttaagtgttt 180
ccatgagttt cattctgaac atcctttatt cattgttttg cgtt 224

<210> SEQ ID NO 233
<211> LENGTH: 333
<212> TYPE: DNA
<213> ORGANISM: Mycobacterium tuberculosis

<400> SEQUENCE: 233
atactcaagc ttggtgaccg gcaccgcgat acgttgcggc aggcatctgg gctggcggtg 60
gttcgccgct ccgaagccgt cgaacaccat cgccagcgcg gcttccacat caacgaccat 120
ttcggccagc ttgcggcgca tcagcggctt gtcgatgagc gccccaccga atgcccgccg 180
ctgcccggcg tatcacatcg attcgaccat cgcgcggcgc gcgttgccga gggcgaacga 240
ggcggtgccc aaccgcaatc tgtttggtca gctccctcat gcgggttgat tccttgccgt 300
ccggacgggc ccgcgtcatg cgctcggttc gcc 333

<210> SEQ ID NO 234
<211> LENGTH: 407
<212> TYPE: DNA
<213> ORGANISM: Mycobacterium tuberculosis

<400> SEQUENCE: 234
ccgttgcgca gcgtgagccg atagttgaca tccggctcgg tgaaggtgaa atcgatggcc 60

-continued aggtcgaggt cccatgcgcg tgggccattg atgctgatcg ccaggacgtc aaagatttgg 120
tccggcgtca gctgggcgaa aaacgtgggc gccgggactt gcccggagct gcccgggttc 180
ccgtcgcgca gctcggcggc cccggtcaga aagaaattgc gccaggtcgc acactccgcg 240
ccgtaggcca gctgctccag ggtgtcggca tagagcccgc gggccgcagc gtgctcgctg 300
tcggcgaaca ccgcatggtc gagaagcgtt gccgcccaac gggaaatcac ctgcgtcgaa 360
agcttcgcgg gccagctcca gcactcggtc gatgccaccc aacgcgt 407

<210> SEQ ID NO 235
<211> LENGTH: 389
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 235
atactcaagc ttgcggatgt tacccctgac agcgtgaact atgtcnaaac acacggcacc 60
ggaacggtgt tgggggaccc catcgagttc gagtcgctgg cggccactta tggcctgggt 120
aaaggccagg gcgagagccc gtgcgcattg ggtcggtca aaaccaacat cggccacctg 180
gaggcggccg ccggtgtggc tggattcatc aaggcggtgc tggcggtgca acgtgggcac 240
attccccgca acttgcactt cacccggtgg aacccggcca tcaacacgtc ggcgacgcgg 300
ctgttcgtgc cgaccgaaag cgccccgtgg ccggcggctg ccggtccacg cagggctgcg 360
gtgtcatcgt tcggcctcag cgggaccaa 389

<210> SEQ ID NO 236
<211> LENGTH: 432
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 236
ccggtaacca gatcagctcg tcgacctcac tgccgggggt gaattcccca ccggtgctgc 60
gcgctgccca gtagtgcacc ttcttgacgc ctcgaaaagg ggagtcggtc gggtaggtca 120
ccgtcaggag ccgcctaccc aggttggcgc ggtgaccggt ctcctcgagt atctcccgca 180
ccgcccccac cggtgcggtc tcgcccggat ccactttgcc cttgggcagc gaccagtcgt 240
cgtaacgggg gcggtgaatg acagcgatct cgaccggccc ttccgaatcg gcactgccgg 300
gtcgccagaa caccgcaccg gcggcgtaca caatccggcc cgccgagcgc cggcgggcgg 360
acganttctg gatcgacacc tcaactcctg caggtcaatt cggccaagct gctcgcggtc 420
gtggatgtgg tc 432

<210> SEQ ID NO 237
<211> LENGTH: 287
<212> TYPE: DNA
<213> ORGANISM: Mycobacterium tuberculosis

<400> SEQUENCE: 237
atactcaagc ttgatgccgc cgaaaccgag cgtgagcacg ccgccaccca ccacgcgcgg 60

-continued

```
gtcgggcgcc gggcccgggc cgccaggctg ctccgctcgg tgatggcacg ccaccgcgac    120

accacccggc tgcgctacgt cgagccatac cgggcggagc tacatcggct cggccgccca    180

gtgttcgggc cctctttcga ggtcgaggtc tataccgatt tgcgcatccg cagccgcacc    240

ctggtcgtct cgtaccgtgc cctacctctg cttgtcgggc ggggcca                  287
```

<210> SEQ ID NO 238
<211> LENGTH: 272
<212> TYPE: DNA
<213> ORGANISM: Mycobacterium tuberculosis

<400> SEQUENCE: 238

```
tccgtacggc ccgggtacgc ttcggtcgca gtgtgcgagt gatagatgac gaccgggacc     60

tcgtcggcat cttccatagc ccgccacacc ttcagttgct caccggaatc caaccggtag    120

aaggtcggcg agcgctcggc attggtcatc gggatatgcc gctcgggacg gtcagagccc    180

tcgggtccgg ccagcactcc gcaggcttcg tcggggtggt cgcgacgcgc atgggccacc    240

atccatccac caggtctgcg cgaatcaccc gc                                  272
```

<210> SEQ ID NO 239
<211> LENGTH: 410
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 239

```
ggacacattg cgaacattga tgacaaaata gaaatcattg atggtttgag tcaccaggcc     60

gatcaagcct tcgccgagcc aaattccaat caagaggccc aagcccgtac caatcagccc    120

ggcaacgagg gattccgtca ttatcagcca aaataactgc tctcgggtta cacccaaaca    180

gcgcaatatg gcgaaaaacg gtcgccgttg cacgacatta aatgtcacgg tattgtaaat    240

taaaaagata cccaccaaca aggcaatcaa actgagagcg gttaaattga ccgtaaaagc    300

gtccgtcatc tgtttgacgg tgtcccgttg ggtntccgac gtttccatac gcacaccggc    360

cggcagtctt tgttggatgc gtgttgcagt ggcctcatct ttgatgatca               410
```

<210> SEQ ID NO 240
<211> LENGTH: 439
<212> TYPE: DNA
<213> ORGANISM: Mycobacterium tuberculosis

<400> SEQUENCE: 240

```
gcctggccca ggtgaaggcc gacctcgacg ccaaagccgc tgatccggca catgagtcgg     60

tggactggga cttgaagtcg ctgcgatggg cgtggaaccg agccaaagat gacgtggcgc    120

cgtggtgggc cgagaattcc aaggagtgct actcgtcggg gttggccgat ctggcccagg    180

gcctggctaa ttggaaagct ggcaagaacg ggacccgcaa aggccggcgg gtgggcttcc    240

cgcgattcaa atccgggcgg cgtgatcctg gcagggtgcg gttcaccacc ggcaccatgc    300

gcatagagga tgaccggcgc acgatcacgg tcccggtgat cgggccgctg cgggccaagg    360

agaacacccg ccgggtgcaa cgccacctcg tgagcgggcg cgcgcagatc ctgaacatga    420

ccttgtcgca gcggtgggg                                                 439
```

<210> SEQ ID NO 241

-continued

<211> LENGTH: 356
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 241
taactcaagc ttcaagtccg cngtccgacc ctgttcgacg gctacctgaa tcaacccgat 60
gccccgccgc ggcgttcgac ccgacagctg gtaccgcacc ggcgacgtcg cggtggtcga 120
cggcagtggg atgcaccgca tcgtgggacg cgagtcggtc gacttgatca agtcgggtgg 180
ataccgggtc ggcgccggtg aaattgaaac ggtgctgctc gggcatccgg acgtggcgga 240
ngcggcagtc gtcggggtgc tcgactatta tctaggccag cggatcgttg cctacgtagt 300
cggctcagcg aatgtcgatg cggacgggct tatcaacttt gttgcccaac aacttt 356

<210> SEQ ID NO 242
<211> LENGTH: 341
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 242
ccatgtcgcc caacatatcg tcgatgttcg cgtcgtccgc ctcgcgcacg tggtctgtca 60
ccagtcaacg ttaacgccgc cgcacatgtc ctgcggccgg gcaaaaacgt gaaaaacgag 120
cgggcgactg caatgtcatg acaccgacgc cgccgatggg cccagggtct ggcagattcg 180
atctgtgcgg ccagtgccag cagcgtcgcc tcgtcatacg gccggccgac gagttgaacc 240
gacatgggca tgccgtcgcc gtcgaagtcc cacggcacca cggccgcggg ctggccggtc 300
agattccana cttgaaagta ctgaagccgc tgcaccacca g 341

<210> SEQ ID NO 243
<211> LENGTH: 336
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 243
cgaaagcgtg aaacagctcg cggcagcccc cgacgtgctg cgtcggatag ccggcgggcg 60
aagatcaatt ccaggcagct cccggacaat gcggctctgc tggcccgcaa cgaaggactc 120
gaggtcaccc cggtgcccgg ggtcgtggtg cacctgccga tcgcacaggt tggcccacaa 180
ccggccgctt gatgcccggt cggcaagccc ggcagttgcc aaacccagcg tgatcntgct 240
cngctctnta nttcggcgaa gaagtggctc gcctgatcac ctaccatcgg ccaggatctg 300
cgtgtcatca caacgctcgc caaggaggtt gttgtg 336

<210> SEQ ID NO 244
<211> LENGTH: 337
<212> TYPE: DNA
<213> ORGANISM: Mycobacterium tuberculosis -continued

<400> SEQUENCE: 244
tccgccacgc ttcgcgccgc ccggcatacg gcgcgtaccg atctccgcgt catacaccgc 60
gggtaatcgc cgacggtgcc ggttcgcgag ccgaaggtga cgacgctgat tgaatcgagt 120
tccaggtcca gcgggtggcg cagcaacggc gcgagctcaa cgacgtcaat cacgttgtcg 180
ctttctacgg tcaccgaccc ggtgaccgta gtcgcccggt gcgctcggcc gagaagctgc 240
accgccacca ccgcgacacc gtcttgcacg cggacccacc ccggatcggt tgttggccaa 300
ggtaattggg tcattccatt tgacgggacg ccgaccc 337

<210> SEQ ID NO 245
<211> LENGTH: 337
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 245
cattctttaa cagttgtttt gggctcggca tggttagcca acgttctgcg gtccaccata 60
tcatcttggt ccggtagcgc tcgtccgggg tatgctgccg ccgggattct cgctgctatt 120
actccccccg aagaaccgcc accggtccag cgcgtgggcc gncgcggtcc catcacaaac 180
tgaaccccca acagggacat gcttatcggt agggcgcgcg ccaaggcggc agcaatcgca 240
tcactgcgct ctgcgcgtca ctattaaccc acccggactt cacttccacc accccgaatg 300
gcgcccggtc attgatcatc tggcgcaccg cggataa 337

<210> SEQ ID NO 246
<211> LENGTH: 343
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 246
cggtgtcctg cagttggtag gcctgcagtt tgtgcatcat gccgatgccg cggcctcgtg 60
gccacgcatg tacagcacca cgccgcgccc ctcacgggcg aacatcgcca gcgcggcgtc 120
cagctgaagc ccgcaatcgc agcggcgtga ccaaacacat cgccggtcaa gcactccgaa 180
tgcaccggac cagcacgtcg tcaccgtcgg cgttgggccc ggcgatctcg ccgcggacca 240
tgcgcgacat gttccacgtc ctcgtanatg ctggtgtagc cgatggcgcg aaactcccca 300
tgacgagtcg gaatccgcgc ctcggcgacc cgctcaatgt gct 343

<210> SEQ ID NO 247
<211> LENGTH: 340
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 247
cggcatctgg cggctgaacc tgttcttggg caacatgccg aggatcgcct cttccaccac 60

-continued

```
gcggtcgggg tggcgttgca ttacctcacc gatggtgcgc ttgtgcaggc cgccgggata    120

ccccgagtgc cggtaaacca tcttgtgctg cagtttgtcg ccgctgatgg cgaccttgtc    180

ggcgttgatc acgatnacna atcaccgcca ncgacattgg gggcgaacgt cggctcgtgc    240

ttgccgcgca gcaggctggc cgccgcgacg caaggcgcca accaccacgt ccgtggcgtc    300

gatgacgtac caccatcgcg tggtgtcacc cgccttgggc                          340


<210> SEQ ID NO 248
<211> LENGTH: 322
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 248

gcggcaaaaa ttgaagcact cntggccact nccgccggga gggacaatct cgggcggcta     60

gggcttctcg cgggaaggcc cgaacgtact gcgtttcaac acgtcgcgtc gccctccgac    120

cgcgaacatt ctgggatggc agcaacctgt tagcaccctg gccgggcgat gatctgcagc    180

gtcgccgcgg gtagtcgccc ccgggcggct acagtctgaa acgcgatgac catcgatgtg    240

tggacgccgc atccgacnca acggttccta cactgtgata tgttcgcctc gctgcgccgg    300

tggacggtgg gtctatcccg ga                                             322


<210> SEQ ID NO 249
<211> LENGTH: 278
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 249

cgcgttgaac tgaaggggtg ccgcccggct cgagcaggca agccatttgt tcgatgcggt     60

taccgaagat ctcttcggtg actgcccgcc gccggccagc tcggctcagt gtccggcgtt    120

ggtcgccgcg gcgacaatct tggcgtccac ggtggtcggg gtcatgcccg cgagcaggat    180

tggcgagcgg ncggtcagcc gggtgaactt cgtcaagagc tgacgctgcg gttggggagg    240

cgaatcatgg tcggtgcgta gcctcgacta ggcccggg                            278


<210> SEQ ID NO 250
<211> LENGTH: 336
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 250

tgacaacgcg gcggcgatta ccccgctacc gcagcagcat gacgcggtag cgaacaccgc     60

cggatgcagc gcaggtgcgt cgatgtgctc acggaatcgc cccggcaccg cgatctcgag    120

gatcaccagt gccacccccct gcagcgcgac accgacgatt ccgtacaccg ccacgccgat   180

caggccctgg gccagctgat tggagctggc gtatatggcg gcgatggtga cgatggtcat    240
```

-continued cgcctcttac attgtggcgg ccagaaccac ggcgttgggg cggcggtcga tgaacactag 300
gcgaccanat ccccggggtc aacaggttga ccatcc 336

<210> SEQ ID NO 251
<211> LENGTH: 95
<212> TYPE: DNA
<213> ORGANISM: Mycobacterium tuberculosis

<400> SEQUENCE: 251
cgcggacatc ccgaacgagg acacgcgacc gcttcggtgt gtgatctatc agggctcgca 60
ccacgcgcaa ccgcttccgg ctacctagac gcggt 95

<210> SEQ ID NO 252
<211> LENGTH: 94
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 252
gcatgcgggt gatgccgttc tcagtgcgca acagcgttcg acgcggcata cccagccgca 60
catgccgtgc acgccggngc cggggcggga atct 94

<210> SEQ ID NO 253
<211> LENGTH: 302
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 253
ctcaagcttc agnccntcta agcggtctgc gcggcgatcg caaagatcgc cctttgccgg 60
cgttgggggc ttctgctcgg gggtgttgta caccttctcg aacacctcgg caccgacacc 120
accaccgtcg gcttgaacac cgccaacatc ggcagcanat cttgatgtcc tggtgaatcc 180
acggtgactt tggagtggaa ggcggccata ctgatcgcgc gcgccaccac atgagctagc 240
ggcaggaaaa ccagcagccg ctcacccttg cgcagcagcg tcgggtgata tgcctggcgc 300
cc 302

<210> SEQ ID NO 254
<211> LENGTH: 291
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 254
agtcgaangt cagtccggtc tcctctccga ctacggccaa gaactggggc gacggtgtca 60
gtgcagaaca gcggaaactg gtggcgccct aggcgagcga acgctcacaa acggcggtga 120
ccgcttctgg tcgtgcacca tcgagccgtg cccagcccgg ccgcgtgccg tcagccgcat 180
ccactggatg cccttctcgg cggtttcaat cangtacagg cgacgttcgc caccatcgtg 240

-continued ccggggcacg gttagcgaga aacgccgact tcaccgattg cctcggtgat g 291

<210> SEQ ID NO 255
<211> LENGTH: 454
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 255
agcttcgcgg cgtggcgatc gcggttcaag gcgcgctctt cgagcacaac gagcgaagac 60
agctcggcga cggagccttt atcgacatcc gttcgggctg gctgaccggc ggcgaagaac 120
tgctggacgc gttgttgtcg acggtgccgt ggcgagccga gcgccgtcag atgtncgacc 180
gggtggtcga tgtgccgcgg ctggtgagtt ttcacgacct gaccatcgaa gatccgccgc 240
atccgcagct ggcgcggatg cgccggcggc tcaacgacat ctacggcggc gaactgggtg 300
agcccttcac caccgccggg ctgtgctact accgcgacgg ctctgacagc gtcgcctggc 360
atggcgacac cattggtcgc ggcagcactg aggacactat ggtggcgatc gtcagcctcg 420
gcgccacccg cgtcttcgcg ctgcggccgc gtgg 454

<210> SEQ ID NO 256
<211> LENGTH: 346
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 256
agcttcagct gatactcgac cagcccca ct cgggccaata cgtgaatgtc tagcatcttc 60
acccgttcac gggctantcg agtagtagac attgattagc ctgaacgtac ctccgacgcc 120
agctgacgaa cgggtatgac ggatggattt cgtggtgtcg cgcccgaggt caattcgtta 180
cggatgtatc tcggggccgg atcggggccg atgttggcgg ccgcggcggc ctgggacgga 240
ctatccgacg aactggcggt ggcggcgtcg tggtttgggt cggtgacctc gggcctggcg 300
gatgcggcgt ggcgcggccc gcggcggttg cgatggcncg cgcggt 346

<210> SEQ ID NO 257
<211> LENGTH: 339
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 257
ctggtcatgg acgttgctcc ggtagtggct cactgccgat cctcctcgtt gagagtgcca 60
cctcagggtt gggtagggtt gggtactcga aaccaagtta cccaccagta acaccgtcaa 120
aatatatccg ttgcataggt caatgcaagt tgatgtgagc tacattgcac caactaacta 180
accaaccggt tgggttagcg gtgatcctgg ccgtgtcggt cctctcacct gcggtgatag 240
cgatcaaatg aagaatatgc ggagtctagg gcggcagcgc ctggcancgt agatcatcgg 300

-continued

```
ctcacgcgga tgcggcctct tggtacggac atgcgcgcg                        339


<210> SEQ ID NO 258
<211> LENGTH: 182
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 258

ctcgtgagta gcacccctgt aatttgggat cggcaaaaag gcgaatcacc gcgtggccac     60

gacacgccgg gagggacnat ctcgggcggc tagggcttct cgcgggaagg cccgaacgta    120

cggcgtttca acacgtcgcg tcgccctccg accgcgaaca ttcggggatg gcagcaacct    180

gg                                                                   182


<210> SEQ ID NO 259
<211> LENGTH: 213
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 259

ggatcaacta ccggccaacg gtgattcttg ggcgccgctg acgcgcgaac gacccagcga     60

cacattcagc agatggccag cgcgtgccgg gccacgatgt tggtgctcgg cggctactcc    120

catggtgcgg cncgtgatcg acatcgtcac cgccgcacca ctgccggcct cgggttcacg    180

cagccgttgc cgcccgcagc ggacgatcac atc                                 213


<210> SEQ ID NO 260
<211> LENGTH: 321
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 260

aggaccgtca gcacggcgac gtgctactcg ccgagcagtg ggaatcgctc tgcagcaaac     60

cattactctg cgcgacgttc gagatgacct tctgaatgga cggatctacc tgccgcgcga    120

cgacctggac cgcgtatgcg tccgcctccg cctggacgac accggggcac tctatgaccc    180

cgacggacgg ctcgcggtac tgctgcggtt caccgccgac gcccgcacgg tacgcgtcgg    240

gactgcgctg agtccancct cgacgccgta gcgctgctgc tgtgcggcca tgtctggcat    300

ctaccgccgt cgctcccttg a                                              321


<210> SEQ ID NO 261
<211> LENGTH: 334
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"
```

-continued

<400> SEQUENCE: 261
cgactctgtt ggccactgcg ggtcgatctt gcggccgccc cggtcgtgga acgcccaggt 60
cacccggcgg cgcaccgcgg tcagcgcgtc gttggccagc gtggtcacat ggaagtggtc 120
gacgacgagc ttggcgttgg gcagcagccc gggcgtgcgg atcgccgagg cgtatgcagc 180
ggcggggtcg atggccaccg tactggatgc tctcccggaa ctgcggtgtg cgcgcttgca 240
gccatgccag caccgccgcg ccgccgcggc cttcatgctg cccataaacc ctgataccgg 300
ccaggtcgac naaccngtat cccacggtca accc 334

<210> SEQ ID NO 262
<211> LENGTH: 208
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 262
cacacggacg gcggtgcgga cgcagctgac gcgcatggtg gtcagcatcg cggccggtct 60
gctgttgtat gcctacttcg cgccgcgcaa atgctggtgg gcggcggtgg tggcgctcgc 120
atggctgggc tgggtgctga cccaactctc gaaccacacc ggtgggtggg ctgggctatg 180
gcctgccata tcggcctggt gttctacn 208

<210> SEQ ID NO 263
<211> LENGTH: 233
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 263
ccgatatccg agccgatagc tggcgggctc gggtggtngc cagcggcgct gcgacgaaag 60
tgtgaccgtc atgaaacaga caccaccggc ggccgtcggc cgtcgtcacc tgctcgagat 120
ctcagcatcc gcagccggtg tgatcgcgct ttcggcgtgt agtgggtcgc cgcccgagcc 180
cggcaaacgc cggcccgaca caaccccgga acaggaagtc cggtcaccgc gcc 233

<210> SEQ ID NO 264
<211> LENGTH: 320
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 264
gcttcaggac aaattgnatc cctatgcacc cgttgtcacg ccgatgagtg aagactgcac 60
gcaatcgccg gaatccggca aaaccctgca caagcgaaat caaccggagg ctgacaaggc 120
aacgtcggtg atccgtaccg cctggttgga caaacggcag aaggcgcctc gtccggtcca 180
tctacgccga gcacactggt gatagcgcca tcggcatcgg tgcggccacg gtggagacga 240
acgtccgcng gcgtctgggt cagtaacccg ccgaccagtt ctcgggcaag ctggtcaaca 300
tcgggcgcca cgtctccaac 320

<210> SEQ ID NO 265
<211> LENGTH: 304
<212> TYPE: DNA
<213> ORGANISM: Mycobacterium tuberculosis

<400> SEQUENCE: 265
gtttggcggc cttattgcac tgaggtcgtc aattgaccca cagcggaaat gccgactatt 60
cgcaggcctc cttcgccttg gctgccggag atgggctccg cgggaaccgc atgcaggtat 120
atgacctcgg tttctcgggt gctaccgcgt gccttgtcga ggatgaactc ggcgttggaa 180
ttgtccagcc ggcccaattc atcgagcgca gattcgtaca catggccggc ggcgacatac 240
cttcaccgtg gatctgctcc acacggaccg ccctgtcggg atctgctcac gggtaaagga 300
atta 304

<210> SEQ ID NO 266
<211> LENGTH: 217
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 266
gcgcactcct ccttatcgct ccgctctgca tcgtcgcggc gcggtcaggt gcaaacgcct 60
tcgggggtgg gggtcctgcg gagcacaccg gatacggagc gcaacgcgtc gcgttgtgcg 120
ggcaaacaag tgtgcaggnn ccaatgccat gtccagcagc ttatcagtgt cgaacgtgcg 180
aacgtcgcgc cttcgccggt gcctgaatct ctacaag 217

<210> SEQ ID NO 267
<211> LENGTH: 174
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 267
cgctgaaagc caccattcgc gggtcgggcg ccgggctcgg gccgccaggc tgctccgctc 60
ggtgatggca cgccaccgcg acaccacccg gctgcgctac gtcgagccat accgggcgga 120
gctacatcgg ctcggccgcc tagtgttcgg gncctctttc gaggtcgagg tcga 174

<210> SEQ ID NO 268
<211> LENGTH: 144
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 268
tgtaatttgg gatgggcaaa aagcaaanca ccgcgtggcc acaaacgcgg ggagggacaa 60
tctcgggcgg ctagggcttc tcgcgggaag cccgaaacgt acggcgtttc aacacgtcgc 120

-continued

```
gtcgcctccg acgcgaaatt cggg                                            144


<210> SEQ ID NO 269
<211> LENGTH: 216
<212> TYPE: DNA
<213> ORGANISM: Mycobacterium tuberculosis

<400> SEQUENCE: 269

cttgggcaac atgctgagga tcgccttttc accacgcggt cggggtggcg ttgcattagc     60

tcaccgatgg tgcgcttgtt gcaggccgcc gggataccg agtgccggta aaccatcttg     120

tgctgcagtt tgtcccgctg atggcgacct tgtcgcgttg atcacgatga cgaagtcacc    180

gccatcgaca ttgggggcga actcggcttg tgcttg                              216


<210> SEQ ID NO 270
<211> LENGTH: 199
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 270

gcatgcttca ttatctaatc tccagccgtg gtttaatcag acgatcgaaa attcatgcag     60

acggtcccaa atagaaagac attctccagg caccagttga agaggttgat caatggtctg    120

ttcaaaaaca agttctcatc cggattgaac tttaccaact tcatccgttt catgtacaac    180

atttttagaa ncatgcttc                                                 199


<210> SEQ ID NO 271
<211> LENGTH: 230
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 271

atactcaagc ttgatgccgc cgaaaccgag cgtgagcacg ccgccagcca ccacgcgcgg     60

gtcgggcgcc gggcccgggc cgccaggctg ctccgctcgg tgatggcacg ccaccgcgac    120

accacccggc tgcgctacgt ctatccatac cgggcggagc tacatcggct cggccgccca    180

ttgttcnggc cctctttcga ggtcgaggtc tataccgatt tgcgcatccg               230


<210> SEQ ID NO 272
<211> LENGTH: 188
<212> TYPE: DNA
<213> ORGANISM: Mycobacterium tuberculosis

<400> SEQUENCE: 272

tccgtactgg tcgggtacgc ttcggtcgca gtgtgcgagt gatagatgac gaccgggacc     60

tcgtcggcat cttccatagc ccgccacacc ttcagttgct caccggaatc caaccggtag    120

aaggtcggcg agcgctcggc attggtcatc gggatatgcc gctcgggacg gtcagaacct    180

cgggtccg                                                             188


<210> SEQ ID NO 273
```

-continued

<211> LENGTH: 158
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 273
gttctcgcac gatttcggat tagcgggatg gtctcaattg ggtatgcggg gaaggcgctg 60
acattcgccg cgattagctg tttgatggac cgggggtgat ttttgatcac ggaaatgggt 120
gtttatncag gtcgcacgct ttcatccggg gcggaacg 158

<210> SEQ ID NO 274
<211> LENGTH: 237
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 274
gggtgtgcct gctgtgtatg cacggcatac ggacatcctt cccctgaaga cccgcggtcg 60
aacagccacg tgtccatcat canggggtca accccggcca agggcgacgg cacgccaagt 120
tcgccgaccg ttaacctagt gctgttagct tcatttgctg cgagcaaaac agctggtcgg 180
ncgttaggaa tgaattgaaa ctcaaccgat ttggtgccgc cgtaggtgtc ctggctg 237

<210> SEQ ID NO 275
<211> LENGTH: 262
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 275
actacccggc caacggtgat ntcttggccg ccgctgacng cgcgaacgac gccagcgacc 60
acattcagca gatggccagc gcgtgccggg ccacgangtt ggtgctcggc ggctactccc 120
anggtgcggn cgtgatcgac atcntcaccg ccgcaccact gcccggcctc gggttcacca 180
gccgttgccg cccgcagcgg acgatcacat cgcttttatt tnntnttcng gaatccctcg 240
ggccgcgctg gcgggctgat ga 262

<210> SEQ ID NO 276
<211> LENGTH: 222
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 276
acgtcgggan actgttcgcg ttcatcctcg tctcggcgga ttggtctgct gcgccggacc 60
gaccgatctt cagcgggggg tcacgctccg tggggtgccg ttacttccga tcgcccagtg 120
tgcgcgtgct gtggctgatg ctgaacctca ccgcgttgan ttggatcggt tcgggatctg 180

-continued

```
gctggtggcc ggaacgcnat ttatgtcgct acgggcgccg gc                        222


<210> SEQ ID NO 277
<211> LENGTH: 166
<212> TYPE: DNA
<213> ORGANISM: Mycobacterium tuberculosis

<400> SEQUENCE: 277

gctcaaaggc actactggca ccaaggccca cacgtcacct gtgactcctg cgccgacccg      60

cccgaggtct ggccgttaca ccgaacgggc gagccgggag ttggtaccat cgaacaagac     120

aaggtgcatg ggcggagttg ttccgccact tcgtcgatga cgggtc                    166


<210> SEQ ID NO 278
<211> LENGTH: 330
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 278

cgataccggc tgcttaccga gacatccacc atgccacccg aatcaccgca cgcgccgaaa      60

tcgcacaaca gcttgacgcc ttgcaggttc cgcgattgga attgccgacg gtctctgacg     120

gcgtcgacct tggcagcctc tacgagctct cggaatcact tgcccagcag ggggttcgat     180

gagtgtcaca ccgaagacct cgatatgggc gcaatcctgg ccgacacatc caaccgggtg     240

gttgtgtgct gcggcgccgg tggggtcngc aanacactac cgcggccgcg ctggcgttgc     300

gcgcggccga atatggccgc actgtggtcg                                      330


<210> SEQ ID NO 279
<211> LENGTH: 332
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 279

cgtcgtcgtc gtggtatgcg atagccatcc cgtcgggcta ctcgccatca ccgatcagct      60

tcgccccgaa gccgccgcgg cgatttccgc tgcgaccaaa ctgaccgggg ccaaaccggt     120

attgcttacc ggcgacaacc gggccaccgc cgatcggctc ggtgtacang ttggcatcga     180

cgacgtacgg gccgggctac tgccgacgac aangtcgcag ccgtgcngcn gctgcaagct     240

ggaggtgcca gattgaccgt ggtcggtgac ggtatcaacg acctccggcc ttagcggccg     300

cgcatgtcgc atcgccatgg gcagcgcccg ac                                   332


<210> SEQ ID NO 280
<211> LENGTH: 222
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 280
```

-continued gcacgcaatc gaagtcaccc aaaccgggcg ggccaggcgt ctnacgccac gtcnaccagc 60
cgcaacctca acccggccac ggcgagctcc tgatcaaggc cgaggccatc ggtgtctact 120
tcatcgacac ctacttccgc tccgggcaat atccgcgcga actcccgttc gtcatctgct 180
ccgaagtatg cggcacggtg gangccgtcg gccaggggtt ac 222

<210> SEQ ID NO 281
<211> LENGTH: 184
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 281
tcgactgtgt ggccacagat cacgccccgc atgccgagca cgagaaatgc gtcgaattcg 60
ccgcgggccg gccggcatgc tcgggttgca gacggcattg tcggtggtgg tgcatacaat 120
ggtggcgccg gcttgttgan ttnggcgcga tatcgcgcgg gtgatgagtg anaaccggcg 180
tgca 184

<210> SEQ ID NO 282
<211> LENGTH: 409
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 282
gaacctgaca ccctggtcac gggtgagcac ggacttgatt tcttcnctat tggtcggcgc 60
tgttgagcac accacgccgc tgacggccgt cgcgtcctcg ctgtgctcgg tctggtggag 120
cgcgctgccc gcggccnaac atcntaaatc aagcgtattc gtcaacagat atcatcaatg 180
tcggcgctgg actattcaaa tcatcgatat actggtgacc tggtccttcg ccatcgatca 240
atggcgatag tcacgcaaat cgtcacggac atcgtcggcg tcccagctgg cccgtgccaa 300
cagatgctgc aacccatcgg ggtggtatca ccgcggtgct cggcgatggt ccacaattct 360
tgcggtccaa gcccnaaaca tcccgggcat gaattcaccg gcatgcgcn 409

<210> SEQ ID NO 283
<211> LENGTH: 413
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 283
ctatcgtacc cgcgccggtc accttctgga tatcgccggc ctggtcaagg gggcgtccga 60
gggagccggg ctgggtnaca agttcctggc tcatatccgc gaatgcgacg ccatttgtca 120
ggtggtgcgg gtgttcgtcg acgacgacgt gactcatgtc accggacggg tcgatcccca 180
gtccgacatt gaggtcgtcg agaccgagct gatcctggca gatctgcaaa ccctggagcg 240
ggccacgggc cggctggaga atgaagcgcg caccaacaag gcgcgcaagc cggtctacga 300

-continued agcggcactg cgtgcccagc angtgctcga cgccgggcaa gacgctgttc gccgcggggg 360
tggatgccgc cgcgttgcgc gactgaaact gctgaccacc aagcccttcc tgt 413

<210> SEQ ID NO 284
<211> LENGTH: 283
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 284
tactcaagct tcaggccgcc acgtccgccg tccgtcggcg acgtgacctc gagcgccgag 60
ttcgactcga catcgccgcc ggcgcatgcc gacatgaacg cggcactcac cgcaagcccg 120
tcggacgtca ggtcgatcga ctccgcttca agcaccggat cgtccgggca actcgcggcc 180
tcggcctgtg cgaacggcac acccgtcgtg gcggcncccc gcgcggaact gggctcatca 240
cggtcgttgc gagccggtcg cgtcaccgcg taccgacgcc gtc 283

<210> SEQ ID NO 285
<211> LENGTH: 397
<212> TYPE: DNA
<213> ORGANISM: Mycobacterium tuberculosis

<400> SEQUENCE: 285
ccgacatcga gtgggctcgc agtgacttgg cgacctccaa gccaccggta cccgccgcgc 60
ggcaagccaa ggacgacgac ggccttgccg gatagctgcg ccaggcgttg cgccaactgg 120
cgtccagcgt cgccacgatc gtcaaagagc ttcatctgcc gagtgtgtcg ccatctcatg 180
gctccaaata tggaattagg tccctgggcc gactgacgac agtccctcag cgaccggatt 240
gcgcatcccg ccttgtacgc tactccgcaa atcccgggct tgcgtccgcg gaagcgaact 300
cggcggcgct acgtggtggt tcacttcggc cgtgcgcact cggatcgacg ggccgatggt 360
ggccgggccc gcgcgcttct tggtcatccg attgagt 397

<210> SEQ ID NO 286
<211> LENGTH: 342
<212> TYPE: DNA
<213> ORGANISM: Mycobacterium tuberculosis

<400> SEQUENCE: 286
atactcaagc ttgtcgcggt aaaccgcacg cagggcggtg ggtgcggtgt caaagacacc 60
cacacttctt tgcggttcgg tgatctcgac accggccgcg agccgaccac catgcgcgcg 120
tagatcggcg atcagcgcgt cggctatcgc ctgggtgccg cccaccggaa tcggccagcc 180
gaccgaatgg gccagcgttg ccagcatcag tccggcgccg gccgacacca gtgacggcaa 240
cggtgaaatc gcgtgggcgg caacgccggt gaacaacgcg cgggcatcct cgcccgccaa 300
cgaccgccag gcagggtgcc tgggccatca tccgcagccc ga 342

<210> SEQ ID NO 287
<211> LENGTH: 430
<212> TYPE: DNA
<213> ORGANISM: Mycobacterium tuberculosis

<400> SEQUENCE: 287
tggactcata acgatcgggt cagcgacgcg ccaacacgaa cggccggacg agtgggccag 60

-continued ggtcgcgcct cccctacaaa caggatccgt tgcctgcgag cgacaggctc cggtgcggcg 120
ttgggcgccg tgctcgtccc agcgtccggt cccgggtcgc cggcgacgct tgtttcctcc 180
atactcgccc cctaatctcg aggcagcccg tacccgcagg caacctccca aaaatgcaat 240
cccccaaaat gcaatgcgtc gagctatttc tcacaccgac cgctagttgc ggatcagaaa 300
tccgttgggc gcggaagtcc agccgaattt gttctcccgc tccgcatcat gcttgtaatc 360
gtttggaaat catcctcata tgcctcgatc gcttcatagg tcaagcccaa acccggcagg 420
atgggtggcc 430

<210> SEQ ID NO 288
<211> LENGTH: 473
<212> TYPE: DNA
<213> ORGANISM: Mycobacterium tuberculosis

<400> SEQUENCE: 288
ctttacactt tatgcttccg gctcgtatgt tgtgtggaat tgtgagcgga taacaatttc 60
acacaggaaa cagctatgac catgattacg ccaagctatt taggtgacac tatagaatac 120
tcaagcttag tggttgcgca cgtaaattcg tcaggtgacc gatcccctgc tgtctcactc 180
gcctcacagc gaccaccacg gctggcgctc aaggcgggca cgtgcggagc agatgaggaa 240
tgtgcgacgt cttgatgcag cctgtcagaa caccgagacc ctcgacgaac ttacgatcga 300
aaccgcttag gccaaccggt gacgggggtg tctttccgcg gctagggcgc cttatcgtcc 360
gaaggccgtg ggtggtgatc gccttctggg tcgcgcttgc gggtctgctt gcgccgacgg 420
tgccgtccct ggaccgatct cccagcggca tccagtggcg attctgccat cgg 473

<210> SEQ ID NO 289
<211> LENGTH: 418
<212> TYPE: DNA
<213> ORGANISM: Mycobacterium tuberculosis

<400> SEQUENCE: 289
caggcatgca agcttgcgat gtatcaacac gccgttgcgc agcgtgagcc gatagttgac 60
atccggctcg gtgaaggtga aatcgatggc caggtcgagg tcccatgcgc gtgggccatt 120
gatgctgatc gccaggacgt caaagatttg gtccggcgtc agctgggcga aaaacgtggg 180
cgccgggact tgcccggagc tgcccgggtt cccgtcgcgc agctcggcgg ccccggtcag 240
aaagaaattg cgccaggtcg cacactccgc gccgtaggcc agctgctcca cggtgtcggc 300
atatagcccg cgggccgcag cgtgctcgct gtcggcgaac accgcatggt cgagaagcgt 360
tgccgcccaa cggaaatcac tgcgtcaaag cttcgccggg ccactccagc actccgtc 418

<210> SEQ ID NO 290
<211> LENGTH: 194
<212> TYPE: DNA
<213> ORGANISM: Mycobacterium tuberculosis

<400> SEQUENCE: 290
atactcaagc ttgaccgacg ctgatcgcac cgcacgcggg aacctcaagg gcactactgg 60
cacaagggcc cacacgtcaa cctgttaact cctgcgccga ccccggccga agtccttggc 120
gttaacaccg aacgggccaa cccgggaatt tgggttccat caaaacaaat agcaggtgcc 180
tgggcggagt gttc 194

<210> SEQ ID NO 291

-continued

```
<211> LENGTH: 166
<212> TYPE: DNA
<213> ORGANISM: Mycobacterium tuberculosis

<400> SEQUENCE: 291

gtcgtcgtgt gctggggcgt ccgtatcagc acgcccacga aatggggcac aagaaggatt     60

cctggaacgg tggctgtcca agatcaccct cgcccaaaac tgctacgggc acttctacat    120

cgagcacaac cgtggccatc acgtccgcgg tgtccacacc gggagg                   166


<210> SEQ ID NO 292
<211> LENGTH: 291
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as “n”

<400> SEQUENCE: 292

atatgccttg ctgagctttt cggatcgcag cgagtcgtac ccgcgccggt caccttcgtg     60

gatatcgccg gcctggtcaa gggggcgtcc gagggagccg ggctgggtaa caagttcctg    120

gctcatatcc gcgaatgcga cgccatttgt caggtggtgc gggtgttcgt cgacaacgac    180

gtgactcatg tcaccggacg ggtcgatccc cagtccgaca ttgaggtcgt cgagaccgag    240

ctgatcctgg cagatctgca agccctggag cgggccacgg ggcggctnga a             291


<210> SEQ ID NO 293
<211> LENGTH: 442
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as “n”

<400> SEQUENCE: 293

gacaccctgg tcacgggtga gcaggactcg atttcttcgc tattggtcgg cgctgttgag     60

gcacagcacg ccgctgaggc cgtcgcgtcc tcgctgtgct cggtctggtg gagcgcgctg    120

cccgcggccg aacatcgtaa atcaagcgta ttcgtcaaca gatatcatca atgtcggcgc    180

tggactattc aaatcatcga tatactggtg acctggtcct tcgccatcga tcaatggcga    240

tagtcacgca gatcgtcacg gacatcgtct gcgtcccagc tggcccgtgc caacagatgc    300

tgcaacccat cggggtggta tcnccgcggt gctcggcgat ggtccaacaa ttcttgcggt    360

ccaagcccga aaccatccgg ccatgagttc accggcatgg cgcaacggct ggtgccgggc    420

aaaacgcggc gcgatcgaat tc                                             442


<210> SEQ ID NO 294
<211> LENGTH: 150
<212> TYPE: DNA
<213> ORGANISM: Mycobacterium tuberculosis

<400> SEQUENCE: 294

tgtagaaggt gggtcccgtc caacttcgcg gcggcggcgc gatatgcctt gctggtcttg     60

ctcatttgat atccaatcta tgggtcgtgg ttactcaacg ggccgaagct ggccctccca    120

cgggtagggt cctattcgac ggtgatgtcc                                     150
```

-continued

<210> SEQ ID NO 295
<211> LENGTH: 321
<212> TYPE: DNA
<213> ORGANISM: Mycobacterium tuberculosis

<400> SEQUENCE: 295
cccgaatccg gtggccggca gggggcctgg cgacgtggac accttctaac ttgtctttac 60
cggtcactgt tgcaccccaa cacctttaac gacgtggacg gacgttacat cggattcgac 120
ggtgtcatcc acagcgttgc cattgggcac acccactacg ccaatttctc cgactgggac 180
acctaccgca gcctcgcccc actgcaggga ctgttgttcc cgcaacgggc catcgacatg 240
atccagtcgt tggtgaccga cgcggagcag actggtgcgt atccgcgttg ggcgctggcg 300
aaattccgcc accggcatga t 321

<210> SEQ ID NO 296
<211> LENGTH: 184
<212> TYPE: DNA
<213> ORGANISM: Mycobacterium tuberculosis

<400> SEQUENCE: 296
ttgagatgct ggtcgggatg ccgatggttg gaacatggtc ccctggcgtc gaatacgcgc 60
gagcgcatga gctcaccggt tcggaacaac gtatcgaaga actcgcactg ctggcagatg 120
gtatctccga tgtggttgta atttgtatcc caactctaac tgtgctatcg gatctgcgtg 180
aata 184

<210> SEQ ID NO 297
<211> LENGTH: 259
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 297
cgtaatcacg atcccgctga gacacttgac cttacggccg aagtgacttc gctgctgcta 60
tgccgacacc cgatttccat acgctgctgt acacgacggc cgggccggtg gcctccatca 120
cgctcaaccg cccggaacag ctcaacacca tcgtcccgcc catgcccgac gagatcgagg 180
ccgctatcgg gttggtcgaa cgcgaccagg acatcaaggt catcntnctg cgcggtggcg 240
ggcgcgcctt ctccggcgg 259

<210> SEQ ID NO 298
<211> LENGTH: 369
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 298
caagcttaag ctggttccgg ccactccatg agccgtagtg caatggttcg tgcacggcga 60
ggccgaactt gccataaaca tccctgacga aagtctccgg caagccgatt gcttcttcgg 120
gccgcttctt gtggattgtc cgataacccg gtccctcatg ctggaagttg tgcgcactct 180
ttccttccgc gatgtgggct aacgactcgt cattgagcaa gaagtacgtg cacaggcatc 240

```
gtccgccggg cttcagcacg cgggagatct cgtccagata gtgctccacg tccggnggga      300

aacatgtggg tgaacaccga ggtnagaaac accncatcca acgacgcatc cgggatatgg      360

aaagcgaaa                                                              369
```

<210> SEQ ID NO 299
<211> LENGTH: 387
<212> TYPE: DNA
<213> ORGANISM: Mycobacterium tuberculosis

<400> SEQUENCE: 299

```
tatggtcttc gtcgaccagt acgtcgtagg cgccatgagc cagcgactga agccgcgcca      60

tgcctgcacg gcccgctcat ccagcgaggc ggccatctcc cgcagatagc ctgccgcctc      120

ggcgcgcacg ctgtccggat cgcgtccgag ctcgtcggcc agcgcacgca gccgctcgtc      180

ataccatcgg gcatccagca gttgggtaac ctcaacgggg tcggtcgcta gcggcgtcat      240

tgattcagca acaataccga tgcgctgcag caactttcgc agtccgatgc ggcccacctc      300

ccgtgcagtc actggctagc ccccgtcatg ccggttgtgt cgatggcacg gcagcgggct      360

cgtaaacctg cggtctcagc tcgctgg                                          387
```

<210> SEQ ID NO 300
<211> LENGTH: 73
<212> TYPE: DNA
<213> ORGANISM: Mycobacterium tuberculosis

<400> SEQUENCE: 300

```
gcttagcggt cttgctcgaa ccgacattgc gtgccactca tgagcgggtg gcggtcgcgg      60

tgcttacaca tct                                                         73
```

<210> SEQ ID NO 301
<211> LENGTH: 156
<212> TYPE: DNA
<213> ORGANISM: Mycobacterium tuberculosis

<400> SEQUENCE: 301

```
gtatctggcg cctctcgaat atccttgaac gtcccgcggt gccacccaga tagatcgcag      60

cgccctgcaa tggagttccc tttatggcct ctctagcctc ccgcttgatc ggctcgaccc      120

gagagatgcc ctcgggcgtt gcgggatctc cctcca                                156
```

<210> SEQ ID NO 302
<211> LENGTH: 394
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 302

```
cttcacgccg atccgcgacc gcgaacgcga cggtgacggt gggcgacaag gttcggttgg      60

tcgccgcggc gctgggcgat atcagctcac ccggtttcga ggtgttcggc gaccggacgg      120

tgctgcagac attcttgagc gtcctcgacc ggcccgattc ggccttcaac atcgtgacgc      180

cgtatttcgg cggtaccgct cggcgccgag tcgaaggcgg cctgagctaa agccgggcat      240

tgcgcgagtg gtaaacaagt tcggtgactt cggttgaccg actcgacggg ctcgatctgg      300

gcgcgctgga ccggtatctg cgttcgctgg ggatcgggcc naccgcnant tgcgttgcga      360
```

-continued nctgattccg gtggagctcc aatctgactt ccgg 394

<210> SEQ ID NO 303
<211> LENGTH: 404
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 303
gcagctaccg accctagcga cgagtgtgtt cgcagcgtcg aatgtgaacg ttcggcgtga 60
ttcggcgcgc gggttcccgc tctcagcgca cgttcggcgc cgaggnggct agtccctggt 120
taagcaatgt ctcggtcgcc gccagcagcg cgcatgtcgc caacccgtcn accgcgttgc 180
gcatgtccgg taccgacgga aacgacggcg cgatccggat gttcttgtcg tccggatcct 240
ttcgatacgg gaacgacccc ccgcctcggt caccgcgata ccaacgtcct tagccaangc 300
tacngtccgg cgcgcggtcc cgggcaacac gtcgaagctg atgaantaac cacccttggg 360
ctcggtccaa gangcgatct tggactcctt aaccgctgat ncaa 404

<210> SEQ ID NO 304
<211> LENGTH: 479
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 304
tccccatcgg cgccggaccg tttgaaagtc caagcacggg tgggatggaa tcgacgacag 60
ttgagcgccg tcggtggccg tggtcagcag ctgttcgcga acgcaccagg tcacatccct 120
tcgacatctc accgacgtgg cacgggcgac atcaacagga agattgacga atccctcgca 180
ggcgcggcac gtccgcaggc caacgccaac tacggggcca ccagcgatcc tccgctcacg 240
caccagccca agccaggctc anccacccaa gtcggcccgc gctctccctc gccccctggt 300
ctccggggcc ttgttaaaca actaccggaa gtccaccaat cctcgctgca tctcgacacc 360
gtccgcctca ctcccttcct cccgccccctc tccacacnac acacctcttg cattaaggtc 420
acggagcggt cacttttcgt cggacgaaat tcgcaatccg gccgctcgcc gccagagat 479

<210> SEQ ID NO 305
<211> LENGTH: 260
<212> TYPE: DNA
<213> ORGANISM: Mycobacterium tuberculosis

<400> SEQUENCE: 305
cggaaagtgg atactcccag caggtagcag gtcgccacca cgctggtcag tgcgcgttca 60
gctcgcttgc ggcgctgcag cagccagtcc gggaaatagc tgccctggcg cagcttgggg 120
atcgcgacgt cgatggttgc ggcacgggtg tcgcaaatca cggtggcggt agccgttgcg 180
ctgattggac cgctcatcgc tgcgttcgcg gtagcccgcc ccgcacaggg cgtcggcttc 240 agccccccatc aaggcggcga 260

<210> SEQ ID NO 306
<211> LENGTH: 464

-continued

<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 306
ggccgagtcc agcacttcgc actatgtgca gaccaaanac ccggtggtcg ccgcgctgcg 60
gcagcggctg gcaacggcgc cggtgatcac cgagtggtgc gnagttgccg accggcagtt 120
cgccgcgggc ttactacgag aagggcctgc gcgacgtcat caggtatcac gtgtcgatga 180
cgtcgagcgt taacttcccc gaccagacgg cgacctcgcc gatggacccc gcgttgtacc 240
tggtgtgggc gcaagctaac gccgccgcan gctatcggta ctcggtcgaa gcgcagccgg 300
ggtcgcaagc gctagcgggc aaggtcgcga cgatctcggt cacctggacc aactacggcg 360
ctgctgccgc caccgaatag tgngtgcccg gctaccggct ggtggattcc acgggacatg 420
tggttcggac ctgccggcag cggtggaact gaagangctg gtct 464

<210> SEQ ID NO 307
<211> LENGTH: 315
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 307
agcttcaagg acatcgtcat cgcgaccaaa accgcgagct aggtcggcat ccgggaagca 60
tcgcgacacc gtggcgccga gcgccgctgc cggcaggccg attaggcggg cagattagcc 120
cgccgcggct cccggctccg attacggcgc cccgaatggc gtcaccggct ggtaaccacg 180
cttgcgcgcc tgggcggcgg cctgccggat caggtggtat atgccgacaa agcctgcgtg 240
atcggtcatc accaacggtg acagcagccg gttgtgcacc atcgcnaacg ccaccccggt 300
ctccgggtct gtcan 315

<210> SEQ ID NO 308
<211> LENGTH: 331
<212> TYPE: DNA
<213> ORGANISM: Mycobacterium tuberculosis

<400> SEQUENCE: 308
gctcgcggtc cagcagcaga cgtgtctgac cccgacgccc ggccgccggt accgaaaccg 60
gatcggcccg ccgatggccg cggccacggc gtctgcctta cccggcccgg ataccagcag 120
ccacacctcg cgggaacgct gaatcgccgg cagggtcaag gtgattcggc gtggcggcgg 180
tttcgcgaat cgtccaccgc caccaccatg cgggtgctct cgaagacgcg gggctgtgcg 240
ggaacagcga gttaatgtgg ccctcgggcc ccatgcccag caggtggacg tcgaaattcg 300
gcccgggtca cctggtgcgg cactggcggc c 331

<210> SEQ ID NO 309
<211> LENGTH: 286
<212> TYPE: DNA
<213> ORGANISM: Mycobacterium tuberculosis
<220> FEATURE:
<221> NAME/KEY: unsure
<222> LOCATION: (various positions within the sequence)

-continued

<223> OTHER INFORMATION: applicants are uncertain of bases designated as "n"

<400> SEQUENCE: 309

```
agcttgtcga tcgtccggca gcgtccggcg agtcaagtcg aagccagtcc ggtctcctct     60

ccgactacgg ccaagaactg ggcgacggtg tcagtgcata ccagcggana ctggtggcgc    120

cctaggcgag cgaccgcctc acaaacggcg gtgaccgcgt tctggtcgtg caccatcgag    180

ccgtgcccat cccggccgcg tgccgtcagc cgcatccact ggatgccctt ctcggcggtt    240

tcaatcaggt acaggcgacg ttcgccanca tcgtgccggg gcangg                   286
```

<210> SEQ ID NO 310
<211> LENGTH: 331
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 310

```
ttggtgatca tcgncccaac gaccccgagg cgatgttctt gcacaccgag gagtgtcgca     60

agctggggct ggccttcgcc gccgatccgt ctcagcagct ggcgaagctg tcggggtgag    120

gaaattcgca ggctcgtcaa cggtgctgct tacttgttca ccaacgacta ctaatgggat    180

ctgctgctgt ccaagaccgg ctggtcagan gccgatgtga tggcgcagat cgacctgcgg    240

gtgaccacat tgggtcctaa gggtgtcgat ttggtagaac ctgacgcacc accatccacg    300

tcggcgttgg tccccgaaac agccagaccg a                                   331
```

<210> SEQ ID NO 311
<211> LENGTH: 458
<212> TYPE: DNA
<213> ORGANISM: Mycobacterium tuberculosis

<400> SEQUENCE: 311

```
ggctcgtatg ttgtgtggaa ttgtgagcgg ataacaattt cacacaggaa acagctatga     60

ccatgattac gccaagctat ttaggtgaca ctatagaata ctcaagcttg attttgatca    120

tcatgatgat catcacccga agtgtggtag ccgcagtggt tatcgtgggt accgtcgtgc    180

tttccatggg cgcctctttc gggctttccg tattggtctg gcaggacatt ctgggtatcg    240

agttgtactg gatggtgttg gcgatgtcgg tgatcctgct cctggcggtg ggatccgact    300

acaatctgct gctgatttcc cggttgaaag aggaaattgg ggccggattg aacaccggaa    360

ttatccgtgc catggctggt accgggggag tggtgacggc tgccggcatg gtgttcgccg    420

ttaccatgtc gttgtttgtg ttcagcgatt tgcgaatt                            458
```

<210> SEQ ID NO 312
<211> LENGTH: 289
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 312

```
caggcatgca agcttggcgt gccgttccaa cccgaattgg ctttcggcgc catcggtgag     60
```

-continued

```
gacggcgtgc gggtgctcaa cgacgacgtc gtccgcggga cacacctcga tgctgccgcc    120

atggacgcgg tcgaacgcaa gcagctgatc gagctacaac gccgcgcgga acgcttccgc    180

cgcgggcgtg accgcatccc gttgaccggg cggatcgcgg tgatcgtcga tgacggcatc    240

gccaccggag cgacggccaa ggcggcgtgc caggtcnccc gggcgcacg                289
```

<210> SEQ ID NO 313
<211> LENGTH: 154
<212> TYPE: DNA
<213> ORGANISM: Mycobacterium tuberculosis

<400> SEQUENCE: 313

```
ggcatcttgg ccgccatgtt agccacactg ccaccggcta tagaagcgat gcgcaccgtc     60

ctgccagcac attgcggcgc tcctccctgg aaagcaagat aaccaagctc atgccgtggt    120

tgtgggtggc gtggtttggt ttgggtaact ttgg                                154
```

<210> SEQ ID NO 314
<211> LENGTH: 324
<212> TYPE: DNA
<213> ORGANISM: Mycobacterium tuberculosis

<400> SEQUENCE: 314

```
tcggctaata atcgtcgacg ccggcctcct ctgcaatcgc cttggcggtc gccgggttgt     60

caccggtgat catcacggtg cggatgctca ttcggcgcat ttcgtcgaat cgttcccgta    120

tgcccacctt gacgatgtcc ttcagatgga cgacgccgat ggcccgcgcg ctgctgttat    180

cggtccattc cgcaacgact aggggtgtcc cccgccggag ctgatgccgt cgacaatggc    240

acccacctcc tcggtggggt gggcaccgtg atcgcgaacc cacttcatca ccgcagccgc    300

ggcaccttgc ggattcgacg gatg                                           324
```

<210> SEQ ID NO 315
<211> LENGTH: 322
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 315

```
ctcaagcttg gaggcgtggc gatcgcggtc caaggcgcgc tctccgagca caacgagcga     60

agacngctcg gcgacggagc ctttatcgac ntccgttcgg gctggctgac ggcggcnaaa    120

taatgctgga ctcgttgttg tcgacggtgc cgtggcgagc cgagcgccgt cagatgtacg    180

accgggtggt ctatgtgccg cggttggtga gtttccacga cctgaccatc gaagatccgc    240

cgcatccgct gctggcgcgg atgcgccggt ggctcaacta attctacggc ggcgaactgg    300

gtnatccctt cnccaccgtc gg                                             322
```

<210> SEQ ID NO 316
<211> LENGTH: 404
<212> TYPE: DNA
<213> ORGANISM: Mycobacterium tuberculosis

<400> SEQUENCE: 316

```
cctaggtcaa ccgtaccgtc atcggatcgg ggtcgaccgc acagatggac tggagcttcg     60

gcgaggtcat cgcctatgcc tcgcgggggg tgacgctgac cccgggtgac gtgttcggct    120
```

-continued cgggcacggt gcccacctgc acgctcgtcg aagcacctca ggccaccgga aatcattccc 180
gggctggctg cacgactgcg acgtggtcac cctccaggtc gaagggctgg gcgagacgat 240
gcagaccgtc cggacgagcg gcactccttt tccgttggct cttcggccga atccggacgc 300
cgaacccgac cggcgcgggg tcaacccggc accgacgcgg gtgccgttta cccgcgggct 360
gcacaaatcc cgacgggtat gggctttgac ctgccgacgg ggga 404

<210> SEQ ID NO 317
<211> LENGTH: 346
<212> TYPE: DNA
<213> ORGANISM: Mycobacterium tuberculosis

<400> SEQUENCE: 317
agcttggcgt gacaccaaca cagggcactt aagatggcaa tgcgccgcct acctgcacgt 60
tttcgcgatg tcagaggatg ccgaggggag aacaatgcga gcacggccgc tgacgttgct 120
caccgctttg gcggcggtga cattggtggt ggttgcgggc tgcgaggccc gagtctaggc 180
cgaagcatat agcgcggccg accgcatttc gtctcgaccg caagcgcgac ctcagccgca 240
gccggtggag ctactgctgc gcgccatcac gccgcctagg gctccggcgg cgtcgccgaa 300
cgtcgggttt ggcgaactgc ctacccgggt ccggcaggca accgat 346

<210> SEQ ID NO 318
<211> LENGTH: 333
<212> TYPE: DNA
<213> ORGANISM: Mycobacterium tuberculosis

<400> SEQUENCE: 318
tcatgccgtt ggaccgacca tcggagttag ttgccgaacc gcgggaccac cgcaagcacc 60
cggtcctggt cgcgcaccgc gtcggccaac cgcttgagca ccaccacgcc gcagccctcg 120
ccgcgcacga atccatccgc gttggcgtcg aagctgttgc atcggccggt cggtgacagc 180
gccgaccact tggacagcgc gatggcggtg aacggtgaca aggtgagctg caccccgccc 240
gccaatgcca cgtcggtttc acgcaggcga agctctgaca cgccaagtga attgccacca 300
gcgacgacga acaagcggta tctacggcga tgg 333

<210> SEQ ID NO 319
<211> LENGTH: 207
<212> TYPE: DNA
<213> ORGANISM: Mycobacterium tuberculosis

<400> SEQUENCE: 319
gggtcgactt tctgcaaggc gaggctacac cgtcgtcgtc gtggtatgcg atagccatcc 60
cgtcgggcta ctcgccatca ccgatcagct tcgccccgaa gccgccgtgg tgatttccgc 120
tgcgaccaaa ctgaacgggg ccaaaccggt attgcttacc ggcgacaacc gggccaccgc 180
cgatcggctc ggtgttcagg ttggcat 207

<210> SEQ ID NO 320
<211> LENGTH: 250
<212> TYPE: DNA
<213> ORGANISM: Mycobacterium tuberculosis

<400> SEQUENCE: 320
aatccgaaat cctgaccgat acttgaacct ggtctcgttc ggcaataact cgtcggcgtg 60
caggacgcgg cgcaaacgta cttcggcatc aacgcgtccg acctgaattg gcagcaagcg 120
gcgctgctgg ccggcatggt gcaatctaac agcacgctct tcccgtacac caaccccgac 180

-continued

```
ggcgcgctgg cccgggcgga acgtggtcct cgacaccatg atcgaaaaac cttcccgggg    240

aggcggatgc                                                           250
```

<210> SEQ ID NO 321
<211> LENGTH: 365
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 321

```
ttccgaattt cgggtccngg tcatatgacc ctcatggaag aagaagcggc cgccccgcgc     60

ccgtgcgacg gcgaatgaaa accctcaccc aggccgcatt gaacgccgac aagacggtgg    120

agcaggtcga agacgtcctg gacggtctgg gtaagaccat ggccgagctg aacagctcgc    180

tgtcacagct gaacagcacc gtggagcgct tggaggacgg tctggaccat ctcgaaggta    240

ccctgcacag cctggacgat ctcgcgaaac ggctcatcgt gttggtcgag ccggtggaag    300

ccatcgtcga tcggatcgac tacatcgtga gcctcggcga aacggtgatg tcaccgctgt    360

cggtc                                                                365
```

<210> SEQ ID NO 322
<211> LENGTH: 413
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 322

```
nctcgatctt ggggtacgtt cgatgaggct gctgaccaac aacccggcca agcgggtggg     60

actggatgga tacggattgc acatcatcga gcgcgtgccg ctgccggtgc gggccaacgc    120

ggaagaacat ccgttacctg atgaccaagc gtgacaaatt ggggcacgac ttggctgggt    180

tggacgattt tcacgaatcc gtgcatctgc ccggagaatt cggcggtgcc ttgtgaaggt    240

ggcgccgggg tgccggatct gccgtcgctg gatcgtctgg tgtgcggctg gcgattgtcg    300

ccagcagctg gcacggaaag atctgcgacg cgctgttgga cggcgcccgc aagtggccgc    360

cgggtgtggc ctcgatgacc gactgtggtt cgggtgctcc gcgcgatcga tat           413
```

<210> SEQ ID NO 323
<211> LENGTH: 364
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 323

```
tcatcccgac caaaacgcga gctaggtcgg catccgggaa gcatcgcgac accgtggcgc     60

cgagcgcgct gccggcaggc cgattaggcg ggcatattat cccgccgcgg ctcccggctc    120

cgagtacggc gccccgaatg gcgtcaccgg ctggtaaccg ctcttgcgcg cctgggcggc    180

ggcctgccgg atcaggtggt agatgccnac aaagcctgcg tgatcggtca tcaccaacgg    240
```

-continued

```
tgacagcagc cggttgtgca ccaagcgcga acgccacccc ggtctccggg tctgtccaac    300

cgatcgaccg cccaagccca catgaacaaa ccccggcatc acgttgccga tcggcatacc    360

gtga                                                                 364
```

<210> SEQ ID NO 324
<211> LENGTH: 488
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 324

```
ttggcgggtt ggcccagcag cccgccggtg acggcgacga tgctgggctg gttgcggccc     60

tgcgccaccg cggcttgcat gctggttggc tgtcttggga cgatcccgaa atagtccacg    120

cggatctggt gattttgcgg gctacccgcg attaccccgc gcggctcgac gagtttttgg    180

cctggactac ccgcgtggcc aatctgctga actcgcggcc ggtggtggcc tggaatgtcg    240

agcgccgtta cctacgtgac ctgatggatc gggggtgcc gaccgtgccc ggcgatgtgt    300

atgtgccggg anagccggtc cggttgccac gcaaaggcca tgtcttcgtc ggtccgacca    360

tcggtaccgg gacacggcgc tgtattgccc ggttcgctgc cgagttcgtc gcgcaactgc    420

acgcnggcgg gccagcggtg ctcgttcanc ccggaggttc cggtgacgat gatcgtgttg    480

gtctccct                                                             488
```

<210> SEQ ID NO 325
<211> LENGTH: 396
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 325

```
gtaggagaga acaaagaccg tcgataggac acgtgttacg ccggtagctg tcattggtat     60

ggggtgccgc tgccgggggg catctactca cccgatcggt tgtgggaggc gttgctgcgg    120

ggcgacaatc tggtcaccga gatccccgcc gaccgctggg acatctacga gtactacgac    180

cccgaacccg gcgtgcccgg acgcaccgac tgcaaatggg gcgcgtacct cgataacgtc    240

ggcgactttg atcccgagtt cttcgggatc ggggagaaag aaacgatagc gatcgatccg    300

cagcaccgct tgttgctgga aacctcctgg gaagccatgg aacacggcgg gctaacaccg    360

aaccatatgc ctcccgacan gggttttcgt ggggtt                              396
```

<210> SEQ ID NO 326
<211> LENGTH: 394
<212> TYPE: DNA
<213> ORGANISM: Mycobacterium tuberculosis

<400> SEQUENCE: 326

```
cgaactgagc ccatagaaag gcagcgacta attcgctggg caaataggaa gacccttttgt    60

cctgccacgt atatttgtcg acctcgttgc gaaggaagcg gctgcgattg gtgccctttt    120

ccctggagaa tctctgcccg gagcaggaag tcttatgagt tgacaagcag gggcgccgcc    180
```

-continued

```
ttcgccggaa atcacattct tggtctcgtg aaatgagagc gctcccaggt cgccgatgct    240

gccgagcgcc cgcccacgat acgacgccat cgcgccttgg gccgcgtctt cgaccaccgc    300

caggttgtgg tgcgtggcga tcttcatgat cgcgtccatc tcgcaggcca cccggcatag    360

tgaacgggga ccatggcctc ggttcgcggg tgaa                                394


<210> SEQ ID NO 327
<211> LENGTH: 140
<212> TYPE: DNA
<213> ORGANISM: Mycobacterium tuberculosis

<400> SEQUENCE: 327

cttagacgcc acctccgggc cgagctccac ggggtggata agtacggccg gatgtggccg     60

caatgggaag ttgttgcccg cttgactgtc cgggttaacg ccggattcca ccacatcccc    120

ttgcgaaagg ccgttgggtt                                                140


<210> SEQ ID NO 328
<211> LENGTH: 242
<212> TYPE: DNA
<213> ORGANISM: Mycobacterium tuberculosis

<400> SEQUENCE: 328

gatcgcgatc gtcgatgtgg ccatccggct tggcgtcgac ccgcgtaagg cagaccagat     60

ggttcgcggc acggtcaacc tgccacacgc actggtaaga ctgcccgcgt cgcggtattc    120

gcggttggtg aaaaggccga tgctgccgtt gccgcggggg ctgatgctgt cggatcgacg    180

atctgatcga gaggatcagg gcggctggct ggaattcgat gccgcgatcg cgataccgga    240

tt                                                                   242


<210> SEQ ID NO 329
<211> LENGTH: 220
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 329

agcttacgcc gctttcgctt cngatttggg acgccgcatc gaaagcgcag ttggaagcgc     60

ggcgcccggc tggtcgagct gctcaagcag ccgcaatccc agcccatgcc cgttgaggag    120

caagtggttt cgatcttcct gggcaccggc ggtcacctgg actcggtgcc cgtcaaggat    180

gtcggcggtt cgaaaccgaa ttactggacc acatgcgggc                          220


<210> SEQ ID NO 330
<211> LENGTH: 328
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 330

cgacgggacc tcgtcgcatc ttccatagcc cgccacacct tcagttgctc accggaatcc     60

aaccggtata aggtcggcga agcgctcggc attggtcatc gggatatgcc gctcgggacg    120

gtcagatgcc ctcgggtccn gccagcactc ctcaggcttc gtcggggtgg tcgcgaccgc    180
```

-continued atgggccaca tcgcattcac caggtctgcg cgaatcacca gcacgtanac ggttcctttc 240
ctaagcaaca ccgaaatttc aggacccgaa tgctccggga aaacatgtca cggtaagtcc 300
ggtattccgg gtaccggttg agcattga 328

<210> SEQ ID NO 331
<211> LENGTH: 366
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 331
cggcatcggt ttgggctgtc accagcagtt ggtagttctt cactactgtt gttcgagcgt 60
cgagccgccg cgcgtgtcga ggtcgccgga cgcgtacccg ccaggccggt cagggtgccc 120
ttccagtcca cgcngctgtg gtcggctaac cgcttatctt caatcgagac natcgccagc 180
ttcatcgtgt tggcgatctt gtccgagggc acctcgaacc ggcgctgcga ntacagccac 240
gcgatcgtgt tgcccttcgc gtcgaccatc gtcgataccg caggcacttg cccctcgagc 300
agctgggccg atccgttggc aacgacctca gaggcacgat tggacatcag ccctagcccg 360
cctgcg 366

<210> SEQ ID NO 332
<211> LENGTH: 407
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 332
ccgtcgangc cgccgacttg gcttgaccga caccaacatg gcctgagggt gttcaacaag 60
accgtggccg acgggctgaa catcaccatg agcggcatga gccacgccac cgagttcatc 120
atgttgatcg ccgaaaacca ttggcgggta gcggaagaac ggtcgaggtg ctctacaccg 180
agtattcgaa gtcgaaaggc caaccgctgc tcaacggcgt caacatcatt ttcgacgggt 240
ttctgcgagg gaggatgcca cgatgaactg gatccaggtg ctgttgatcg cgtcgatcat 300
cgggttgctg ttctacctgt tgcggtcgcg ccgaagcgcg cggtccgtgc ctgggtcaag 360
gtgggctatg tcttgttcgt gctcccggca tctatgccgt gctgaga 407

<210> SEQ ID NO 333
<211> LENGTH: 473
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 333
ttacacgncc tgcttccggc tcgtatgttg tgtggaattg tgagcggata acaatttcac 60
acaggaaaca gctatgacca tgattacgcc aagctattta ggtgacacta tagaatactc 120
aagctttttg agcgtcgcgc ggggcagctt cgccggcaat tctactagcg agaagtctgg 180

-continued

```
cccgatncgg atctgaccga agtcgctgcg gtgcagccca ccctcattgg cgatggcgcc    240

gacnatggcg cctggaccga tcttgtgccg cttgccgacg gngacgcggt angtggtcaa    300

gtccggtcta cncttgggcc tttgcggacg gtcccgacgc tggtcgcggt tgcgccgcgg    360

aaagcggcgg gtcgggtgcc atcaggaatg cctcaccgcc gcggcactgn acggccagtg    420

ccgcggcgat gtcngccatc gggacatcat gctcgcgttc atactcctcg acc           473
```

<210> SEQ ID NO 334
<211> LENGTH: 305
<212> TYPE: DNA
<213> ORGANISM: Mycobacterium tuberculosis

<400> SEQUENCE: 334

```
caggcatgca agctttgtca caccaagtgt ttcgaccagg cgctccatcc ggcgagtgga     60

tactcccagc aggtagcagg tcgccaccac gctggtcagt gcgcgttcag ctcgcttgcg    120

gcgctgcagc agccagtccg ggaaatagct gccctggcgc agcttgggga tcgcgacgtc    180

gatggttgcg gcacgggtgt cgaaatcacg gtggcggtag ccgttgcgct gattggaccg    240

ctcatcgctg cgttcgcggt agcccgcccc gcacagggcg tcggcttcag cccccatcaa    300

ggcgg                                                                305
```

<210> SEQ ID NO 335
<211> LENGTH: 432
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 335

```
agcttagcca gtttttctac tcttgggccc acacccacag tgcttcgacg gtacggtcac     60

ccatgatggc catccagttg gcatcggtga gctgataaat gccagctggt ttcgccaacc    120

cggtagcgat cttggcgcgc tgcttgttgt cactgatacc tatcgagcaa gacagcccgg    180

tttgcgacaa gatgactttt cggatctctt cggcgacttc gatggggtcg tcgggagtcc    240

cgggcgccac cgcgaggtaa gcctcgtccc agccccatac ctcgaccggg tatcccaggt    300

cgcgcaataa cgccaccacc tcctcggacg ccgcgttgta ggcggctggg ttcgacggca    360

agaagtggcc tcagggcatc gtcggcgcgg tcccaacggc ntgccggcgc gcacaccgta    420

ggcgcggggc tc                                                        432
```

<210> SEQ ID NO 336
<211> LENGTH: 429
<212> TYPE: DNA
<213> ORGANISM: Mycobacterium tuberculosis

<400> SEQUENCE: 336

```
ccggcggaac tcagacgtgc tggtggtgcg gcatggcacc gcgggcagca aagcgcactt     60

ctccggggac gacagcaagc gaccgctaga caagaggggt cgtgcgcagg cagaagcgtt    120

ggtaccacag ctgctggcgt tcggcgccac cgatgtttat gccgccgacc gggtgcgctg    180

ccaccagacg atggagccac tcgccgcgga actgaacgtg accatacaca acgagcccac    240

cctgaccgaa gagtcctacg ccaacaaccc caaacgcggc cgacaccgag tgctgcagat    300

cgtcgagcaa gtaggcacac ccgtgatctg cacgcagggc aaggtcattc ccgatctgat    360
```

-continued

```
cacgtggtgg tgcgagcgcg accgtgtgcc cccgacagtc ccgcaatcgc aaaggcagca    420

cgttggtgt                                                            429


<210> SEQ ID NO 337
<211> LENGTH: 94
<212> TYPE: DNA
<213> ORGANISM: Mycobacterium tuberculosis

<400> SEQUENCE: 337

gtatggtcag ctgtccatcc ggcgctgtcg gccgagctgc cagatctcgt cagccgtaac     60

cgggttgcgg gatccacgcg tgcgggttgt ctac                                 94


<210> SEQ ID NO 338
<211> LENGTH: 351
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 338

ccgactttcc gcgggtaccc gctcaacttt gtgtcnacct caacgccatt gccggcacct     60

actacgtgca ctccaactac ttcatcctga cgccggaaca aattgacgca gcggttccgc    120

tgaccaatac ggtcggtccc acgatgaccc agtactacat cattcgcacg gagaacctgc    180

cgctgctaga gccactgcga tcggtgccga tcgtggggaa cccactggcg aacctggttc    240

aaccaaactt gaaggtgatt gttaacctgg gctacgcgac ccggcctatg gttattcgac    300

ctcgccgccc aatgttgcga ctccgttcgg ttgttccaga angtcagccc g             351


<210> SEQ ID NO 339
<211> LENGTH: 152
<212> TYPE: DNA
<213> ORGANISM: Mycobacterium tuberculosis

<400> SEQUENCE: 339

gcaccgatgt cggcgagcac ttcgtcaact tccaggggtg cccgcaccaa gtatttcgac     60

gagtatttcc gtcgggccgc cgccgccggt gcgcggcagg tggtcatcct ggcggcgggg    120

ctgggactcg cgcgcgtacc ggctgcctcg gc                                  152


<210> SEQ ID NO 340
<211> LENGTH: 263
<212> TYPE: DNA
<213> ORGANISM: Mycobacterium tuberculosis

<400> SEQUENCE: 340

tgcacccaac ttactgagca tgctaacgct ggtcgtgcgg gtcttgttcc cgcgtgtcgg     60

cagggcacac gctcggggcg tagctgggag aggccccggt caagcccgga gagcagtgct    120

cagtccgcca gcttgaccga ctttcgatga gaacgcgctt ctcgccgtat tgaactggcg    180

tgctgacggt cgctgagcag cgctcgccga gtgcggccgc tgattctttc atcgagccag    240

gacgcgcatt cgtgttcggc cgc                                            263


<210> SEQ ID NO 341
<211> LENGTH: 249
<212> TYPE: DNA
<213> ORGANISM: Mycobacterium tuberculosis
```

-continued

<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 341
agcttacggc cggtcgacgc gacgagtggt tcatgacacc acaaaccgtc aacgcctact 60
acaacccggg gatgaacgaa atcgtcttcc cgcagcgatt ttacagccac catttttcga 120
tccgcaggcc gacgaggccg ccaactacgg cgggatcggg gcgcgtgatc gggcacgatg 180
atcgggcacg gtttcgacga tagggcgcca aatacgangg cgacgcaatc tggtcnattg 240
gtggatcga 249

<210> SEQ ID NO 342
<211> LENGTH: 269
<212> TYPE: DNA
<213> ORGANISM: Mycobacterium tuberculosis

<400> SEQUENCE: 342
atgtcgtcac gtcaccacaa tcgcgaggac ccaatcatgc cgcccagggc ggccaaccca 60
atggtggccg cgaagcggca gctcgatcgc agcgcggagg tgccggccgc cagttgattc 120
acgaacaggg tgaggtcata ggcgggcagg atagtgacga acgcaagacc tatatctgcc 180
gtcggagtaa gaatcgagta gccggtcgac caacggaagc gaaagtgtcc gcgatgttga 240
tgagcgtcgc cggttgtggc ggcggtggc 269

<210> SEQ ID NO 343
<211> LENGTH: 336
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 343
agcttcacca gcgtgccgat gctgttcgcn acacctccct actatgcgca attcgccgac 60
acgggtggca tcaacacggg cgataaggtg gacatcgctg gggtgaacgt cgggctggtg 120
cgctcgctgg caatccgcgg caaccgcgtg ttgatcggat tctcgttgcc cggcaagaca 180
atcgggatgc aaagccgggc agcaattcgc accgacacca ttcttggccg taagaacctg 240
gaaatcgaac cccgcggttc ggagccgttg aaacccaacg gtttcctgcc gttggcgcag 300
aacactacgc cataccaaat ctatgacgcg ttcgtc 336

<210> SEQ ID NO 344
<211> LENGTH: 417
<212> TYPE: DNA
<213> ORGANISM: Mycobacterium tuberculosis

<400> SEQUENCE: 344
ctgccgcggt ggcggtcagc gcctggcaag tcaccgcacc gccgtccggt tcatcggcag 60
gctcccccga aaagggccct ggcaacagaa ggtgatcaat gagctcccgc agaccttcgc 120
cgatctggga ccgacatacg tgaagttcgg ccagatcatc gcgtccagcc cgggagcatt 180
cggtgagtcg ctgtcgcggg gaattccgcg gcctgctcga ccgggtgccg cccgcaaaaa 240
ccgacgaggt gcacaagctc ttcgtcgagg aactcggcga cgagccggcc cggctgttcg 300

-continued

```
cctccttcga ggaagaaccg ttcgcgtctg cgtccatcgc ccaagtgcac tacgcgacct    360

gcgcagcggc gaagaagtgt ggtcaagatc cacggccggg catccgccgc cgcgttt       417


<210> SEQ ID NO 345
<211> LENGTH: 405
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 345

gatcgtgccg gccccccggc ggcagtagca gatcagctcg tcgaaatcgc ggcaaccagt     60

ccagtcgatt tccatacggg cgccgtcaat caactctgcg aacatcgcga tcggcaccgg    120

aaaccggcga gccgcgtcag ccagcgcaac cagcaccggg atcggatgaa tcatcaatat    180

tatcaagtga tttcctgatg gcatcgagct cggtgatctt ggtctcgggg gccagctcgc    240

cgtcggcgac gtcgtcgatc cggcggccga gcgcatagac cgcaaatagt gccgctcgct    300

tttcgcgcgg caagagtcgg atgccgtaat atangtttct ggcggccgtg cgcgtgatcn    360

actcggtgat tcgatacgcc tgttcatctc ggtcatgccg tcctc                    405


<210> SEQ ID NO 346
<211> LENGTH: 414
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 346

ggtggcgcaa tgaccgaaac caccccagcc ccgcaaaccc cggcggcccc ggccgggccc     60

gcacaatcgt tcgtgttgga gcggcccatc cagaccgttg ggcgccgtaa ggaggccgtg    120

gtacgagtgc ggctggtgcc cggcaccggc aagttcgacc tcaacggccg cagcttggag    180

gactacttcc caaacaaggt gcaccagcag ttgatcaagg cacccctggt caccgtggat    240

cgggtggaaa gtttcgacat ctttgcccac ctgggcggcg gcggcccgtc gggtcatggc    300

cggcgcgctg cgcctgggta tcgcccgggc attgattctn gtatcgccgg atgaccggcc    360

cgcgctgaat aangccggct tcttgaccgt gatccacgcg ccaccgaacg caaa          414


<210> SEQ ID NO 347
<211> LENGTH: 331
<212> TYPE: DNA
<213> ORGANISM: Mycobacterium tuberculosis

<400> SEQUENCE: 347

cacaatagat tactcaagct tcgaaccagc ggccttatca cgtatccccg ctgagacctt     60

gacccttagg gccgaagtga cttcgctgct gctatgccga cacccgattt ccagacgctg    120

ctgttacacg acggccgggc cggtggccac catcacgctc aaccgcccgg aacagctcaa    180

caccatcgtc ccgcccatgc ccgacgagat cgaggccgct atcgggttgg ccgagcgcga    240

ccaggacatc aaggtcatcg tgctgcgcgg tgccggccgc gccttctccg gcggttacaa    300

cttcggcggc gggttccaac attgggggca t                                   331
```

-continued

<210> SEQ ID NO 348
<211> LENGTH: 386
<212> TYPE: DNA
<213> ORGANISM: Mycobacterium tuberculosis

<400> SEQUENCE: 348
tcaggacgct tatggttggc agatggtcgc cctggcgtcg aatacgcgcg agcgcatgag 60
ctcaccggtt cggaacaacg tatcgaagaa cgtcgcactg ctggcagatg gtatctccga 120
tgtggttgta atttgtatcc caactctaac tgtgctatcg gatcagcgtg aatatcgaga 180
tattgcgaat gcgatgacag gccgccattc ggtttattcg cttacgcttc ccgggttcga 240
ttcgtctgat gcactgccgc aaaacgcgga tatgattgtt gaaaccgtat ctaacgcaat 300
tattgatgtg gtaggcggca gctgccgttt tgtgctgtcg ggctattcat cgggtggggg 360
tgtttggcta tgccctctgc tcccat 386

<210> SEQ ID NO 349
<211> LENGTH: 187
<212> TYPE: DNA
<213> ORGANISM: Mycobacterium tuberculosis

<400> SEQUENCE: 349
cgcagctgtc gccgatctgg tccggaatac ctagctccag gttctgagtg gagatgagtg 60
cggccatcga agtgttgtca atgtactcca ggatgtcagg tgccaggccg ctggcgagga 120
tcttgggcac cgccgccatg acttggtcga agtcggcgaa cggggcgagc acgctggcgt 180
cgtggtc 187

<210> SEQ ID NO 350
<211> LENGTH: 241
<212> TYPE: DNA
<213> ORGANISM: Mycobacterium tuberculosis

<400> SEQUENCE: 350
gtagttcgtt catccaaaca cagtgcggta ccggctcaag cggatcaccg acttcaccgg 60
gcgcgatccc acccagccac gcgatgccta tgtccttcgg gtggcggcca ccgtgggtca 120
actcaactat ccgacgccgc actgaagcat cgacagcaat gccgtgtcat agattccctc 180
gccggtcaga gggggtccag caggggcccc ggaaaagata ccaggggcgc cgtcggaccg 240
a 241

<210> SEQ ID NO 351
<211> LENGTH: 335
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 351
tccgctcgct tctccgagag gttgagtgcc aacgctctgc cgatgcccga agccggcccc 60
ggtgatgacg gcgaccttgc cttcgaatga gctcatttga ctactccccg tggttgtccc 120
tgcgattggt ggaggtggcc gcgcagcctt gccccgaggt cggcgatcgc gtctcgggct 180
tcggggagca gactgacctg cagatggaag tcgtgccaca tgcccgcgaa ccggcgatgc 240
tcgatgcttg ttttcgaagc ggcgcaggcg gtttcgatct tgtccgcgtc aacacngatc 300
ggatcgtcgc ccgcggtctg catgacgaat gggcg 335

-continued

<210> SEQ ID NO 352
<211> LENGTH: 441
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 352
atgggaggcc accgattacc atcttgcaca caccgattcc gggctattga tgtccacgtt 60
cggtccgcga accgcgctgt ggctgctgct ggccaaaggc ggaggcgata ccgaagtcag 120
tgcccaagct tgggttccac gctcgcgcag ccacgccgtc acctttccac gagacctcac 180
ctgccgatcc gaaatggaat cggccgtgac ggaattggcg cagcgaacac tcaacgaggt 240
ggtggcttcg tcgcgaaccg tcacccgagt cgcggtcacc gtgcgcacgg cgacgttcta 300
cacccgcacc aagatccgaa agctgcaagc tcccagcacc gatcccgacg tcatcaccgc 360
tgccgcccgg cacgttcttg aacctattcg agctggaatc ggccgtccgg ttgctgggaa 420
ttgcngttaa gaactgggcc t 441

<210> SEQ ID NO 353
<211> LENGTH: 332
<212> TYPE: DNA
<213> ORGANISM: Mycobacterium tuberculosis

<400> SEQUENCE: 353
gctttgcgcg cttctccgag aggttggagt gccaacgctc tgccgatgcc cgagccggcc 60
ccggtgatga cggcgacctt gccttcgaat gagctcattt gactactccc cgtggttgtc 120
cctgcgattg gtggaggtgg ccgcgcagcc ttgccccgag gtcggcgatc gcgtcgcggg 180
cttcggggag caaactgacc tgcagatgga agtcgtgcca catgcccgcg aaccggcgat 240
gctcgatgct tgttttcgaa gcggcgcagg cggttcgatc ttgtccgcgt caacgcagat 300
cggatcgtcg cccgcgggtc tgcatgaaga at 332

<210> SEQ ID NO 354
<211> LENGTH: 334
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 354
ctcacgcagc cacgccgtca cctttccacg aagacctcac ctgccgatcc gaaatggaat 60
cggccgtgac ggaaattggc gcagcgaaac actcaacgag gtggtggctt cgtcgcgaac 120
cgtcacccga gtcgcggtca ccgtgcgcac ggcgacgttc tacacccgca ccaacatccg 180
aaagctgcaa gctcccagca ccgatcccga cgtcatcacc gctgccgccc ggcacgttct 240
tgacctattc gagctggatc ggcccgtccg gttgctggga gtgcggttag aaactggcct 300
agaaaccggc gggcacaccg cacctgggcg gggn 334

<210> SEQ ID NO 355
<211> LENGTH: 341
<212> TYPE: DNA

-continued

<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 355

```
tgcttccggc tcgtatgttg tgtggaattg tgagcggata acaatttcac acaggaaaca     60

gctatgacca tgattacgcc aagctattta ggtgacacta tagaatactc aagcttgatg    120

ccgccgaaac cgagcgtgag cacgccgcca gccaccacnc gcgggtcggg cgccgggccc    180

gggtcgccan gctgctccgc tcggtgatgg cacgccaccg cgacaccacc cggctgcgct    240

acgtcgagcc ataccgggcg gagctacatc ggctcggccg cccagtgttc gggccctctt    300

tcgaagtcga agtcgatacc gattgcgcat ccgcngccgc a                         341
```

<210> SEQ ID NO 356
<211> LENGTH: 259
<212> TYPE: DNA
<213> ORGANISM: Mycobacterium tuberculosis

<400> SEQUENCE: 356

```
caggcatgca agcttcacgt ccgtacggct cgggtacgct tcggtcgcag tgtgcgagtg     60

atagatgacg accgggacct cgtctgcatc ttccatagcc cgccacacct tcagttgctc    120

accggaatcc aaccggtaga aggtcggcga gcgctcggca ttggtcatcg ggatatgccg    180

ctcgggacgg tcagaaccct cgggtccggc cagcactccg caggcttcgt cggggtggtc    240

gcgacgcgca tgggccacc                                                  259
```

<210> SEQ ID NO 357
<211> LENGTH: 349
<212> TYPE: DNA
<213> ORGANISM: Mycobacterium tuberculosis

<400> SEQUENCE: 357

```
gcttgtctat cgtcccggcc aggtccggcc agtcaaggtc gaaggccagt ccggtctcct     60

ctccgactac ggccaagaac tgggcgacgg tgtcagtgca gaccagcgga aactggtggc    120

gccctaggcg agcgaccgcc tcacaaacgg cggtgaccgc gttctggtcg tgcaccatcg    180

agccgtgccc agcccggccg cgtgccgtca gccgcatcca ctggatgccc ttctcggcgg    240

tttcaatcag gtacaggcga cgttcgccac catcgtgccg gggcacggtt agcgagaaac    300

cgccgacttc acgattgcct cggtgatgcc gtcgaaacag atcgggcct                 349
```

<210> SEQ ID NO 358
<211> LENGTH: 325
<212> TYPE: DNA
<213> ORGANISM: Mycobacterium tuberculosis

<400> SEQUENCE: 358

```
gcgcgccatg ttgaggttgt ccgacggtga cgacggtgaa ccacaactgt ttgacctgtc     60

cgcacacacc gtgtggatcg gcgagcggac ccgacaaatc gatggcgcgc acatcgcgtt    120

tgcccaggtg attgctaatc cggtcggggt caagttgggc cccaacatga ccccggaact    180

ggccgtggag tacgtcgagc ggctcgaccc gcacaataag ccgggccggc tgacttggtg    240

agcaggatgg gcaaccacaa ggtccgcgat ctgttgccac cgatcgtgga gaacgtccat    300

gccaccgggc atcaggtcat ctggc                                           325
```

-continued

<210> SEQ ID NO 359
<211> LENGTH: 191
<212> TYPE: DNA
<213> ORGANISM: Mycobacterium tuberculosis

<400> SEQUENCE: 359
ttgccttcca tgccgagcaa ggtcgactca gcgatgacga attgttcttc ttcgcgggtg 60
ttgctgctgg ttgcgggcta tgagagcact gctcatatga ttagcacatt gtttctgacg 120
ctggccgact atccagatca gctgacactc cttgcgcagc aaccagacct gatcccgccg 180
gcgatcgagg a 191

<210> SEQ ID NO 360
<211> LENGTH: 74
<212> TYPE: DNA
<213> ORGANISM: Mycobacterium tuberculosis

<400> SEQUENCE: 360
cgacgctggg cccaactgcg accaccaggt cctggtatgg caggacatgg ccgggttcag 60
cggcgccaat accg 74

<210> SEQ ID NO 361
<211> LENGTH: 312
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 361
taacgactcg ggtccagcga ccgcgccaac acnaacggcc ggacnacgtg ggccagggtc 60
gcggcctccc ctacaaacag gatccgttgc ctgcgaacga caggctccgg tgcggcgttg 120
ggcgccgtgc tcgtcccagc gtccggtccc gggtcgccgg cgacgcttgt ttcctccata 180 ctcgcccccct aatctcgagg cagcccgtac ccgcaggcaa cctcccaaaa atgcaatccc 240
ccaaaatgca atgcgtcnag ctatttctca caccgaccgc tagttgcgga tcanaaatcc 300
gttgggcgcg ga 312

<210> SEQ ID NO 362
<211> LENGTH: 335
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 362
cntggcggtg ggtgcggtgt cgaacacgac cacacttctt tgcggttcgg tgatctcgac 60
accggccgcg agccgaccac catgcgcgcg tagatcggcg atcagcgcgt cggctatcgc 120
ctgggtgccg cccaccggaa tcggccagcc gaccgaatgg gccagcgttg ccatcatcag 180
tccggcgccg gccgacacca gtgacggcaa cggtgaaatc ncgtgggcgg caacgccggt 240
gaacaacgcg cgggcatcct cgcccgccag cgaccgccag gcaggggtgc cctgggccag 300
catccgcagc ccgagacnca ggaccgancc cagtg 335

-continued

<210> SEQ ID NO 363
<211> LENGTH: 386
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 363
gcttttcnga tcgcagcgag tcgtacccgc gccggtcacc ttcgtggata tcgccggcct 60
ggtcaagggg gcgtccgagg gagccgggct gggtaacaag ttcctggctc atatccgcga 120
atgcnacgcc atttgtcagg tggtgcgggt gttcgtcaac aacnacttga ctcatgtcac 180
cggacgggtc gatccccant ccgacattga ggtcgtcgan accgagctga tcctggcana 240
tctgcaaacc ctggagcggg ccacgggccg gctggagaag gaancgcgca ccaacaaggc 300
gcgcaagccg gtctacgacg cggcactgcg tgcccagcag gtgctcgacg ccggcaanac 360
gctgttcgcc gcgggggtgg atgccg 386

<210> SEQ ID NO 364
<211> LENGTH: 386
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 364
gtcgtacgcc attngtcggt gtgcgcatac cagtacgacg cgccgggcac ctgacgcggc 60
ggccgcgacc agtcggtggc catcgccatc gtctgccacc cggtcaacgg acgcaccttc 120
tcctggccga cgtagtgcgc ccacccgccg ccgttgcgtc ccatcnatcc ggtcaacatg 180
agcagcgcca acaccgagcg gtacatgaca tcgctgtgga accagtgaca gattccgccg 240
cccatgatga tcatcgaccg tcctccggat tcggtcgcgt tgcgggcgaa attccttggc 300
aaaccggatt gcctgcgcgg ccggcacacc ggtgatcgac tcctgccagg ccggggtgtt 360
ctgctgggtt cggtcgtggt accggt 386

<210> SEQ ID NO 365
<211> LENGTH: 335
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 365
gcgaggcggt atcgcttccc gtcgtaccgg cgaccgccag ccgagaagct cgttttccca 60
gtgttgctgg ggattctcac gctgctgctg antgcgtgcc anaccgcttc cgcttcgggt 120
tacaacgagc cgcggggcta cgatcgtgcg acgctgaant tggtgttctc catggacttg 180
gggatgtgcc tgaaccggtt cacctacnac tccaagctgg cgccgtctcg tccgcaggtc 240
gttgcttgcg atagccggga ggcccggatc cgcaatgacg gattccatgc caacgctccg 300
agttgcatgc ggatcgaata cnaattgatc accca 335

-continued

<210> SEQ ID NO 366
<211> LENGTH: 396
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 366

```
tgggtcttgc cggcgagccc agcgaagtcg ctagcgtggc cgtgtttctt ggcttcggat     60

ctatcctcgt tacatgaccg gcaccgtgtt ggacgtgact ggcggccggt tcatatgaca    120

ccgagatcat tgccacggta cggcaattcg tcaagaagga aatctttccc natgcaccgg    180

ccctcgaacg tggcaacagc tacccgcaag aaatcgtcga tcggctgggt gttattggct    240

tgctcggtcg ccggctgcaa gggtatcgac accaccgagt tcattctcgg gcgtgccggc    300

gcattcgagc tggcggtgcg cgctgcccag caccgtcata agtacttgan gatggtcaaa    360

cgtcggacga accgccacca cgtcgctgcc gaacgg                              396
```

<210> SEQ ID NO 367
<211> LENGTH: 262
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 367

```
tagatgccca agcttgccnt tanagacctc gtcgaccaag cacggacgcg accgtcgaag     60

gtggcgaatc cgggcttggc gtcnacccgc gtaaggcaga ccagatggtt cgcggcacgg    120

tcaacctgcc acacggcact ggtaagactg cccgcgtcgc ggtattcgcg gttggtgaaa    180

aggccgatgc tgccgttgcc gcgggggcgg atgttgtcgg gagtgacgat ctgatcgaga    240

ggattcaggg cggctggctg ga                                             262
```

<210> SEQ ID NO 368
<211> LENGTH: 303
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 368

```
tctccacggc gtggatcaag gtaccggccg ggatgttgcg caatggcagg ttgttgcccg     60

gcttgatgtc tgcgttagcg ccggattcca ccacatcccc ttgcgaaaag tccgttgggt    120

gcaatgatgt agcgcttctc cccatcgaga tagtggagca acgcaatccg tgcggtacgg    180

ttcgggtcgt actcgatgtg cgcgaccttg gcgttgacac catctttgtc attgcggcga    240

aagtcgatca tccggtaagc gcgcttatga ccgccgcctt tgtgccgggt nggtaatccg    300

gcc                                                                  303
```

<210> SEQ ID NO 369
<211> LENGTH: 367
<212> TYPE: DNA
<213> ORGANISM: Mycobacterium tuberculosis -continued
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 369
gcccggttcg atcgggcatg tccgcagtcg tcgttaccgg aggcggtcgt ggccgcgcta 60
atcggcgtcg gcgccgacaa gatgtgggat atccgcaatc ggggcgtcat ccctgcgggc 120
gcgctccccc gcgtccgagc cttcgtcgac gcaatcgagg caagtcacga cgcggatgag 180
gggcagcagt gaattacagc gaggtcgagc tgttgagtcg cgctcatcaa ctgttcgccg 240
gaaacagtcg gcgaccgggg ttggatgcgg gcaccacacc ctacggggga tctgctgtct 300
cgggctgccg acctgaatgt nggtgcgggc ancgccggta tcnactcccg tggaacacag 360
ccggggc 367

<210> SEQ ID NO 370
<211> LENGTH: 366
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 370
ctcggcgtgg atatcggtgt agccggcgcc ggtgaangtc ggctccttac gtccactcga 60
caacagctca tagcgatcca accagtangc aaccgccttc agcagtacaa ccgcgccggc 120
gaacactgcg agttgaacgc gagctgcctg ggtcagcatg cctctgccgg ttgtcagccg 180
aaggccgccg aacaggtaat gcgtcaacag gctcgctaga aacgccagaa ccacggccac 240
gaacagccag ttcagcaccg accggtagaa cggcagatcg aagacgaaaa aacccaatgt 300
catagccgaa ttcggggtcc acgatgccaa aggtgccccc gtgtacaaca actgaacctt 360
caccca 366

<210> SEQ ID NO 371
<211> LENGTH: 455
<212> TYPE: DNA
<213> ORGANISM: Mycobacterium tuberculosis

<400> SEQUENCE: 371
tccggctcgt atgttgtgtg gaattgtgag cggataacaa tttcacacag gaaacagcta 60
tgaccatgat tacgccaagc tatttaggtg acactataga atactcaagc ttcacgtccg 120
tacggctcgg gtacgcttcg gtcgcagtgt gcgagtgata gatgacgacc gggacctcgt 180
cggcatcttc catagcccgc cacaccttca gttgctcacc ggaatccaac cggtagaagg 240
tcggcgagcg ctcggcattg gtcatcggga tatgccgctc gggacggtca gagccctcgg 300
gtccggccag cactccgcag gcttcgtcgg ggtggtcgcg acgcgcatgg gccaccatcg 360
cattcaccag gtctgcgcga atcaccagca cgtagacggt tcctttccta agcaacaccg 420
aagtttcagg accgaatgct ccgggaaaca tgtca 455

<210> SEQ ID NO 372
<211> LENGTH: 196
<212> TYPE: DNA
<213> ORGANISM: Mycobacterium tuberculosis -continued

<400> SEQUENCE: 372
caggcatgca agcttgatgc cgccgaaacc gagcgtgagc acgccgccag ccaccacgcc 60
cgggtcgggc gccgggcccg ggccgccagg ctgctccgct cggtgatggc acgccaccgc 120
gacaccaccc ggctgcgcta cgtcgagcca taccgggcgg agctccatcc gctcggccgc 180
cagtgtccgg gccctc 196

<210> SEQ ID NO 373
<211> LENGTH: 443
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 373
cctgcatccg gctcgtatgt tgtgtggaat tgtgancgga taacaatttc acacaggaaa 60
cagctatgac catgattacg ccaagctatt taggtgacac tatagaatac tcaagcttcc 120
aatccccctg ccctgatacg cgtcggcaac cgtgaacgcg atctcggcga ccgtcggatc 180
ggtttcatcc cgcacaaaac gcgcgtcggc tacggggtcg cttccgtcgg tcaccaccca 240
gacgaagtgg tcgacgtagt cgacttccga caggtagtgc atcaacgccg gactgggaac 300
acnagccgac atgaaccgtc gatacagcgt ctcnccggag aactggatgt gtccgtgcac 360
ggtccgctcg cggtcaccgg gcagcacggg gcgtaacatc agttgagtcc cgtcggcaag 420
ccgtaccgga atcggggaga cga 443

<210> SEQ ID NO 374
<211> LENGTH: 445
<212> TYPE: DNA
<213> ORGANISM: Mycobacterium tuberculosis

<400> SEQUENCE: 374
caagatgatc gccggtgcca ccccgatccg tgcctcggtc agcgcgaacg tgctttccgg 60
tccggcgacc accatgtcgc acgcaccgac caggccgaac ccgccggccc gcacatgccc 120
gttgatggcg ccgaccaccg gcagcggcga ctcgacgatg gcgcgcaaca gcgccgtcat 180
ttcccgcgcc cgcgccaccg ccatccggta cggatcacca ccaccaccgc cggcctcgct 240
gaggtccgcg ccggcgcaga acgttccgcc ggtatgcccc agcacgacca gccgcaccgc 300
cggatctgct tcggccgcac tcagcccttg atgtagttgg ctgaccagcg tgctcgacag 360
cgcgttgcgg ttgtgcggag agttcagtgt cagcctggcg aaggggccgc cgcaggcggc 420
cgggccagcg tagtcgacgg ggctg 445

<210> SEQ ID NO 375
<211> LENGTH: 308
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 375
ctcaagcttc gatcgacagt actcccgcct tgggtctggt cttcgagctg gtcggtcatg 60
gtcggacctg ctggtagtgg ggatctaacg caacatggtc gggattcatc atggtgtacc 120

-continued cgtgataccc attcgcagct gccggtgaaa ccccgcgatg ccgggatttc cagccgcact 180
aggatgtcta gccggccagc cgctgccgcc ggacttcggg atgttcggta taccaccgat 240
cggcaatctt gcntatccgc cgatgctcga acgctagcca ccccaaacca accactgtga 300 cnacaatc 308

<210> SEQ ID NO 376
<211> LENGTH: 239
<212> TYPE: DNA
<213> ORGANISM: Mycobacterium tuberculosis

<400> SEQUENCE: 376
tgaatttccc gatcccacaa tctcggttca gatacaggtc gccatacccc ttacttcggc 60
aacgctgggc ggattggccc tgccgctgca gcagaccatc gacgccatcg aattgccggc 120
aatctcgttc agccaatcca tacccatcga cattccgccg atcgacatcc cggcctccac 180
tatcaacgga atttcgatgt cggaggtcgt gccgatcgat gtgtccgtcg acattccgg 239

<210> SEQ ID NO 377
<211> LENGTH: 431
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 377
tactcaagct tgaacgctgc gagcgagccc atgtagagcg tttggtacca aaccgatcgg 60
tgggccaact tgccatgggc tcacagcggc tatcgcgagc gtgtagccga tcatcggcca 120
ggcgacggtg gcctgagcgg caggggttgc cttatccatc ctcttgcggc atggttgccg 180
cagggagtgc cggtaagtct ggtcggcaac ctggcccgct gcgggttggg ttcggattcc 240
ctcggctagt aaggtgctcg cctggtgtta caacgaatcg ctagacagct cttatcggga 300
gtggccgtcg cgatcgttgc gctgccgctg gcgatcgcgt tcggcnttac cgccaccgga 360
acgtcccaag gtgcgctcat cgggctctac ggcgccatct tcgccggatt cttcccngcc 420
gtgttcggtg g 431

<210> SEQ ID NO 378
<211> LENGTH: 334
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 378
gcggtgtctg aacttcgccc gttccctcca gcgcattgag cttcagcccg accggcaggt 60
agggagtcgg catgcggtcc ttcgccccga ccccgctggc taaatagcca cccccgagcg 120
cggtcacggt ctttgcaccg ggacgacggc ataccggcag cgcgaacatc gccgcgggct 180
gcagcgtgaa cgtcgaatac gagtcgaaca gtgtcggcgc gtaaaaaccc gagccggcgg 240
tcgcttcggt aatcaacggc tcctgcgcaa ccagctgcaa ntcnccggtg ccaccggcgt 300
tgacaatctt gatntcggcg acctcgcgca ccan 334

<210> SEQ ID NO 379
<211> LENGTH: 302
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 379

```
tactcagctt cggctcaggt ggtgctgctg gtaaagttcn ctgaacggtg caggtttcga     60

caatgtggtg ccggttcggc gggtactgcc atcgagacac tggcgcaggc tatcgcaccc    120

gttatcggct acaaacaaat cgcggtatgc gttcttgagc atgagtcggc gaccgtcgtc    180

atggtcgaca cccacgacgg aaagacgcag atcgccgtca agcntgtgtg ccgcggatta    240

tcaggactga cctcctggct gaccggcntg tttggtcncg atgcctggcg cccggccggc    300

gt                                                                   302
```

<210> SEQ ID NO 380
<211> LENGTH: 240
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 380

```
catcacctgg ttcatgaaac tggaagcagc gcagcgcttc cttttcggcc gcaacatgag     60

ccagcctctc gtcggcggtc gggtgcaggt gctcgggcag ctcggccgcg acagccgcct    120

gaccctgaaa ccagcttcca tatcccgcga cgaacgacgc cagtccgcta cgtaacccct    180

ccgcgactgt ccatggacaa cancgcgttc tccaccgacc gggcccgggt gtggggtgtt    240
```

<210> SEQ ID NO 381
<211> LENGTH: 362
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 381

```
ctcaagcttc ccggcggcca gtaccgaaag cgcgaacagc tcgcggcagc ccacaacntg     60

ctgcgtcgga ttgccggcgg cganatcaat tccaggcagc tcccggacaa tgcggctctg    120

ctggcccgca acgaaggact cgaggtcacc ccggtgcccg gggtcgtggt gcacctgccg    180

atcgcacagg ttggcccaca accggccgct tgatgcccgg tcggcaagcc cggcagttgc    240

caaacccagc gtgatcaggc tcggctcgcg agttcggcga agaagtggct cgcctgatca    300

cctaccatcg gccaggatct gcgtgtcatc acnacgctcg ccaaggaggt tgttgtggtg    360

ct                                                                   362
```

<210> SEQ ID NO 382
<211> LENGTH: 411
<212> TYPE: DNA
<213> ORGANISM: Mycobacterium tuberculosis -continued

<400> SEQUENCE: 382
gccacgtttc gcgccgcccg gcatacggcg gcgtaccgat ctccgcgtca tacacccgcg 60
ggtaatcgcc gacggtgccg gttcgcgagc cgaaggtgac gacgctgatt gaatcgagtt 120
ccaggtccag cgggtggcgc agcaacggcg cgagctcaac gacgtcaatc acgttgtcgc 180
tttctacggt caccgacccg gtgaccgtag tcgcccggtg cgctcggccg agaagttgca 240
ccgccaccac cgcgacaccg tcttgcacgc ggacgccacc cccggatcgg ttgttggcca 300
aggtaattgg gtcattccat ttgacgggac gccgaccccg cagccccagt accgcccacg 360
accacgccgg ctgaccccac cactgtacga acaccaaggc gacgccgacc a 411

<210> SEQ ID NO 383
<211> LENGTH: 331
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 383
ctcaagcttg atgccgccta aaccgaagcg tgagcacgcc gccacccacc acgcgcgggt 60
cgggcgccgg gcccgggccg ccaggctgct ccgctcggtg atggcacgcc accgcgacac 120
cacccggctg cgctacgtca agccataccg ggcggagcta catcggctcg gccgcccagt 180
gttcgggccc tctttcgagg tcnaggtcna taccgatttg cgcatccgca gccgcaccct 240
ggacgacaga accgtgccct acgagtgctt gtcgggcggg gccaaagaac ancttggcat 300
cctggcgcga ttggccggcg cggtcctggt c 331

<210> SEQ ID NO 384
<211> LENGTH: 254
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 384
ctcgggtacg cttcggtcgc agtgtgcgag tgatagatga cgaccgggac ctcgtcggca 60
tcttccatag cccgccacac cttcagttgc tcaccggaat ccaaccggta naangtcggc 120
gagcgctcgg cattggtcat cgggatatgc cgctcgggac ggtcagagcc ctcgggtccg 180
gccagcactc cgcaggcttc gtcggggtgg tcgcgacncg catgggccac catcgcattc 240
accaggtctg cgcg 254

<210> SEQ ID NO 385
<211> LENGTH: 346
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 385
ctcaagcttc aattcctcca cgacgcgttc ccaaatgaat ttcccgatcc cacaatctcg 60

-continued

```
gttcagatac aggtcgccat acccttact tcggcaacgc tgggcggatt ggccctgccg    120

ctgcagcaaa ccatcgacgc catcgaattg ccggcaatct cgttcagcca atccataccc    180

atcgacattc cgccgatcga catcccggcc tccactatca acggaatttc gatgtcggag    240

gtcgtgccga tcgatntntc cgtcnacatt ccggnggtca ccatcaccgg caccagnatc    300

gacccgattc cgctgaactt cgacgttctc agcagcgccg gaacca                   346
```

<210> SEQ ID NO 386
<211> LENGTH: 287
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 386

```
ttaacccccg tggcctctac gccgcctncg ggtcgaacat gcatcccgag canatgctcg     60

agcgcgcacc ccactcgccg atggccggaa ccggctggtt acccgggtgg cggctgacgt    120

tcggcggcga ggacatcggc tgggaagggg cgcttgccac cgtcgtcgaa gacccagatt    180

cgaaggtgtt cgtcgtgctc tacgacatga ccccggcgga cgagaagaac cttgaccggt    240

gggaaggctc cgagttcggc atccaccana agatccgatg ccgcgtt                  287
```

<210> SEQ ID NO 387
<211> LENGTH: 370
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 387

```
ctcaagcttg attttgatca tcatggatga tcatcacccg aagtgtggta gccgcagtgg     60

ttatcgtggg taccgtcgtg ctttccatgg gcgcctcttt cgggctttcc gtattggtct    120

ggcaggacat tctgggtatc gagttgtact ggatggtgtt ggcgatgtcg gtgatcctgc    180

tcctggcggt gggatccgac tacaatctgc tgctgatttc ccggttgaaa aangaaattg    240

gggccggatt gaacaccgga attatccgtg ccatggctgg taccggggga gtggtgacgg    300

ctgccggcat ggtgttcgcc gttaccatgt cgttgtttgt gttcagcgat ttgcgaatta    360

ttggtcagat                                                           370
```

<210> SEQ ID NO 388
<211> LENGTH: 330
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 388

```
cgnccaaccc gaattggttt tcggcgccnt cggtgaggac ggcgtgcggg tgctcaacga     60

cgacgtcgtc cgcgggacac acctcgatgc tgccgccatg gacgcggtcg aacgcaagca    120

gctgatcgag ctacaacgcc gcgcggaacg cttccgccnc nggcgttacc gcatcccgtt    180
```

-continued

```
gaccgggcgg atcgcggtga tcgtcgatga cggcatcgcc accggagcga cggccaaggc    240

ggcgtgccag gtcgcccggg cgcacggtgc ggacaaggtg gtgctggcgg tcccgatcgg    300

cccanacgac atcgtggcga gattcgccgg                                     330
```

<210> SEQ ID NO 389
<211> LENGTH: 346
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 389

```
cgtgactgcc accggggcca ctccgcagaa tctgtacccg accaagatct acaccatcga     60

atacgacggc gtcgccgact ttccgcggta cccgctcaac tttgtgtcna ccctcaacgc    120

cattgccggc acctactacg tgcactccaa ctacttcatc ctgacgccgg aacaaattga    180

cncagcggtt ccnctgacca atacggtcgg tcccacgatg acccantact acntcattcg    240

cacgganaac ctgccgctgc tagagccact gcgatcggtg ccgatcgtgg ggaacccact    300

ggcgaacctg gttcaaccaa acttgaaggt gattgttaac ctgggg                   346
```

<210> SEQ ID NO 390
<211> LENGTH: 355
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 390

```
tcgctcaagc gcntgaggcc gaancggctg gttacgactc cctgtttgtg atggaccact     60

tctaccaact gcccatgttg gggacgcccg accagccgat gctggaggcc tacacggccc    120

ttggtgcgct ggccacggcg accgagcggc tgcaactggg cgcgttggtg accggcaata    180

cctaccgcag cccgaccctg ctggcaaaga tcatcaccac gctcgacgtg gttagcgccg    240

gtcgagcgat cctcggcatt ggagccggtt ggtttgagct ggaacaccgc cagctcggct    300

tcgagttcgg cactttcagt gaccggttca accggctcga aaaggcgcta canat         355
```

<210> SEQ ID NO 391
<211> LENGTH: 403
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 391

```
atactcaagc ttccgctggg gcctgttcaa ccatggcgat cccgttggtc ccggacatcc     60

cgaacgagga caccgcgacc cncttcggtg tgtgatcatt accgttgggc cactgcgtaa    120

ccgcttgcgg cacaaagagc ccggtctcga cgtcggaaag ctcatcgggc acccgattga    180

aatgcagcag cggcggcacc accccgtgcc gcagtgacag aattgccttg atcagcccga    240

cggtccccgc cgatgccgtg ctgtgcccca tgttgctctt ggccgatcca agcgcgcagg    300
```

-continued gggtgcccgc gccatacacc cgcgccaggc tgcggtactc aatcgggtcg ccgattggcg 360
taccggtgcc gtgcgcctcc accacaccga ccgtttcggg ctg 403

<210> SEQ ID NO 392
<211> LENGTH: 440
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 392
caacagcgtt ccagcggcat accaccgcac atgccgtgca cccggcgccg ggcggagtcg 60
ccgcataaca cangtacacc ttgggaatcg gtgtgcgcca gggattcnac cgcggggtgg 120
ggccggcgat cgcgcgccag gtcgagttgg cgccgaccgt gatntcaccg ccgacgtagt 180
tggcgttgtg gtccgccatc cgcgcggcgg gcacggcgcg ggccgccacc acgatgtcac 240
ggaagccggg ggcgaacgct cgacgacctg gttaccgtct cngtcgcntc nancgtggac 300
ccgacngcac gtgggcatat gtccanaacg gacgnggccg gtttcntcga tgcngccggg 360
gtccgcgacn tgcggacncn cngncacacc atccgccagt ccgcgtggcg tcccgccgcg 420
actctgcctc ggccgcgcca 440

<210> SEQ ID NO 393
<211> LENGTH: 353
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 393
ctcaagcttt gncgacgatc gggcgatgtc gatganagga aaccccagcg cacaaccgac 60
nattttggcg tagccggcgg acntctgctc gattccgatc acgtcggcgc tcgcatcgag 120
catggcgccg gcgacggcta gcagcgatcc gccgtcgtcg aggaacacga cacgagccgt 180
acgcccggcc gtaagccgcg cccaggattc ggcgaaaaac cgttctacgt ggcgggtgta 240
ctgggtgtcc aatgattcgt ggggtgcgta ggcgtcgctg caatcgtcga cataaatgcc 300
gtcggcccgc atcgcgtcaa caactcccgg gtgagtggaa tancacttgc cga 353

<210> SEQ ID NO 394
<211> LENGTH: 340
<212> TYPE: DNA
<213> ORGANISM: Mycobacterium tuberculosis

<400> SEQUENCE: 394
tccaacgcgg tgacagattt gtctatcctg gacctgacgg tgaggtcgaa gttttccagg 60
aattcggcaa aatcggtaag agcctgaaga attcggtatc gccggacgaa atctgcgacg 120
catacggggc agatacgctt cgggtttacg agatgtcgat ggggccgctg gaggcttcac 180
gtccatgggc cacaaaggat gttgtcggcg cgtaccgttt tctgcagcgg gtgtggcgct 240
tggtcgtcga cgagcacacc ggcgaaactc gggtggctga cggcgtggaa ctcgacatcg 300
atacgctacg ggcgttgcac cgcaccatcg tcggcgtgtc 340

-continued

<210> SEQ ID NO 395
<211> LENGTH: 362
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 395

```
ctcgtccttg actacgccca gtatcgaaan cctcctgtgc cggtncgcta aacacccggc     60

ggacactcan acggtgctgg tggtgcggca tggcaccgcg ggcagcaaag cgcacttctc    120

cggggacgac agcaagcgac cgctagacaa gaggggtcgt gcgcaggcag aagcgttggt    180

accacagctg ctggcgttcg gcgccaccga tgtttatgcc gccgaccggg tgcgctgcca    240

ccanacnatg gagccactcg ccgcggaact gaacgtgacc atacacaacg agcccncccct    300

gaccgaagag tcctacgcca acaaccccaa acgcggccga caccgagtgc tgcagatctt    360

cg                                                                   362
```

<210> SEQ ID NO 396
<211> LENGTH: 356
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 396

```
gtatcgcctc cncctttggc caccagcagc cacagcgcgg ttcgcggacc gaacgtggac     60

atcaatagcc cggaatcggt gtgtgcaagt tggtaaacgg tgttgatccc aagctttgcc    120

agccttttcg tagtcttggg ccccacaccc cacagtgctt cgacggtacg gtcacccatg    180

atggccatcc agttggcatc ggtgagctga tagatgccag ctggtttcgc caacccggta    240

gcgatcttgg cgcgctgctt gttgtcactg atacctatcg agcaagacag cccggtttgc    300

gacaagatga cttttcggat ctcttcngcg aacttccaat gggggtctcc gggant        356
```

<210> SEQ ID NO 397
<211> LENGTH: 350
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 397

```
ctcaagcttt tggtctagcc ggccgagcac gatacgggtg tccttggcca ccggcggcgg     60

ctgtccggga aatggcgggt ccccggtggt tttgctgang antgctgaac cgtagtcgaa    120

gtgggcggcg tcagactcca cccagccagc aggcagcgcg aagctgaatc ctccaaccgg    180

gttgtcgatc cggacaggtt ggggtgcgtt tggggcaatg acaggtggcg gcggtgcgtt    240

cgggtcggcc ggcggaggtg ctgcgttggg atcncccggc tgggcattcg gcntnttggc    300

ggcggccggt ggtggggggg caacangtgt cccggtgcgg gtggcgctgc               350
```

<210> SEQ ID NO 398
<211> LENGTH: 355

-continued

<212> TYPE: DNA
<213> ORGANISM: Mycobacterium tuberculosis

<400> SEQUENCE: 398
atctgtaccc gaccaagatc tacaccatcg aatacgacgg cgtcgccgac tttccgcggt 60
acccgctcaa ctttgtgtcg accctcaacg ccattgccgg cacctactac gtgcactcca 120
actacttcat cctgacgccg gaacaaattg acgcagcggt tccgctgacc aatacggtcg 180
gtcccacgat gacccagtac tacatcattc gcacggagaa cctgccgctg ctagagccac 240
tgcgatcggt gccgatcgtg gggaacccac tggcgaacct ggttcaacca aacttgaagg 300
tgattgttaa cctgggctac ggcgacccgg cctatggtta ttcgacctcg ccgcc 355

<210> SEQ ID NO 399
<211> LENGTH: 360
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 399
ctcaagcttg caatgcgggt cgggatgccc atggttggaa natggtcgcc ctggcgtcna 60
atacgcgcga gcgcatgagc tcaccggttc ggaacaacgt atcgaaaaac gtcgcactgc 120
tggcagatgg tatctccgat gtggttgtaa tttgtatccc aactctaact gtgctatcgg 180
atcagcgtga atatcganat attgcgaatg cgatgacagg ccgccattcg gtttattcgc 240
ttacgcttcc cgggttcgat tcgtctgatg cactgccgca aaacgcggat atgattgttg 300
aaaccgtatc taacgcaatt attgatgtgg taggcggcag ctgccgtttt gtgctgtcgg 360

<210> SEQ ID NO 400
<211> LENGTH: 272
<212> TYPE: DNA
<213> ORGANISM: Mycobacterium tuberculosis

<400> SEQUENCE: 400
caaatacacg ccggacgcac aggcggacat cgccatcccg agcacaccca aaacgggata 60
caggatggag gccaacgcca cggccgcgcc caggatcacc aaccacaccg gcttggtcag 120
cttgtcggcg gcggtatagg catcgggccg ctgcaacgca gcatgcacaa acgcgtacac 180
cgctgtcacc aagacggcga ccagcaatac cagcatgacg gtacccacga ggtggctcac 240
gcattcagac tatgcggttt gcatccaaca cg 272

<210> SEQ ID NO 401
<211> LENGTH: 306
<212> TYPE: DNA
<213> ORGANISM: Mycobacterium tuberculosis

<400> SEQUENCE: 401
ctcgtccttc ggcctcgctg caggagtggg agccgcaggg ctggaaatcc gaaaaacgag 60
ccggtgatcg cactgtcgcc gatcggcgcc gcacctggtt ggtgttacgg atgaatccgc 120
agcgaaatgt ggctgcggtg gcgtgtcgtg actcgttggc gtcgacgctg gtggcagcca 180
ccgagcggtt ggtccaggat ctggatgggc aaagttgtgc ggcccggccg gtgacggccg 240
atgagctgac cgaggtcgac agcgccgtgt tggctgactt ggaaccgaca tggagtcgcc 300
ccggtt 306

-continued

<210> SEQ ID NO 402
<211> LENGTH: 300
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 402
gtctagnccg ccgaacacga tacgggtgtc attggccacc ggcggcggct gtccgggaaa 60
tggcgggtcc ccggtggttt tgctgaagan tgctgaaccg tagtcgaagt gggcggcgtc 120
agactccacc cagccagcag gcagcgcgaa gctgaatcct ccaaccgggt tgtcgatccg 180
gacaggttgg ggtgcgtttg gggcaatgac aggtggcggc ggtgcgttcg ggtcggccgg 240
cggaagtgct gcgttgggat cgcccggctg ggcattcggc gtgttggcgg cggccggtgg 300

<210> SEQ ID NO 403
<211> LENGTH: 396
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 403
actcaagctt gagattggcg tcaacgggtg tcggcaccgg cgtcctgcag ttggtaggcc 60
tgcagtttgt gcatcaggcc gatgccgcgg ccctcgtggc cacgcatgta cancaccacg 120
ccgcgcccct cacgggcgac catcgccagc gcggcgtcca gctgaggccc gcaatcgcag 180
cggcgtgacc caaacacatc gccggtcaag cactccgaat gcacccggac cagcacgtcg 240
tcaccgtcgg cgttgggccc ggcgatctcg ccgcggacca gcgcgacatg ttccacgtcc 300
tcgtaaatgc tggtgtancc gatggcgcga aactccccat gacaantcgg aatcccgcgc 360
ctcggcgacc ccgctcaatg ttgcttctcn tgcttg 396

<210> SEQ ID NO 404
<211> LENGTH: 352
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 404
tcgacnagca ttcttgacng ttgttttggc tcggcatggt tagccaaggt tctgcggtcc 60
caccagatca tcttggtccg gtagcgctcg tccgggtatg ctgccgccgg gattctcgct 120
gctattactc cccccgaaga acgccaccgg tccagcgcgt gggccgccgc ggtccccatc 180
acaaactgaa cccccaacag gggacatgct tagcggtagg gcgcgcgcca aggcggcagc 240
aatcgcatca ctgcgctgcg cgtcactatt aacccacccg gacttcactt ccacgacccc 300
gaatggcgcc cggtcattga tcatcttgcg caccgcggat aatccgggat tg 352

<210> SEQ ID NO 405
<211> LENGTH: 420

-continued

<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 405
accggggcca ctccgcacaa tctgtacccg accaanatct acaccatcga atacgacggc 60
gtcgccgact ttccgcggta cccgctcaac tttgtgtcna ccctcaacgc cattgccggc 120
acctactacg tgcactccaa ctacttcatc ctgacgccgg aacaaattga cgcngcggtt 180
ccgctgacca atacggtcgg tcccacnatg acccantact acatcattcg cacgganaac 240
ctgccgctgc taaagccact gcgatcggtg ccgatcgtgg ggaacccact ggcgaacctg 300
gttcaaccaa acttgaaggt nattgttnac ctgggctacg gcganccggc ctntggttat 360
tccacctcnc cgcccaatgt ttgcnactcc cgttcggggt tgttcccnna aggtcaaccc 420

<210> SEQ ID NO 406
<211> LENGTH: 328
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 406
cgctcaagcg cntgaggccg aancggctgg ttacgactcc ctgtttgtga tggaccactt 60
ctaccaactg cccatgttgg ggacgcccga ccagccgatg ctggaggcct acacggccct 120
tggtgcgctg gccacggcga ccgagcggct gcaactgggc gcgttggtga ccggcaatac 180
ctaccgcagc ccgaccctgc tggcaaagat catcaccacg ctcgacgtgg ttagcgccgg 240
tcgagcgatc ctcggcattg gagccggttg gtttganctg gaacaccgcc agctcggctt 300
cgagttcggc actttcagtg accggttc 328

<210> SEQ ID NO 407
<211> LENGTH: 315
<212> TYPE: DNA
<213> ORGANISM: Mycobacterium tuberculosis

<400> SEQUENCE: 407
ctcaagcttg cgttcgatga agtagtcgtc ggtcagcgcc gcctcttcga gctccttggc 60
gatgcccagc aaggagtcat cgccgccgag cttggccagg atcttgtcgg cctgttcctt 120
gacgatgcgg gcccgcggat cgtagttctt gtagacacga tgaccgaaac ccatcaattt 180
gaccccggcc tcgcggttct tgaccttgcg tacaaactcg ctgacgtcgt cgccgctgtc 240
gcgaatgccc tcgagcatct ccaggacagc ctgattggcg ccgccatgaa gcggacccca 300
tagtgcgttg atgcc 315

<210> SEQ ID NO 408
<211> LENGTH: 329
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

-continued

<400> SEQUENCE: 408
ggtcaggccg agcaggcgcg aggaacgacg aacccaacaa gccatggtgg ttggcgccgt 60
cgagaggtcg gcggtcgcca caacgggaag atcgccttga gcgtcgctcg accgccgcct 120
cgagttgggt cataacgaag tagctgatgc cgatcatgtc gacgtttccg tcgcatcagc 180
gtgcagcggc gacccactcn acgaggtctc ggtgccgccg cggccagggc accagcagtg 240
acgagtccag gcgccgtcgg gccaagcagt cgcggtgcca nccgtggtgg gtcgggcgat 300
ggttgggtgt gctcatttcg ggaacgcca 329

<210> SEQ ID NO 409
<211> LENGTH: 294
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 409
ctcgaagctt taacagcatc aaccccgccc cgcaccagca ccgacacnat gtcgatgcca 60
tcgaggtgaa tgtcgaactg gcgcaaacca tcggcgaccg cgaccaccgg caacatgggt 120
accggcgatt tccggtgcca atgccgaccc gacgggccgc tctcaccgca ggtgacctcg 180
atcaccgaga ccanccggcc gttntnntca cgcaccccta ccgtgtcacg cccaaaacgg 240
cgctggtggt cgattgccgg agtgcacccc ncacccagtg tcgtgcccgg atcc 294

<210> SEQ ID NO 410
<211> LENGTH: 288
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 410
tgatgccgca cccgatcgac ggtcgttggt cggggttgac tggccgcccg gcgaagcagg 60
gcgtcgaccg cggcccggac gtcggcggcc gtcaccggtc ggccattgcc cgggcgggag 120
tcgtcgagct gaccacggta gacaagtcgg cgctggccgt cgaagacnaa cgtgtcgggt 180
gtgcaggccg cggagaaggc gcgggcgacn tcttgggttt cgtcgtanag atacgggaac 240
gtccagccgt ggcggcgggc ctcggcgacc atctgatcgg gcccgtcc 288

<210> SEQ ID NO 411
<211> LENGTH: 420
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 411
tttcgggcga ggcggtatan cttcccntcg taccggcgac cgccagccga naagctcgtt 60
ttcccagtgt tgctggggat tctcacgctg ctgctgantg cgtgccaaac cgcttccgct 120
tcgggttaca acgagccgcg gggctacnat cgtgcgacgc tgaagttggt gttctccatg 180

-continued gacttgggga tgtgcctgaa ccggttcacc tacnactcca agctggcgcc gtctcgtccg 240
caggtcgttg cttgcgatag ccgggaggcc cggatccgca atgacggatt ccntgccanc 300
gctccgagtt gcntgcggat cgactacnaa ttgatcaccc anaaccatcg ggcgtnttac 360
tgcctgaagt acctggtgcg ggtcggatac tgctatccgg cggtgacaac cccggcaagc 420

<210> SEQ ID NO 412
<211> LENGTH: 378
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 412
gttttggctc ggcatggtta gccaaggttc tgcggtccca ccagatcatc ttggtccggt 60
agcgctcgtc cgggtatgct gccgccggga ttctcgctgc tattactccc cccgaagaac 120
gccaccggtc cagcgcgtgg gccgccgcgg tccccatcac aaactgaacc cccaacaggg 180
acatgcttag cggtagggcg cgcgccaagg cggcagcaat cgcatcactg cgctgcgcgt 240
cactattaac ccacccggac ttcacttcca cgaccccgaa tggcgcccgg tcattgatca 300
tcttgcgcac cgcggataat ccgggattgc cagcccattc nactaccgca tgcgagtcat 360
cggctgaccg cagcggtc 378

<210> SEQ ID NO 413
<211> LENGTH: 347
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 413
tcgcctaggc gggcttcccc ttccgtccga gcngtcagaa gctcctatga caatgcacta 60
cccgagacna tcaacggcct atgcaatacc nagctgatca aacccggcaa gccctggcgg 120
tccatcgagg atgtcgagtt ggccaccgcg cgctgggtcg actggttcaa ccatcgccgc 180
ctctaccggt actgcggcga catcccgccg gtctaactcg acgccgcctc actacgctca 240
acgccagaga ccanccgccg gctgacgtct cagatcagag agtctccgga ctcaccgggg 300
cggttcatcc ccactgtcga tagcgtctgt ggataacttt gtctgca 347

<210> SEQ ID NO 414
<211> LENGTH: 165
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 414
gcgcgtngaa ctgataggtg cggcccggct cgagcangcc ggccatttgt tcgatgcggt 60
taccgaagat ctcttcggtg acctgcccgc cgccggccag ctcggcccag tgcccggcgt 120
tggccgccgc ggcgacaatc ttggcgtcca cggtggtctg ggtca 165

-continued

<210> SEQ ID NO 415
<211> LENGTH: 317
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 415
ctcaagcttc aatacagagt tataaactgt gataatcaac cctcatcaat gatgacnaac 60
taacccccga tatcaggtca catgacgaag ggaaagagaa ggaaatcaac tgtgacaaac 120
tgccctcaaa tttggcttcc ttaaaaatta cagttcaaaa agtatgagaa aatccatgca 180
ggctgaagga aacagcaata actgtgacaa attaccctca gtaggtcaga acaaatgtga 240
cgaaccaccc tcaaatctgt gacagataac cctcagacta tcctgtcgtc atggaagtga 300
tatcgcggaa ggaaaat 317

<210> SEQ ID NO 416
<211> LENGTH: 379
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 416
ctcaagcttc gatcgacatt actcccgcct tgggtctggt ctccgagctg gtcggtcatg 60
gtcggacctg ctggtagtgg ggatctaacg caacatggtc gggattcatc atggtgtacc 120
cgtgataccc attcgcagct gccggtgaaa ccccgcgatg ccgggatttc cagccgcact 180
aggatgtcta gccggccagc cgctgccgcc ggacttcggg atgttcggta taccancgat 240
cggcaatctt gcgtatccgc cgatgctcga acgctancca cgccaaacca accactgtga 300
cnacaatcgc caccacacca aaggtcatgc cctcggcgtg atgtccggtg ccgaaagccg 360
caagagctcc gacgccgcc 379

<210> SEQ ID NO 417
<211> LENGTH: 420
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 417
cattcccaat tgaatttccc natcccacaa tctcggttca gatacaggtc gccataccc 60 ttacttcggc aacgctgggc ggattggccc tgccgctgca gcanaccatc gacgccatcg 120
aattgccggc aatctcgttc agccaatcca tacccatcga cattccgccg atcgacatcc 180
cggcctccac tatcaacgga atttcgatgt cggaggtcgt gccgatcgat gtgtccgtcg 240
acattccggc ggtcaccatc accggcacca ggatcgaccc gattccgctg aacttcgacg 300
ttctcagcag cgccggaccc atcaacatct cgatcatcga cattccggcg ctgccgggct 360
ttggcaactc gaccgagctg ccgtcgtcgg gcttcttcaa caccggcggc ggtggcggct 420

-continued

<210> SEQ ID NO 418
<211> LENGTH: 255
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 418
ctcaagcttt cggcggagac ggacannttg cgaacattga tgacaaaata gaaatcattg 60
atggtttgag tcaccaggcc gatcaagcct tcgccgagcc aaattccaat caagaggccc 120
aagcccgtac caatcagccc ggcaacgagg gattccgtca ttatcagcca aaataactgc 180
tctcgggtta cacccaaaca gcgcaatatg gcgaaaaacg gtcgccgttg cacgacatta 240
aatgtcacgg tattg 255

<210> SEQ ID NO 419
<211> LENGTH: 359
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 419
agcttaactg ctccctaata cctggggctg tgcctgcggt gtatgcacgg catacggaca 60
tccntcccct gagacccncg gtctaatcag ccacgtgtcc accatcaggg gtcaaccccg 120
gccaagggcg acggcacccc aagttcgccg accgttaacc tattgctgtg agcttcattt 180
gctgcgagca aaacagttgg tcggccgtta ggaactgaat tgacactcaa ccgatttggt 240
gccnccgtag gtgtcctggc tgcgggtgcg ctggtgttgt ccgcgtgtgg taacgaccac 300
aatgtgaccg ggggaggtgc aaccactggc cacgcgtccg cgaatgtcta ttgcggggg 359

<210> SEQ ID NO 420
<211> LENGTH: 314
<212> TYPE: DNA
<213> ORGANISM: Mycobacterium tuberculosis

<400> SEQUENCE: 420
ctcaagcttg gggtggcgct gtcggtcggt gtgcttggcg gcgtcggtat caacaccgcc 60
cacgaaatgg ggcacaagaa ggattcgctg gagcggtggc tgtccaaaat caccctcgcc 120
cagacctgct acgggcactt ctacatcgag cacaaccgtg gccatcacgt ccgggtgtcc 180
acaccggagg acccggcgtc ggcgcggttc ggcgaaacgt tgtgggagtt cctgccccgc 240
agtgttatcg gcggcttgcg ctcggccgtt catttggagg cccaacggct gcgtcggctc 300
ggcgtcagcc ccct 314

<210> SEQ ID NO 421
<211> LENGTH: 280
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

-continued

<400> SEQUENCE: 421
gcaccaaggc cccacacgtc accctgtgac ctcctgcgcc gaccccgccc gaggtcctgg 60
ccgttaccac ctgaacgggc gagccgggag tctggtacgc atcgaacaaa gagcaaggtg 120
catgggcgga gttgttccgc cacttcgtcg atgacggggt cnatccattc gaggtccgtc 180
gccgcgtcgg tcgagtggcg gtcacactcc aggtactcga cctcacagac gagaggactc 240
gatcccatct aggtgtggac gaaacagatc ttctgtccga 280

<210> SEQ ID NO 422
<211> LENGTH: 230
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 422
tcgcctccgc atatgggtcg acgccaagcg ggtccggatt tctgggcttc atcgctcgcg 60
ccgtcgcgac aaacagcgcg gtcgaaccga cactcgttgt gatgtcccag ctatcacctt 120
cggtacgcac ccaatcgacc ctacncggct atctcagccg cgatctccag gctccgccga 180
gccaggtgca tcccggtccg gatcccacta acccggcacc attggcgtcn 230

<210> SEQ ID NO 423
<211> LENGTH: 272
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 423
gtcctcgagt gccgccgtcg ncacncccag cgcccgcgcg gccacttgga tgcgacccgt 60
ttcaagtccc ttcatcatct gcgaaaagcc ttgacccatg gctccgccca ggatcgccga 120
gaccggcacc cggaggttgt cgaacgacag ctcgcaggat tcgacgccct tgtaacccaa 180
cttcggcaag tcccgcgaca ccgtgagtcc cggcccgggt tcgacgagca cgatcgacat 240
gccttggtgc cgcggtgtgg cgttcgggtc gg 272

<210> SEQ ID NO 424
<211> LENGTH: 423
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 424
ggcataccaa tgtggacttc tgctcaccca cgatatccgt ggtctgatcc gctgctgcgg 60
cgggctgcna cctgcntctc ngcggcaccc gtnactacat ggcncgcgcc gcacgcatac 120
gtcgcggcgg gacccactcc nactggtcga cggtgctggc cgcgtgtccg cangtcccna 180
acccggccgc accgacgaaa ccggccgccg tccgttctgg accaacgctc atgtgccgtc 240
ggggtccatg ctcgacgcca tcgagaccgt aaccagcgtc ctcgagcggt tcgcctccgg 300

-continued

```
cttccgtgac atcttcgtgg ctgctcgcgc cgtgccgccg cgcggatggt cgaccacaac    360

gccaaccacc tcggcggtga catcaccgtc cgcgccactc gacctggcgc gcgatcgcgg    420

ccc                                                                  423
```

<210> SEQ ID NO 425
<211> LENGTH: 315
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 425

```
gtgagcagac ctacgccncc tggttgcgcc aactcggtac cgatcatggc gcgcngcctg     60

tcgtcaccga tacccagcga acaagacagc ccggtccgcg acaagatgac tttcccgatc    120

tcttcggcga cttccatggg gtcgtccgga gtcccgggcg ccaccgcgag gtaaccctcg    180

tctcagtccc atacgcgacc gggtatccac gtcgcgcaac aacgccacca cctccccaga    240

cgccncgttg tacgcggctg ggttccacng caataagtgg cctcanggca tcgtccggcg    300

gcggtccnca acgca                                                     315
```

<210> SEQ ID NO 426
<211> LENGTH: 335
<212> TYPE: DNA
<213> ORGANISM: Mycobacterium tuberculosis

<400> SEQUENCE: 426

```
ctcaagcttg aggttaactt tgaacggatc gagctggacg ttcgagacgg tgatcgggcc     60

gaacctgaat tgtccggtaa tgcccaacgc aaaaagcagg gtggtggccg gggcggtgaa    120

accggcgtcg gcggcaccgt cgaaatctat gtggattgcc ggaatgggga tgtccggcac    180

ggcgaaaccg tagttcgctt gtcccgtgag gcccaggtgg atggggggaa agatcctggt    240

gtccgggata ataatggggc cgatgccgcc ggttgaagtc cactggatcg ggaattccgg    300

aatcttgatc cgacgttcag gccgaacagg ccctc                               335
```

<210> SEQ ID NO 427
<211> LENGTH: 346
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 427

```
cggcgacgtc gcgatacgcc gagcagttgg gaatcgctct gcagcaaacc aatattctgc     60

gcgacgttcg agaggacttt ttgaatggac ggatctacct gccgcgcgac gagctggacc    120

gattaggcgt acgcctccgc ctggacgaca ccggggcact cgatgacccc gacggacggc    180

tcgcggcnct gctgcggttc agtgccgacc gcgccgcaga ctggtnttcg ctgggactgc    240

ggctgattcc acacctcgac cgccgcagcg ctgcctgctg tgcggccatg tctggcatct    300

accgccgtca gctcgccttg atcagagcat cgccggcggt cgtcta                   346
```

<210> SEQ ID NO 428

-continued

<211> LENGTH: 332
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 428

```
ctataaaata ctcaagcttg atgccgccga aaccgagcgt gagcacgccg ccagccacca     60

cgcgcgggtc gggcgccggg cccgggccgc caggctgctc cgctcggtga tggcacgcca    120

ccgcgacacc acccggntgc gctacgtcna gccataccgg gcggagctac atcggctcgg    180

ccgcccagtg ttcgggccct ctttcgaggt cnaggtcnat accgatttgc gcatccgcag    240

ccgcaccctg aacnacanaa ccgtgcccta ctattgcttg tcnggcgggg ccaaaaaaca    300

gcttggcatc ctggcccnat tggccggcgc gg                                  332
```

<210> SEQ ID NO 429
<211> LENGTH: 276
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 429

```
cttcggtcgc agtgtgcgag tgatagatga cgaccgggac ctcgtcggca tcttccatag     60

cccgccacac cttcagttgc tcaccggaat ccaaccggta gaaggtcggc gagcgctcgg    120

cattggtcat cgggatatgc cgctcgggac ggtcagagcc ctcgggtccg gccagcactc    180

cgcaggcttc gtcggggtgg tcgcgacgcg catgggccac catcgcattc accaggtctg    240

cgcgaatcnc cancacgtan acngttcctt tcctaa                              276
```

<210> SEQ ID NO 430
<211> LENGTH: 420
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 430

```
ctggcaccaa ggccccacac gtcaccctgt gacctcctgc gccgaccccg cccgaggtcc     60

tggccgttac caccgaacgg gcgagccggg agtctggtnc gcatcgaaca aanagcaagg    120

tgcatgggcg gagttgttcc gccacttcgt cgatgacggg gtcnatccat tcgaggtccg    180

tcgccgcgtc ggtcnagtgg cggtcacact ccaggtactc gacctcacag acnaaaggac    240

tcnatcccat ctaggtgtgg acnaaacaga tcttctgtcc gacnactaca ccaccaccca    300

ggccatcgcc gccgcccgcg atgccaactt cgacgccgta ctggccccgg cggggggcgc    360

tccccggttg tcaacacttg ccgtgttcnt tcacgcnctg ccccacatcc aaccccaacg    420
```

<210> SEQ ID NO 431
<211> LENGTH: 130
<212> TYPE: DNA
<213> ORGANISM: Mycobacterium tuberculosis -continued

<400> SEQUENCE: 431
gttcttgggc ccatgcggag gtatcgccgt ttccaccacg cggtcggggt ggcgttgcat 60
tagctcaccg atggtgcgct tgtgcaggcc gccgggatac cccgagtgcc ggtaaaccat 120
cttgtgctgc 130

<210> SEQ ID NO 432
<211> LENGTH: 215
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 432
caatactcaa gcttggcgtg ccgttccaac ccgaattggc tttcggcgcc atcggtgagg 60
acggcgtgcg ggtgctcaac nacnacgtcg tccgcgggac acacctcgat gctgccgcca 120
tggacgcggt cgaacgcaag cagctgatcg agctacaacg ccgcgcggaa cgcttccgcc 180
gcgggcgtga ccgcatcccg ttgaccgggc ggatc 215

<210> SEQ ID NO 433
<211> LENGTH: 360
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 433
cntcatgatg atcatcaccc gaagtgtggt agccgcagtg gttatcgtgg gtaccgtcgt 60
gctttccatg ggcgcctctt tcgggctttc cgtattggtc tggcaggaca ttctgggtat 120
cgagttgtac tggatggtgt tggcgatgtc ggtgatcctg ctcctggcgg tgggatccga 180
ctacaatctg ctgctgattt cccggttgaa agaggaaatt ggggccggat tgaacaccgg 240
aattatccgt gccatggctg gtaccggggg agtggtgacg gctgccggca tggtgttcgc 300
cgttaccatg tcgttgtttg tgttcagcga tttgcgaatt attggtcaga tcggtaccac 360

<210> SEQ ID NO 434
<211> LENGTH: 265
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 434
atactcaagc ttttacggtg atcgcncatc acctggttca tgaactggaa gcagcgcagc 60
gcttcctttt cggccgcaac atgagccagc ctctcgtcgg cggtcgggtg caggtgctcg 120
ggcagctcgg ccgcnacagc cgcctgaccc tgaaaccagc ttccatatcc cgcgannaac 180
gacgccagtc cgctacgtna cccctccgcg actgtccatg gacaacagcg cgttctccac 240
cgaccgggcc cgggtgtggg gtntt 265

<210> SEQ ID NO 435

-continued

<211> LENGTH: 264
<212> TYPE: DNA
<213> ORGANISM: Mycobacterium tuberculosis

<400> SEQUENCE: 435
gctggtagag tcgctgaccg gtgcaggttt cgacaatgtg gtgccggttc ggcggctacg 60
tgccatcgag acactggcgc aggctatcgc acccgttatc ggctacgagc aaatcgcggt 120
atgcgttctt gagcatgagt cggcgaccgt cgtcatggtc gacacccacg acggaaagac 180
gcagatcgcc gtcaagcatg tgtgccgcgg attatcagga ctgacctcct ggctgaccgg 240
catgtttggt cgcgatgcct ggcg 264

<210> SEQ ID NO 436
<211> LENGTH: 335
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 436
gctttccgcc gatacccgcc atgtcncgca catccaggac ttctgggggg atccgctgac 60
agcggcggga tcccaaagtg cggatgatcg ggccgcctac gtcgtggtgt acctcgtcgg 120
taacaacgaa accgaagcgt atgactcggt ccacgcggtg cggcacatgg tggacaccac 180
accgccaccg cacggggtga aggcctatgt caccggtccg gcancactca atgccgacca 240
ggccgaggcc gganacaaaa ntatcgctaa ggtcaccgcg atcacnagca tggtgatcgc 300
agcaatgttg ctagtgatct atcgctccgt aatta 335

<210> SEQ ID NO 437
<211> LENGTH: 304
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 437
cttccaaccc gaattggctt tcggcgccat cggtgaggac ggcgtgcggg tgctcaacga 60
cgacgtcgtc cgcgggacac acctcgatgc tgccgccatg gacgcggtcg aacgcaagca 120
gctgatcgag ctacaacgcc gcgcggaacg cttccgccgc gggcgtgacc gcatcccgtt 180
gaccgggcgg atcgcggtga tcgtcgatga cggcatcgcc accggagcga cggccaaggc 240
ggcgtgccan gtcgcccggg cgcacggtgc ggacaaggtg gtgctggcgg tcccgatcgg 300
ccca 304

<210> SEQ ID NO 438
<211> LENGTH: 223
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 438

-continued

```
tactcaagct tcgcgagatc cggatggcac tcacgctgga caagaccttc acaaaatctg     60

aaatcctgac ccgatacttg aacctggtct cgttcggcaa taactcgttc ggcgtgcagg    120

acgcggcgca aacgtncttc ggcatcaacg cgtccganct gaattggcag caagcggcgc    180

tgctggccgg catggtgcaa tcnaccagca cgctcaaccc gta                      223


<210> SEQ ID NO 439
<211> LENGTH: 263
<212> TYPE: DNA
<213> ORGANISM: Mycobacterium tuberculosis

<400> SEQUENCE: 439

cccacgactt tctcctcgat cagttggatt tgtacgaaga ggcaacgaaa gcagtgatcc     60

tcgggatggt cgacgcctac atcgacccgc cgttcacgcc gcacagcctg ctagatgcgc    120

tgggcgagca ggtcccacag ttcgccgcta aggcacggcg tctgttcccg tccggatcgc    180

cattcggcct cggcgtcctg ctcccattcg atcaataggg ctggcagctc cgtcggcagg    240

ggcctacgcc tcaccccgtc acg                                            263


<210> SEQ ID NO 440
<211> LENGTH: 301
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as “n”

<400> SEQUENCE: 440

ctcaagctta tgcgcgccgg ccgaggtctg ctcacggcaa cccctgaagt ttaggggacn     60

acctactcag cgcaaaattt cgctaatgtg agtccgcccc accaggggna natcaaccca    120

tgtcgatcat gatctacccg gataccggat tggcggtagc gcccacgatc gtcnaaatnt    180

ccgcctgaat catcggatag ctgatccggc gtcaacgcgt tttganttca ccgcgcaaca    240

gccgccaggc cggcccgcan cganccgatc tcntcgggcc gcatgggccc caatcttntc    300

g                                                                    301


<210> SEQ ID NO 441
<211> LENGTH: 90
<212> TYPE: DNA
<213> ORGANISM: Mycobacterium tuberculosis

<400> SEQUENCE: 441

gtgtgtggtg gaacccatct gagcagtgtg ccaaaccggg gcagacagct cccaattgac     60

gtgagcccgc tcacttgctg ggtaagcgtc                                      90


<210> SEQ ID NO 442
<211> LENGTH: 183
<212> TYPE: DNA
<213> ORGANISM: Mycobacterium tuberculosis

<400> SEQUENCE: 442

ctttacactt cctgcatccg gctcgtatgt tgtgtggaat tgtgagcgga taacaatttc     60

acacaggaaa cagctatgac catgattacg ccaagctatt taggtgacac tatagaatac    120

tcaagcttgg gcgtgacggc caccggggcc actccgcacc atctgtaccc gaccaagatc    180

tac                                                                  183
```

-continued

<210> SEQ ID NO 443
<211> LENGTH: 348
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 443
caggcatgca agctttagct gcccgaatgc gtcaccccga tgcgcccaga tcggggcttc 60
gcagataaag cacgaacagg cgggcaaaac gtcnatctcg gagccggaag ggcaatcagc 120
cgaccgtcga cgaacgacac cggcgagacc acttaggcag tgacggccgg cccgaacatt 180
acgcgctcgt tgattaggcg ttcggtctcg tccgcggtca tgccgagcag cttgcggcag 240
atctgaacgc tgtcctgtcc gggcagcggc gccgggcgtt ggggtgcctg cccgaatgtg 300
acgaaacgga gccggacccg tctcggcggg ccgcggacgg cgatccgc 348

<210> SEQ ID NO 444
<211> LENGTH: 335
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 444
cncaagcttg cggatgttac ccctgacagc ctgaactatg tcnaaacaca cggcaccgga 60
acggtgttgg gggaccccat cganttcgag tcgctggcgg ccacttatgg cctgggtaaa 120
ggccagggcn anagcccgtg cgcattgggg tcggtcaaaa ccaacatcgg ccacctggag 180
gcggccgccg gtgtggctgg atncatcaag gcggtgctgg cggtgcaacg tgggcacatt 240
ccccgcaact tgcacttcac ccggtggaac ccggccatcn acgcgtcggc nacgcggctg 300
ttcgtgccna ccnaaaaccc cccgtggccg gcggc 335

<210> SEQ ID NO 445
<211> LENGTH: 289
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 445
ggaaccggta accagatcag ctcgtcgacc tcactgccgg gggtgaattc cccaccggtg 60
ctgcgcgctg cccagtagtg caccttcttg acgcctcgaa aaggggagtc ggtcgggtag 120
gtcaccgtca ggagccgcct acccaggttg gcgcnatagc cggtctcctc gagtatctcc 180
cgcaccgccc ccaccggtgc ggtctcaccc anatccactt tgcccttggg cagcgaccag 240
tcgtcgtanc nggggcggtg aatgacaacg atctcgaccg gcccttccn 289

<210> SEQ ID NO 446
<211> LENGTH: 263
<212> TYPE: DNA
<213> ORGANISM: Mycobacterium tuberculosis
<220> FEATURE:

-continued

<221> NAME/KEY: unsure
<222> LOCATION: (various positions within the sequence)
<223> OTHER INFORMATION: applicants are uncertain of bases designated as "n"

<400> SEQUENCE: 446

```
tactcaagct tcagaacagg cctgttgtgg gcncacccgg ctcgccgagt tctgcacgca     60

ccgcctcaag tgcggcccgc accgccggca tctcccggtc acgcagggcc gcggcccgcg    120

ccgcagcgac ggcgtgttcg cgcagttcgc cgtcaatgat gctgacctga tcggccaccc    180

gggcgttctc ggcgtcgtcg cgttcactaa tcgcggtgct cagcagcgtc tcgacagcca    240

ccacccgagt ggcgaccagc tgc                                            263
```

<210> SEQ ID NO 447
<211> LENGTH: 279
<212> TYPE: DNA
<213> ORGANISM: Mycobacterium tuberculosis

<400> SEQUENCE: 447

```
taatgtcttg ccaacgtcac cacaatcgcg atgaattcaa tcatgccgcc cagggcggcc     60

aacccaatgg tggccgcgag cggcagctcg atcgcagcgc ggaggttgcc ggccgccagt    120

tgattcacga acagggtgag gtcataggcg ggcaggatag tgacgaaggc aagacctata    180

tctgccgtcg gaagaagaat cgagtagccg gtcgacacaa cggaagcgaa agtgtccgcg    240

atgttgatga gcgtcgccgg ttgtggcggc ggtggcggc                           279
```

<210> SEQ ID NO 448
<211> LENGTH: 295
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 448

```
tactcaagct ttcgtcagtt catcgcgcca gcagaccaac aagagcatcg ggacatacgg     60

agtcaactac ccggccaacg gtgatttctt ggccgccgct gacggcgcga acgacgccag    120

cgaccacatt cagcanatgg ccagcgcgtg ccgggccacg aggttggtgc tcggcggcta    180

ctcccagggt gcggccgtga tcgacatcgt caccgccgca ccactgcccg gcctcgggtt    240

cacgcagccg ttgccgcccg cagcgganna tcacatcgcc gcgatcgccc tgttc         295
```

<210> SEQ ID NO 449
<211> LENGTH: 280
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 449

```
ccacccgtgt aatttgggat gggcnaaaag gcnaagcacc gcgtggccac gaacgccggg     60

agggacaatc tcgggcggct agggcttctc gcgggaaggc ccgaacgtac ggcgtttcaa    120

cacgtcgcgt cgccctccga ccgcgaacat tcggggatgg cagcaacctg gtagcaccct    180

ggccgggcga tgatctgcag cgtcgccgcg ggtagtcgcc gcccgggcgg ctacagtctg    240
```

-continued

```
aaacgcgatg accatcgatg tgtggatgca gcatccgacg                        280


<210> SEQ ID NO 450
<211> LENGTH: 320
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 450

tcaagcttta gctgcccgaa tccgtcancc cgatgcnccc agatcggggc ttcgcanata     60

aagcacnaac aggcgggcaa aacgtcnatc tcggagccgg aagggcaatc anccgaccgt    120

cnacaaacga caccggcgan accacttagg cagtgacggc cggcccgaac attacncgct    180

cgttgattag gcgttcggtc tcgtccgcgg tcatgccgag cagcttgcgg canatctgaa    240

cgctgtcctg tccgggcagc ggcgccgggc gttggggtgc ctgcggaatg tgacnaaacg    300

gagccggacc cntctcggcg                                                320


<210> SEQ ID NO 451
<211> LENGTH: 203
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 451

ccggggccac tccgcacaat cngtaccnna ccaanatcta caccatcgaa tacgacggcg     60

tcgccgantt tccgcggtac ccgctcaact ttgtgtcgac cctcaacgcc attgccggca    120

cctactacgt gcactccaac tacttcatcc tgacgccgga acaaatngac gcntcggttc    180

cgctgaccaa tacggtcggt ccc                                            203


<210> SEQ ID NO 452
<211> LENGTH: 287
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 452

nctggccttt ggtccacact aanacaatac tcaagcttcc ggccgcagag ccgccaactc     60

acgatatcgt taaccgatat cccgagccga tagctggcgg gctcgggtgg tggccagcgg    120

cgctgcgacn aaaggtgtga ccgtcatgaa acagacacca ccggcggccg tcggccgtcg    180

tcacctgctc ganatctcag catccgcagc cggtgtgatc gcgctttcgg cgtgtngtgg    240

gtcnccgccc gagcccggca aaggccggcc cgacacaacc ccggaac                  287


<210> SEQ ID NO 453
<211> LENGTH: 272
<212> TYPE: DNA
<213> ORGANISM: Mycobacterium tuberculosis

<400> SEQUENCE: 453
```

-continued

```
catctgccca ccacacggac cgcggtgcgg acgcggctga cgcgcctggt ggtcagcatc     60

gtggccggtc tgctgttgta tgccagcttc ccgccgcgca actgctggtg ggcggcggtg    120

gttgcgctcg cattgctggc ctgggtgctg acccaccgcg cgacgacacc ggtgggtggg    180

ctgggctacg gcctgctatt cggcctggtg ttctacgtct cgttgttgcc gtggatcggc    240

gagctggtgg gccccgggcc ctggttggca ct                                   272
```

<210> SEQ ID NO 454
<211> LENGTH: 364
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 454

```
gacaatactc aagcttgact ggccacccac cggcatgacc accgacaggc ccgactggtc     60

gtaccactcg aacgccgggg tgttgatgtc ccagccgctg aantcgtcct gcgcgcgcag    120

gccgtcnaac aggtacaggg cgggcgaatt ggcaccacca ctttggaatt ggaccttgat    180

gtcacggccc atcgacggcg acggcacctg caggtactcc accggcaagc ccggccggga    240

aaatgccccc gcggtcnccg tgccaccgac ggcgccganc aaacccgaca ctagggccgc    300

gccnacggcc ccgaccacna ntcnacgcga catacccgtg acggcgccac naaccctgtc    360

aaca                                                                  364
```

<210> SEQ ID NO 455
<211> LENGTH: 360
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 455

```
cctccaactc ggcggggaag cgacnccagc ctaccgagct tggagtccan gacgccagcg     60

gcggcgtcgg tctgcgtcgt ggtgccgccg gggtggcgtt ggctggcaac gatctccacc    120

cagccggtcg ggttacccac gatctcggca tanacgcggg ccgaggccgg tgcgataccg    180

tattgcgtca attgggacgc ggttgtgcat tcggctagct cggttgccac acccgtcagg    240

ggttcgacgt tggcgggttc ggcgggcccc ancaccgctg tcaccatgcc cgccaagccg    300

acctgcggcg ccaccaactg cagcaccanc atgtcgccgt cgcgcgccgc gatcacatgg    360
```

<210> SEQ ID NO 456
<211> LENGTH: 311
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 456

```
ctcaagcttt ttgagcgtcg cgcggggcan cttcgccggc aattctacta ncgagaantc     60

tggcccgata cggatctgac cgaantcgct gcggtgcanc ccaccctcat tggcgatggc    120
```

-continued

```
gccgacnatg gcgcctggac cgatcttgtg ccgcttgccg acggcgacgc ggtaggtggt    180

caagtccggt ctacgcttgg gcctttgcgg acggtcccga cgctggtcgc ggttgcgccg    240

cnaaagcggc gggtcgggtg ccatcaggaa tgcctcnccg ccgcggcact gcacggccag    300

tgccgcggcg a                                                         311


<210> SEQ ID NO 457
<211> LENGTH: 288
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 457

cnccagcttg attggtctgg ttgcattggc cagctgcgcg agcctggctc acttcaacta     60

cgacgaccgc aaacaattgc cgccttcgga tccgagttcg gttgggtacg cggcaatgga    120

gcaccatttc tcggtgaatc agactattcc tgagtacttg atcatccact ctgcacacga    180

cctgcgaacc ccgcgcggcc ttgccgacct ggagcagctg gcgcaacgtg tgagccagat    240

cccaggcgtt gccatggttc gcggtgtgac ccggccaaac ggggaaac                 288


<210> SEQ ID NO 458
<211> LENGTH: 256
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 458

caatactcaa gcttgactgg gcccgcacct tcggcgccac ccacaccgtc aacgcccgcg     60

aagtcnacgt cgtccaggcc atcggcggcc tcacggatgg attcggcgcg gacgtggtga    120

tcgacgccgt cggccgaccg gaaacctacc agcaggcctt ctacgcccgc gatctcgccg    180

gaaccgttgt gctggtgggt gttccnacgc ccgacatgcg cctggacatg ccgctggtcn    240

acttcttctc tcacgg                                                    256


<210> SEQ ID NO 459
<211> LENGTH: 327
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 459

tcgacggttt ggcggcctta aatgcactga ggtcgtcaat tgaccccaca gcggaaatgc     60

cgactattcg caggcctcct tcgccttggc tgccggagag gggctccgcg ggaaccgcat    120

gcaggtatat gacctcggtt tctcgggtgc taccgcgtgc cttgtntang atnanctcgg    180

cgttggaatt gtccagccgg cccaattcat cgagcgcana ttcgtacacn tggccggcgg    240

cgacatacgc ttcaccgtgg atctgctcca cacggaccgc cctgtcggga tcctgctcac    300

gggtaangga acttacgtgg cactcgg                                        327
```

-continued

<210> SEQ ID NO 460
<211> LENGTH: 100
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 460
gaccacgcca ggctaatcac gtgacgctac cgaataccct ncctagtggt gcaggctccc 60
gctggaaatg gccctgtacc aactcgcgca ccggtgccag 100

<210> SEQ ID NO 461
<211> LENGTH: 114
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 461
cggcacccga cccctttgag ccgtccgccg tggccgcggt ggaactggcc gacgagggac 60
tgatcgtgct gggcaaattg gtcgatggca cgctggccgc cgatctgaag gtcn 114

<210> SEQ ID NO 462
<211> LENGTH: 287
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 462
ctcaagcttg ccgttacccc gacttccgga gggacaccat gagcaccgcc agccgagcac 60
gaggccaaac tccgccgacg caggccggtt ggacttgtcg tgctggacaa ggggtttagc 120
cgccgaagca gtgacgtaca tcggcgaaaa gcagttcgcc tgtcgaccga cggngcnnac 180
cgtgaggcta gggaagcgag gagcacatgg ccgccgaccc gcaatgtaca cgctgcaagc 240
aaaccatcga acccggatgg ctatncntca ccgcccatcg ccgcggt 287

<210> SEQ ID NO 463
<211> LENGTH: 288
<212> TYPE: DNA
<213> ORGANISM: Mycobacterium tuberculosis

<400> SEQUENCE: 463
catgtcgcgc acatccagga cttctggggg gatccgctga cagcggcggg atcccaaagt 60
gcggatgatc gggccgccta cgtcgtggtg tacctcgtcg gtaacaacga aaccgaagcg 120
tatgactcgg tccacgcggt gcggcacatg gtggacacca caccgccacc gcacggggtg 180
aaggcctatg tcaccggtcc ggcagcactc aatgccgacc aggccgaggc cggagacaaa 240
agtatcgcta aggtcaccgc gatcacgagc atggtgatcg cagcaatg 288

<210> SEQ ID NO 464
<211> LENGTH: 255
<212> TYPE: DNA

-continued

<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 464
atactcaagc ttcggtacgg tggcgggccg tgctgctggc cgcggtcgcg gcgtgcgcgg 60
cctgcggtct cgtttacnag ctcgcgctgc tgacactggc ggcnagcctg aacggcggcg 120
ggatcgtggc cacctccctg atcgtcgcgg gctacatagc cgcgctggga gcaggcgcct 180
tgctgatcaa gccgctactt gcacacgcgg ccatcgcgtt catcgccgtg gaggcggtgc 240
tgggcatcat cggcg 255

<210> SEQ ID NO 465
<211> LENGTH: 288
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 465
tgtcaagtcc tttcagatct cntttttatg acatgactgg agatctgtct agattgcagc 60
tcctgtgagc gtgggtaccg gattcaagcc ggtcggtcac gccgcggtgg taccggcttt 120
gcggcagtgc tcggcctcga gttcggcgat cgcgcgcgaa gtgcgttcgc gcagcaagat 180
cgcggccgta atgccggcga tgaccgcgat gaccagcgcg atccaggaga accgttccaa 240
ccagtgctgg gcggccatcc cggcgaagta gaccagtgca gtggtgcc 288

<210> SEQ ID NO 466
<211> LENGTH: 224
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 466
caatactcaa gcttcaaaac aggcctgttg tgggcgcacc cggctcgccg agttctgcac 60
gcaccgcctc aantgcggcc cgcaccgccg gcatctcccg gtcacgcagg gccgcggccc 120
gcgccgcanc gacggngtgt tcgcgcagtt cgccgtcaat gatgctgacc tgatcggcca 180
cccgggcgtt ctcggcgtcg tcncgttcac taatcgcggt gctc 224

<210> SEQ ID NO 467
<211> LENGTH: 320
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 467
tacgctggcg ctggagggag ccanntacaa catccacgcc aatgctcttg ccccgatcgc 60
ggcgaccagg atgacccagg acatcctgcc gcccgaagta ctggaaaagc tcacacccga 120

-continued

```
gttcgtcgca ccggtggtgg cctacctgtg caccgaggag tgtgccgaca acgcatcggt    180

gtacgtcgtc ggtggtggca aggtgcagcg agttgcgctg tttggcaacg acggcgccaa    240

cttcgacaaa ccgccgtcgg tacaagatgt tgcggcgcgg tgggccgaga tcaccgatct    300

gtccggtgcg aaaattgctg                                                320


<210> SEQ ID NO 468
<211> LENGTH: 303
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 468

gcttttcccg tccgtcnncg ctcaaccgcg tgaggccgaa gcggntggtt acgactccct     60

gtttgtgatg gaccacttct accaactgcc catgttgggg acncccgacc agccgatgct    120

ggaggcctac acggcccttg gtgcgctggc cacggcgacc gancggctgc nnntgggcgc    180

gttggtgacc ggcaatacct accgcagccc gaccctgctg gcaaanatca tcaccacgct    240

cgacgtggtt agcgccggtc gagcgatcct cggcattgga gccggttggt ttganctgga    300

aca                                                                  303


<210> SEQ ID NO 469
<211> LENGTH: 391
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 469

cngcttttta atggccttga cntgggcgng ccggccaccg gggccactcc gcacaatctg     60

tacccgacca agatctacac catcgaatac gacggcgtcg ccgactttcc gcggtacccg    120

ctcaactttg tgtcgaccct caacgccatt gccggcacct actacgtgca ctccaactac    180

ttcatcctga cgccggaaca aattgacgca gcggttccgc tgaccaatac ggtcggtccc    240

acgatgaccc agtactacat cattcgcacg gagaacctgc cgctgctaga gccactgcga    300

tcggtgccga tcgtggggaa cccactggcg aacctggttc aaccaaactt gaaggtgatt    360

gttaacctgg gctacggcga cccggcctat g                                   391


<210> SEQ ID NO 470
<211> LENGTH: 343
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 470

ctcaagcttg ccgggagggt gcatggccga ctcggattta cccaccangg ggcgccaacg     60

cggtgtccgc gccgtcnagc tgaacgttgc tgcccgcctg gagaacctgg cgctgctgcg    120

caccctggtc ggcgccatcg gcaccttcga ggacctggat ttcgacgccg tggccgacct    180
```

-continued gaggttggcg gtggacgagg tgtgcacccg gttgattcgc tcggccttgc cggatgccac 240
cctgcgcctg gtggtcgatc cgcgaaaana cgaanttgtg gtggaggctt ctgctgcctg 300
cgacacccac nacgtggtgg caccgggcag ctttagctgg cat 343

<210> SEQ ID NO 471
<211> LENGTH: 303
<212> TYPE: DNA
<213> ORGANISM: Mycobacterium tuberculosis

<400> SEQUENCE: 471
ccgacgccgt cgtggccacc aacaccgcga ccagcaccgt gacccggacc ggggtgccgc 60
gcgaaccggt cttggccaat tgccgcggca ccaagccgtc gcgcgccatg gcgaacagca 120
cgcggcattg cccgagcatc aacaccatca ccaccgtggt aagcccggcc agcgcgccga 180
cggagatgat gccgctggcc cagtacaccc cgttggcctg gaacgcggtg gccagatttg 240
ccggcccgcg gcccggtacg gtccgcagtt gggtgtatgg aaccatgccc gacagcacca 300
ccg 303

<210> SEQ ID NO 472
<211> LENGTH: 264
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 472
ttnactggcc tttggtccac actagacaat actcaagctt ccaggacatc gtcatcgcga 60
ccaaaaccgc gagctaggtc ggcatccggg aagcatcgcg acaccgtggc gccgagcgcc 120
gctgccggca ggccgattag gcgggcaaat tagcccgccg cggctcccgg ctccgantac 180
ggcgccccga atggcgtcac cggctggtaa ccacgcttgc gcgcctgggc ggcggcctgc 240
cggatcaggt ggtaaatgcc gaca 264

<210> SEQ ID NO 473
<211> LENGTH: 280
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 473
ngacgtcttc catccgcgcg tcgttttggc gggttggcca cagcagcccg ccggtgacgg 60
cgacgatgct gggctggttg cggccctgcg ccaccgcggc ttgcatgctg gttggctgtc 120
ttgggacgat cccgaaatag tccacgcgga tctggtgatt ttgcgggcta cccgcgatta 180
ccccgcgcgg ctcgacgagt ttttggcctg gactacccgc gtggccaatc tgctgaactc 240
gcggccggtg gtggcctgga atgtcgagcg ccgttaccta 280

<210> SEQ ID NO 474
<211> LENGTH: 153
<212> TYPE: DNA
<213> ORGANISM: Mycobacterium tuberculosis
<220> FEATURE:

<221> NAME/KEY: unsure
<222> LOCATION: (various positions within the sequence)
<223> OTHER INFORMATION: applicants are uncertain of bases designated
      as "n"

<400> SEQUENCE: 474
cttcctcctg agtaccnccc gtntactttg ggatgggtaa aaaggcgaat cnccgtttgg    60
tcacgaacgc cgggagggac aatctcgggc ggctggggcc tctcgcggga angcccgaat  120
gtacggtgtc tcgacacttc ccntccccct ccg                               153

<210> SEQ ID NO 475
<211> LENGTH: 247
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 475
gagcatcggg acntacggag tcaactaccc ggccaacggt gatttcttgg ccgccgctga   60
cggcgcgaac gacgccngcg accacattca gcagatggcc agcgcgtgcc gggccacgag  120
gttggtgctc ggcggctact cccagggtgc ggccntgatc nacatcgtca ccgccgcacc  180
actgcccggc ctcgggttca cgcagccgtt gccgcccnca gcggacgatc acntcgccgc  240
gatcgcc                                                             247

<210> SEQ ID NO 476
<211> LENGTH: 264
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 476
tactcatgan catcctttaa tcanngcttt gcgttttttt attaaatctt gcaatttact   60
gcaaagcaac aacaaaatcg caaagtcatc aaaaaaccgc aaagttgttt aaaataagag  120
cancactaca aaaggagata agaagagcac atacctcagt cacttattat cactagcgct  180
cgccgcagcc gtgtaaccga gcatagcgag cgaactggcg aggaagcaaa gaagaactgt  240
tctgtcagat agctcttacg cnca                                          264

<210> SEQ ID NO 477
<211> LENGTH: 264
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 477
ctcaagcttc aggtcaatgt gcnccaagcc ctgacgctgg ccgaccaggc caccgccgcc   60
gganacnctg ccaaggccac cgaatacaac aacgccgccg aggcgttcgc ancccagctg  120
gtgaccgccg agcanancgt caaaaacctc aagacgctgc atgaccaggc gcttancncc  180
gcanctcagg ccaagaaggc cgtcnaacga aatgcgatgg tgctgcacca naagatcgcc  240

-continued gagcgaacca agctgctcag ccng 264

<210> SEQ ID NO 478
<211> LENGTH: 352
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 478
catggtggca ctgtagcgac gtgctgcaat caaggtcatg cccgactctg gtcagctcgg 60
anccgctgac accccgctaa ggctgctcag ctcggtgcat tacctcaccg acggcgaact 120
cccccagctt tacgactatc cggatgacgg cacctggttg cgggcgaact tcatcatcag 180
cttggacggc ggcgctaccg tcgatggcac cagcggggcg atggccgggc ccggcgaccg 240
attcgtcttc aacctgttgc gtgaacttgc cgacgtcatc gtggtcggcg tgggcaccgt 300
gcgcattgag ggctactccg gcgtccggat gggtgtcgtc cagcgccagc ac 352

<210> SEQ ID NO 479
<211> LENGTH: 207
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 479
tactcaagct tgcgggtgat cgccttggtc aacggcaccg tgatcggatc ggggtcnacc 60
gcacaaatgg actggagctt cggcgaantc atcgcctatg cctcgcgggg ggtgacgctg 120
accccgggtg acntgttcgg ctcgggcacg gtgcccacct gcacgctcgt ctatcacctc 180
nggccaccgg aatcattccc gggctgg 207

<210> SEQ ID NO 480
<211> LENGTH: 256
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 480
gttggngcct cgtcggcgaa cagttctcgc acgatttccg gattagcggg actggtcacc 60
agttgggtat gcgggaaggc gctgacgttc gccgcgatta gctgtttgat ggacgcggtg 120
gtgatgttct gatcacggaa ctggctgtaa tagcccaggg tcgccacgct ttcatccggg 180
cccggacccg gcgcaccgag cgtgtcgcgc aggtatgcga cgtgattttc gctgaagtcc 240
ccgtacccgg agaact 256

<210> SEQ ID NO 481
<211> LENGTH: 397
<212> TYPE: DNA
<213> ORGANISM: Mycobacterium tuberculosis
<220> FEATURE:
<221> NAME/KEY: unsure -continued
<222> LOCATION: (various positions within the sequence)
<223> OTHER INFORMATION: applicants are uncertain of bases designated as “n”

<400> SEQUENCE: 481

```
tgcttccggc tcgtatgttg tgtggaattg tgancggata acaatttcac acaggaaaca     60
gctatgacca tgattacgcc aagctattta ggtgacacta tagaatactc aagctccagg    120
tcaatgtgcg ccaagccctg acgctggccg accaggccac cgccgccgga gacgctgcct    180
ttgtcaccga atacaacaac gccgccgagg cgttcgcagc ccagctggtg accgccgagc    240
agagcgtcga agacctcaag acgctgcatg accaggcgct tagcgccgca gctcaggcca    300
agaatgccgt cgaacgaaat gcgatggtgc tgcggcataa gatcgccgag cgaaccaagc    360
tgctcagcca gctcgagcag gcgaagatgc acgagca                              397
```

<210> SEQ ID NO 482
<211> LENGTH: 379
<212> TYPE: DNA
<213> ORGANISM: Mycobacterium tuberculosis

<400> SEQUENCE: 482

```
caggcatgca agcttcggag gcagacccgt gcatggtggc actgtagcga cgtgctgcaa     60
tcaaggtcat gcccgactct ggtcagctcg gagccgctga caccccgcta aggctgctca    120
gctcggtgca ttacctcacc gacggcgaac tcccccagct ttacgactat ccggatgacg    180
gcacctggtt gcgggcgaac ttcatcagca gcttggacgg cggcgctacc gtcgatggca    240
ccagcggggc gatggccggg cccggcgacc gattcgtctt caacctgttg cgtgaacttg    300
ccgacgtcat cgtggtcggc gtgggcaccg tgcgcattga aggctactcc ggcgtccgga    360
tgggtgtcgt ccatcgcca                                                  379
```

<210> SEQ ID NO 483
<211> LENGTH: 264
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 483

```
tactcaagct tggggtggcg ctgtcggtcg gtgtgcttgg cggcgtcggt atcaacaccg     60
cccacgaaat ggggcacaag aaggattcgc tggagcggtg gctgtccaaa atcaccctcg    120
cccanacctg ctacgggcac ttctacatcg agcacaaccg tggccatcac gtccgggtgt    180
ccacaccgga ggacccggcg tcggcgcggt tcggcnaaac gttgtgggan ttcctgcccc    240
gcantgttat cggcggcttg cgct                                            264
```

<210> SEQ ID NO 484
<211> LENGTH: 351
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 484

```
ggccatcgcc accgcnccgc ggcgaacgct caaaggcacc tactggcacc aaggccccac     60
```

-continued

```
acgtcaccct gtgacctcct gcgccgaccc cgcccgaggt cctggccgtt accaccgaac    120

gggcgagccg ggagtctggt acgcatcgaa caaagagcaa ggtgcatggg cggagttgtt    180

ccgccacttc gtcgatgacg gggtcgatcc attcgaggtc cgtcgccgcg tcggtcgagt    240

ggcggtcaca ctccangtac tcgacctcac agacgagagg actcgatccc atctaggtgt    300

ggacgaaaca gatcttctgt ccgacgacta caccaccacc caggccatcg c             351


<210> SEQ ID NO 485
<211> LENGTH: 328
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 485

gcttgcgggt gatcgccttg gtcaacggca ccgtgatcgg atcggggtcn accgcncaga     60

tggactggan cttcggcgaa ntcntcgcct atgcctcgcg gggggtgacc ctgaccccgg    120

gtgacntgtt cggctcgggc acggtgccca cctgcacgct cgtcaagcac ctcnggccac    180

cggaatcatt cccgggctgg ctgcacnacg gcgacntggt cnccctccag gtcgaagggc    240

tgggcnaaac aangcagacc gtccggacaa ncggcactcc ttttccgttg gctcttcggc    300

cgaatccgga cgccnaaccc gaccggcg                                       328


<210> SEQ ID NO 486
<211> LENGTH: 344
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 486

gttctcgcac gatttccgga ttagcgggac tggtcaccag ttgggtatgc gggaaggcgc     60

tgacgttcgc cgcgattagc tgtttgatgg acgcggtggt gatgtnctga tcacggaact    120

ggctgtaata ncccagggtc gccncgcttt catccgggcc cggacccggc gcaccgagcg    180

tgtcgcgcag gtatgcgacg tgattttcgc tgaagtcccc gtacccggag aactcgaaca    240

cgctgaggcg ctcgtcaccg tcgtnncggc gaccaagcgc ggcgagcaac tgcgcaaaat    300

cgttaagana ggtcgaatcg ttgaaattcg gcaccacctg cacc                     344


<210> SEQ ID NO 487
<211> LENGTH: 285
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 487

cacaagacaa tactcaagct tcaggtcaat gtgcnccaag ccctgacgct ggccgaccag     60

gccaccgccg ccgganacgc tgccaaggcc accgaataca acaacgccgc cgaggcgttc    120

gcagcccagc tggtgaccgc cgagcanano gtcnaaaacc tcaagacgct gcatgaccag    180
```

-continued

```
gcgcttancg ccncagctca ggccaagaag gccgtcgaac gaaatgcgat ggtgctgcag    240

canaanatcg ccgancgaac caagctgctc agccagctcg agcag                    285


<210> SEQ ID NO 488
<211> LENGTH: 280
<212> TYPE: DNA
<213> ORGANISM: Mycobacterium tuberculosis

<400> SEQUENCE: 488

ccacccgtgc atggtggcac tgtagcgacg tgctgcaatc aaggtcatgc ccgactctgg     60

tcagctcgga gccgctgaca ccccgctaag gctgctcagc tcggtgcatt acctcaccga    120

cggcgaactc ccccagcttt acgactatcc ggatgacggc acctggttgc gggcgaactt    180

catcagcagc ttggacggcg gcgctaccgt cgatggcacc agcggggcga tggccgggcc    240

cggcgaccga ttcgtcttca acctgttgcg tgaacttgcc                          280


<210> SEQ ID NO 489
<211> LENGTH: 160
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as “n”

<400> SEQUENCE: 489

gctttccgcc gatacccncc atgtcccgca catccaggac ttctgggggg atccgctgac     60

agcggcggga tcccaaagtg cggatgatcg ggccgcctac gtcgtggtgt acctcgncgg    120

taacaacgaa accgaancgt atgactcngt ccacgcggtg                          160


<210> SEQ ID NO 490
<211> LENGTH: 176
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as “n”

<400> SEQUENCE: 490

caacccgant tggctttcgg cgccntcggt gaggacggcg tgcgggtgct caacgacgac     60

gtcgtccgcg ggacacacct cgatgctgcc gccatggacg cggtcgaacg caagcagctg    120

atcgatctac nacgccgngn ggaacgcttc ngccgcgggc gtgaccgcnt cccgtt        176


<210> SEQ ID NO 491
<211> LENGTH: 216
<212> TYPE: DNA
<213> ORGANISM: Mycobacterium tuberculosis

<400> SEQUENCE: 491

gggatgggca aaaaggcgaa gcaccgcgtg gccacgaacg ccgggaggga caatctcggg     60

cggctagggc ttctcgcggg aaggcccgaa cgtacggcgt ttcaacacgt cgcgtcgccc    120

tccgaccgcg aacattcggg gatggcagca acctggtagc accctggccg ggcgatgatc    180

tgccagcgtc cccgcgggta gtcgccgccc gggcgg                              216


<210> SEQ ID NO 492
```

-continued

<211> LENGTH: 163
<212> TYPE: DNA
<213> ORGANISM: Mycobacterium tuberculosis

<400> SEQUENCE: 492
cagcagacca acaagagcat cgggacatac ggagtcaact acccggccaa cggtgatttc 60
ttggccgccg ctgacggcgc gaacgacgcc agcgaccaca ttcagcagat ggccagcgcg 120
tgccgggcca cgaggttggt gctcggcggc tactcccacg gtt 163

<210> SEQ ID NO 493
<211> LENGTH: 80
<212> TYPE: DNA
<213> ORGANISM: Mycobacterium tuberculosis

<400> SEQUENCE: 493
ctcaagcttg actggccacc caccggcatg accaccgaca ggcccgactg gtcgtaccac 60
tcgaacgccg gggtgtttga 80

<210> SEQ ID NO 494
<211> LENGTH: 248
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 494
ttggtgcccg gaatggcgag tcccatttan tcgctgattt gtttgaacag cgacgaaacc 60
ggtgttgaaa atgtcgcctg ggtcggggat tccctctcca agcaagagta actggcccca 120
aataaagtta ctcgtcgtct tgcaaagacc gctacccgat gccatttatg tgtttcctta 180
cgctcnnnnt tccggtgcgc catcattatc tgcacctttg cactgcacat tgagcttagc 240
agcgctcg 248

<210> SEQ ID NO 495
<211> LENGTH: 341
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 495
gaattngctt tcggcgccat cggcccagga ccgcgtgcgg gtgctcaacg acgacgtcgt 60
ccgcgggaca cacctcgatg ctgccgccat ggacgcggtc gaacgcaagc agctgatcga 120
gctacaacgc cgcgcggaac gcttccgccg cgggcgtgac cgcatcccgt tgaccgggcg 180
gatcgcngtg atcgtcgatg acggcatcgc caccggagcg acggccaagg cggcgtgcca 240
ggtcgcccgg gcgcacggtg cggacaaggt ggtgctggcg gtcccgatcg gcccagacga 300
catcgtggcg agattcgccg ggtacgccga tgaagtggtg t 341

<210> SEQ ID NO 496
<211> LENGTH: 420
<212> TYPE: DNA
<213> ORGANISM: Mycobacterium tuberculosis
<220> FEATURE:
<221> NAME/KEY: unsure -continued
<222> LOCATION: (various positions within the sequence)
<223> OTHER INFORMATION: applicants are uncertain of bases designated as "n"

<400> SEQUENCE: 496
taaagctttc gtcagttcat ngngcccccg gaccaacaaa agcatcggga catacggagt 60
caactacccg gccaacggtg atttcttggc cgccgctgac ggcgcnaacg acgccagcga 120
ccacattcag cagatggcca gcgcgtgccg ggccacgagg ttggtgctcg gcggctactc 180
ccagggtgcg gccgtgatcn acatcgtcac cgccgcacca ctgcccggcc tcgggttcac 240
gcagccgttg ccgcccgcag cggacgatca cntcgccgcg atcgccctgt tcgggaatcc 300
ctcgggccgc gctggcgggc tgatgagcgc cctgacccct caattcgggt ccaanaccat 360
cnacctctgc aacaacggcg acccgatttg ttcggacggc aaccggtggc gancgcacct 420

<210> SEQ ID NO 497
<211> LENGTH: 135
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 497
ccgggaggga ccatcncggg cggctncggc ttctctccgg aaggttctan ngtnnngcgt 60
ttcnacnctt cccgtcgccc tgcgaccgcc gaacattcgg ggtatggnng cancctgtna 120
gcatccnggc cgggc 135

<210> SEQ ID NO 498
<211> LENGTH: 277
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 498
ctcaagcttc cgcatcagat cgctatagaa ccggtgcgcg tccccaccga gtggctggtc 60
gccttccagc acgatcgtta ccgcgttatc ggaatcaaac tcnccgaaca cctgaccaac 120
gcgcttgatc gcctgaatcg atgcggcgtc gctggggctc atcgataccg agtgtgcttt 180
tccgaccact tccagttgcg gtacggcgag attgacaaag gcggtgaagc ccagccagag 240
caggacgatc accnccgcaa accggcggat ttgcccg 277

<210> SEQ ID NO 499
<211> LENGTH: 323
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 499
gcttggcagc ctgcggctgg gcgccctnga gctcttcgat ctggatctcc ggactcgaga 60
tgctcacttg cccggccgtg gacgtaccca ttgcggccgg gaccccagcg ccccaggtga 120

-continued

```
ccagcgagtt gggctgcacg ctgaccggcc cgtcggggtc gacgccggta acggtcagca    180

gctccgangt ccnnctgatc ccgaccgcag ctgccaatgc gcggctggca gccgacgtgg    240

atgtgccggg gcctagatcg cggggcagca gcgagaccgc gtcaccgacg gtcatcacct    300

tgccgagttt nggcctgccg can                                            323
```

<210> SEQ ID NO 500
<211> LENGTH: 148
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 500

```
gcttccggct cgtatgttgt gtggaattgt gagcggataa caattncaca caggaaacag     60

ctatgaccat gattacgcca agctatctag gtgacactat agaatactca agcttgagcc    120

atcgggctat cagctggttg atgtcccg                                       148
```

<210> SEQ ID NO 501
<211> LENGTH: 242
<212> TYPE: DNA
<213> ORGANISM: Mycobacterium tuberculosis

<400> SEQUENCE: 501

```
caggcatgca agcttgtcgt ctatcacatc cgaccaccaa ccgcccgacg gctcggcaga     60

acgcctccgc atatgggtcg acgaccagcg ggtcggactt ctgggctgcc agcgctcgcg    120

ccgtcgcgac aaacagcgcg gtcgaaccga cactccttgt gatgtcccac ctatcacctt    180

cggtacgcac ccaatcgacc ctacgcggct agctcagccc cgatcttcca gagctccgcc    240

cg                                                                   242
```

<210> SEQ ID NO 502
<211> LENGTH: 230
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 502

```
gctttttgag cgtcgcgcgg ggcggcttcc ccggcaattc tactagcgag aagtctggcc     60

cgatacggat ctgaccgaag tcgctgcggt gcagcccacc ctcattggcg atggcgccga    120

cnatggcgcc tggaccgatc ttgtgccgct tgccgacggc gacgcggtag gtggtcaatt    180

ccggtctacg cttgggcctt tgcggacggt cccgacgctg gtcgcggttg               230
```

<210> SEQ ID NO 503
<211> LENGTH: 235
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 503

-continued

```
cgancctgtt cgacggctac ctgaatcacc ccgatnccac cgccgcggcg ttcgacgccg     60

acagctggta ccgcaccggc gacgtcgcgg tggtcgacgg cagtgggatg caccgcatcg    120

tgggacgcga gtcggtcgac ttgatcaagt cgggtggata ccgggtcggc gccggtgaaa    180

ttgaaacggt gctgctcggg catccggacg tggcggaggc ggcagtcgtc ggggt         235


<210> SEQ ID NO 504
<211> LENGTH: 152
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 504

naagctttgt cacaccaagt gtttcnacca gncgctccat ccggcgaagt ggatactccc     60

agcaggtagc aggtcgccac cacgctggtc agtgcgcgtt cagctcgctt gcggcgctgc    120

agcagccagt ccgggaaata gctgccctgg cg                                  152


<210> SEQ ID NO 505
<211> LENGTH: 192
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 505

cgctggncgc cggcgctggg ctgcggtaac caattaccac aacacttttc ggtagccgaa     60

cagcggcgcg taccagcgaa atggcacagc caccgcagtc gccgacatcc cgcgaagatg    120

tggcagattt tcgtgcggtc gagccggcga aggcctagcg tcattgttgc ctggcaaggt    180

tgctgggccc gg                                                        192


<210> SEQ ID NO 506
<211> LENGTH: 312
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 506

ctcaagcttc ttctgcccct tgccgttncg gatnacatcc cgcagcgact cggcttcggc     60

gtcgatgtcg aagttctcga tcagcttctg gatcgactcc gcgcccatgg caccggtgaa    120

gtactcgccg tagcggtcga cnagttcgcg gtagaggttt tcgtcnacna tcagctgctt    180

gggcgccanc ttggtgaaag tgctccaaat gtcctccaac cggtccagct cacgctgcgc    240

gcggtcacgg atctggcgca tctcgcgctc gccgccgtcg cgaacttgcg ccgcgcatcg    300

gccttggggc cc                                                        312


<210> SEQ ID NO 507
<211> LENGTH: 296
<212> TYPE: DNA
<213> ORGANISM: Mycobacterium tuberculosis
<220> FEATURE:
```

-continued

<221> NAME/KEY: unsure
<222> LOCATION: (various positions within the sequence)
<223> OTHER INFORMATION: applicants are uncertain of bases designated
as "n"

<400> SEQUENCE: 507
gttcacacct acctactatg ccncaattcn ccgacacggg tggcatcaac acgggcgata 60
aggtggaaat cgctggggtg aacgtcgggc tggtgcgctc gctggcaatc cgcggcaacc 120
gcgtgttgat cggattctcg ttgcccggca agacaatcgg gatgcaaagc cgggcagcaa 180
ttcncnccna caccattctt ggccgtaaga acctggagat cgaaccccgc ggttcggagc 240
cgttgaaacc caacggtttc ctgccgttgg cgcanaccac tacgccatac caaatc 296

<210> SEQ ID NO 508
<211> LENGTH: 208
<212> TYPE: DNA
<213> ORGANISM: Mycobacterium tuberculosis

<400> SEQUENCE: 508
ctcaagcttt acgccgacgc cggcctacac aacaccaagg aaacgattgc ctactgccga 60
atcggggaac ggtcctcgca cacctggttc gtgttgcggg aattactcgg acaccaaaac 120
gtcaagaact acgacggcag ttggacagaa tacggctccc tggtgggcgc cccgatcgag 180
ttgggaagct gatatgtgct ctggaccc 208

<210> SEQ ID NO 509
<211> LENGTH: 278
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 509
tcccncatgg gataacgggt ttagatttcn acaacggcac cgtgtttctc aacaagccgg 60
tcatcagctg ggccggcgac aacggtatct acttcacccg ctttcgcccg tacaagaaaa 120
accactaggc caccatcgag tccaagaaca accacctggt ccgcaagtac gcgttctact 180
accgctatga caccgccgag gaacgcgccg tgctcaaccg gatgtggaag ctggtcaacg 240
accgcctcaa ctacctcacc ccgaccatca aaccgatc 278

<210> SEQ ID NO 510
<211> LENGTH: 177
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 510
ctcaagcttg ggtgttgccg atcaccggaa gccncatgat cagccacgtt tcgcgccgcc 60
cggcatacgg cggcgtaccg atctccgcgt catacacccg cgggtaatcg ccgacggtgc 120
cggttcgcga gccgaaggtg acaacgctga ttgaatcnag ttccangtcc agcgggt 177

<210> SEQ ID NO 511
<211> LENGTH: 296
<212> TYPE: DNA

-continued

<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 511
tnaacagctc gcggcagccc acgacctgct gcgtcggatt gccggcggcg agatcaattc 60
caggcagctc ccggacaatg cggctctgct ggcccgcaac gaangactcg aggtcacccc 120
ggtgcccggg gtcgtggtgc acctgccgat cgcacaggtt ggcccacaac cggccgcttg 180
atgnnnngtc ggcaagcccg gcagtngcca aacccagcgt gatcangctc ggctcgcgag 240
ttcggcgaan aagtggctcg cctgatcacc taccatcggc cangatctgc gtgtca 296

<210> SEQ ID NO 512
<211> LENGTH: 223
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 512
gccanccggc ttggcgtcga ctcccgttcn gcacatcata cggtccccgg tactgtccaa 60
ctgcgccggt gcgctagcca aacgtcacga ctctcagtga tcccagttcg tgatccggcc 120
ggtggcgccg ctgcggcggg ggctnatnta cttcggactn attatctcat ccaaaggaca 180
ccgggccggt ggctggaatc ccatggtgcg atcggccaca can 223

<210> SEQ ID NO 513
<211> LENGTH: 147
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 513
ccgacctggt atcttccgat agcgcgcgtt gatatccggt ctgatctcct gcccttaacg 60
ccggatctca gcaggtcccc atgcaaagat ccgaggtgtc ccngatctag gggtcctcgt 120
cctccagatg atggagcaag tcggccc 147

<210> SEQ ID NO 514
<211> LENGTH: 149
<212> TYPE: DNA
<213> ORGANISM: Mycobacterium tuberculosis

<400> SEQUENCE: 514
ctcaagcttc ggctcaggcg gcgctgccgg taacgtcgct gaccggtgca ggtttcgaca 60
atgtggtgcc ggttcggcgg ctacgtgcca tcaagacact ggcgcaggct atcgcacccg 120
ttatcggcta caaacaaatc gcggtatgc 149

<210> SEQ ID NO 515
<211> LENGTH: 238
<212> TYPE: DNA
<213> ORGANISM: Mycobacterium tuberculosis
<220> FEATURE:

-continued

<221> NAME/KEY: unsure
<222> LOCATION: (various positions within the sequence)
<223> OTHER INFORMATION: applicants are uncertain of bases designated as "n"

<400> SEQUENCE: 515

```
catcacctgn ttcatgaact ggaagcaccg cagcgcttcc ttttcggccg caacatgagc     60

cagcctctcg tcggcggtcg ggtgcaggtg ctcgggcagc tcggccgcga cagccgcctg    120

accctgaaac cagcttccat atcccgcgac gaacgacgcc agtccgctac gtaacccctc    180

cgcgactgtc catggacaac agcgcgttct ccaccgaccg ggcccgggtg tggggtgt      238
```

<210> SEQ ID NO 516
<211> LENGTH: 175
<212> TYPE: DNA
<213> ORGANISM: Mycobacterium tuberculosis

<400> SEQUENCE: 516

```
agcttagctt cccgccccgg caatagggct ccagctcatc cggtgtgacc agataggggc     60

ccagggtgat accgctgtct ttgcccttgg cctgtccgat gcgcagctgg ccctccagca    120

tctgcaggtc ccgtgcggac cagtcgttga aaatggtata gccgatgatc gaccg         175
```

<210> SEQ ID NO 517
<211> LENGTH: 144
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 517

```
ccngaacaga agcggnggtt cctaccgcgg tgtgcggccg gcgcgatatc ggccttttta     60

ctaaccgaac ccgatgtggg ctccgatccg gcgcgcatgg catcgacggc gacgccgatc    120

gatgaccgcc aggcttacca cctt                                           144
```

<210> SEQ ID NO 518
<211> LENGTH: 174
<212> TYPE: DNA
<213> ORGANISM: Mycobacterium tuberculosis

<400> SEQUENCE: 518

```
ctcaagcttg cgcgactcga caagcattct tgacagttgt tttggctcgg catggttagc     60

caaggttctg cggtcccacc agatcatctt ggtccggtag cgctcgtccg ggtatgctgc    120

cgccgggatt ctcgctgcta ttactccccc cgaagaacgc caccggtcca gcgc          174
```

<210> SEQ ID NO 519
<211> LENGTH: 187
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 519

```
gcnaggcggt atagcttccc gtcgtaccgg cgaccgccag ccgagaagct cgttttccca     60

gtgttgctgg ggattctcac gctgctgctg agtgcgtgcc agaccgcttc cgcttcgggt    120
```

-continued

```
tacaacgagc cgcggggcta cgatcgtgcg acgctgaagt tggtgttctc catggacttg    180

gggatgt                                                              187


<210> SEQ ID NO 520
<211> LENGTH: 215
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as “n”

<400> SEQUENCE: 520

gtgtggaacc gtgagcggat aacaatttca cacaggaaac agctntgacc ttgattacgc     60

caagctattt aggtgaggct atattaatac tcaagattgc ggtcgagcac atcggcccaa    120

gaaccgccga aggcacggcg gaacgcctgc ggcacatggg gcgacgacca gcgggtcgga    180

cttctgggct gtccagccgg atcgcgccgt cgcga                               215


<210> SEQ ID NO 521
<211> LENGTH: 406
<212> TYPE: DNA
<213> ORGANISM: Mycobacterium tuberculosis

<400> SEQUENCE: 521

cactgtcagt acatatgcgc cgctcctcct catcgctgcg ctcggcatcg tcgccggcgg     60

tcatggcgtc accctaccca agccgaacgc gaaacgagaa cgtgttccat tattagggtg    120

tgagcaccaa taccagattg ctcaccagga actcacgcag caccgggacg gatgtcagcc    180

accacgccca tctggggtgg tagcggggaa atacggctaa cgcggctccg gtgccggcag    240

cccagcgcag accctcggcg gcggacacgg caaacaacga cgacccatag ttgttctttg    300

ccggatggcc gtgtttgcgg acatatcggg cggcggcgcg ggcgccgccg aggtagtggc    360

tgaggcccat ctcgtgcccg ccgaatggcc ccagccaaac cgtgta                   406


<210> SEQ ID NO 522
<211> LENGTH: 180
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as “n”

<400> SEQUENCE: 522

ctcaagcttt tacggtgatc gcgcatcacc tggttcatga actggaagca gcgcagcgct     60

tccttttcgg ccgcaacatg agccancctc tcgtcggcgg tcgggtgcag gtgctcgggc    120

agctcggccg cgacagccgc ctgaccctga aaccagcttc catatcccgc gacnaacgac    180


<210> SEQ ID NO 523
<211> LENGTH: 69
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as “n”

<400> SEQUENCE: 523
```

-continued ctcagaagcc gctagctggt agagtcgctg accggtgcac gtggcgncaa tgtgcgctgc 60
cggttcgcg 69

<210> SEQ ID NO 524
<211> LENGTH: 168
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 524
ctcaagcttg cgctcatcaa gcgcgaacag cagggcggtc ggctggtcgc catgacgggt 60
gacgggacca atgacgcacc cgcgctcgcg caagccgatg tcggggtggc natnaatacc 120
ggcacccagg cggcccggga agccggcaac atggtcnatc tccactcc 168

<210> SEQ ID NO 525
<211> LENGTH: 83
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 525
acttctattt cgactggtgt gctgtggcgc gatccgactg ccggcgtggt caaggccggc 60
cagttgtggg atnccacagg cac 83

<210> SEQ ID NO 526
<211> LENGTH: 173
<212> TYPE: DNA
<213> ORGANISM: Mycobacterium tuberculosis

<400> SEQUENCE: 526
gcttgtcgta ttccgtggca ctgtcagaca tatgcgccgc tcctcctcat cgctgcgctc 60
ggcatcgtcg ccggcggtca tggcgtcacc ctacccaagc cgaacgcgaa acgagaacgt 120
gttccattat tagggtgtga gcaccaatac cagattgctc accaggaact cac 173

<210> SEQ ID NO 527
<211> LENGTH: 38
<212> TYPE: DNA
<213> ORGANISM: Mycobacterium tuberculosis

<400> SEQUENCE: 527
cgatattcgt cggccgcgtt gtctcgactg ggtcgcgt 38

<210> SEQ ID NO 528
<211> LENGTH: 136
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 528
gacctcggcc accaagccgg acgcgaccgt cgaggtggcg atccggcttg gcgtcgaccc 60

-continued gcgtaaggca gaccacatgg tccgcggcac ggccancctg ccacacggca ctggtaagac 120
tgcccgcgtc gcggcn 136

<210> SEQ ID NO 529
<211> LENGTH: 114
<212> TYPE: DNA
<213> ORGANISM: Mycobacterium tuberculosis

<400> SEQUENCE: 529
ccggaagtct aggggacgac ctactcagcg caaaatgtcg ctaatgtgag tccgccccac 60
cagggcagat caacccatgt cgatgatgac ctacccggat accggattgg cggt 114

<210> SEQ ID NO 530
<211> LENGTH: 119
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 530
agcttcagtt cctccacgac gcgttcccaa atgaatttcc cgatcccaca atctcggttc 60
agatacaggt cgccataccc cttacttcgg naacgctggg cggattggcc ctgccgctg 119

<210> SEQ ID NO 531
<211> LENGTH: 99
<212> TYPE: DNA
<213> ORGANISM: Mycobacterium tuberculosis

<400> SEQUENCE: 531
ccgcctacgg gtcgaacatg catcccgaga ccgatgctcg agcgcgcacc ccactcgccg 60
atggccggaa ccggctggtt acccgggtgg cggctgacc 99

<210> SEQ ID NO 532
<211> LENGTH: 308
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 532
gcggctggtt acgactccct gtttgtgatg gaccacttct accaactgcc catgttgggg 60
acgcccgacc agccgatgct ggaggcctac acggcccttg gtgcgctggc cacggcgacc 120
gagcggctgc aactgggcgc nttggtnacc ggcaatacct accgcagccc gaccctgctg 180
gcaaagatca tcaccacgct cgacgtggtt agcgccggtc gagcgatcct cggcattgga 240
gccggttggt ttgagctgga acaccgccag ctcggcttcg agttcggcac tttcagtgac 300 cggttcan 308

<210> SEQ ID NO 533
<211> LENGTH: 328
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated -continued as “n”

<400> SEQUENCE: 533
gcctttccgc acaatctgta ccccaggacc ntctaaaaaa tcgaatacga cggcgtcgcc 60
gactttccgc ggtacccgct caactttgtg tcgaccctca acgccattgc cggcacctac 120
tacgtgcact ccaactactt catcctgacg ccggaacaaa ttgacgcagc ggttccgctg 180
accantnntg tcggtcccac gatgacccag tactacatca ttcgcacgga gaacctgccg 240
ctgctagagc cactgcgatc ggtgccgatc gtggggaacc cactggcgaa cctggttcaa 300
ccaaacttga aggtgattgt taacctgg 328

<210> SEQ ID NO 534
<211> LENGTH: 75
<212> TYPE: DNA
<213> ORGANISM: Mycobacterium tuberculosis

<400> SEQUENCE: 534
gcagaccaac aagatgcatc gggatcatac gccgtcaact acccggccaa cggtgatttc 60
ttggccgccg cccac 75

<210> SEQ ID NO 535
<211> LENGTH: 319
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 535
ctcaagcttg ccaaagagac ctcgtccacc aagcnggacg cgaccgtcna ggtggcgatc 60
cggcttggcg tccacccgcg taaggcanac canatggttc gcggcacggt caacctgcca 120
cacggcactg gtaanactgc ccgcgtcgcg gtattcgcgg ttggtgaaaa ggccgatgct 180
gccgttgccg cgggggcgga tgttgtcggg agtgacaatc tgatcganag gattcagggc 240
ggctggctgg aattcgatgc cgcgatcgcg acaccggatc agatggccaa agtcggtcnc 300
atcgctcggg tgctgggtc 319

<210> SEQ ID NO 536
<211> LENGTH: 312
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 536
ccacggcgtg gatcaaggta ccggccggga tgttgcgcaa tggcaggttg ttgcccggct 60
tgatgtcggc gttagcgccg gattccacca catccccttg cgaaagtccg ttgggtgcaa 120
tgatgtagcg cttctcccca tcgagatagt ggagcaacgc aatccgtgcg gtacggttcg 180
ggtcntactc gatgtgcgcg accttggcgt tgacaccatc tttgtcattg cggcgaaagt 240
cgatcatccg gtaagcgcgc ttatgaccgc cgcctttgtg ccgggtggta atccggccat 300
gcgcgttgcg tc 312

-continued

<210> SEQ ID NO 537
<211> LENGTH: 105
<212> TYPE: DNA
<213> ORGANISM: Mycobacterium tuberculosis

<400> SEQUENCE: 537
ggcggctgcg tcggcgagat gatcgcccgg tgccaccccg atccgtgcct cggtcagcgc 60
caacgtgctt tccggtccgg cgaccaccat gtcgcatgcg ccgac 105

<210> SEQ ID NO 538
<211> LENGTH: 144
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 538
gcaatcgcct tggcggtcgc cgggttgtca ccggtgatca tcncggngcg gatgctcatn 60
cggcgcattt cgtcnaatcg ttcccgtatg cccaccttga cgatgtcctt catatggacc 120
acgccgatgg cccncgcgct nctg 144

<210> SEQ ID NO 539
<211> LENGTH: 431
<212> TYPE: DNA
<213> ORGANISM: Mycobacterium tuberculosis

<400> SEQUENCE: 539
ccggctcgta tgttgtgtgg aattgtgagc ggataacaat ttcacacagg aaacagctat 60
gaccatgatt acgccaagct atttaggtga cactatagaa tactcaagct tccacatcgg 120
tatgccaaag cattgcgccg ctatcgattt cgcgctggca tcgccaaggt ggacttcttg 180
ctcagcgacg agatcccgtg gtcggatccg cggctgcggc gggctgcgac cctgcatctc 240
ggcggcaccc gtgaccagat ggcgcgcgcc gaggcagacg tcgcggcggg acgccacgcc 300
gactggccga tggtgctggc cgcgtgtccg cacgtcgccg accccggccg catcgacgaa 360
accggccgcc gtccgttctg gacctatgcc cacgtgccgt cggggtccac gctcgacgcg 420
accgagaccg t 431

<210> SEQ ID NO 540
<211> LENGTH: 462
<212> TYPE: DNA
<213> ORGANISM: Mycobacterium tuberculosis

<400> SEQUENCE: 540
cgcgtccacc gcagcgtgag attggtggcg ccattcgtcg tggtgtagct gctgttggcg 60
gcgtcgccgt attgtgcggg ccagccttgt gcgggggccg cttctaccca cgagtcggca 120
cttccgcaac cgcccagctc gaccgcgatt acggcggccg caacggccgc cggaaggcgt 180
ctcgcaagcg ccttatcctt tcgcaggttc ccagatcctt ccgctacgtg ggtcgctcat 240
cggcgggccc ggccgaatga gtacaggtga gggtaaccgc tacaaatgaa gttggtcagt 300
gctggccaac tgtgtaatgg ttgcccggct cgggtcacca cgtacattct ggcaaggcgg 360
gcgagattcg gttcctcgcg tccttggccg gtggcggttc ccggttgtcc gtgggcgtgt 420
cgtgtacgtg gtgtaagtgt cgtgaactcc tcagtttggg ct 462

-continued

<210> SEQ ID NO 541
<211> LENGTH: 307
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 541
ctcaagcttg cgctggatct ggcggctgag cctgttcttg ggcaacatgc cgagggatcg 60
ccttttccac cacgcggtcg gggtggcgtt gcattagctc accgatggtg cgcttgtgca 120
ggccgccggg ataccccgag tgccggtaaa ccatcttgtg ctgcagtttg tcgccgctga 180
tggcgacctt gtcggcgttg atcacnatga cnaagtcacc gccatcgaca ttgggggcga 240
acgtcggctt gtgcttgccg cgcagcaggt tggccgccgc gacggcaagg cggccaanca 300
ccacgtc 307

<210> SEQ ID NO 542
<211> LENGTH: 333
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 542
tttgggatgg gcaaaaaggc gaagcnccgc gtggccacga acgccgggag ggacaatctc 60
gggcggctag ggcttctcgc gggaaggccc gaacgtacgg cgtttcaaca cgtcgcgtcg 120
ccctccgacc gcgaacattc ggggatggca gcaacctggt agcaccctgg ccgggcgatg 180
atctgcagcg tcgccgcggg tagtcgccgc ccgggcggct acagtctgaa acgcgatgac 240
catcgatgtg tggatgcagc atccgacgca acggttccta cacggcgata tgttcgcctc 300
gctgcgccgg tggaccggtg ggtctatccc gga 333

<210> SEQ ID NO 543
<211> LENGTH: 234
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 543
ctcaagcttc gtcataagac catggtgcgc tttctttcac ccgtccanag tcgggggcat 60
ccgcaccggc tcgcatcgca tcatcctccc acgacgggcc gctcatcagc ttgggccatt 120
tcaatgtact tgataccccg cgctgcgggt aggccactgc nacaattcaa acacggtgtc 180
acacggtgaa tantgtcnan atgggctctg atcaaccgtc ncaaacccgg tttc 234

<210> SEQ ID NO 544
<211> LENGTH: 440
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated -continued as “n”

<400> SEQUENCE: 544
gaattctgcg tgcaccgcta tgggttgcag cagcggctgg cgccgcacac cccactggcc 60
cgggtgtttt cgccccgaac ccggatcatg gtgagcgaaa aggagattcg cctgttcgat 120
gctgggattc gccaccgcga ggccatcgac cgattactcg ccaccggggt gcgagaggtg 180
ccgcagtccc gctccgtcga cgtctccgac gatccatccg gcttccgccg tcgggtggcg 240
gtagccgtcg atgaaatcgc tgccggccgc taccacaagg tgattctgtc ccgttgtgtc 300
gaagtgcctt tcgcgatcga ctttccgttg acctaccggc tggggcgtct gcacaacacc 360
ccggtgaggt cgtttttgtt gcagttgggc ggaatccgtg ctctgggtta cagccccgaa 420
ctcgtcncgg cggtgcgcgc 440

<210> SEQ ID NO 545
<211> LENGTH: 425
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 545
gcagttggga atcgctctgc agcaaaccan tattctgcgc gacgttcgag aggactnttt 60
gaatggacgg atctacctgc cgcgcgacga gctggaccga ttaggcgtac ncctccgcct 120
ggacgactcc ggggcactcg atgaccccga cggacggctc gcggcactgc tgcggttcan 180
tgccnaccgc gccgcanact ggtattcgct gggactgcgg ctgattccac acctcgaccg 240
ccgcagcgct gcctgctgtg cggccatgtc tggcatctac cgccgtcngc tcgccttgat 300
cagaccatcg ccggcggtcg tctaccatcg gcgaatctct ctgttcggga ctgaanaang 360
cccaagtggc ggcggcagca ctggnctctt cggtaacctg cngaccgccc attggaccgc 420
taccg 425

<210> SEQ ID NO 546
<211> LENGTH: 401
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 546
ttgatctgga cgtctgagac ggtgatcggn ccgaacctga attgtccggt aatgcccagc 60
gcagaaagca nggtggtggc cggggcggtg aanccggcgt cggcggcacc gtcgaagtcg 120
atgtggattg ccggaatggg gatgtccggc acggcgaagc cgtagttcgc ttgtcccgtg 180
aggcccangt ggatgggggg aaggatcgtg gtgtccggga tgataatggg gccgatgccg 240
ccggttgaag tccagtggat cgggaattcg ggaatcgtga tgccgacgtt caggccgaac 300
aggccctcca agttgcctcg ccacnagatg ccgttgctga agttgcccga catgagggcg 360
ccggtgtcca cattgcccga attggcgacg ccggtgttgg c 401

<210> SEQ ID NO 547
<211> LENGTH: 391

-continued

```
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 547

cacgtaggcg ccgtccataa atnactccgc cgcgcttcgc acatcctcgt ancgatcctt     60

ggcgagcagg tcaaccgggc gctgcccgtc naggagccgg tttttggcgt gcagccactg    120

gccgacacct cggggggtaa gcgaatccga gagcaggagg acnaggtcac gaanctgcgc    180

cagccggtcg taccgctcag ggcggatgtc gccggtccgc cacccgcgta ccgcccgatc    240

ggacacctgt atgaccgcgg cgacntcgac ctgggtgacg ccgaagggtt tcagggcatc    300

nacnatctcg ctggcctcga ccgcccggtc cagggtgacc gccatcgtgg ttcctccgca    360

acttccggtt ctactaccgt aaacgctacc g                                   391


<210> SEQ ID NO 548
<211> LENGTH: 369
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 548

cggggaacgg tcctcgcaca cctggttcgt gttgcgggaa ttactcggac ancaaaacgt     60

caagaactac gacggcagtn ggacagaana cggctccctg gtgggcgccc cgatcgagtt    120

gggaagctga tatgtgctct ggacccaagc aaggactgac attgccggcc agcgtcgacc    180

tggaaaaaga aacggtgatc accggccgcg tagtggacgg tgacggccag gccgtgggcg    240

gcgcgtttcg tgcggctgct gggacncctc cgacgagttc accgccggga ggtcgtcgcg    300

tcggccaccg ggcgaatttc cggttcttcg ccgcgccccg ggatcctggg accgcnggcg    360

cgcgctgtt                                                            369


<210> SEQ ID NO 549
<211> LENGTH: 85
<212> TYPE: DNA
<213> ORGANISM: Mycobacterium tuberculosis

<400> SEQUENCE: 549

ctcaagcttt gtccgacaag cgttcccggg cggtcagcaa gcgaacgtcg gttggcccac     60

tgcgggtcga tattgccgcc aggga                                           85


<210> SEQ ID NO 550
<211> LENGTH: 101
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 550

cgtcagcacg gcgacgtcgc gntacgccga gcagttacac aatcgctctg cagcaaacca     60

atattctgcg cgacgttcga gaggacttct tgattggact g                        101
```

-continued

<210> SEQ ID NO 551
<211> LENGTH: 458
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 551
ctgcatccgg ctcgtatgtt gtgtggaatt gtgagcggat aacaatttca cacaggaaac 60
agctatgacc atgattacgc caagctattt aggtgacact atagaatact caagcttcgc 120
gcagcggcgg gttgacccgg ttcacgccgt catagctggc caatctggca tcgtcgatca 180
ncatgtggtg gggggtgacc tcggcggtga tcgaaatacc ctggtcctta tcccatttca 240
ggatttcgac ggtgcccgcg gccgacgcgt gacagatgtg cacccgggcg ccggcgtcac 300
gggccagcaa ggcgtcgcgg gcgacgatcg attcctcggc ggcccgcggc catcccgcca 360
ggcccagccg cgccgccatg ggtccctcgt gcgcgacggc gccgaccgtc agccggggct 420
cctcggcgtg ctgggcgatc agcacgccca aaccggtg 458

<210> SEQ ID NO 552
<211> LENGTH: 463
<212> TYPE: DNA
<213> ORGANISM: Mycobacterium tuberculosis

<400> SEQUENCE: 552
ccgacgcgca ctacgtgctg gtgtccaccc gcgacccgca ccggcacgag ctacgcagct 60
accgcatcgt cgatggcgct gtcaccgagg aacctgtcaa tgtcgtcgag cagtactgaa 120
ccgttccgag aaaggccagc atgaacgtca ccgtatccat tccgaccatc ctgcggcccc 180
acaccggcgg ccagaagagt gtctcggcca gcggcgatac cttgggtgcc gtcatcagcg 240
acctggaggc cagctattcg ggcatttccg agcgcctgat ggacccgtct tccccaggta 300
agttgcaccg cttcgtgaac atctacgtca acgacgaaga cgtgcggttc tccggcggct 360
tggccaccgc gatcgctgac ggtgactcgg tcaccatcct ccccgccgtg gccggtgggt 420
gagcggacac atgacacgat acgactcact gttgcatgcc ttg 463

<210> SEQ ID NO 553
<211> LENGTH: 453
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 553
tgcttccggc tcgtatgttg tgtggaattg tgagcggata acaatttcac acaggaaaca 60
gctatgacca tgattacgcc aagctattta ggtgacacta tagaatactc aagcttgccg 120
ggagggtgca tggccgactc ggatttaccc accaaggggc gccaacgcgg tgtccgcgcc 180
gtcgagctga acgttgctgc ccgcctggag aacctggcgc tgctgcgcac cctggtcggc 240
gccatcggca ccttcgagga cctggatttc gacgccgtgg ccgacctgag gttggcggtg 300
gacgangtgt gcacccggtt gattcgctcg gccttgccgg atgccaccct gcgcctggtg 360

-continued

```
gtcgatccgc gaaaagacga agttgtggtg gaggcttctg ctgcctgcga cacccacgac    420

gtggtggcac gggcagcttt agctggcatt cct                                 453


<210> SEQ ID NO 554
<211> LENGTH: 466
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 554

ggaaacaccg ncgccgtcgt ggccaccaac accgcgacca gcaccgtgac ccggaccggg     60

gtgccgcgcg aaccggtctt ggccaattgc cgcggcacca agccgtcgcg cgccatggcg    120

aacagcacgc ggcattgccc gagcatcaac accatcacca ccgtggtaag cccggccagc    180

gcgccgacgg agatgatgcc gctggcccag tacaccccgt tggcctggaa cgcggtggcc    240

agatttgccg gcccgcggcc cggtacggtc cgcagttggg tgtatggaac catgcccgac    300

agcaccaccg ataccgcgac gtagagaagg gtcacgaccc ccagcgacgc gagaatccct    360

cgagggacgt ctcgttgagg acgcttggtc tcctcggcca tggtggccac gatgtcaaac    420

ccgataaacg cgaagaacac gatcgatgcc cggccagcac gccgta                   466


<210> SEQ ID NO 555
<211> LENGTH: 466
<212> TYPE: DNA
<213> ORGANISM: Mycobacterium tuberculosis

<400> SEQUENCE: 555

cctgcttccg gctcgtatgt tgtgtggaat tgtgagcgga taacaatttc acacaggaaa     60

cagctatgac catgattacg ccaagctatt taggtgacac tatagaatac tcaagcttgt    120

cctcgggcgt ggcctcggcc aagaaatcgt cgacgccggc ctcctgtgca atcgccttgg    180

cggtcgccgg gttgtcaccg gtgatcatca cggtgcggat gctcattcgg cgcatttcgt    240

cgaagcgttc ccgtatgccc accttgacga tgtccttcag atggacgacg ccgatggccc    300

gcgcgctgct gttatcggtc cattccgcaa cgactagggg tgtccccccg ccggagctga    360

tgccgtcgac aatggcaccc acctcctcag tggggtggcc accgtgatcg caaaaccact    420

tcatcaccgc agccgcggca ccttgcggat ccgaacggat gcgctc                   466


<210> SEQ ID NO 556
<211> LENGTH: 467
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 556

ttcgttcgat ggcgccgccc cggctacggt ttgacctgtg ggtgtcgaat tggggtcaaa     60

ttccgaggtc ggcgcgctaa gagtggtcat cctgcaccgc ccgggggccg aactgcgccg    120

gctcacaccg cgcaacaccg accagctgct gttcgacggc ctgccctggg tatcccgcgc    180

gcatgacgag cacgacgaat tcgccgagct gctggcttcc cgcggtgcgg aagtgctgtt    240

gctgtcggac ctgttgactg aggcactaca tcacagcggg gccgcccgca tgcaggggat    300
```

-continued cgccgctgcc gtcgacgcac cgcggctggg actgccgctg gcgcaagaac tttcggccta 360
cctgcgtatc tcgacccaag cangttggcg catgtgctga cgccggcatg acttcaacga 420
actcccntcc gacacgccga acgaagtgtc gttggtgttg cgtatgc 467

<210> SEQ ID NO 557
<211> LENGTH: 142
<212> TYPE: DNA
<213> ORGANISM: Mycobacterium tuberculosis

<400> SEQUENCE: 557
gcggcgagtg tggtgggtgc cgaacacgaa tccaacgacg cactggcgga gagataccac 60
ttgctgtact ggaagcacgt gctgatgatc tcccgtggaa tgtgcctcgc cgccgtctat 120
cgaaaacagt gagcatgctg cg 142

<210> SEQ ID NO 558
<211> LENGTH: 217
<212> TYPE: DNA
<213> ORGANISM: Mycobacterium tuberculosis

<400> SEQUENCE: 558
caaccgcgct cggcgcgtct gggccttccg ccggctccgc cgacaattct atctctggat 60
cagcggggct ctccgggccg gcctccgcga actcaacagg ccgcgccttc cggccgaaac 120
attccctagc catatatgat cgcacctcga tacacgatct ggcggcaaca ccgcaaagcg 180
tccgacgggc ccaacctccg caattcaggt atccggg 217

<210> SEQ ID NO 559
<211> LENGTH: 147
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 559
gaaggtcggc gaaggtgtgg ctggntgccg atcacgaatc caatgatgca gtggtcggaa 60
gatattagcc acttgctgtt ctggagacag gtgctgatga tctcccgtgg aatgtccctc 120
gactccgtct atcgaaatct gtgaaca 147

<210> SEQ ID NO 560
<211> LENGTH: 177
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 560
tcctgcgctc tgggccattc tcgggtctgc cgacaattct atctctggat ctgtggggct 60
ctcttggccg gcctcngcga tctcttcang gcgcgccttc cggccgaaac attccctatc 120
catatatgat cgcacctcta tacaccgttt ggcggcaaca ccgcaaagtg tctgtcg 177

<210> SEQ ID NO 561
<211> LENGTH: 128
<212> TYPE: DNA

-continued

<213> ORGANISM: Mycobacterium tuberculosis

<400> SEQUENCE: 561
agctttacgc tggcgtatca gcgttggggc cgctgccatt tcggtcgccc aacgcgttgc 60
cagctccctg cgctgtcagg gcttgcgcgc caaactggcc accgcaacaa acttggctga 120
gcttgatc 128

<210> SEQ ID NO 562
<211> LENGTH: 142
<212> TYPE: DNA
<213> ORGANISM: Mycobacterium tuberculosis

<400> SEQUENCE: 562
ctctatctgg cgtcacattc gcaatcttta gattgcagat atcgataaaa tcacccgcgc 60
gacaagaccg ccatgtcatc ctttcgatgt tatttcgccg gcctggggaa agcgcaacga 120
cgttgcctac acgttccgcc gt 142

<210> SEQ ID NO 563
<211> LENGTH: 406
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 563
agctttncct tgcatctgca ccccgatcca cgtcagccac gtcggcgttc tccaccaaga 60
agttgcgggc attctccttg ccctggccga gctgctcgcc ctcgtaggtg aaccaggcac 120
ccgacttgcg gatgaggccc tgatccacac ccatgtcgat cagcgagccc tccctgctga 180
ttcccttgcc gtagaggatg tcgaactcgg cctgcttgaa ggggggcgaa cagttgtgca 240
cgacaacccc ttcggcgacg agggtgtgca gttcctcgac ctcgaggtcg aacgttcgtg 300
cccgccgcgt tggcagcact tctcggatca cggaatagcg ganttcttcc gccagcatgt 360
cgtgcaggaa tttgtcatcc agggcatccg cgagcgcctg cacgcg 406

<210> SEQ ID NO 564
<211> LENGTH: 311
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 564
actgtcnagg gaatgcttcg cagcatctac ctgcagtcgc ttgtgcataa gcggacggcc 60
cnacctgttc gtgttccggg acaccagacg cgggagcacc ggcagtacgg cgaaaggttt 120
gagcggaagg agttgcgcaa atcggggcgc cccaacaccc gtccgcaaga cgcggtcaac 180
gacctgtttc aggcgatcag ggtcaccgac tcacctgcac tgagaacaag cgatctgctg 240
atctgccaga agatggacat gaatgtccac ggcaagcctg atggcctgcc gctcttccgg 300
gaatgtttgg c 311

<210> SEQ ID NO 565
<211> LENGTH: 310

-continued

<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 565
tgaattatga tcccgacaca actgcatcan tttagccgcg tcgngatgct atccgccgac 60 ggtttggtanc nggtccgtgt cgttcgtgtt gatctcaccc gaagttgtgt ccgccgccgc 120
cggggatcta gcgaacgtgg gatcgacaat cagcgccgcc aacaaggcgg cagcggctgc 180
gaccacgcag gtgctggccg cgggcgccga tnaggtgtca gcgcgcatcg cggcgctgtt 240
tggtatgtac ggcctgnaat atccggcgat cagtgcgcaa gttgccgcgt atcaccanca 300
gtccgtgcag 310

<210> SEQ ID NO 566
<211> LENGTH: 326
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 566
aacggggacc ncaagaaacc attcaanaac gaggggtcgt caccaacgtc gaaaccgacg 60
gttgccagcc ggcccacgat attgcgtgct cgagggtccg ctgtaccctc accgaacgtg 120
agtcccacac cgcggaggcg ggcgactctg gcgtcgttag cagccgagct caaggtgtcc 180
cgcaccactg tctcgaatgc ttttaaccga ccggatcagc tctccgccga tctacgtgaa 240
cgagtgcttg ccacggccaa gcgactgggc tatgccggac cggatccggt ggcgcgatcg 300
ttgcggaccc gcaaagccgg tgcggt 326

<210> SEQ ID NO 567
<211> LENGTH: 374
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 567
agctttggag ccncnccgan ccnccggtac gccccgccac cgccgtaccc ggcacccgac 60
ccctttgagc cgttcgccgt ggccgcggtg ganctggccg acgagggact gatcgtgctg 120
ggcaaagtgg tcgatggcac gctggccgcc gatctgaagg tcggcatgga gatggagctg 180
acgaccatgc cgctgttcgc cgacnacgac ggtgtgcagc gcatcgtcta cgcgtggcgg 240
atcccatcgc gcgccggcga cnatgcanag cgcancgatg ctgaggagcg gcgccgatga 300
ggatgagcgc gccggaaccc gtttacntcc tgggtgccgg tatgcacccg tgggggaaat 360
ggggtaatga cttc 374

<210> SEQ ID NO 568
<211> LENGTH: 422
<212> TYPE: DNA
<213> ORGANISM: Mycobacterium tuberculosis -continued
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 568

```
ttctcncatc gttcgtactn ngatgggacg ctgctgcccg aggcgatcct ggccaaccgg     60
ctctcgccgg cgctgacctt cggcggggcg aacctgaact tctttccgat gggcgcttgg    120
gccaaacgta ccggggctat cttcattcgg cgtcagacga aagatattcc cgtctaccgc    180
ttcgtattac gtgcttacgc cgcgcagctg gtgcaaaacc atgtcaacct cacctggtcg    240
atcgaagggg gtcggaccag aacgggcaag ctacggccac cggtgttcgg gatcctgcgt    300
tacatcaccg atgcggtcga cgaaatcgac ggtcccgaag tgtatttggt gccgacctcg    360
atcgtgtacg aacagctgca cgaagtggaa gccatgacca ccgaagccta tggcgccgtg    420
aa                                                                   422
```

<210> SEQ ID NO 569
<211> LENGTH: 300
<212> TYPE: DNA
<213> ORGANISM: Mycobacterium tuberculosis

<400> SEQUENCE: 569

```
ttcttccggg taccgctgat cggcggcacc atcacgcacc cggtgcaggg cgaggcggcc     60
gccggtgtgg tgttgctacg gccggccagc ccgggtaccg gtgtgatcgc cggtggtgcg    120
gcccgcgcgg tgctggaatg tgcgggggtg cacgacatct tggccaagtc gctgggcagt    180
gacaacgcga tcaatgtggt gcacgccacc gtggccgcgc tcaagctgct gcaccgtccg    240
gaggaggtgg cggcgcgccg cggtttgcca atagaagacg tccccccggc cgggatgctg    300
```

<210> SEQ ID NO 570
<211> LENGTH: 343
<212> TYPE: DNA
<213> ORGANISM: Mycobacterium tuberculosis

<400> SEQUENCE: 570

```
gtcgaaagtg accatctcta ccttgagtgc cataccgccc gaccctatgc ctcggatagc     60
tcggcggaaa gaaacgcttg cagtgccgcc gaataggcgg ctacgtcgtg agcgcccatc    120
aactctcgcg cggagtgcat cgccagctgg gcggcgccga cgtcgaccgt ggggattccg    180
gtgcgcgccg cggccaacgg cccgatcgtc gacccgcacg gcagatcggc gcgatgttcg    240
taacgctgca taggcactcc cgcgcgctgg caggccagtt gcgaaacgcc cccgccgggt    300
gccttccgtc ggttggcttt accgcaaatt tggggttgcc cct                      343
```

<210> SEQ ID NO 571
<211> LENGTH: 220
<212> TYPE: DNA
<213> ORGANISM: Mycobacterium tuberculosis

<400> SEQUENCE: 571

```
aaagccacgg aaacgattgc ctactgccga atcggggaac ggtcctcgca cacctggttc     60
gtgttgcggg aattactcgg acaccaaaac gtcaagaact acgacggcag ttggacagaa    120
tacggctccc tggtgggcgc cccgatcgag ttgggaaact gatatgtgct ctggacccaa    180
gcaaggactg acattgccgg ccagcgtcta cctggaaaaa                          220
```

-continued

<210> SEQ ID NO 572
<211> LENGTH: 254
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 572
tttcgccacc gcnaggtcgt gcgcgttcca gaaaagcgtg gtttcgccgg gcgcgaggat 60
tcgacggtcc aactgaccag ccggtcccgc cacccgttag gcaggatcgc ggtgtctata 120
tgttcgccct cggcataaac gccattgctg cggtgaaaat cggacatctc gccgattgcc 180
acgtctacat gatccgcttt gtcccgcgcc gggtcgttga caaacgcgat gtcngcctcc 240
tgggaagcgg tggc 254

<210> SEQ ID NO 573
<211> LENGTH: 329
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 573
tcgccaagtg gattcgtgct caccnacgag atccgtggtc ggatccgcng ctgcggcggg 60
ctgcgaccct gcatctcggc ggcacccgtg accaaatggc gcgcgccgaa gcagacgtct 120
cggcgggacg ccacgccgac tggccgatgg tgctggccgc gtgtccgcnc gtcnccgacc 180
ccggccgcat cnaccaaacc ggccgccgtc cgttctggac ctatcccacg tgccntcggg 240
gtccacgctc gacgcgaccg anaacgtaac cagcgtcctc gancggttcg cccccggctt 300
ccgtgacatc gtggtggcgg ccgcgccgt 329

<210> SEQ ID NO 574
<211> LENGTH: 297
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 574
gtaccgtcac catgatcgcc cccatcggca tcggtgagct gatagatccc agccggtttc 60
gccaaccccg gagcgatctt ggcgcgctgc tngtngtcnc tganacntag ccaccaacag 120
agcccggtgt gcgacaagan gactgatcgg atctctccgg acacntcgag ggggtcntca 180
ggagnccggg cgccaccccg aggtaagcct ccgcccagcc tcacaccgcg accgggtatc 240
ncaagtcgcg caataanccc accacctcct cggaccccac gttgtatgcg gctgggt 297

<210> SEQ ID NO 575
<211> LENGTH: 401
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated -continued as “n”

<400> SEQUENCE: 575
atactcaagc ttagacctca ctgatgtggc gggacgcggg agataaccgc ggttcgagcc 60
gttcaacagt ggtggttccc acaccagttg tttgcctttg cgaagtaaag cgattcgatt 120
tgctcgaaaa gagggctggc tgctcgtgag ggacatccat ggccgatacc tcagcgatct 180
caacggtcaa gcgactgcat gtttggcgca aggtatcgct aagcataggt tcgtgacgga 240
tttgacagca agagctttcc aaagattgct gtccacatan tgattcgcat ctctacacct 300
cttcgccggt gctgtcaaga gccattcgaa tcagttatct cgctcgtgct tggaanaaat 360
tttcccagcc tgcgttggac aaaccgcgtc gccaaagcgg t 401

<210> SEQ ID NO 576
<211> LENGTH: 453
<212> TYPE: DNA
<213> ORGANISM: Mycobacterium tuberculosis

<400> SEQUENCE: 576
agcttcccga gaaacagtgc attccctaag cagcccgttg tcacgccgat gagtgaagag 60
tgcacgcaat cgccggaatc cggcaaagcc ctgcacaagc gaaatcaacc cggaggctga 120
caaggcaacg tcggtgatcc gtaccgcctg gttggacaaa cggcagaagg cggcctcgtc 180
cggtccatct acgccgagca cactggtgat agcgcgcatc ggcatcggtg cggccacggt 240
ggagacgacg tccgcgggcg tctgggtcag taacccgccg accagttctc gggcaagctg 300
gtcgaccatc gggcgccacg tctccaacgc gccacgcgcc atacctggtg ccagttgctt 360
gcgcatccgg gtgtgcgccg gcggatcgga cgtcgcagaa acgcagccac cccgtgagaa 420
gtgacccacg gcgctggaca cgtgtctggt tac 453

<210> SEQ ID NO 577
<211> LENGTH: 474
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 577
cggccgggat gtgcgcaatg gcaggttgtc gcccggcttg atgtcggcgt tagcgccgga 60
ttccaccaca tccccttgcg aaagtccgtt gggtgcaatg atgtancgct tctccccatc 120
gagatagtgg agcaacgcaa tccgtgcggt acggttcggg tcgtactcga tgtgcgcgac 180
cttggcgttg acaccatctt tgtcatggcg gcgaaagtcg atcatccggt aagcgcgctt 240
atgaccgccg cctttgtgcc nggtggtaat ccggccatgc gcgttgcgtc caccgcgacc 300
gtgcagcggg cgcaccagcg acntctccgg ggttgaccgg gtgatctcgg cgaaatcaga 360
tacgctggcg ccgcgacgac caggcgtcgt gggcttgtac ttgcgaattg ccatggtcta 420
atcaggtctt tctctcacct ctcgtcgccg ggctagggcg cattgcctgc tcct 474

<210> SEQ ID NO 578
<211> LENGTH: 357
<212> TYPE: DNA
<213> ORGANISM: Mycobacterium tuberculosis
<220> FEATURE:
<221> NAME/KEY: unsure
<222> LOCATION: (various positions within the sequence)

-continued

<223> OTHER INFORMATION: applicants are uncertain of bases designated as "n"

<400> SEQUENCE: 578

```
tagcggtgta accaactccc gggtcaccac ccgcaaacct cttgcggcaa cagcaccgtc     60

gacgcgtcaa ccgggctgcc cggaatcctg tggatgggca tcgagtgcat ggtcacgacg    120

tccccgacgc ggccggtggc aacgacaagt ggcccggatg caccacaaat gacggccgca    180

caccggtggg gacggccagc acgagagccg tgtcgccgaa gtcgacgcta atgccgtagg    240

cattggccgt cacaacaggc gacgccccgc gtaccaccga gtccacggng gttgggcggt    300

ctcctcggcc aaccaggcgt gaacccggcg gatccgaatg cagcaagacc cgtgggc       357
```

<210> SEQ ID NO 579
<211> LENGTH: 269
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 579

```
ccattggtcg gtgtgcgcat accantacna cgcgccgggc acctgacgcg gcggccgcaa     60

ccattcggtg gccatcgcca tcgtctgcca cccggtcaac ggacgcacct tctcctggcc    120

gacctagtgc gcccacccgc cgccgttgcg tcccatcgat ccggtcaaca tgagcagcgc    180

caacaccgag cggtacatga catctgctgt ggaaccagtg acanattccg ccgcccatga    240

tgatcntcga ccgtcctccg gattcggtc                                      269
```

<210> SEQ ID NO 580
<211> LENGTH: 272
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 580

```
gccggcctgg tcaaaggggc gtccgaagga nccgggctgg gtaacaagtt cctggctcat     60

atccgcgaat gcgacgccat ttgtcaggtg gtgcgggtgt tcgtcgacga cnacgtgact    120

catgtcaccg gacgggtcga tccccagtcc gacattgagg tcgtcgagac cgagctgatc    180

ctggcagatc tgcaaaccct ggagcgggcc acgggccggc tggagaanga agcncgcacc    240

aacaaggcgc gcaagccggt ctacgacccg gc                                  272
```

<210> SEQ ID NO 581
<211> LENGTH: 373
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 581

```
gatccactga ccacgatgac atatcgaaat gctcgacgat tccgatggcg atcaaggcca     60

cgatgccctg gccgttgggc ggtatctggt ggatggtgta cccgcggtag gttcccgtga    120
```

-continued

```
tcgtgtcgac ccagtccacg cgatgggcgg cgaggtcgtc ggcacgcatc accccgccgt    180

ntgccgccga gtgcgcctcg agtttggcgg ccagctctcc ccggtagaac tctcaccgtt    240

ggtcgccgcg atcttctcta ncgtcgccgc gtggtcagga aaggtaaaca gctcaccggg    300

tttcggcgct cgtccgccgg gcatgaacgc atctgcgaat ccgggctggg atgcgaacaa    360

cggacctgtg ccg                                                       373
```

<210> SEQ ID NO 582
<211> LENGTH: 314
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 582

```
tctactgccg aatcggggaa cggtcctcgc ccaccnggtt cgtgttgccg gaattactca     60

ggacaccgaa acgtcgagaa ctacgagcgg agttggacan aataccgctc ccnggtgggc    120

gcccccatcg anttgggaag cngaaatgtg ctctggaccc cacccaagaa tgacattgcc    180

ggccgccctc caactggaaa tagaaacngt gatcacccgc cgcgttcttg gaaggaatgg    240

catgccctgg gccgggcgtt ccttccgctg ccggactcct cccaccaatt caccgccgaa    300

ggcgtcccgt ctgc                                                      314
```

<210> SEQ ID NO 583
<211> LENGTH: 135
<212> TYPE: DNA
<213> ORGANISM: Mycobacterium tuberculosis

<400> SEQUENCE: 583

```
atactcaagc ttctgtcacc gaaatcccgc atgggataac gggtttagat ttcgacaacg     60

ggaccgtgtt tctcaacaag ccggtcatca gctgggccgg cgacaacggt atctacttca    120

cccgctttcg cccgt                                                     135
```

<210> SEQ ID NO 584
<211> LENGTH: 221
<212> TYPE: DNA
<213> ORGANISM: Mycobacterium tuberculosis

<400> SEQUENCE: 584

```
ctggctcaag cgctcggcgc gcaggtgaac tcggaccggc tcgacgtcgc cgaacgcgag     60

gcggtgctgg cccacgccga cgccgtcgtc gcacatatcg gcaccgtgca caagtctaca    120

acaacgccgg catcgcgtac aacggcaacg tcgacaagtc ggagttcaag gacatcgagc    180

gcatcatcga cgtcgacttc tggggcgtcc tccacgggcc c                        221
```

<210> SEQ ID NO 585
<211> LENGTH: 70
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 585

-continued

```
ccgccctccg cattatgggt caagaaccat cgggtcggac ttctgggctt ccaacgctcg     60

cgccgtcccn                                                            70


<210> SEQ ID NO 586
<211> LENGTH: 241
<212> TYPE: DNA
<213> ORGANISM: Mycobacterium tuberculosis

<400> SEQUENCE: 586

ccgtggcact gtcagacata tgcgccgctc ctcctcatcg ctgcgctcgg catcgtcgcc     60

ggcggtcatg gcgtcaccct acccaagccg aacgcgaaac gagaacgtgt tccattatta    120

gggtgtgagc accaatacca gattgctcac caggaactca cgcagcaccg ggacggatgt    180

cggccaccac gcccatctgg ggtggtagcg gggaaatacc gctaacgcgg ctccggtgcc    240

g                                                                    241


<210> SEQ ID NO 587
<211> LENGTH: 492
<212> TYPE: DNA
<213> ORGANISM: Mycobacterium tuberculosis

<400> SEQUENCE: 587

tactcaagct tgtccaaata tcgaagcgtc gggtcgcgag gctcggtcgg cagctccagc     60

aaaacccgct ccacccctag atgccggtat ccctcaaggt ctttatccgc cgcttcaccc    120

cactggcaca cggtcaccgg cacgtcgccc ccggccatgg cgcgcaaccg ctgaagcgga    180

cccgacagcc gctgcggtga tggactgatc gcgatccacc cggcattgag ccgggctatc    240

cgcgggaagt tcgccggtcc cccgcccaca tacagcggag gatagggctt tgtcaccggc    300

ttcggccagc agtagatcgg atcgaagtcc acatatgtcc catggaattc cgcctgctcc    360

tgcgttcaga tctcgattat cgcgcgcaac cgctcatcga tcacacgtcc gcgcaccgca    420

gggtccacac catggttggc gacttcttcg cgcaaccagc cacacccacg ccgaaacgaa    480

accgtccctg cg                                                        492


<210> SEQ ID NO 588
<211> LENGTH: 313
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 588

caggcatgca agcttggcca actcctcatc ggacttgaag gtgccgtcct cgttggcggc     60

cctgctccac ggcacgttga tggcaccagg aatgtgtccg ggccgctggc tttgttcctg    120

cggcaggtgc gcgggggcca ggatcttgcc ggagaactcg tcgggagagc gcacgtcgat    180

gaggttcttg acgttgatgg ccgccaggac ctcgtcgcgg aatgcccgaa tcgtgttatc    240

cggcggggan gcggtgtagg aagtcaccgg ccggctgacc gggtcgctgg acagcgggcg    300

tccgtcgagc tcc                                                       313


<210> SEQ ID NO 589
<211> LENGTH: 305
<212> TYPE: DNA
<213> ORGANISM: Mycobacterium tuberculosis
<220> FEATURE:
```

-continued

<221> NAME/KEY: unsure
<222> LOCATION: (various positions within the sequence)
<223> OTHER INFORMATION: applicants are uncertain of bases designated as "n"

<400> SEQUENCE: 589

```
atactcaagc ttcaaaacag gcctgttgtg ggcgcacccg gctcgccgag ttctgcacgc     60
accgcctcaa gtgcggcccg caccgccggc atctcccggt cacgcagggc cgcggcccgc    120
gccgcagcga cggcgtgttc gcgcagttcg ccgtcaatga tgctgacctg atcggccacc    180
cgggcggtct cggcgtcgtc ccgttcacta atcgcggtgc tcagcagcgt ctcgacagcc    240
accacccgag tggagaccag atgcnccacc acggaccgca gcgatgccag tcacctcacc    300
cgtcc                                                                305
```

<210> SEQ ID NO 590
<211> LENGTH: 394
<212> TYPE: DNA
<213> ORGANISM: Mycobacterium tuberculosis

<400> SEQUENCE: 590

```
caggcatgca agctttgcag ttgctgagta atgtcggcca acgtcaccac aatcgcgatg     60
aattcaatca tgccgcccag ggcggccaac ccaatggtgg ccgcgagcgg cagctcgatc    120
gcagcgcgga ggttgccggc cgccagttga ttcacgaaca gggtgaggtc ataggcgggc    180
aggatagtga cgaaggcaag acctagatct gccgtcggaa gaagaatcga gtatccggtc    240
gacacaacgg aagcgaaagt gtccgcgatg ttgatgagcg tcgccggttg tggcggcggt    300
ggcggcggta gcaccgtccg cacataccgc gggaacgcgg gcatccgaat ttggggcagg    360
gtgttcaagg cggctggcaa ctcaccatga atct                                394
```

<210> SEQ ID NO 591
<211> LENGTH: 457
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 591

```
ccggctcgta tgttgtgtgg aattgtgacc ggataacaat ttcacacagg aaacagctat     60
gaccatgatt acgccaagct atttaggtga cactatagaa tactcaagct tggccgcagg    120
gccgagtcga ttggtcgcgg tcgcctcgac agttagctta tgcaatgcta acttcggggc    180
aaagttcagg cggatcggcc gatggcgggc gtaggtgaag gagacagcgg aggcgtggag    240
cgtgatgaca ttggcatggt ggccgcttcc cccgtcgcgt ctcgggtaaa tggcaaggta    300
gacgctgacg tcgtcggtcg atttgccacc tgctgccgtg ccctgggcat cgcggtttac    360
cagcgtaaac gtccgccgga cctggctgcc gcccggtctg gtttcgccgc gctgacccgc    420
gtcgcccatg acagtgcgac cctgnaccgg gctggcc                             457
```

<210> SEQ ID NO 592
<211> LENGTH: 438
<212> TYPE: DNA
<213> ORGANISM: Mycobacterium tuberculosis

<400> SEQUENCE: 592

```
gtgtgctgtc aattcagagc tgagcctgat gcactcaact tactgagcat gctaacgctg     60
```

-continued gtcgtgcggg tcttgttccc gcgtgtcggc agggcacacg ctcggggcgt agctgggaga 120
ggccccggtc aagcccggag agcagtgctc agtccgccag cttgaccgac tttcgatgag 180
aacgcgcttc tcgccgtatt gaactggcgt gctgacggtc gctgagcagc gctcgccgag 240
tgcggccgct gattctttca tcgagccagg aggcgcattc gtgttcggcc gcctgcgggt 300
cggccccatc gtcgacgcga tccgtcaccc actcctcgat caggtctgcc tcatcgaacg 360
ggccaacggt gctgtcggag taagtgtgcg tgggcacgcg agccgggtgc tgtggtacac 420
ccaccgttgc atgaacaa 438

<210> SEQ ID NO 593
<211> LENGTH: 220
<212> TYPE: DNA
<213> ORGANISM: Mycobacterium tuberculosis

<400> SEQUENCE: 593
atactcaagc ttcaccaggc gccggcgggc cgcggcgcca agccaggcag ccgcgctcgg 60
cgcgtcgggg ccttccgccg gctcggccga cagttcgatc tctggatcgg cggggctctc 120
cgggccggcc tcggcgacct cagcgggccg cgccttccgg ccgaaccatt ccctagccat 180
agataaccgc acctcaatgc acggtttggc ggcaacccgg 220

<210> SEQ ID NO 594
<211> LENGTH: 266
<212> TYPE: DNA
<213> ORGANISM: Mycobacterium tuberculosis

<400> SEQUENCE: 594
agcttccgtc acgacccgcc ctcgccggtg ccggcgccat cggtcatcgg atctcatgac 60
gacgtcacgt aggcccgcta gccgcgagcg ggcgcggtca actggcgagg cggcggcgac 120
gtgactgagc tggccgagct ggaccggttc accgcggaac taccgttctc gctcgacgac 180
tttcagcagc gggcttgcag cgcgctggaa cgcggccacg gtgttgctgg tgtgcgcgcc 240
gaccggcgct ggcaagacgg tggtcg 266

<210> SEQ ID NO 595
<211> LENGTH: 105
<212> TYPE: DNA
<213> ORGANISM: Mycobacterium tuberculosis

<400> SEQUENCE: 595
atactcaagc ttgccgggac cgcggaacag aaccggcggt tcctaccgcg gtgtgcggcc 60
ggcgcgatat cggcctcccg actaaccgaa cccgatgtgg gctcc 105

<210> SEQ ID NO 596
<211> LENGTH: 141
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 596
acgttggctc tgccggaacg tatttccagc ggcacgcatt cggcgtgggt gccgggcgcc 60
gagttgcgtc gctgggatca cgcagcagtc gccggcggct gccgtcgggc tatgaattgc 120
accgagccgg aaaatccnca c 141

-continued

<210> SEQ ID NO 597
<211> LENGTH: 234
<212> TYPE: DNA
<213> ORGANISM: Mycobacterium tuberculosis

<400> SEQUENCE: 597
atactcaagc ttgtcgtatt ccgtggcact gtcagacata tgcgccgctc ctcctcatcg 60
ctgcgctcgg catcgtcgcc ggcggtcatg gcgtcaccct acccaagccg aacgcgaaac 120
gagaacgtgt tccattatta gggtgtgagc accaatacca gattgctcac caggaactca 180
cgcagcaccg ggacggatgt cagccaccac ccccatctgg ggtggtagcg ggga 234

<210> SEQ ID NO 598
<211> LENGTH: 184
<212> TYPE: DNA
<213> ORGANISM: Mycobacterium tuberculosis

<400> SEQUENCE: 598
cgttggtagc ccgatatgca tagtgtatct tactgaacat gatttccatt atggagcccg 60
gggtgccggc agcgcgaacg gtgcgccgtc agacgcgggc ggcactgacc agggtgttgc 120
gggcgaacat cggcccggct tcggattccg gtccgggtac cgggcgaccc accgcttcga 180
ggta 184

<210> SEQ ID NO 599
<211> LENGTH: 351
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 599
atactcaagc ttggccaact cctcatcgga cttgaaggtg ccgtcctcgt tggcggccct 60
gctccacggc acgttgatgg caccaggaat gtgtccgggc cgctggcttt gttcctgcgg 120
caggtgcgcg ggggccatga tcttgccgga aaactcgtcg ggagagcgca cgtcgatgag 180
gttcttgacg ttgatggccg ccaggacctc gtcgcggaat gcccgaatcg tgttatccgg 240
cggggaggcg gtgtatgagg tcaccggccg gctgaccggg tcgctggaca gcgggcgtcc 300
gtccagctcc cacttcttgc gggcgccgtc caacnacttg acttctcctg g 351

<210> SEQ ID NO 600
<211> LENGTH: 438
<212> TYPE: DNA
<213> ORGANISM: Mycobacterium tuberculosis

<400> SEQUENCE: 600
atatcttaag cgtcgggtcc cgaggctcgg tcggcagctc cagcaaaacc cgctccaccc 60
ctagatgccg gtatccctca aggtctttag ccgccgcttc accccactgg cacacggtca 120
ccggcacgtc gcccccggcc atggcgcgca accgctgaag cggacccgac agccgctgcg 180
gtgatggact gatcgcgatc cacccggcat tgagccgggc tatccgcggg aagttcgccg 240
gtcccccgcc cacatacagc ggaggatagg gctttgtcac cggcttcggc cagcagtaga 300
tcggatcgaa gtccacatat gtcccatgga attccgcctg ctcctgcgtc cagatctcga 360
ttatcgcgcg caaccgctca tcgatcacac gtccgcgcac cgcagggtcc acaccatggt 420

-continued tggcgacttc ttcgcgca 438

<210> SEQ ID NO 601
<211> LENGTH: 410
<212> TYPE: DNA
<213> ORGANISM: Mycobacterium tuberculosis

<400> SEQUENCE: 601
atactcaagc ttgtcgcggt aaacccgcag cagggcggtg ggtgcggtgt caaaaacaac 60
cacacttctt tgcggttcgg tgatctcgac accggccgcg agccgaccac catgcgcgcg 120
taaatcggcg atcagcgcgt cggctatcgc ctgggtgccg cccaccggaa tcggccagcc 180
gaccgaatgg gccagcgttg ccagcatcag tccggcgccg gccgacacca gtgacggcaa 240
cggtgaaatc gcgtgggcgg caacgccggt gaacaacgcg cgggcatcct cgcccgccag 300
cgaccgccag gcaggggtgc cctgggccag catccgcagc ccgagacgca ggaccgagcc 360
cagtgcagta ggcaaagacc gcttgtcgga gacatgaact ccacgaccgt 410

<210> SEQ ID NO 602
<211> LENGTH: 456
<212> TYPE: DNA
<213> ORGANISM: Mycobacterium tuberculosis

<400> SEQUENCE: 602
agcttattga accgcgggtc gcaggcaaag tggacctcat aacgactcgg gtccagcgac 60
cgcgccaaca cgaacggccg gacgacgtgg gccagggtcg cggcctcccc tacaaacagg 120
atccgttgcc tgcgagcgac aggctccggt gcggcgttgg gcgccgtgct cgtcccagcg 180
tccggtcccg ggtcgccggc gacgcttgtt tcctccatac tcgcccccta atctcgaggc 240
agcccgtacc cgcaggcaac ctcccaaaaa tgcaatcccc caaaatgcaa tgcgtcgagc 300
tatttctcac accgaccgct agttgcggat cagaaatccg ttgggcgcgg aagtccagcc 360
gaatttgttc tcccgctccg catcatgctt gtaatcgttt ggaaattcat cctcatatgc 420
ctcgatcgct tcatagggtc caggccaaac cgggca 456

<210> SEQ ID NO 603
<211> LENGTH: 217
<212> TYPE: DNA
<213> ORGANISM: Mycobacterium tuberculosis

<400> SEQUENCE: 603
cttccggctc gtatgttgtg tggaattgtg agcggataac aatttcacac aggaaacagc 60
tatgaccatg attacgccaa gctatttagg tgacactata gaatactcaa gcttggccac 120
ctcgcggtgt gtggtggaac ccatctgagc agtgtgccaa accggggcag acagctccca 180
attgacgtga gcccgctcac ttgctgggta agcgtcg 217

<210> SEQ ID NO 604
<211> LENGTH: 478
<212> TYPE: DNA
<213> ORGANISM: Mycobacterium tuberculosis

<400> SEQUENCE: 604
tagcgccccc tcccgggcgg agctccacgg cgtggatcaa ggtaccggcc gggatgttgc 60
gcaatggcag gttgttgccc ggcttgatgt cggcgttagc gccggattcc accacatccc 120
cttgcgaaag tccgttgggt gcaatgatgt agcgcttctc cccatcgaga tagtggagca 180

-continued

```
acgcaatccg tgcggtacgg ttcgggtcgt actcgatgtg cgcgaccttg gcgttgacac    240

catctttgtc attgcggcga aagtcgatca tccggtaagc gcgcttatga ccgccgcctt    300

tgtgccgggt ggtaatccgg ccatgcgcgt tgcgtccacc gcgaccgtgc agcgggcgca    360

ccagcgactt ctccggggtt gaccgggtga tctcggcgaa atcagatacg ctggcgccgc    420

gacgaccaag cgtcgtgggc ttgttcttgc gaattgcatg tctaatcagg tctttctc      478


<210> SEQ ID NO 605
<211> LENGTH: 459
<212> TYPE: DNA
<213> ORGANISM: Mycobacterium tuberculosis

<400> SEQUENCE: 605

tgaaactata taatactcaa gcttgccaaa gaagacctcg tcgaccaagc aggacgcgac     60

cgtcgaggtg gcgatccggc ttggcgtcga cccgcgtaag gcaaaccaga tggttcgcgg    120

cacggtcaac ctgccacacg gcactggtaa gactgcccgc gtcgcggtat tcgcggttgg    180

tgaaaaggcc gatgctgccg ttgccgcggg ggcggatgtt gtcgggagtg acgatctgat    240

cgaaaggatt cagggcggct ggctggaatt cgatgccgcg atcgcgacac cggatcagat    300

ggccaaagtc ggtcgcatcg ctcgggtgct gggtccgcgc ggcctgatgc ccaacccgaa    360

aaccggcacc gtcaccgccg acgtcgccaa ggccgtcgcg gacatcaagg gcggcaagat    420

caacttccgg gttgacaagc aggccaacct gcacttctc                           459


<210> SEQ ID NO 606
<211> LENGTH: 464
<212> TYPE: DNA
<213> ORGANISM: Mycobacterium tuberculosis

<400> SEQUENCE: 606

gctgagctcc acggcgtgga tcaaggtacc ggccgggatg ttgcgcaatg gcaggttgtt     60

gcccggcttg atgtcggcgt tagcgccgga ttccaccaca tccccttgcg aaagtccgtt    120

gggtgcaatg atgtagcgct tctccccatc gagatagtgg agcaacgcaa tccgtgcggt    180

acggttcggg tcgtactcga tgtgcgcgac cttggcgttg acaccatctt tgtcattgcg    240

gcgaaagtcg atcatccggt aagcgcgctt atgaccgccg cctttgtgcc gggtggtaat    300

ccggccatgc gcgttgcgtc caccgcgacc gtgcagcggg cgcaccagcg acttctccgg    360

ggttgaccgg gtgatctcgg cgaaatcaga tacgctggcg ccgcgacgac caggcgtcgt    420

gggcttgtac ttgcgaattg ccatgtctaa tcaggtcttt ctct                     464


<210> SEQ ID NO 607
<211> LENGTH: 205
<212> TYPE: DNA
<213> ORGANISM: Mycobacterium tuberculosis

<400> SEQUENCE: 607

atactcaagc ttgttggtga cctcgccggc gaacagttct cgcacgattt ccggattagc     60

gggactggtc accagttggg tatgcgggaa ggcgctgacg ttcgccgcga ttagctgttt    120

gatggacgcg gcggtgatgt cctgatcacg gaactggctg taatagccca gggtcgccac    180

gcttccatcc gggcccggac ccggc                                          205


<210> SEQ ID NO 608
<211> LENGTH: 244
<212> TYPE: DNA
<213> ORGANISM: Mycobacterium tuberculosis
```

<400> SEQUENCE: 608
gatgatcgcc ggtgccaccc cgatccgtgc ctcggtcagc gcgaacgtgc tttccggtcc 60
ggcgaccacc atgtcgcacg caccgaccag gccgaacccg ccggcccgca catgcccgtt 120
gatggcgccg accaccggca gcggcgactc gacgatggcg cgcaacagcg ccgtcatttc 180
ccgcgcccgc gccaccgcca tccggtacgg atcaccacca cctccgccgg cctcgctgag 240
gtcc 244

<210> SEQ ID NO 609
<211> LENGTH: 289
<212> TYPE: DNA
<213> ORGANISM: Mycobacterium tuberculosis

<400> SEQUENCE: 609
atactcaagc ttgccgcaat cgaaaccaac ctgtttgtgc cgcaagaaat tacgccgtgg 60
cccggcgccg atcaagaaac gccccggcgc gcggcggtgt cgtcgtatgg catgacgggc 120
accaatgtgc acgccattgt cgagcaggca ccggtgccag cccccgaatc cggtgcacca 180
ggcgacaccc cggccacacc cggtatcgac ggcgcgctgc tgttcgcgct gtcggccagc 240
tcgcaggacg cgctgcggca aaccgccgcg cggctggccg attgggtct 289

<210> SEQ ID NO 610
<211> LENGTH: 282
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 610
ttggcgggtt ggccacanca ncccgccggt gacggcgacg atgctgggct ggttgcggcc 60
ctgcgccacc gcggcttgca tgctggttgg ctgtcttggg acgatcccga aatagtccac 120
gcggatctgg tgattttgcg ggctacccgc gattaccccg cgcggctcga cgagtttttg 180
gcctggacta cccgcgtggc caatctgctg aactcgcggc cggtggtggc ctggaatgtc 240
cancgccgtt cacctacgtg accttgatgg gatccggggg nt 282

<210> SEQ ID NO 611
<211> LENGTH: 312
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 611
ncgtggacac cggtgtcgan cgccaccagc cgcatgtctg cangtcnatt ccgtcctcgg 60
caacatcttg aatgccgagc agcgcctggg cgtgatcggc aaccggggat gaccgctcgc 120
cgatccgctc gacaatcccg gcggcacgtg acatgccggc ggacggctcg acgagctgga 180
acttcagcga cgacgatccg gaattgatca ccagcacggt gctactcatg gacccctgcg 240
cctgaatccc gtgatggcca cggtgttgac tattcgtcga cagtgcaccc gagatagtct 300
tcacggctgc gt 312

-continued

<210> SEQ ID NO 612
<211> LENGTH: 349
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 612
catgtattgc cgtgctcacg gcgccacgct cgatggtttc tcgaagtctc cgggctggtg 60
tacagcttct cgttgatctc gttcgccacg ccgtcctctt cccgccgacg acccgatctc 120
gatctccana atgatcttgg cggccgccgc cgccttgagc agctcctggg cgatggccag 180
gttctcatcg atgggcactg ccgaccgtcc cacatgtgcg acggaacaaa gatgtcacct 240
tgctcacgcg tgcgcnagat cncanaaggg ccggacatac tgtcnacttg tccttgggca 300
gtggtccgtg tcagcccacg tgacgggtac ttggcgcgat aacgtggtg 349

<210> SEQ ID NO 613
<211> LENGTH: 350
<212> TYPE: DNA
<213> ORGANISM: Mycobacterium tuberculosis

<400> SEQUENCE: 613
gccaccacga cccggccgta actctgctca cggaaatgcg gccaggccgc gcgtagcacg 60
tggtatccgc cataaaggtg caccttaagc acggcgtccc aattctcgaa cgacatcttg 120
tggaaggtgc cgtcgcgcaa gatcccggcg ttgctcacca caccgtgcac ggcgccgaat 180
tcgtcaagcg cggtcttgat gatgttcgct gcgccgtcct cggtggcgac gctgtcctta 240
gttggcgacc gcccggcccc ccttgtcgcg aatctcggcg acgacctcat cggccatcgc 300
cgaacggcgc ccgtgcccgt cgcgggcgcc accgaggtcg ttgaccacga 350

<210> SEQ ID NO 614
<211> LENGTH: 126
<212> TYPE: DNA
<213> ORGANISM: Mycobacterium tuberculosis

<400> SEQUENCE: 614
caggcatgca acctttgtcc acacggcgtc tactccgtgc aaggtccgac cgcttccacg 60
tcccgccgtg acggtgctcc atctccctca gcaacgcgtg aagtggtccg atcccgcggc 120
ttcagg 126

<210> SEQ ID NO 615
<211> LENGTH: 395
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 615
gttgagacgc aaccagcgca caacgacgat ttggcgtagc ggcggacgtc tgctcgattc 60
gatcacgtcg cgctcgcatc gagcatggcc cgcgacgcta cacgatcgcc gtcgtcgatg 120
acacgaccga gccgtacgcc ggccgtaagc cgcgccagga ttcggcgaaa aacgtctacg 180
tggcgggtgt actgggtgtc gaatgattcg tggggtgcgt atgcgtcctg caatcgtcga 240

-continued

```
catagatccg tcgccgcatc gcgtcgacaa ctccgggtga gtggaataca cttgccgatc    300

acgcgacgtg cgcggatcga tgccgaccga aatacgacca catggctctt gttgcncagt    360

gttggcggca tcaaataccc tcagtgccgt ccgac                               395


<210> SEQ ID NO 616
<211> LENGTH: 371
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 616

ttnccgcctt nacgcctact ccnagacgat gctcgacgcg tgtgagcaca cggcgctgct     60

gtagacggca cggcgcagct ggatcgcgct tggtgcaccc aagcctctac gcgcgtcgct    120

gcgtcgtcat cgggtaccga acatattccg gtcgttgcgc agagtgtgca tgtgcggctc    180

ttgtgaacga acatagcaaa gcgtatatgt ctgtggcggc tctgcagata tcgcgataat    240

acgtatatac ataaggtggc gcgcgatcta tcggtatatc cgttatggcg gacgtgcgtg    300

agcgtgagtc gcggcgcatc gcgcacttcg cgatcgcgtg actggtcctc gcgactgcgc    360

gcatgcgtag c                                                         371


<210> SEQ ID NO 617
<211> LENGTH: 423
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 617

ggtgatgacg cacttgcttc gaatgagtca ttgactactc ccgtggttgt cctgcgatgg     60

tggagtgccg cgcagccttg cccgangtcg cgatcgcgtc gcgggcttcg gggagcagac    120

tgacctgcag atggaagtcg tgccacatgc ccgcgaacgg cgagctcgat gcttgttttc    180

gaagngcgca ngcggtttcg atcttgtccg cgtcaacgca gatcggatct cgccgcggtc    240

tgcatgacga tgggcgcagg cccgctcatg tcccgtagac ggggagatac gggcagccgc    300

ggatcgagac ctacgtagcg cggcgcccat cgtgccatcg acgaagaatg acggatcgcg    360

cagcgccgtc gcgtcgcttc gatgtcacgc gagatcgcca cggcagatca gcgatgcgcg    420

ggc                                                                  423


<210> SEQ ID NO 618
<211> LENGTH: 354
<212> TYPE: DNA
<213> ORGANISM: Mycobacterium tuberculosis

<400> SEQUENCE: 618

cggtacgccg gcaacaaacg ccttgtgacg agcgcgtccg agcggtcatc ggcctccacc     60

gtcatgcaca gctccttctc caggtctacg ccgacgtcgc ggtccacatt ggtgagcttg    120

gcgaatgcct cggcaacctc gtcgaaatgc gcctccgcgt ccgcatcgaa ggtcgccatg    180

tcaaagatca actcgacgta gtagctagtt accgcatcag gtcagtgttt gctggcctcg    240
```

-continued

```
gagtccggcc gaacaatggc catttcccgc gactctagaa tccagtcatc gtctcggtga    300

cgacgccttg ccgatcacat agctcgaccg gatcggagag aatctggttc tcgt          354


<210> SEQ ID NO 619
<211> LENGTH: 128
<212> TYPE: DNA
<213> ORGANISM: Mycobacterium tuberculosis

<400> SEQUENCE: 619

atactcaagc ttaagcgcag cagtaccggc ggtgcctggg catcccagca aaacggggag     60

ctcaacgaac gattcctgaa cgaagggtcg tccaccaacc tccaaaccga acggttgcca    120

gccccggc                                                             128


<210> SEQ ID NO 620
<211> LENGTH: 295
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 620

gcaagtccgc tcaatgtggt tgtgatcaca ngactacgtc gcctcaatca gctcaaacgt     60

caccccgtgg cgtgctgcgc agcatgaagg tcggcgcccg cacgatgtgg gcgaagcaac    120

aggtaataac tggtcggcat gggtcaaccc tcattgggcc gttgcggatc gggtgcacgc    180

ccggagtgcc ggtcgaactc aacaccgcct tcaccgatct tttcgtcgaa aatggcggtc    240

gtgtcggggt atacgtccgc gatcccacga ggcggaatcc gctgagccgc actga         295


<210> SEQ ID NO 621
<211> LENGTH: 361
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 621

atactcaagc ttcgcgccct caagcggctg aaggtggttc cggcgtncca acngtcgggc     60

aactcgccga tgggcatggt gctcgacncc gtcccggtga tcccgccgga gctgcgcccg    120

atggtgcagc tcgacggcgg ccggttcgcc ncgtccgact tgaacgacct gtaccgcagg    180

gtgatcaacc gcnacnncnn gntgaaaagg ctgatcgatc tgggtgcgcc ggaaatcatc    240

gtcaacaacn agaancggat gctgcnggaa tccgtggacg cgctgttcga caatggccgc    300

cgcggccggc ccgtcaccgg gccgggcaac cgtccgctca agtcgctttc cgatctgctc    360

a                                                                    361


<210> SEQ ID NO 622
<211> LENGTH: 361
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"
```

-continued

<400> SEQUENCE: 622
tgcgcatggc agttgttgcc ggcttgagtc gcgttagcgc ggattccacc acatcccttg 60
cgaagtcgtg ggtgcaatga tgtagcgctt ctcccatcga gatagtggag caacgcaatc 120
cgtgcgtacg ttgggtcgta ctcgagtgcg cancttggcg ttgacaccat ctttgtcatt 180
gcggcgaagt cgatcatccg gtaagcgcgc ttatcgacgc cgcctctgtg ccgggtggta 240
atccggccat gcgcttgcgt ccaccgcgac gtgcagcggg cgcacaccga cttctccggg 300
tgacgggtga tctcggcgaa tcagaacctg gcgcgcgaca cagcgtcgtg gctgtacttg 360
c 361

<210> SEQ ID NO 623
<211> LENGTH: 312
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 623
tgggtgatca gatactggct agttggtcgg gtggggtgat cgaagatcgc ggtggccggc 60
agcgttactg cggtgacgct gttaagcggt tacgtactcc acggcactca angaattana 120
tcccgaatcg gcaaaccctg gccagcgtcg agtccgcagc gccgtcgcgc cccccaccgc 180
tgcggcatgc tcacatacca cctcgatcgc tgcgggagtt gctcgtcggc cgaccgaccg 240
gccagccggg cggcaaaccg gaggacccaa gattcagcac caccatcgct agcccgatct 300
ggccgcgcgt gg 312

<210> SEQ ID NO 624
<211> LENGTH: 454
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 624
tcgtagcggt tgcgaccant ccgcggacag ctccgccacg cgacgggtcg ggatcaccgc 60
ggtcaaacca ccgagcggcg aggatctctg gccgtcgacg tgaccgcgca cggccgcggt 120
gatggccagt cccgaccgcc gttccacttg gcgtacgcgc tggatgtgtt gtgccgcaac 180
ggaatcccac ctcaattatg acctcgttgt gggcgagcgc ggtatcgtac gcccgaccag 240
gaatcgtcga tgctatctca cgtcaccgaa ggcctctccc agcacaccgc atccagaacg 300
tgcacacngt cgacatgtct cggcggatcc gcctgcagaa cgaacgccan gtgcgctgtg 360
cgacacgggt cgcgatcacc gctcgcacgc ggagatcggc acacgcgcag cgcatcgatc 420
ataatctctc gatgcggtct ccaccaccga acag 454

<210> SEQ ID NO 625
<211> LENGTH: 366
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated -continued as “n”

<400> SEQUENCE: 625
atactcaagc ttcgctgagg tggtggggca cgatcacgtc accgcaccgc tgtcggtggc 60
gctggatgcc ggccggatca accacgcgta cctgttctct gggccgcgtg gctgcggaaa 120
gacgtcgtca gcgcgtatcc tggcncggtc gttgaactgt gcgcagggcc ctaccgccaa 180
cccgtgcggg gtctgcgaat cctgcgtttc gttggcgccc aacgcccccg gcagcatcga 240
cgtggtagag ctggatgccg ccagccacgg cggcgtggac gacacccgcg agctgcggga 300
ccgcgcgttc tatgcgccgg tccactcacg gtaccgggta tttatcgtcg acgaggcgca 360
catggt 366

<210> SEQ ID NO 626
<211> LENGTH: 363
<212> TYPE: DNA
<213> ORGANISM: Mycobacterium tuberculosis

<400> SEQUENCE: 626
gcactcacgc tggtacaaga ccttcacaaa atctgaaatc ctgacccgat acttgaacct 60
ggtctcgttc ggcaataact cgttcggcgt gcaggacgcg gcgcaaacgt acttcggcat 120
caacgcgtcc gacctgaatt ggcagcaagc ggcgctgctg gccggcatgg tgcaatcgac 180
cagcacgctc aacccgtaca ccaaccccga cggcgcgctg gcccggcgga acgtggtcct 240
cgacaccatg atcgagaacc ttcccgggga ggcggaggcg ttgcgtgccg ccaaggccga 300
tccgctgggg gtactgccgc agcccaatga gttgccgcgc ggctgcatcg cggccggcga 360
ccg 363

<210> SEQ ID NO 627
<211> LENGTH: 367
<212> TYPE: DNA
<213> ORGANISM: Mycobacterium tuberculosis

<400> SEQUENCE: 627
atactcaagc ttgtataaaa agatcggtga gcgcatcgat tcgctccgcc gggtttgccg 60
ctgcggcggc ggagctgccg tgaccgtcta tttgggtgat cagatactgg gctagttcgg 120
tcggggtggg gtgatcgaag atcgcggtgg ccggcagcgt tactgcggtg acggctgtta 180
agcggttacg tacctccacg gcactcaagg aattaaatcc cgaatcggca aacgcctggc 240
cagcgtcgaa tccggcagcg ccgtcgcgcc ccagcaccgc tgcggcatgc tcacatacca 300
cctccatcgc tgcggcgaat tgctcgtcgg ccgaccgacc ggccagccgg gcggcaaacc 360
cggaaga 367

<210> SEQ ID NO 628
<211> LENGTH: 518
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as “n”

<400> SEQUENCE: 628
cctcatcata tgccgataga gctctacata ttcaggagat caccatggct cgtgcggtcg 60
ggatcgactc gggaccacca actccgtcgt ctcggttctg gaangtggcg accnggtcgt 120

-continued

```
cgtcgccaac tccggagggc tccaggacca cccgtcaatt gtcgcgttcg cccgcaacgg    180

tgaggtgctg gtcngccagc ccgccaagaa caggcagtga ccaacgtcga tcgcaccgtg    240

cgctcggtca agcgaccatg ggcagcgact ggtccataga gattgacgca agaaatacac    300

gcccggagat ctcgccgcat tctgatgaac tgaacgcgac ccgaggctac tcggtganga    360

catnacgacg cgttatcaca ccccgcctnc ttcaatgacc ccacgtcngg caccaaggac    420

ccggcaatcg cggctcactt gngcgatngt cnacaaccaa cgcgncgcct ggctacgggc    480

tcaacaaggc anaagacaca atccgctctc gattggtg                            518
```

<210> SEQ ID NO 629
<211> LENGTH: 435
<212> TYPE: DNA
<213> ORGANISM: Mycobacterium tuberculosis

<400> SEQUENCE: 629

```
atactcaagc ttatcgaggc ggcgcatacc gaagcgtggg aaatccagac cgaataccgc     60

gacgtgctgg acactttggc cggcgagctg ctggaaaagg agaccctgca ccgacccgag    120

ctggaaagca tcttcgctga cgtcgaaaag cggccgcggc tcaccatgtt cgacaacttc    180

ggtggccgga tcccgtcgga caaaccgccc atcaagacac ccggcgagct cgcgatcgaa    240

cgcggcgaac cttggcccca gccggtcccc gagccggcgt tcaaggcggc gattgcgcat    300

gctacccaag ccgctgaggc cgcccggtcc gacccggcca aaccgggcac ggcgccaacg    360

gttcgcccgc cggcaccacc ggtccggtga ccgcagtacg gtccccccag cctgactacc    420

gtgccccggc gggct                                                     435
```

<210> SEQ ID NO 630
<211> LENGTH: 398
<212> TYPE: DNA
<213> ORGANISM: Mycobacterium tuberculosis

<400> SEQUENCE: 630

```
tggccgggct ggtagcccgc gtatggcaag gttccgctca atgtggttgt gatgcagcag     60

gactacgttc gcctcaatca gctcaaacgt cacccccgtg gcgtgctgcg cagcatgaag    120

gtcggcgccc gcacgatgtg ggcgaaggca acaggtaaga acctggtcgg catgggtcga    180

gccctcattg ggccgttgcg gatcgggttg cagcgcgccg gagtgccggt cgaactcaac    240

accgccttca ccgatctttt cgtcgaaaat ggcgtcgtgt ccggggtata cgtccgcgat    300

tcccacgagg cggaatccgc tgagccgcag ctgatccggg ctcgccgcgg cgtgatcctg    360

gcctgtggtg gtttcgagca taacgagcag atgcgaat                            398
```

<210> SEQ ID NO 631
<211> LENGTH: 464
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 631

```
gtccagtcaa gcatcggtcc tctccgacta cgccaagant ggcgacgtgt cagtgcanac     60

agcgganatg gtggcgccta tgcgtcgacg ctcacaaacn gcggtgancg cgttctggtc    120

gtgcaccatc gagccgtgcc agcccggccg cgtgccgtca gccgcatcca ctggatgcct    180
```

-continued

```
tctcggngtt tcaatcangt acangcgacg ttcgccacca tcgtgccggg gcacggttag    240

cgagaaaccg ccgacttcac cgattgcctc ggtgatgccg tcgaacagat cgggcctatt    300

gtcgacagcc agtgtgatnc gtatttgccg ccgtgctcct cgtcgcaacg atgcgaacac    360

agatccgtgg nggacgatag cggctgacaa ngtgggggca acacaatcac atgccacatt    420

tcttcatttc acgcccacaa cccagacttc gtctcgatgn gccg                     464
```

<210> SEQ ID NO 632
<211> LENGTH: 499
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 632

```
cacgcggtct ggcccgatcc gaagatccct ttgccggcgt ggcggctctg ctcggcggtg     60

ttgtacactt ctcgaacacc tcggcaccga caccaccacc gtngcttgaa caccgccaac    120

atcggcagca gatcttgatg gtcctggtga atcccacggt gactttggag tggaaggcgc    180

catactgatc gccgcgccag cacatgagct agcggcagga aaaccagcag ccgctcacct    240

tgcgcagcag cgtcnggtga tatgcctggc gcccttaatc tcgtgaacca gttggattgg    300

gtcaactggc agccttgggt ctccggtggt gccgangtgt anataagctc ccgggtccgt    360

caacgtantg cgcaggcggc ggttactcgg cgggtcaacg agccccgctc gtgagcnatc    420

agcctttgga ccgaacggga ttcatactcc gcaggcggcc ctccgaaatc ggcacatgtc    480

ctttgatcgt tcgcaacan                                                 499
```

<210> SEQ ID NO 633
<211> LENGTH: 343
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 633

```
ggccatgtca catcggtggt acaggtaaac cgcgccgtgt gcgcggtctc ggagatcaga     60

acgtggtcgc agttgaaccg cgggctttca gccagtcgcg ataatcggcg gaagtcggcg    120

cctgccgccc caactagcgc gactcgccac ctagcacacc gatggcgaag gccatgtntc    180

cggccacgcc gccgcggtgc atcaccaagt catcgactag gaagctaagc gacancttgt    240

gcaggtgttc gggcagtagc tgctcggaaa atcggctgga aaccgcatca aatggtcggt    300

ccaatcgaac cggttacccg atcgtcacaa aaatctccgt cct                      343
```

<210> SEQ ID NO 634
<211> LENGTH: 192
<212> TYPE: DNA
<213> ORGANISM: Mycobacterium tuberculosis

<400> SEQUENCE: 634

```
gggtctacaa ccaccgggtc tgacttctgg gcttccaccg ctcgcgccgt cgcgacaaac     60

agcgcggtcg aaccgacact cgttgtgatg tcccagctat cacctccggt aggcacccaa    120

tcgaccctac ccggctatct cacccccgat ctccaggctc cgccgatcca tgcgcatccc    180
```

-continued

```
ggtccggatc cc                                                          192


<210> SEQ ID NO 635
<211> LENGTH: 376
<212> TYPE: DNA
<213> ORGANISM: Mycobacterium tuberculosis

<400> SEQUENCE: 635

caggcatgca agcttgtcgt attccgtggc actgtcagac atatgcgccg ctcctcctca      60

tcgctgcgct cggcatcgtc gccggcggtc atggcgtcac cctacccaag ccgaacgcga     120

aacgagaacg tgttccatta ttagggtgtg agcaccaata ccagattgct caccaggaac     180

tcacgcagca ccgggacgga tgtcagccac cacgcccatc tggggtggta gcggggaaat     240

acggctaacg cggctccggt gccggcagcc cagcgcagac cctcggcggc ggacacggct     300

aacaacgacg acccatagtt gttctttgcc ggatggccgt gtttgctgac atatcgggcg     360

cggcgccggc gccgcc                                                      376


<210> SEQ ID NO 636
<211> LENGTH: 83
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 636

nctacgctgc tgaatgttgt gcgccggagg anctcaagac ccacgcggtt gtacgcggac      60

ntgcgacatg ttcaaccgcc gga                                              83


<210> SEQ ID NO 637
<211> LENGTH: 319
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 637

ctaaccaaca agccatggtg gttggcgccg tcgagaggtc ggcggtcgcc acaacgggaa      60

gatcgccttg agcgtcgctc gaccgccgcc tcgagttggg tcataacgaa gtactgatgc     120

cgatcatgtc gacgtgtccg tcgcatcagc gtgcagcggc gacccctcga cgagcctcgg     180

tgccgccgcg gccagggcac cagctgtttt agcgcattgt gctccgccgg taataaagga     240

ngtcggtcgc ctccgctgct gtggttgcgg aataacatct tcccttcctg caacaggatg     300

agaatggttt taattgctc                                                   319


<210> SEQ ID NO 638
<211> LENGTH: 94
<212> TYPE: DNA
<213> ORGANISM: Mycobacterium tuberculosis

<400> SEQUENCE: 638

ctaagctttc gggtccgccg ccactagtac cgcgttgccg gccccgccga cctagaatgt      60

tccgcccatt gccgtttcct cccgccgccg ggtt                                  94
```

-continued

<210> SEQ ID NO 639
<211> LENGTH: 122
<212> TYPE: DNA
<213> ORGANISM: Mycobacterium tuberculosis

<400> SEQUENCE: 639
tctggtgccg ggtgtgccga cgggtccgtc cgcctctgct tcagtgattc tgtgatgcga 60
ccggcaacgt cctcgttgtt cggtgtctat gtggtccgtc tctccttgtt ccgcatacga 120
tt 122

<210> SEQ ID NO 640
<211> LENGTH: 210
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 640
gcgatcgntn accacaaggg cgcaaccgtt cgcgcgtcga ctgaacgtgc tgccgcctgg 60
agaactggcg ctgctgccac ctggtcggcg catcggcact tcgaggactg gatttcgacg 120
cgtggcccga cctgangtng gcggtggacn ngtgtgcacc cggttgattc ctcggccttg 180
ccgggatgcc acctgcgcct ggtggtcgat 210

<210> SEQ ID NO 641
<211> LENGTH: 328
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 641
cgtgaccgga cggggtgccg cgcgaaccgg tcttggccaa ttgccgggga ctggggctgg 60
agtataaagc gggcctgttg ccggaagata aagtcaaagc ggtgaccgag ctgaatcaac 120
atgcgccgct ggcgatggtc ggtgacggta ttaacgaccg ccagcgatga aagctgccgc 180
catcgggatt gcaatgggta gcggcacaga ctggcgctgg aaaccgccga cgcacattaa 240
ccataaccac ctgcgcggct ggtgcaaatg attgaactgg cacgnccact cacgccaata 300
tccgccagaa catcactatt gcgctggg 328

<210> SEQ ID NO 642
<211> LENGTH: 553
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 642
atactcaagc ttcttaccca nagcatgaac cccgccgtcc aatgccgcca ccgtggtgct 60
gtcggccggc cgggtgcggg cacaatcgcc gagttcggcg aacagatcct cgaaggtctt 120
cacggccagc gattgttgca cgtgtcagcc agccaagtca cggtggtttg acgccacacg 180

-continued

```
ttcgccaccg ccgcgccgcg cattagggca tcctaatata ggttaggcta ccctanttat    240

tcctgtggtc naaggaggca gccgaacgtg accttcccga tgtggttcgc agttccgccg    300

gaagtgccgt cagcatggct gtccaccggc atgggccccg gtccgctgct ggccgcggcc    360

agggcgtggc acgcgctggc cgcgcaatac accgaaattg caacggaact cgcaagcgtg    420

ctcgctgcgg tgcaggcaac tcgtggcagg ggcccagcgc cgacggttcg tcntccccat    480

caaccgttcc gtattggcta accacctgca cggtggcacc gcacaacgcc gccacaaacg    540

cgccccggta tac                                                       553
```

```
<210> SEQ ID NO 643
<211> LENGTH: 486
<212> TYPE: DNA
<213> ORGANISM: Mycobacterium tuberculosis

<400> SEQUENCE: 643

ggccgaactt aatcggttgt tggcggctgc cgagttgggt cactcggggg gtgtgcactg     60

gcacatggtg ggccggattc aacgcaacaa agccgggtcg ctggctcgct gggcgcacac    120

cgctcactcg gtggacagct cgcggttggt gaccgcgctg gatcgggcgg ttgttgcggc    180

gctggccgaa caccgtcgtg gcgagcggct gcgggtttac gtccaggtca gcctcgacgg    240

tgacggatcc cggggcggcg tcgacagcac gacgcccggc gccgtagacc ggatttgcgc    300

gcaggtgcag gagtcagagg gcctcgaact ggtcgggttg atgggcattc cgccgctgga    360

ttgggacccg acgaagcctt tgaccggctg caatcggagc acaaccgggt gcgtgcgatg    420

ttcccgcacg cgatcggtct gtcgcgggca tgtccaacaa cttgaaatcc cgtcaacatg    480

gtcgac                                                               486
```

```
<210> SEQ ID NO 644
<211> LENGTH: 146
<212> TYPE: DNA
<213> ORGANISM: Mycobacterium tuberculosis

<400> SEQUENCE: 644

gcttcccctg atactcgacc agccccactc gggccaatac gtgaatgtcc tagcattttt     60

cacccgttca cgggctagtc gagtagtaga cgattgatta gcctgaacgt acctccgacg    120

gccagctgac gaacgggttt gacgga                                         146
```

```
<210> SEQ ID NO 645
<211> LENGTH: 204
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 645

tcagctgtct gtagaagggc tggcgatact gtgcactgtc tgatatcgcn ncgtngtggg     60

actatncagn ccatnangat gcggttcngn nnntgcagag natcctggna cacatncggt    120

tcacgttaat cancatcgcg anttnctncg tnttcgatta nttctgctaa cgnntctnnn    180

agtgcctgcg ggtcgactct agag                                           204
```

```
<210> SEQ ID NO 646
<211> LENGTH: 209
<212> TYPE: DNA
```

-continued

<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 646
nctctgccgg gcnagagcgc agagtcggac ggcttcgtcg atcgtgaagc gaccntgcga 60
tgancagata tcgntnacac tgctcanaaa cttcggatca tcgntgatac acaggccaac 120
gggtagcggt tgtccaaccg cttcgtcaac ganatgggat cgtgacganc ctacgctcgc 180
aggatatgtc gcngaccngn tctaganan 209

<210> SEQ ID NO 647
<211> LENGTH: 183
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 647
cacttcatgc tcgtgcgttg gcntcgattt gcncgagngg ttagctcctc gagtgngtga 60
cgtatcactc cggcngacta nccgtatcng cgtcccgcac cggtcaactg gtctagccac 120
accggggaga atncncgacc ggngctatcg accnatcacg gcttgtcgnn aagatagnca 180
gcc 183

<210> SEQ ID NO 648
<211> LENGTH: 154
<212> TYPE: DNA
<213> ORGANISM: Mycobacterium tuberculosis

<400> SEQUENCE: 648
atactcaagc ttgccaaccg ccaccctgca tccgggggc gagcactgct ccgccgacca 60
gtacgaacca acctgcggtg cccaggccat tgacaatgtg ctggtcggcg cccgcgagtt 120
ctagcacagc aacgccgcgg ccaccacagg ggcg 154

<210> SEQ ID NO 649
<211> LENGTH: 219
<212> TYPE: DNA
<213> ORGANISM: Mycobacterium tuberculosis

<400> SEQUENCE: 649
cggtcggtgt gcttggcggc gtcggtatca acaccgccca cgaaatgggg cacaagaagg 60
attcgctgga gcggtggctg tccaagatca ccctcgccca gacctgctac gggcacttct 120
acatcgagca caaccgtggc catcacgtcc gggtgtccac accggaagac ccggcgtcgg 180
cgcggttcgg caaaactttg tgggatttcc cgccccccc 219

<210> SEQ ID NO 650
<211> LENGTH: 307
<212> TYPE: DNA
<213> ORGANISM: Mycobacterium tuberculosis

<400> SEQUENCE: 650
aatactcaag cttcgcggag gtggtggggc aggagcacgt caccgcgccg ctgtcggtgg 60
cgctggatgc cggccggatc aaccacgcgt acctgttctc tgggccgcgt ggctgcggaa 120

-continued agacgtcgtc agcgcgtatc ctggcgcggt cgttgaactg tgcgcagggc cctaccgcca 180
acccgtgcgg ggtctgcgaa tcctgcgttt cgttggcgcc caacgccccc ggcagcatcg 240
acgtggtaga gctggatgcc gccagccacg gcggcgtgga gcaaccccgc gagctgcggg 300
accgccc 307

<210> SEQ ID NO 651
<211> LENGTH: 252
<212> TYPE: DNA
<213> ORGANISM: Mycobacterium tuberculosis

<400> SEQUENCE: 651
gatggcactc acgctggaca agaccttcac aaaatctgaa atcctgaccc gatacttgaa 60
cctggtctcg ttcggcaata actcgttcgg cgtgcaggac gcggcgcaaa cgtacttcgg 120
catcaacgcg tccgacctga aattggcagc aaaccggcgc tgctgggccg ggcatggtgc 180
aatccgaaca agcacgctca acccgtacac caaccccgaa gggccgctgg cccggcggaa 240
ccttgtcctc ca 252

<210> SEQ ID NO 652
<211> LENGTH: 402
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 652
aacagctatg accatgatta cgccaagcta tttaggtgac actatagaat actcaagctt 60
ctgggcgtcg tggtgcccgg cctgccggtg caggaactgg attttactgc catctctcgc 120
gaccctgagg tggtccaggc ttacaacacc gacccactcg tgcaccacgg acgggttccg 180
gccgggattg gccgcgcgct gctgcangtg ggcgagacca tgccgcggcg ancaccggca 240
ttgaccgcgc cgctgctagt gctgcacggc accgatgacc ggctgatccc catcgaaggc 300
agccgtcgcc tggtcnaatg tntnggatcn gccgacgtgc anctgaanga ntatccccgg 360
ctgtnccacn aggtgttcaa cgaaccggan cgcaaccaag tg 402

<210> SEQ ID NO 653
<211> LENGTH: 429
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 653
caaggcatac gccaagaccc aagggatcgc agtcacctcc gtcaacggcc tggtcgccgg 60
ccacgggtcc gtgcaggaga cgtggctggc catgcaaagc gccgccgcct tatcaggaac 120
gccccggctt gtcggctttt cctgcatcga cacatttccg gaggtgttgt ggttggcgca 180
ncgcgcgaga caggcctggg atggcgtgcg catcgtcatc gggaatgcga tggcaacact 240
gaactacgag cgcatcctgc gccagcatga ctgtttcgac tacgtcgtcg ttggcgacgg 300
ggangtagcg ttcaccaagc tggccttggc cctggcgaat gacctgcggt tgacgactcc 360

-continued

```
cgggactaac ccgccgtant gagcaaggac agattctgcg cacaccctcc tcgctggtcg    420

accttgaca                                                            429


<210> SEQ ID NO 654
<211> LENGTH: 353
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 654

aacagctatg accatgatta cgccaagcta tttaggtgac actatagaat actcaagctt     60

gccggtgatc tgggtggcca actcggcggg caccatctcc atcacgacng caaacgctcc    120

ggcttcggcg acagcgatcg cgtctgcgat ngtttgttcg gcggcgtctc cgcggccctg    180

cacccggaag ccgcccaagg tgttgacnct ttgcggggtg aagccgatgt gtgccatcac    240

cgggatnccc gccgcggtca gacangcgat ttgctcggcc acccgctcac cgccctcgan    300

cttgacngca tgtgcgccgc cgtccttgaa gaaaccggtg gcggnggcaa ccc           353


<210> SEQ ID NO 655
<211> LENGTH: 464
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 655

cgttgagatc cagctgcgca ctgtgcagcg cctcggtggt ctgctcggcc tgccgggata     60

actcgttgag cttggccagc gcgtcgtcgg ccggatcagc cagcacattc gcggccagga    120

cgccggagga gacggtgaag ctcgcaaaga aacctatggc ggaccgcatg attacacgcg    180

cgatcaacca cctctggtcg agcctcaaaa tttgcttcct taaacgggcc atcgacggat    240

gacgtcgagc tggtttaggt ctcaaacagg ttacgaaacg atctcggaat tgtccaaaag    300

gggaagttaa gaaaatggat agatttctac catttcgctg tggacgatcg tacttctgct    360

atagggctcc aggggcatcg acacgcaacg accttacgcg acaccggatc cgcgctggcg    420

gcggaacggc accangcgca accgaagggc caatccgaca tcgg                     464


<210> SEQ ID NO 656
<211> LENGTH: 515
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 656

atactcaagc ttatctaggc gccagcttga ttggtctggt tgcattggcc agctgcgcga     60

gcctggctca cttcaactac aacaaccgca aacaattgcc gccttcggat ccgagttcgg    120

ttgggtacgc ggcaatggan caccatttct cggtgaatca gactattcct gagtacttga    180

tcatccactc tgcacacgac ctgcgaaccc cgcgcggcct tgccgacctg gagcagctgg    240
```

-continued

```
cgcaacgtgt gagccanatc ccaggcgttg ccatggttcg cggtgtgacc cggccaaacg    300

gggaaaccct tgaacaggcc cgggcgacat accaagccgg ccaagttggc aaccggctgg    360

gcggcgcgtc gcgaatgatc gatgagcgca ccggcgacct gaatcggctg gcatcgggtg    420

ccaacctgtt ggccgacaat ctcggtgact tcgcggtcaa gtcagccggg ccgttgcggg    480

tgtccgcagc cttgtccagc ccctcgctta ctcca                               515


<210> SEQ ID NO 657
<211> LENGTH: 403
<212> TYPE: DNA
<213> ORGANISM: Mycobacterium tuberculosis

<400> SEQUENCE: 657

caggcatgca agctttttga gcgtcgcgcg gggcagcttc gccggcaatt ctactagcga     60

gaagtctggc ccgatacgga tctgaccgaa gtcgctgcgg tgcagcccac cctcattggc    120

gatggcgccg acgatggcgc ctggaccgat cttgtgccgc ttgccgacgg cgacgcggta    180

ggtggtcaag tccggtctac gcttgggcct ttgcggacgg tcccgacgct ggtcgcggtt    240

gcgccgcgaa agcggcgggt cgggtgccat caggaatgcc tcaccgccgc ggcactgcac    300

ggccagtgcc cgcggcgatt cagccatcgg gacatcatgc tcgcttcata ctcctcgacc    360

agtcggcgga acagctcgat tcccggaacg cccacgcatg gtg                      403


<210> SEQ ID NO 658
<211> LENGTH: 444
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 658

aacagctatg accatgatta cgccaagcta tttaggtgac actatagaat actcaagctt     60

gtagaaaaag atcggtgagc gcatcgattc gctccgccgg gtttgccgct gcggcggcgg    120

agctgccgtg accgtctatt tgggtgatca gatactgggc tagttcggtc ggggtggggt    180

gatcgaagat cgcggtggcc ggcagcgtta ctgcggtgac agctgttaag cggttacgta    240

tctccacggc actcaaggaa ttaaatcccg aatcggcaaa cgcctggcca gcgtcnagtc    300

cggcagcgcc gtcncgcccc agcaccgctg cggcatgctc acataccacc tcgatcgctg    360

cggcganttg ctcgtcngcc gaccgaccgg ccanccgggc ggcaaacccn gaagacccaa    420

gaattcatca ccaccatcgc tagc                                           444


<210> SEQ ID NO 659
<211> LENGTH: 437
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 659

ccttcttgac acccacctcg ccatcgacct tgagcactcc gtcgtagttg gtgaacatgt     60

gaccggcgat cgggcgggtg aacgcgtact gggtgtcggt gtcgacgttc atcttcacca    120

cgccgtagcg cagcgcctcc tcgatctccg acttaagcga acccgagccg ccgtggaaca    180
```

-continued

```
cgaaatcnaa cggcttggcg tcngccggca gtccgagctt ggccgccgcc acctgttgcc    240

cttgcgcaag gatgtcnggg cgaancttga cgttgccggg cttgtanacg ccatgcacgt    300

tgccgaacgt cncggccagc angtatttgc cgtgctcacc ggcgcccanc gcctcgatgg    360

ttttctcgaa gtcctccggg ctggtgtaca gcttctcgtt gatctcgttc gccacgccgt    420

cctcttcgcc gccgacg                                                    437
```

<210> SEQ ID NO 660
<211> LENGTH: 422
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 660

```
aacagctatg accatgatta cgccaagcta tttaggtgac actatagaat actcaagctt     60

ggaaaggaga tccccgggaa cctggtggca accccgccat tggggttgtt gggattgccg    120

atcagcgtga angaaagctc gtctggagac agcgggtcgg ccgaagccgc aagattggcc    180

atcactagtg acganatcgt ggcgctctgc gagtanccna agacagtgac gttgttnccg    240

gcggcaattt gctgccgaat cgcactttcg agaatgacng caccctgcgc caccgangaa    300

tcnaaagtga ggttcttgat cacgaccacc gggtngagcc cttggggcgt gaagancgcc    360

tgcgcnataa cacccgggac gctgccactc atgtncagcg cgttcgcgan ctcnacatat    420

ct                                                                    422
```

<210> SEQ ID NO 661
<211> LENGTH: 412
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 661

```
tcctggtgat cganggccgc ggttccggcc gaaaatccgg ttcgggttcg ggtcgcggtt     60

ccaacttgan cgcggtccgc agctgattca ccgtggcaac gccggccaac tgcgcataat    120

gcgcatccga accctcaccc gcccgccccg cgatcacccc aacctgatcc aacgacaacc    180

gcccctcccg cataccccgg gcgcagcgcg gaaactccgg caaccgccgc gccaccgtgg    240

cgatcgtgtg ggcgttgcct gacgaacanc ccatcttcca ggccaccaac cccgccaccg    300

accgcgcccc cgtcacaccc cacaacccgt cgcgatccag ctcagccacg atctccacaa    360

tgcgcccatc aatcgcattg cgctgaacgg gcaactccgc caactcctcc aa            412
```

<210> SEQ ID NO 662
<211> LENGTH: 467
<212> TYPE: DNA
<213> ORGANISM: Mycobacterium tuberculosis

<400> SEQUENCE: 662

```
aacagctatg accatgatta cgccaagcta tttaggtgac actatagaat actcaagatc     60

tggtacccat ccgtgataca ttgaggctgt tccctggggg tcgttacctt ccacgagcaa    120
```

-continued

```
aacacgtagc ccccttcagag ccagatcctg agcaagatga acagaaactg aggttttgta    180

aacgccacct ttatgggcag caaccccgat caccggtgga aatacgtctt cagcacgtcg    240

caatcgcgta ccaaacacat cacgcatatg attaatttgt tcaattgtat aaccaacacg    300

ttgctcaacc cgtcctcgaa tttccatatc cgggtgcggt agtcgccctg ctttctcggc    360

atctctgata gcctgagaag aaaccccaac taaatccgct gcttcaccta ttctccagcg    420

ccgggttatt ttcctcgctt ccgggctgtc atcattaaac tgtgcaa                  467
```

<210> SEQ ID NO 663
<211> LENGTH: 452
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 663

```
aacagctatg accatgatta cgccaagcta tttaggtgac actatagaat actcaagctt     60

ancgccacct cccgggcgga actccacggc gtggatnaag gtaccggccg ggatgttgcg    120

caatggcagg ttgttgcccg gcttgangtc cgcgttagcg ccggattcca ccacatcccc    180

ttgcgaaant ccgttgggtn cnatgatgtn ncgcttctcc ccntcnanat aatggancaa    240

cgcnatccgt gcggtacggt tcgggtcnta ctccatgtnc gcgaccttgg cgttganacc    300

atctttgtca ttgcggcgaa agtcnatcat ccggtnagcn cgcntatgan cgccgccttt    360

gtgccgggtg gtaatccggc catgcgcntt gcgtccaccg cgaacgtgca acgggggcnc    420

caacganttc tccngggttg aaccggtnat ct                                  452
```

<210> SEQ ID NO 664
<211> LENGTH: 93
<212> TYPE: DNA
<213> ORGANISM: Mycobacterium tuberculosis

<400> SEQUENCE: 664

```
tgtgtgtggt ggtaacccat ctgagcagtg tgccaaaccg gggcagccag ctcccaattg     60

acgtgagccc gctcacttgc tgggtaagcg tcg                                  93
```

<210> SEQ ID NO 665
<211> LENGTH: 352
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 665

```
aacagctatg accatgatta cgccaagcta tttaggtgac actatanaat actcaagctt     60

gcgggtnatn gccttggtca acggcaccgt gatcggatcn gggtctaccg cacacatnga    120

ctggagcttc ggcgaantca tcgcctatgc ctcgcggggg gtgacgctga ncccnggtga    180

cntgttcngc tcnggcacgg tgcccacctg cacgctcntc naacacctca ngccaccgga    240

atcattcccn ggctggctgc acganagcga nnttgtcncc ctccaagtct aaaggctggg    300

cganananagc anaacgtccc gacnaacggc actccttttc cntttgctct tc           352
```

-continued

```
<210> SEQ ID NO 666
<211> LENGTH: 448
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 666

gaaatcattg atggtttgag tcaccaggcc gatcaagcct tcgccgagcc aaattccaat     60

caagaggccc aagcccgtac caatcagccc ggcaacgagg gattccgtca ttatcagcca    120

aaataactgc tctcgggtta cacccaaaca gcgcaatatg gcgaaaaacg gtcgccgttg    180

cacgacatta aatgtcacgg tattgtagat taaaaagata cccaccaaca angcaatcaa    240

actgagagcg gttaaattga ccgtaaaagc gtccgtcatc tgtttgacng tgtcccgttg    300

ggtatccgac gtttccatac gcacaccggc cggcagtctt tgttggatgc gtnttgcaat    360

ggcctcatct ttgatgatca aatcgatgtn gctcagtctt ccgggcatat ggaacaactc    420

ttgggccgtg gaaatatcag caatgata                                       448


<210> SEQ ID NO 667
<211> LENGTH: 386
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 667

ctttcgccca ggccggcgcg gatgtcctca tcgcttcacg aacatcatcc gagcttgacg     60

ctgtcgccga acagatccgc gctgccggcc gccgcgccca caccgttgcc gccgatctgg    120

cccatcccga ggtgaccgcg cagctggctg gtcaggccgt cggagctttc gggaagctcg    180

acatcgtcgt caacaacgtt ggcggcacca tgcccaacac gctgctaagc acctcgacca    240

angacctcgc ggacgccttc gccttcaacg tgggcaccgc ccacgcgctg accgtcgcgg    300

cggtgccgtt gatgctggaa cactccggcg gcggcagcgt gatcaacatc agctccacca    360

tgggccggct ggcggcgcgg ggtttc                                         386


<210> SEQ ID NO 668
<211> LENGTH: 378
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 668

tgtgggctcc gatccggcgc gcatggcatc gacggcgacg ccgatcgatg acggccaggc     60

ttacgagctt gagggtgtga agttgtggac caccaacggt gtggtagcgg acctgctagt    120

ggttatggcg cgggtaccgc gcagtgaagg gcnccgaggg ggaatcancg cctttgtcgt    180

cgaggctgat tcgcccggga tcaccgtgga gcggcgcaac aagttcatgg gactgcgtgg    240

catcgaaaac ggcgtgaccc ggcttcntcg cgtcagggtg cccaaagaca acttgatcgc    300

anggaagcga cggtctgaag atcgcgctga ccacactcaa cgccggacgg ctgtccctac    360
```

-continued

```
cggcgatcca accggagt                                              378


<210> SEQ ID NO 669
<211> LENGTH: 344
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 669

gagctggccg agctggaccg gttcaccgcg gaactaccgt tctcgctcga cgactttcag     60

cagcgggctt gcagcgcgct ggaacgcggc cacggtgtgc tggtgtgcgc gccgaccggc    120

gctggcaaga cagtggtcgg cgagttcgcc gtgcacctgg cgctggcggc cggcagtaaa    180

tgtttctaca ccacgccgct gaaagccctg agcaaccaaa agcacaccga tctcacagca    240

cgctacggcc gtgaccagat ctggctgctg accggtgacc tgtcngtcaa cggcaaccgc    300

cggtggtggt gatgaccacc gaaatgctgc gcaacatgct ctac                     344


<210> SEQ ID NO 670
<211> LENGTH: 411
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 670

gatctctgga tcggcggggc tctccgggcc ggcctcggcg acctcagcgg gccgcgcctt     60

ccggccgaac cattccctag ccatagatga ccgcacctcg atgcacggtt tggcggcaac    120

gcggcaaggc gtcngtcggg cccagccgcg gcaatgcggg tacccgggag cgcgggtcng    180

tanaccancg ctggactgcg tcgcgcggtg cgtcnacntc aaagtccccg gcgtcccata    240

tcgcgtatga cgcgggcgcg cccggcacca ngggtgccga tccggccgtc tcgaacacca    300

ccggcccgcc agccgccgcg ggtccggcag cnaacccgcc cgcgccgata cccgctgccc    360

gcgtgcgtga ttgaccgccg cgcgcacgct ggccanggat caaagcccgt g             411


<210> SEQ ID NO 671
<211> LENGTH: 473
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 671

ggacgcgtag cccgccaggc cggtcagggt gcccttccag tccacgccgc tgtggtcggc     60

gaaccgctta tcttcaatcg agacgatcgc cagcttcatc gtgttggcga tcttgtccga    120

gggcacctcg aaccggcgct gcgagtncag ccacgcgatc gtgttgccct tcgcgtcgac    180

catcgtcgat accgcaggca cttgcccctc gagcagctgg gccgagccgt tggcaacgac    240

ctcagangca cgattggaca tcagccctag cccgcctgcg aacgggaacg tcagcgcagt    300

ggcgacgaca ctggccaaca gacagcaccc agccagcttc agaacggtga tcgcggccgg    360
```

```
gaagcgctcg ggcatgcgtn ctacagtagc gacctcctgt cactccacgt gccgctcggt    420

ccaatagaat ctttccgcgg gcgggtgaat ctctgcngga tcggggcngg cgc           473
```

<210> SEQ ID NO 672
<211> LENGTH: 357
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 672

```
gctcgttgcc ggcggcgatc tcgtcgagct cgtcttccat cgccgcggtg aagtcgtagt     60

cgacgagccg accgaaatgc tgctcgagca gaccggttac cgcgaacgcc acccatgacg    120

gcaccagtgc actgcccttc ttgtgcacgt ngccgcgatc ctggatggtc ttgatgatcg    180

acgantaggt cgacgggcgg ccgatgccca gctcctcgag cgctttgacc agcgacgcct    240

cngtgtnncg ggccggcggg ttggtggcat ggccgtctgg ggtcaactcg acnatgtcca    300

accgttgacc cggggtcaga tggggcagtc gccgctcggc atcgtcagcc tcgccgc       357
```

<210> SEQ ID NO 673
<211> LENGTH: 402
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 673

```
gtctttcgat ggctgcttct tcggcgctga cgctggcgat ctatcacccc cagcagttcg     60

tctacgcggg agcgatgtcg ggcctgttgg acccctccca ggcgatgggt cccaccctga    120

tcggcctggc gatgggtgac gctggcggct acaaggcctc cgacatgtgg ggcccgaagg    180

aggacccggc gtggcagcgc aacgacccgc tgttgaacgt cnggaanctg atcgccaacn    240

acacccncgt ctgggtgtac tgcggcaacn gcaagccgtc ggatctgggt ggcaacaacc    300

tgccggccaa gttcctcgag ggcttcgtgc ggaccatcaa catcaagttc caagacgcct    360

acaacgccng tggcggccac aaccgcgtgt tcgacttccc gg                       402
```

<210> SEQ ID NO 674
<211> LENGTH: 336
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 674

```
gccaggtcga ggtcccatgc gcgtgggcca ttgatgctga tcgccaggac gtcaaanatt     60

tggtccggcg tcagctgggc gaaaaacgtg ggccccagga cttgcccgga gctgcccggg    120

ttcccgtcgc gcagctcggc ggccccggtc agaaanaaat tgcgccaggt cgcacactcc    180

gcgccgtang ccagctgctc cagggtgtcg gcatagagcc cgcgggccgc agcgtgctcg    240

ctgtcggcga acaccgcatg gtcgagaagc gttgccgccc aacggaaatc acctgcgtcn    300
```

-continued aangcttcgc gggccaactc cagcactcgg tcgatg 336

<210> SEQ ID NO 675
<211> LENGTH: 405
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 675
naaacgttcc ggcttnggtg ccgggcgctt atttgcgtct ctgggatcac nctcagtcgc 60
cggcggctgc cgttgggcta tnanttgcac cganccggaa aatccgcacn anaactgcna 120
gtagcggcct gcagaantgc atcctcggcg aancngacta ccggtggaca ncnacaagcg 180
ccgccgaaca acgcactggc ccgagggatn ggcgtctatc ggccccgccc gtcgaactng 240
gaacagacng tgcggttcta ccgtgatctg gtgggaatgc tcnaccanac cttcccnann 300
gctacggaac nacggcgcga tattcngccn tcccanctcg agcctgacnc tngatatcgt 360
cgannctcac catcncgatc ngctgtgccg gtnttgctcg gactn 405

<210> SEQ ID NO 676
<211> LENGTH: 389
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 676
cgaacgacga acnccncaag ccatggtggt tggcgccgtc aaaaggtccg cggtcgccac 60
tactggaaaa tcgccttgag cgtcnctcga ccnccgcctc gagttgggtc ntaacgaaat 120
acctgatgcc gatcangtcn acgtctccgt cgcnncaacg tgcagcggcg acccactcta 180
cnangtctcg gtnccgccnc ggccagngca ccaccagtga cnaatccntg cgccntcggg 240
ccnagcantc ccggtgcnac cgnggtgggt ccggcgatgg tngggtgtnc tcnntacngg 300
aacgccagcg cnatcancat cggcanactc ncgtcgatgt gccgcggcgc aaccatcccc 360
cacaatgatc nggtgcgtct gatcaggcn 389

<210> SEQ ID NO 677
<211> LENGTH: 135
<212> TYPE: DNA
<213> ORGANISM: Mycobacterium tuberculosis

<400> SEQUENCE: 677
ttaggcgtga cggccaccgg ggccactccg cacaatctgt acccgaccaa gatctacacc 60
atcgaatacg acggcgtcgc cgactttccg cggtacccgc tcaactttgt gtcgaccctc 120
aacgccattg ccggc 135

<210> SEQ ID NO 678
<211> LENGTH: 140
<212> TYPE: DNA
<213> ORGANISM: Mycobacterium tuberculosis

<400> SEQUENCE: 678

-continued

```
cgtcaccccg atgcgcccag atcggggctt cgcagataaa gcacgaactg gcgggcaaaa     60

cgtcgatctc ggagccggaa gggcaatcag ccgaccgtcg acgaacgaca ccggcgagac    120

cacttaggca gtgacggcct                                                140


<210> SEQ ID NO 679
<211> LENGTH: 272
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 679

cttttcncga tgtctcatga tnccnangga gaacnntgcn ancncngccg ctgacntngc     60

ncaccgctnt ggcngnggtg acattggtgg tggttgcggg ctgcnacgcc cgactcgang    120

ccganccatn tnttgcggcc gaccgcntnt cgtctcnacc gcannccena tctcngccgc    180

ncccggtgga nctacngctn cttcgccatc tctcgccnat ggctccngcg nntcgcncaa    240

cgtntggttt ggtnanctgc ctacctggtc nt                                  272


<210> SEQ ID NO 680
<211> LENGTH: 507
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 680

gctgcgccag tcgttcggtg cggtcatgcc gttggaccna ccatcggagt tagttgccga     60

accgcggacc accgcaagca cccggtcctg gtcgcgcacc gcgtcggcca accgcttgag    120

caccaccacg ccgcagccct cgccgcgcac gaatccatcc gcgttggcgt cnaanctgtn    180

gcatcggtcg gtcggtgaca gcgccgacca cttggacagc gcgatggcgg tgaacggtna    240

ntaggtgacc tgccnccncg cccgccaatg cccacctccg cttcacncat gcgaatggtc    300

tgacacgccn agtgaattgc caccagcgac aacaaaaatc ggtatctncn gcgacggcgg    360

acacgcnatc ccnactgata ctcgatccgc cccaccgctt gnanctccgg gttccngtgc    420

tcatgtaccn tcatgtcggt ctgcgcncga tattgacgat cgtgtttccc acgannanag    480

ancctcatca cgccggttcg agtgccg                                        507


<210> SEQ ID NO 681
<211> LENGTH: 470
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated
      as "n"

<400> SEQUENCE: 681

ctgtgtgcgg ncggcgcgat atcggccttt ttactaaccg aacccgatgt gggctccgat     60

ccggcgcgca tggcatctac ngcgacgccg atcgatgacg gccaggctta cgagcttgag    120

ggtgtgaant tgtggaccnc caacggtgtg gtagcggacc tgctantggt tatggcgcgg    180
```

-continued

```
gtaccgcgca gtgaanggca ccgaggggga atcancgcct ttgtcgtcta ngctgattct    240

cccgggatca ccntggagcg cnccncnant tcatgggact gcgtggcatc caanacggcg    300

tgaccggctt catccntcng ggtgcccaaa gacaacttga tcngcnngga agcgacgtct    360

gaanatcgcg ctgatcncac tcaacgccgg acgctgtcct accggcgatc gcaccggant    420

tgccaanccg cgctnannat ncgcgngaat gnccgtccac nantgcatgg                470
```

<210> SEQ ID NO 682
<211> LENGTH: 346
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 682

```
tggggtgccg ggcgccgagt tgcgtccctg ggatcacgca gagtcgccgg cggctgccgt     60

tgggctatga attgcaccga gccggaaaat ccgcancaaa actgcgagta gcggcctgca    120

gaagtgcanc ctcggcgaaa cggagtacgg tggacaacga aaagcgccgc cgaacnacgc    180

actggcccga gggattggcg tcaatcggcc ccgcccgtcg aacttggaag anacantgcg    240

gttctaccgt gatctggtgg gaatgctcca acnnaccttc nccgaaagct acggaagcna    300

cggcgcgatn ttcggccttc ccagctcgac ctgacgctgg aaatcg                    346
```

<210> SEQ ID NO 683
<211> LENGTH: 453
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 683

```
nggcngggaa gttaatgccc tactggttcn atgctcncac ntcnccngtg acnncctgcn     60

ccgacccgcc gaggtcctgn ccgtnaccac cgancnggcg atccgggact ctngtacgca    120

tccaacanng ancaacgtgc acgggcggag tngtnccgcc acttcgncna tgacggggtc    180

gatccnttcg acgtccgtcg ccgcgtcggt cgagtggcgg tcacnctccn ngtactcgac    240

cncacngacg agaggactcg ancccatcta cgtgtggacg aaacanatct tctgtccnac    300

gactacacca ccacccaggc catcgccgnc gcccgcgang cccccttcgac gccntactgg    360

tccngnggng gcgctctccg gttgtctnnc ncntgncgtg ttccttcacn cactgcccna    420

catcganccc gagcnatncn angtccgtca atc                                  453
```

<210> SEQ ID NO 684
<211> LENGTH: 382
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 684

```
ggacactgtt cgcgtgcccc tcgtcaaagc cggagtggtc gtgctgcgcc ggacccgacc     60
```

-continued

```
cgaccttcag cgggggttca cagctccgtg ggtgccgtta cttccgatcg ccgcagtgtg    120

cgcgtgcctg tggctgatgc tgaacctcac cgcgttgact tggatccggt tcgggatctg    180

gctggtggcc ggaaccgcga tttatgtcng ctacgggcgc cggcactcgg cgcatggcct    240

tcggcaagcn cnananaacg cgacccggag gtgttgaact agcttcgccg cgtatttaca    300

aattgcntta tatgtctaca cataagacgc aaactgctct attgtcaant cccancgtgg    360

tgtggcncat gaagatgttt gg                                              382
```

<210> SEQ ID NO 685
<211> LENGTH: 408
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 685

```
tccttctcgg tatcggtttg ggctgtcacc ancagttggt agttcttcac gtnctgttgt     60

tcgagcgtcn agccgtcgcg cgtgtcnang tcnccggacg cgtatcccgc caggccggtc    120

anggtgccct tccantccac gccgctgtgg tcggcgaacg ctnatcttca atcgagacca    180

tcgccagctt catcntgttg gcgatcttgt cnnacggcac ctcnaaccgg cgctnctagt    240

acnccacncn atcntgttnc cttcncgtcn acatcctcga tnccncntgc actttccctc    300

gancncctgg gccgagccgt tggcantnac ctcngagccc cattggacat cancccancc    360

cgcctgcgaa cgggaacgtc agcncnctgg cgacaacctg gccaacan                  408
```

<210> SEQ ID NO 686
<211> LENGTH: 372
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 686

```
cacnccgtga tcgcnagccc cngtagaaat ngttgagcca gttggtgcgg cgctcgttgc     60

cggcggtnat ctcgtcgagc tcntcttcca tcgccgcggt gaagtcgtac tcgacnagcc    120

gaccnaaatg ctgctcnagc agaccggtta ccnnnaacnc cncctcntga cngcaccagt    180

gcnctgccct tcttgtgcac gtacccgcna tcctggatgg tcttgatgat cnactantnt    240

gtcgacgggc ggccgatgcc catctcctcn agcgctttga ccagcgacnc ctcggtgtat    300

cgggccggcg ggttngtggc atggccgtct ggggtcanct cnacnatntt canccgttga    360

cccggggtca ca                                                         372
```

<210> SEQ ID NO 687
<211> LENGTH: 403
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 687

-continued tggccttctt gncangggcn nacatnngct atngcgagcg tgtaaccgat catcntccng 60
gcgactgtgg cctgancggc aagggtngcc tnattcntcc tcctgnggca tggttnccac 120
acggaatgnc ggtaagtctg gtcggcaacc tggcccgctg cgggttgggt tcggattcgc 180
tcggctanta aggtgctcgc ctggtgtnac nactaatcnc natatacnct tancgggagt 240
ngncgtcccg atcctngccc tgccgcnggc gatcncgttc gcancaccgc caccggaact 300
cncaangtgc gctcatcggg ctctacgcgc catcttcccc ggattcttcg cggcngngtn 360
ccgngggacc ccggactgtg acnggcccaa cggctcatca tcg 403

<210> SEQ ID NO 688
<211> LENGTH: 356
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 688
ccggatagcg gtgtctgaac ttcgcccgtt ccctccancg cattgagctt cagcccgacc 60
ggcaggtnng gagtcggcat gcggtccttc gccccgaccc cgctggctaa atanccaccc 120
ccgagcgcgg tcacggtctt tgcaccggga cgacgcatac cggcagcgcg aacatcnccg 180
cgggctgcag cntgaacgtc caataccant cnaacagtgt ccgcgcgtna aaacccganc 240
cggcggtcgc ttcngtaatc aacggctcct gcgcaaccag ctgcaagtcg ccggtgccac 300
cggcgttgac gatcttgatg tctgcganct cgcgcaccag ctcgacggcc cgggca 356

<210> SEQ ID NO 689
<211> LENGTH: 439
<212> TYPE: DNA
<213> ORGANISM: Mycobacterium tuberculosis

<400> SEQUENCE: 689
cctcccgacc acatacaggc aaagtaatgg cattaccgcg agccattact cctacgcgcg 60
caattaacga atccaccatc ggggcagctg gtgtcgataa cgaagtatct tcaaccggtt 120
gagtattgag cgtatgtttt ggaataacag gcgcacgctt cattatctaa tctcccagcg 180
tggtttaatc agacgatcga aaatttcatt gcagacaggt tcccaaatag aaagagcatt 240
tctccaggca ccagttgaag agcgttgatc aatggcctgt tcaaaaacag ttctcatccg 300
gatctgacct ttaccaactt catccgtttc acgtacaaca ttttttagaa ccatgcttcc 360
ccaggcatcc cgaatttgct cctccatcca cggggactga gagccattac tattgctgta 420
tttggtaagc aaaatacgt 439

<210> SEQ ID NO 690
<211> LENGTH: 442
<212> TYPE: DNA
<213> ORGANISM: Mycobacterium tuberculosis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 690
cttcacntcc gtacggctcg ggtacgcttc ggtcncattg tgcgagtgat agatgacgac 60
cgggacctcg tcggcatctt ccatagcccg ccacaccttc agttgctcac cggaatccaa 120

-continued

```
ccggtanaag gtcggcganc gctcngcatt ggtcatcggg atatgccgct cgggacggtc    180

anagccctcg ggtccggcca gcactccgca ggcttcgtcg gggtggtcgc gacgcgcatg    240

ggccaccatc gcattcacca ggtctgcgcg aatcaccagc acgtanacgg ttcctttcct    300

aagcaacacc gaantttcag gacccgaatg ctccgggaaa catgtcacgg taggtcggta    360

ttccggctac cggctganca ttgagcacgc cggccagcac cgcacgaacc aggcaatcag    420

ccgccgccgc acccgaccgc gg                                             442
```

<210> SEQ ID NO 691
<211> LENGTH: 365
<212> TYPE: DNA
<213> ORGANISM: Mycobacterium tuberculosis

<400> SEQUENCE: 691

```
caggcatgca agcttgatgc cgccgaaacc gagcgtgagc acgccgccag ccaccacgcg     60

cgggtcgggc gccgggcccg ggccgccagg ctgctccgct cggtgatggc acgccaccgc    120

gacaccaccc ggctgcgcta cgtcgagcca taccgggcgg agctacatcg gctcggccgc    180

ccagtgttcg ggccctcttt cgaggtcgag gtcgataccg atttgcgcat ccgcagccgc    240

accctggacg acagaaccgt gccctacgaa ttgcttgtcg ggcggggcca aagaacagct    300

tggcatcctg gcgcgattgg ccggcgcggc gctggtcgcc aaggaagacc cgttccggtg    360

ctgat                                                                365
```

<210> SEQ ID NO 692
<211> LENGTH: 307
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 692

```
aagntcgggt ttccacacgc gcggtttgac cctagtcata tgtaatcatg tgtaccatgt     60

gcgggcgctt ttcgacggcc gcgaaccacc gganatttcc tgtgatttca ctgcatgcgt    120

accatctggc acaattgagc anttgtctnt cgcggtggtc ggncgggttg cgtgccgcct    180

gctgcganat gcaccantaa gcccgaaccc accggcttgg tgaccaccgc acgctgcgtg    240

tggggggtaa ccactccgcg accccaagga tggtcatttc caatgaaccg gctggacttc    300

gtccana                                                              307
```

<210> SEQ ID NO 693
<211> LENGTH: 414
<212> TYPE: DNA
<213> ORGANISM: Mycobacterium bovis

<400> SEQUENCE: 693

```
gtcgcggttc gatcgacccg atcttcacct cgtaacctcg atgcttagca ggatccagct     60

tgaccgcgtt tggctctacc cactctttga gtggcgccgt cgcctgtgcc ccatcggtgt    120

tcatgacgaa cgcttcgaaa gacttcctct tgtgagccgg aatgtctgcg taaagaagtt    180

ccatgtccgg gaagtagacc cggtcgccct ccacgtggta ctccttcgag gtccgcttct    240

cgccggatcc gataaacacc ggccccaggc accgcagcgt gagttcgaac ggcttcaggt    300

aggtgttcat gcggcggact ccgggagtgc gagaaatagc ggtcgcgcgt agctgtagac    360
```

-continued cggatggttt ccgcccaggc tgacgtcgaa gatgcctcct tggaaggggc gcga 414

<210> SEQ ID NO 694
<211> LENGTH: 256
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 694
aactcaagtt tttacggtga tcgcgcatca cctggttcat gaactggaag cagcgcagcg 60
cttccttttc ggccgcaaca tgagccagcc tctcgtcggc ggtcgggtgc aggtgctcgg 120
gcagctcggc cgcgacagcc gcctgaccct gaaaccagct tccatatccc gcgacnaacg 180
acgccagtcc gctacgtaac ccctccgcga ctgtccatgg acaacagcgc gttctccacc 240
gaccgggccc gggtgt 256

<210> SEQ ID NO 695
<211> LENGTH: 328
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 695
gtgcaggttt cgacaatgtg gtgccggttc ggcggctacg tgccatcgag acactggcgc 60
angctatcgc acccgttatc ggctgcgagc aaatcgcggt atgcgttctt gagcatgagt 120
cggcgaccgt cgtcatggtc gacacccacg acggaaagac gcagatcgcc gtcaagcatg 180
tgtgccgcgg attatcagga ctgacctcct ggctgaccgg catgtttggt cgcgatgcct 240
ggcgcccggc cggcgtggtc gtggtcggct cggatagcga ggtcagcgaa ttctcgtggc 300
agctcgaaag ggtcctgccg gtgccggt 328

<210> SEQ ID NO 696
<211> LENGTH: 278
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 696
ttcgagtcat gcgcccgcct cgaccacgaa natgcacgtc gnggttcgat cgacccgatc 60
ttcacctcgt aacctcgatg cttagcagga tccagcttga ccgcgtttgg ctctacccac 120
tctttgagtg gcgccgtcgc ctgtgcccca tcggtgttca tgacgaacgc ttcgaaagac 180
ttcctcttgt gagccggaat gtctgcgtaa agaagttcca tgtccgggaa gtagacccgg 240
tcgccctcca cgtggtactc cttcgaggtc cgcttctc 278

<210> SEQ ID NO 697
<211> LENGTH: 264
<212> TYPE: DNA
<213> ORGANISM: Mycobacterium bovis -continued
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 697
gtcatgtgta ccatttgcgg gcgcttttcg acggccgcga aacaccggag atttcctgtg 60
atttcactgc atgcgtaccg tctggcacaa ttgagcagtt gtctgtcgcg gtggtcggcc 120
gggttgcgtg ccgcctgctg cgagatgcac caataagccc gaacccaccg gcttggtgac 180
caccgcacgc tgcgtgtggg gggtaaccac gccgcgaccc caaggatggt catttccaat 240
gaaccggctg gacttcntca acaa 264

<210> SEQ ID NO 698
<211> LENGTH: 169
<212> TYPE: DNA
<213> ORGANISM: Mycobacterium bovis

<400> SEQUENCE: 698
aacagcgcgg ttgaactgat aggtgcggcc cggctcgagc aggccgggcc atttgttcga 60
tgcggttacc gaaagatctc ttcggtgacc tgcccgccgc cggccagctc ggcccagtgc 120
ccggcgttgg ccgccgcggc gacgatcttg gcgtccacgg tggtcgggg 169

<210> SEQ ID NO 699
<211> LENGTH: 256
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 699
gcatctgggc tggcggtggt tcgccgctcc gaagccgtcg aacaccatcg ccagcgcggc 60
ttccacatca acgaccattt cggccagctt gcggcgcatc agcggcttgt cgatgagcgc 120
cccaccgaat gcccgccgct gcccggcgta ncacagcgat tcgaccagcg cgcggcgcgc 180
gttgccgagg gcgaacgaag cggtgcccaa ccgcaatctg ttggtcagct ccatcatgcg 240
ggtgagtccc ttgccg 256

<210> SEQ ID NO 700
<211> LENGTH: 291
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated
as "n"

<400> SEQUENCE: 700
atcggtttcc agcaacagcc gatcgacggc ttcgcccagg ccgctcccgg gcgacccgac 60
cattgctgtc gccgcgtaac gccatcacgg atgacgcgca gttcgtcgct gtctagctcc 120
accatcgcct gcacaccggc ggccagnacc cattggccgt cgcactcgta nagcaggtaa 180
tcctcgtcga cggactcggt aaccaccgcc gccagctccg ctgccaggtc ggcggggttg 240
acaccggcgg gcatcgggat ggacgacgac gcggtgctga cggcgcctgt c 291

-continued

<210> SEQ ID NO 701
<211> LENGTH: 315
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 701
agcggtttcc cangcgggat gtgctgtgag cgccgcacca ccagcgccga cgctaaggat 60
ggaacgcacg gcatcttctg acgcgtaacc gcgttgtgat cgcgagctga ggagacggta 120
tgggggaggg ttctcggagg ccatctggga tgttgatgtc tgtcgatctt gagccggtgc 180
aactcgtcgg cccggacggt acgccgacgg ccgaacgccg ctaccaccgt gaccttcctg 240
aggaaacgct gcgttggctc tacgagatga tggtggtcac ccgcgagctg gataccgaat 300
tcgtcaatct gcacg 315

<210> SEQ ID NO 702
<211> LENGTH: 328
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 702
caagcttcca caggtaggga tcgaggaaca gcgcgttgaa ctgataggtg cggcccggct 60
cgagcaggcc ggccatttgt tcgatgcggt taccgaaaat ctcttcggtg acctgcccgc 120
cgccggccag ctcggcccag tgcccggcgt tggccgccgc ggcaacgatc ttggcgtcca 180
cggtggtcgg ggtcatgccc gcgagcagga tcggcgagcg gccggtcagc cgggtgaact 240
tcgtcgaaag cttgaccctg ccgtcgggga ggcgaaccac ggtcggtgcg tanctccacc 300
aagcccgggc aacctcgggg gtggcgcc 328

<210> SEQ ID NO 703
<211> LENGTH: 352
<212> TYPE: DNA
<213> ORGANISM: Mycobacterium bovis

<400> SEQUENCE: 703
tggacctcat gacaacgcgg cggcgattac ccccgctacc gccagcagca tgacggcggt 60
agcgaacacc gccggatgca gcgcaggtgc gtcgatgtgc tcacggaatc gccccggcac 120
cgcgatctcg aggatcacca gtgccacccc ctgcagcgcg acaccgacga ttccgtacac 180
cgccacgccg atcaggccct gggccagctg gcgtatatgg cggcgatggt gacgatggcc 240
agcgccacat acattgtggc ggccagaacc acggcgttgg ggcggcggtc gatgaacact 300
aggcgacgca gatcgcccgg ggtcaacagg ttgaccatca gaaagcctgc ga 352

<210> SEQ ID NO 704
<211> LENGTH: 315
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

-continued

<400> SEQUENCE: 704
tttggtgcgg ccggcaatca acttcngctc ncagcggttt cccaggcggg atgtgctgtg 60
agcgccgcac caccagcgcc gacgctaagg atggaacgca cggcatcttc tgacgcgtaa 120
ccgcgttgtg atcgcgagct gaggagacgg tatgggggag ggttctcgga ggccatctgg 180
gatgttgatg tctgtcgatc ttgagccggt gcaactcgtc ggcccggacg gtacgccgac 240
ggccgaacgc cgctaccacc gtgaccttcc tgaggaaacg ctgcgttggc tctacgatat 300
gatggtggtc acccg 315

<210> SEQ ID NO 705
<211> LENGTH: 390
<212> TYPE: DNA
<213> ORGANISM: Mycobacterium bovis

<400> SEQUENCE: 705
cgcccagggc cgctcccggg cgacccgacc attgctgtcg ccgcgtaacg ccatcacgga 60
tgacgcgcag ttcgtcgctg tctagctcca ccatcgcctg cacaccggcg gccaggaccc 120
attggccgtc gcactcgtag agcaggtaat cctcgtcgac ggactcggta accaccgccg 180
ccagctccgc tgccaggtcg gcggggttga caccggcggg catcgggatg gacgacgacg 240
cggtgctgac ggcgcctgtc gcgacgctga gctcggacac agctagtaaa tgtagcctaa 300
cctacttaat gggtcgcagc cccccggggt cgtcgcatgt ccaacgttgc tcgactggaa 360
gaaaatgctc gtcggggagc aaatggcacc 390

<210> SEQ ID NO 706
<211> LENGTH: 322
<212> TYPE: DNA
<213> ORGANISM: Mycobacterium bovis

<400> SEQUENCE: 706
aatactcaat cttgatcggt ttccagcaac agccgatcga cggcttcgcc cagggccgct 60
cccgggcgac ccgaccattg ctgtcgccgc gtaacgccat cacggatgac gcgcagttcg 120
tcgctgtcta gctccaccat cgcctgcaca ccggcggcca ggacccattg gccgtcgcac 180
tcgtagagca ggtaatcctc gtcgacggac tcggtaacca ccgccgccag ctccgctgcc 240
aggtcggcgg ggttgacacc ggcgggcatc gggatggacg acgacgcggt gctgacggcg 300
cctgtcgcga ctctgagctc gg 322

<210> SEQ ID NO 707
<211> LENGTH: 398
<212> TYPE: DNA
<213> ORGANISM: Mycobacterium bovis

<400> SEQUENCE: 707
ggatgtgctg tgagcgccgc accaccagcg ccgacgctaa ggatggaacg cacggcatct 60
tctgacgcgt aaccgcgttg tgatcgcgag ctgaggagac ggtatggggg agggttctcg 120
gaggccatct gggatgttga tgtctgtcga tcttgagccg gtgcaactcg tcggcccgga 180
cggtacgccg acggccgaac gccgctacca ccgtgacctt cctgaggaaa cgctgcgttg 240
gctctacgag atgatggtgg tcacccgcga gctggatacc gaattcgtca atctgcagcg 300
ccagggggaa gctggcgttg tacacgccct gtcgcgggca ggaagccgcg caggtgggtg 360
cggcggcttg cctacgcaaa accgactggt tgttcccc 398

-continued

<210> SEQ ID NO 708
<211> LENGTH: 175
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 708
atcacgacaa cagcgacggt gtgtcggatc agcggccccc gttgccgggc aatgttgagg 60
cgtttctgcg tctggttgag gccggctggg acnccgaggt ggctcgtcgg ccacatgggc 120
agcacaccac cgtggtgatg catctagacg tgcaggaccg tgccgctggc ctgca 175

<210> SEQ ID NO 709
<211> LENGTH: 210
<212> TYPE: DNA
<213> ORGANISM: Mycobacterium bovis

<400> SEQUENCE: 709
gcggctacgt gccatcgaga cactggcgca ggctatcgca cccgttatcg gctgcgagca 60
aatcgcggta tgcgttcttg agcatgagtc ggcgaccgtc gtcatggtcg acacccacga 120
cggaaagacg cagatcgccg tcaagcatgt gtgccgcgga ttatcaggac tgacctcctg 180
gctgaccggc atgtttggtc gcgatgcctg 210

<210> SEQ ID NO 710
<211> LENGTH: 312
<212> TYPE: DNA
<213> ORGANISM: Mycobacterium bovis

<400> SEQUENCE: 710
tacaagcggc acctcgccgg tgaactgacc gttcgcacgc tgcgcaccgc cgccgggcgc 60
gtgctcggcg cgccggcggc ccccgaggcc tgagaggggga accaaccatg caggtgaaca 120
tgacggtaaa cggcgagccc gtcaccgccg aggtcgaacc ccggatgctg ctggtccatt 180
ttctccgtga tcagctgcgg ctcaccggaa ctcactgggg ctgtgatacc agcaactgcg 240
ggacatgcgt ggtggaggtc gacggcgtgc cggtgaaatc ctgcacgatg ctcgccgtga 300
tggcctccgg gc 312

<210> SEQ ID NO 711
<211> LENGTH: 255
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 711
agcggctggt tacgactccc tgtttgtgat ggaccacttc taccaactgc ccatgttggg 60
gacgcccgnc cntccgatgc tggaagccta cactgccctt ggtgcgctgg ccncngcgac 120
cgagcggctg caactgggcg cnttggtgac cngcaatacc taccgcaccc cnaccctgct 180 ggncaaaanat catcaccacg ctcgacttgg ttagcgccgg tcgancgatc ctcggcattg 240
gaaccggttg gtttn 255

-continued

<210> SEQ ID NO 712
<211> LENGTH: 304
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 712
acgcgcgccg atcatatctg ctatggatgt acaattcagc tcttgctgtt ataccagtat 60
atggtgtact atttgatcta tgctgacgtg tgagatgcgg gaatcggccc tggctcgact 120
cggccgggct ctggctgatc cgacgcggtg ccggattctg gtggcgttgc tggatggcgt 180
ttgctatccc ggccagctag ctgcgcacct cgggttgacc cgatcgaatg tgtccaacca 240
tctgtcgtgt ttgcggggct gcgggctggt antcccaacc tatgagggcc ggcaggttcg 300
gtat 304

<210> SEQ ID NO 713
<211> LENGTH: 352
<212> TYPE: DNA
<213> ORGANISM: Mycobacterium bovis

<400> SEQUENCE: 713
ccgcgctgct gctgacgtcg gtcgaacgtg cgacacgtct gcgaataccg gccgaacgct 60
gggtttatcc acaggctggc accgacgccc acgacacacc ggccgtcgcc gaccgccacc 120
gactgcatcg gtcgacggcc attcggatcg ccggtgcccg ggcgctggaa ctggctgggc 180
tggggctcga tgacatcgaa tacgtcgacc tgtattcgtg ctttccctcc gctgtccaag 240
tcgccgcaat cgaactcggc ctggacaccg acgatcctgc ccgcccgctg accgtcaccg 300
ggggcctgac cttcgccggc gggccgtgga gcaattacgt cacgcactcc at 352

<210> SEQ ID NO 714
<211> LENGTH: 233
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 714
caggcgtgca atgacctgca ctgcgccgga nantccctaa cccactaaac cggggccgct 60
cacaagccgt gcagctcggt cagcgtcagg tgcgcgacca ggaantaaat gagcagaccc 120
gtgccgtcaa cgatggtggc gatcatcggc cccgaaacga tggccgggtc natgcgcaac 180
ttcttcagca gcggcggaag gacggcancc accagcgacn accacaccac gat 233

<210> SEQ ID NO 715
<211> LENGTH: 335
<212> TYPE: DNA
<213> ORGANISM: Mycobacterium bovis

<400> SEQUENCE: 715
gcgaacactt cgtcaacttc cagggctgcc cgcaccaagt atttcgacga gtatttccgt 60
cgggccgccg ccgccggcgc gcggcaggtg gtcatcctgg cggcggggct ggactcgcgc 120
gcgtaccggc tgccttggcc cgacgggacc acggtttttg agctggaccg cccgcaggtc 180

-continued

```
cttgatttca agcgcgaggt gctcgccagc cacggtgccc aaccgcgcgc cctgcgccgc    240

gagatcgccg tcgacctgcg tgacgattgg ccacaagcct tgcgggacag tggtttcgat    300

gcggctgcac cgtcggcatg gattgccgaa gggct                               335
```

<210> SEQ ID NO 716
<211> LENGTH: 274
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 716

```
ttgggcnttg cccncaatan ggccccaatc aaaagccgag caggtggaac ctanncgcat     60

tcgcctcntc gtntgtgcac ccgagccatc gcacgcgcgg gaattcccgg atntcnccgt    120

attctccggc ggccgggcta acccatccca ngccgaacgg ttggctcntg ccgtgggtcc    180

cgtgttggcc gatcggggcg tcaccggggg tgctcgggtg cggntgacca tggcnaactg    240

ccccnatggg ccgaccctgg tgcagataaa cctg                                274
```

<210> SEQ ID NO 717
<211> LENGTH: 327
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 717

```
tggtggaggt ccccaccaan acccggccgt aactctgctc acggaaatgc ggncaggccg     60

cgcgtagcac gtggtatccg ccataaaggt gcaccttaag cacggcgtcc caattctcga    120

acgacatctt gtggaaggtg ccgtcgcgca agatcccggc gttgctcacc acaccgtgca    180

cggcgccgaa ttcgtcaagc gcggtcttga tgatgttcgc tgcgccgtcc tcggtggcga    240

cgctgtcggt anttggcgac cgcccggccc cccttgtcgc gaaatctcgg cgacgacctc    300

atcggccatc gccgaaccgg gcgcccg                                        327
```

<210> SEQ ID NO 718
<211> LENGTH: 344
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 718

```
gccggccaaa ctggccggcg gggttgctgt cntcaaggtg ggttccgcca ccaanaccnc     60

actcaaggat cgcaaggaaa gcntcaagga tgcggtcgcg gccgccaagg ccgcggtcaa    120

ggagggcatc gtccctggtg gggganccctc cctcatccac caggcccgca aggcgctgac   180

cgaactgcnt gcgtcncnga ccggtgacaa ngtcctcggt gtccacgtgt nctccgaagc    240

ccttgccgct ccgttgttct ggatcnccnc caacnctggc ttggacggct cngtggtggt    300

caacaaggtc agcgagctac ccgccgggca tgggctgaac gtga                     344
```

-continued

<210> SEQ ID NO 719
<211> LENGTH: 271
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 719
cgaacctnaa ttgtcctgta atgcccagct caccaangca tggctggtgg ccggggcggt 60
gaagccggcg tctgcggcac cgtccaactc natgtggatn gccggaatgg ggatgtccgg 120
nacggcgaat ccgtanttcg cttgtcccgt gaggcccagg tggatggggg gaaggatcnt 180
ggtgtccggg atgatnatgg ggccgatgcc gccggttgaa gtccactgga tcgggaattc 240
gggaatcgtg atnccgacgt tcaggccgaa c 271

<210> SEQ ID NO 720
<211> LENGTH: 302
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 720
ctaacggaat gaaagccctg gtggccgtnt cggcggtggc cgtcgtcgca ctgctcggtg 60
tatcttccgc ccaagctgat cccgaggcgg atcccggcgc aggtgaggcc aactatggtg 120
gccccccaag ttccccacgt cttgtcgatc acaccgaatg ggcgcantgg ggaattctgc 180
ccagcctccg ggtctacccg tcccaagttg ggcgtacanc ctcccgccgc ctcgggatgg 240
ccgctgccga cccggcctgg gccnaggttc tcgcgctgtc accggaagcc gacactgccg 300
gc 302

<210> SEQ ID NO 721
<211> LENGTH: 303
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 721
ccgcgggaca cncctcnatg ctgccgccat ggacgcggtc gaacgcaagc agctgatcga 60
gctacaacgc cgcgcggaac gcttccgccg cgggcgtgac cgcatcccgt tgaccgggcg 120
gatcgcggtg atcgtcgatg acggcatcgc caccggagcg acggccaagg cggcgtgcca 180
ggtcgcccgg gcgcacggtg cggacaaggt ggtgctggcg gtcccgatcg gcccanacga 240
catcgtggcg aagattcgcc gggtacgccg atgatgtggt gtgtttggcg acgccggcgt 300
tgt 303

<210> SEQ ID NO 722
<211> LENGTH: 280
<212> TYPE: DNA
<213> ORGANISM: Mycobacterium bovis
<220> FEATURE:

-continued

<221> NAME/KEY: unsure
<222> LOCATION: (various positions within the sequence)
<223> OTHER INFORMATION: applicants are uncertain of bases designated as "n"

<400> SEQUENCE: 722

```
ctctgggacc ggccacggtg ccnccggcgt tcccggacgt gctgcgccag gtgtccggcg     60

gccgcgtgca tggtgttccc ggatcggccg ctggccagag cccaccggtg aatctggcgc    120

ctggccgacc accgtgcgcc gtaggcttgc gatcgtgcag cgctggcgtg gccaggacga    180

gatcccgacg gattggggca gatgcgtgct caccatcggg gtatttgacg gcgtgcaccg    240

cgggcacgcc gaactgatcg cgcacgcggt caaaggcggc                          280
```

<210> SEQ ID NO 723
<211> LENGTH: 333
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 723

```
aatactcaag ctttcgtcag ttcattgcgc cagcagacca acaanagcat cgggacatac     60

ggantcaact acccggccaa cggtgatttc ttggccgccg ctgacggcgc gaacgacgcc    120

agcgaccacn ttcagcaaat ggccancgcg tgccgggcca cgaggttggt gctcggcggc    180

tactcccagg gtgcggccgt gatcnacatc ntcaccgccg caccactgcc cggcctcggg    240

ttcacgcagc cgttgccgcc cgcagcggac natcacatcg ccgcgatcgc cctgttcggg    300

aatccctcng gccgcgctgg cgggctgatt aac                                 333
```

<210> SEQ ID NO 724
<211> LENGTH: 320
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 724

```
tgccgcggat ttggctggct gcccaatatt cagaatcggg cctttctttt tgcgcgacaa     60

taaggtcaca gtaaaccctc gttttgtgag atgcggggcg ggccgggcga antcgacctc    120

gagtgaatgg atctcgagtg aatggacagg gcatcgccta cgagtcgcat ccccatccaa    180

cagaccggtg ctcttgcatc ggaccctgaa ggtcccgcac ggagggtgtg gttgccggcg    240

cggggtcacg gtgcggtagc gacgtagtgt ttgaacgaat ttcttgatgc tccaacctgt    300

ttggtgttca atccagttct                                                320
```

<210> SEQ ID NO 725
<211> LENGTH: 296
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as "n"

<400> SEQUENCE: 725

-continued

```
aancttgcgc gctcggccgg gtcnagcatc cagctgctcg gcaaggaggc cagctacncn      60

tcgctgcgta tgcccagcgg tgagatccgc cgggtcnacg tccgctgccg cgcgaccgtc     120

ggcgaagtgg gcaatgccga gcaggcaaac atcaactggg gcaaggccgg tcggatgcgg     180

tggaagggca agcgcccgtc ggtccggggc gtggtgatna acccggtcna ccacccgcac     240

ggcggtggtg agggtaaaac ctccggcggc cgtcacccgg ttagcccgtg ggcaa          296
```

<210> SEQ ID NO 726
<211> LENGTH: 304
<212> TYPE: DNA
<213> ORGANISM: Mycobacterium bovis
<220> FEATURE:
<221> NAME/KEY: unsure
<222> LOCATION: (various positions within the sequence)
<223> OTHER INFORMATION: applicants are uncertain of bases designated as “n”

<400> SEQUENCE: 726

```
antcgaaagt gaccatctct accttgagtg ccataccgcc cgaccctatg cctcggatag      60

ctcggcggaa agaaacgctt gcagtgccgc cgaataggcg gctacgtcgt gagcgcccat     120

caactctcgc gcggagtgca tcgccagctg ggcggcgccg acgtcgaccg tggggattcc     180

ggtgcgcgcc gcggccaacg gcccgatcgt cgacccgcac ggcagatcgg cgcgatgttc     240

gtaacgctgc ataggcactc ccgcgcgctg gcaggccagt gcgaacgccg ccgcggtgcg     300

tccg                                                                  304
```

<210> SEQ ID NO 727
<211> LENGTH: 318
<212> TYPE: PRT
<213> ORGANISM: Mycobacterium sp.

<400> SEQUENCE: 727

```
Pro Thr Gln Thr Leu Thr Gly Arg Pro Leu Ile Gly Asn Gly Thr Pro
  1               5                  10                  15

Gly Ala Val Gly Ser Gly Ala Thr Gly Ala Pro Gly Gly Trp Leu Leu
             20                  25                  30

Gly Asp Gly Gly Ala Gly Gly Ser Gly Ala Ala Gly Ser Gly Ala Pro
         35                  40                  45

Gly Gly Ala Gly Gly Ala Ala Gly Leu Trp Gly Thr Gly Gly Ala Gly
     50                  55                  60

Gly Ala Gly Gly Ser Ser Ala Gly Gly Gly Gly Ala Gly Gly Ala Gly
 65                  70                  75                  80

Gly Ala Gly Gly Trp Leu Leu Gly Asp Gly Gly Ala Gly Gly Ile Gly
                 85                  90                  95

Gly Ala Ser Thr Val Leu Gly Gly Thr Gly Gly Gly Gly Gly Val Gly
            100                 105                 110

Gly Leu Trp Gly Ala Gly Gly Ala Gly Gly Ala Gly Gly Thr Gly Leu
        115                 120                 125

Val Gly Gly Asp Gly Gly Ala Gly Gly Ala Gly Gly Thr Gly Gly Leu
    130                 135                 140

Leu Ala Gly Leu Ile Gly Ala Gly Gly Gly His Gly Gly Thr Gly Gly
145                 150                 155                 160

Leu Ser Thr Asn Gly Asp Gly Gly Val Gly Gly Ala Gly Gly Asn Ala
                165                 170                 175

Gly Met Leu Ala Gly Pro Gly Gly Ala Gly Gly Ala Gly Gly Asp Gly
            180                 185                 190
```

-continued

```
Glu Asn Leu Asp Thr Gly Gly Asp Gly Gly Ala Gly Gly Ser Ala Gly
        195                 200                 205

Leu Leu Phe Gly Ser Gly Gly Ala Gly Gly Ala Gly Gly Phe Gly Phe
    210                 215                 220

Leu Gly Gly Asp Gly Gly Ala Gly Gly Asn Ala Gly Leu Leu Leu Ser
225                 230                 235                 240

Ser Gly Gly Ala Gly Gly Phe Gly Gly Phe Gly Thr Ala Gly Gly Val
                245                 250                 255

Gly Gly Ala Gly Gly Asn Ala Gly Trp Leu Gly Phe Gly Gly Ala Gly
            260                 265                 270

Gly Val Gly Gly Ser Ala Gly Leu Ile Gly Thr Gly Gly Asn Gly Gly
        275                 280                 285

Asn Gly Gly Thr Gly Ala Asn Ala Gly Ser Pro Gly Thr Gly Gly Ala
    290                 295                 300

Gly Gly Leu Leu Leu Gly Gln Asn Gly Leu Asn Gly Leu Pro
305                 310                 315


<210> SEQ ID NO 728
<211> LENGTH: 334
<212> TYPE: PRT
<213> ORGANISM: Mycobacterium sp.

<400> SEQUENCE: 728

Pro Thr Gln Thr Leu Thr Gly Arg Pro Leu Ile Gly Asn Gly Thr Pro
  1               5                  10                  15

Gly Ala Val Gly Ser Gly Ala Thr Gly Ala Pro Gly Gly Trp Leu Leu
            20                  25                  30

Gly Asp Gly Gly Ala Gly Gly Ser Gly Ala Ala Gly Ser Gly Ala Pro
        35                  40                  45

Gly Gly Ala Gly Gly Ala Ala Gly Leu Trp Gly Thr Gly Gly Ala Gly
    50                  55                  60

Gly Ile Gly Gly Ala Ser Thr Val Leu Gly Gly Thr Gly Gly Gly Gly
 65                  70                  75                  80

Gly Val Gly Gly Leu Trp Gly Ala Gly Gly Ala Gly Gly Ala Gly Gly
                 85                  90                  95

Thr Gly Leu Val Gly Gly Asp Gly Gly Ala Gly Gly Ala Gly Gly Thr
            100                 105                 110

Gly Gly Leu Leu Ala Gly Leu Ile Gly Ala Gly Gly Gly His Gly Gly
        115                 120                 125

Thr Gly Gly Leu Ser Thr Asn Gly Asp Gly Gly Val Gly Gly Ala Gly
    130                 135                 140

Gly Asn Ala Gly Met Leu Ala Gly Pro Gly Gly Ala Gly Gly Ala Gly
145                 150                 155                 160

Gly Asp Gly Glu Asn Leu Asp Thr Gly Gly Asp Gly Gly Ala Gly Gly
                165                 170                 175

Ser Ala Gly Leu Leu Phe Gly Ser Gly Gly Ala Gly Gly Ala Gly Gly
            180                 185                 190

Phe Gly Phe Leu Gly Gly Asp Gly Gly Ala Gly Gly Asn Ala Gly Leu
        195                 200                 205

Leu Leu Ser Ser Gly Gly Ala Gly Gly Phe Gly Gly Phe Gly Thr Ala
    210                 215                 220

Gly Gly Val Gly Gly Ala Gly Gly Asn Ala Gly Trp Leu Gly Phe Gly
225                 230                 235                 240

Ala Gly Gly Ile Gly Gly Ile Gly Gly Asn Ala Asn Gly Gly Ala Gly
```

-continued

```
            245                 250                 255

Gly Asn Gly Gly Thr Gly Gly Gln Leu Trp Gly Ser Gly Gly Ala Gly
        260                 265                 270

Val Glu Gly Gly Ala Ala Leu Ser Val Gly Asp Thr Gly Gly Ala Gly
    275                 280                 285

Gly Val Gly Gly Ser Ala Gly Leu Ile Gly Thr Gly Gly Asn Gly Gly
290                 295                 300

Asn Gly Gly Thr Gly Ala Asn Ala Gly Ser Pro Gly Thr Gly Gly Ala
305                 310                 315                 320

Gly Gly Leu Leu Leu Gly Gln Asn Gly Leu Asn Gly Leu Pro
            325                 330


<210> SEQ ID NO 729
<211> LENGTH: 650
<212> TYPE: DNA
<213> ORGANISM: Mycobacterium sp.

<400> SEQUENCE: 729

gcggccgcaa ggggttcgcg tcagcgggtg ttggcgggtg tcggggctgg cttaactatg      60

cggcatcaga gcagattgta ctgagagtgc accatatgcg gtgtgaaata ccgcacagat     120

gcgtaaggag aaaataccgc atcaggcgcc attcgccatt caggctgcgc aactgttggg     180

aagggcgatc ggtgcgggcc tcttcgctat tacgccagct ggcgaaaggg ggatgtgctg     240

caaggcgatt aagttgggta acgccagggt tttcccagtc acgacgttgt aaaacgacgg     300

ccagtgaatt gtaatacgac tcactatagg gcgaattcga gctcggtacc cggggatcct     360

ctagagtcga cctgcaggca tgcaagcttg agtattctat agtgtcacct aaatagcttg     420

gcgtaatcat ggtcatagct gtttcctgtg tgaaattgtt atccgctcac aattccacac     480

aacatacgag ccggaagcat aaagtgtaaa gcctggggtg cctaatgagt gagctaactc     540

acattaattg cgttgcgctc actgcccgct ttccagtcgg gaaacctgtc gtgccagctg     600

cattaatgaa tcggccaacg cgaacccctt gcggccgccc gggccgtcga                650


<210> SEQ ID NO 730
<211> LENGTH: 8
<212> TYPE: PRT
<213> ORGANISM: Mycobacterium sp.
<220> FEATURE:
<221> NAME/KEY: Unsure
<222> LOCATION: (1-8)
<223> OTHER INFORMATION: applicants are uncertain of residues
      designated as "xaa"

<400> SEQUENCE: 730

Asn Xaa Gly Xaa Gly Asn Xaa Gly
  1               5


<210> SEQ ID NO 731
<211> LENGTH: 9
<212> TYPE: PRT
<213> ORGANISM: Mycobacterium sp.
<220> FEATURE:
<221> NAME/KEY: Unsure
<222> LOCATION: (1-9)
<223> OTHER INFORMATION: applicants are unsure of residues
      designated as "xaa"

<400> SEQUENCE: 731

Gly Xaa Xaa Ser Val Pro Xaa Xaa Trp
  1               5
```

-continued

<210> SEQ ID NO 732
<211> LENGTH: 29
<212> TYPE: PRT
<213> ORGANISM: Mycobacterium sp.

<400> SEQUENCE: 732

```
Gly Gly Ala Gly Gly Ala Gly Gly Ser Ser Ala Gly Gly Gly Gly Ala
  1               5                  10                  15

Gly Gly Ala Gly Gly Ala Gly Gly Trp Leu Leu Gly Asp
             20                  25
```

<210> SEQ ID NO 733
<211> LENGTH: 45
<212> TYPE: PRT
<213> ORGANISM: Mycobacterium sp.

<400> SEQUENCE: 733

```
Gly Ala Gly Gly Ile Gly Gly Ile Gly Gly Asn Ala Asn Gly Gly Ala
  1               5                  10                  15

Gly Gly Asn Gly Gly Thr Gly Gly Gln Leu Trp Gly Ser Gly Gly Ala
             20                  25                  30

Gly Val Glu Gly Gly Ala Ala Leu Ser Val Gly Asp Thr
         35                  40                  45
```

<210> SEQ ID NO 734
<211> LENGTH: 21
<212> TYPE: DNA
<213> ORGANISM: Mycobacterium sp.

<400> SEQUENCE: 734
agttagctca ctcattaggc a 21

<210> SEQ ID NO 735
<211> LENGTH: 21
<212> TYPE: DNA
<213> ORGANISM: Mycobacterium sp.

<400> SEQUENCE: 735
ggatgtgctg caaggcgatt a 21

<210> SEQ ID NO 736
<211> LENGTH: 27
<212> TYPE: DNA
<213> ORGANISM: Mycobacterium sp.

<400> SEQUENCE: 736
aaacagctat gaccatgatt acgccaa 27

<210> SEQ ID NO 737
<211> LENGTH: 24
<212> TYPE: DNA
<213> ORGANISM: Mycobacterium sp.

<400> SEQUENCE: 737
tcctctagag tcgacctgca ggca 24

<210> SEQ ID NO 738
<211> LENGTH: 18
<212> TYPE: DNA
<213> ORGANISM: Mycobacterium sp.
<220> FEATURE:
<221> NAME/KEY: variation
<222> LOCATION: (1-18)

-continued

```
<223> OTHER INFORMATION: bases designated as "n" may be A,T,C or G

<400> SEQUENCE: 738

tctagannnn nntccggc                                               18


<210> SEQ ID NO 739
<211> LENGTH: 18
<212> TYPE: DNA
<213> ORGANISM: Mycobacterium sp.
<220> FEATURE:
<221> NAME/KEY: variation
<222> LOCATION: (1-18)
<223> OTHER INFORMATION: bases designated as "n" may be A, T, C or G

<400> SEQUENCE: 739

tctagannnn nngggccc                                               18


<210> SEQ ID NO 740
<211> LENGTH: 20
<212> TYPE: DNA
<213> ORGANISM: Mycobacterium sp.
<220> FEATURE:
<221> NAME/KEY: variation
<222> LOCATION: (1-20)
<223> OTHER INFORMATION: bases designated as "n" may be A, T, C, or G

<400> SEQUENCE: 740

cgtttaaann nnnwaggccg                                             20


<210> SEQ ID NO 741
<211> LENGTH: 21
<212> TYPE: DNA
<213> ORGANISM: Mycobacterium sp.
<220> FEATURE:
<221> NAME/KEY: variation
<222> LOCATION: (1-21)
<223> OTHER INFORMATION: bases designated as "n" may be A, T, C, or G

<400> SEQUENCE: 741

ggtactagtn nnnnwtccgg c                                           21


<210> SEQ ID NO 742
<211> LENGTH: 22
<212> TYPE: DNA
<213> ORGANISM: Mycobacterium sp.

<400> SEQUENCE: 742

acgacctcat attccgaatc cc                                          22


<210> SEQ ID NO 743
<211> LENGTH: 23
<212> TYPE: DNA
<213> ORGANISM: Mycobacterium sp.

<400> SEQUENCE: 743

gcatctgttg agtacgcact tcc                                         23
```